United States Patent
Masse et al.

(10) Patent No.: US 10,781,204 B2
(45) Date of Patent: Sep. 22, 2020

(54) TYK2 INHIBITORS AND USES THEREOF

(71) Applicant: Nimbus Lakshmi, Inc., Cambridge, MA (US)

(72) Inventors: Craig E. Masse, Cambridge, MA (US); Jeremy Robert Greenwood, Brooklyn, NY (US); Donna L. Romero, Chesterfield, MO (US); Geraldine C. Harriman, Charlestown, RI (US); Ronald T. Wester, Ledyard, CT (US); Mee Shelley, Tigard, OR (US); Joshua Jahmil Kennedy-Smith, New York, NY (US); Markus Dahlgren, Stratford, CT (US); Sayan Mondal, New York, NY (US); Shaughnessy Robinson, Westerly, RI (US)

(73) Assignee: Nimbus Lakshmi, Inc., Cambridge, MA (US)

( * ) Notice: Subject to any disclaimer, the term of this patent is extended or adjusted under 35 U.S.C. 154(b) by 0 days.

(21) Appl. No.: 16/007,099

(22) Filed: Jun. 13, 2018

(65) Prior Publication Data

US 2018/0354949 A1 Dec. 13, 2018

Related U.S. Application Data

(62) Division of application No. 15/254,071, filed on Sep. 1, 2016, now Pat. No. 10,023,571.

(60) Provisional application No. 62/213,475, filed on Sep. 2, 2015, provisional application No. 62/214,018, filed on Sep. 3, 2015.

(51) Int. Cl.
  *C07D 471/04* (2006.01)
  *A61P 37/00* (2006.01)
  *A61P 35/00* (2006.01)
  *C07D 519/00* (2006.01)

(52) U.S. Cl.
  CPC ............ *C07D 471/04* (2013.01); *A61P 35/00* (2018.01); *A61P 37/00* (2018.01); *C07D 519/00* (2013.01); *C07B 2200/05* (2013.01)

(58) Field of Classification Search
  CPC ..................... A61K 31/437; C07D 471/04
  See application file for complete search history.

(56) References Cited

U.S. PATENT DOCUMENTS

| | | |
|---|---|---|
| 4,650,750 A | 3/1987 | Giese |
| 4,709,016 A | 11/1987 | Giese |
| 5,360,819 A | 11/1994 | Giese |
| 5,516,931 A | 5/1996 | Giese et al. |
| 5,602,273 A | 2/1997 | Giese et al. |
| 5,604,104 A | 2/1997 | Giese et al. |
| 5,610,020 A | 3/1997 | Giese et al. |
| 5,650,270 A | 7/1997 | Giese et al. |
| 7,390,799 B2 | 6/2008 | Bruncko et al. |
| 7,521,557 B2* | 4/2009 | Devasthale ......... C07D 471/04 546/113 |
| 8,138,347 B2 | 3/2012 | Knight et al. |
| 10,196,390 B2 | 2/2019 | Masse et al. |
| 2007/0088163 A1* | 4/2007 | Pryor .................. C07D 405/12 546/113 |
| 2017/0305933 A1 | 10/2017 | Dahlgren et al. |
| 2018/0134700 A1 | 5/2018 | Greenwood et al. |
| 2018/0155349 A1 | 6/2018 | Greenwood et al. |
| 2018/0258086 A1 | 9/2018 | Greenwood et al. |
| 2019/0031664 A1 | 1/2019 | Masse et al. |

FOREIGN PATENT DOCUMENTS

| | | |
|---|---|---|
| EP | 2108642 A1 | 10/2009 |
| JP | 63-107966 A | 5/1998 |
| WO | 2001042246 A2 | 6/2001 |
| WO | 2002088112 A1 | 11/2002 |
| WO | 2003063794 A2 | 8/2003 |
| WO | 2004019973 A1 | 3/2004 |
| WO | 2004089925 A1 | 10/2004 |
| WO | 2004106328 A1 | 12/2004 |
| WO | 2005007623 A2 | 1/2005 |
| WO | 2005113554 A2 | 12/2005 |
| WO | 2006078846 A1 | 7/2006 |
| WO | 2006122806 A2 | 11/2006 |
| WO | 2007016176 A2 | 2/2007 |
| WO | 2007044729 A2 | 4/2007 |
| WO | 2007053452 A1 | 5/2007 |
| WO | 2007070514 A1 | 6/2007 |
| WO | 2007084786 A1 | 7/2007 |
| WO | 2007129161 A2 | 11/2007 |
| WO | 2008039218 A2 | 4/2008 |
| WO | 2008109943 A1 | 9/2008 |
| WO | 2008118802 A1 | 10/2008 |
| WO | 2009114512 A1 | 9/2009 |
| WO | 2011079051 A1 | 6/2011 |
| WO | 2011090760 A1 | 7/2011 |
| WO | 2016138352 A1 | 9/2016 |

OTHER PUBLICATIONS

Nishioka et al. (Dermatology, 2012, 224(1), abstract).*

(Continued)

*Primary Examiner* — Susanna Moore
(74) *Attorney, Agent, or Firm* — Andrea L. C. Reid; Paul R. Fleming; Dechert LLP

(57) ABSTRACT

The present invention provides compounds of formula I, compositions thereof, and methods of using the same for the inhibition of TYK2, and the treatment of TYK2-mediated disorders.

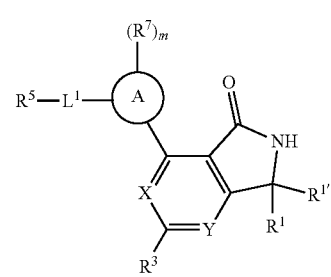

8 Claims, No Drawings

(56) References Cited

OTHER PUBLICATIONS

Bacon et al., "Interleukin 12 (IL-12) induces tyrosine phosphorylation of JAK2 and TYK2: differential use of Janus family kinases by IL-2 and IL-12," The Journal of Experimental Medicine, vol. 181, No. 1, Jan. 1995 (pp. 399-404).

Ban et al., "Replication analysis identifies TYK2 as a multiple sclerosis susceptibility factor," European Journal of Human Genetics, vol. 17, Mar. 2009 (pp. 1309-1313).

Berge et al., "Pharmaceutical Salts," Journal of Pharmaceutical Sciences, vol. 66, No. 1, Jan. 1977 (pp. 1-19).

Cho et al., "Genomics and the multifactorial nature of human auto-immune disease," The New England Journal of Medicine, vol. 365, No. 17, Oct. 27, 2011 (pp. 1612-1623).

Duerr et al., "A Genome-Wide Association Study Identifies IL23R as an Inflammatory Bowel Disease Gene," Science, vol. 314, No. 5804, Dec. 2006 (pp. 1461-1463).

Finbloom et al., "IL-10 induces the tyrosine phosphorylation of tyk2 and Jak1 and the differential assembly of STAT1 and STAT3 complexes in human T cells and monocytes," The Journal of Immunology, vol. 155, No. 3, Aug. 1995 (pp. 1079-1090).

Fontan et al. "Discovering What Makes STAT Signaling TYK in T-ALL," Cancer Discovery, vol. 3, No. 5, May 2013 (pp. 494-496).

Graham et al., "Association of NCF2, IKZF1, IRF8, IFIH1, and TYK2 with Systemic Lupus Erythematosus," PLoS Genetics, vol. 7, No. 10, Oct. 2011 (9 pages).

International Search Report and Written Opinion issued by the United States Patent and Trademark Office as International Searching Authority for International Application No. PCT/US2016/049852 dated Nov. 3, 2016 (10 pages).

Ishizaki et al., "Tyk2 deficiency protects joints against destruction in anti-type II collagen antibody-induced arthritis in mice," International Immunology, vol. 23, No. 9, Sep. 2011 (pp. 575-582).

Ishizaki et al., "Tyk2 is a therapeutic target for psoriasis-like skin inflammation," International Immunology, vol. 26, No. 5, May 2014 (11 pages).

Oyamada et al., "Tyrosine Kinase 2 Plays Critical Roles in the Pathogenic CD4 T Cell Responses for the Development of Experimental Autoimmune Encephalomyelitis," The Journal of Immunology, vol. 183, No. 11, Dec. 2009 (pp. 7539-7546).

Parham et al., "A receptor for the heterodimeric cytokine IL-23 is composed of IL-12Rβ1 and a novel cytokine receptor subunit, IL-23R," The Journal of Immunology, vol. 168, No. 11, Jun. 2002 (pp. 5699-5708).

Ramirez et al "Defining causative factors contributing in the activation of hedgehog signaling in diffuse large B-cell lymphoma," Leukemia Research, vol. 36, No. 10, Oct. 2012 (15 pages).

Remmers et al., "Genome-wide association study identifies variants in the MHC class I, IL10, and IL23R-IL 12RB2 regions associated with Behçet's disease," Nature Genetics, vol. 42, No. 8, Aug. 2010 (20 pages).

Rostovetsev et al., "A Stepwise Huisgen Cycloaddition Process: Copper(I)-Catalyzed Regioselective "Ligation" of Azides and Terminal Alkynes," Angewandte Chemie International Edition, vol. 41, No. 14, Jul. 2002 (pp. 2596-2599).

Sanda et al. "TYK2-STAT1-BCL2 Pathway Dependence in T-Cell Acute Lymphoblastic Leukemia," Cancer Discovery, vol. 3, No. 5, May 2013 (pp. 564-577).

Sigurdsson et al., "Polymorphisms in the Tyrosine Kinase 2 and Interferon Regulatory Factor 5 Genes Are Associated with Systemic Lupus Erythematosus," American Journal of Human Genetics, vol. 76, No. 3, Mar. 2005 (pp. 528-537).

Simma et al. "Identification of an Indispensable Role for Tyrosine Kinase 2 in CTL-Mediated Tumor Surveillance," cancer Research, vol. 69, No. 1, Jan. 2009 (pp. 203-211).

Stahl et al., "Association and activation of Jak-Tyk kinases by CNTF-LIF-OSM-IL-6 beta receptor components," Science, vol. 263, No. 5143, Jan. 1994 (pp. 92-95).

Strange et al., "A genome-wide association study identifies new psoriasis susceptibility loci and an interaction between HLA-C and ERAP1," Nature Genetics, vol. 42, No. 11, Nov. 2010 (16 pages).

Sun et al., "Carbohydrate and Protein Immobilization onto Solid Surfaces by Sequential Diels-Alder and Azide-Alkyne Cycloadditions," Bioconjugate Chemistry, vol. 17, No. 1, Jan. 2006 (pp. 52-57).

Velazquez et al., "A protein tyrosine kinase in the interferon αβ signaling pathway," Cell, vol. 70, No. 2, Jul. 1992 (pp. 313-322).

Velusamy et al., "A novel recurrent NPM1-TYK2 gene fusion in cutaneous CD30-positive lymphoproliferative disorders," Blood, vol. 124, No. 25, Dec. 2014 (pp. 3768-3771).

Wan et al. "Tyk2/STAT3 Signaling Mediates β-Amyloid-Induced Neuronal Cell Death: Implications in Alzheimer's Disease," The Journal of Neuroscience, vol. 30, No. 20, May 2010 (pp. 6873-6881).

Welham et al., "Interleukin-13 signal transduction in lymphohemopoietic cells: similarities and differences in signal transduction with interleukin-4 and insulin," The Journal of Biological Chemistry, vol. 270, No. 20, May 1995 (pp. 12286-12296).

Zhang et al., "Docking protein Gab2 regulates mucin expression and goblet cell hyperplasia through TYK2/STAT6 pathway," The FASEB Journal, vol. 26, No. 11, Nov. 2012 (pp. 4603-4613).

Bhandari et al., "Solid-phase synthesis of pyrrolo[3,4-b]pyridines and related pyridine-fused heterocycles," Synthesis. 1999; 11: 1951-1960.

Office Action issued in Japanese Patent Application No. 2018-512319, dated May 15, 2020 (7 pages).

* cited by examiner

TYK2 INHIBITORS AND USES THEREOF

CROSS-REFERENCE TO RELATED APPLICATIONS

The present application is a divisional application of U.S. Ser. No. 15/254,071 filed on Sep. 1, 2016, now issued as U.S. Pat. No. 10,023,571, which claims priority to U.S. provisional patent application Ser. No. 62/214,018, filed Sep. 3, 2015, and U.S. provisional patent application Ser. No. 62/213,475, filed Sep. 2, 2015, the entirety of each of which is incorporated herein by reference.

TECHNICAL FIELD OF THE INVENTION

The present invention relates to compounds and methods useful for inhibiting non-receptor tyrosine-protein kinase 2 ("TYK2"), also known as Tyrosine kinase 2. The invention also provides pharmaceutically acceptable compositions comprising compounds of the present invention and methods of using said compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is the protein kinase family.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxins, and $H_2O_2$), cytokines (e.g., interleukin-1 (IL-1), interleukin-8 (IL-8), and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by kinase-mediated events. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

It has now been found that compounds of this invention, and pharmaceutically acceptable compositions thereof, are effective as inhibitors of TYK2 kinase. Such compounds have the general formula I:

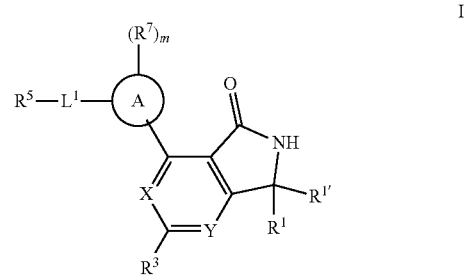

or a pharmaceutically acceptable salt thereof, wherein each variable is as defined and described herein.

Compounds of the present invention, and pharmaceutically acceptable compositions thereof, are useful for treating a variety of diseases, disorders or conditions, associated with regulation of signaling pathways implicating TYK2 kinases. Such diseases, disorders, or conditions include those described herein.

Compounds provided by this invention are also useful for the study of TYK2 enzymes in biological and pathological phenomena; the study of intracellular signal transduction pathways occurring in bodily tissues; and the comparative evaluation of new TYK2 inhibitors or other regulators of kinases, signaling pathways, and cytokine levels in vitro or in vivo.

DETAILED DESCRIPTION OF CERTAIN EMBODIMENTS

1. General Description of Certain Embodiments of the Invention:

Compounds of the present invention, and compositions thereof, are useful as inhibitors of TYK2 protein kinase.

The binding pocket of TYK2 contains a plurality of hydration sites, each of which is occupied by a single molecule of water. Each of these water molecules has a stability rating associated with it. As used herein, the term "stability rating" refers to a numerical calculation which incorporates the enthalpy, entropy, and free energy values associated with each water molecule. This stability rating allows for a measurable determination of the relative stability of water molecules that occupy hydration sites in the binding pocket of TYK2.

Water molecules occupying hydration sites in the binding pocket of TYK2 having a stability rating of >2.5 kcal/mol are referred to as "unstable waters."

Without wishing to be bound by any particular theory, it is believed that displacement or disruption of an unstable water molecule (i.e., a water molecule having a stability rating of >2.5 kcal/mol), or replacement of a stable water (i.e., a water molecule having a stability rating of <1 kcal/mol), by an inhibitor results in tighter binding of that inhibitor. Accordingly, inhibitors designed to displace one or more unstable water molecules (i.e., those unstable water molecules not displaced by any known inhibitor) will be a tighter binder and, therefore, more potent inhibitor as compared to an inhibitor that does not displace unstable water molecules.

It was surprisingly found that provided compounds displace or disrupt one or more unstable water molecules. In some embodiments, a provided compound displaces or disrupts at least two unstable water molecules.

In certain embodiments, the present invention provides a compound of formula I:

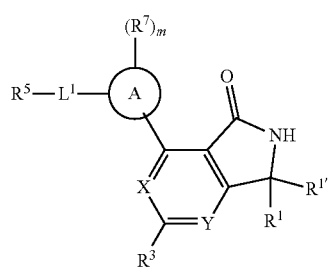

I or a pharmaceutically acceptable salt thereof, wherein:
each of X and Y is independently =C($R^6$)— or =N—;
Ring A is phenyl; a 5-6 membered partially unsaturated monocyclic heterocyclic ring having 1-4 heteroatoms independently selected from nitrogen, oxygen, and sulfur; a 6-12 membered partially unsaturated bicyclic heterocyclic ring having 1-4 heteroatoms independently selected from nitrogen, oxygen, and sulfur; a 5-6 membered monocyclic heteroaryl ring having 1-4 heteroatoms independently selected from nitrogen, oxygen, and sulfur; or a 7-12 membered bicyclic heteroaryl ring having 2-4 heteroatoms independently selected from nitrogen, oxygen, and sulfur;
each of $R^1$ and $R^{1'}$ is independently hydrogen, —$R^2$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)S(O)$_2$R; or
$R^1$ and $R^{1'}$ are taken together with their intervening atoms to form an optionally substituted 3-7 membered spiro-fused ring having 0-2 heteroatoms independently selected from nitrogen, oxygen, and sulfur;
each $R^2$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
$R^3$ is $C_{2-6}$ aliphatic or $Cy^1$; wherein $R^3$ is substituted with n instances of $R^8$;
$R^5$ is halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)S(O)$_2$R, and $Cy^2$; wherein $R^5$ is substituted with p instances of $R^9$; or when Ring A is bicyclic or partially unsaturated, $L^1R^5$, taken together, may also be absent;
each of $Cy^1$ and $Cy^2$ is independently phenyl; a 3-7 membered saturated or partially unsaturated monocyclic carbocyclic ring; a 6-12 membered bicyclic carbocyclic ring; a 3-7 membered saturated or partially unsaturated monocyclic heterocyclic ring having 1-2 heteroatoms independently selected from nitrogen, oxygen, and sulfur; a 6-12 membered saturated or partially unsaturated bicyclic heterocyclic ring having 1-3 heteroatoms independently selected from nitrogen, oxygen, and sulfur; or a 5-6 membered heteroaryl ring having 1-4 heteroatoms independently selected from nitrogen, oxygen, and sulfur;
each instance of $R^6$ is independently hydrogen, —$R^2$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)S(O)$_2$R;
each instance of $R^7$ and $R^8$ is independently oxo, —$R^2$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)S(O)$_2$R;
each instance of $R^9$ is independently oxo, $C_{1-6}$ hydroxyaliphatic, —$R^2$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)S(O)$_2$R;
$L^1$ is a covalent bond or a $C_{1-6}$ bivalent saturated or unsaturated, straight or branched hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—;
m is 0-2;
n is 0-4;
p is 0-3; and
each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

2. Compounds and Definitions:

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

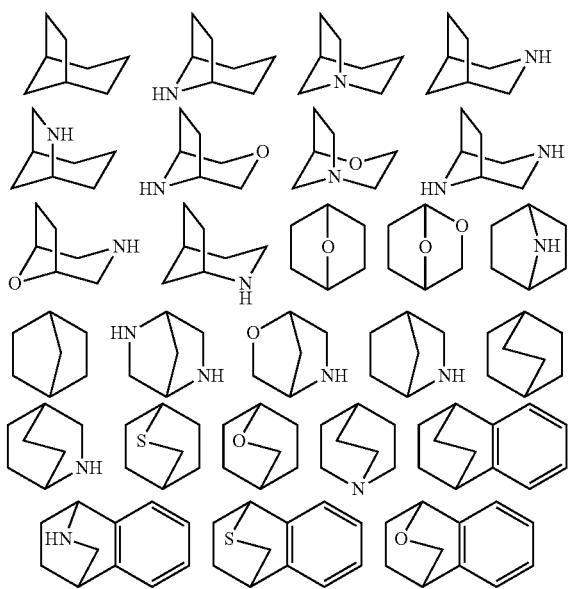

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^-$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

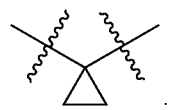

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —O$(CH_2)_{0-4}R^\circ$, —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$(CH_2)_{0-4}O(CH_2)_{0-1}$-pyridyl which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR^\circ$; —$SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched alkylene)O—$N(R^\circ)_2$; or —$(C_{1-4}$ straight or branched alkylene)C(O)O—$N(R^\circ)_2$, wherein each $R^\circ$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, -(haloR$^\bullet$), —$(CH_2)_{0-2}OH$, —$(CH_2)_{0-2}OR^\bullet$, —$(CH_2)_{0-2}CH(OR^\bullet)_2$; —O(haloR$^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —$(C_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, a warhead moiety, R$^1$, of a provided compound comprises one or more deuterium atoms. In certain embodiments, Ring B of a provided compound may be substituted with one or more deuterium atoms.

As used herein, the term "inhibitor" is defined as a compound that binds to and/or inhibits TYK2 with measurable affinity. In certain embodiments, an inhibitor has an IC$_{50}$ and/or binding constant of less than about 50 µM, less than about 1 µM, less than about 500 nM, less than about 100 nM, less than about 10 nM, or less than about 1 nM.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}P$, $^{33}P$, $^{35}S$, or $^{14}C$), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360, 8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in a TYK2 protein kinase activity between a sample comprising a compound of the present invention, or composition thereof, and a TYK2 protein kinase, and an equivalent sample comprising an TYK2 protein kinase, in the absence of said compound, or composition thereof.

3. Description of Exemplary Embodiments:

As described above, in certain embodiments, the present invention provides a compound of formula I:

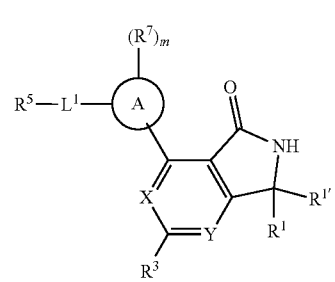

or a pharmaceutically acceptable salt thereof, wherein:

each of X and Y is independently $=C(R^6)-$ or $=N-$;

Ring A is phenyl; a 5-6 membered partially unsaturated monocyclic heterocyclic ring having 1-4 heteroatoms independently selected from nitrogen, oxygen, and sulfur; a 6-12 membered partially unsaturated bicyclic heterocyclic ring having 1-4 heteroatoms independently selected from nitrogen, oxygen, and sulfur; a 5-6 membered monocyclic heteroaryl ring having 1-4 heteroatoms independently selected from nitrogen, oxygen, and sulfur; or a 7-12 membered bicyclic heteroaryl ring having 2-4 heteroatoms independently selected from nitrogen, oxygen, and sulfur;

each of $R^1$ and $R^{1'}$ is independently hydrogen, $-R^2$, halogen, $-CN$, $-NO_2$, $-OR$, $-SR$, $-NR_2$, $-S(O)_2R$, $-S(O)_2NR_2$, $-S(O)R$, $-C(O)R$, $-C(O)OR$, $-C(O)NR_2$, $-C(O)N(R)OR$, $-OC(O)R$, $-OC(O)NR_2$, $-N(R)C(O)OR$, $-N(R)C(O)R$, $-N(R)C(O)NR_2$, or $-N(R)S(O)_2R$; or $R^1$ and $R^{1'}$ are taken together with their intervening atoms to form an optionally substituted 3-7 membered spirofused ring having 0-2 heteroatoms independently selected from nitrogen, oxygen, and sulfur;

each $R^2$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$R^3$ is $C_{2-6}$ aliphatic or $Cy^1$; wherein $R^3$ is substituted with n instances of $R^8$;

$R^5$ is halogen, $-CN$, $-NO_2$, $-OR$, $-SR$, $-NR_2$, $-S(O)_2R$, $-S(O)_2NR_2$, $-S(O)R$, $-C(O)R$, $-C(O)OR$, $-C(O)NR_2$, $-C(O)N(R)OR$, $-OC(O)R$, $-OC(O)NR_2$, $-N(R)C(O)OR$, $-N(R)C(O)R$, $-N(R)C(O)NR_2$, $-N(R)S(O)_2R$, and $Cy^2$; wherein $R^5$ is substituted with p instances of $R^9$; or when Ring A is bicyclic or partially unsaturated, $L^1R^5$, taken together, may also be absent;

each of $Cy^1$ and $Cy^2$ is independently phenyl; a 3-7 membered saturated or partially unsaturated monocyclic carbocyclic ring; a 6-12 membered bicyclic carbocyclic ring; a 3-7 membered saturated or partially unsaturated monocyclic heterocyclic ring having 1-2 heteroatoms independently selected from nitrogen, oxygen, and sulfur; a 6-12 membered saturated or partially unsaturated bicyclic heterocyclic ring having 1-3 heteroatoms independently selected from nitrogen, oxygen, and sulfur; or a 5-6 membered heteroaryl ring having 1-4 heteroatoms independently selected from nitrogen, oxygen, and sulfur;

each instance of $R^6$ is independently hydrogen, —$R^2$, halogen, —CN, —$NO_2$, —OR, —SR, —$NR_2$, —$S(O)_2R$, —$S(O)_2NR_2$, —S(O)R, —C(O)R, —C(O)OR, —C(O)NR_2$, —C(O)N(R)OR, —OC(O)R, —OC(O)NR_2$, —N(R)C(O)OR, —N(R)C(O)R, —N(R)C(O)NR_2$, or —$N(R)S(O)_2R$;

each instance of $R^7$ and $R^8$ is independently oxo, —$R^2$, halogen, —CN, —$NO_2$, —OR, —SR, —$NR_2$, —$S(O)_2R$, —$S(O)_2NR_2$, —S(O)R, —C(O)R, —C(O)OR, —C(O)NR_2$, —C(O)N(R)OR, —OC(O)R, —OC(O)NR_2$, —N(R)C(O)OR, —N(R)C(O)R, —N(R)C(O)NR_2$, or —$N(R)S(O)_2R$;

each instance of $R^9$ is independently oxo, $C_{1-6}$ hydroxyaliphatic, —$R^2$, halogen, —CN, —$NO_2$, —OR, —SR, —$NR_2$, —$S(O)_2R$, —$S(O)_2NR_2$, —S(O)R, —C(O)R, —C(O)OR, —C(O)NR_2$, —C(O)N(R)OR, —OC(O)R, —OC(O)NR_2$, —N(R)C(O)OR, —N(R)C(O)R, —N(R)C(O)NR_2$, or —$N(R)S(O)_2R$;

$L^1$ is a covalent bond or a $C_{1-6}$ bivalent saturated or unsaturated, straight or branched hydrocarbon chain wherein one or two methylene units of the chain are optionally and independently replaced by —N(R)—, —N(R)C(O)—, —C(O)N(R)—, —N(R)S(O)_2—, —S(O)_2N(R)—, —O—, —C(O)—, —OC(O)—, —C(O)O—, —S—, —S(O)— or —S(O)_2—;

m is 0-2;

n is 0-4;

p is 0-3; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

As defined generally above, each of X and Y is =C($R^6$)— or =N—. In some embodiments, each of X and Y is =C($R^6$)— or =N—, provided that X and Y are not simultaneously =C($R^6$)—. In some embodiments, both X and Y are =N—. In some embodiments, X is =N—, and Y is =C($R^6$)—. In some embodiments, X is =C($R^6$)—, and Y is =N—. In some embodiments, both X and Y are =C($R^6$)—.

As defined generally above, Ring A is phenyl; a 5-6 membered partially unsaturated monocyclic heterocyclic ring having 1-4 heteroatoms independently selected from nitrogen, oxygen, and sulfur; a 6-12 membered partially unsaturated bicyclic heterocyclic ring having 1-4 heteroatoms independently selected from nitrogen, oxygen, and sulfur; a 5-6 membered heteroaryl ring having 1-4 heteroatoms independently selected from nitrogen, oxygen, and sulfur; or a 7-12 membered bicyclic heteroaryl ring having 2-4 heteroatoms independently selected from nitrogen, oxygen, and sulfur.

In some embodiments, Ring A is phenyl. In some embodiments, Ring A is a 5-6 membered partially unsaturated monocyclic heterocyclic ring having 1-4 heteroatoms independently selected from nitrogen, oxygen, and sulfur. In some embodiments, Ring A is a 6-12 membered partially unsaturated bicyclic heterocyclic ring having 1-4 heteroatoms independently selected from nitrogen, oxygen, and sulfur. In some embodiments, Ring A is a 5-6 membered heteroaryl having 1-4 heteroatoms independently selected from nitrogen, oxygen, and sulfur. In some embodiments, Ring A is a 7-12 membered bicyclic heteroaryl ring having 2-4 heteroatoms independently selected from nitrogen, oxygen, and sulfur. In some embodiments, Ring A is a 5-membered heteroaryl having 1-2 heteroatoms selected from nitrogen, oxygen, and sulfur. In some embodiments, Ring A is a 5-membered heteroaryl having 1-4 nitrogens. In some embodiments, Ring A is a 6-membered heteroaryl having 1-4 nitrogens. Ring A is phenyl, pyridin-2-yl, pyridin-3-yl, pyridin-4-yl, pyrazinyl, pyridaziny-3-yl, pyridazin-4-yl pyrazol-1-yl, pyrazol-2-yl, pyrazol-3-yl, pyrazol-4-yl, 1,2, 4-triazol-1-yl, imidazol-1-yl, imidazol-2-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, or isothiazol-5-yl. In some embodiments, Ring A is pyridyl. In some embodiments, Ring A is pymidinyl. In some embodiments, Ring A is pyrazinyl. In some embodiments, Ring A is pyrazolyl. In some embodiments, Ring A is imidazolyl. In some embodiments, Ring A is oxazolyl. In some embodiments, Ring A is isoxazolyl. In some embodiments, Ring A is isothiazolyl. In some embodiments, Ring A is imidazoline. In some embodiments, Ring A is oxazoline. In some embodiments, Ring A is thiazoline. Exemplary Ring A groups include those depicted in Table 1.

One of skill in the art will appreciate that multiple regioisomers of a given Ring A are possible. Unless otherwise stated, all regioisomers are intended to be encompassed. For example, Ring A can be 1-pyrazolyl, 2-pyrazolyl, 3-pyrazolyl, 4-pyrazolyl, or 5-pyrazolyl. In some embodiments, Ring A is connected to the bicyclic core via one of its nitrogens. In some embodiments, Ring A is connected to the bicyclic core via one of its carbon atoms.

Likewise, when Ring A is phenyl, multiple attachment points are possible. In some embodiments, when Ring A is phenyl, $L^1$ is para to the point of attachment to the rest of the molecule. In some embodiments, $L^1$ is meta to the point of attachment to the rest of the molecule. In some embodiments, $L^1$ is ortho to the point of attachment to the rest of the molecule.

In some embodiments, when Ring A is partially unsaturated, it is selected from the structures in Table A, below, each of which may be unsubstituted, or substituted by $L^1R^5$ or m instances of $R^7$ as indicated above:

TABLE A

Exemplary Partially Unsaturated
Ring A Groups

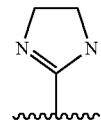

TABLE A-continued
Exemplary Partially Unsaturated
Ring A Groups
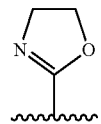 [SMILES: *C1=NCCO1]
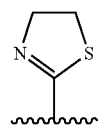 [SMILES: *C1=NCCS1]
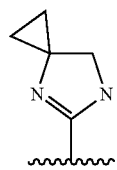
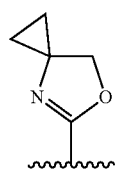
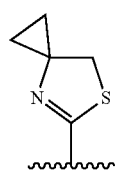 [SMILES: *C1=NC2(CC2)CS1]
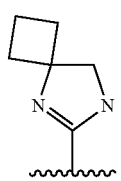 [SMILES: *C1=NC2(CCC2)CN1]
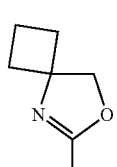
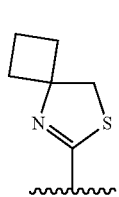 [SMILES: *C1=NC2(CCC2)CS1]
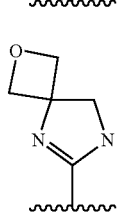
TABLE A-continued
Exemplary Partially Unsaturated
Ring A Groups
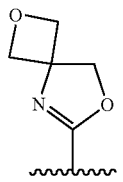 [SMILES: *C1=NC2(COC2)CO1]
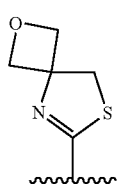 [SMILES: *C1=NC2(COC2)CS1]
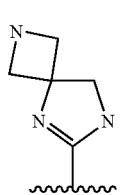 [SMILES: *C1=NC2(CNC2)CN1]
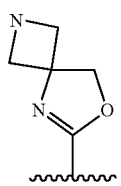 [SMILES: *C1=NC2(CNC2)CO1]
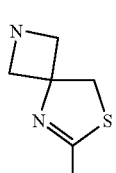
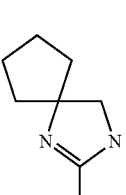
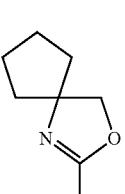
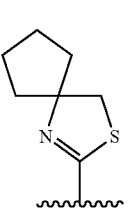 [SMILES: *C1=NC2(CCCC2)CS1]

TABLE A-continued
Exemplary Partially Unsaturated Ring A Groups
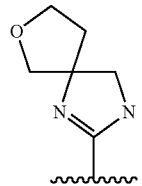
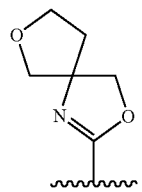 [SMILES: *C1=NC2(CCOC2)CO1]
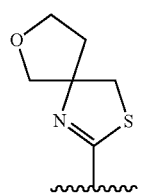 [SMILES: *C1=NC2(CCOC2)CS1]
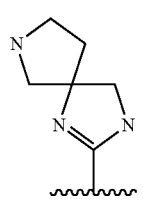 [SMILES: *C1=NC2(CCNC2)CN1]
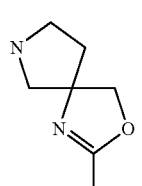
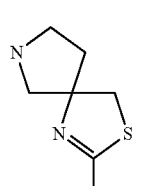
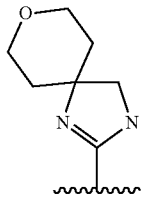 [SMILES: *C1=NC2(CCNCC2)CN1]
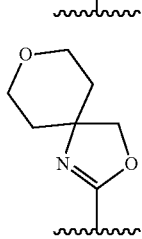
TABLE A-continued
Exemplary Partially Unsaturated Ring A Groups
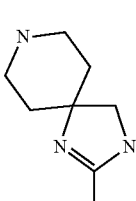
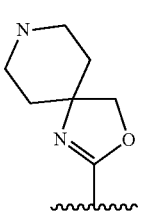 [SMILES: *C1=NC2(CCNCC2)CO1]
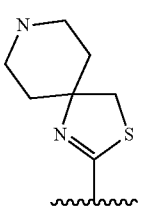 [SMILES: *C1=NC2(CCNCC2)CS1]
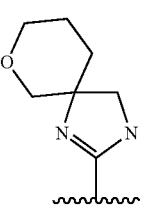 [SMILES: *C1=NC2(CCCOC2)CN1]
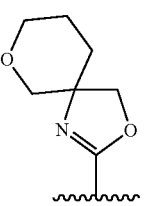 [SMILES: *C1=NC2(CCCOC2)CO1]
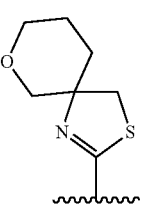 [SMILES: *C1=NC2(CCCOC2)CS1]

TABLE A-continued
Exemplary Partially Unsaturated Ring A Groups
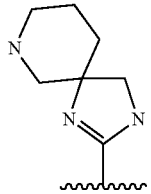 [SMILES: *C1=NC2(CCCNC2)CN1]
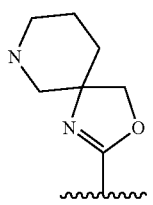 [SMILES: *C1=NC2(CCCNC2)CO1]
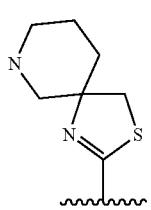 [SMILES: *C1=NC2(CCCNC2)CS1]
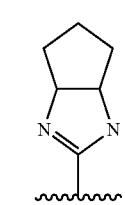 [SMILES: *C1=NC2CCCC2N1]
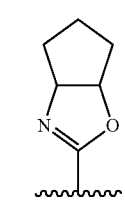 [SMILES: *C1=NC2CCCC2O1]
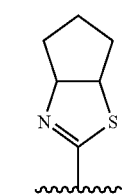
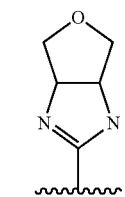 [SMILES: *C1=NC2COCC2N1]
TABLE A-continued
Exemplary Partially Unsaturated Ring A Groups
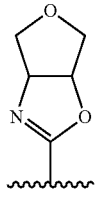 [SMILES: *C1=NC2COCC2O1]
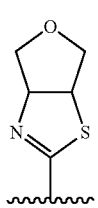
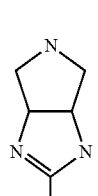
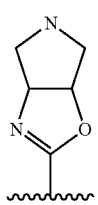
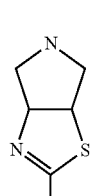
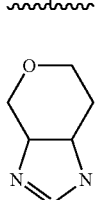
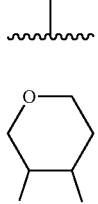
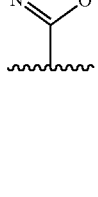

TABLE A-continued

Exemplary Partially Unsaturated Ring A Groups

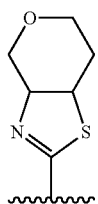

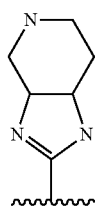 [SMILES: *C1=NC2CNCCC2N1]

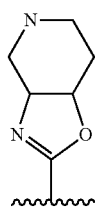 [SMILES: *C1=NC2CNCCC2O1]

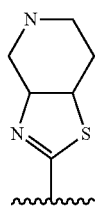 [SMILES: *C1=NC2CNCCC2S1]

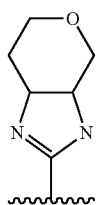 [SMILES: *C1=NC2CCOCC2N1]

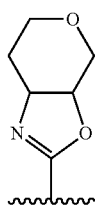 [SMILES: *C1=NC2CCOCC2O1]

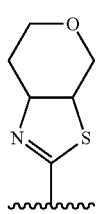 [SMILES: *C1=NC2CCOCC2S1]

TABLE A-continued

Exemplary Partially Unsaturated Ring A Groups

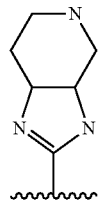

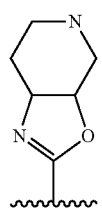

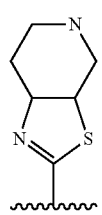 [SMILES: *C1=NC2CCNCC2S1]

As defined generally above, each of $R^1$ and $R^{1'}$ is independently hydrogen, —$R^2$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$; or $R^1$ and $R^{1'}$ are taken together with their intervening atoms to form an optionally substituted 4-7 membered spiro-fused ring having 0-2 heteroatoms independently selected from nitrogen, oxygen, and sulfur.

In some embodiments, both of $R^1$ and $R^{1'}$ are hydrogen. In some embodiments, each of $R^1$ and $R^{1'}$ is independently —$R^2$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$. In certain embodiments, each of $R^1$ and $R^{1'}$ are methyl. In some embodiments, one of $R^1$ and $R^{1'}$ is methyl, and the other is hydrogen. In some embodiments, $R^1$ and $R^{1'}$ are taken together with their intervening atoms to form an optionally substituted 3-7 membered spiro-fused ring having 0-2 heteroatoms independently selected from nitrogen, oxygen, and sulfur. In some embodiments, $R^1$ and $R^{1'}$ are taken together with their intervening atoms to form an optionally substituted 3-7 membered spiro-fused carbocyclic ring. In some embodiments, $R^1$ and $R^{1'}$ are taken together with their intervening atoms to form an optionally substituted spirocyclopropyl ring. In some embodiments, $R^1$ and $R^{1'}$ are taken together with their intervening atoms to form an optionally substituted 3-7 membered spiro-fused heterocyclic ring having 1-2 heteroatoms independently selected from nitrogen, oxygen, and sulfur.

As defined generally above, $R^3$ is $C_{2-6}$ aliphatic or $Cy^1$; wherein $R^3$ is substituted with n instances of $R^8$. In some embodiments, $R^3$ is $C_{2-6}$ aliphatic. In some embodiments, $R^3$ is $Cy^1$. Exemplary $R^3$ groups include those depicted in Table 1. In some embodiments, $R^3$ is selected from those depicted in Table B1 below:

TABLE B1

Exemplary R³ Groups

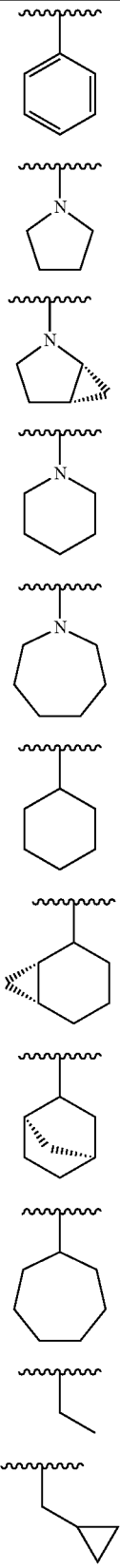

In some embodiments, $R^3(R^8)_n$, taken together, is selected from the structures depicted in Table B2 below:

TABLE B2

Exemplary $R^3(R^8)_n$ Groups

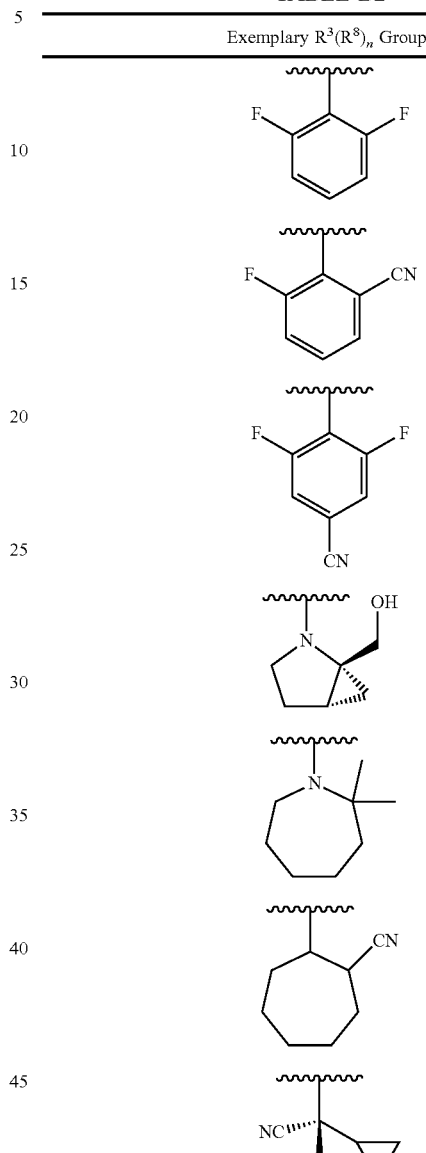

As defined generally above, $R^5$ is halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, —N(R)S(O)₂R, and Cy²; wherein $R^5$ is substituted with p instances of $R^9$; or when Ring A is bicyclic or partially unsaturated, $L^1R^5$, taken together, may also be absent.

In some embodiments, $R^5$ is halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, —N(R)S(O)₂R. In some embodiments, $R^5$ is Cy². In some embodiments, Ring A is partially unsaturated, and $L^1R^5$, taken together, is absent. In some embodiments, Ring A is bicyclic, and $L^1R^5$, taken together, is absent. Exemplary $R^5$ groups include those depicted in Table 1. In some embodiments, $R^5$, taken together is selected from those depicted in Table B3 below:
TABLE B3
Exemplary $R^5$ Groups
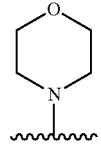
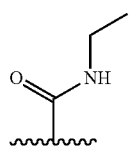
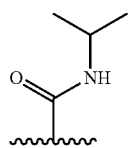
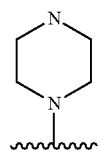

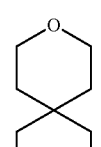
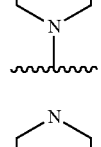
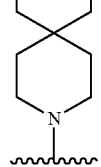
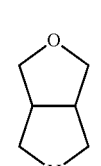
TABLE B3-continued
Exemplary $R^5$ Groups
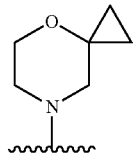 [SMILES: *N1CCOC2(CC2)C1]
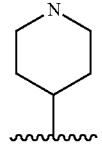 [SMILES: *C1CCNCC1]
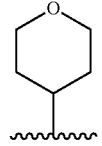 [SMILES: *C1CCOCC1]
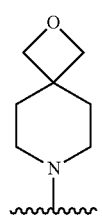 [SMILES: *N1CCC2(CC1)COC2]
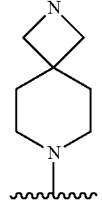 [SMILES: *N1CCC2(CC1)CNC2]
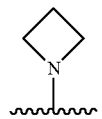
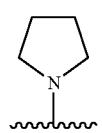
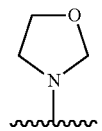 [SMILES: *N1CCOC1]
In some embodiments, $R^5(R^9)_p$, taken together, is selected from the structures depicted in Table B4 below:

TABLE B4
Exemplary $R^5(R^9)_p$ Groups
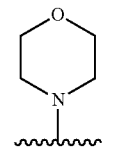
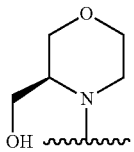 [SMILES: *N1CCOC[C@@H]1CO]
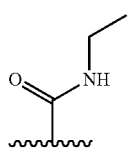
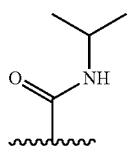
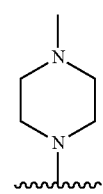
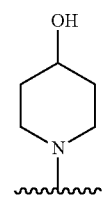
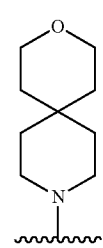
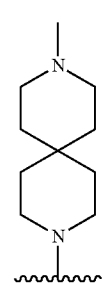
TABLE B4-continued
Exemplary $R^5(R^9)_p$ Groups
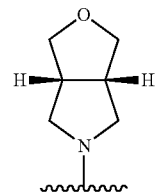 [SMILES: *N1C[C@H]2COC[C@H]2C1]
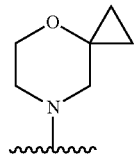 [SMILES: *N1CCOC2(CC2)C1]
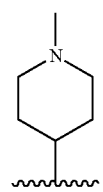
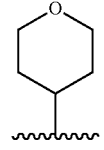
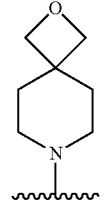
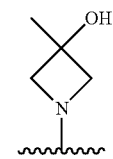
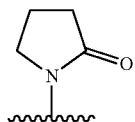 [SMILES: *N1CCCC1=O]

TABLE B4-continued
Exemplary R⁵(R⁹)ₚ Groups
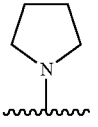 [SMILES: *N1CCCC1]
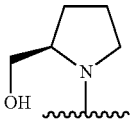
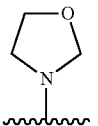
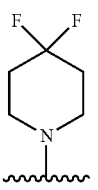
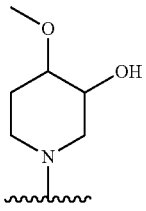 [SMILES: *N1CCC(OC)C(O)C1]
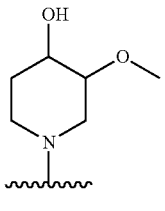
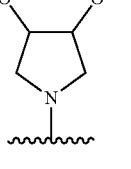
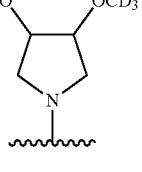
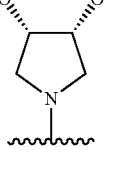
TABLE B4-continued
Exemplary R⁵(R⁹)ₚ Groups
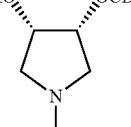
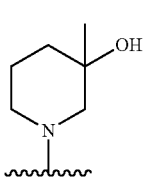 [SMILES: *N1CCCC(C)(O)C1]
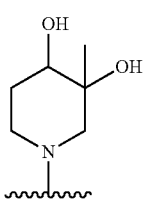 [SMILES: *N1CCC(O)C(C)(O)C1]
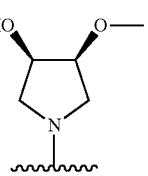
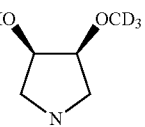
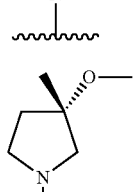
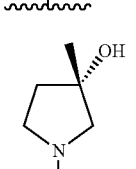
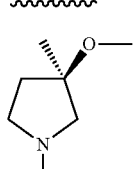
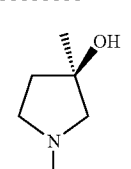

TABLE B4-continued

Exemplary $R^5(R^9)_p$ Groups

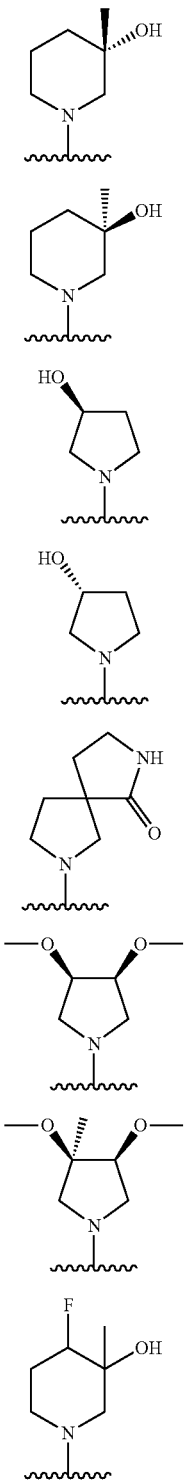

As defined generally above, each of $Cy^1$ and $Cy^2$ is independently phenyl; a 3-7 membered saturated or partially unsaturated monocyclic carbocyclic ring; a 6-12 membered bicyclic carbocyclic ring; a 3-7 membered saturated or partially unsaturated monocyclic heterocyclic ring having 1-2 heteroatoms independently selected from nitrogen, oxygen, and sulfur; a 6-12 membered saturated or partially unsaturated bicyclic heterocyclic ring having 1-3 heteroatoms independently selected from nitrogen, oxygen, and sulfur; or a 5-6 membered heteroaryl ring having 1-4 heteroatoms independently selected from nitrogen, oxygen, and sulfur.

In some embodiments, $Cy^1$ is phenyl. In some embodiments, $Cy^1$ is a 3-7 membered saturated or partially unsaturated monocyclic carbocyclic ring. In some embodiments, $Cy^1$ is a 3-7 membered saturated monocyclic carbocyclic ring. In some embodiments, $Cy^1$ is a 3-7 membered partially unsaturated monocyclic carbocyclic ring. In some embodiments, $Cy^1$ is a 6-12 membered bicyclic carbocyclic ring. In some embodiments, $Cy^1$ is a 3-7 membered saturated or partially unsaturated monocyclic heterocyclic ring having 1-2 heteroatoms independently selected from nitrogen, oxygen, and sulfur. In some embodiments, $Cy^1$ is a 3-7 membered saturated monocyclic heterocyclic ring having 1-2 heteroatoms independently selected from nitrogen, oxygen, and sulfur. In some embodiments, $Cy^1$ is a 3-7 membered partially unsaturated monocyclic heterocyclic ring having 1-2 heteroatoms independently selected from nitrogen, oxygen, and sulfur. In some embodiments, $Cy^1$ is a 6-12 membered saturated or partially unsaturated bicyclic heterocyclic ring having 1-3 heteroatoms independently selected from nitrogen, oxygen, and sulfur. In some embodiments, $Cy^1$ is a 6-12 membered saturated bicyclic heterocyclic ring having 1-3 heteroatoms independently selected from nitrogen, oxygen, and sulfur. In some embodiments, $Cy^1$ is a 6-12 membered partially unsaturated bicyclic heterocyclic ring having 1-3 heteroatoms independently selected from nitrogen, oxygen, and sulfur. In some embodiments, $Cy^1$ is a 5-6 membered heteroaryl ring having 1-4 heteroatoms independently selected from nitrogen, oxygen, and sulfur. In some embodiments, $Cy^1$ is a 5-membered heteroaryl ring having 1-4 heteroatoms independently selected from nitrogen, oxygen, and sulfur. In some embodiments, $Cy^1$ is a 6-membered heteroaryl ring having 1-4 heteroatoms independently selected from nitrogen, oxygen, and sulfur.

In some embodiments, $Cy^2$ is phenyl. In some embodiments, $Cy^2$ is a 3-7 membered saturated or partially unsaturated monocyclic carbocyclic ring. In some embodiments, $Cy^2$ is a 3-7 membered saturated monocyclic carbocyclic ring. In some embodiments, $Cy^2$ is a 3-7 membered partially unsaturated monocyclic carbocyclic ring. In some embodiments, $Cy^2$ is a 6-12 membered bicyclic carbocyclic ring. In some embodiments, $Cy^2$ is a 3-7 membered saturated or partially unsaturated monocyclic heterocyclic ring having 1-2 heteroatoms independently selected from nitrogen, oxygen, and sulfur. In some embodiments, $Cy^2$ is a 3-7 membered saturated monocyclic heterocyclic ring having 1-2 heteroatoms independently selected from nitrogen, oxygen, and sulfur. In some embodiments, $Cy^2$ is a 3-7 membered partially unsaturated monocyclic heterocyclic ring having 1-2 heteroatoms independently selected from nitrogen, oxygen, and sulfur. In some embodiments, $Cy^2$ is a 6-12 membered saturated or partially unsaturated bicyclic heterocyclic ring having 1-3 heteroatoms independently selected from nitrogen, oxygen, and sulfur. In some embodiments, $Cy^2$ is a 6-12 membered saturated bicyclic heterocyclic ring having 1-3 heteroatoms independently selected from nitrogen, oxygen, and sulfur. In some embodiments, $Cy^2$ is a 6-12 membered partially unsaturated bicyclic heterocyclic ring having 1-3 heteroatoms independently selected from nitrogen, oxygen, and sulfur. In some embodiments, $Cy^2$ is a 5-6 membered heteroaryl ring having 1-4 heteroatoms independently selected from nitrogen, oxygen, and sulfur. In some embodiments, $Cy^2$ is a 5-membered heteroaryl ring having 1-4 heteroatoms independently selected from nitrogen, oxygen, and sulfur. In some embodiments, $Cy^2$ is a 6-membered heteroaryl ring having 1-4 heteroatoms independently selected from nitrogen, oxygen, and sulfur.

As defined generally above, each instance of $R^6$ is independently hydrogen, —$R^2$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —N(R)C(O)$NR_2$, or —N(R)S(O)$_2$R. In some embodiments, both instances of $R^6$ are hydrogen. In some embodiments, one instance of $R^6$ is hydrogen, and the other is —$R^2$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —N(R)C(O)$NR_2$, or —N(R)S(O)$_2$R. In some embodiments, both instances of $R^6$ are —$R^2$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —N(R)C(O)$NR_2$, or —N(R)S(O)$_2$R.

As defined generally above, $L^1$ is a covalent bond or a $C_{1-6}$ bivalent saturated or unsaturated, straight or branched hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—. In some embodiments, when $L^1$ is a covalent bond, $R^5$ is not unsubstituted alkyl. In some embodiments, $L^1$ is a covalent bond. In other embodiments, $L^1$ is a $C_{1-6}$ bivalent hydrocarbon chain wherein one or two methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—.

In some embodiments, $L^1$ is a $C_1$ bivalent hydrocarbon chain wherein one methylene unit of the chain is replaced by —C(O)— (e.g, —C(O)—). In some embodiments, $L^1$ is —$CH_2$C(O)— (wherein the carbonyl is adjacent to $R^5$). In some embodiments, $L^1$ is —C(O)$CH_2$— (wherein the carbonyl is adjacent to Ring A). Exemplary $L^1$ groups include those depicted in Table 1.

As defined generally above, each instance of $R^8$ is independently —$R^2$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —N(R)C(O)$NR_2$, or —N(R)S(O)$_2$R. In some embodiments, at least one instance of $R^8$ is a halogen. In some embodiments, at least one instance of $R^8$ is fluorine. In some embodiments, at least one instance of $R^8$ is chlorine. In some embodiments, at least one instance of $R^8$ is —OR. In some embodiments, at least one instance of $R^8$ is —OH. In some embodiments, at least one instance of $R^8$ is —$NR_2$. In some embodiments, at least one instance of $R^8$ is —$NH_2$. In some embodiments, at least one instance of $R^8$ is —CN. In some embodiments, at least one instance of $R^8$ is optionally substituted $C_{1-6}$ aliphatic. In some embodiments, at least one instance of $R^8$ is $C_{1-6}$ alkyl. In some embodiments, at least one instance of $R^8$ is methyl. In some embodiments, at least one instance of $R^8$ is $C_{1-6}$ alkyl substituted by one or more halogens. In some embodiments, at least one instance of $R^8$ is $C_{1-6}$ alkyl substituted by one or more —OH groups. In some embodiments, at least one instance of $R^8$ is hydroxymethyl. In some embodiments, at least one instance of $R^8$ is halogen, and at least one instance of $R^8$ is —CN. In some embodiments, at least one instance of $R^8$ is $CF_3$. In some embodiments, each $R^8$ is a halogen. In some embodiments, each $R^8$ is fluorine, chlorine, methyl, or $CF_3$. Exemplary $R^8$ groups include those depicted in Table 1.

One of ordinary skill in the art will appreciate that an $R^8$ substituent on a saturated carbon of $R^3$ forms a chiral center. In some embodiments, that chiral center is in the (R) configuration. In other embodiments, that chiral center is in the (S) configuration.

As defined generally above, each instance of $R^9$ is independently oxo, $C_{1-6}$ hydroxyaliphatic, —$R^2$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —N(R)C(O)$NR_2$, or —N(R)S(O)$_2$R.

In some embodiments, at least one instance of $R^9$ is oxo. In some embodiments, at least one instance of $R^9$ is —$R^2$. In some embodiments, at least one instance of $R^9$ is optionally substituted $C_{1-6}$ aliphatic. In some embodiments, at least one instance of $R^9$ is $C_{1-6}$ alkyl. In some embodiments, at least one instance of $R^9$ is methyl. In some embodiments, at least one instance of $R^9$ is $C_{1-6}$ hydroxyaliphatic. In some embodiments, $R^9$ is hydroxymethyl. In some embodiments, $R^9$ is hydroxyethyl. In some embodiments, $R^9$ is hydroxycyclobutyl. In some embodiments, $R^9$ is hydroxycyclobutyl. In some embodiments, $R^9$ is N,N-dimethylaminoethyl. In some embodiments, $R^9$ is a 3-7 membered saturated or partially unsaturated heterocyclic ring having 1-2 heteroatoms independently selected from nitrogen, oxygen, and sulfur. In some embodiments, $R^9$ is selected from —OH, —OEt, —$NH_2$, NHEt, aziridinyl, azetidinyl, pyrrolidinyl, piperidinyl, morpholinyl, thiomorpholinyl, oxetanyl, tetrahydrothiopyranyl, and tetrahydrofuranyl. In some embodiments, when $L^1$ is absent, at least one $R^9$ is oxo.

As defined generally above, m is 0-4. In some embodiments, m is 0. In some embodiments, m is 1-4. In some embodiments, m is 1. In some embodiments, m is 2. In some embodiments, m is 3. In some embodiments, m is 4.

As defined generally above, n is 0-4. In some embodiments, n is 0. In some embodiments, n is 1-4. In some embodiments, n is 1. In some embodiments, n is 2. In some embodiments, n is 3. In some embodiments, n is 4. In some embodiments, n is 0-1. In some embodiments, n is 0-2. In some embodiments, n is 0-3. In some embodiments, n is 1-3. In some embodiments, n is 2-3.

As defined generally above, p is 0-3. In some embodiments, p is 0. In some embodiments, p is 1-3. In some embodiments, p is 1. In some embodiments, p is 2. In some embodiments, p is 3.

In certain embodiments, the present invention provides a compound of formula I, wherein when X is =N—, $R^3$ is phenyl.

In certain embodiments, the present invention provides a compound of formula I, wherein $R^1$ and $R^{1'}$ are each hydrogen, thereby forming a compound of formula II:

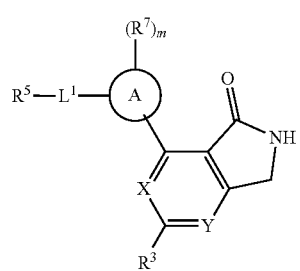

II or a pharmaceutically acceptable salt thereof, wherein each of X, Y, Ring A, $L^1$, $R^3$, $R^4$, and $R^5$ is as defined above and described in embodiments herein, both singly and in combination.

In certain embodiments, the present invention provides a compound of formula I, wherein X is =N— and Y is =C(R⁶)—; X is =C(R⁶)—; and Y is =N—; each of X and Y are =N—, or each of X and Y are =C(R⁶)—; thereby forming a compound of formula III-a, III-b, III-c, or III-d respectively:

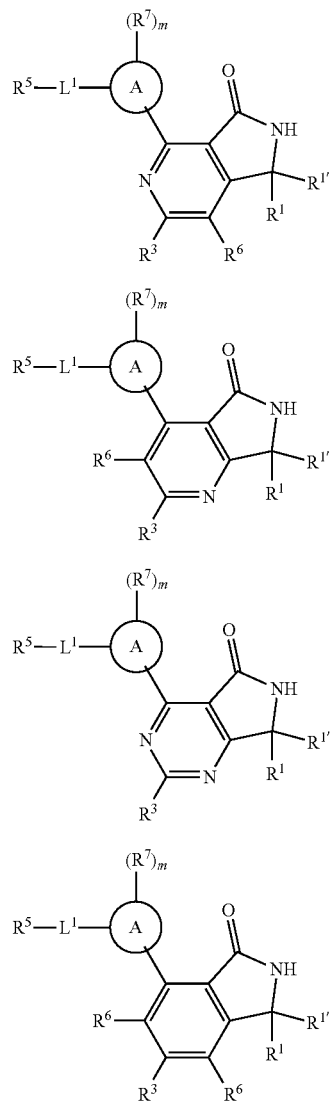

or a pharmaceutically acceptable salt thereof, wherein each of Ring A, L¹, R¹, R¹', R³, R⁵, R⁶, R⁷, and m is as defined above and described in embodiments herein, both singly and in combination.

In certain embodiments, the present invention provides a compound of formulae III-a, III-b, III-c, or III-d wherein R¹ and R¹' are each hydrogen, thereby forming a compound of formulae IV-a, IV-b, IV-c, and IV-d respectively:

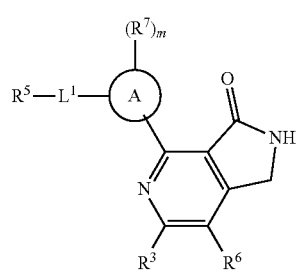

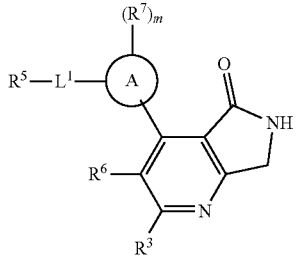

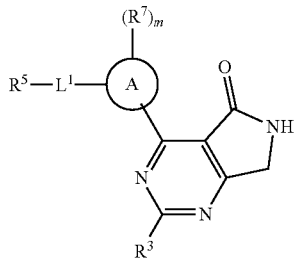

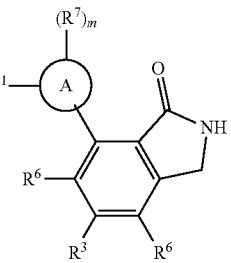

or a pharmaceutically acceptable salt thereof, wherein each of Ring A, L¹, R³, R⁵, R⁶, R⁷, and m is as defined above and described in embodiments herein, both singly and in combination.

In some embodiments, the present invention provides a compound of formula IV-a, IV-b, or IV-d wherein each R⁶ is hydrogen.

In certain embodiments, the present invention provides a compound of formula I, wherein Ring A is phenyl, pyridinyl, pyrazinyl, pyridazinyl, pyrazolyl, triazolyl, imidazolyl, oxazolyl, isoxazolyl, thiazolyl, or isothiazolyl. In certain embodiments, the present invention provides a compound of formula I, wherein Ring A is phenyl, pyridin-2-yl, pyridin-3-yl, pyridin-4-yl, pyrazinyl, pyridaziny-3-yl, pyridazin-4-yl pyrazol-1-yl, pyrazol-2-yl, pyrazol-3-yl, pyrazol-4-yl, 1,2,4-triazol-1-yl, imidazol-1-yl, imidazol-2-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, or isothiazol-5-yl thereby forming a compound of formulae VI-a, VI-b, VI-c, VI-d, VI-e, VI-f, VI-g, VI-h, VI-i, VI-j, VI-k, VI-l, VI-m, VI-n, VI-o, VI-p, VI-q, VI-r, VI-s, VI-t, VI-v, VI-x, VI-y, VI-z, and VI-aa respectively:

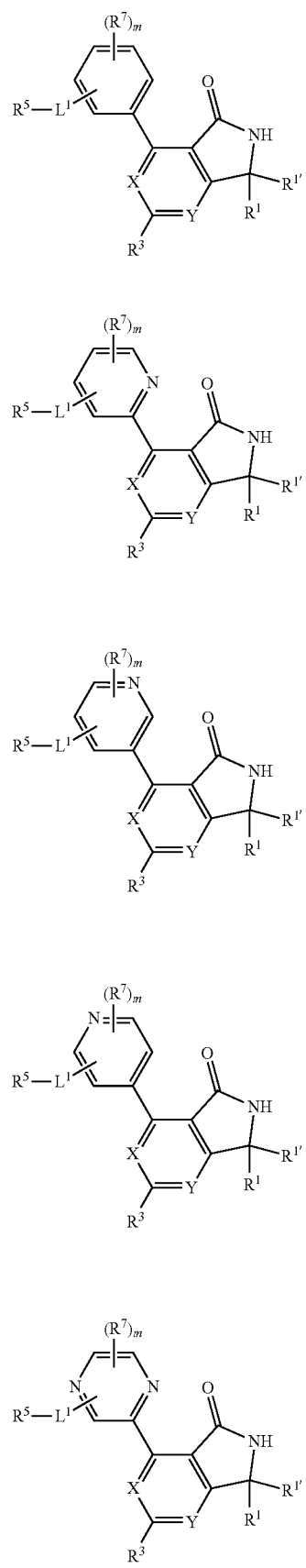

VI-l
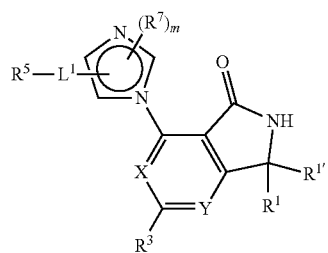
VI-m
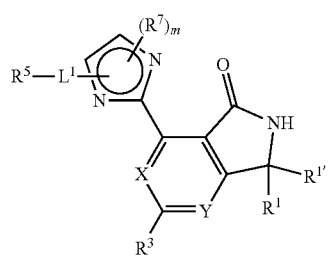
VI-n
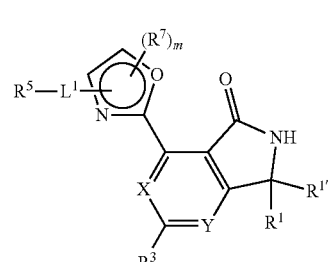
VI-o
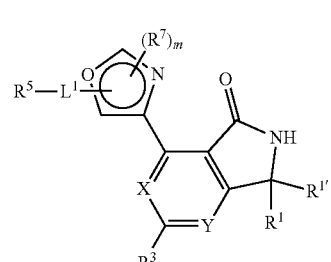
VI-p
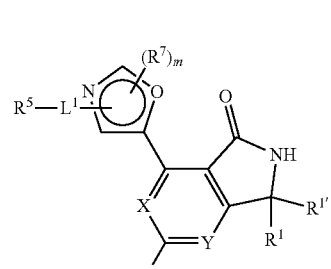
VI-q
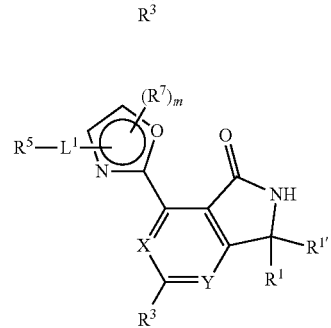
VI-r
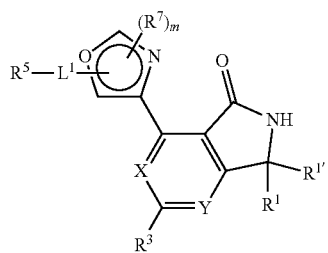
VI-s
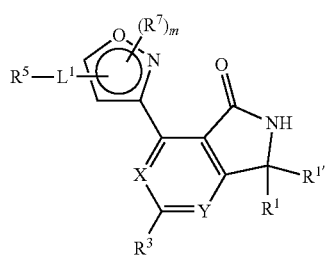
VI-t
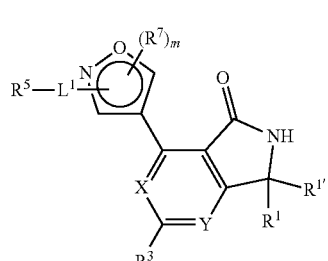
VI-u
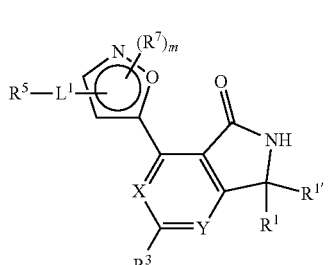
VI-v
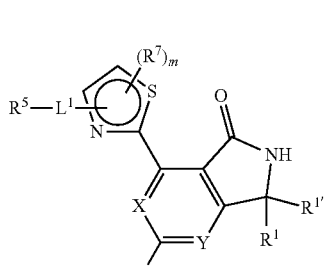
VI-w
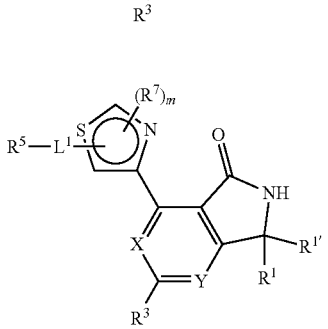

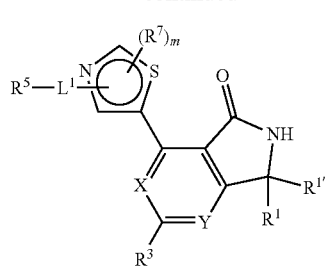
VI-x

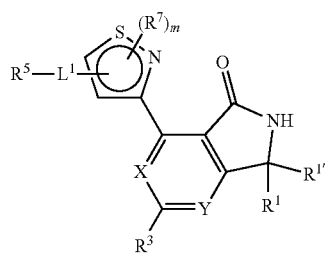
VI-y

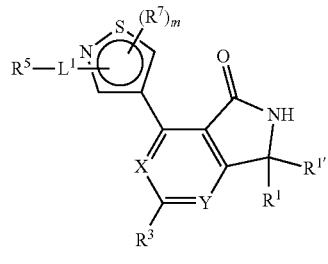
VI-z

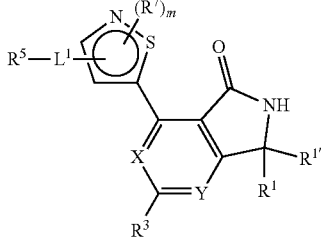
VI-aa or a pharmaceutically acceptable salt thereof, wherein each of, X, Y, $L^1$, $R^1$, $R^{1'}$, $R^3$, $R^5$, $R^7$, and m is as defined above and described in embodiments herein, both singly and in combination.

In some embodiments, the present invention provides a compound of any one of formulae VI-a, VI-b, VI-c, VI-d, VI-e, VI-f, VI-g, VI-h, VI-i, VI-j, VI-k, VI-l, VI-m, VI-n, VI-o, VI-p, VI-q, VI-r, VI-s, VI-t, VI-v, VI-x, VI-y, VI-z, or VI-aa wherein m is 0. In some embodiments, the present invention provides a compound of any one of formulae VI-a, VI-b, VI-c, VI-d, VI-e, VI-f, VI-g, VI-h, VI-i, VI-j, VI-k, VI-l, VI-m, VI-n, VI-o, VI-p, VI-q, VI-r, VI-s, VI-t, VI-v, VI-x, VI-y, VI-z, or VI-aa wherein m is 1.

In some embodiments, the present invention provides a compound of any one of formulae VI-a, VI-b, VI-c, VI-d, VI-e, VI-f, VI-g, VI-h, VI-i, VI-j, VI-k, VI-l, VI-m, VI-n, VI-o, VI-p, VI-q, VI-r, VI-s, VI-t, VI-v, VI-x, VI-y, VI-z, or VI-aa wherein $R^5$ is $Cy^2$.

In some embodiments, the present invention provides a compound of any one of formulae VI-a, VI-b, VI-c, VI-d, VI-e, VI-f, VI-g, VI-h, VI-i, VI-j, VI-k, VI-l, VI-m, VI-n, VI-o, VI-p, VI-q, VI-r, VI-s, VI-t, VI-v, VI-x, VI-y, VI-z, or VI-aa wherein both X and Y are $=C(R^6)$—. In some embodiments, the present invention provides a compound of any one of formulae VI-a, VI-b, VI-c, VI-d, VI-e, VI-f, VI-g, VI-h, VI-i, VI-j, VI-k, VI-l, VI-m, VI-n, VI-o, VI-p, VI-q, VI-r, VI-s, VI-t, VI-v, VI-x, VI-y, VI-z, or VI-aa wherein both X and Y are $=N$—. In some embodiments, the present invention provides a compound of any one of formulae VI-a, VI-b, VI-c, VI-d, VI-e, VI-f, VI-g, VI-h, VI-i, VI-j, VI-k, VI-l, VI-m, VI-n, VI-o, VI-p, VI-q, VI-r, VI-s, VI-t, VI-v, VI-x, VI-y, VI-z, or VI-aa wherein X is $=N$— and Y is $=C(R^6)$—. In some embodiments, the present invention provides a compound of any one of formulae VI-a, VI-b, VI-c, VI-d, VI-e, VI-f, VI-g, VI-h, VI-i, VI-j, VI-k, VI-l, VI-m, VI-n, VI-o, VI-p, VI-q, VI-r, VI-s, VI-t, VI-v, VI-x, VI-y, VI-z, or VI-aa wherein X is $=C(R^6)$— and Y is $=N$—. In some embodiments, the present invention provides a compound of any one of formulae VI-a, VI-b, VI-c, VI-d, VI-e, VI-f, VI-g, VI-h, VI-i, VI-j, VI-k, VI-l, VI-m, VI-n, VI-o, VI-p, VI-q, VI-r, VI-s, VI-t, VI-v, VI-x, VI-y, VI-z, or VI-aa wherein X is $=C(R^6)$— and Y is $=N$—, thereby forming a compound of formulae VII-a, VII-b, VII-c, VII-d, VII-e, VII-f, VII-g, VII-h, VII-i, VII-j, VII-k, VII-l, VII-m, VII-n, VII-o, VII-p, VII-q, VII-r, VII-s, VII-t, VII-v, VII-x, VII-y, VII-z, and VII-aa respectively:

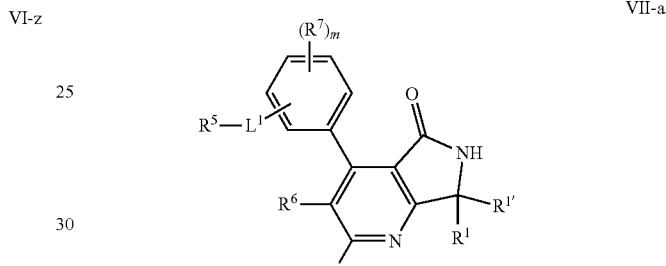

-continued
VII-e
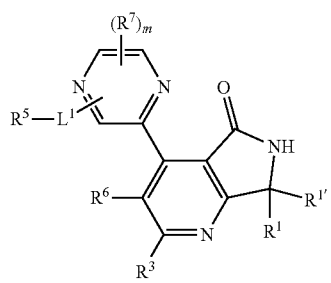
VII-f
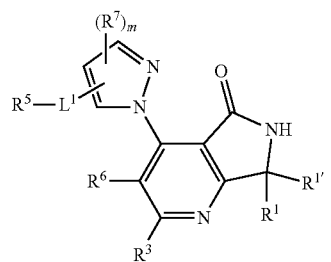
VII-g
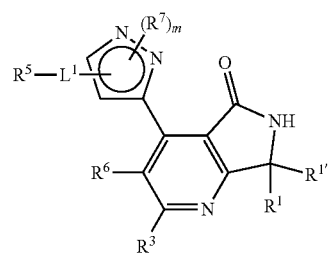
VII-h
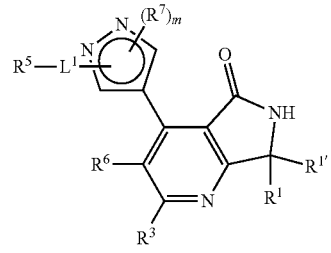
VII-i
VII-j
VII-k
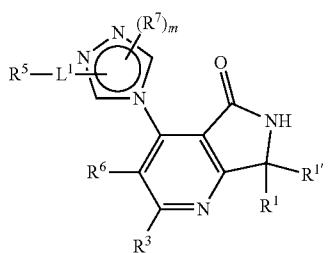
VII-l
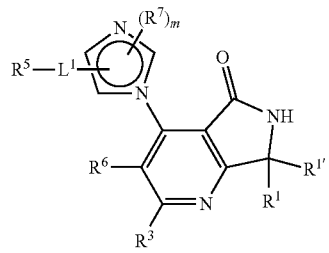
VII-m
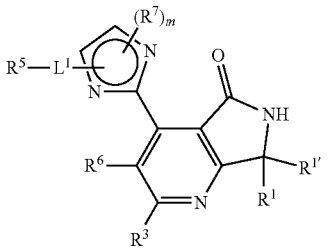
VII-n
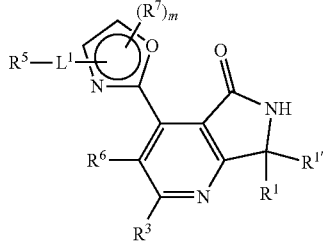
VII-o
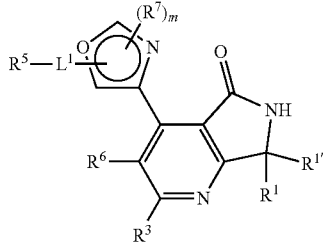
VII-p
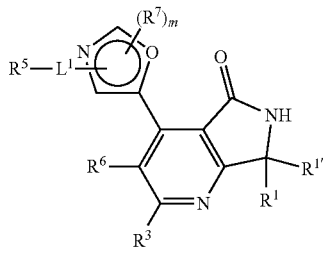

VII-q 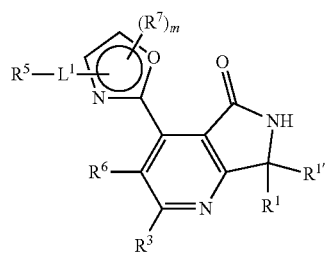

VII-r 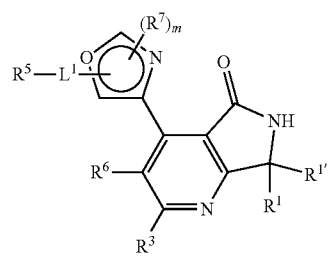

VII-s 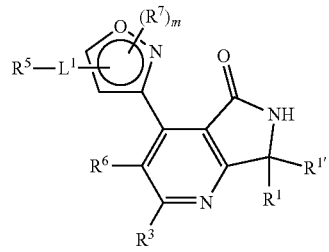

VII-t 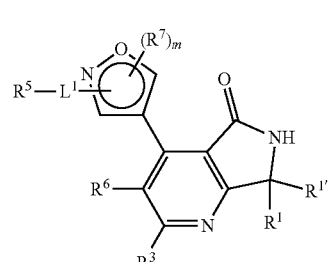

VII-u 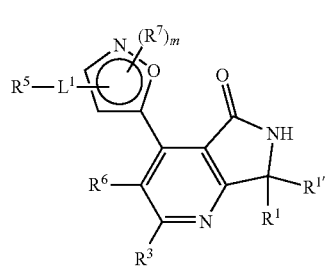

VII-v 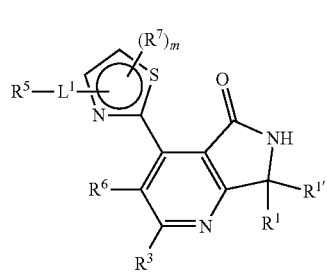

VII-w 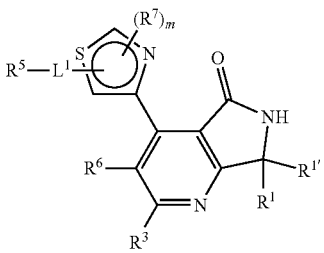

VII-x 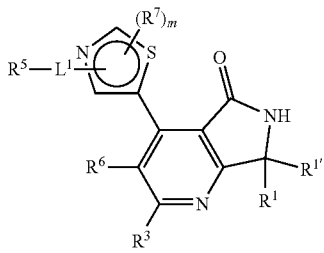

VII-y 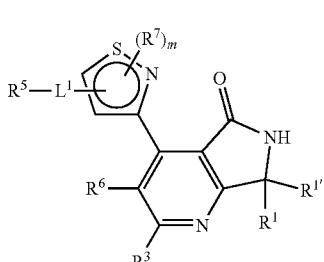

VII-z 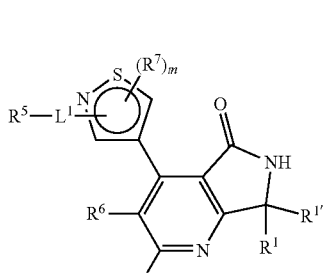

VII-aa 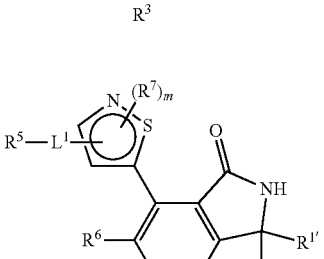

or a pharmaceutically acceptable salt thereof, wherein each of, $L^1$, $R^1$, $R^{1'}$, $R^3$, $R^4$, $R^5$, $R^6$, $R^7$, and m is as defined above and described in embodiments herein, both singly and in combination.

In some embodiments, the present invention provides a compound of one of formulae VII-a, VII-b, VII-c, VII-d, VII-e, VII-f, VII-g, VII-h, VII-i, VII-j, VII-k, VII-l, VII-m, VII-n, VII-o, VII-p, VII-q, VII-r, VII-s, VII-t, VII-v, VII-x, VII-y, VII-z, or VII-aa, wherein m is 0. In some embodiments, the present invention provides a compound of one of formulae VII-a, VII-b, VII-c, VII-d, VII-e, VII-f, VII-g, VII-h, VII-i, VII-j, VII-k, VII-l, VII-m, VII-n, VII-o, VII-p, VII-q, VII-r, VII-s, VII-t, VII-v, VII-x, VII-y, VII-z, or VII-aa, wherein m is 1.

In some embodiments, the present invention provides a compound of one of formulae VII-a, VII-b, VII-c, VII-d, VII-e, VII-f, VII-g, VII-h, VII-i, VII-j, VII-k, VII-l, VII-m, VII-n, VII-o, VII-p, VII-q, VII-r, VII-s, VII-t, VII-v, VII-x, VII-y, VII-z, or VII-aa, wherein $R^6$ is hydrogen. In some embodiments, the present invention provides a compound of one of formulae VII-a, VII-b, VII-c, VII-d, VII-e, VII-f, VII-g, VII-h, VII-i, VII-j, VII-k, VII-l, VII-m, VII-n, VII-o, VII-p, VII-q, VII-r, VII-s, VII-t, VII-v, VII-x, VII-y, VII-z, or VII-aa, wherein m is 0, and $R^6$ is hydrogen.

In some embodiments, the present invention provides a compound of one of formulae VII-a, VII-b, VII-c, VII-d, VII-e, VII-f, VII-g, VII-h, VII-i, VII-j, VII-k, VII-l, VII-m, VII-n, VII-o, VII-p, VII-q, VII-r, VII-s, VII-t, VII-v, VII-x, VII-y, VII-z, or VII-aa, wherein $R^3$ is $C_{2-6}$ aliphatic. In some embodiments, the present invention provides a compound of one of formulae VII-a, VII-b, VII-c, VII-d, VII-e, VII-f, VII-g, VII-h, VII-i, VII-j, VII-k, VII-l, VII-m, VII-n, VII-o, VII-p, VII-q, VII-r, VII-s, VII-t, VII-v, VII-x, VII-y, VII-z, or VII-aa, wherein $R^3$ is $Cy^1$.

In some embodiments, the present invention provides a compound of one of formulae VII-a, VII-b, VII-c, VII-d, VII-e, VII-f, VII-g, VII-h, VII-i, VII-j, VII-k, VII-l, VII-m, VII-n, VII-o, VII-p, VII-q, VII-r, VII-s, VII-t, VII-v, VII-x, VII-y, VII-z, or VII-aa, wherein $R^5$ is $Cy^2$.

In some embodiments, the present invention provides a compound of one of formulae VII-a, VII-b, VII-c, VII-d, VII-e, VII-f, VII-g, VII-h, VII-i, VII-j, VII-k, VII-l, VII-m, VII-n, VII-o, VII-p, VII-q, VII-r, VII-s, VII-t, VII-v, VII-x, VII-y, VII-z, or VII-aa, wherein $R^1$ and $R^{1'}$ are both hydrogen.

In certain embodiments, the present invention provides a compound of one of formulae III-a, III-b, III-c, or III-d, wherein $R^3$ is $C_{2-6}$ aliphatic. In certain embodiments, the present invention provides a compound of one of formulae III-a, III-b, III-c, or III-d, wherein $R^3$ is $Cy^1$. In certain embodiments, the present invention provides a compound of one of formulae III-a, III-b, III-c, or III-d, wherein $R^3$ is phenyl; thereby forming a compound of formula VIII-a, VIII-b, VIII-c, or VIII-d respectively:

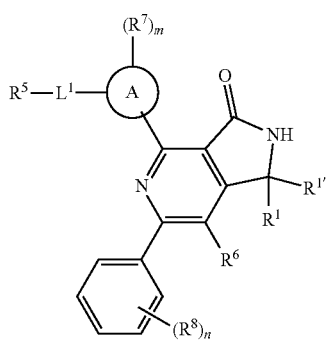

VIII-a

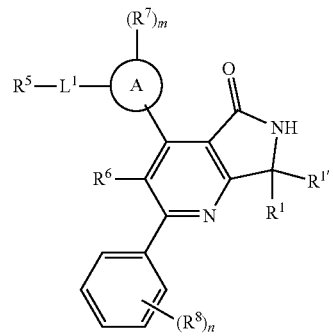

VIII-b

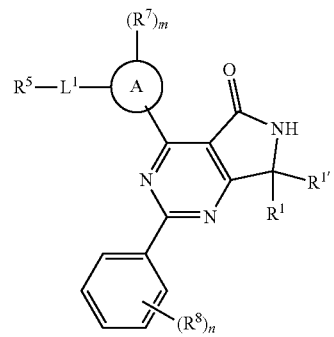

VIII-c

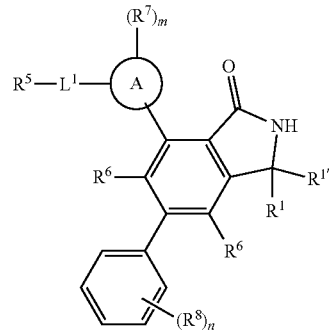

VIII-d

In some embodiments, the present invention provides a compound of one of formulae VIII-a, VIII-b, VIII-c, or VIII-d wherein $R^5$ is $Cy^2$. In some embodiments, the present invention provides a compound of one of formulae VIII-a, VIII-b, VIII-c, or VIII-d wherein $L^1$ is absent and $R^5$ is $Cy^2$. In some embodiments, the present invention provides a compound of one of formulae VIII-a, VIII-b, VIII-c, or VIII-d wherein $L^1$ is —C(O)— and $R^5$ is $Cy^2$.

In some embodiments, the present invention provides a compound of one of formulae VIII-a, VIII-b, VIII-c, or VIII-d wherein m is 0. In some embodiments, the present invention provides a compound of one of formulae VIII-a, VIII-b, VIII-c, or VIII-d wherein m is 1.

Exemplary compounds of the invention are set forth in Table 1, below.

TABLE 1
Exemplary Compounds
I-1
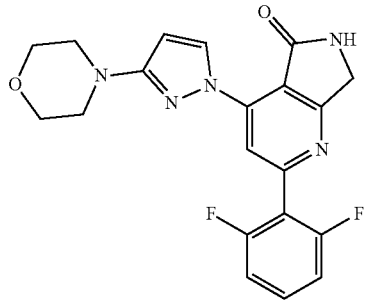 [SMILES: O=C1NCc2nc(-c3c(F)cccc3F)cc(-n3ccc(N4CCOCC4)n3)c21]
I-2
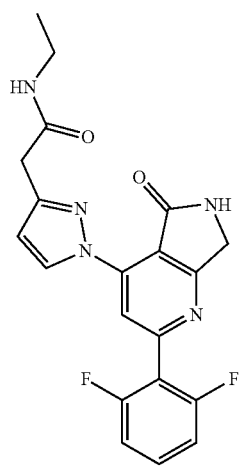 [SMILES: CCNC(=O)Cc1ccn(-c2cc(-c3c(F)cccc3F)nc3c2C(=O)NC3)n1]
I-3
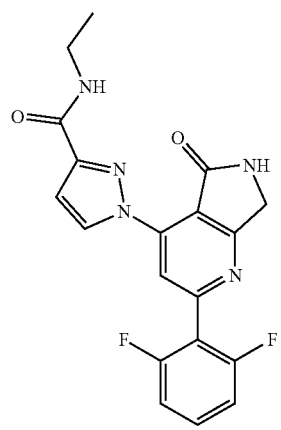 [SMILES: CCNC(=O)c1ccn(-c2cc(-c3c(F)cccc3F)nc3c2C(=O)NC3)n1]
I-4
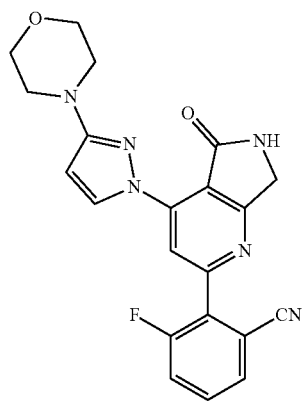 [SMILES: N#Cc1cccc(F)c1-c1cc(-n2ccc(N3CCOCC3)n2)c2c(n1)CNC2=O]
TABLE 1-continued
Exemplary Compounds
I-5
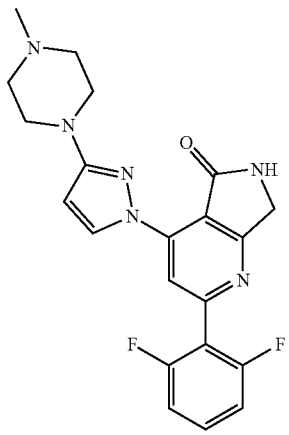 [SMILES: CN1CCN(c2ccn(-c3cc(-c4c(F)cccc4F)nc4c3C(=O)NC4)n2)CC1]
I-6
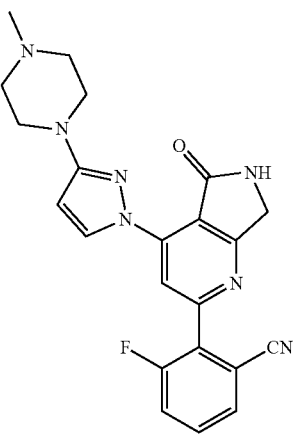 [SMILES: CN1CCN(c2ccn(-c3cc(-c4c(F)cccc4C#N)nc4c3C(=O)NC4)n2)CC1]
I-7
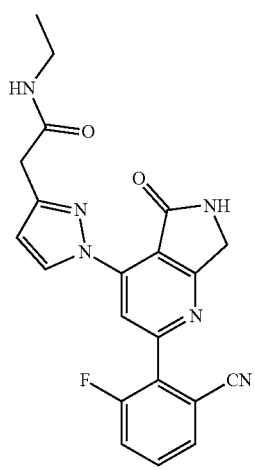 [SMILES: CCNC(=O)Cc1ccn(-c2cc(-c3c(F)cccc3C#N)nc3c2C(=O)NC3)n1]

TABLE 1-continued

Exemplary Compounds

I-8, I-9, I-10, I-11, I-12, I-13, I-14, I-15, I-16, I-17

TABLE 1-continued

Exemplary Compounds

I-18
I-19
I-20
I-21
I-22
I-23
I-24
I-25
I-26

TABLE 1-continued

Exemplary Compounds

I-27, I-28, I-29, I-30, I-31, I-32, I-33, I-34, I-35, I-36

TABLE 1-continued
Exemplary Compounds
I-37 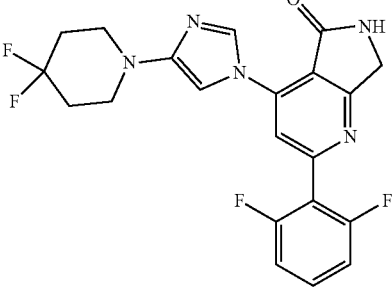
I-38 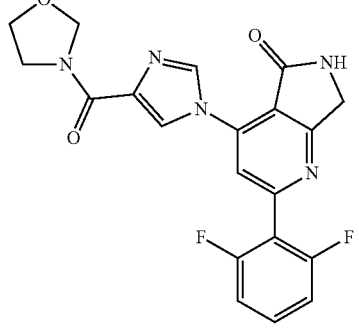
I-39 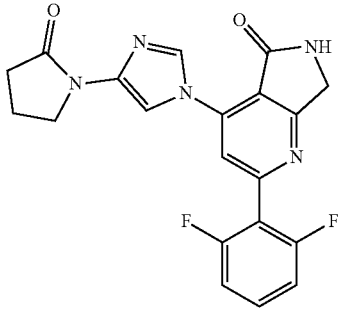 [SMILES: O=C1NCc2nc(-c3c(F)cccc3F)cc(-n3cnc(N4CCCC4=O)c3)c21]
I-40 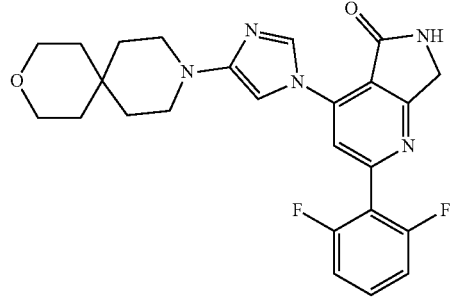 [SMILES: O=C1NCc2nc(-c3c(F)cccc3F)cc(-n3cnc(N4CCC5(CCOCC5)CC4)c3)c21]
I-41 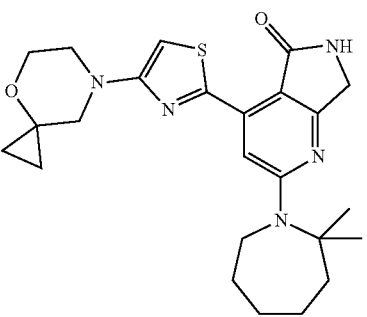 [SMILES: CC1(C)CCCCCN1c1cc(-c2nc(N3CCOC4(CC4)C3)cs2)c2c(n1)CNC2=O]
I-42 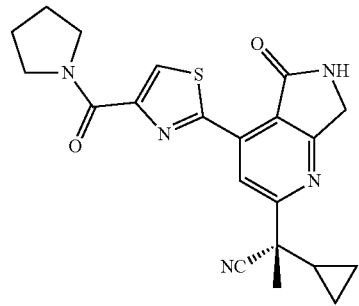 [SMILES: C[C@@](C#N)(c1cc(-c2nc(C(=O)N3CCCC3)cs2)c2c(n1)CNC2=O)C1CC1]
I-43 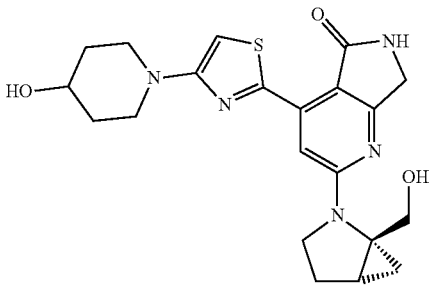
I-44 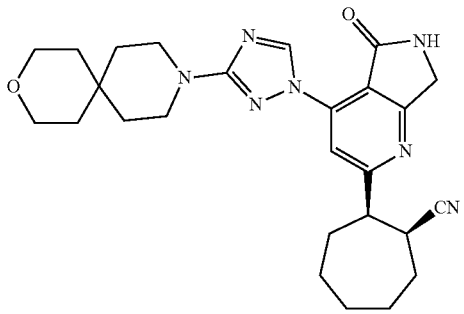 [SMILES: N#C[C@H]1CCCCC[C@H]1c1cc(-n2cnc(N3CCC4(CCOCC4)CC3)n2)c2c(n1)CNC2=O]
I-45 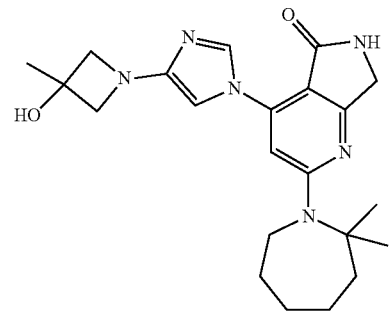
I-46 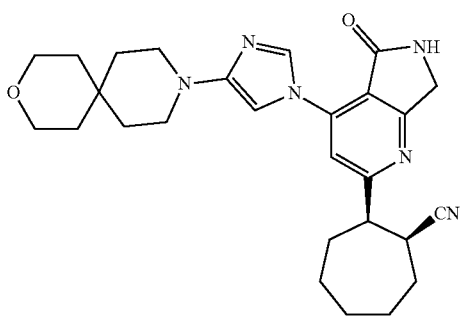 [SMILES: N#C[C@H]1CCCCC[C@H]1c1cc(-n2cnc(N3CCC4(CCOCC4)CC3)c2)c2c(n1)CNC2=O]

TABLE 1-continued
Exemplary Compounds
I-47 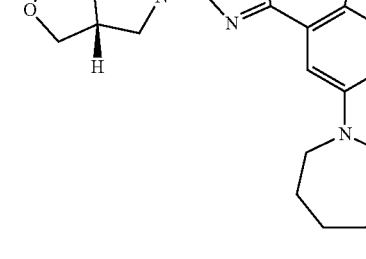
I-48
I-49
I-50
I-51
TABLE 1-continued
Exemplary Compounds
I-52 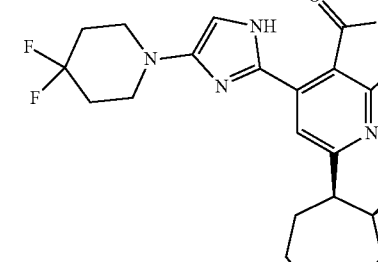
I-53
I-54
I-55

TABLE 1-continued
Exemplary Compounds
I-56
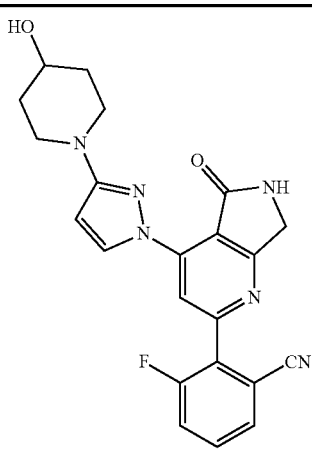
I-57
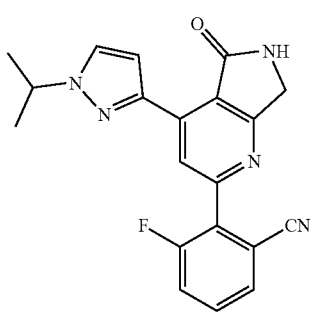 [SMILES: CC(C)n1ccc(-c2cc(-c3c(F)cccc3C#N)nc3c2C(=O)NC3)n1]
I-58
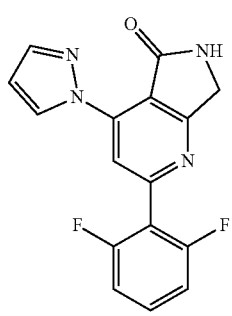 [SMILES: O=C1NCc2nc(-c3c(F)cccc3F)cc(-n3cccn3)c21]
I-59
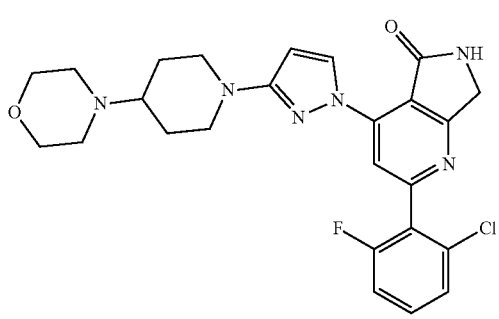 [SMILES: O=C1NCc2nc(-c3c(F)cccc3Cl)cc(-n3ccc(N4CCC(N5CCOCC5)CC4)n3)c21]
TABLE 1-continued
Exemplary Compounds
I-60
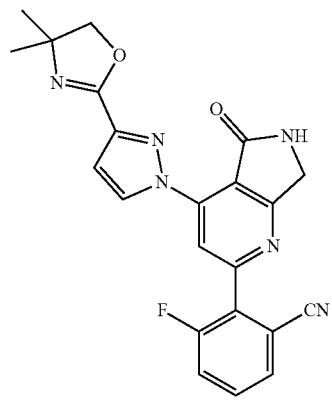 [SMILES: CC1(C)COC(c2ccn(-c3cc(-c4c(F)cccc4C#N)nc4c3C(=O)NC4)n2)=N1]
I-61
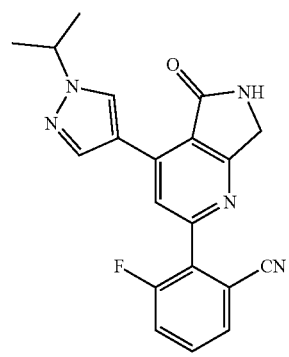 [SMILES: CC(C)n1cc(-c2cc(-c3c(F)cccc3C#N)nc3c2C(=O)NC3)cn1]
I-62
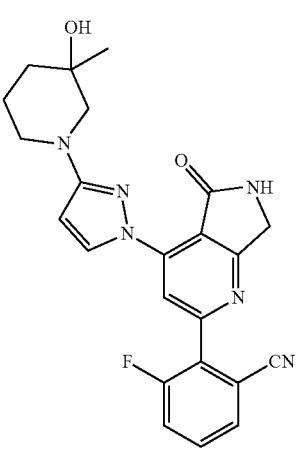 [SMILES: CC1(O)CCCN(c2ccn(-c3cc(-c4c(F)cccc4C#N)nc4c3C(=O)NC4)n2)C1]
I-63
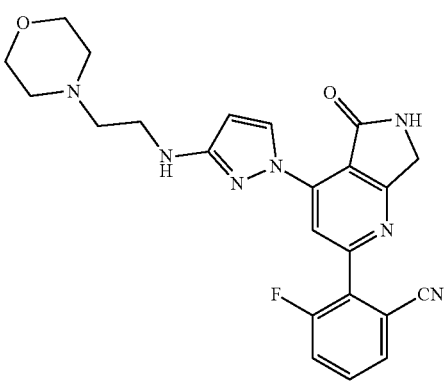 [SMILES: N#Cc1cccc(F)c1-c1cc(-n2ccc(NCCN3CCOCC3)n2)c2c(n1)CNC2=O]

TABLE 1-continued

Exemplary Compounds

I-64

I-65

I-66

I-67

I-68

I-69

I-70

TABLE 1-continued
Exemplary Compounds
I-71 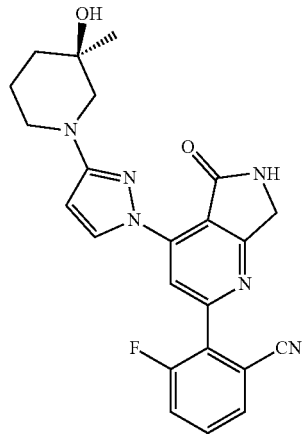 [SMILES: C[C@@]1(O)CCCN(c2ccn(-c3cc(-c4c(F)cccc4C#N)nc4c3C(=O)NC4)n2)C1]
I-72 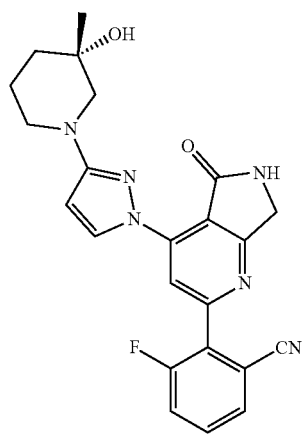 [SMILES: C[C@]1(O)CCCN(c2ccn(-c3cc(-c4c(F)cccc4C#N)nc4c3C(=O)NC4)n2)C1]
I-73 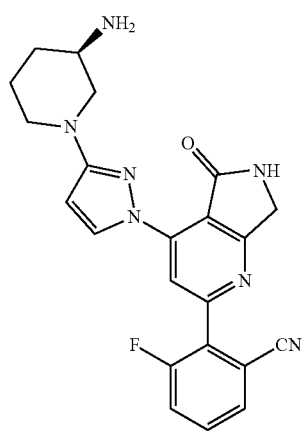 [SMILES: N#Cc1cccc(F)c1-c1cc(-n2ccc(N3CCC[C@@H](N)C3)n2)c2c(n1)CNC2=O]
TABLE 1-continued
Exemplary Compounds
I-74 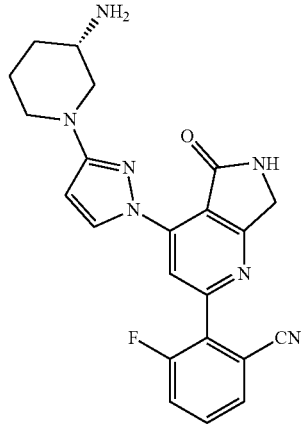 [SMILES: N#Cc1cccc(F)c1-c1cc(-n2ccc(N3CCC[C@H](N)C3)n2)c2c(n1)CNC2=O]
I-75 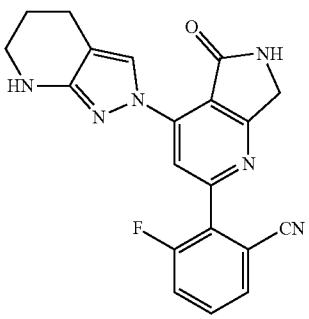 [SMILES: N#Cc1cccc(F)c1-c1cc(-n2cc3c(n2)NCCC3)c2c(n1)CNC2=O]
I-76 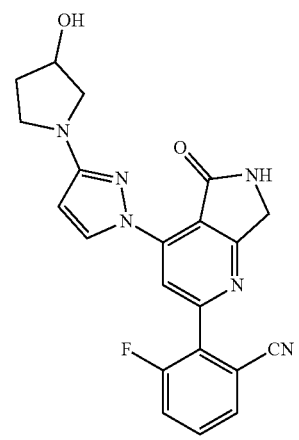
I-77 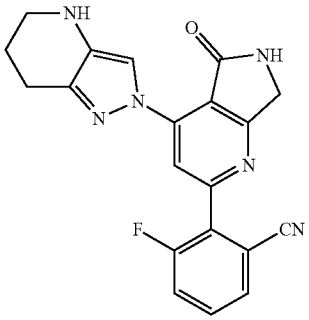 [SMILES: N#Cc1cccc(F)c1-c1cc(-n2cc3c(n2)CCCN3)c2c(n1)CNC2=O]

TABLE 1-continued

Exemplary Compounds

I-78, I-79, I-80, I-81, I-82, I-83, I-84

TABLE 1-continued
Exemplary Compounds
I-85
I-86
I-87
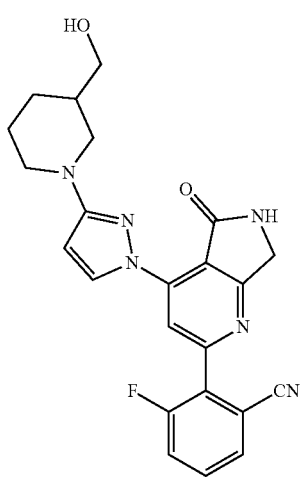
I-88
I-89
I-90
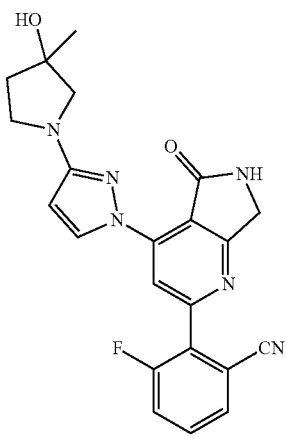 [SMILES: CC1(O)CCN(c2ccn(-c3cc(-c4c(F)cccc4C#N)nc4c3C(=O)NC4)n2)C1]

TABLE 1-continued
Exemplary Compounds
I-91 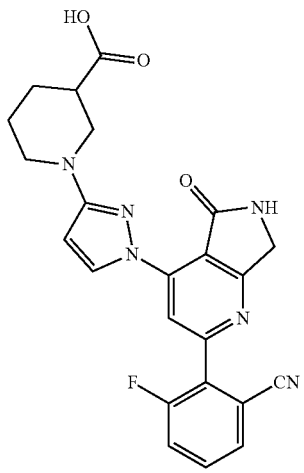 [SMILES: N#Cc1cccc(F)c1-c1cc(-n2ccc(N3CCCC(C(=O)O)C3)n2)c2c(n1)CNC2=O]
I-92 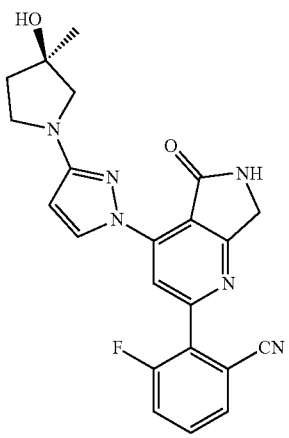 [SMILES: C[C@@]1(O)CCN(c2ccn(-c3cc(-c4c(F)cccc4C#N)nc4c3C(=O)NC4)n2)C1]
I-93 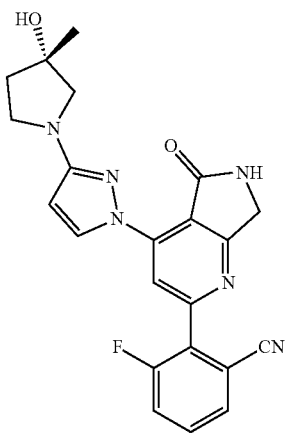 [SMILES: C[C@]1(O)CCN(c2ccn(-c3cc(-c4c(F)cccc4C#N)nc4c3C(=O)NC4)n2)C1]
I-94 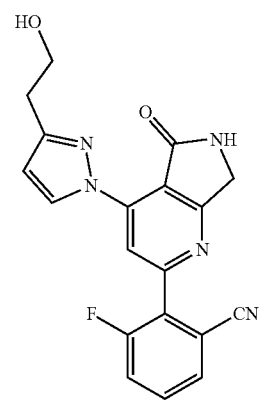 [SMILES: N#Cc1cccc(F)c1-c1cc(-n2ccc(CCO)n2)c2c(n1)CNC2=O]
I-95 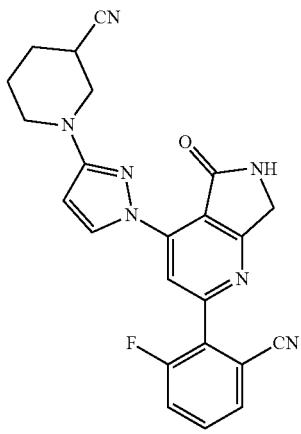 [SMILES: N#Cc1cccc(F)c1-c1cc(-n2ccc(N3CCCC(C#N)C3)n2)c2c(n1)CNC2=O]
I-96 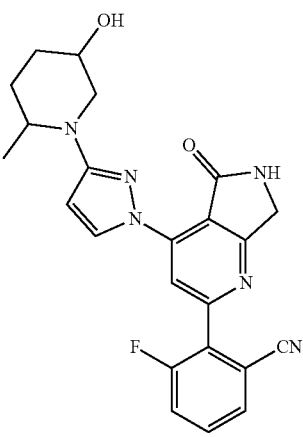 [SMILES: CC1CCC(O)CN1c1ccn(-c2cc(-c3c(F)cccc3C#N)nc3c2C(=O)NC3)n1]

TABLE 1-continued
Exemplary Compounds
I-97
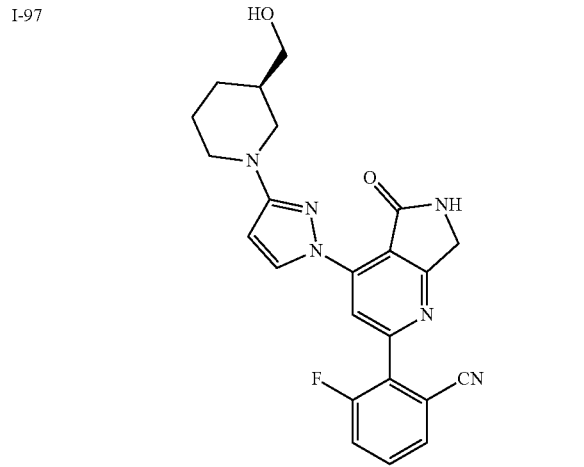
I-98
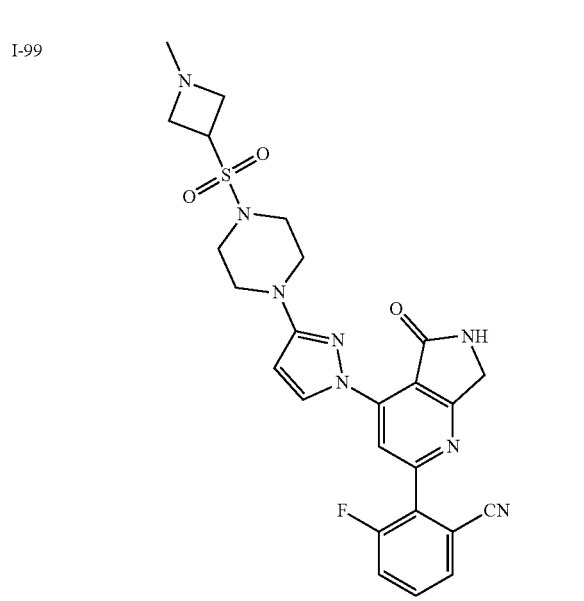
I-99
TABLE 1-continued
Exemplary Compounds
I-100
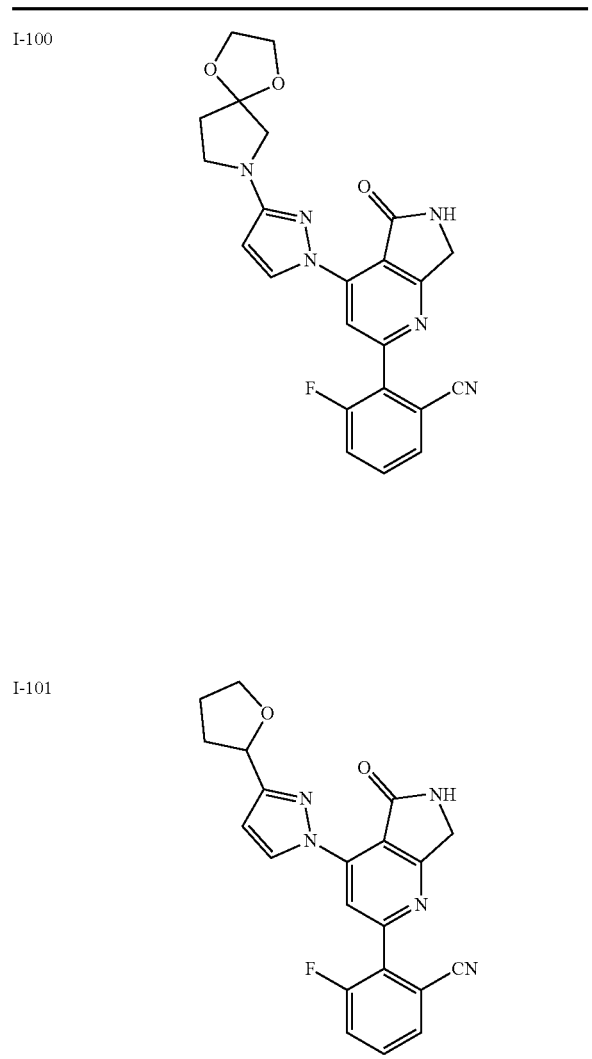
I-101
I-102
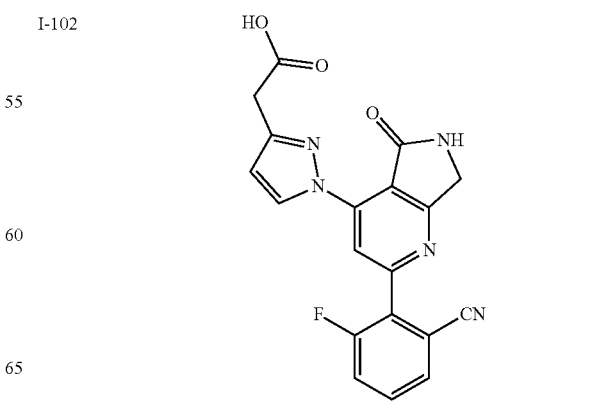

TABLE 1-continued
Exemplary Compounds
I-103 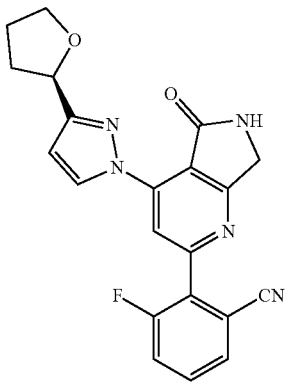 [SMILES: N#Cc1cccc(F)c1-c1cc(-n2ccc([C@H]3CCCO3)n2)c2c(n1)CNC2=O]
I-104 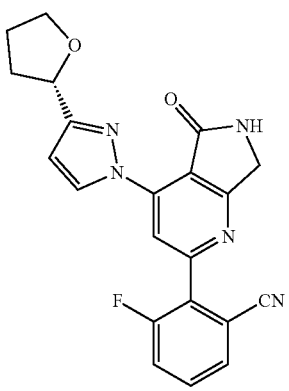 [SMILES: N#Cc1cccc(F)c1-c1cc(-n2ccc([C@@H]3CCCO3)n2)c2c(n1)CNC2=O]
I-105 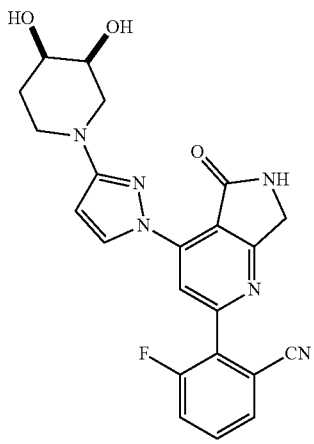 [SMILES: N#Cc1cccc(F)c1-c1cc(-n2ccc(N3CC[C@@H](O)[C@@H](O)C3)n2)c2c(n1)CNC2=O]
TABLE 1-continued
Exemplary Compounds
I-106 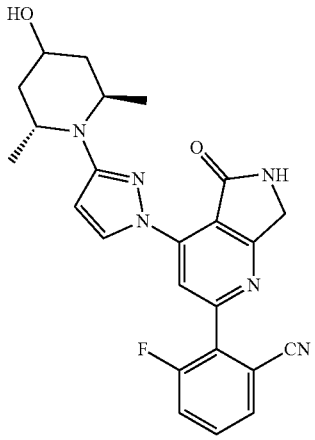 [SMILES: C[C@@H]1CC(O)C[C@@H](C)N1c1ccn(-c2cc(-c3c(F)cccc3C#N)nc3c2C(=O)NC3)n1]
I-107 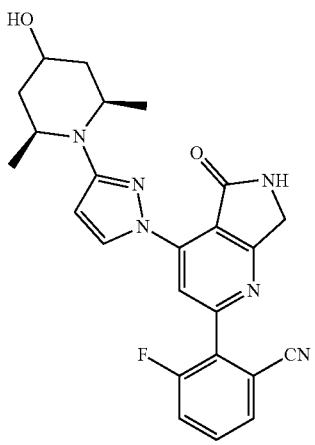 [SMILES: C[C@@H]1CC(O)C[C@H](C)N1c1ccn(-c2cc(-c3c(F)cccc3C#N)nc3c2C(=O)NC3)n1]
I-108 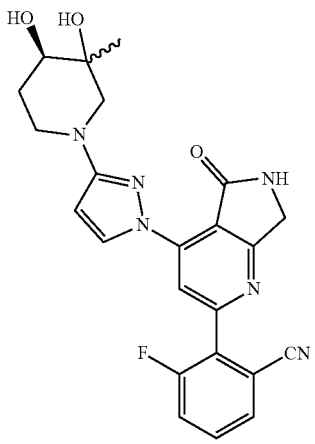 [SMILES: CC1(O)CN(c2ccn(-c3cc(-c4c(F)cccc4C#N)nc4c3C(=O)NC4)n2)CC[C@H]1O]

TABLE 1-continued

Exemplary Compounds

I-109

I-110

I-111

I-112

I-113

I-114

I-115

TABLE 1-continued
Exemplary Compounds
| I-116 | 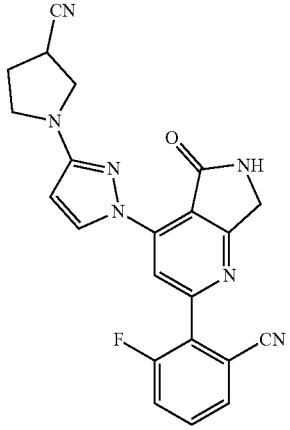 [SMILES: N#Cc1cccc(F)c1-c1cc(-n2ccc(N3CCC(C#N)C3)n2)c2c(n1)CNC2=O] |
| I-117 | 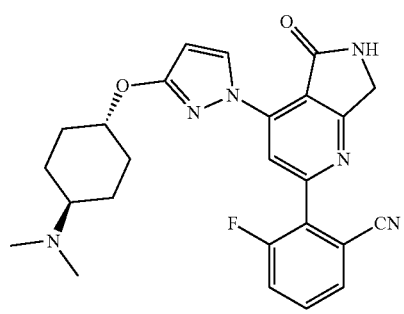 [SMILES: CN(C)[C@H]1CC[C@H](Oc2ccn(-c3cc(-c4c(F)cccc4C#N)nc4c3C(=O)NC4)n2)CC1] |
| I-118 | 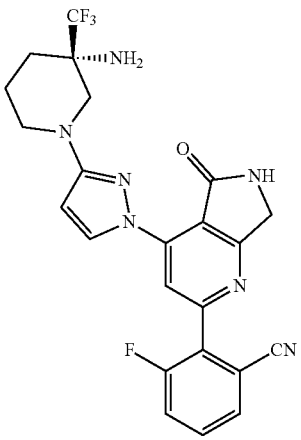 [SMILES: N#Cc1cccc(F)c1-c1cc(-n2ccc(N3CCC[C@@](N)(C(F)(F)F)C3)n2)c2c(n1)CNC2=O] |
| I-119 | 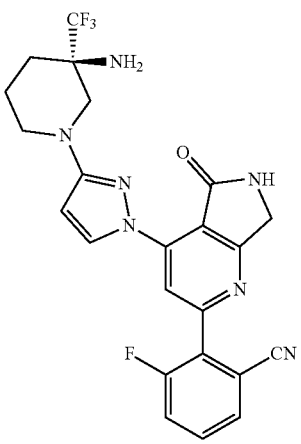 [SMILES: N#Cc1cccc(F)c1-c1cc(-n2ccc(N3CCC[C@](N)(C(F)(F)F)C3)n2)c2c(n1)CNC2=O] |
| I-120 | 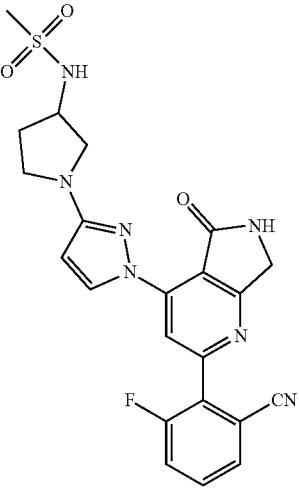 [SMILES: CS(=O)(=O)NC1CCN(c2ccn(-c3cc(-c4c(F)cccc4C#N)nc4c3C(=O)NC4)n2)C1] |
| I-121 | 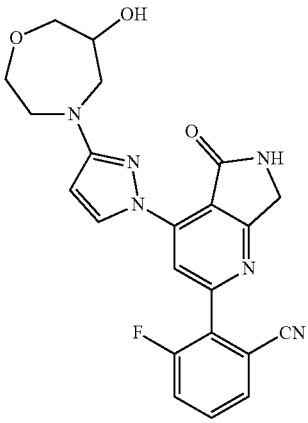 [SMILES: N#Cc1cccc(F)c1-c1cc(-n2ccc(N3CCOCC(O)C3)n2)c2c(n1)CNC2=O] |
| I-122 | 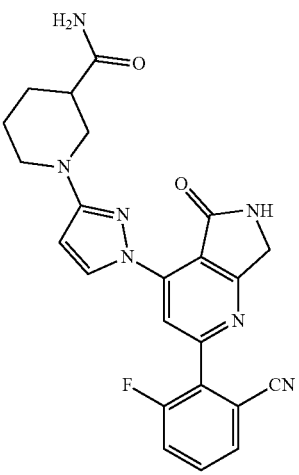 [SMILES: N#Cc1cccc(F)c1-c1cc(-n2ccc(N3CCCC(C(N)=O)C3)n2)c2c(n1)CNC2=O] |

TABLE 1-continued
Exemplary Compounds
I-123
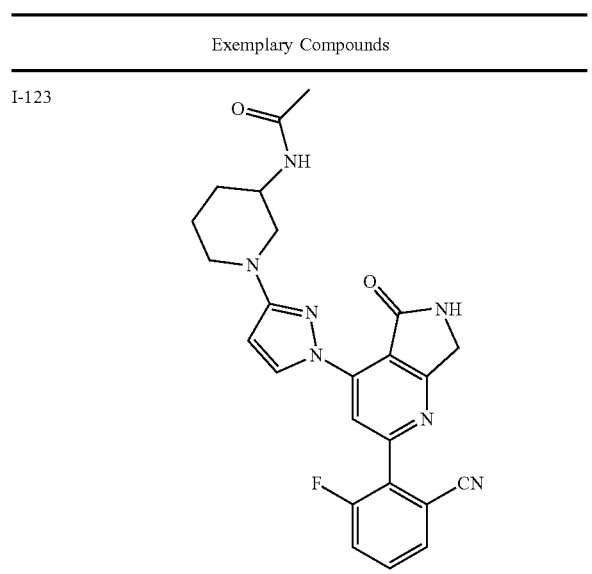
I-124
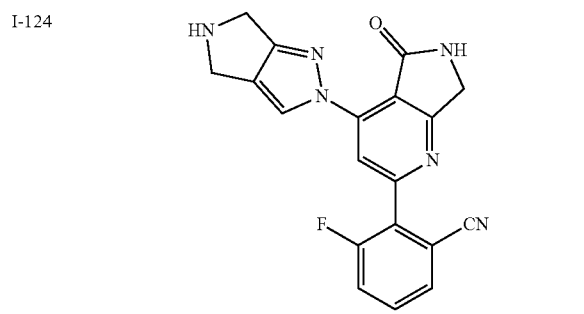
I-125
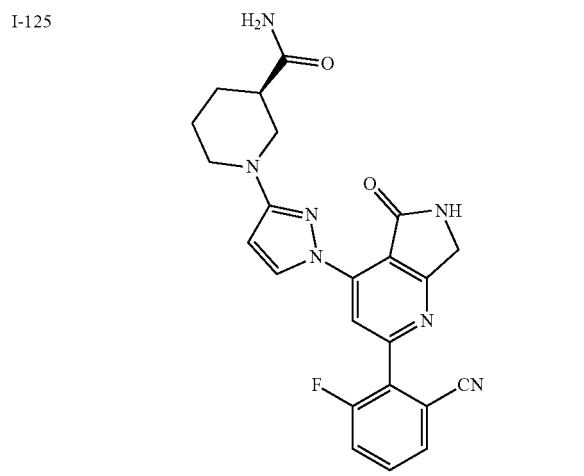
TABLE 1-continued
Exemplary Compounds
I-126
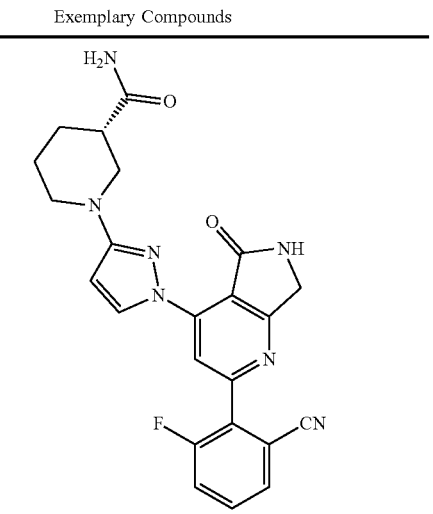
I-127
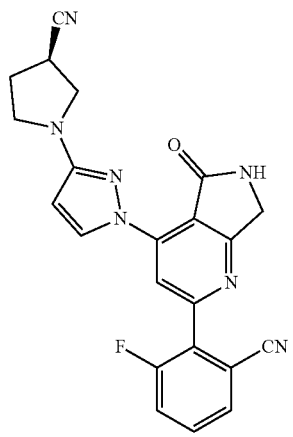 [SMILES: N#Cc1cccc(F)c1-c1cc(-n2ccc(N3CC[C@@H](C#N)C3)n2)c2c(n1)CNC2=O]
I-128
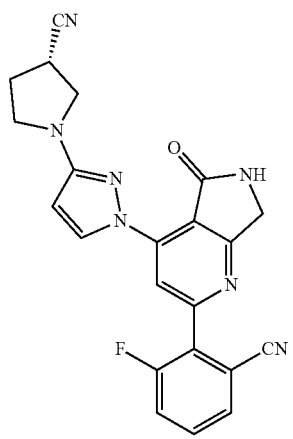 [SMILES: N#Cc1cccc(F)c1-c1cc(-n2ccc(N3CC[C@H](C#N)C3)n2)c2c(n1)CNC2=O]

TABLE 1-continued

Exemplary Compounds

I-129

I-130

I-131

I-132

I-133

I-134

TABLE 1-continued
Exemplary Compounds
I-135
I-136
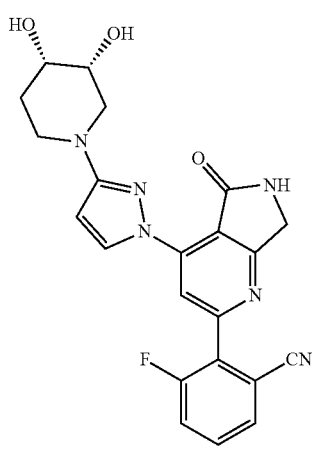 [SMILES: N#Cc1cccc(F)c1-c1cc(-n2ccc(N3CC[C@H](O)[C@H](O)C3)n2)c2c(n1)CNC2=O]
I-137
I-138
I-139
I-140
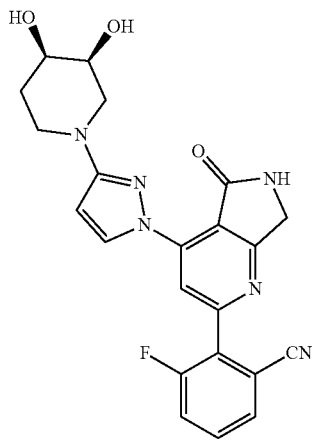 [SMILES: N#Cc1cccc(F)c1-c1cc(-n2ccc(N3CC[C@@H](O)[C@@H](O)C3)n2)c2c(n1)CNC2=O]

TABLE 1-continued
Exemplary Compounds
I-141
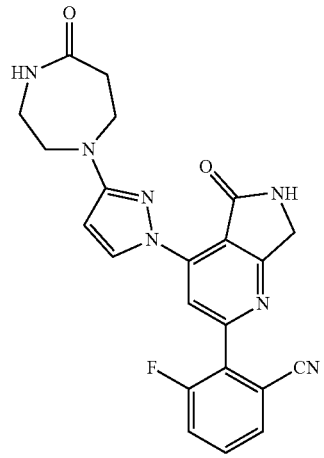 [SMILES: N#Cc1cccc(F)c1-c1cc(-n2ccc(N3CCNC(=O)CC3)n2)c2c(n1)CNC2=O]
I-142
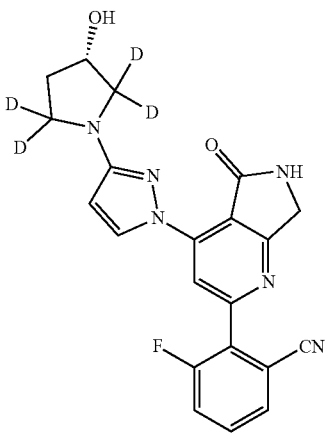 [SMILES: [2H]C1([2H])C[C@H](O)C([2H])([2H])N1c1ccn(-c2cc(-c3c(F)cccc3C#N)nc3c2C(=O)NC3)n1]
I-143
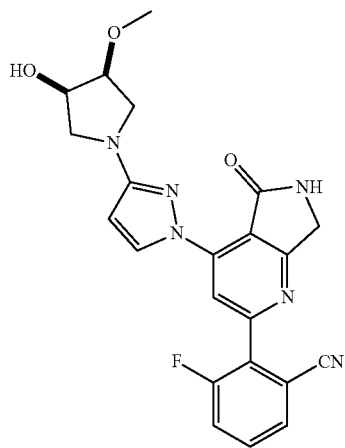 [SMILES: CO[C@H]1CN(c2ccn(-c3cc(-c4c(F)cccc4C#N)nc4c3C(=O)NC4)n2)C[C@H]1O]
TABLE 1-continued
Exemplary Compounds
I-144
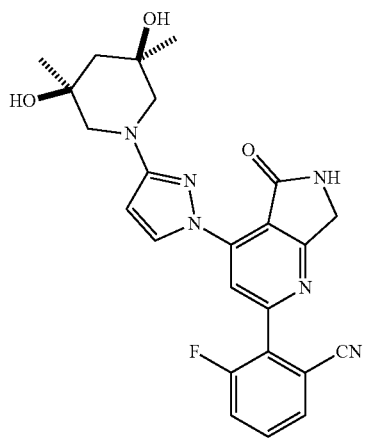 [SMILES: C[C@]1(O)CN(c2ccn(-c3cc(-c4c(F)cccc4C#N)nc4c3C(=O)NC4)n2)C[C@@](C)(O)C1]
I-145
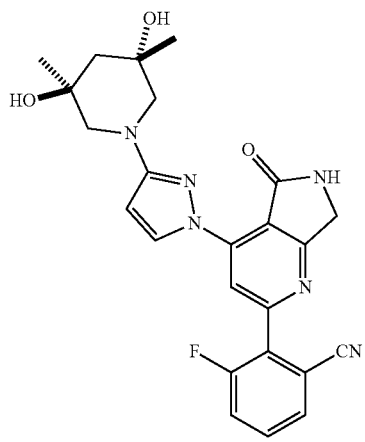 [SMILES: C[C@@]1(O)CN(c2ccn(-c3cc(-c4c(F)cccc4C#N)nc4c3C(=O)NC4)n2)C[C@@](C)(O)C1]
I-146
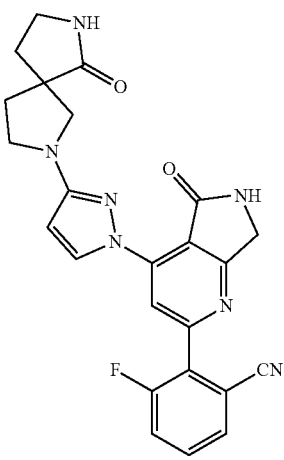 [SMILES: N#Cc1cccc(F)c1-c1cc(-n2ccc(N3CCC4(CCNC4=O)C3)n2)c2c(n1)CNC2=O]

TABLE 1-continued
Exemplary Compounds
I-147
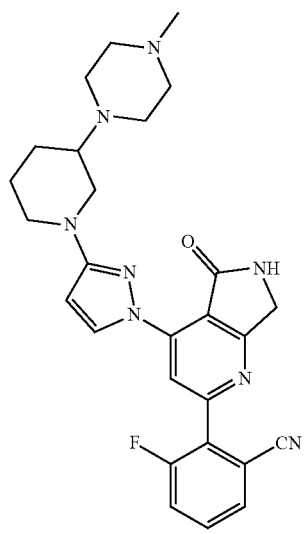 [SMILES: CN1CCN(C2CCCN(c3ccn(-c4cc(-c5c(F)cccc5C#N)nc5c4C(=O)NC5)n3)C2)CC1]
I-150
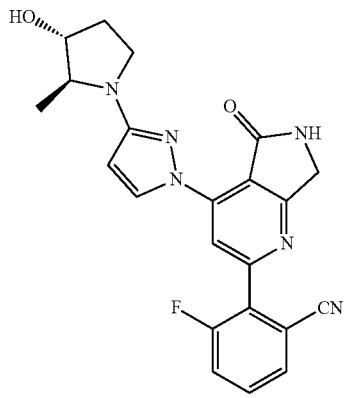
I-148
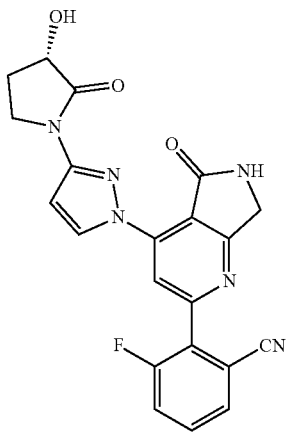 [SMILES: N#Cc1cccc(F)c1-c1cc(-n2ccc(N3CC[C@H](O)C3=O)n2)c2c(n1)CNC2=O]
I-151
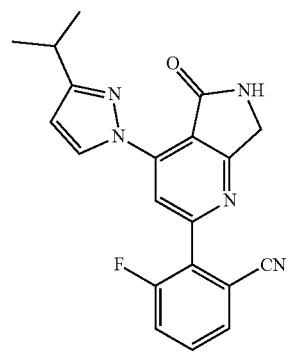 [SMILES: CC(C)c1ccn(-c2cc(-c3c(F)cccc3C#N)nc3c2C(=O)NC3)n1]
I-149
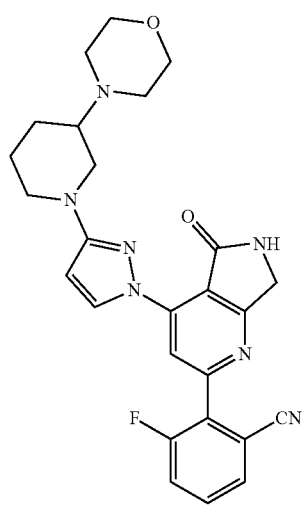 [SMILES: N#Cc1cccc(F)c1-c1cc(-n2ccc(N3CCC[C@H](N4CCOCC4)C3)n2)c2c(n1)CNC2=O]
I-152
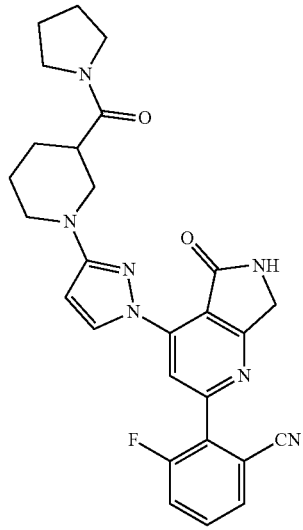

TABLE 1-continued

Exemplary Compounds

I-153, I-154, I-155, I-156, I-157, I-158 (chemical structures)

TABLE 1-continued
Exemplary Compounds
I-159
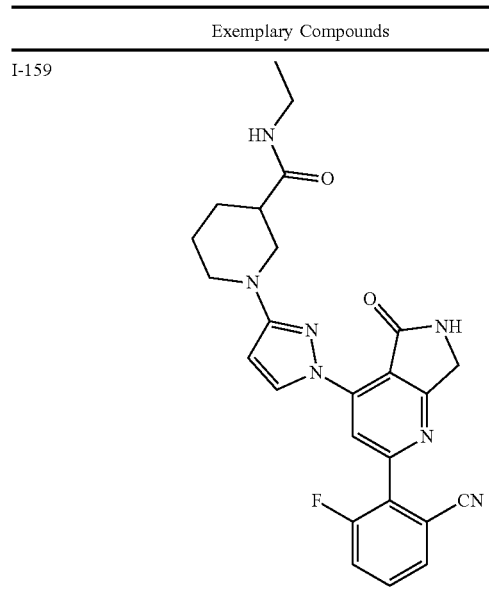
I-160
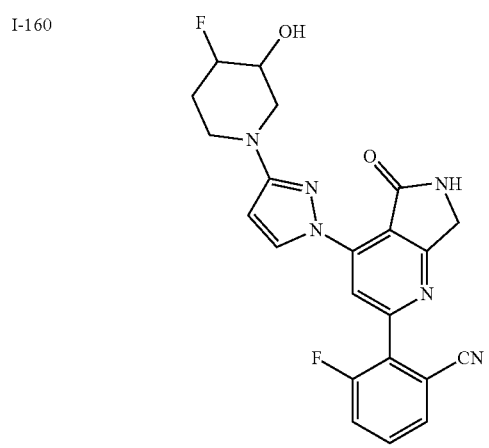
I-161
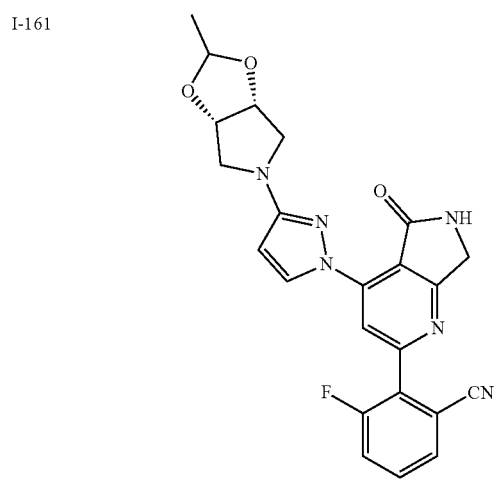
I-162
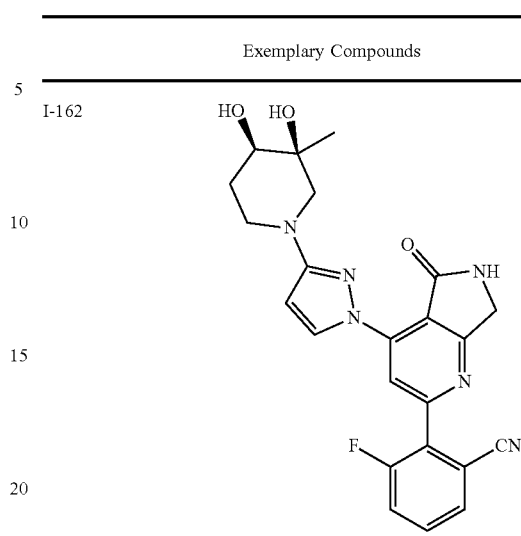
I-163
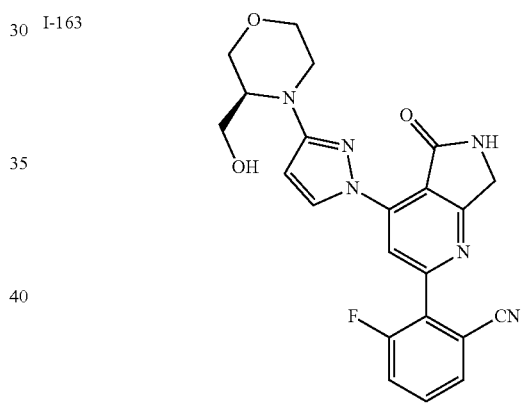
I-164
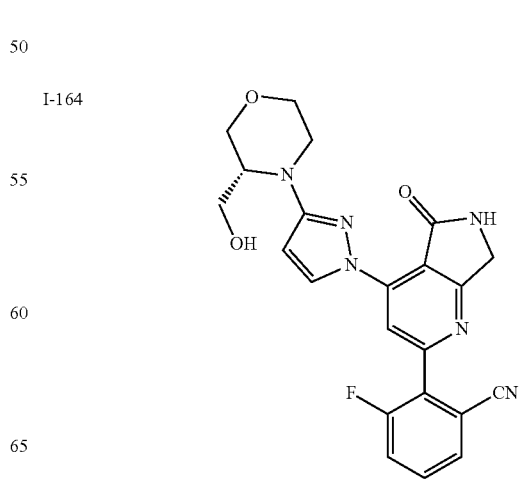

TABLE 1-continued
Exemplary Compounds
I-165
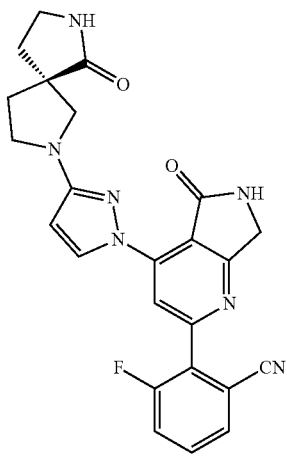 [SMILES: N#Cc1cccc(F)c1-c1cc(-n2ccc(N3CC[C@]4(CCNC4=O)C3)n2)c2c(n1)CNC2=O]
I-166
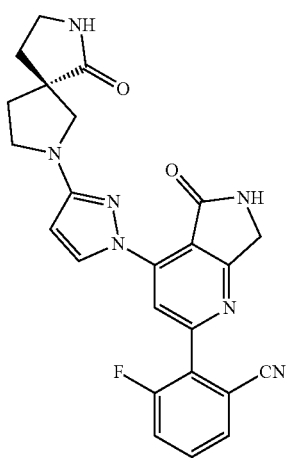 [SMILES: N#Cc1cccc(F)c1-c1cc(-n2ccc(N3CC[C@@]4(CCNC4=O)C3)n2)c2c(n1)CNC2=O]
I-167
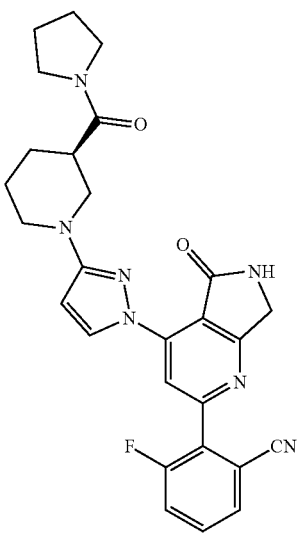 [SMILES: N#Cc1cccc(F)c1-c1cc(-n2ccc(N3CCC[C@@H](C(=O)N4CCCC4)C3)n2)c2c(n1)CNC2=O]
I-168
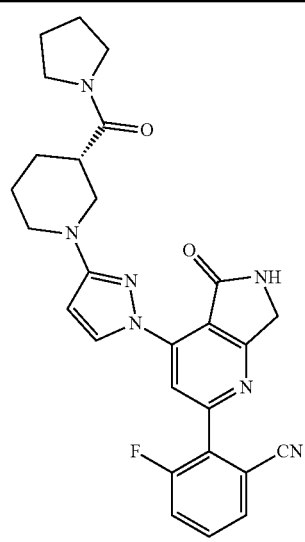
I-169
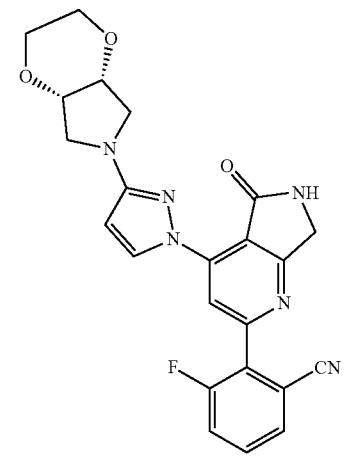 [SMILES: N#Cc1cccc(F)c1-c1cc(-n2ccc(N3C[C@@H]4OCCO[C@@H]4C3)n2)c2c(n1)CNC2=O]
I-170
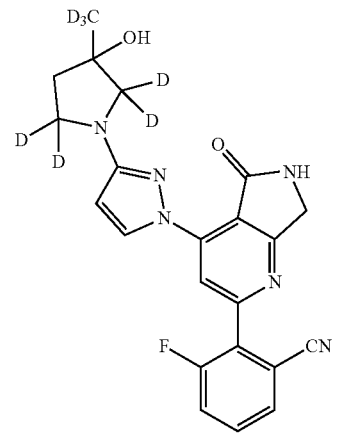 [SMILES: [2H]C1([2H])CC(O)(C([2H])([2H])[2H])C([2H])([2H])N1c1ccn(-c2cc(-c3c(F)cccc3C#N)nc3c2C(=O)NC3)n1]

TABLE 1-continued
Exemplary Compounds
I-171
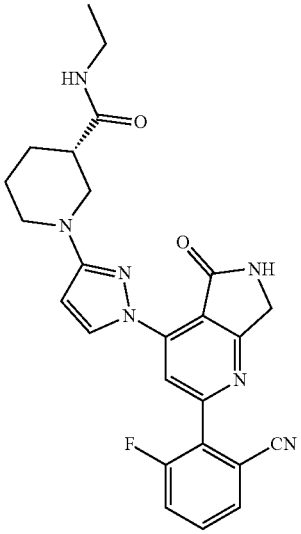 [SMILES: CCNC(=O)[C@H]1CCCN(c2ccn(-c3cc(-c4c(F)cccc4C#N)nc4c3C(=O)NC4)n2)C1]
I-172
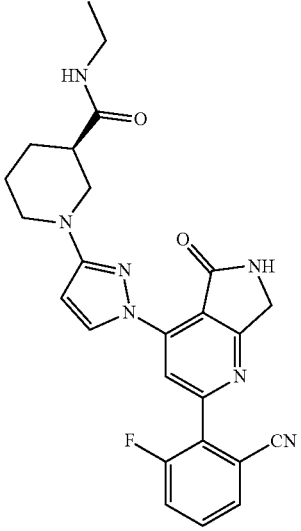 [SMILES: CCNC(=O)[C@@H]1CCCN(c2ccn(-c3cc(-c4c(F)cccc4C#N)nc4c3C(=O)NC4)n2)C1]
I-173
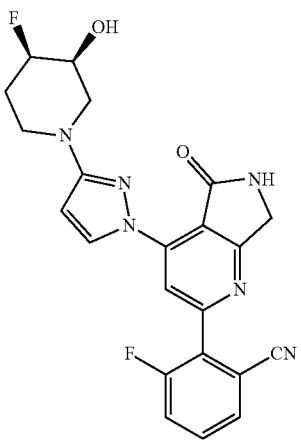 [SMILES: N#Cc1cccc(F)c1-c1cc(-n2ccc(N3CC[C@@H](F)[C@@H](O)C3)n2)c2c(n1)CNC2=O]
TABLE 1-continued
Exemplary Compounds
I-174
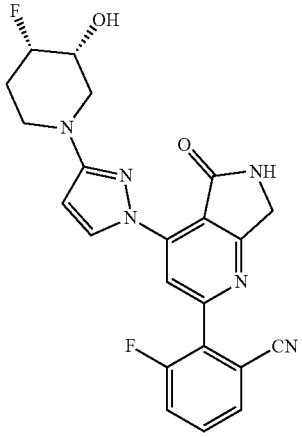 [SMILES: N#Cc1cccc(F)c1-c1cc(-n2ccc(N3CC[C@H](F)[C@H](O)C3)n2)c2c(n1)CNC2=O]
I-175
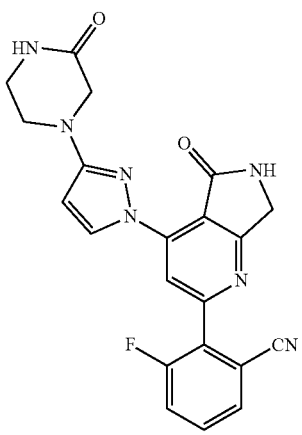 [SMILES: N#Cc1cccc(F)c1-c1cc(-n2ccc(N3CCNC(=O)C3)n2)c2c(n1)CNC2=O]
I-176
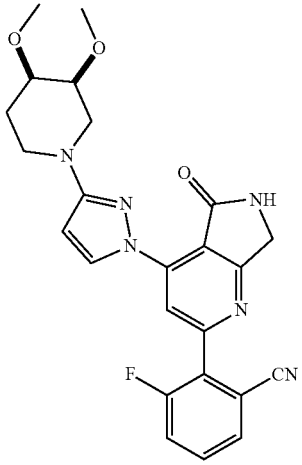 [SMILES: CO[C@H]1CN(c2ccn(-c3cc(-c4c(F)cccc4C#N)nc4c3C(=O)NC4)n2)CC[C@H]1OC]

TABLE 1-continued
Exemplary Compounds
I-177
I-178
I-179
I-180
I-181
I-182
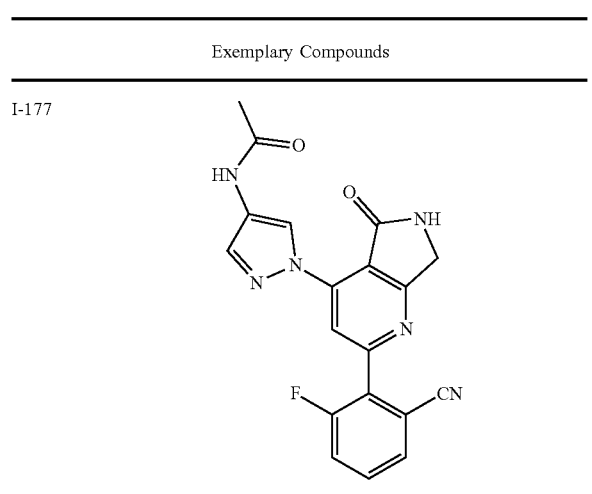
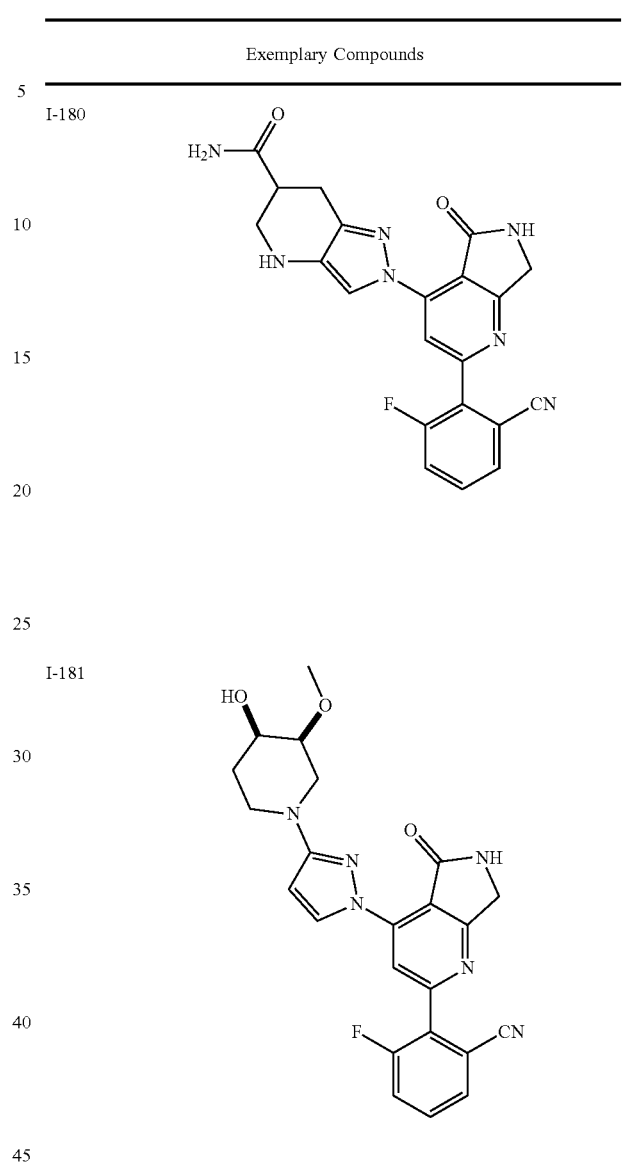

TABLE 1-continued
Exemplary Compounds
I-183
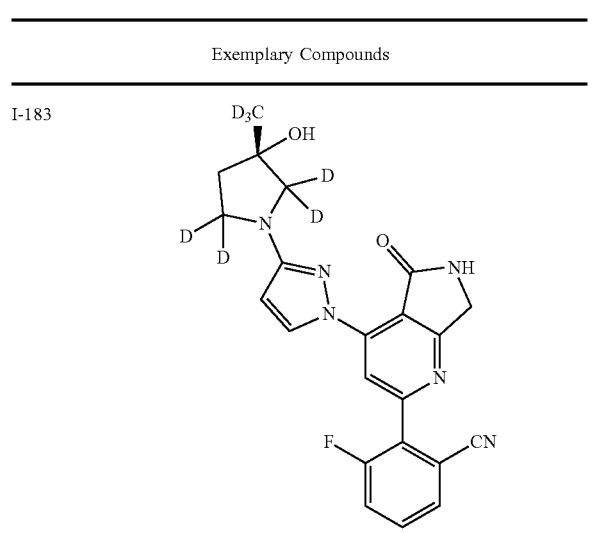
I-184
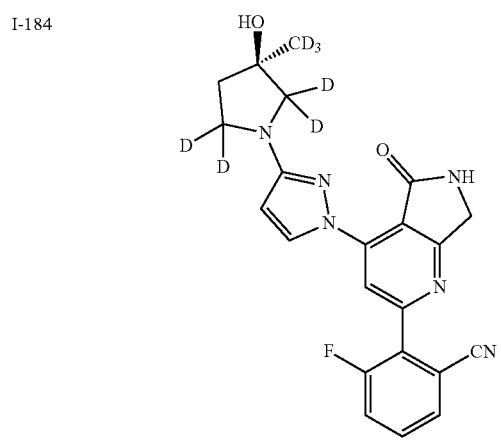
I-185
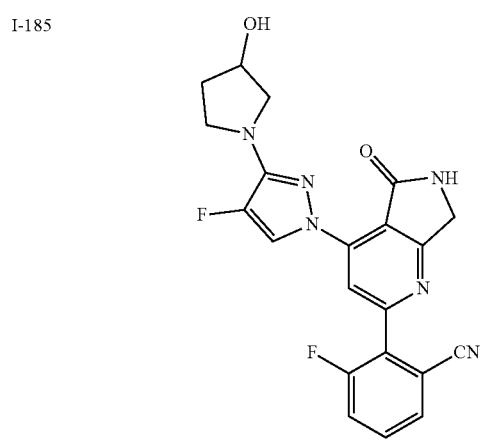
TABLE 1-continued
Exemplary Compounds
I-186
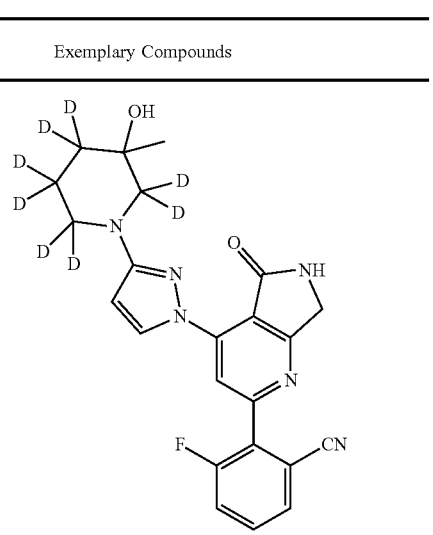
I-187
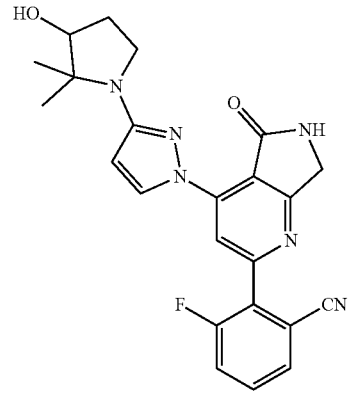 [SMILES: CC1(C)C(O)CCN1c1ccn(-c2cc(-c3c(F)cccc3C#N)nc3c2C(=O)NC3)n1]
I-188
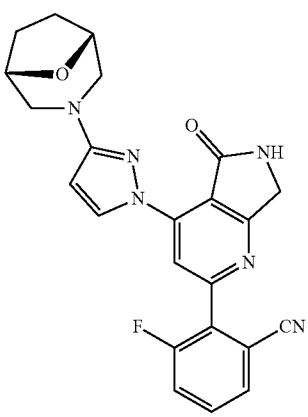 [SMILES: N#Cc1cccc(F)c1-c1cc(-n2ccc(N3C[C@H]4CC[C@@H](C3)O4)n2)c2c(n1)CNC2=O]

TABLE 1-continued
Exemplary Compounds
I-189
I-190
I-191
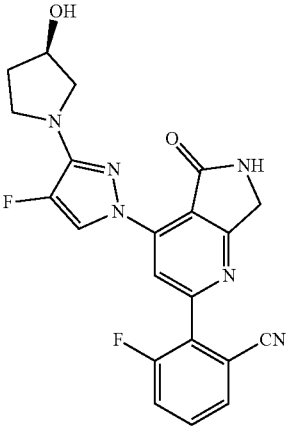 [SMILES: N#Cc1cccc(F)c1-c1cc(-n2cc(F)c(N3CC[C@@H](O)C3)n2)c2c(n1)CNC2=O]
I-192
I-193
I-194
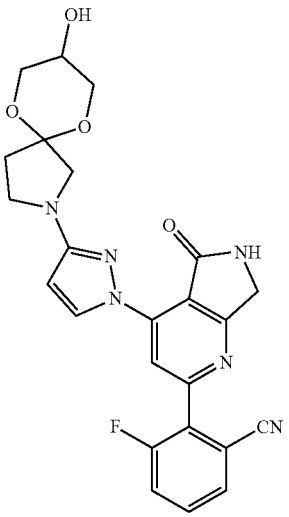 [SMILES: N#Cc1cccc(F)c1-c1cc(-n2ccc(N3CCC4(C3)OCC(O)CO4)n2)c2c(n1)CNC2=O]

TABLE 1-continued
Exemplary Compounds
I-195
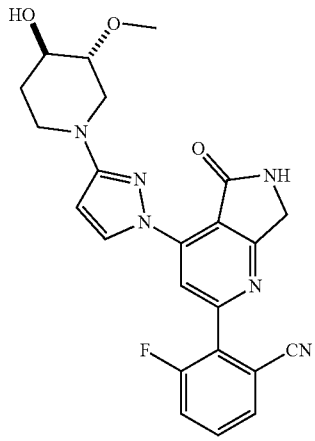 [SMILES: CO[C@@H]1CN(c2ccn(-c3cc(-c4c(F)cccc4C#N)nc4c3C(=O)NC4)n2)CC[C@H]1O]
I-196
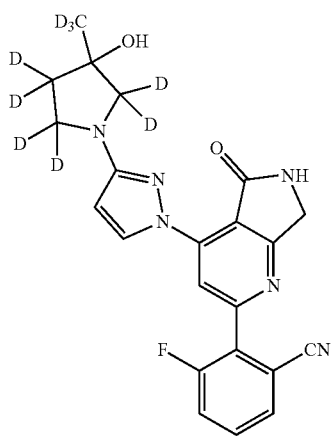 [SMILES: [2H]C([2H])([2H])C1(O)C([2H])([2H])N(c2ccn(-c3cc(-c4c(F)cccc4C#N)nc4c3C(=O)NC4)n2)C([2H])([2H])C1([2H])[2H]]
I-197
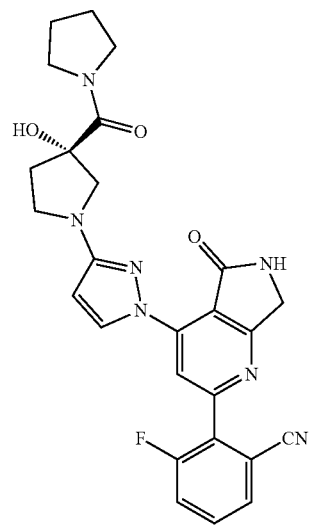 [SMILES: N#Cc1cccc(F)c1-c1cc(-n2ccc(N3CC[C@@](O)(C(=O)N4CCCC4)C3)n2)c2c(n1)CNC2=O]
I-198
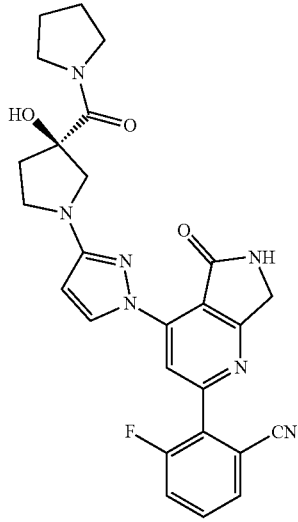 [SMILES: N#Cc1cccc(F)c1-c1cc(-n2ccc(N3CC[C@](O)(C(=O)N4CCCC4)C3)n2)c2c(n1)CNC2=O]
I-199
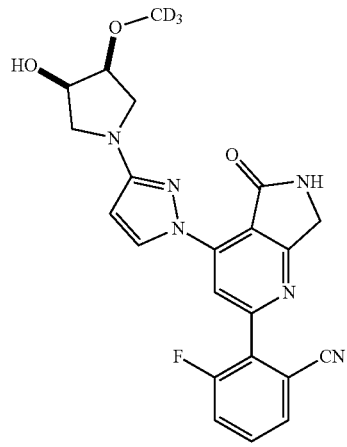 [SMILES: [2H]C([2H])([2H])O[C@H]1CN(c2ccn(-c3cc(-c4c(F)cccc4C#N)nc4c3C(=O)NC4)n2)C[C@H]1O]
I-200
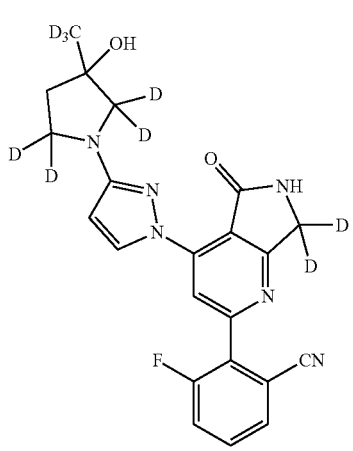 [SMILES: [2H]C1([2H])NC(=O)c2c(-n3ccc(N4C([2H])([2H])CC(O)(C([2H])([2H])[2H])C4([2H])[2H])n3)cc(-c3c(F)cccc3C#N)nc21]

TABLE 1-continued
Exemplary Compounds
I-201 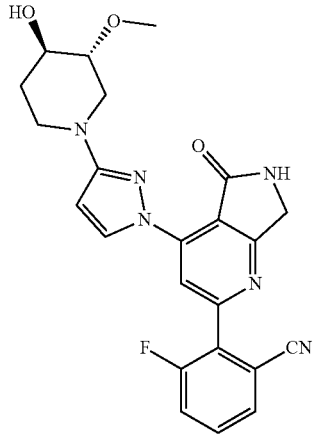 [SMILES: CO[C@@H]1CN(c2ccn(-c3cc(-c4c(F)cccc4C#N)nc4c3C(=O)NC4)n2)CC[C@H]1O]
I-202 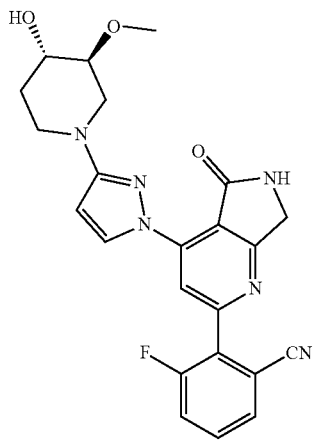 [SMILES: CO[C@H]1CN(c2ccn(-c3cc(-c4c(F)cccc4C#N)nc4c3C(=O)NC4)n2)CC[C@@H]1O]
I-203 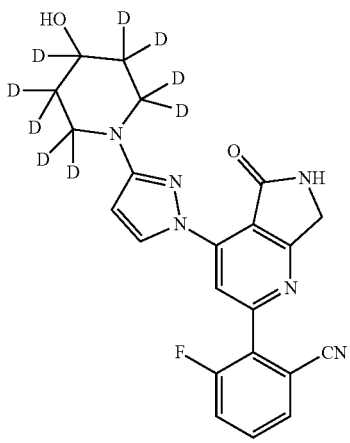 [SMILES: [2H]C1([2H])N(c2ccn(-c3cc(-c4c(F)cccc4C#N)nc4c3C(=O)NC4)n2)C([2H])([2H])C([2H])([2H])C([2H])(O)C1([2H])[2H]]
I-204 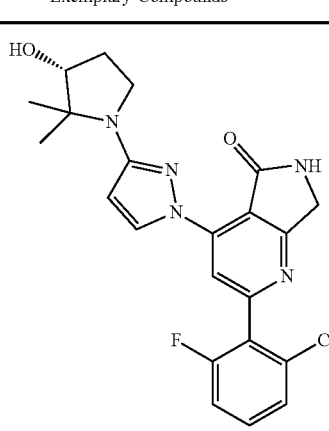
I-205 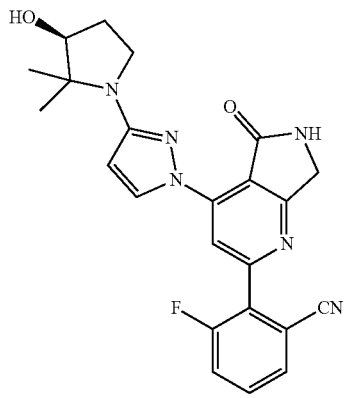 [SMILES: CC1(C)[C@@H](O)CCN1c1ccn(-c2cc(-c3c(F)cccc3C#N)nc3c2C(=O)NC3)n1]
I-206 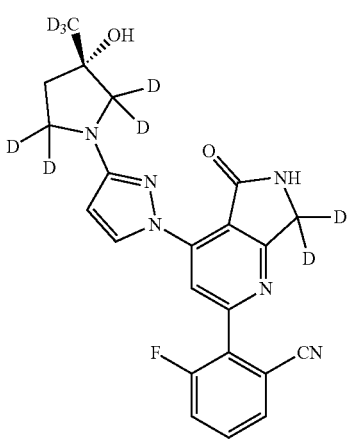 [SMILES: [2H]C1([2H])NC(=O)c2c(-n3ccc(N4C([2H])([2H])C[C@@](O)(C([2H])([2H])[2H])C4([2H])[2H])n3)cc(-c3c(F)cccc3C#N)nc21]

TABLE 1-continued
Exemplary Compounds
I-207
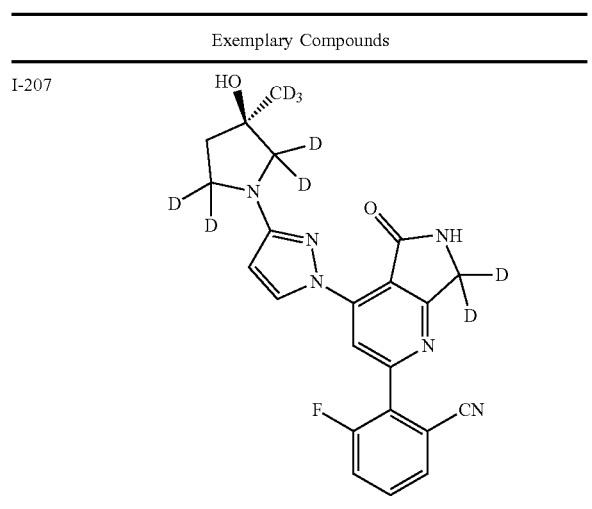
I-210
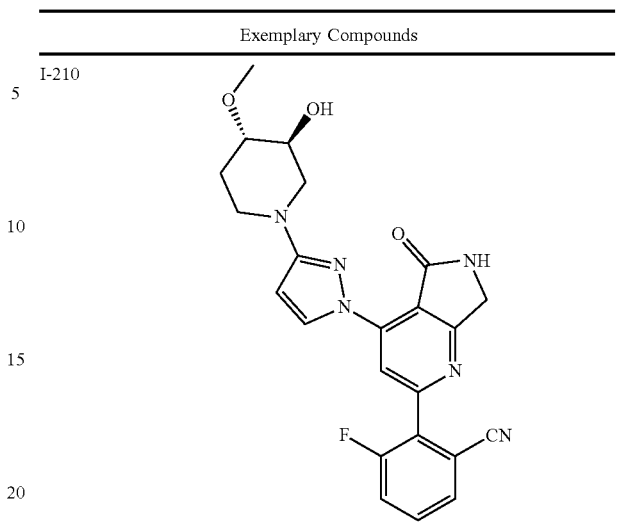
I-208
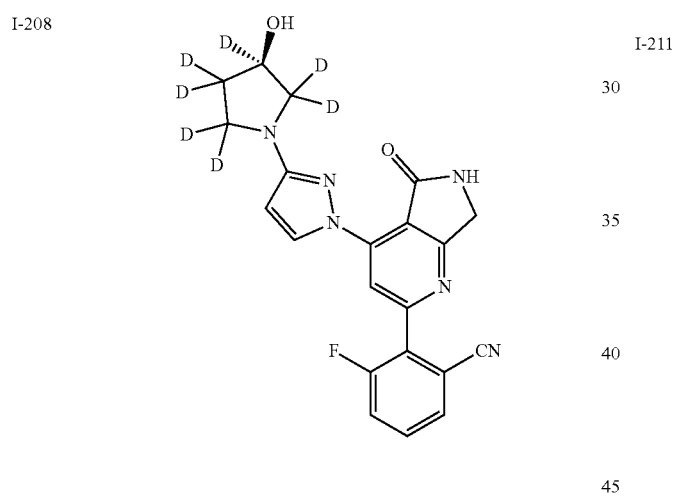
I-211
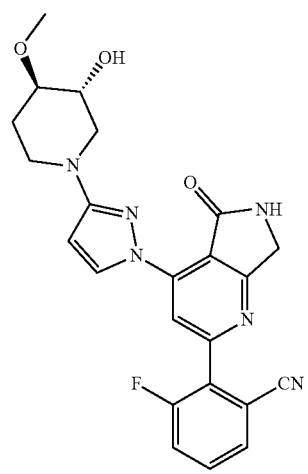 [SMILES: CO[C@@H]1CCN(c2ccn(-c3cc(-c4c(F)cccc4C#N)nc4c3C(=O)NC4)n2)C[C@H]1O]
I-209
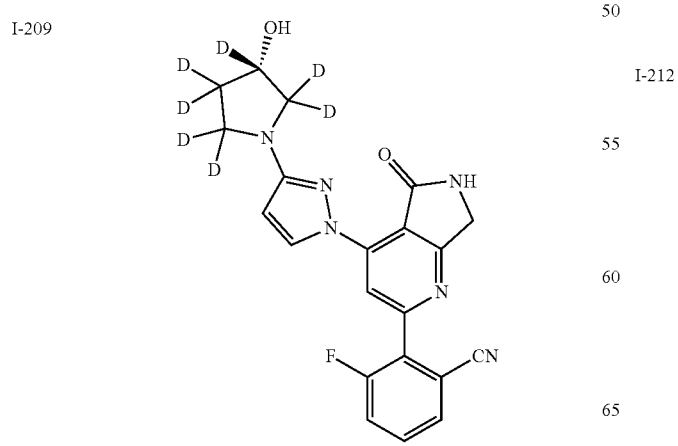
I-212
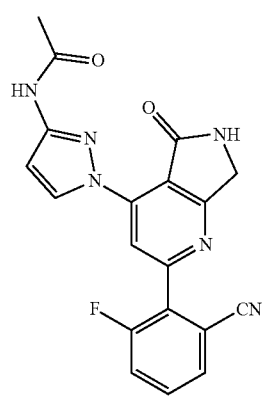 [SMILES: CC(=O)Nc1ccn(-c2cc(-c3c(F)cccc3C#N)nc3c2C(=O)NC3)n1]

TABLE 1-continued
Exemplary Compounds
I-213
I-214
I-215
I-216
I-217
I-218
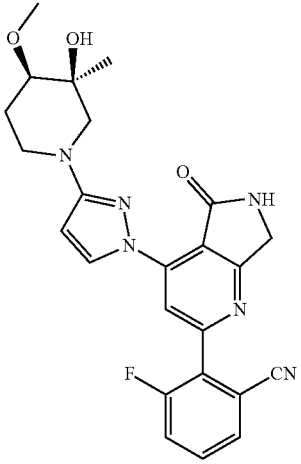 [SMILES: CO[C@@H]1CCN(c2ccn(-c3cc(-c4c(F)cccc4C#N)nc4c3C(=O)NC4)n2)C[C@]1(C)O]

TABLE 1-continued
Exemplary Compounds
I-219 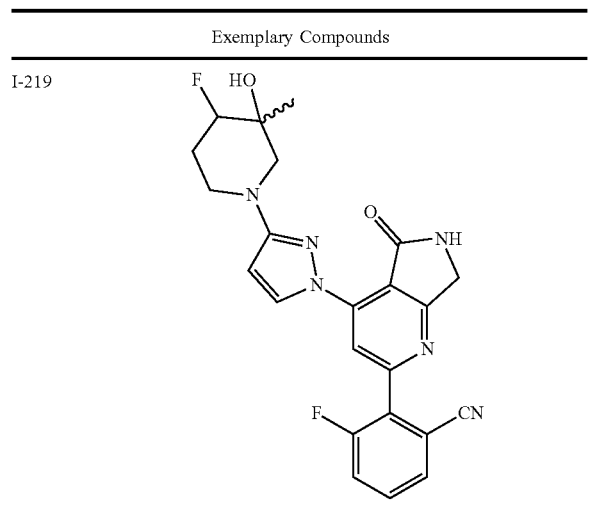
I-220 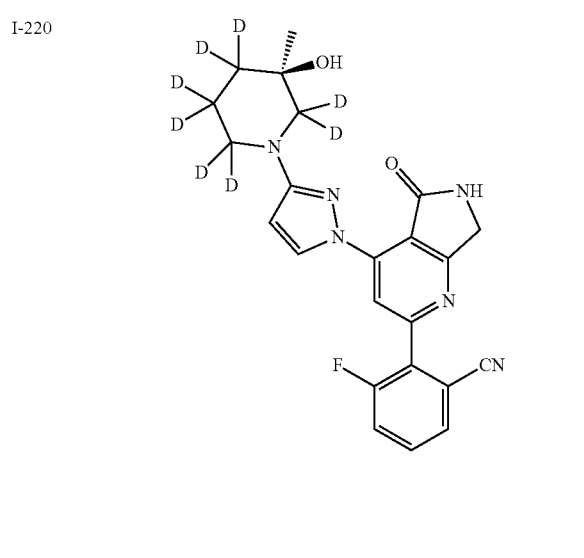
I-221 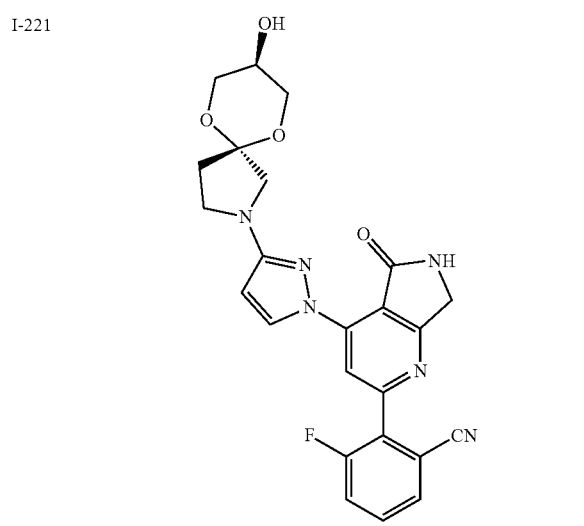
TABLE 1-continued
Exemplary Compounds
I-222 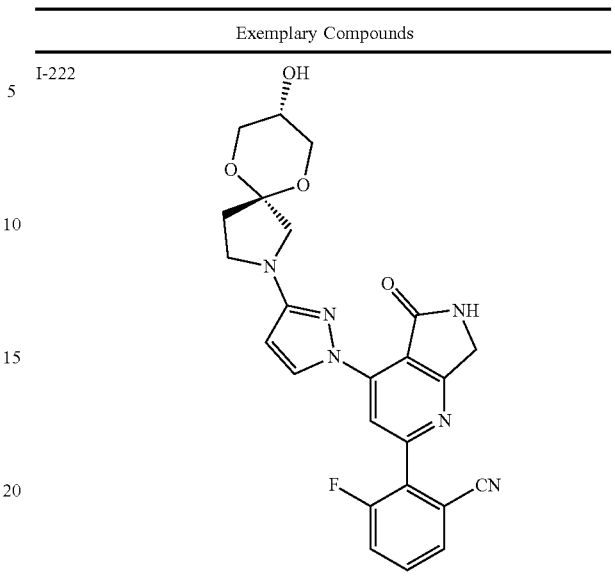
I-223 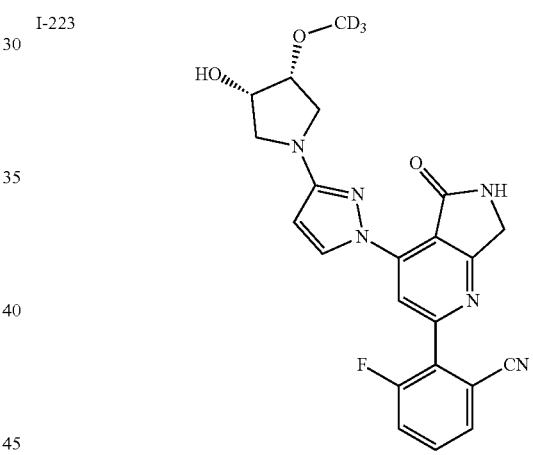
I-224 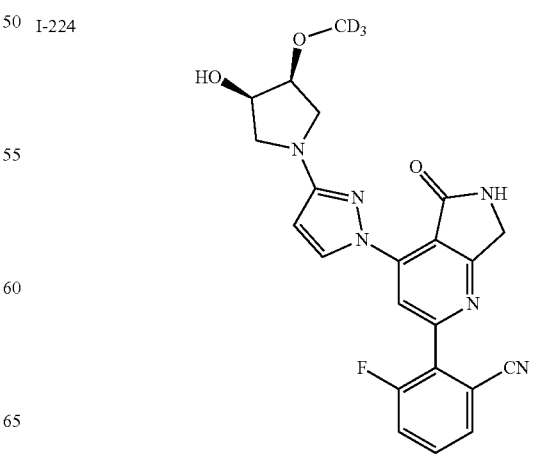

TABLE 1-continued
Exemplary Compounds
I-225 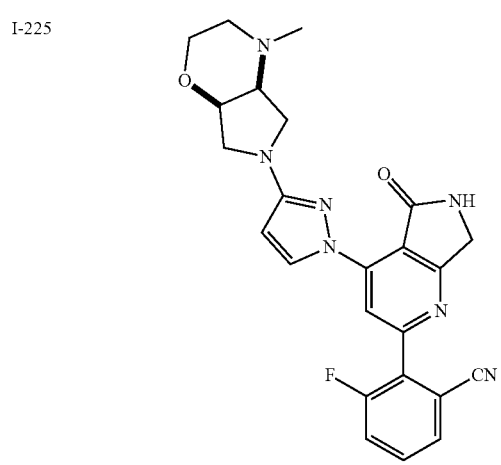
I-226 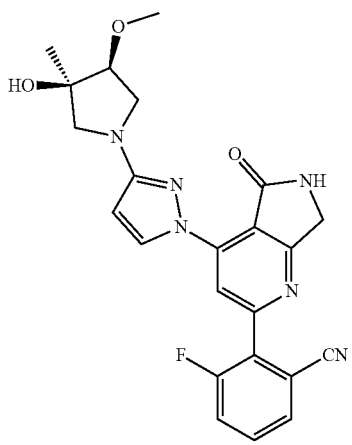 [SMILES: CO[C@H]1CN(c2ccn(-c3cc(-c4c(F)cccc4C#N)nc4c3C(=O)NC4)n2)C[C@@]1(C)O]
I-227 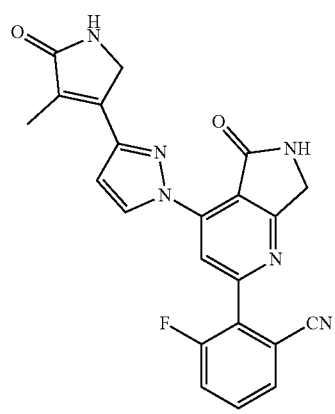 [SMILES: CC1=C(c2ccn(-c3cc(-c4c(F)cccc4C#N)nc4c3C(=O)NC4)n2)CNC1=O]
TABLE 1-continued
Exemplary Compounds
I-228 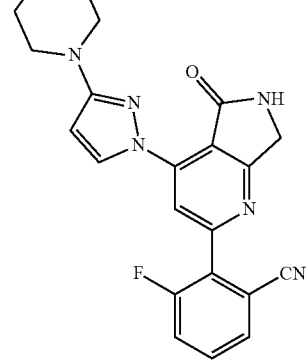
I-229 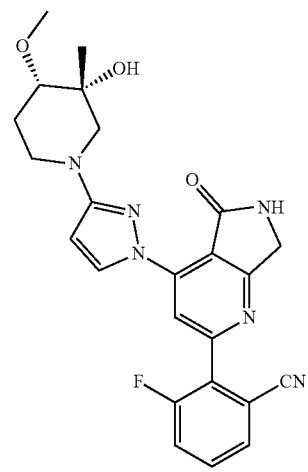 [SMILES: CO[C@H]1CCN(c2ccn(-c3cc(-c4c(F)cccc4C#N)nc4c3C(=O)NC4)n2)C[C@@]1(C)O]
I-230 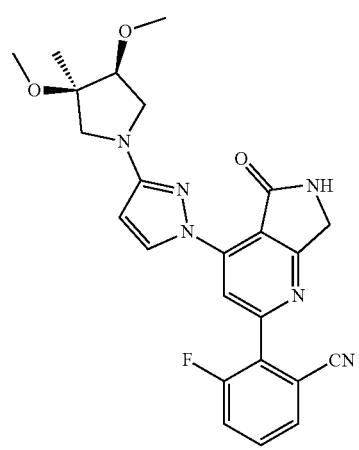 [SMILES: CO[C@H]1CN(c2ccn(-c3cc(-c4c(F)cccc4C#N)nc4c3C(=O)NC4)n2)C[C@@]1(C)OC]

TABLE 1-continued

Exemplary Compounds

I-231

I-232

I-233

I-234

I-235

In some embodiments, the method employs a compound set forth in Table 1, above, or a pharmaceutically acceptable salt thereof.

Without wishing to be bound by any particular theory, it is believed that proximity of an inhibitor compound, or pendant moiety of an inhibitor compound, to the water of interest facilitates displacement or disruption of that water by the inhibitor compound, or pendant moiety of an inhibitor compound. In some embodiments, a water molecule displaced or disrupted by an inhibitor compound, or pendant moiety of an inhibitor compound, is an unstable water molecule.

In certain embodiments, the method employs a complex comprising TYK2 and an inhibitor, wherein at least one unstable water of TYK2 is displaced or disrupted by the inhibitor. In some embodiments, at least two unstable waters selected are displaced or disrupted by the inhibitor.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit a TYK2 protein kinase, or a mutant thereof, in a biological sample or in a patient. In certain embodiments, the amount of compound in compositions of this invention is such that is effective to measurably inhibit a TYK2 protein kinase, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of a TYK2 protein kinase, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of kinase activity of one or more enzymes. In some embodiments the kinase inhibited by the compounds and methods of the invention is TYK2

TYK2 is a non-receptor tyrosine kinase member of the Janus kinase (JAKs) family of protein kinases. The mammalian JAK family consists of four members, TYK2, JAK1, JAK2, and JAK3. JAK proteins, including TYK2, are integral to cytokine signaling. TYK2 associates with the cytoplasmic domain of type I and type II cytokine receptors, as well as interferon types I and III receptors, and is activated by those receptors upon cytokine binding. Cytokines implicated in TYK2 activation include interferons (e.g. IFN-α, IFN-β, IFN-κ, IFN-δ, IFN-ε, IFN-τ, IFN-ω, and IFN-ζ (also known as limitin), and interleukins (e.g. IL-4, IL-6, IL-10, IL-11, IL-12, IL-13, IL-22, IL-23, IL-27, IL-31, oncostatin M, ciliary neurotrophic factor, cardiotrophin 1, cardiotrophin-like cytokine, and LIF). Velasquez et al., "A protein kinase in the interferon α/β signaling pathway," Cell (1992) 70:313; Stahl et al., "Association and activation of Jak-Tyk kinases by CNTF-LIF-OSM-IL-6β receptor components," Science (1994) 263:92; Finbloom et al., "IL-10 induces the tyrosine phosphorylation of Tyk2 and Jak1 and the differential assembly of Stat1 and Stat3 complexes in human T cells and monocytes," J. Immunol. (1995) 155:1079; Bacon et al., "Interleukin 12 (IL-12) induces tyrosine phosphorylation of Jak2 and Tyk2: differential use of Janus family kinases by IL-2 and IL-12," J. Exp. Med. (1995) 181:399; Welham et al., "Interleukin-13 signal transduction in lymphohemopoietic cells: similarities and differences in signal transduction with interleukin-4 and insulin," J. Biol. Chem. (1995) 270:12286; Parham et al., "A receptor for the heterodimeric cytokine IL-23 is composed of IL-12Rβ1 and a novel cytokine receptor subunit, IL-23R," J. Immunol. (2002) 168:5699. The activated TYK2 then goes on to phosphorylate further signaling proteins such as members of the STAT family, including STAT1, STAT2, STAT4, and STAT6.

TYK2 activation by IL-23, has been linked to inflammatory bowel disease (IBD), Crohn's disease, and ulcerative colitis. Duerr et al., "A Genome-Wide Association Study Identifies IL23R as an Inflammatory Bowel Disease Gene," Science (2006) 314:1461-1463. As the downstream effector of IL-23, TYK2 also plays a role in psoriasis, ankylosing spondylitis, and Behçet's disease. Cho et al., "Genomics and the multifactorial nature of human auto-immune disease," N. Engl. J. Med (2011) 365:1612-1623; Remmers et al., "Genome-wide association study identifies variants in the MHC class I, IL10, and IL23R-IL12RB2 regions associated with Behçet's disease," Nat. Genet. (2010) 42:698-702. A genome-wide association study of 2,622 individuals with psoriasis identified associations between disease susceptibility and TYK2. Strange et al., "A genome-wide association study identifies new psoriasis susceptibility loci and an interaction between HLA-C and ERAP1," Nat. Genet. (2010) 42:985-992. Knockout or tyrphostin inhibition of TYK2 significantly reduces both IL-23 and IL-22-induced dermatitis. Ishizaki et al., "Tyk2 is a therapeutic target for psoriasis-like skin inflammation," Intl. Immunol. (2013), doi: 10.1093/intimm/dxt062.

TYK2 also plays a role in respiratory diseases such as asthma, chronic obstructive pulmonary disease (COPD), lung cancer, and cystic fibrosis. Goblet cell hyperplasia (GCH) and mucous hypersecretion is mediated by IL-13-induced activation of TYK2, which in turn activates STAT6. Zhang et al., "Docking protein Gab2 regulates mucin expression and goblet cell hyperplasia through TYK2/STAT6 pathway," FASEB J. (2012) 26:1-11.

Decreased TYK2 activity leads to protection of joints from collagen antibody-induced arthritis, a model of human rheumatoid arthritis. Mechanistically, decreased Tyk2 activity reduced the production of $T_h1/T_h17$-related cytokines and matrix metalloproteases, and other key markers of inflammation. Ishizaki et al., "Tyk2 deficiency protects joints against destruction in anti-type II collagen antibody-induced arthritis in mice," Intl. Immunol. (2011) 23(9):575-582.

TYK2 knockout mice showed complete resistance in experimental autoimmune encephalomyelitis (EAE, an animal model of multiple sclerosis (MS)), with no infiltration of CD4 T cells in the spinal cord, as compared to controls, suggesting that TYK2 is essential to pathogenic CD4-mediated disease development in MS. Oyamada et al., "Tyrosine Kinase 2 Plays Critical Roles in the Pathogenic CD4 T Cell Responses for the Development of Experimental Autoimmune Encephalomyelitis," J. Immunol. (2009) 183:7539-7546. This corroborates earlier studies linking increased TYK2 expression with MS susceptibility. Ban et al., "Replication analysis identifies TYK2 as a multiple sclerosis susceptibility factor," Eur J. Hum. Genet. (2009) 17:1309-1313. Loss of function mutation in TYK2, leads to decreased demyelination and increased remyelination of neurons, further suggesting a role for TYK2 inhibitors in the treatment of MS and other CNS demyelination disorders.

TYK2 is the sole signaling messenger common to both IL-12 and IL-23. TYK2 knockout reduced methylated BSA injection-induced footpad thickness, imiquimod-induced psoriasis-like skin inflammation, and dextran sulfate sodium or 2,4,6-trinitrobenzene sulfonic acid-induced colitis in mice.

Joint linkage and association studies of various type I IFN signaling genes with systemic lupus erythematosus (SLE, an autoimmune disorder), showed a strong, and significant correlation between loss of function mutations to TYK2 and decreased prevalence of SLE in families with affected members. Sigurdsson et al., "Polymorphisms in the Tyrosine Kinase 2 and Interferon Regulatory Factor 5 Genes Are Associated with Systemic Lupis Erythematosus," Am. J. Hum. Genet. (2005) 76:528-537. Genome-wide association studies of individuals with SLE versus an unaffected cohort showed highly significant correlation between the TYK2 locus and SLE. Graham et al., "Association of NCF2, IKZF1, IRF8, IFIH1, and TYK2 with Systemic Lupus Erythematosus," PLoS Genetics (2011) 7(10):e1002341.

TYK2 has been shown to play an important role in maintaining tumor surveillance and TYK2 knockout mice showed compromised cytotoxic T cell response, and accelerated tumor development. However, these effects were linked to the efficient suppression of natural killer (NK) and cytotoxic T lymphocytes, suggesting that TYK2 inhibitors would be highly suitable for the treatment of autoimmune disorders or transplant rejection. Although other JAK family members such as JAK3 have similar roles in the immune system, TYK2 has been suggested as a superior target because of its involvement in fewer and more closely related signaling pathways, leading to fewer off-target effects. Simma et al. "Identification of an Indispensable Role for Tyrosine Kinase 2 in CTL-Mediated Tumor Surveillance," Cancer Res. (2009) 69:203-211.

However, paradoxically to the decreased tumor surveillance observed by Simma et al., studies in T-cell acute lymphoblastic leukemia (T-ALL) indicate that T-ALL is highly dependent on IL-10 via TYK2 via STAT1-mediated signal transduction to maintain cancer cell survival through upregulation of anti-apoptotic protein BCL2. Knockdown of TYK2, but not other JAK family members, reduced cell growth. Specific activating mutations to TYK2 that promote cancer cell survival include those to the FERM domain (G36D, S47N, and R425H), the JH2 domain (V731I), and the kinase domain (E957D and R1027H). However, it was also identified that the kinase function of TYK2 is required for increased cancer cell survival, as TYK2 enzymes featuring kinase-dead mutations (M978Y or M978F) in addition to an activating mutation (E957D) resulted in failure to transform. Sanda et al. "TYK2-STAT1-BCL2 Pathway Dependence in T-Cell Acute Lymphoblastic Leukemia," Cancer Disc. (2013) 3(5):564-577. Whole transcriptome sequencing studies have implicated the potential role of Tyk2 in pathogenesis of cutaneous CD30-positive lymphoproliferative disorders (e.g. lymphomatoid papulosis, anaplastic large cell lymphoma), by genetic mutations leading to Tyk2 fusion proteins with constitutive Tyk2 activity. "A novel recurrent NPM1-TYK2 gene fusion in cutaneous CD30-positive lymphoproliferative disorders," Blood (2014) doi:10.1182/blood-2014-07-588434.

Thus, selective inhibition of TYK2 has been suggested as a suitable target for patients with IL-10 and/or BCL2-addicted tumors, such as 70% of adult T-cell leukemia cases. Fontan et al. "Discovering What Makes STAT Signaling TYK in T-ALL," Cancer Disc. (2013) 3:494-496.

TYK2 mediated STAT3 signaling has also been shown to mediate neuronal cell death caused by amyloid-β (Aβ) peptide. Decreased TYK2 phosphorylation of STAT3 following Aβ administration lead to decreased neuronal cell death, and increased phosphorylation of STAT3 has been observed in postmorterm brains of Alzheimer's patients. Wan et al. "Tyk/STAT3 Signaling Mediates β-Amyloid-Induced Neuronal Cell Death: Implications in Alzheimer's Disease," J. Neurosci. (2010) 30(20):6873-6881.

Accordingly, compounds that inhibit the activity of TYK2 are beneficial, especially those with selectivity over JAK2. Such compounds should deliver a pharmacological response that favorably treats one or more of the conditions described herein without the side-effects associated with the inhibition of JAK2.

Even though TYK2 inhibitors are known in the art, there is a continuing need to provide novel inhibitors having more effective or advantageous pharmaceutically relevant properties. For example, compounds with increased activity, selectivity over other JAK kinases (especially JAK2), and ADMET (absorption, distribution, metabolism, excretion, and/or toxicity) properties. Thus, in some embodiments, the present invention provides inhibitors of TYK2 which show selectivity over JAK2.

The activity of a compound utilized in this invention as an inhibitor of TYK2, or a mutant thereof, may be assayed in vitro, in vivo or in a cell line. In vitro assays include assays that determine inhibition of either the phosphorylation activity and/or the subsequent functional consequences, or ATPase activity of activated TYK2, or a mutant thereof. Alternate in vitro assays quantitate the ability of the inhibitor to bind to TYK2. Inhibitor binding may be measured by radiolabeling the inhibitor prior to binding, isolating the inhibitor/TYK2 complex and determining the amount of radiolabel bound. Alternatively, inhibitor binding may be determined by running a competition experiment where new inhibitors are incubated with TYK2 bound to known radioligands. Representative in vitro and in vivo assays useful in assaying a TYK2 inhibitor include those described and disclosed in, e.g., each of which is herein incorporated by reference in its entirety. Detailed conditions for assaying a compound utilized in this invention as an inhibitor of TYK2, or a mutant thereof, are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of TYK2 and are therefore useful for treating one or more disorders associated with activity of TYK2 or mutants thereof. Thus, in certain embodiments, the present invention provides a method for treating a TYK2-mediated disorder comprising the step of administering to a patient in need thereof a compound of the present invention, or pharmaceutically acceptable composition thereof.

As used herein, the term "TYK2-mediated" disorders, diseases, and/or conditions as used herein means any disease or other deleterious condition in which TYK2 or a mutant thereof is known to play a role. Accordingly, another embodiment of the present invention relates to treating or lessening the severity of one or more diseases in which TYK2, or a mutant thereof, is known to play a role. Such TYK2-mediated disorders include but are not limited to autoimmune disorders, inflammatory disorders, proliferative disorders, endocrine disorders, neurological disorders and disorders associated with transplantation.

In some embodiments, the present invention provides a method for treating one or more disorders, wherein the disorders are selected from autoimmune disorders, inflammatory disorders, proliferative disorders, endocrine disorders, neurological disorders, and disorders associated with transplantation, said method comprising administering to a patient in need thereof, a pharmaceutical composition comprising an effective amount of a compound of the present invention, or a pharmaceutically acceptable salt thereof.

In some embodiments, the disorder is an autoimmune disorder. In some embodiments the autoimmune disorder is type 1 diabetes, systemic lupus erythematosus, multiple sclerosis, psoriasis, Behçet's disease, POEMS syndrome, Crohn's disease, ulcerative colitis, ankylosing spondylitis, axial spondyloarthritis, primary biliary cirrhosis, autoimmune hepatitis, or inflammatory bowel disease.

In some embodiments, the disorder is an inflammatory disorder. In some embodiments, the inflammatory disorder is rheumatoid arthritis, asthma, chronic obstructive pulmonary disease, psoriasis, hepatomegaly, Crohn's disease, ulcerative colitis, ankylosing spondylitis, axial spondyloarthritis, primary biliary cirrhosis, polymyalgia rheumatica, giant cell arteritis, or inflammatory bowel disease.

In some embodiments, the disorder is a proliferative disorder. In some embodiments, the proliferative disorder is a hematological cancer. In some embodiments, the proliferative disorder is a lymphoproliferative disorder. In some embodiments the proliferative disorder is a leukemia. In some embodiments, the leukemia is a T-cell leukemia. In some embodiments the T-cell leukemia is T-cell acute lymphoblastic leukemia (T-ALL). In some embodiments, the lymphoproliferative disorder is lymphomatoid papulosis or anaplastic large cell lymphoma. In some embodiments the proliferative disorder is polycythemia vera, myelofibrosis, essential or thrombocytosis.

In some embodiments, the disorder is an endocrine disorder. In some embodiments, the endocrine disorder is polycystic ovary syndrome, Crouzon's syndrome, or type 1 diabetes.

In some embodiments, the disorder is a neurological disorder. In some embodiments, the neurological disorder is Alzheimer's disease.

In some embodiments the proliferative disorder is associated with one or more activating mutations in TYK2. In some embodiments, the activating mutation in TYK2 is a mutation to the FERM domain, the JH$_2$ domain, or the kinase domain. In some embodiments the activating mutation in TYK2 is selected from G36D, S47N, R425H, V731I, E957D, and R1027H.

In some embodiments, the disorder is associated with transplantation. In some embodiments the disorder associated with transplantation is transplant rejection, or graft versus host disease.

In some embodiments the disorder is associated with type I interferon, IL-10, IL-12, or IL-23 signaling. In some embodiments the disorder is associated with type I interferon signaling. In some embodiments the disorder is associated with IL-10 signaling. In some embodiments the disorder is associated with IL-12 signaling. In some embodiments the disorder is associated with IL-23 signaling. In some embodiments the disorder is a type I interferonopathy. In some embodiments the type I interferonopathy is Aicardi-Goutières syndrome, bilateral striatal necrosis, chronic atypical neutrophilic dermatosis with lipodystrophy and elevated temperature (CANDLE), complete non-penetrance, dyschromatosis symmetrica hereditaria, familial chilblain lupus, Japanese autoinflammatory syndrome with lipodystrophy (JASL), joint contractures, muscle atrophy, microcytic anaemia, panniculitis, and lipodystrophy (JMP), Mendelian susceptibility to mycobacterial disease (MSMD), Nakajo-Nishimura syndrome, retinal vasculopathy with cerebral leukodystrophy (RVCL), spastic paraparesis, STING-associated vasculopathy with onset in infancy (SAVI), Singleton-Merten syndrome, or spondylochondromatosis (SPENCD).

Compounds of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic juvenile idiopathic arthritis (SJIA), Cryopyrin Associated Periodic Syndrome (CAPS), and osteoarthritis.

In some embodiments the inflammatory disease which can be treated according to the methods of this invention is a $T_h1$ or $T_h17$ mediated disease. In some embodiments the $T_h17$ mediated disease is selected from psoriasis, systemic lupus erythematosus, multiple sclerosis, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis.

Furthermore, the invention provides the use of a compound according to the definitions herein, or a pharmaceutically acceptable salt, or a hydrate or solvate thereof for the preparation of a medicament for the treatment of an autoimmune disorder, an inflammatory disorder, or a proliferative disorder, or a disorder commonly occurring in connection with transplantation.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I and one or more additional therapeutic agents. The therapeutic agent may be administered together with a compound of formula I, or may be administered prior to or following administration of a compound of formula I. Suitable therapeutic agents are described in further detail below. In certain embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a compound of formula I and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating rheumatoid arthritis comprising administering to a patient in need thereof a compound of formula I and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating systemic lupus erythematosus comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating Crohn's disease, ulcerative colitis, or inflammatory bowel disease comprising administering to a patient in need thereof a compound of formula I and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound of formula I and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In some embodiments, the present invention provides a method of treating COPD comprising administering to a patient in need thereof a compound of formula I and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In another embodiment, the present invention provides a method of treating a hematological malignancy comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a solid tumor comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a hematological malignancy comprising administering to a patient in need thereof a compound of formula I and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of formula I and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating or lessening the severity of a disease comprising administering to a patient in need thereof a compound of formula I and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of formula I and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleredoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments the present invention provides a method of treating or lessening the severity of a disease comprising administering to a patient in need thereof a compound of formula I and a Bcl-2 inhibitor, wherein the disease is an inflammatory disorder, an autoimmune disorder, a proliferative disorder, an endocrine disorder, a neurological disorder, or a disorder associated with transplantation. In some embodiments, the disorder is a proliferative disorder, lupus, or lupus nephritis. In some embodiments, the proliferative disorder is chronic lymphocytic leukemia, diffuse large B-cell lymphoma, Hodgkin's disease, small-cell lung cancer, non-small-cell lung cancer, myelodysplastic syndrome, lymphoma, a hematological neoplasm, or solid tumor.

The compounds and compositions, according to the method of the present invention, may be administered using any amount and any route of administration effective for treating or lessening the severity of an autoimmune disorder, an inflammatory disorder, a proliferative disorder, an endocrine disorder, a neurological disorder, or a disorder associated with transplantation. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting TYK2, or a mutant thereof, activity in a biological sample comprising the step of contacting said biological sample with a compound of this invention, or a composition comprising said compound. In certain embodiments, the invention relates to a method of irreversibly inhibiting TYK2, or a mutant thereof, activity in a biological sample comprising the step of contacting said biological sample with a compound of this invention, or a composition comprising said compound.

In another embodiment, the invention provides a method of selectively inhibiting TYK2 over one or more of JAK1, JAK2, and JAK3. In some embodiments, a compound of the present invention is more than 2-fold selective over JAK1/2/3. In some embodiments, a compound of the present invention is more than 5-fold selective over JAK1/2/3. In some embodiments, a compound of the present invention is more than 10-fold selective over JAK1/2/3. In some embodiments, a compound of the present invention is more than 50-fold selective over JAK1/2/3. In some embodiments, a compound of the present invention is more than 100-fold selective over JAK1/2/3.

The term "biological sample", as used herein, includes, without limitation, cell cultures or extracts thereof biopsied material obtained from a mammal or extracts thereof; and blood, saliva, urine, feces, semen, tears, or other body fluids or extracts thereof.

Inhibition of TYK2 (or a mutant thereof) activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting activity of TYK2, or a mutant thereof, in a patient comprising the step of administering to said patient a compound of the present invention, or a composition comprising said compound. According to certain embodiments, the invention relates to a method of reversibly or irreversibly inhibiting one or more of TYK2, or a mutant thereof, activity in a patient comprising the step of administering to said patient a compound of the present invention, or a composition comprising said compound. In other embodiments, the present invention provides a method for treating a disorder mediated by TYK2, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other therapeutic compounds. In some embodiments, the other therapeutic compounds are antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j)

compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; ALK inhibitors, which are compounds which target, decrease or inhibit anaplastic lymphoma kinase, and Bcl-2 inhibitors.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412. In some embodiments, the present invention provides a method of treating AML associated with an ITD and/or D835Y mutation, comprising administering a compound of the present invention together with a one or more FLT3 inhibitors. In some embodiments, the FLT3 inhibitors are selected from quizartinib (AC220), a staurosporine derivative (e.g. midostaurin or lestaurtinib), sorafenib, tandutinib, LY-2401401, LS-104, EB-10, famitinib, NOV-110302, NMS-P948, AST-487, G-749, SB-1317, S-209, SC-110219, AKN-028, fedratinib, tozasertib, and sunitinib. In some embodiments, the FLT3 inhibitors are selected from quizartinib, midostaurin, lestaurtinib, sorafenib, and sunitinib.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID(™) CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1

Synthesis of I-1 2-(2,6-difluorophenyl)-4-(3-morpholino-1H-pyrazol-1-yl)-6,7-dihydro-5H-pyrrolo[3,4-b]pyridin-5-one

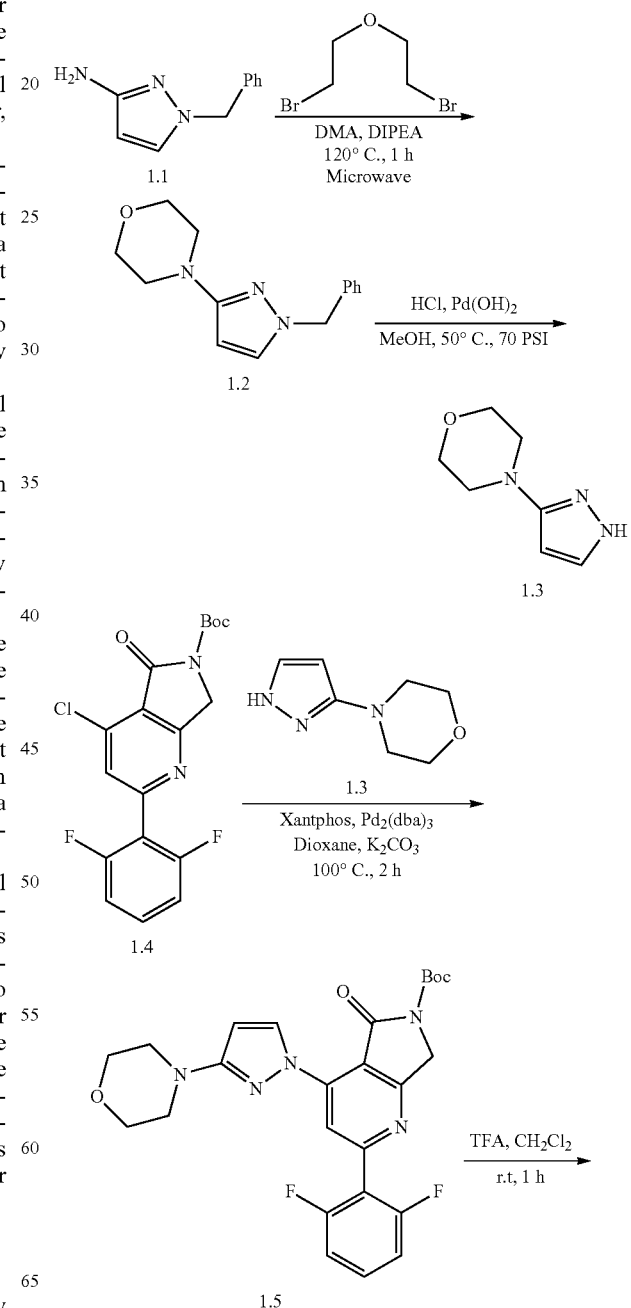

149

-continued

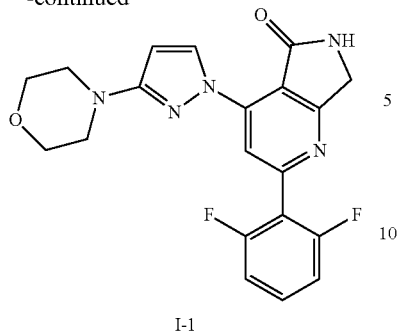

I-1

Synthesis of compound 1.2. A mixture of 1.1 (0.3 g, 1.73 mmol, 1.0 eq), 1-bromo-2-(2-bromoethoxy)ethane (0.441 g, 1.90 mmol, 1.1 eq), DIPEA (0.55 g, 4.32 mmol, 2.5 eq) and dimethyl amine (2.0 mL) was heated in microwave for 1 h. Upon completion of the reaction, mixture was poured into water and product was extracted with EtOAc. Organic layers were combined, washed with brine, dried over sodium sulphate and concentrated under reduced pressure to obtain crude material. The crude was purified by column chromatography to furnish compound 1.2 (0.34 g, 80.7%). MS (ES): m/z 243.31 [M+H]$^+$.

Synthesis of compound 1.3. A mixture of compound 1.2 (0.190 g), Pd(OH)$_2$ (0.190 g), 1N HCl solution (0.2 mL) and methanol (5.0 mL) were stirred in autoclave at 3 kg pressure of H$_2$ and 50° C. for 1 h. Upon completion of the reaction, the mixture was filtered through celite and concentrated to get residue which was taken in ethyl acetate. pH was adjusted to 7.0 by saturated NaHCO$_3$. Organic layer was separated, washed with brine solution, dried over sodium sulphate and concentrated under reduced pressure to obtain crude material. The crude was purified by column chromatography to furnish 1.3 (0., 62.7%). MS(ES): m/z 153.19 [M+H]$^+$.

Synthesis of compound 1.5. To a mixture of 1.4 (0.075 g, 0.196 mmol, 1.0 eq) in 1,4-dioxane (2.5 mL) was added compound 1.3 (0.036 g, 0.236 mmol, 1.2 eq) and K$_2$CO$_3$ (0.081 g, 0.588 mmol, 3.0 eq). The reaction mixture was degassed for 10 min. under argon atmosphere, then Pd$_2$(dba)$_3$ (0.017 g, 0.019 mmol, 0.1 eq) and Xantphos (0.022 g, 0.038 mmol, 0.2 eq) were added, again degassed for 5 min. The reaction was stirred at 100° C. for 2 h. Upon completion of the reaction, mixture was poured into water and product was extracted with EtOAc. Organic layers were combined, washed with brine solution, dried over sodium sulphate and concentrated under reduced pressure to obtain crude material. This crude was purified by column chromatography to furnish pure 1.5 (0.070 g, 71.4%). MS(ES): m/z 497.50 [M+H]$^+$.

Synthesis of compound I-1. Compound 1.5 (0.070 g, 0.140 mmol, 1.0 eq) was dissolved in CH$_2$Cl$_2$ (2 mL) and trifluoroacetic acid (0.5 mL) was added. The reaction was stirred at room temperature for 1 h. Upon completion of the reaction, mixture was poured into water, basified with saturated bicarbonate solution and extracted with EtOAc. Organic layers were combined, washed with brine solution, dried over Na$_2$SO$_4$ and concentrated under reduced pressure to obtain crude material. Crude was purified by column chromatography to furnish I-1 (0.040 g, 71.5%). MS(ES): m/z 397.39 [M+H]$^+$, $^1$H NMR (DMSO-d$_6$, 400 MHz): 9.76 (s, 1H), 9.09 (m, 1H), 8.05 (s, 1H), 7.63-7.59 (m, 1H), 7.31-7.27 (t, 2H), 6.36 (s, 1H), 4.49 (s, 2H), 3.71-3.69 (t, 4H), 3.27-3.24 (t, 4H).

150

Example 2

Synthesis of 2-(1-(2-(2,6-difluorophenyl)-5-oxo-6,7-dihydro-5H-pyrrolo[3,4-b]pyridin-4-yl)-1H-pyrazol-3-yl)-N-ethylacetamide, I-2

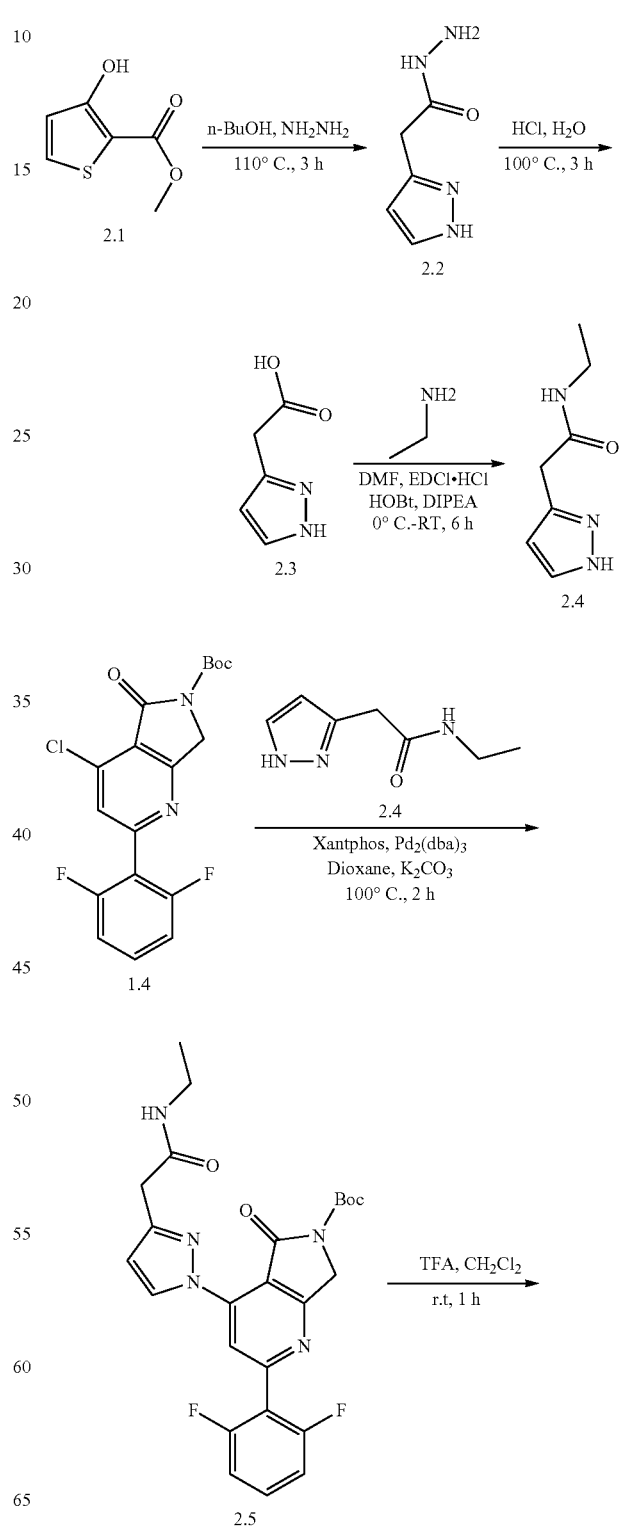

-continued

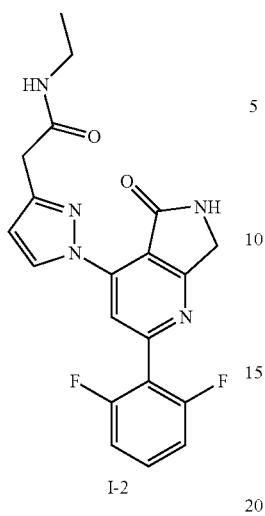

I-2

Synthesis of compound 2.2. To a solution of 2.1 (1.0 g, 6.3 mmol, 1.0 eq) in n-Butanol (15 mL) was added hydrazine hydrate (1.58 g, 31.6 mmol, 5.0 eq) and the reaction mixture was heated at 110° C. for 3 h. Upon completion of the reaction, excess solvent was concentrated under reduced pressure to get crude which was purified by trituration to provide 2.2 (0.70 g, 79.0%). MS(ES): m/z 140.15 [M+H]$^+$.

Synthesis of compound 2.3. To a solution of compound 2.2 (0.7 g, 4.99 mmol, 1.0 eq) was added concentrated HCl (20 mL) and the reaction was heated at 100° C. for 3 h. Upon completion of the reaction, insoluble particles were filtered off and the filtrate was distilled under reduced pressure to get crude material which was purified by preparative HPLC to furnish 2.3 (0.40 g, 63.5%). MS(ES): m/z 126.12 [M+H]$^+$.

Synthesis of compound 2.4. To a solution of compound 2.3 (0.250 g, 1.984 mmol, 1.0 eq) and ethyl amine (0.178 g, 3.96 mmol, 2.0 eq) in dry $CH_2Cl_2$ (4 mL) at 0° C., were added EDCI-HCl (0.571 g, 2.97 mmol, 1.5 eq) and HOBt (0.151 g, 0.99 mmol, 0.5 eq) and DIPEA (17 mL, 9.92 mmol, 5.0 eq). The reaction was stirred at room temperature for 6 h. Upon completion of the reaction, mixture was poured into water and extracted with EtOAc. Aqueous layer separated was concentrated under reduced pressure to obtain crude material which was purified by preparative HPLC to furnish 2.4 (0.1 g, 32.9%). MS(ES): m/z 153.19 [M+H]$^+$.

Synthesis of compound 2.5. To a mixture of 1.4 (0.082 g, 0.215 mmol, 1.0 eq) in 1,4-dioxane (3 ml) was added 2.4 (0.033 g, 0.215 mmol, 1.0 eq) and $K_2CO_3$ (0.074 g, 0.539 mmol, 2.5 eq). The reaction mixture was degassed for 10 min. under argon atmosphere, then $Pd_2(dba)_3$ (0.020 g, 0.021 mmol, 0.1 eq) and Xantphos (0.025 g, 0.043 mmol, 0.2 eq) were added, again degassed for 5 min. The reaction was then heated at 100° C. for 2 h. Upon completion of the reaction, mixture was poured into water and product was extracted with EtOAc. Organic layers were combined, washed with brine, dried over $Na_2SO_4$ and concentrated under reduced pressure to obtain crude material. Crude was purified by column chromatography to furnish 2.5 (0.035 g, 32.67%). MS(ES): m/z 497.50 [M+H]$^+$.

Synthesis of compound I-2. Compound 2.5 (0.035 g, 0.070 mmol, 1.0 eq) was dissolved in $CH_2Cl_2$ (2 mL) and trifluoroacetic acid (0.5 mL) was added to the reaction mixture. The reaction was stirred at room temperature for 1 hour. Upon completion of the reaction, mixture was poured in water, basified with saturated $Na_2CO_3$ solution and product was extracted with EtOAc. Organic layers were combined, dried over sodium sulphate and concentrated under reduced pressure to obtain crude material. The crude was purified by trituration to furnish I-2 (0.021 g, 75.1%).

MS(ES): m/z 397.39 [M+H]$^+$; $^1$H NMR (DMSO-$d_6$, 400 MHz): 9.62-9.61 (d, 1H), 9.18 (s, 1H), 8.12-8.10 (m, 2H), 7.65-7.61 (m, 1H), 7.32-7.28 (t, 2H), 6.53 (d, 1H), 4.54 (s, 2H), 3.51 (s, 2H), 3.12-3.05 (m, 2H), 1.03-1.00 (t, 3H).

Example 3

Synthesis of 1-(2-(2,6-difluorophenyl)-5-oxo-6,7-dihydro-5H-pyrrolo[3,4-b]pyridin-4-yl)-N-ethyl-1H-pyrazole-3-carboxamide, I-3

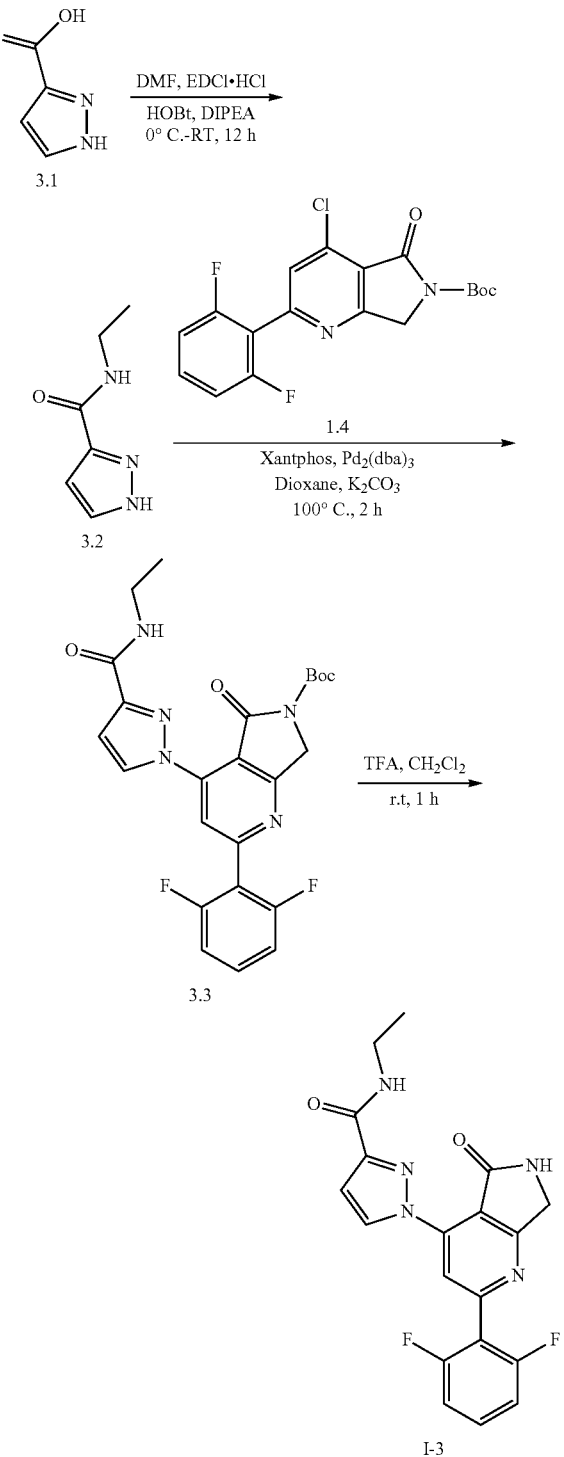

Synthesis of compound 3.2. To a solution of compound 1 (0.5 g, 4.46 mmol, 1.0 eq) and ethyl amine (3.5 mL, 6.69 mmol, 1.5 eq) in dry DMF (5 mL) at 0° C., EDCI (1.28 g, 6.69 mmol, 1.5 eq) and HOBt (0.341 g, 2.23 mmol, 0.5 eq) were added and stirred for 15 min. then DIPEA (2.3 mL, 13.4 mmol, 3.0 eq) was added. The reaction mixture was stirred at room temperature for 12 hours. Upon completion of the reaction, mixture was poured into water and product was extracted with EtOAC. Organic layers were combined, washed with brine solution, dried over sodium sulphate and concentrated under reduced pressure to obtain crude material. Crude was purified by column chromatography to furnish 3.2 (0.3 g, 48.3%). MS (ES): m/z 139.16 [M+H]+.

Synthesis of compound 3.3. To a mixture of 1.4 (0.1 g, 0.262 mmol, 1.0 eq) in 1,4-dioxane (3 mL) was added compound 3.2 (0.036 g, 0.262 mmol, 1.0 eq) and $K_2CO_3$ (0.090 g, 0.656 mmol, 2.5 eq). The reaction mixture was degassed for 10 min. under argon atmosphere, then $Pd_2(dba)_3$ (0.030 g, 0.026 mmol, 0.1 eq) and Xantphos (0.030 g, 0.051 mmol, 0.2 eq) were added and again degassed for 5 min. The reaction was stirred at 100° C. for 2 hours. Upon completion of the reaction, mixture was poured into water and extracted with EtOAc. Organic layers were combined, washed with brine, dried over $Na_2SO_4$ and concentrated under reduced pressure to obtain crude material. Crude was purified by column chromatography to furnish 3.3 (0.075 g, 59.1%). MS(ES): m/z 483.48 [M+H]+.

Synthesis of compound I-3. Compound 3.3 (0.075 g, 0.155 mmol, 1.0 eq) was dissolved in $CH_2Cl_2$ (2 mL) and trifluoroacetic acid (0.5 mL) was added to the reaction mixture. The reaction was stirred at room temperature for 1 hour. Upon completion of the reaction, mixture was poured in water, basified with saturated bicarbonate solution and extracted with EtOAc. Organic layers were combined, dried over $Na_2SO_4$ and concentrated under reduced pressure to obtain crude which was purified by column chromatography to furnish pure I-3 (0.035 g, 58.9%). MS (ES): m/z 383.36 [M+H]+; 1H NMR (DMSO-$d_6$, 400 MHz): 9.74 (d, 1H), 9.28 (s, 1H), 8.60-8.57 (m, 1H), 8.38 (s, 1H), 7.67-7.61 (m, 1H), 7.37-7.32 (dd, 2H), 6.95-6.94 (d, 1H), 4.57 (s, 2H), 3.34-3.25 (m, 2H), 1.13-1.09 (t, 3H).

Example 4

Synthesis of 3-fluoro-2-(4-(3-morpholino-1H-pyrazol-1-yl)-5-oxo-6,7-dihydro-5H-pyrrolo[3,4-b]pyridin-2-yl)benzonitrile, I-4

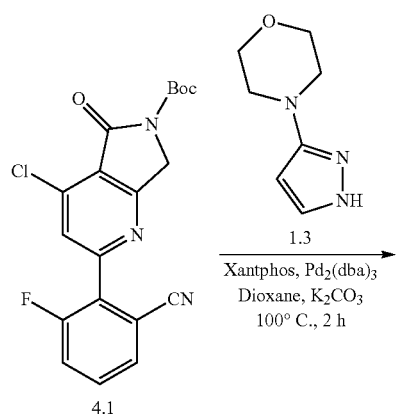

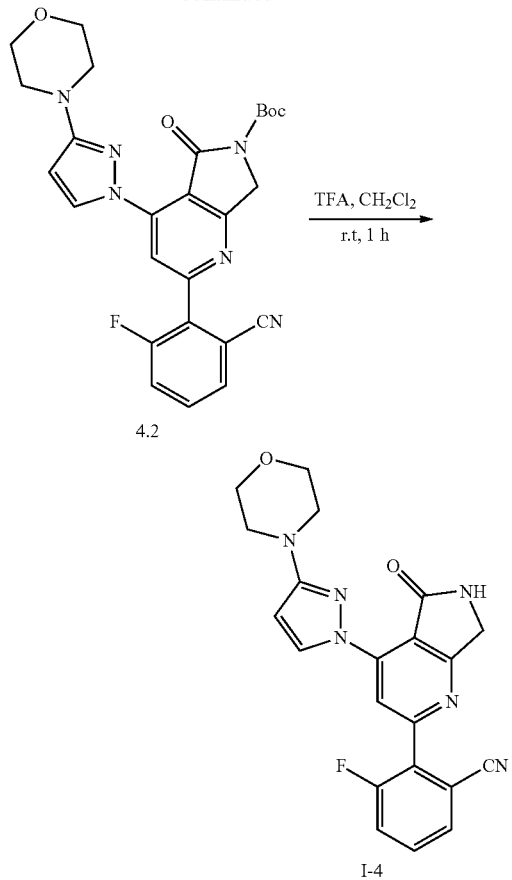

Synthesis of compound 4.2. To a mixture of 4.1 (0.073 g, 0.185 mmol, 1.0 eq) in 1,4-dioxane (3 ml) was added 1.3 (0.034 g, 0.222 mmol, 1.0 eq) and $K_2CO_3$ (0.077 g, 0.555 mmol, 3.0 eq). The reaction was degassed for 10 minutes using argon, then $Pd_2(dba)_3$ (0.018 g, 0.018 mmol, 0.1 eq) and Xantphos (0.026 g, 0.044 mmol, 0.2 eq) were added, again degassed for 5 minutes. The reaction was stirred at 110° C. for 0.5 h. Upon completion of the reaction, mixture was poured into water and product was extracted with EtOAc. Organic layers were combined, washed with brine solution, dried over $Na_2SO_4$ and concentrated under reduced pressure to obtain crude material. This crude was purified by column chromatography to get pure 4.2 (0.080 g, 84.2%). MS(ES): m/z 505.27 [M+H]+.

Synthesis of compound I-4. Compound 4.2 (0.080 g, 0.158 mmol, 1.0 eq) was dissolved in $CH_2Cl_2$ (2 mL) and trifluoroacetic acid (0.5 mL) was added to the reaction mixture. The reaction was stirred at room temperature for 1 h. Upon completion of reaction, mixture was poured into water, basified with saturated bicarbonate solution and extracted with EtOAc. Organic layers were combined, dried over $Na_2SO_4$ and concentrated under reduced pressure to obtain crude which was purified by column chromatography to furnish I-4 (0.038 g, 59.3%). MS(ES): m/z 405.43 [M+H]+; 1H NMR (DMSO-$d_6$, 400 MHz): 9.78-9.77 (d, 1H), 9.15 (s, 1H), 8.19 (s, 1H), 7.92-7.90 (d, 1H), 7.83-7.75 (m, 2H), 6.38 (d, 1H), 4.50 (s, 2H), 3.71-3.69 (t, 4H), 3.27-3.25 (t, 4H).

Example 5

Synthesis of 2-(2,6-difluorophenyl)-4-(3-(4-methyl-piperazin-1-yl)-1H-pyrazol-1-yl)-6,7-dihydro-5H-pyrrolo[3,4-b]pyridin-5-one, I-5

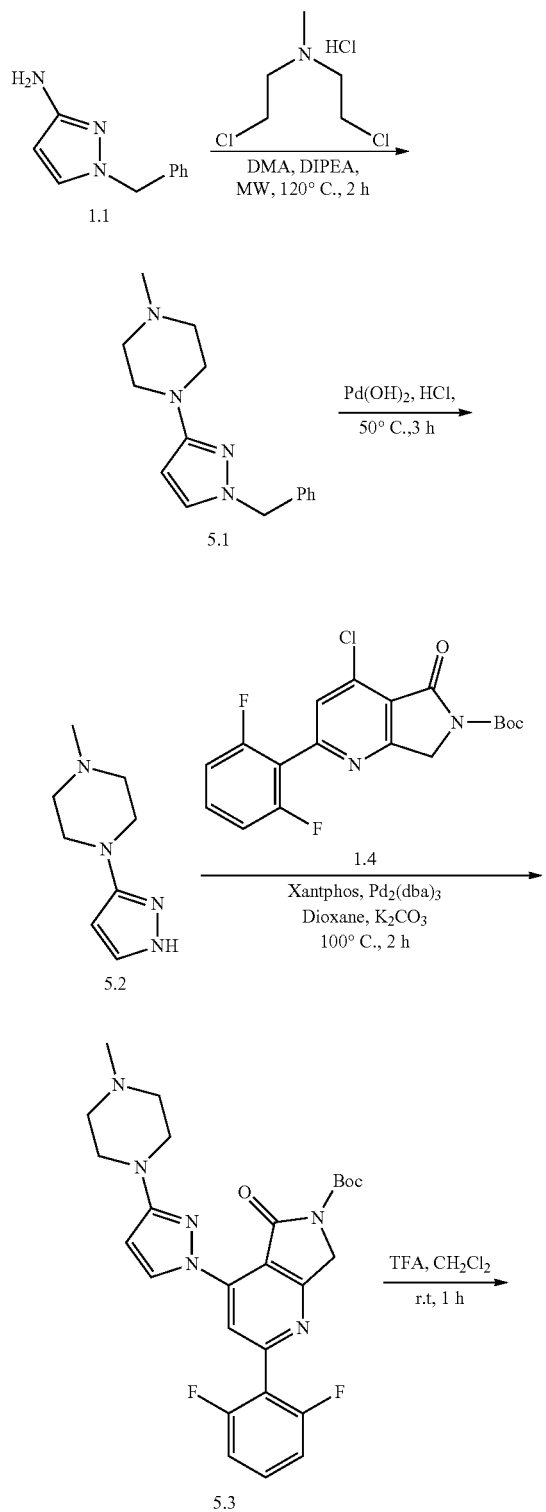

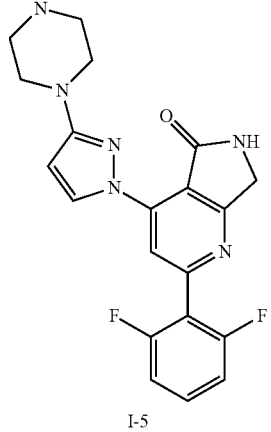

I-5

Synthesis of compound 5.1. To a solution of compound 1.1 (0.1 g, 0.578 mmol, 1.0 eq) in dimethylacetamide (5 mL) were added 2-chloro-N-(2-chloroethyl)-N-methylethan-1-amine (0.132 g, 0.693 mmol, 1.2 eq) and DIPEA (0.5 mL, 2.77 mmol, 4.0 eq). The reaction was heated under microwave irradiation at 120° C. for 2 h. Upon completion of the reaction, mixture was quenched with water and the product was extracted with EtOAc. Organic layers were combined, washed with brine, dried over $Na_2SO_4$ and concentrated under reduced pressure to get crude material. This crude was purified by column chromatography to provide 5.1 (0.061 g, 41.22%). MS(ES): m/z 256.35 [M+H]$^+$.

Synthesis of compound 5.2. To a suspension of Pd(OH)$_2$ (0.061 g) in MeOH (3 mL) was added compound 5.1 (0.061 g, 0.238 mmol, 1.0 eq) and 1N HCl solution (0.1 mL) under nitrogen. The reaction was heated at 50° C. for 3 hours. Upon completion of the reaction, mixture was filtered through celite, washed with methanol and obtained filtrate was concentrated under reduced pressure to get crude material. Crude was neutralized with tetra alkyl ammonium carbonate and filtered through Millipore and concentrated under reduced pressure to get pure 5.2 (0.027 g, 68.26%). MS(ES): m/z 166.23 [M+H]$^+$.

Synthesis of compound 5.3. To a mixture of 1.4 (0.068 g, 0.178 mmol, 1.0 eq) in 1,4-dioxane (2.5 mL) was added 5.2 (0.030 g, 0.178 mmol, 1.0 eq) and $K_2CO_3$ (0.061 g, 0.447 mmol, 2.0 eq). The reaction mixture was degassed for 10 minutes under argon, then Pd$_2$(dba)$_3$ (0.016 g, 0.017 mmol, 0.1 eq) and Xantphos (0.021 g, 0.035 mmol, 0.2 eq) were added, and again degassed for 5 min. The reaction was stirred at 100° C. for 2 hours. Upon completion of the reaction, mixture was poured into water and product was extracted with EtOAc. Organic layers were combined, washed with brine solution, dried over $Na_2SO_4$ and concentrated under reduced pressure to obtain crude material. This crude was purified by column chromatography to furnish 5.3 (0.04 g, 43.9%). MS(ES): m/z 510.55 [M+H]$^+$.

Synthesis of compound I-5. Compound 5.3 (0.040 g, 0.078 mmol, 1.0 eq) was dissolved in $CH_2Cl_2$ (2 mL) and trifluoroacetic acid (0.5 mL) was added to the reaction mixture. The reaction was stirred at room temperature for 1 hour. Upon completion of the reaction, mixture was poured into water, basified with saturated $NaHCO_3$ solution and product was extracted with EtOAc. Organic layers were combined, dried over $Na_2SO_4$ and concentrated under reduced pressure to obtain crude material. Obtained crude was purified by column chromatography to get pure I-5 (0.02 g, 62.2%). MS(ES): m/z 410.43 [M+H]$^+$; $^1$H NMR (DMSO-d$_6$, 400 MHz): 9.76-9.75 (d, 1H), 9.01 (s, 1H), 8.04 (s, 1H), 7.63-7.59 (m, 1H), 7.31-7.27 (t, 2H), 6.35-6.34 (d, 1H), 4.48 (s, 2H), 3.28-3.26 (t, 4H), 2.40 (t, 4H), 2.21 (s, 3H).

Example 6

Synthesis of 3-fluoro-2-(4-(3-(4-methylpiperazin-1-yl)-1H-pyrazol-1-yl)-5-oxo-6,7-dihydro-5H-pyrrolo[3,4-b]pyridin-2-yl)benzonitrile, I-6

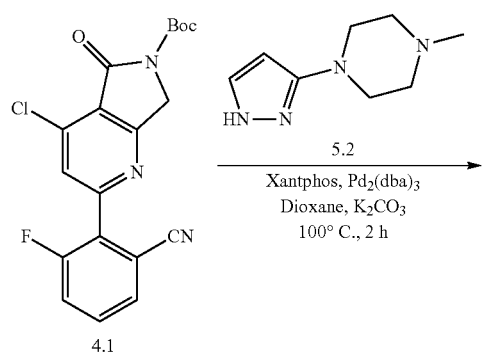

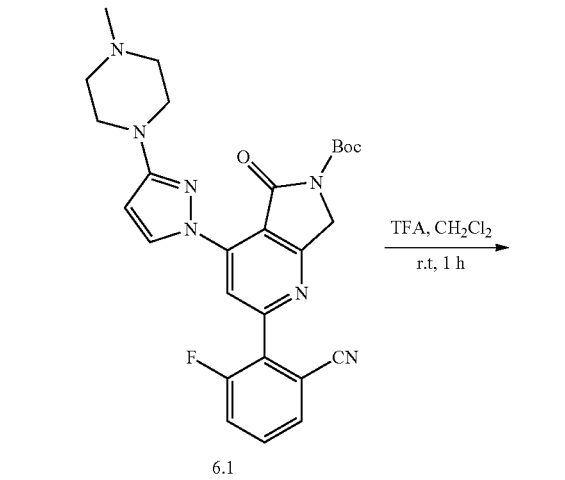

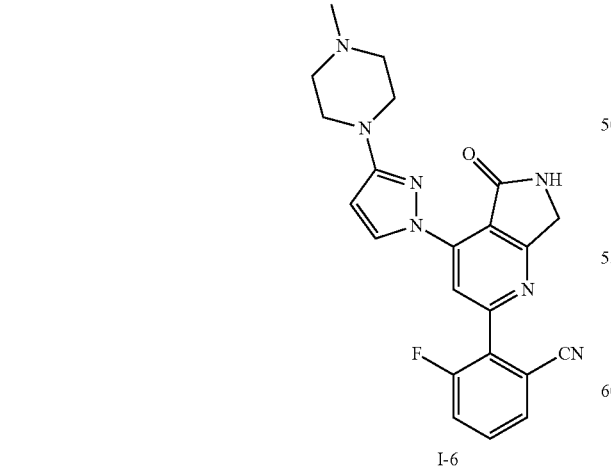

Synthesis of compound 6.1. To a mixture of 4.1 (0.070 g, 0.180 mmol, 1.0 eq) in 1,4-dioxane (3.0 mL) was added 5.2 (0.030 g, 0.180 mmol, 1.0 eq) and K$_2$CO$_3$ (0.062 g, 0.452 mmol, 2.5 eq). The reaction mixture was degassed for 10 minutes using argon, then Pd$_2$(dba)$_3$ (0.017 g, 0.018 mmol, 0.1 eq) and Xantphos (0.020 g, 0.036 mmol, 0.2 eq) were added and again degassed for 5 min. The reaction was stirred at 100° C. for 2 h. Upon completion of the reaction, mixture was poured into water and product was extracted with EtOAc. Organic layers were combined, washed with brine, dried over Na$_2$SO$_4$ and concentrated under reduced pressure to obtain crude material. Crude was purified by column chromatography to furnish 6.1 (0.065 g, 69.6%). MS(ES): m/z 517.57 [M+H]$^+$.

Synthesis of compound I-6. Compound 6.1 (0.065 g, 0.125 mmol, 1.0 eq) was dissolved in CH$_2$Cl$_2$ (2 mL) and trifluoroacetic acid (0.5 mL) was added to the reaction mixture. The reaction was stirred at room temperature for 1 h. Upon completion of the reaction, mixture was poured into water, basified with satd. NaHCO$_3$ solution and extracted with EtOAc. Organic layers were combined, dried over Na$_2$SO$_4$ and concentrated under reduced pressure to obtain crude which was purified by column chromatography to furnish I-6 (0.025 g, 47.7%). MS(ES): m/z 417.45 [M+H]$^+$; $^1$H NMR (DMSO-d$_6$, 400 MHz): 9.77 (d, 1H), 9.13 (s, 1H), 8.18 (d, 1H), 7.92-7.73 (m, 3H), 6.37-6.36 (s, 1H), 4.50 (s, 2H), 3.29 (t, 4H), 2.42 (t, 4H), 2.22 (s, 3H).

Example 7

Synthesis of 2-(1-(2-(2-cyano-6-fluorophenyl)-5-oxo-6,7-dihydro-5H-pyrro-lo[3,4-b]pyridin-4-yl)-1H-pyrazol-3-yl)-N-ethylacetamide, I-7

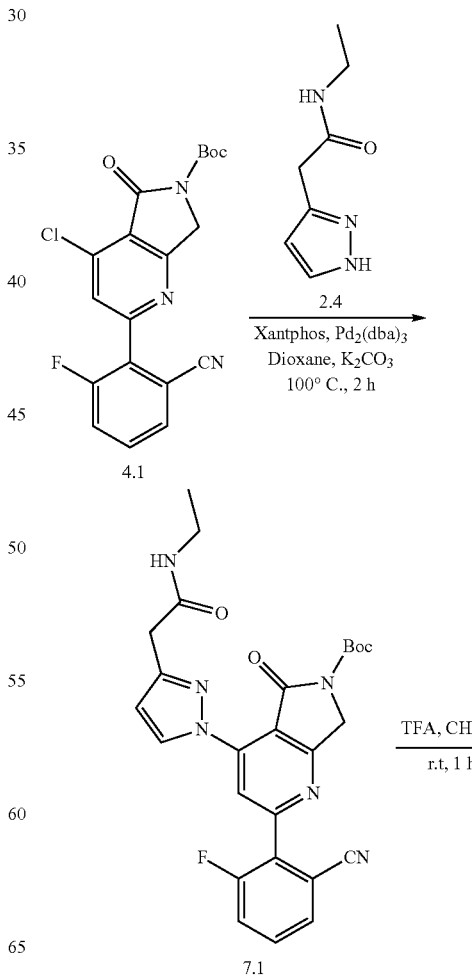

-continued

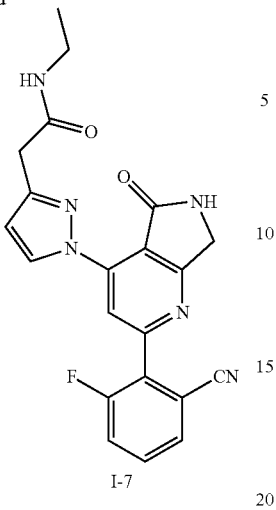

I-7

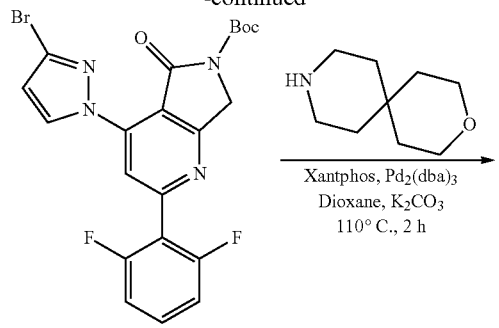

9.2

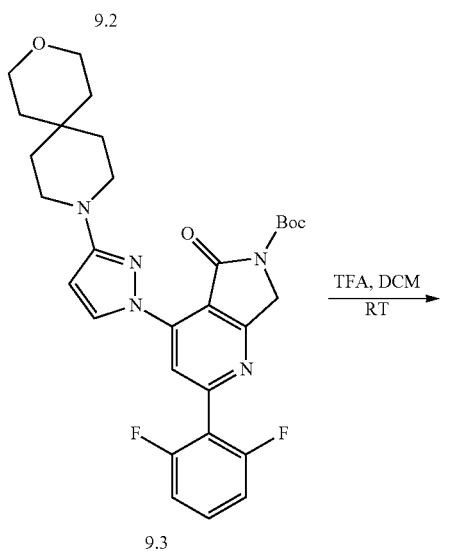

9.3

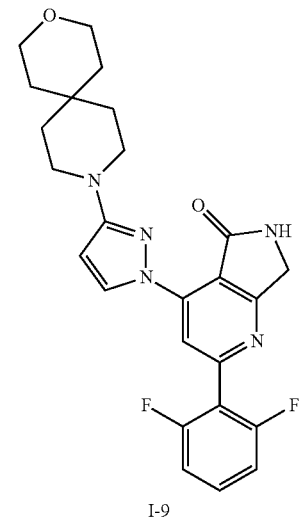

I-9

Synthesis of compound 7.1. To a mixture of 4.1 (0.1 g, 0.25 mmol, 1.0 eq) in 1,4-dioxane (3.0 mL) was added 2.4 (0.039 g, 0.25 mmol, 1.0 eq) and K$_2$CO$_3$ (0.086 g, 0.625 mmol, 2.5 eq). The reaction mixture was degassed for 10 minutes using argon, then Pd$_2$(dba)$_3$ (0.022 g, 0.025 mmol, 0.1 eq) and Xantphos (0.028 g, 0.05 mmol, 0.2 eq) were added and again degassed for 5 min. The reaction was stirred at 100° C. for 2 h. Upon completion of the reaction, mixture was poured into water and product was extracted with EtOAC. Organic layers were combined, washed with brine, dried over sodium sulphate and concentrated under reduced pressure to obtain crude material. The crude was purified by column chromatography to furnish 7.1 (0.06 g, 46.1%). MS(ES): m/z 504.52 [M+H]$^+$.

Synthesis of compound I-7. The compound 1.1 (0.060 g, 0.098 mmol, 1.0 eq) was dissolved in CH$_2$Cl$_2$ (2 mL) and trifluoroacetic acid (0.5 mL) was added to the reaction mixture. The reaction was stirred at room temperature for 1 hour. Upon completion of the reaction, reaction mixture was poured in water, basified with satd. NaHCO$_3$ solution and product was extracted with EtOAc. Organic layers were combined, dried over Na$_2$SO$_4$ and concentrated under reduced pressure to obtain crude material. Crude was purified by column chromatography to get pure I-7 (0.052 g, 86.7%). MS(ES): m/z 404.41 [M+H]$^+$; $^1$H NMR (DMSO-d$_6$, 400 MHz): 9.63-9.62 (d, 1H), 9.24 (s, 1H), 8.27-8.26 (d, 1H), 8.11 (m, 1H), 7.94-7.92 (dd, 1H), 7.84-7.77 (m, 2H), 6.55-6.54 (d, 1H), 4.55 (s, 2H), 3.52 (s, 2H), 3.12-3.05 (q, 2H), 1.04-1.00 (t, 3H).

Example 9

Synthesis of 4-(3-(3-oxa-9-azaspiro[5.5]undecan-9-yl)-1H-pyrazol-1-yl)-2-(2,6-difluorophenyl)-6,7-dihydro-5H-pyrrolo[3,4-b]pyridin-5-one, I-9

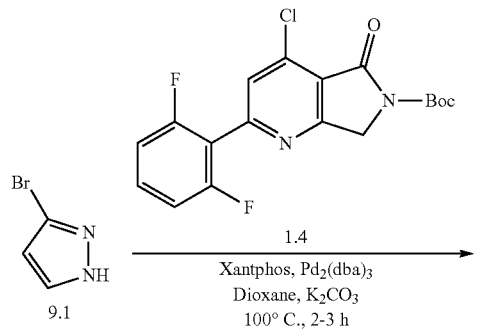

Synthesis of compound 9.2. To a mixture of 1.4 (0.4 g, 1.05 mmol, 1.0 eq) in 1,4-dioxane (5.0 ml) was added 3-Bromo-1H-pyrazole (0.169 g, 1.15 mmol, 1.1 eq) and K$_2$CO$_3$ (0.29 g, 2.10 mmol, 2.5 eq). The reaction mixture was degassed for 10 min. under argon atmosphere, then Pd$_2$(dba)$_3$ (0.096 g, 0.01 mmol, 0.1 eq) and Xantphos (0.121 g, 0.2 mmol, 0.2 eq) were added, and again degassed for 5 min. The reaction was then heated at 100° C. for 2 h. Upon completion of the reaction, reaction mixture was poured into water and product was extracted with EtOAc. Organic layers were combined, washed with brine solution, dried over Na$_2$SO$_4$ and concentrated under reduced pressure to obtain crude which was purified by column chromatography to provide 9.2 (0.11 g, 21.4%). MS(ES): m/z 491 [M+H]$^+$.

Synthesis of compound 9.3. To a mixture of 9.2 (0.05 g, 0.10 mmol, 1.0 eq) in 1,4-dioxane (2.0 ml) was added 3-oxa-9-azaspiro[5.5]undecane (0.02 g, 0.12 mmol, 1.2 eq) K₂CO₃ (0.03 g, 0.20 mmol, 2.5 eq). The reaction mixture was degassed for 10 min. under argon atmosphere, then Pd₂(dba)₃ (0.010 g, 0.01 mmol, 0.1 eq) and Xantphos (0.011 g, 0.02 mmol, 0.2 eq) were added, and again degassed for 5 min. The reaction was then heated at 110° C. for 2 hours. Upon completion of the reaction, reaction mixture was transferred into water and product was extracted with EtOAc. Organic layers were combined, washed with brine, dried over Na₂SO₄ and concentrated under reduced pressure to obtain crude which was purified by column chromatography to furnish 9.2 (0.011 g, 19.29%). MS(ES): m/z 566 [M+H]⁺.

Synthesis of compound I-9. Compound 9.2. (0.011 g, 0.019 mmol, 1.0 eq) was dissolved in DCM (2.0 mL) and TFA (0.1 mL) was added to the reaction mixture. Reaction was stirred at room temperature for 1 hour. Upon completion of the reaction, mixture was poured into water, basified with satd. NaHCO₃ and extracted with EtOAc. Organic layers were combined and dried over Na₂SO₄ and concentrated under reduced pressure to obtain crude which was purified by column chromatography to furnish I-9 (0.005 g, 55.6%). MS(ES): m/z 466 [M+H]⁺; ¹H NMR (DMSO-d₆, 400 MHz): 9.70-9.69 (d, 1H), 8.24 (s, 1H), 7.45-7.41 (m, 1H), 7.08-7.04 (m, 2H), 6.09-6.08 (d, 1H), 6.46 (s, 1H), 4.61 (s, 2H), 3.72-3.69 (m, 4H), 3.38-3.35 (m, 4H), 1.82-1.66 (m, 4H), 1.58-1.56 (m, 4H).

Example 16

Synthesis of 3-fluoro-2-(5-oxo-4-(3-(tetrahydro-2H-pyran-4-yl)-1H-pyrazol-1-yl)-6,7-dihydro-5H-pyrrolo[3,4-b]pyridin-2-yl)benzonitrile, I-16

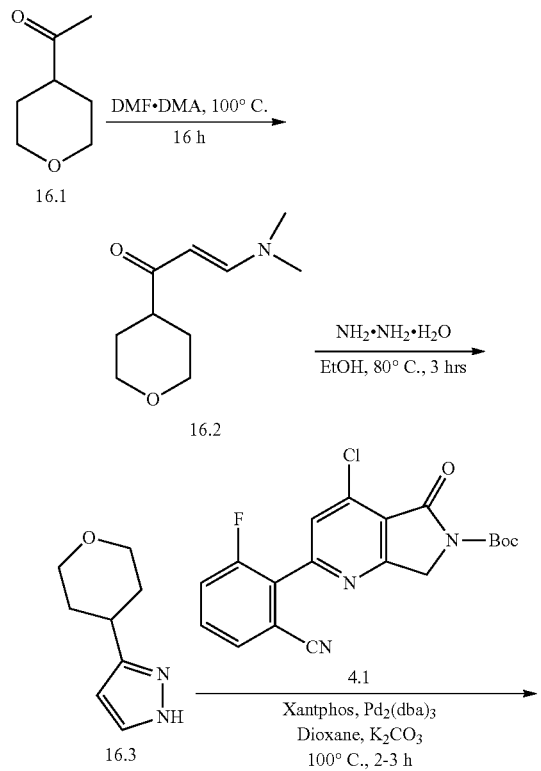

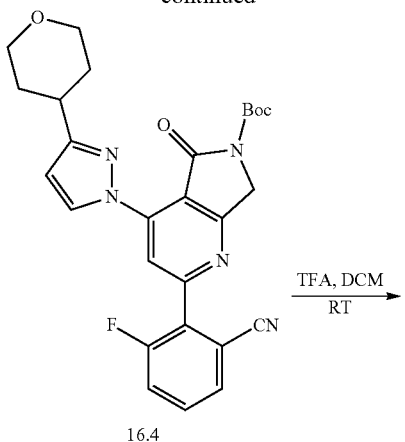

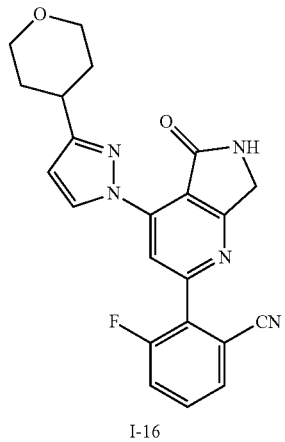

Synthesis of compound 16.2. Solution of 16.1 (0.5 g, 3.9 mmol, 1 eq) in DMF-DMA (5 mL) was heated to 100° C. for 16 h. Upon completion of the reaction was reaction, solvents were removed under reduced pressure to get crude 16.2 (0.45 g, 62.95%), MS(ES): m/z 184.12 [M+H]⁺. The crude product was used in to next step without further purification.

Synthesis of compound 16.3. To a solution of 16.2 (0.45 g, 2.45 mmol, 1 eq) in EtOH (5.0 mL) was added hydrazine hydrate in water (0.147 g, 2.9 mmol, 1.2 eq).). The reaction mixture was heated to 80° C. for 3 h. Upon completion, reaction was quenched with water and extracted with EtOAc. Organic layers were washed with brine, dried over Na₂SO₄ and concentrated under reduced pressure to get crude which was purified by column chromatography to provide 16.3 (0.27 g, 72.24%). MS(ES): m/z 153.10 [M+H]⁺.

Synthesis of compound 16.4. Compound was prepared from 16.3 and 4.1 using the procedure described in Example 7.

Synthesis of compound I-16. Compound was prepared from 16.4 using the procedure described in Example 7. MS(ES): m/z 404.56 [M+H]⁺; ¹H NMR (DMSO-d₆, 400 MHz): 9.64-9.63 (d, 1H), 9.22 (s, 1H), 8.29 (s, 1H), 7.93-7.91 (m, 1H), 7.84-7.75 (m, 2H), 6.60-6.59 (d, 1H), 4.54 (s, 2H), 3-2.94 (m, 1H), 1.88-1.84 (m, 2H), 1.76-1.66 (m, 2H).

Example 55

Synthesis of 3-fluoro-2-(5-oxo-4-(3-(pyrrolidine-1-carbonyl)-1H-pyrazol-1-yl)-6,7-dihydro-5H-pyrrolo[3,4-b]pyridin-2-yl)benzonitrile, I-55

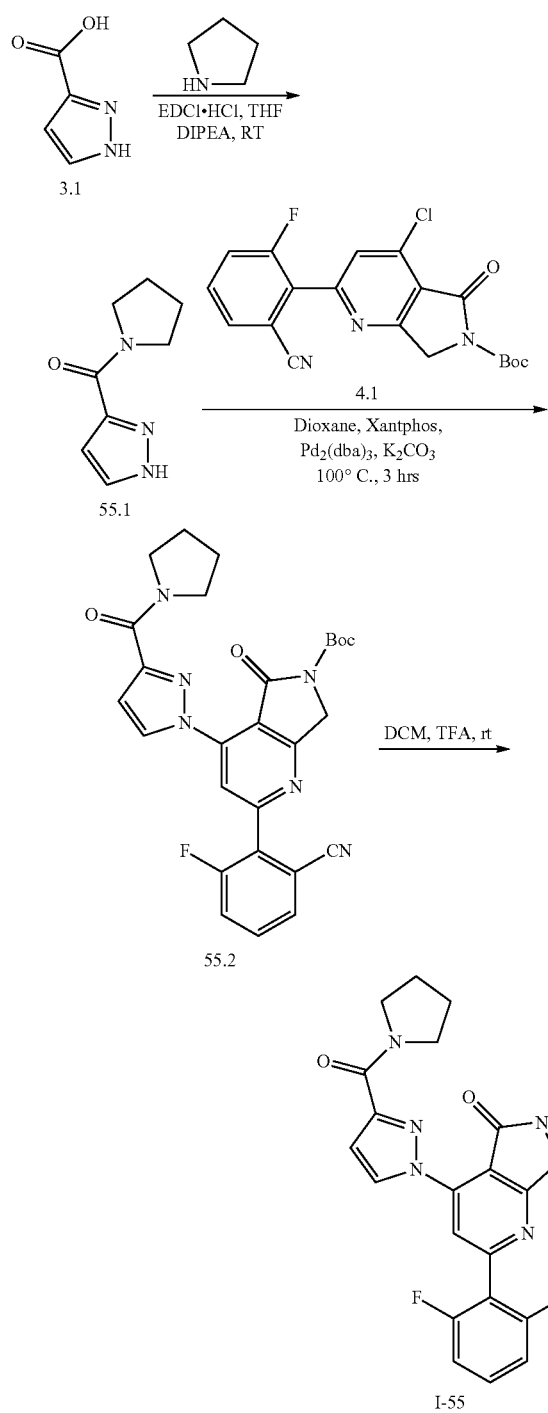

15 minutes and to it pyrrolidine (0.19 g, 2.67 mmol, 1.0 eq) was added at 0° C. Reaction was stirred overnight. Upon completion of the reaction, mixture was transferred into ice and with EtOAc. Organic layers were combined, washed with brine solution, dried over sodium sulphate and concentrated under reduced pressure to obtain crude which was purified by column chromatography to provide 54.1 (0.12 g, 27.0%) MS(ES): m/z 166.5 [M+H]⁺.

Synthesis of compound 54.2. To a mixture of 4.1 (0.13 g, 0.33 mmol, 1.0 eq) in 1,4-dioxane (3.0 ml) was added 1.2 (0.050 g, 0.33 mmol, 1.0 eq) and $K_2CO_3$ (0.116 g, 1.839 mmol, 2.5 eq). The reaction mixture was degassed for 10 min. under argon atmosphere, then $Pd_2(dba)_3$ (0.031 g, 0.033 mmol, 0.1 eq) and Xantphos (0.039 g, 0.067 mmol, 0.2 eq) were added, again degassed for 5 min. The reaction was stirred at 120° C. for 1 hour. Upon completion of the reaction, mixture was transferred in water and product was extracted with EtOAc. Organic layers were combined, washed with brine, dried over $Na_2SO_4$ and concentrated under reduced pressure to obtain crude which was purified by column chromatography to provide 54.2 (0.050 g, 21.6%). MS(ES): m/z 517. [M+H]⁺.

Synthesis of compound I-54. Compound 54.2 (0.06 g, 0.116 mmol, 1.0 eq) was dissolved in DCM (5 mL) and TFA (0.5 mL) was added to the reaction mixture. The reaction was stirred at room temperature for 2 hours. Upon completion of the reaction, mixture was poured into water, basified with satd. $NaHCO_3$ and was extracted with EtOAc. Organic layers were combined and dried over $Na_2SO_4$ and concentrated under reduced pressure to obtain crude which was purified by column chromatography to provide I-54 (0.020 g, 60.17%). MS(ES): m/z 417.7 [M+H]⁺, ¹H NMR (DMSO-d₆, 400 MHz): 9.66-9.67 (d, 1H), 8.45 (d, 1H), 7.82-7.83 (m, 1H), 7.69-7.75 (m, 3H), 7.00 (d, 1H), 4.63-4.65 (s, 2H), 4.04-4.07 (t, 2H), 3.65-3.68 (t, 2H), 1.98-2.08 (m, 5H).

Example 56

Synthesis of 3-fluoro-2-(4-(3-(4-hydroxypiperidin-1-yl)-1H-pyrazol-1-yl)-5-oxo-6,7-dihydro-5H-pyrrolo[3,4-b]pyridin-2-yl)benzonitrile, I-56

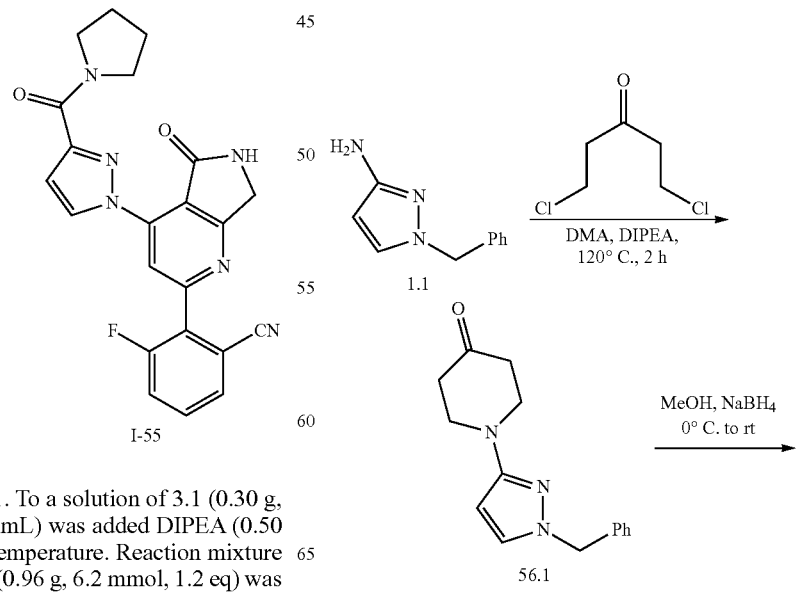

Synthesis of compound 54.1. To a solution of 3.1 (0.30 g, 2.67 mmol, 1.0 eq) in THF (3 mL) was added DIPEA (0.50 g, 4.0 mmol, 1.5 eq) at room temperature. Reaction mixture was cooled to 0° C. and EDCI (0.96 g, 6.2 mmol, 1.2 eq) was added. Reaction mixture was stirred at room temperature for

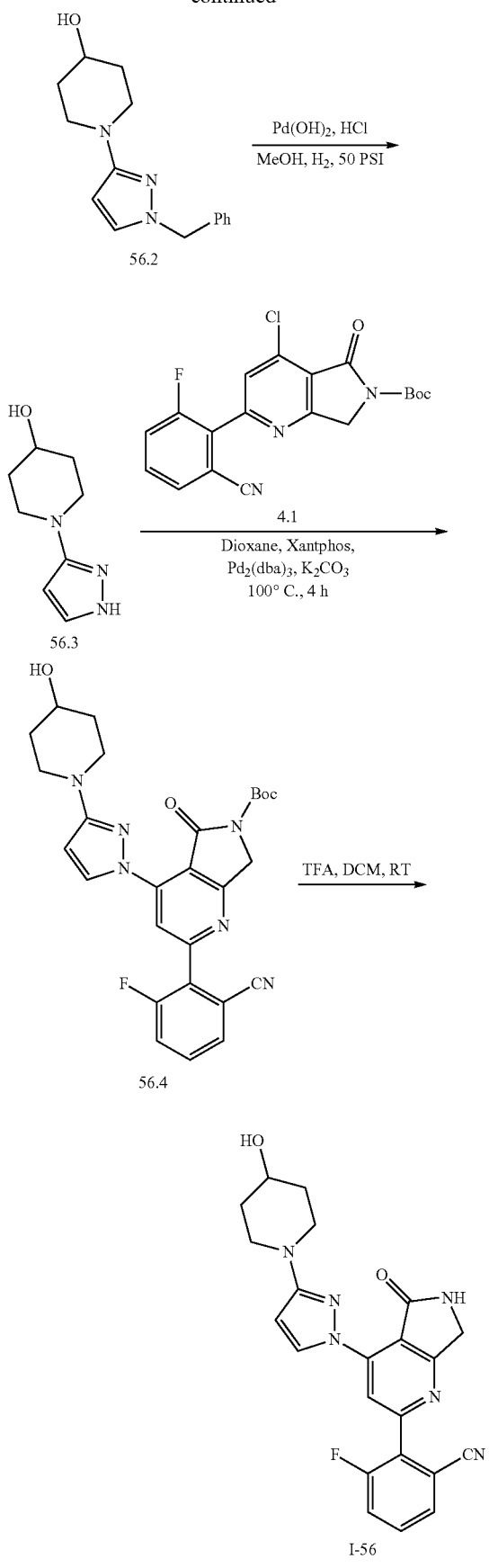

Synthesis of compound 56.1. To a solution of 1.1 (0.3 g, 1.73 mmol, 1.0 eq.) in DMA (3 mL) was added 1,5-dichloropentan-3-one (0.295 g, 1.9 mmol, 1.1 eq.) and DIPEA (0.447 g, 3.46 mmol, 2.0 eq.). The reaction mixture was kept in microwave at 120° C. for 2 hours. Upon completion of the reaction, mixture was transferred into water and product was extracted with EtOAc. Organic layers were combined, washed with brine solution, dried over sodium sulphate and concentrated under reduced pressure to get crude material. The crude purified by column chromatography to get pure 56.1 (0.2 g, 45.23%). MS(ES): m/z 256.5 [M+H]$^+$.

Synthesis of compound 56.2. To 56.2 (0.2 g, 0.784 mmol, 1.0 eq) in MeOH (5.0 mL) at 0° C. was added NaBH$_4$ (0.15 g, 3.92 mmol, 5.0 eq). Reaction mixture was stirred at for 3 hours. Upon completion of the reaction, mixture was poured into water and product was extracted with ethyl acetate. Organic layers were combined, washed with brine, dried over Na$_2$SO$_4$ and concentrated under reduced pressure to get pure 56.2 (0.15 g, 74.41%). MS(ES): m/z 258.4 [M+H]$^+$.

Synthesis of compound 56.3. To a suspension of Pd(OH)$_2$ (0.15 g) in MeOH (5.0 mL) was added 56.2 (0.15 g, 0.58 mmol, 1.0 eq) followed by 1N HCl (catalytic). Reaction was stirred under 50 psi of H$_2$ gas for 6 hours. Reaction mixture was filtered through celite and concentrated under reduced pressure to get crude material. The crude was purified by column chromatography to get pure 56.3 (0.051 g, 52.33%). MS(ES): m/z 168 [M+H]$^-$.

Synthesis of compound 56.4. To a mixture of 4.1 (0.140 g, 0.374 mmol, 1.0 eq) in 1,4-dioxane (3.0 ml) was added 56.3 (0.055 g, 0.29 mmol, 1.0 eq) and K$_2$CO$_3$ (0.129 g, 0.936 mmol, 2.5 eq). The reaction mixture was degassed for 10 min. under argon atmosphere, then Pd$_2$(dba)$_3$ (0.034 g, 0.037 mmol, 0.1 eq) and Xantphos (0.043 g, 0.074 mmol, 0.2 eq) were added and again degassed for 5 minutes. The reaction was stirred at 100° C. for 4 h. Upon completion of the reaction, reaction mixture was transferred into water and product was extracted with EtOAc. Organic layers were combined, washed with brine solution, dried over Na$_2$SO$_4$ and concentrated under reduced pressure to obtain the crude which was purified by column chromatography to furnish 56.4 (0.080 g, 41.9%). MS(ES): m/z 519.5 [M+H]$^+$.

Synthesis of compound I-56. The compound 1.4 (0.080 g, 0.154 mmol, 1.0 eq) was dissolved in CH$_2$Cl$_2$ (1.0 mL) and TFA (0.5 mL) was added to the reaction mixture. The reaction was stirred at room temperature for 1 hour. Upon completion of the reaction, mixture was poured into water, basified with saturated bicarbonate solution and extracted with EtOAc. Organic layers were combined and dried over Na$_2$SO$_4$ and concentrated under reduced pressure to obtain crude which was purified by column chromatography to provide I-56 (0.030 g, 66.4%). MS(ES): m/z 419.61[M+H]$^+$; $^1$H NMR (MeOD, 400 MHZ): 9.71-9.70 (d, 1H), 8.29-8.28 (d, 1H), 7.80-7.78 (m, 1H), 7.74-7.63 (m, 2H), 6.28 (s, 1H), 4.56 (s, 2H), 3.84-3.77 (m, 3H), 3.09-3.01 (m, 3H), 1.97-1.93 (m, 2H), 1.65-1.58 (m, 2H).

Example 57

Synthesis of 3-fluoro-2-(4-(1-isopropyl-1H-pyrazol-3-yl)-5-oxo-6,7-dihydro-5H-pyrrolo[3,4-b]pyridin-2-yl)benzonitrile, I-57

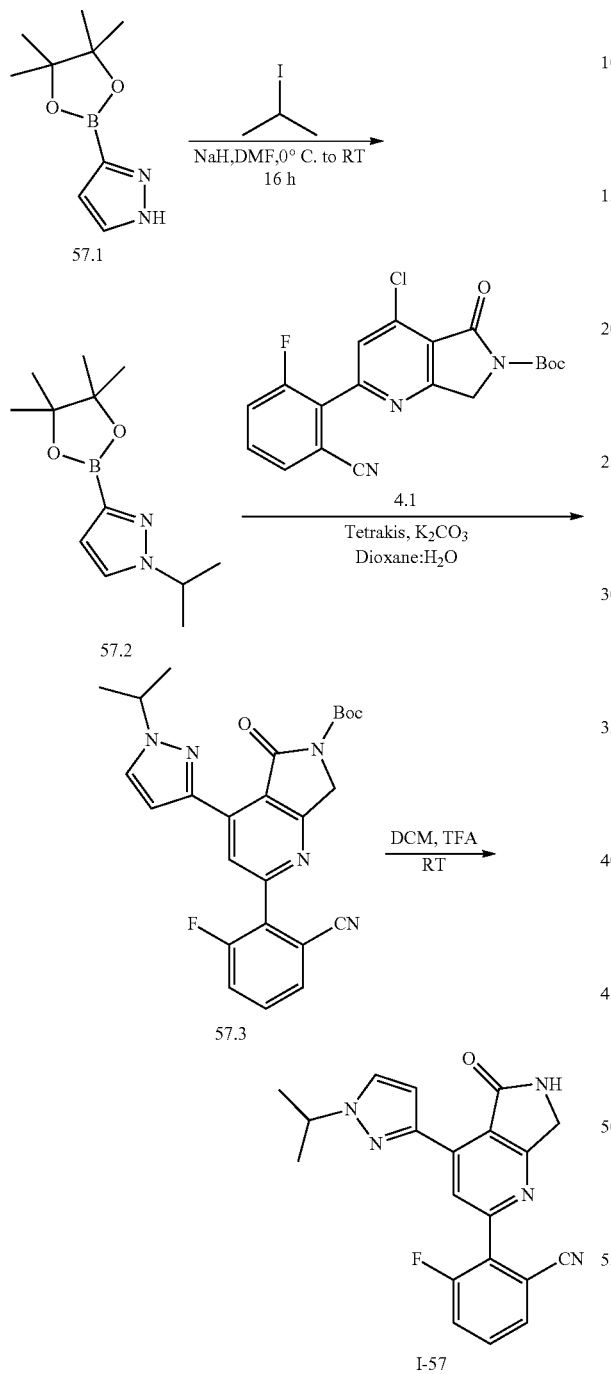

Synthesis of compound 57.2. To a solution of 57.1 (1.0 g, 5.14 mmol, 1.0 eq) in DMF (5 mL) was added NaH (0.180 g, 7.7 mmol, 1.5 eq) at 0° C. Reaction mixture was stirred at room temperature for 1 h. Reaction mixture was cooled to 0° C. and 2-iodopropane was added dropwise, with stirring at room temperature for 16 h. Upon completion of the reaction, reaction mixture was transferred into ice. Resulting mixture was extracted with EtOAc. Organic layers were combined, washed with brine, dried over $Na_2SO_4$ and concentrated under reduced pressure to obtain 57.2 (0.39 g, 32%). Crude compound was used for next step without any purification.

Synthesis of compound 57.3. To a mixture of 4.1 (0.46 g, 1.18 mmol, 1.0 eq) in 1,4-dioxane (10.0 ml) and water (2.5 mL) was added 57.2 (0.365 g, 1.54 mmol, 1.3 eq) and $K_2CO_3$ (0.492 g, 3.56 mmol, 3.0 eq). Reaction mixture was degassed for 10 min. under argon atmosphere, then Pd(PPh3)$_4$ (0.068 g, 0.059 mmol, 0.1 eq) was added, and again degassed for 5 min. The reaction was then heated at 110° C. for 1 h. Upon completion of the reaction, reaction mixture was transferred into water and product was extracted with EtOAc. Organic layers were combined, washed with brine, dried over $Na_2SO_4$ and concentrated under reduced pressure to obtain crude which was purified by column chromatography to provide 57.3 (0.21 g, 38.3%). MS(ES): m/z 462.5 [M+H]$^-$.

Synthesis of compound I-57. Compound was prepared using the procedure described in Example 56. (0.098 g, 60.2%). MS(ES): m/z 362.38 [M+H]$^+$; $^1$H NMR (DMSO-d$_6$, 400 MHz): 8.96 (s, 1H), 8.27 (s, 1H), 7.92-7.90 (m, 2H), 7.82-7.75 (m, 3H), 4.64-4.58 (m, 1H), 4.50 (s, 2H), 1.48-1.46 (d, 6H).

Example 58

Synthesis of 2-(2,6-difluorophenyl)-4-(1H-pyrazol-1-yl)-6,7-dihydro-5H-pyrrolo[3,4-b]pyridin-5-one, I-58

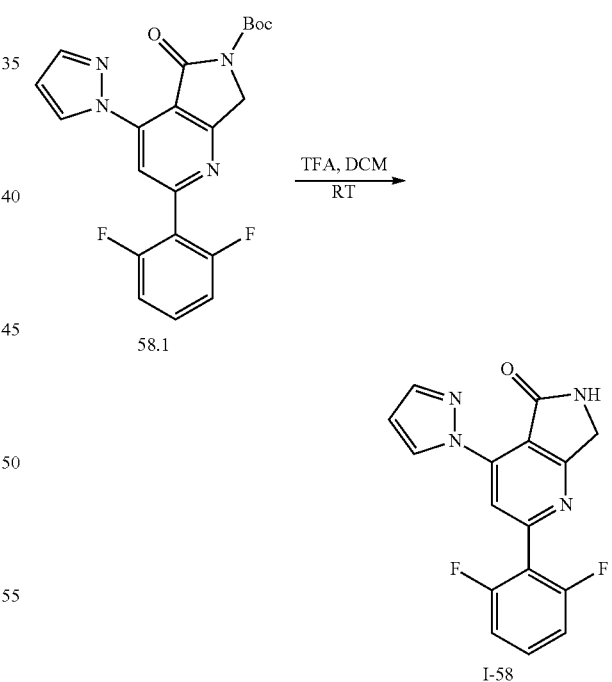

Compound 58.1 (0.025 g, 0.06 mmol, 1.0 eq) was dissolved in DCM (2.0 mL) and TFA (0.1 mL) was added to the reaction mixture. The reaction was stirred at room temperature for 1 h. Upon completion of the reaction, mixture was poured into water, basified with satd. NaHCO$_3$ solution and extracted with EtOAc. Organic layers were combined, dried over $Na_2SO_4$ and concentrated under reduced pressure to obtain crude which was purified by column chromatography to furnish I-58 (0.015 g, 83.3%). MS(ES): m/z 313 [M+H]$^+$; $^1$H NMR (DMSO-d$_6$, 400 MHz): 9.69-9.68 (d, 1H), 9.20 (s, 1H), 8.19 (s, 1H), 7.93-7.92 (d, 1H), 7.64-7.60 (m, 1H), 7.33-7.28 (m, 2H), 6.66-6.65 (m, 1H), 4.54 (m, 2H).

Example 59

Synthesis of 3-fluoro-2-(4-(3-(4-morpholinopiperidin-1-yl)-1H-pyrazol-1-yl)-5-oxo-6,7-dihydro-5H-pyrrolo[3,4-b]pyridin-2-yl)benzonitrile, I-59

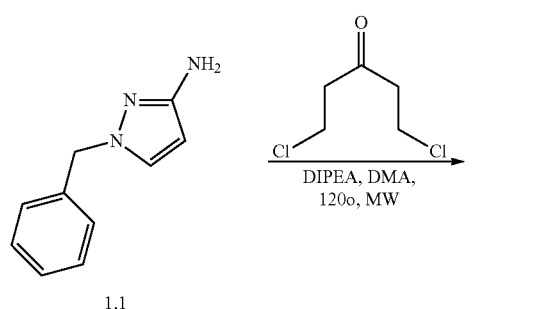

1.1

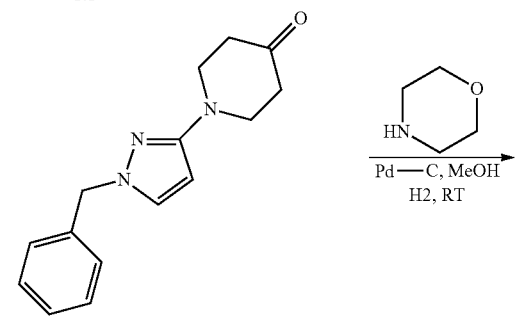

56.1

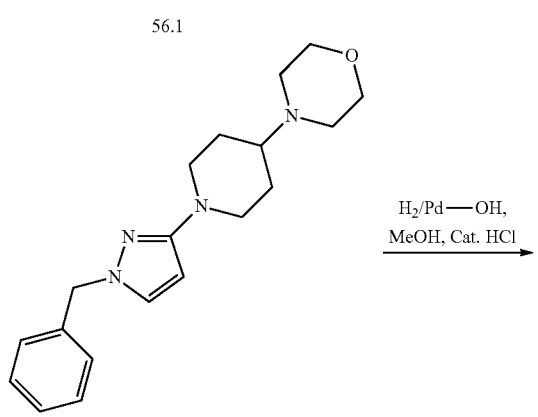

59.2

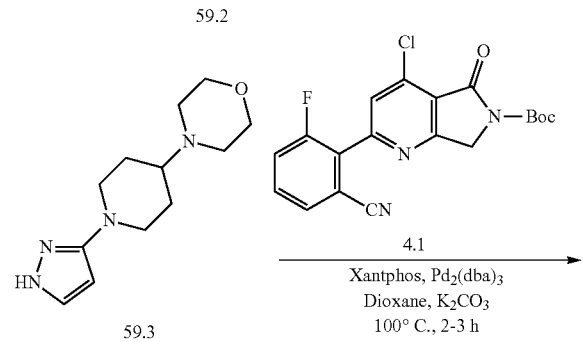

59.3

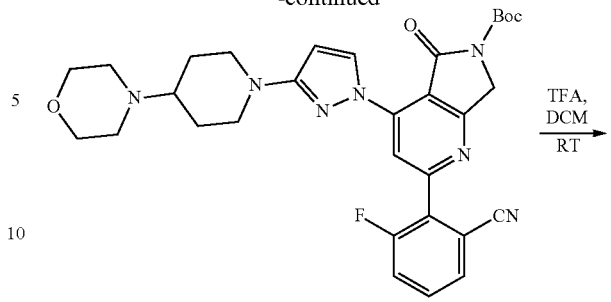

59.4

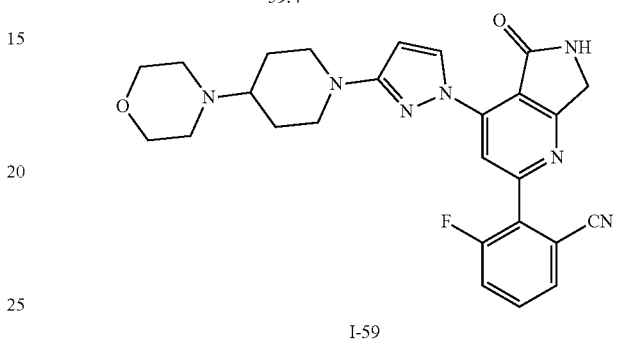

I-59

Synthesis of compound 59.2. To a solution of 56.1. (0.2 g, 0.92 mmol, 1.0 eq) and morpholine (0.161 g, 1.85 mmol, 2.0 eq) in MeOH (5.0 mL), 10% Pd/C (0.1 g) was added. Reaction mixture was stirred H$_2$ pressure of 40 psi for 15 h. Upon completion of the reaction, mixture was filtered through celite-bed and washed with methanol, concentrated under reduced pressure to obtain crude 59.2 (0.19 g, 73.1%). MS(ES): m/z 327 [M+H]$^+$.

Synthesis of compound 59.3. To a solution of 59.2. (0.19 g, 0.58 mmol, 1.0 eq) in MeOH (5.0 mL), 20% Pd(OH)$_2$/C (0.1 g) and 1N HCl (catalytic amount) were added into reaction. Reaction mixture was stirred 40 psi of H$_2$ for 15 h. Upon completion of the reaction, mixture was filtered through celite-bed and washed with methanol, concentrated under reduced pressure to obtain crude which was purified by column chromatography to provide 59.3. (0.07 g, 51.1%). MS (ES): m/z 237 [M+H]$^+$.

Synthesis of compound 59.4. Compound 59.4 was prepared from compounds 59.3 and 4.1 using the procedure described in Example 56.

Synthesis of compound I-59. Compound I-59 was prepared from compound 59.4 using the procedure described in Example 56. MS(ES): m/z 488 [M+H]$^+$; $^1$H NMR (DMSO-d$_6$, 400 MHz): 9.76-9.75 (d, 1H), 9.12 (s, 1H), 8.18 (s, 1H), 7.92-7.90 (m, 1H), 7.83-7.73 (m, 2H), 6.37 (s, 1H), 4.49 (s, 2H), 3.89-3.86 (m, 2H), 3.56 (s, 4H), 2.83-2.75 (t, 2H), 2.50-2.45 (m, 4H), 1.82-1.80 (m, 2H), 1.46-1.40 (m, 2H).

Example 60

Synthesis of 2-(4-(3-(4,4-dimethyl-4,5-dihydrooxazol-2-yl)-1H-pyrazol-1-yl)-5-oxo-6,7-dihydro-5H-pyrrolo[3,4-b]pyridin-2-yl)-3-fluorobenzonitrile, I-60

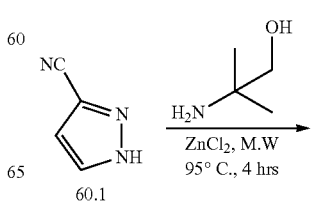

60.1

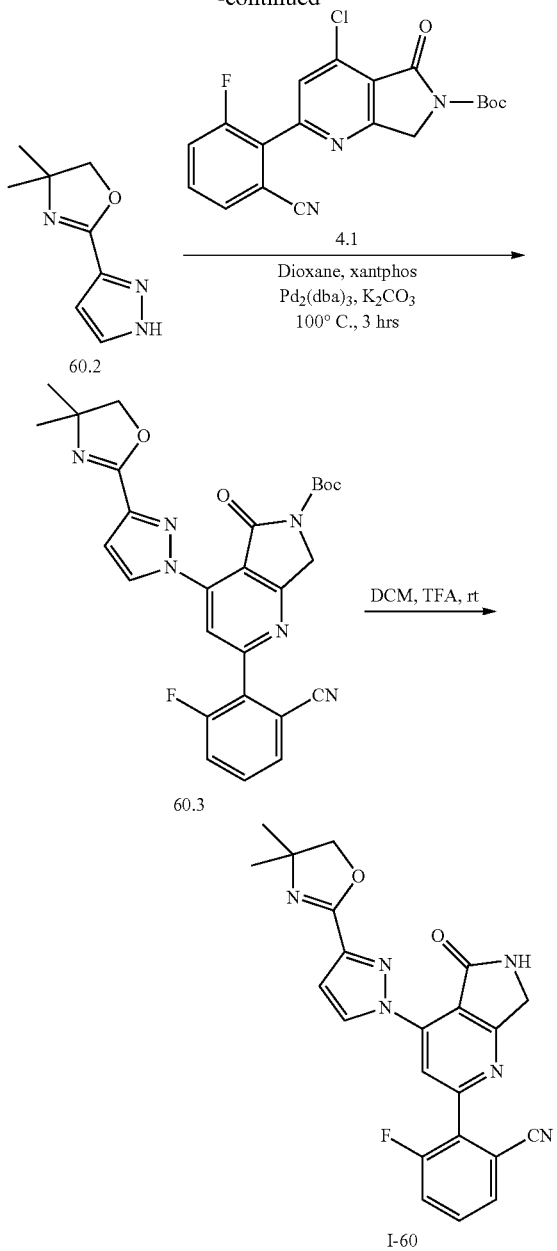

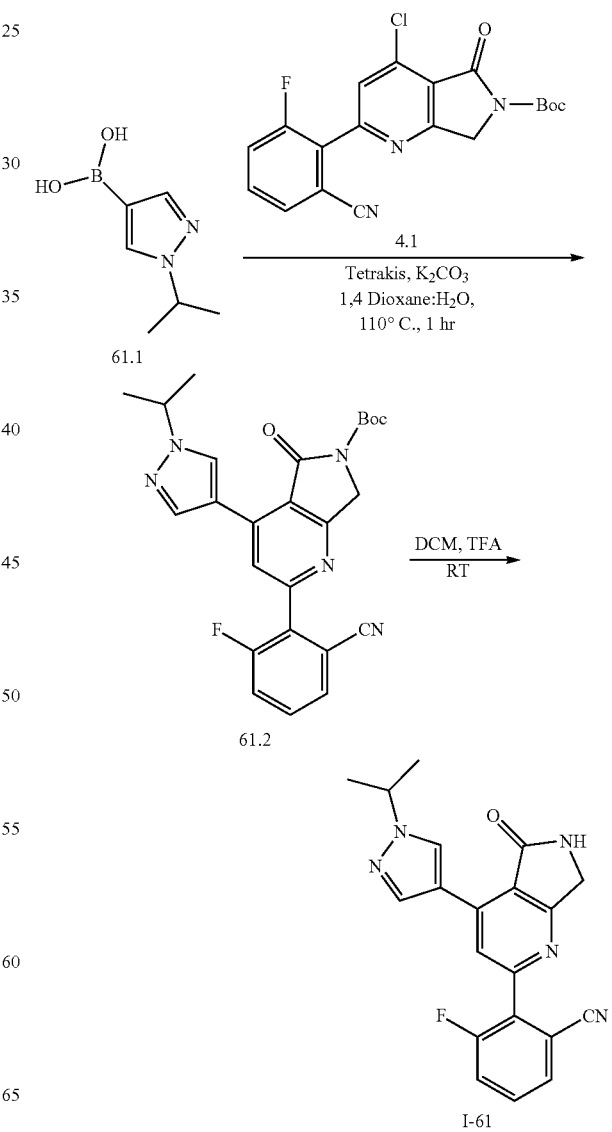

was extracted with EtOAc. Organic layers were combined, washed with brine solution, dried over sodium sulphate and concentrated under reduced pressure to obtain the crude which was purified by column chromatography to furnish 60.3 (0.070 g, 53.2%). MS(ES): m/z 517.5 [M+H]⁺.

Synthesis of compound I-60. Compound 60.3 (0.070 g, 0.135 mmol, 1.0 eq) was dissolved in DCM (2.0 mL) and TFA (0.5 mL) was added to the reaction mixture. The reaction was stirred at room temperature for 1 hour. Upon completion of the reaction, mixture was poured into water, basified with satd. NaHCO₃ solution and extracted with EtOAc. Organic layers were combined, dried over Na₂SO₄ and concentrated under reduced pressure to obtain crude which was purified by column chromatography to furnish I-60 (0.026 g, 53.2%). MS(ES): m/z 417.44 [M+H]⁺; ¹H NMR (DMSO-d₆, 400 MHZ): 9.70-9.71 (d, 1H), 9.33 (s, 1H), 8.30 (s, 1H), 7.92-7.94 (m, 1H), 7.78-7.85 (m, 2H), 7.01-7.02 (d, 1H), 4.59 (s, 2H), 4.12 (s, 2H), 1.13 (s, 6H).

Example 61

Synthesis of 3-fluoro-2-(4-(1-isopropyl-1H-pyrazol-4-yl)-5-oxo-6,7-dihydro-5H-pyrrolo[3,4-b]pyridin-2-yl)benzonitrile, I-61

Synthesis of compound 60.2. To a mixture of 60.1 (0.14 g, 1.50 mmol, 1.0 eq) and aminoalcohol (0.20 g, 2.25 mmol, 1.5 eq) was added ZnCl₂ (0.041 g, 0.30 mmol, 0.2 eq) and stirred at 95° C. under microwave irradiation for 4 h. Upon completion of the reaction, mixture was quenched with water. Resulting mixture was extracted with EtOAc. Organic layers were combined, washed with brine, dried over Na₂SO₄ and concentrated under reduced pressure. The residue was purified by flash column chromatography to obtain pure 60.2 (0.10 g, 41.6%). MS(ES): m/z 166.2 [M+H]⁺.

Synthesis of compound 60.3. To a mixture of 4.1 (0.15 g, 0.387 mmol, 1.0 eq) in 1,4-dioxane (3.0 ml) was added 60.2 (0.058 g, 0.348 mmol, 0.9 eq) and K₂CO₃ (0.133 g, 0.968 mmol, 2.5 eq). The reaction mixture was degassed for 10 min. under argon atmosphere, then Pd₂(dba)₃ (0.035 g, 0.0387 mmol, 0.1 eq) and Xantphos (0.045 g, 0.077 mmol, 0.2 eq) were added then again degassed for 5 min. The reaction was stirred at 120° C. for 1 h. Upon completion of the reaction, mixture was transferred into water and product Compound I-61 was prepared from 61.1 and 4.1 using the procedures described in Example 57. (0.035 g, 44.7%). MS(ES): m/z 362.27 [M+H]$^+$; $^1$H NMR (DMSO-d$_6$, 400 MHz): 9.08 (s, 1H), 8.91 (s, 1H), 8.53 (s, 1H), 8.09 (s, 1H), 7.92-7.91 (m, 1H), 7.83-7.75 (m, 2H), 4.58-4.55 (m, 1H), 4.46 (s, 2H), 1.48-1.46 (d, 6H).

Example 62

Synthesis of 3-fluoro-2-(4-(3-(3-hydroxy-3-methyl-piperidin-1-yl)-1H-pyrazol-1-yl)-5-oxo-6,7-dihydro-5H-pyrrolo[3,4-b]pyridin-2-yl)benzonitrile, I-62

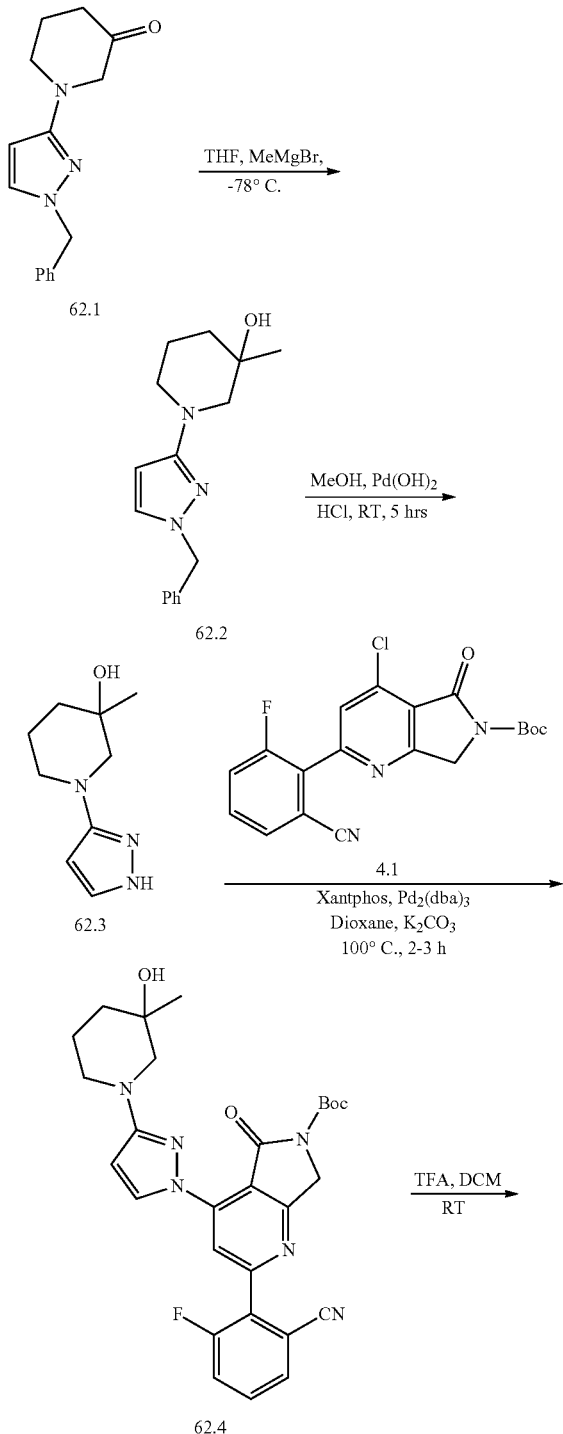

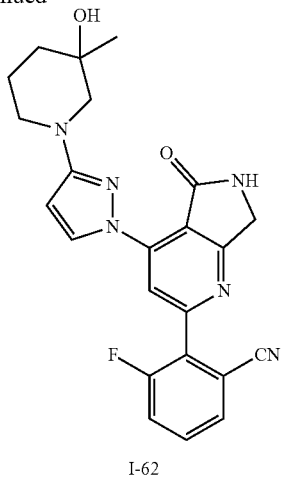

Synthesis of compound 62.2. To a solution of 62.1 (0.75 g, 2.93 mmol, 1.0 eq) in THF (10.0 mL) was added MeMgBr (1.05 g, 8.80 mmol, 3 eq) at −78° C. Reaction was stirred at −78° C. for 3 h, then cooled to 0° C. Upon completion of reaction, reaction mixture was quenched using NH$_4$Cl solution. Resulting mixture was extracted with EtOAc. Organic layers were combined, washed with brine, dried over Na$_2$SO$_4$ and concentrated under reduced pressure to provide crude that was purified by column chromatography to provide 62.2 (0.35 g, 43.9%). MS(ES): m/z 272 [M+H]$^+$.

Synthesis of compound 62.3. To a solution of 62.2 (0.35 g, 1.29 mmol, 1.0 eq) in MeOH (5.0 mL). 20% Pd(OH)$_2$/C (0.75 g) and 1N HCl (catalytic amount) waere added. Reaction mixture was stirred at 40 psi of H$_2$ gas for 4 h. Upon completion of reaction, reaction mixture was filtered, concentrated under reduced pressure to obtain crude which was purified by column chromatography to furnish 62.2. (0.2 g, 86.5%). MS(ES): m/z 182 [M+H]$^+$.

Synthesis of compound 62.4. Compound 62.4 was prepared from compounds 4.1 and 62.3 using the procedure in Example 56.

Synthesis of compound I-62. Compound I-62 was prepared from compound 62.4 using the procedure described in Example 56. MS(ES): m/z 433 [M+H]$^+$; $^1$H NMR (DMSO-d$_6$, 400 MHz): 9.76 (d, 1H), 9.11 (s, 1H), 8.16 (s, 1H), 7.92-7.90 (m, 1H), 7.83-7.76 (m, 2H), 6.34-6.33 (d, 1H), 4.49 (s, 3H), 3.31-3.28 (m, 1H), 3.24-3.20 (m, 1H), 3.11 (s, 2H), 1.78-1.77 (m, 1H), 1.52 (s, 3H), 1.13 (s, 3H).

Example 63

Synthesis of 3-fluoro-2-(4-(3-((2-morpholinoethyl)amino)-1H-pyrazol-1-yl)-5-oxo-6,7-dihydro-5H-pyrrolo[3,4-b]pyridin-2-yl)benzonitrile, I-63

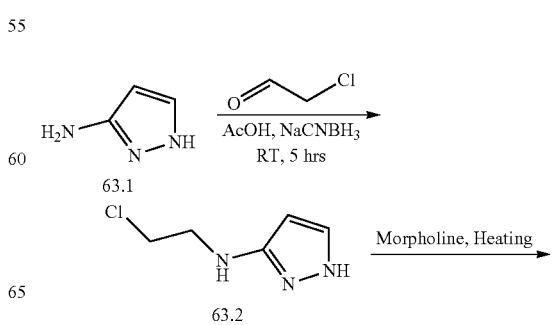

-continued

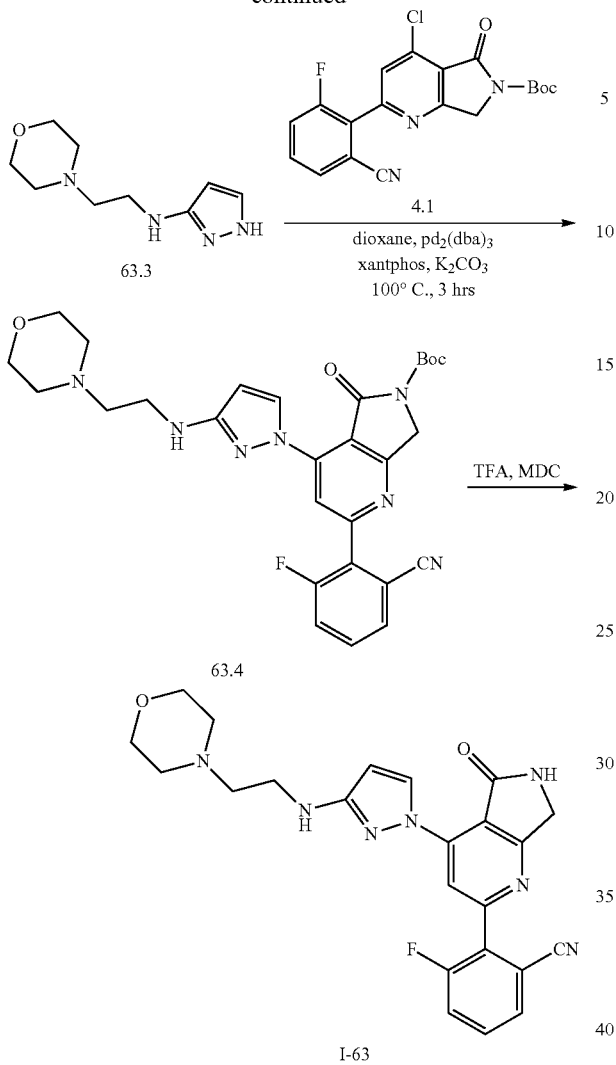

56.81%). MS(ES): m/z 448 [M+H]+; 1H NMR (DMSO-$d_6$, 400 MHz): 9.73 (d, 1H), 9.08 (s, 1H), 8.14 (d, 1H), 7.92 (d, 1H), 7.83-7.75 (m, 2H), 6.11-6.04 (m, 2H), 4.48 (d, 2H), 3.55 (t, 4H), 3.30-3.26 (m, 2H), 2.51-2.33 (m, 6H).

Example 64

Synthesis of 3-fluoro-2-(4-(3-((2-hydroxyethyl)amino)-1H-pyrazol-1-yl)-5-oxo-6,7-dihydro-5H-pyrrolo[3,4-b]pyridin-2-yl)benzonitrile, I-64

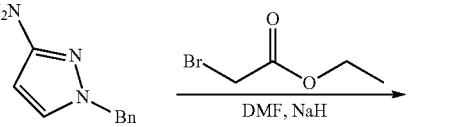

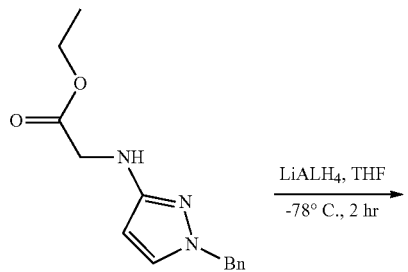

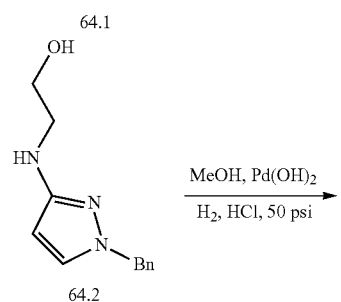

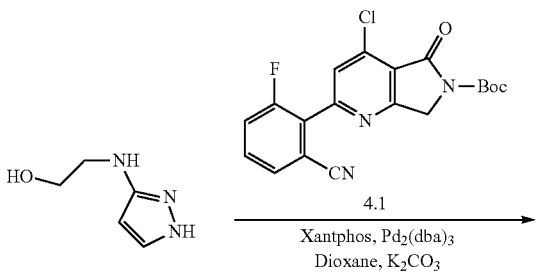

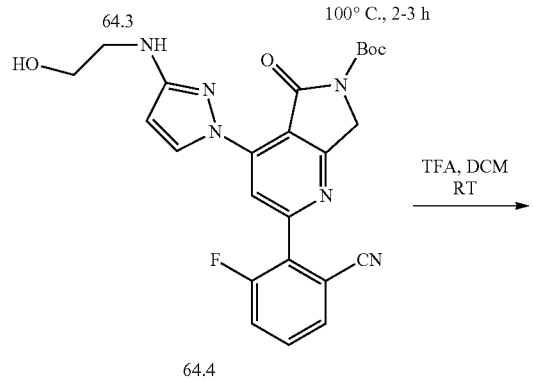

Synthesis of compound 63.2. To a mixture of 63.1 (1.0 g, 12.0 mmol, 1.0 eq) and acetic acid (5 ml) was added Chloroacetaldehyde (1.6 ml, 12.0 mmol, 1.1 eq) at 0° C. Sodium cyanoborohydride (0.9 g, 14.4 mmol, 1.2 eq) was added slowly at 0° C. The reaction was stirred at room temperature for 5 h. Upon completion of reaction, reaction mixture was transferred into water, then extracted with EtOAc. Organic layers were combined, washed with brine, dried over sodium sulphate and concentrated under reduced pressure to obtain crude which was purified by column chromatography to get pure 63.2 (0.2 g, 11.4%). MS(ES): m/z 146 [M+H]+.

Synthesis of compound 63.3. A solution of 63.2 (0.1 g, 0.68 mmol, 1.0 eq) in Morpholine (1 mL) was stirred at 100° C. for 2 h. Upon completion of the reaction, reaction mixture was transferred into water, extracted with EtOAc. Organic layers were combined, washed with brine, dried over sodium sulphate and concentrated under reduced pressure to obtain crude which was purified by column chromatography to provide 63.3 (0.065 g, 48.1%). MS(ES): m/z 197 [M+H]+.

Synthesis of compound 63.4. Compound was prepared using the procedure described in Example 56.

Synthesis of compound I-63. Compound was prepared using the procedure described in Example 56. (0.025 g,

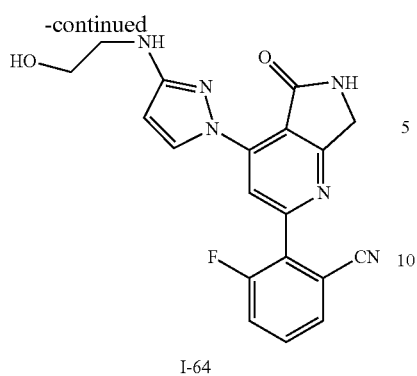

I-64

Synthesis of compound 64.1. To a solution of 1.1 (0.35 g, 2.023 mmol, 1.0 eq) in DMF (5 mL) was added 60% NaH (0.089 g, 2.225 mmol, 1.1 eq) at 0° C. Reaction mixture was stirred at 0° C. for 30 minutes and ethyl bromoacetate (0.37 g, 2.225 mmol, 1.1 eq) was added at same temperature. The reaction mixture was stirred at 70° C. for 1 h. Upon completion of the reaction; mixture was transferred into water and extracted with EtOAc. Organic layers were combined, washed with brine s, dried over $Na_2SO_4$ and concentrated under reduced pressure to obtain crude which was purified by column chromatography to get pure 64.1 (0.30 g, 60.0%). MS(ES): m/z 260.3 $[M+H]^-$.

Synthesis of compound 64.2. To a solution of 64.1 (0.30 g, 1.158 mmol, 1.0 eq) in dry THF (5.0 mL) was added $LiAlH_4$ (1.0 M in THF) (3 mL, 3.474 mmol, 3.0 eq.) at −78° C. Reaction mixture was stirred at 0° C. for 2 h. Upon completion of reaction; reaction mixture was transferred into ice water, extracted with EtOAc. Organic layers were combined, washed with brine, dried over $Na_2SO_4$ and concentrated under reduced pressure to pressure to obtain crude which was purified by column chromatography to provide 64.2 (0.2 g, 79.0%). MS(ES): m/z 218.2 $[M+H]^+$.

Synthesis of compound 64.3. To a solution of 64.2. (0.20 g, 0.621 mmol, 1.0 eq) in MeOH (5.0 mL). 20% $Pd(OH)_2/C$ (0.25 g) and 1N HCl (catalytic) was added into reaction. Reaction mixture was stirred at 40 psi of $H_2$ for 20 h. Upon completion of the reaction, reaction mixture was filtered through celite-bed and washed with MeOH and concentrated under reduced pressure to obtain crude material. The crude was purified by column chromatography to get pure to get 64.3 (0.025 g, 21.34%). MS(ES): m/z 128.5 $[M+H]^+$.

Synthesis of compound 64.4. To a mixture of 4.1 (0.080 g, 0.206 mmol, 1.0 eq) in 1,4-dioxane (4.0 ml) was added 64.3 (0.023 g, 0.186 mmol, 0.9 eq) followed by $K_2CO_3$ (0.071 g, 0.51 mmol, 2.5 eq). The reaction mixture was degassed for 10 min. under argon atmosphere, then $Pd_2(dba)_3$ (0.019 g, 0.02 mmol, 0.1 eq) and Xantphos (0.024 g, 0.04 mmol, 0.2 eq) were added and again degassed for 5 min. The reaction was then heated at 100° C. for 2 h. Upon completion of the reaction, reaction mixture was poured into water and product was extracted with EtOAc. Organic layers were combined, washed with brine solution, dried over $Na_2SO_4$ and concentrated under reduced pressure to obtain crude which was purified by column chromatography to get pure 64.4 (0.043 g, 43.4%). MS(ES): m/z $[M+H]^+$.

Synthesis of compound I-64. The compound 1.4 (0.040 g, 0.168 mmol, 1.0 eq) was dissolved in $CH_2Cl_2$ (2.0 mL) and TFA (0.2 mL) was added to the reaction mixture. The reaction was stirred at room temperature for 2 h. Upon completion of reaction, reaction mixture was poured into water, basified with satd. $NaHCO_3$ solution and extracted with EtOAc. Organic layers were combined, dried over Na2SO4 and concentrated under reduced pressure to obtain crude material. The crude was purified by column chromatography to provide I-64 (0.020 g, 63.23%). MS(ES): m/z 379.51 $[M+H]^+$; $^1$H NMR (DMSO-$d_6$, 400 MHz): 9.72 (d, 1H), 9.07 (s, 1H), 8.12 (s, 1H), 7.92-7.90 (d, 1H), 7.81-7.77 (m, 2H), 6.03 (d, 1H), 4.47 (s, 2H), 3.56-3.53 (t, 2H), 3.25-3.22 (t, 2H).

Example 65

Synthesis of 3-fluoro-2-(4-(3-(3-hydroxypiperidin-1-yl)-1H-pyrazol-1-yl)-5-oxo-6,7-dihydro-5H-pyrrolo[3,4-b]pyridin-2-yl)benzonitrile, I-65

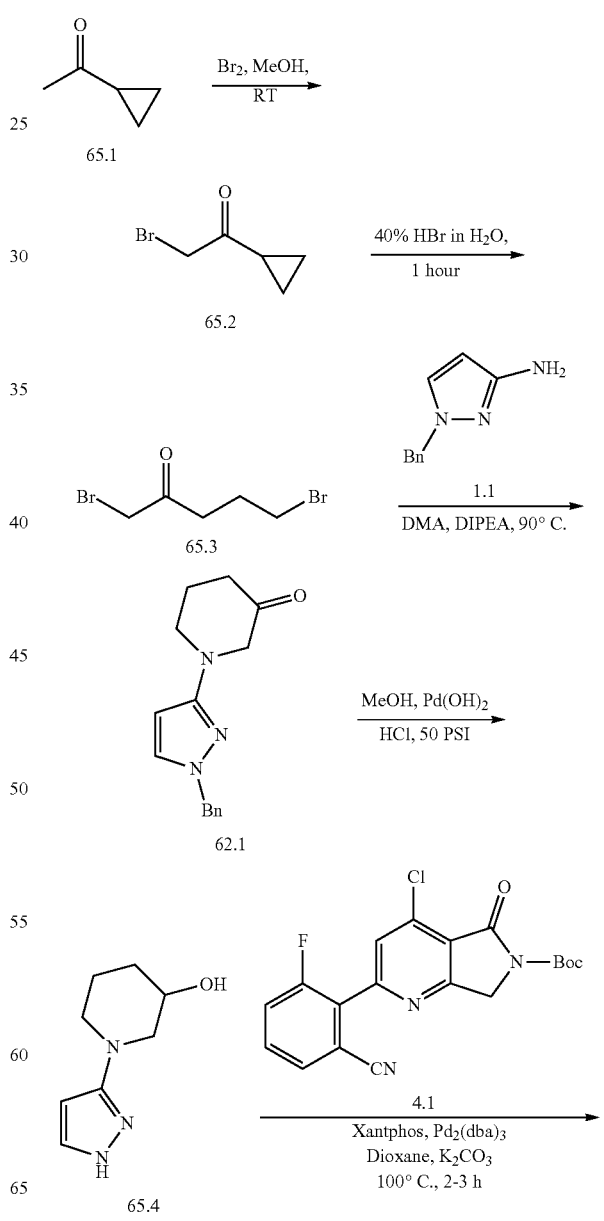

-continued

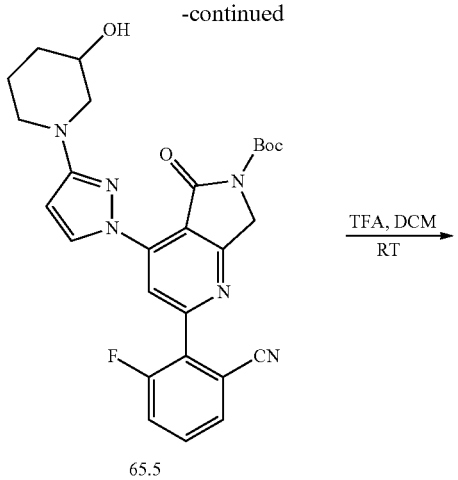

65.5

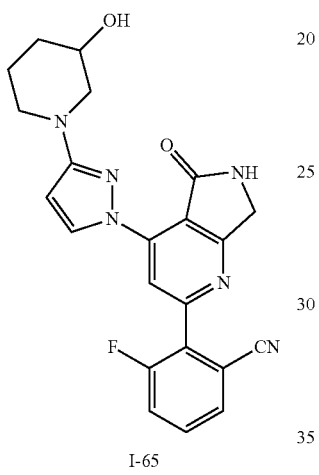

I-65

Synthesis of compound 65.2. To a solution of 65.1 (15 g, 178.5 mmol, 1.0 eq) in MeOH (75 mL) was added Br$_2$ (28.6 g, 178 mmol, 1 eq) drop wise at 0° C. over a period of 20 minutes. The reaction was stirred at room temperature for 18 h. Upon completion of the reaction, reaction mixture was transferred into water and extracted with Et$_2$O. Combined organic layers were washed with satd. NaHCO$_3$, dried over Na$_2$SO$_4$ and concentrated under reduced pressure to get crude 65.2 (14.4 g, 49.54%). MS(ES): m/z 163.97 [M+H]$^-$. The crude compound 65.2 was used in next step without further purification.

Synthesis of compound 65.3. To 65.2 (14.4 g, 88.9 mmol, 1 eq) was added 40% HBr in water (45 mL) at 50° C. The resulting mixture was stirred at 50° C. for 1 h. Upon completion of the reaction, mixture was poured into ice water and extracted with Et$_2$O. Combined organic layers were washed with brine, dried over Na$_2$SO$_4$ and concentrated under reduced pressure to get crude 65.3 (11.7 g, 54.19%). MS(ES): m/z 241.89 [M+H]$^+$. Crude compound was used in next step without further purification.

Synthesis of compound 62.1. To a solution of 65.3 (1 g, 5.78 mmol, 1 eq), in DMA (10 mL) was added 1.1 (1.56 g, 6.2 mmol, 1.1 eq) followed by DIPEA (2 mL, 14.44 mmol, 2.5 eq). The resulting mixture was heated 90° C. in microwave for 1 h. Upon completion, reaction was quenched with water and extracted with EtOAc. Organic layers were combined, washed with brine and solvents were removed under reduced pressure to provide crude that was purified by column chromatography to furnish 62.1 (0.6 g, 41.2%). MS(ES): m/z 256.14 [M+H]$^+$.

Synthesis of compound 65.4. To a solution of 62.1 (0.6 g, 2.34 mmol, 1.0 eq) in MeOH (3.0 mL) was added Pd(OH)$_2$ (0.05 g), 1N HCl (0.05 mL), in hydrogenator. Reaction mixture was stirred under hydrogen (50 psi) at room temperature for 18 h. Upon completion of the reaction, reaction mixture was filtered, solvents removed and resulting crude purified by column chromatography to provide 65.4 (0.17 g, 43.4%). MS(ES): m/z 168.11 [M+H]$^+$.

Synthesis of compound 65.5. Compound was prepared from 4.1 and 65.4 using the procedure described in Example 64.

Synthesis of compound I-65. Compound was prepared from 65.5 using the procedure described in Example 64. MS(ES): m/z 419.51 [M+H]$^+$; $^1$H NMR (DMSO-d$_6$, 400 MHz): 9.77-9.76 (d, 1H), 9.12 (s, 1H), 8.16 (s, 1H), 7.92-7.9 (dd, 1H), 7.83-7.73 (m, 2H), 6.35-6.34 (d, 1H), 4.86-4.85 (d, 1H), 4.49 (s, 2H), 3.79-3.75 (m, 1H), 3.62-3.53 (m, 2H), 2.85-2.78 (m, 1H), 2.68-2.65 (m, 1H), 1.91-1.88 (m, 1H), 1.75-1.72 (m, 1H), 1.53-1.48 (m, 1H), 1.35-1.29 (m, 1H)

Example 66

Synthesis of 3-fluoro-2-(5-oxo-4-(3-(4-(pyrrolidin-1-yl)piperidin-1-yl)-1H-pyrazol-1-yl)-6,7-dihydro-5H-pyrrolo[3,4-b]pyridin-2-yl)benzonitrile, I-66

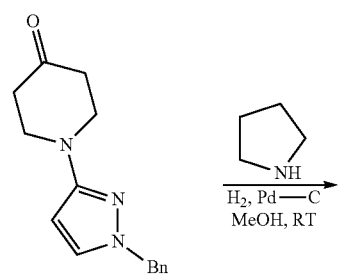

56.1

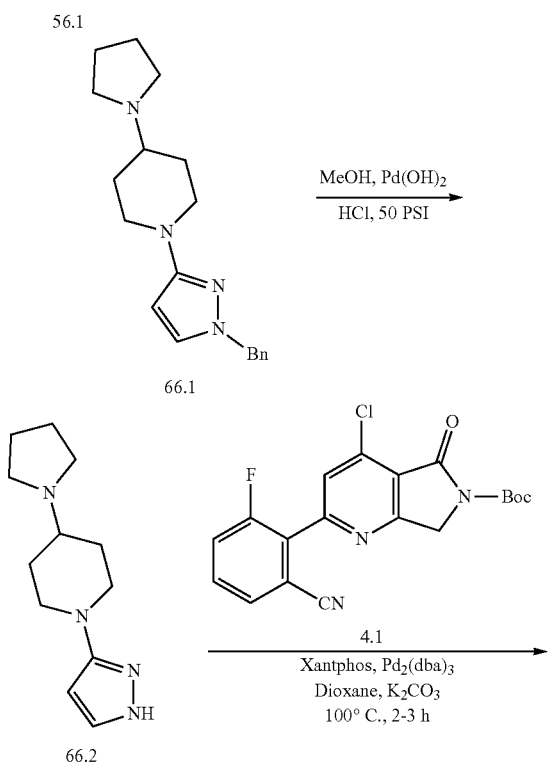

-continued

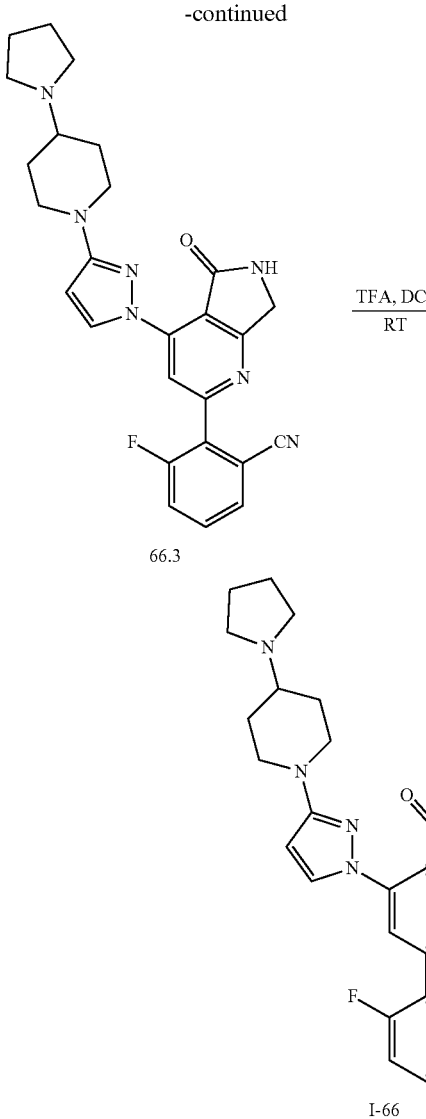

(0.023 g, 44.2%). MS(ES): m/z 472.61 [M+H]⁻; ¹H NMR (MeOD, 400 MHz): 9.73-9.72 (d, 1H), 8.29 (s, 1H), 7.81-7.79 (m, 1H), 7.76-7.64 (m, 2H), 6.29 (d, 1H), 4.57 (s, 2H), 4.12-4.09 (m, 2H), 3.36 (m, 3H), 3.00-2.94 (m, 2H), 2.21-2.17 (m, 2H), 2.0 (bs, 4H), 1.82-1.73 (m, 3H).

Example 67

Synthesis of 2-(4-(3-(((1r,4r)-4-(dimethylamino)cyclohexyl)amino)-1H-pyrazol-1-yl)-5-oxo-6,7-dihydro-5H-pyrrolo[3,4-b]pyridin-2-yl)-3-fluorobenzonitrile, I-67

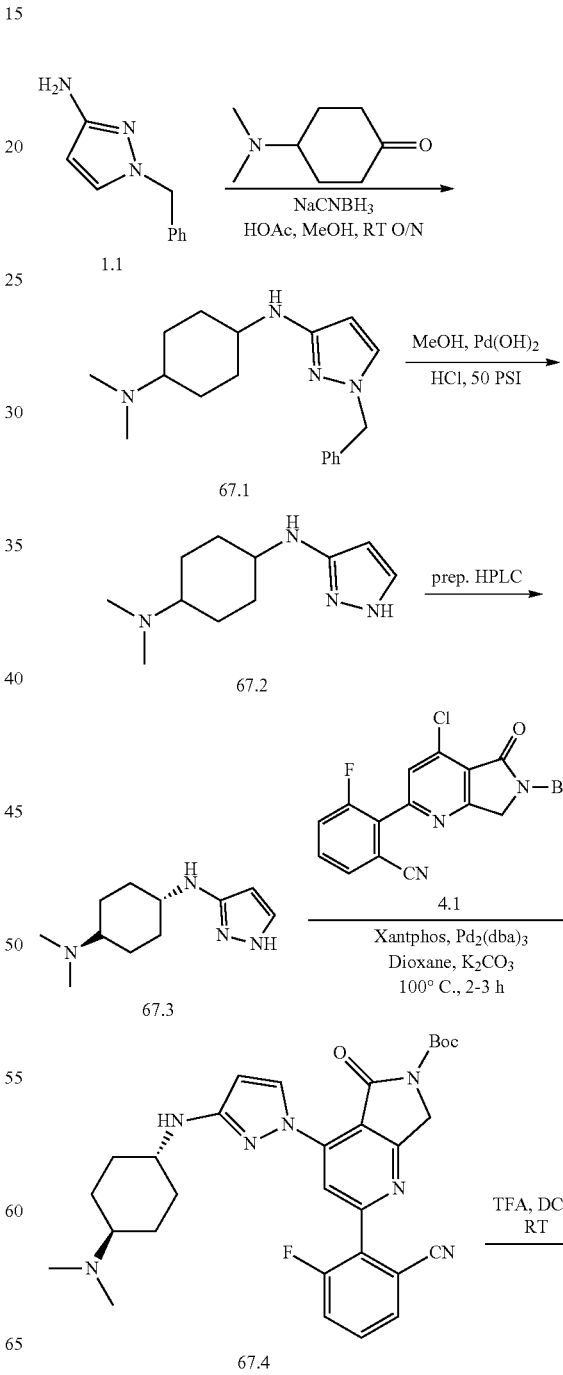

Synthesis of compound 66.1. To a solution of 56.1 (0.3 g, 1.17 mmol, 1.0 eq) in MeOH (10 ml) was added pyrrolidine (0.091 g, 1.29 mmol, 1.1 eq) and 10% Pd/C (0.1 g). Reaction mixture was stirred under 40 psi hydrogen pressure at room temperature for 16 h. Upon completion of the reaction, reaction mixture was filtered concentrated under reduced pressure to obtain crude which was purified by column chromatography to furnish 66.1. (0.22 g, 60.3%). MS(ES): m/z 311.5 [M+H]⁺.

Synthesis of compound 66.2. To a solution of 66.2 (0.2 g, 0.708 mmol, 1.0 eq) in MeOH (10 mL), 20% Pd(OH)₂ on charcoal (0.1 g) and 1N HCl (catalytic) were added. Reaction mixture was stirred under H₂ at 50 psi for 24 h. Upon completion of the reaction, reaction mixture was filtered and concentrated under reduced pressure to obtain crude material. The crude was purified by column chromatography to ge puret 1.2. (0.12 g, 76.9%). MS(ES): m/z 221.4 [M+H]⁺.

Synthesis of compound 66.3. Compound was prepared from 4.1 and 66.2 using the procedure described in Example 64.

Synthesis of compound I-66. Compound was prepared from 66.3 using the procedure described in Example 64.

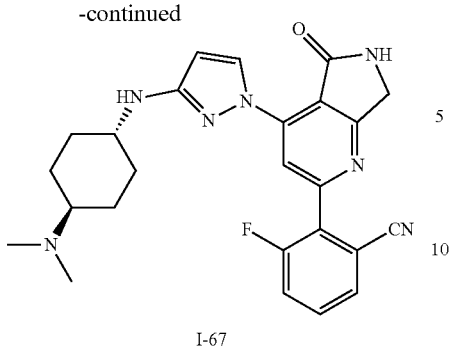

I-67

Synthesis of compound 67.1. To a solution of 1-benzyl-1H-pyrazol-3-amine (0.5 g, 2.89 mmol, 1.0 eq) in MeOH (15 mL) was added glacial acetic acid (1.5 mL) and mixture was stirred at room temperature for 2 h. Reaction mixture cooled to 0° C. and NaCNBH$_3$ (0.911 g, 14.45 mmol, 5.0 eq) was added portionwise. The reaction mixture was stirred at room temperature for 12 h. Upon completion of reaction, reaction mixture was transferred into water and product was extracted with EtOAc. Organic layers were combined, washed with brine, dried over Na$_2$SO$_4$ and concentrated under reduced pressure to get crude material which purified by column chromatography to get pure 67.1 (0.4 g, 46%). MS(ES): m/z 299.5 [M+H]$^+$.

Synthesis of compound 67.2. To the suspension of Pd(OH)$_2$ (0.5 g) in MeOH (10 mL) was added compound 67.1 (0.4 g, 1.34 mmol, 1.0 eq) followed by 1N HCl (catalytic) in hydrogenator and stirred under hydrogen pressure at 50 psi for 12 h. Reaction mixture filtered through celite and concentrated under reduced pressure to get 67.2 (0.220 g, 78%). MS(ES): m/z 209.4 [M+H]$^-$.

Synthesis of compound 67.3. Racemic mixture of 67.2 (0.22 g) was separated out using chiral column chromatography to furnish 67.3 (0.073 g), MS (ES): m/z 209.3 [M+H]$^+$, Synthesis of compound 67.4. Compound 67.4 was prepared from 67.3 and 4.1 using the procedure described in Example 64.

Synthesis of compound I-67. Compound I-67 was prepared using the procedure described in Example 64. MS(ES): m/z 460.20 [M+H]$^{+1}$H NMR (MeOD, 400 MHz): 9.61-9.60 (d, 1H), 8.21 (s, 1H), 7.81-7.79 (m, 1H), 7.76-7.64 (m, H), 6.00 (s, 1H), 4.56 (s, 2H), 2.85 (s, 6H), 2.40-2.37 (m, 3H), 2.14-2.11 (m, 3H), 1.73-1.65 (m, 2H), 1.43-1.34 (m, 3H).

Example 68

Synthesis of 2-(4-(3-(3-aminopiperidin-1-yl)-1H-pyrazol-1-yl)-5-oxo-6,7-dihydro-5H-pyrrolo[3,4-b]pyridin-2-yl)-3-fluorobenzonitrile I-68

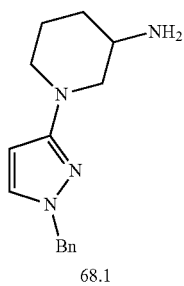

68.1

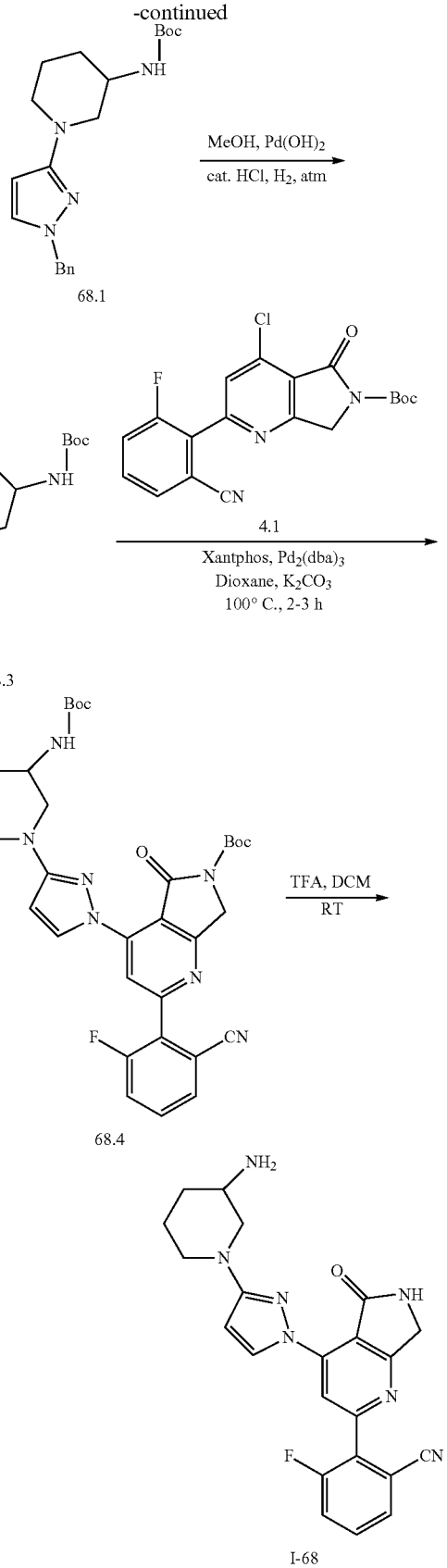

Synthesis of compound 68.2. To a solution of 68.1 (0.5 g, 1.9 mmol, 1.0 eq) in THF (10 mL) was added Et$_3$N (0.42 g, 39 mmol, 2.0 eq) and Di-tert-butyl dicarbonate (0.64 g, 2.9 mmol, 1.5 eq) at room temperature. Reaction mixture was stirred at room temperature for 16 h. Upon completion of the reaction; reaction mixture was transferred into water and extracted with DCM. Combined organic layers were washed with brine, dried over $Na_2SO_4$ and concentrated under reduced pressure to obtained crude which was purified by column chromatography 68.2. (0.35 g, 50.6%). MS(ES): m/z 357.35 $[M+H]^+$.

Synthesis of compound 68.3. To a solution of 68.2 (0.35 g, 0.981 mmol, 1.0 eq) in MeOH (5.0 mL), 20% $Pd(OH)_2$ (0.06 g) and 1N HCl (catalytic) were added. Reaction mixture was stirred under hydrogen at 40 psi for 24 h. Upon completion of the reaction, reaction mixture was filtered through celite and washed with MeOH. Solvents were removed under reduced pressure to afford crude which was purified by column chromatography to yield 68.3 (0.16 g, 61.2%). MS(ES): m/z 167.21 $[M+H]^+$.

Synthesis of compound 68.4. Compound was prepared from 68.3 and 4.1 using the procedure described in Example 64.

Synthesis of compound I-68. Compound was prepared from 68.4 using the procedure described in Example 64. MS(ES): m/z 418.3 $[M+H]^+$; $^1H$ NMR (DMSO-d6, 400 MHz): 9.77-9.76 (d, 1H), 9.11 (s, 1H), 8.16 (s, 1H), 7.92-7.90 (m, 1H), 7.81-7.76 (m, 2H), 6.33 (d, 1H), 4.49 (s, 2H), 3.77 (d, 1H), 3.68 (d, 1H), 2.79-2.67 (m, 1H), 1.85-1.82 (m, 1H), 1.72-1.68 (m, 1H), 1.55-1.49 (m, 1H), 1.37-1.35 (m, 4H).

Example 69

Synthesis of (R)-3-fluoro-2-(4-(3-(3-hydroxypiperidin-1-yl)-1H-pyrazol-1-yl)-5-oxo-6,7-dihydro-5H-pyrrolo[3,4-b]pyridin-2-yl)benzonitrile, I-69

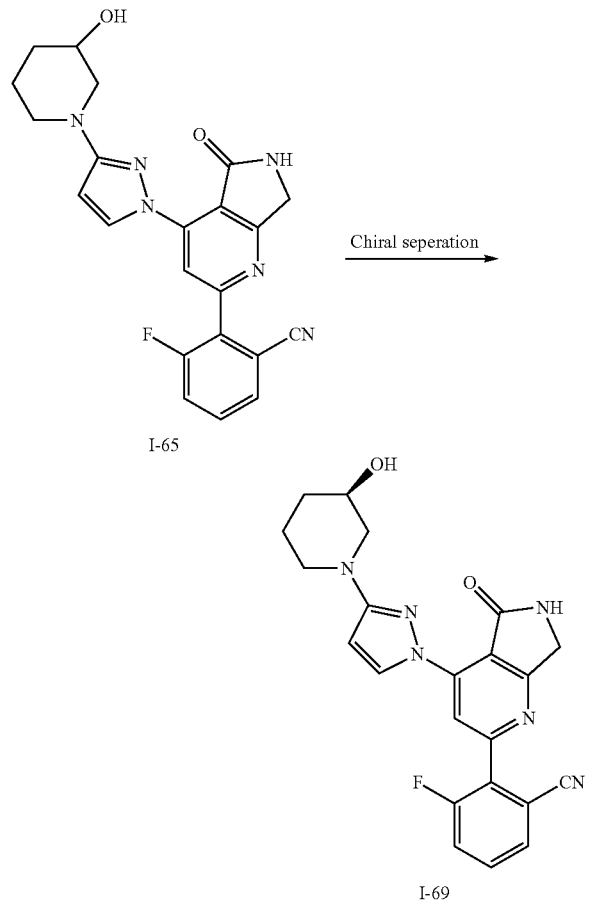

Compound I-69 was prepared by chiral purification of compound I-65. MS(ES): m/z 434 $[M+H]^+$; $^1H$ NMR (DMSO-d6, 400 MHz): 9.76-9.75 (d, 1H), 9.1 (s, 1H), 8.16 (s, 1H), 7.91-7.89 (dd1H), 7.82-7.75 (m, 2H), 6.34-6.33 (d, 1H), 4.84-4.83 (d, 1H), 4.49 (s, 2H), 3.79-3.75 (m, 1H), 3.62-3.52 (m, 2H), 2.85-2.78 (m, 1H), 2.68-2.65 (m, 1H), 1.91-1.88 (m, 1H), 1.75-1.72 (m, 1H), 1.53-1.48 (m, 1H), 1.35-1.29 (m, 1H).

Example 70

Synthesis of (S)-3-fluoro-2-(4-(3-(3-hydroxypiperidin-1-yl)-1H-pyrazol-1-yl)-5-oxo-6,7-dihydro-5H-pyrrolo[3,4-b]pyridin-2-yl)benzonitrile, I-70

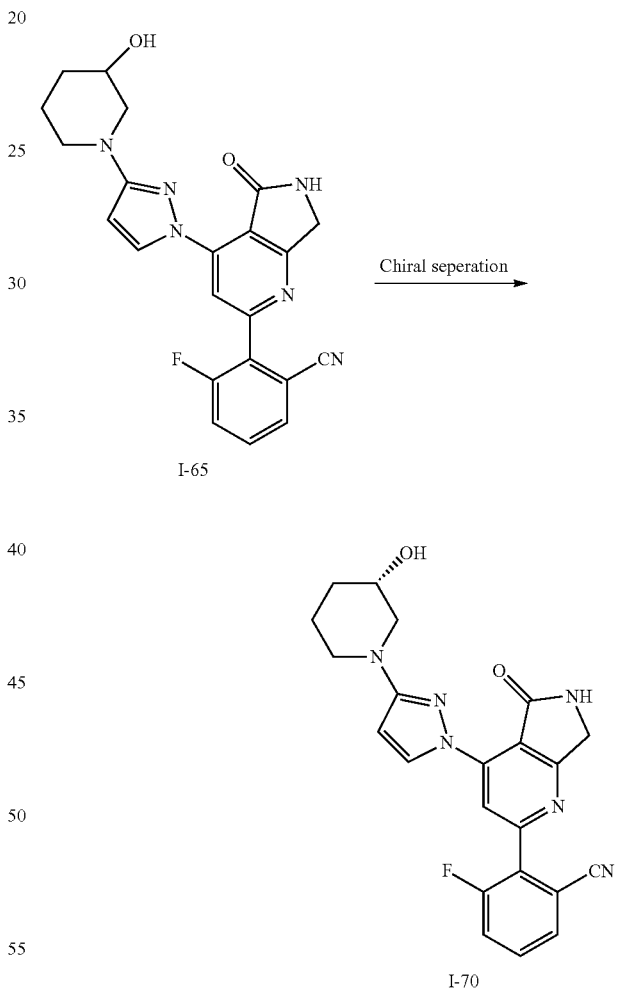

Compound I-70 was prepared by chiral purification of compound I-65. MS(ES): m/z 434 $[M+H]^+$; $^1H$ NMR (DMSO-d6, 400 MHz): 9.76-9.75 (d, 1H), 9.1 (s, 1H), 8.16 (s, 1H), 7.91-7.89 (dd, 1H), 7.82-7.75 (m, 2H), 6.34-6.33 (d, 1H), 4.84-4.83 (d, 1H), 4.49 (s, 2H), 3.79-3.75 (m, 1H), 3.62-3.52 (m, 2H), 2.85-2.78 (m, 1H), 2.68-2.65 (m, 1H), 1.91-1.88 (m, 1H), 1.75-1.72 (m, 1H), 1.53-1.48 (m, 1H), 1.35-1.29 (m, 1H).

Example 71

Synthesis of (R)-3-fluoro-2-(4-(3-(3-hydroxy-3-methylpiperidin-1-yl)-1H-pyrazol-1-yl)-5-oxo-6,7-dihydro-5H-pyrrolo[3,4-b]pyridin-2-yl)benzonitrile, I-71

Example 72

Synthesis of (S)-3-fluoro-2-(4-(3-(3-hydroxy-3-methylpiperidin-1-yl)-1H-pyrazol-1-yl)-5-oxo-6,7-dihydro-5H-pyrrolo[3,4-b]pyridin-2-yl)benzonitrile, I-72

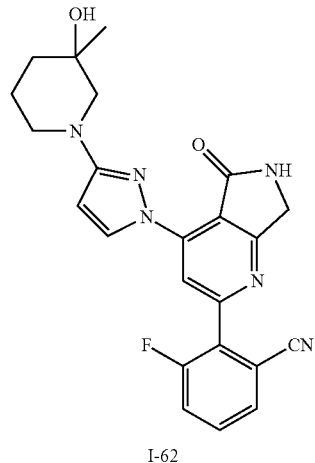

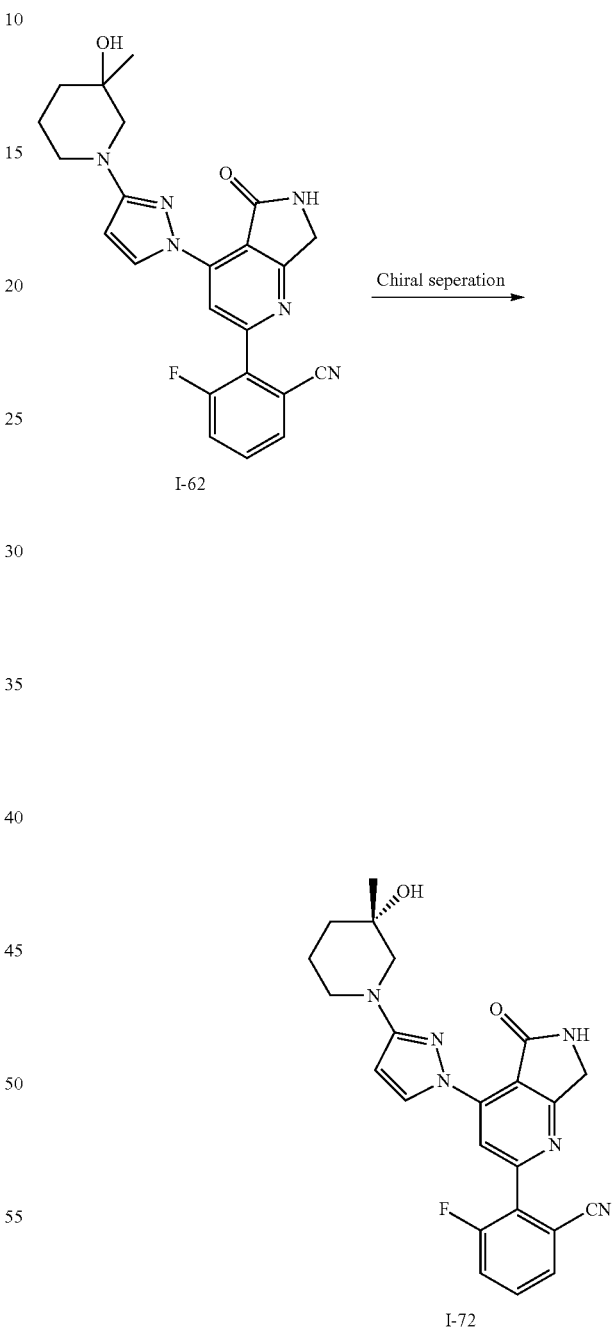

Compound I-71 was prepared by chiral purification of compound I-62. MS(ES): m/z 433 [M+H]$^+$; $^1$H NMR (DMSO-d$_6$, 400 MHz): 9.76 (d, 1H), 9.09 (s, 1H), 8.16 (s, 1H), 7.92-7.90 (m, 1H), 7.83-7.73 (m, 2H), 6.33 (d, 1H), 4.49 (s, 3H), 3.31-3.28 (m, 1H), 3.24-3.20 (m, 1H), 3.11 (s, 2H), 1.78-1.77 (m, 1H), 1.52 (s, 3H), 1.13 (s, 3H).

Compound I-72 was prepared by chiral purification of compound I-62. MS(ES): m/z 433 [M+H]$^+$; $^1$H NMR (DMSO-d$_6$, 400 MHz): 9.76 (d, 1H), 9.09 (s, 1H), 8.16 (s, 1H), 7.92-7.90 (m, 1H), 7.81-7.75 (m, 2H), 6.33 (d, 1H), 4.49 (s, 3H), 3.31-3.28 (m, 1H), 3.24-3.20 (m, 1H), 3.11 (s, 2H), 1.78-1.77 (m, 1H), 1.52 (s, 3H), 1.13 (s, 3H).

Example 73

Synthesis of (R)-2-(4-(3-(3-aminopiperidin-1-yl)-1H-pyrazol-1-yl)-5-oxo-6,7-dihydro-5H-pyrrolo[3,4-b]pyridin-2-yl)-3-fluorobenzonitrile, I-73

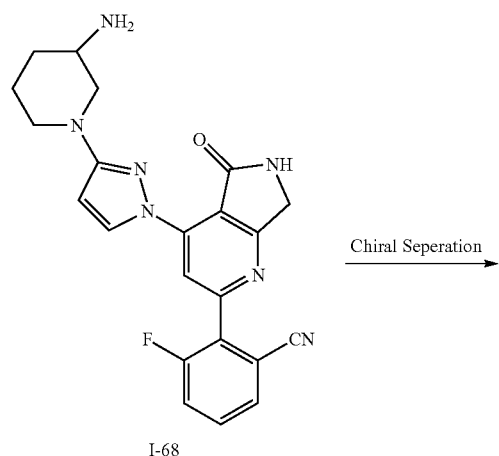

I-68

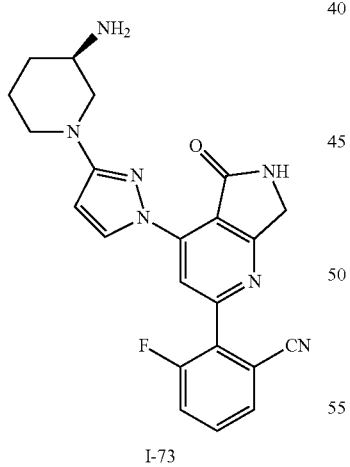

I-73

Compound I-73 was prepared by chiral purification of compound I-68. MS(ES): m/z 418.6 [M+H]$^+$; $^1$H NMR (DMSO-d$_6$, 400 MHz): 9.78-9.77 (d, 1H), 9.11 (s, 1H), 8.16 (s, 1H), 7.91 (d, 1H), 7.83-7.76 (m, 2H), 6.17-6.16 (d, 1H), 5.80-5.75 (m, 2H), 4.49 (s, 2H), 3.80-3.72 (m, 4H), 3.48-3.45 (m, 4H), 2.38-2.33 (m, 1H), 2.08 (s, 1H), 1.86-1.83 (m, 2H), 1.75-1.72 (m, 2H).

Example 74

Synthesis of (S)-2-(4-(3-(3-aminopiperidin-1-yl)-1H-pyrazol-1-yl)-5-oxo-6,7-dihydro-5H-pyrrolo[3,4-b]pyridin-2-yl)-3-fluorobenzonitrile, I-74

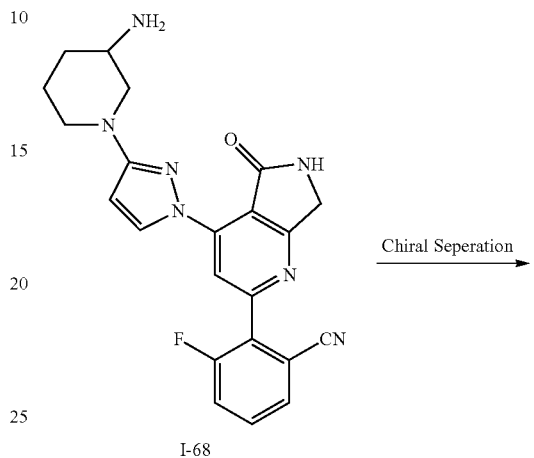

I-68

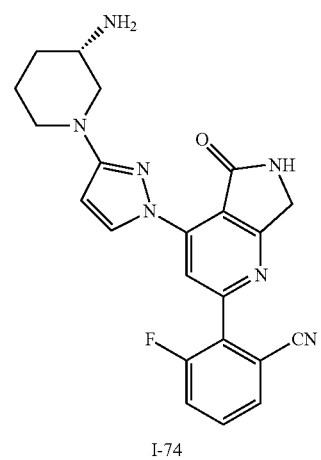

I-74

Compound I-68 was prepared by chiral purification of compound I-68. MS(ES): m/z 418.6 [M+H]$^+$; $^1$H NMR (DMSO-d$_6$, 400 MHz): 9.78-9.77 (d, 1H), 9.12 (s, 1H), 8.16 (s, 1H), 7.92 (d, 1H), 7.83-7.74 (m, 2H), 6.17-6.16 (d, 1H), 5.80-5.75 (m, 2H), 4.49 (s, 2H), 3.80-3.72 (m, 4H), 3.48-3.45 (m, 4H), 2.38-2.33 (m, 1H), 2.08 (s, 1H), 1.86-1.83 (m, 2H), 1.75-1.72 (m, 2H).

Example 75

Synthesis of 3-fluoro-2-(5-oxo-4-(4,5,6,7-tetra-hydro-2H-pyrazolo[3,4-b]pyridin-2-yl)-6,7-dihydro-5H-pyrrolo[3,4-b]pyridin-2-yl)benzonitrile, I-75

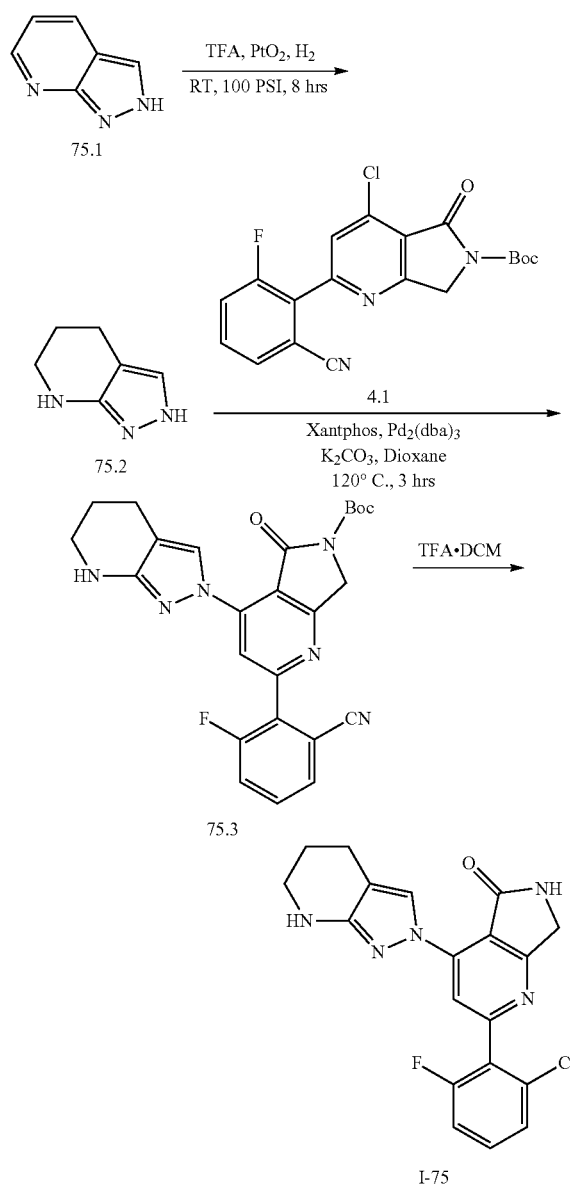

Synthesis of compound I-75. Compound I-75 was prepared from compound 75.3 using the procedure described in Example 64. MS(ES): m/z 375.46[M+H]+; $^1$H NMR (DMSO-$d_6$, 400 MHz): 9.53 (s, 1H), 9.03 (s, 1H), 8.04 (s, 1H), 7.90-7.88 (m, 1H), 7.79-7.74 (m, 2H), 6.40 (s, 1H), 4.45 (s, 2H), 3.19 (br, 2H), 2.67-2.61 (m, 2H), 1.79 (br, 2H).

Example 76

Synthesis of 3-fluoro-2-(4-(3-(3-hydroxypyrrolidin-1-yl)-1H-pyrazol-1-yl)-5-oxo-6,7-dihydro-5H-pyrrolo[3,4-b]pyridin-2-yl)benzonitrile, I-76

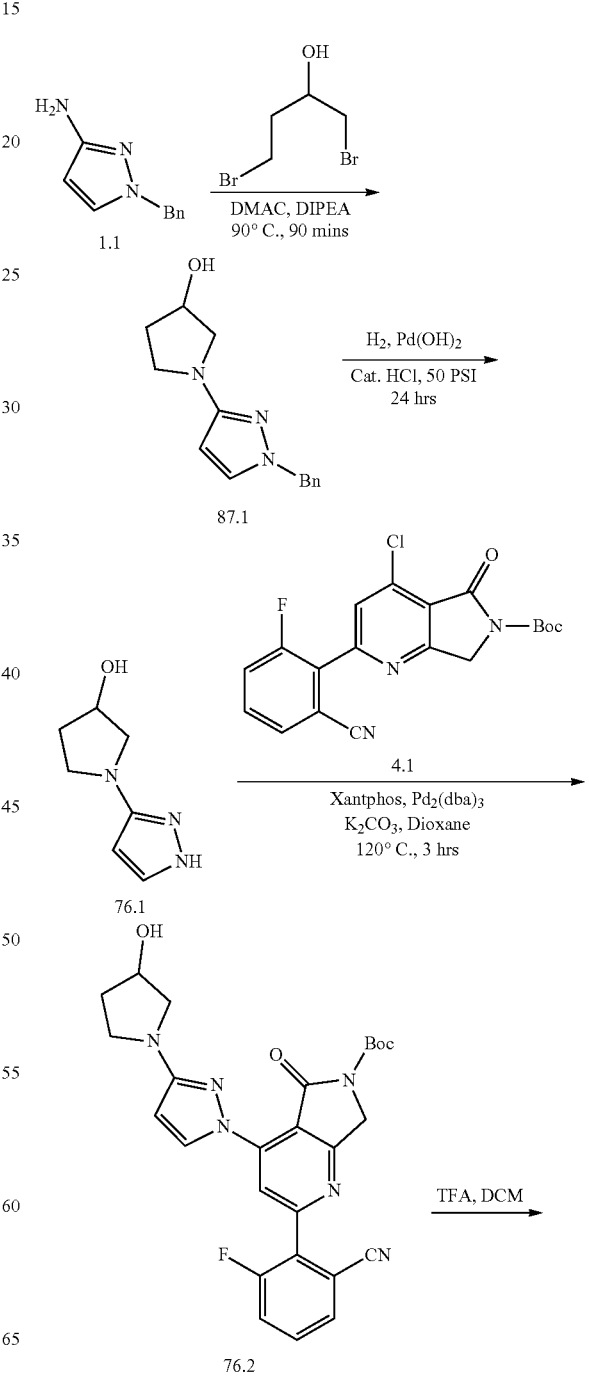

Synthesis of compound 75.2. To the solution of compound 75.1 (0.5 g, 4.2 mmol, 1.0 eq) in TFA (5.0 mL) was added PtO$_2$ (0.095 g, 0.42 mmol, 0.1 eq.) in hydrogenator and stirred under hydrogen pressure at 100 psi for 8 h. Reaction mixture was filtered through celite and concentrated under reduced pressure to get material which is diluted with DCM and basified with methanolic ammonia. Solvents were removed under reduced pressure and resulting crude was purified by column chromatography to furnish 75.2 (0.4 g, 77.33%). MS(ES): m/z 124.5 [M+H]+.

Synthesis of compound 75.3. Compound 75.3 was prepared from compound 75.2 and 4.1 using the procedure described in Example 64

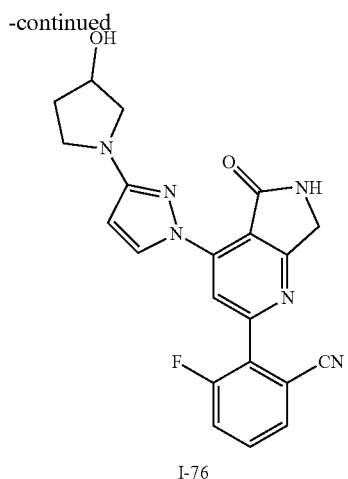

I-76

Synthesis of compound 87.1. To a solution of 1.1 (2 g, 11.56 mmol, 1 eq) in DMA (10 mL) was added 1,4-dibromobutan-2-ol (3 g, 12.66 mmol, 1.1 eq) followed by DIPEA (5.0 mL, 28.9 mmol, 2.5 eq). Reaction was stirred at 90° C. in microwave for 1 h. Upon completion of the reaction, mixture was transferred into water and extracted with EtOAc. Organic layers were washed with brine, dried over $Na_2SO_4$ and concentrated under reduced pressure to get crude which was purified by chromatography to furnish 87.1 (2.0 g, 71.2%). MS(ES): m/z 244.14 [M+H]$^+$.

Synthesis of compound 76.1 To a Solution of 87.1 (2 g, 8.23 mmol, 1.0 eq) in MeOH (3.0 mL) was added Pd(OH)$_2$ (0.5 g) and 1N HCl (0.5 mL). The mixture was stirred in hydrogenator under hydrogen (50 psi) at room temperature for 24 h. Upon completion of the reaction, mixture was filtered, solvents removed under reduced pressure to provide 76.1 (0.65 g, 51.6%). MS(ES): m/z 154.09 [M+H]$^+$.

Synthesis of compound 76.2 Compound was prepared from 76.1 and 4.1 using the procedure described in Example 64.

Synthesis of compound I-76. Compound was prepared from 76.2 using the procedure described in Example 64. MS(ES): m/z 405.12 [M+H]$^+$; $^1$H NMR (DMSO-$d_6$, 400 MHz): 9.79-9.78 (d, 1H), 9.09 (s, 1H), 8.17 (s, 1H), 7.924-7.904 (d, 1H), 7.81-7.77 (m, 2H), 6.14 (d, 1H), 4.94-4.93 (d, 1H), 4.48 (s, 2H), 4.36 (s, 1H), 3.48-3.41 (m, 3H), 3.23-3.21 (m, 1H), 2.09 (s, 1H), 2.01-1.99 (s, 1H), 1.87-1.85 (m, 1H).

Example 77

Synthesis of 3-fluoro-2-(5-oxo-4-(4,5,6,7-tetra-hydro-2H-pyrazolo[4,3-b]pyri-din-2-yl)-6,7-dihydro-5H-pyrrolo[3,4-b]pyridin-2-yl)benzonitrile, I-77

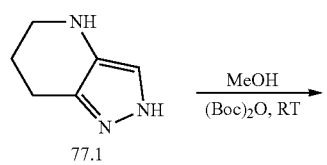

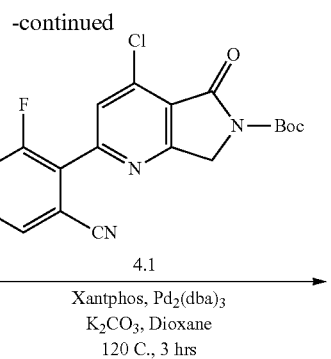

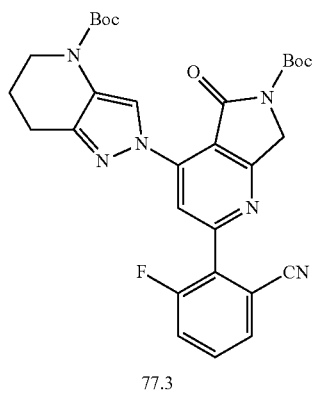

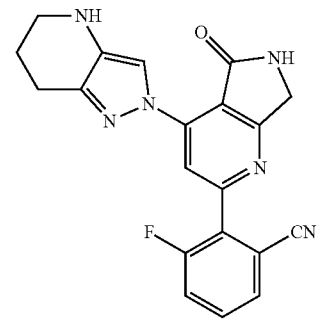

I-77

Synthesis of compound 77.2. To a solution 77.2 (0.1 g, 0.81 mmol, 1.0 eq) in MeOH (4 mL) was added (BOC)$_2$O (0.212 g, 0.975 mmol, 1.2 eq). The reaction was stirred at room temperature for 1 h. Upon completion of the reaction, mixture was transferred into water and extracted with EtOAc. Organic layers were combined, washed with brine, dried over $Na_2SO_4$ and concentrated under reduced pressure to obtain crude which was purified by column chromatography to provide 77.2 (0.105 g, 57.9%). MS(ES): m/z 224.14 [M+H]$^+$.

Synthesis of compound 77.3. Compound was prepared from 77.2 and 4.1 using the procedure described in Example 64.

Synthesis of compound I-77. Compound was prepared from 77.3 using the procedure described in Example 64. MS(ES): m/z 375.12[M+H]$^+$; $^1$H NMR (DMSO-$d_6$, 400 MHz): 9.16 (s, 1H), 9.08 (s, 1H), 8.2 (s, 1H), 7.9 (m, 1H), 7.81-7.74 (m, 2H), 5.27 (s, 1H), 4.47 (m, 2H), 3.07 (m, 2H), 2.74-2.67 (m, 2H), 1.87-1.86 (m, 2H).

Example 78

Synthesis of (R)-3-fluoro-2-(4-(3-(3-hydroxypyrrolidin-1-yl)-1H-pyrazol-1-yl)-5-oxo-6,7-dihydro-5H-pyrrolo[3,4-b]pyridin-2-yl)benzonitrile, I-78

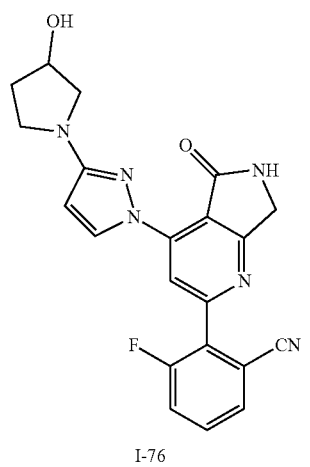

I-76

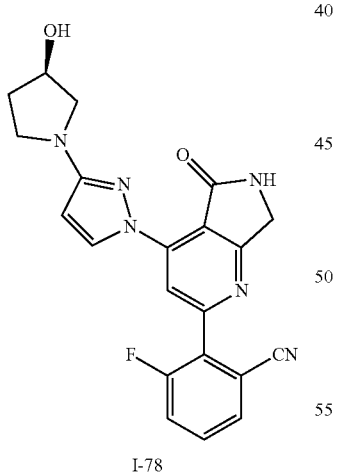

I-78

Compound I-78 was prepared by chiral purification of compound I-76. MS(ES): m/z 434 [M+H]−; $^1$H NMR (DMSO-d$_6$, 400 MHz): 9.79-9.78 (d, 1H), 9.1 (s, 1H), 8.17 (s, 1H), 7.91-7.89 (d, 1H), 7.83-7.73 (m, 2H), 6.14-6.13 (d, 1H), 4.95-4.94 (d, 1H), 4.48 (s, 2H), 4.36 (s, 1H), 3.47-3.44 (m, 3H), 3.23-3.2 (m, 1H), 2.09 (s, 1H), 2.01-1.99 (s, 1H), 1.87-1.85 (m, 1H).

Example 79

Synthesis of (S)-3-fluoro-2-(4-(3-(3-hydroxypyrrolidin-1-yl)-1H-pyrazol-1-yl)-5-oxo-6,7-dihydro-5H-pyrrolo[3,4-b]pyridin-2-yl)benzonitrile, I-79

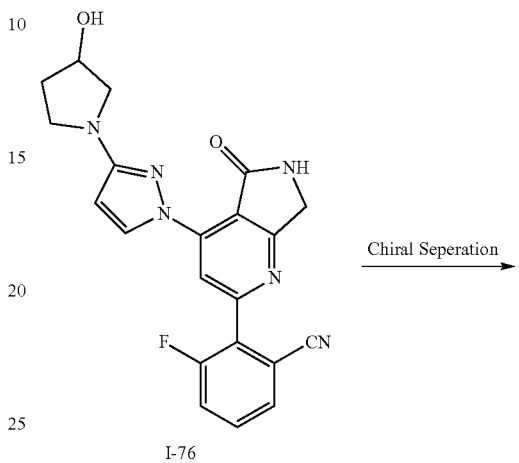

I-76

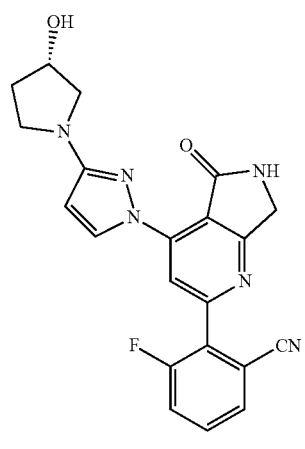

I-79

Compound I-79 was prepared by chiral purification of compound I-76. MS(ES): m/z 434 [M+H]+; $^1$H NMR (DMSO-d$_6$, 400 MHz): 9.79-9.78 (d, 1H), 9.1 (s, 1H), 8.17 (s, 1H), 7.91-7.89 (d, 1H), 7.83-7.73 (m, 2H), 6.14-6.13 (d, 1H), 4.95-4.94 (d, 1H), 4.48 (s, 2H), 4.36 (s, 1H), 3.47-3.44 (m, 3H), 3.23-3.2 (m, 1H), 2.09 (s, 1H), 2.01-1.99 (s, 1H), 1.87-1.85 (m, 1H).

Example 80

Synthesis of 3-fluoro-2-(4-(3-(3-hydroxy-3-(trifluoromethyl)piperidin-1-yl)-1H-pyrazol-1-yl)-5-oxo-6,7-dihydro-5H-pyrrolo[3,4-b]pyridin-2-yl)benzonitrile, I-80

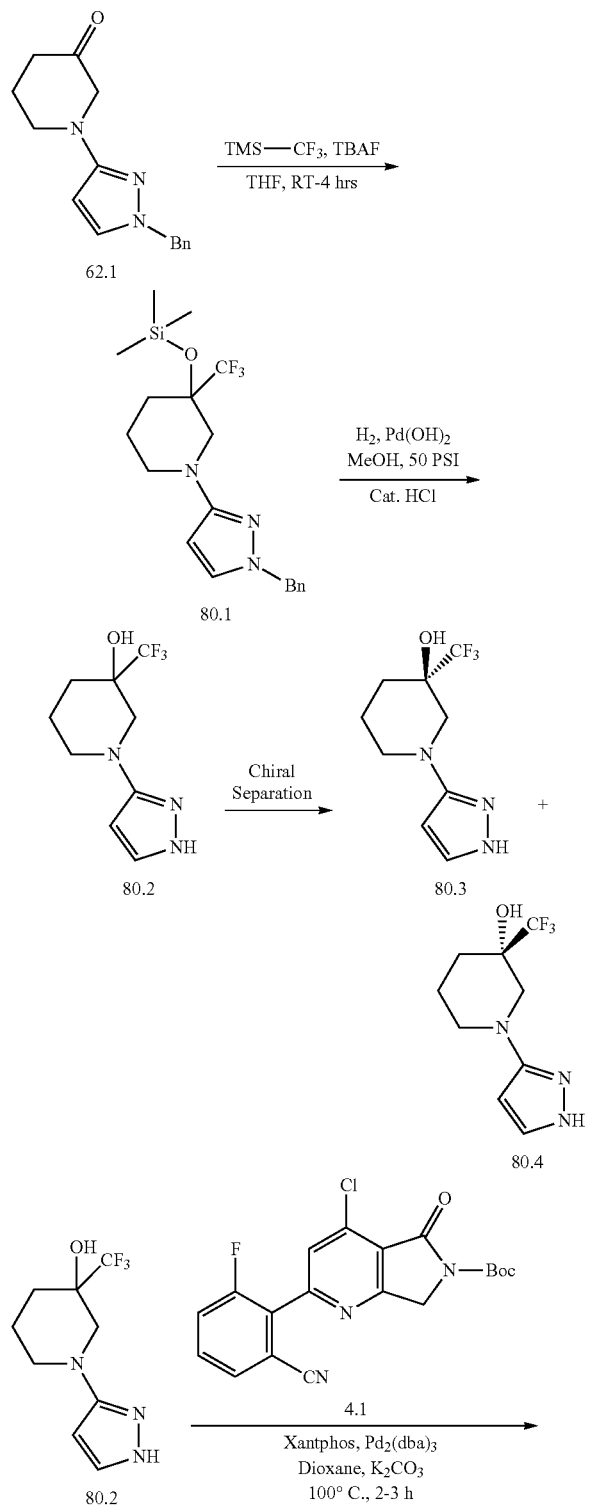

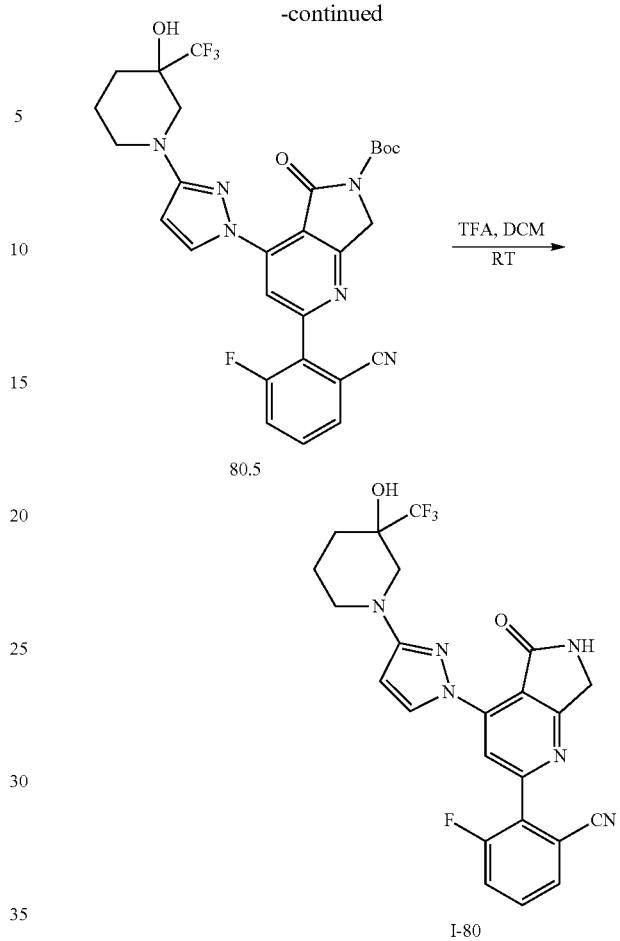

Synthesis of compound 80.1. To a solution of 62.1 (2.0 g, 7.83 mmol, 1.0 eq) in THF (20.0 ml), Trifluoromethyltrimethylsilane (5.56 g, 39.1 mmol, 5.0 eq) and TBAF (0.204 g, 0.78 mmol, 0.1 eq) were added. Reaction was stirred at room temperature for 6 hr. Upon completion of the reaction, mixture was transferred into water, extracted with EtOAc, dried over $Na_2SO_4$ and concentrated under reduced pressure to obtain crude which was purified by column chromatography to provide 80.1 (2.1 g, 67.7%). MS(ES): m/z 398 [M+H]$^+$.

Synthesis of compound 80.2. To a solution of 80.1 (2.0 g, 5.03 mmol, 1.0 eq) in MeOH (20.o mL). Pd(OH)$_2$/C (0.4 g) and 1.0 NHCl (catalytic amount) were added. Reaction mixture was stirred at 40 psi of $H_2$ for 15 h. Upon completion of the reaction, mixture was filtered through concentrated under reduced pressure to obtain crude which was purified by column chromatography to get 80.2. (0.32 g, 27.11%). MS(ES): m/z 236 [M+H]$^+$.

Synthesis of compounds 80.3 and 80.4. Compounds were prepared by chiral purification of 80.2.

Synthesis of compound 80.5. Compound 80.5 was prepared from compounds 80.2 and 4.1. using the procedure described in Example 56.

Synthesis of compound I-80. Compound was prepared from 80.5 using the procedure described in using the procedure described in Example 56. MS(ES): m/z 487 [M+H]$^+$; $^1$H NMR (DMSO-d$_6$, 400 MHz): 9.75 (d, 1H), 9.11 (s, 1H), 8.16 (d, 1H), 7.92-7.90 (m, 1H), 7.83-7.73 (m, 2H), 6.38 (d, 1H), 6.02 (s, 1H), 4.49 (s, 2H), 3.85 (d, 1H), 3.75 (d, 1H), 3.08 (d, 1H), 2.88-2.82 (m, 1H), 1.90-1.79 (m, 2H), 1.73-1.70 (m, 1H), 1.66-1.60 (m, 1H).

Example 81

Synthesis of 3-fluoro-2-(4-(3-(methylsulfonyl)-1H-pyrazol-1-yl)-5-oxo-6,7-dihydro-5H-pyrrolo[3,4-b]pyridin-2-yl)benzonitrile, I-81

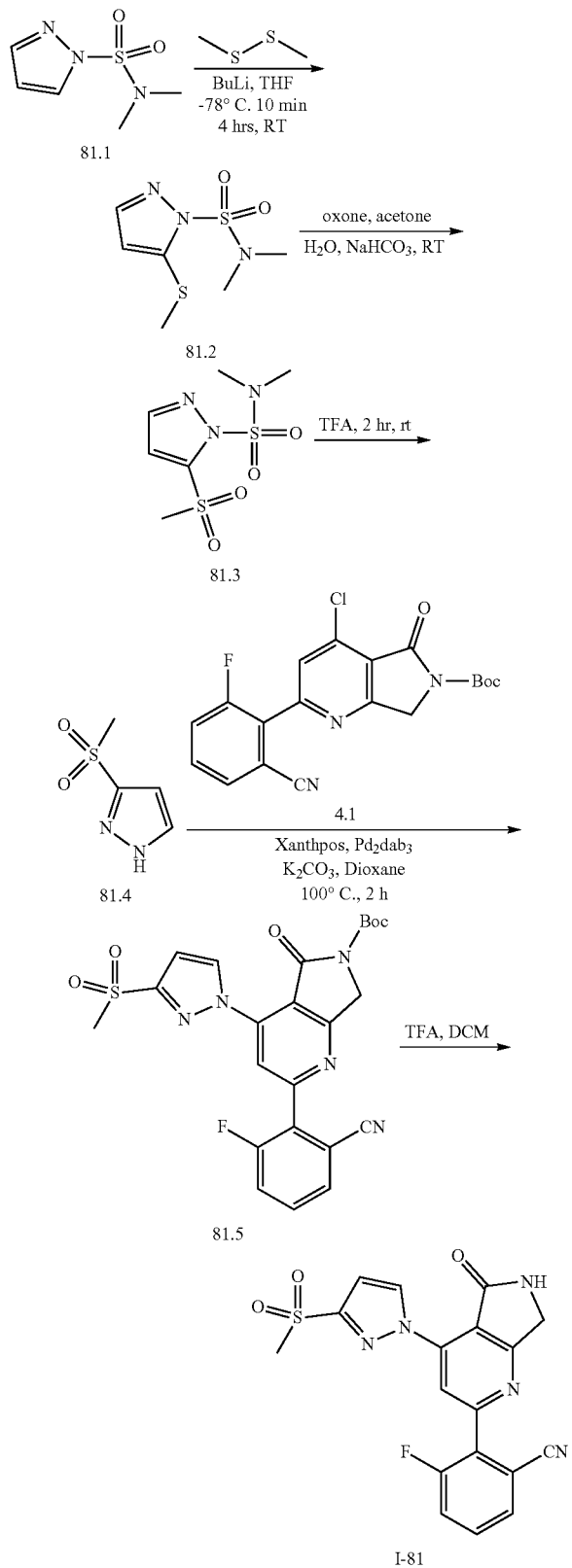

Synthesis of compound 81.2. To a solution of n-butyl lithium (3.9 mL, 1.1 eq) in THF (4.0 mL) was added 81.1 (1 g, 5.71 mmol, 1 eq) in tetrahydrofuran (2 mL) at −78° C. To this mixture was added 1,2-dimethyldisulfane (0.6 mL, 1.5 eq) and the resulting mixture was stirred at room temperature for 4 h. Upon completion of the reaction, reaction mixture was transferred into water and extracted with EtOAc. Organic layers were combined, washed with brine, dried over $Na_2SO_4$ and concentrated under reduced pressure to obtain crude which was purified by column chromatography to provide 81.2 (1.0 g, 79.2%). MS(ES): m/z 223.10 $[M+H]^+$.

Synthesis of compound 81.3. To a solution of 81.2 (0.4 g, 1.8 mmol, 1 eq) in acetone (8 mL) was added $NaHCO_3$ (0.76 g, 9.04 mmol, 5.0 eq), oxone (2.77 g, 4.52 mmol, 2.5 eq) at 0° C. and the resulting mixture was stirred at room temperature for 2 h. Upon completion of the reaction, reaction mixture was transferred into water and extracted with EtOAc. Organic layers were combined, washed with brine, dried over $Na_2SO_4$ and concentrated under reduced pressure to obtain crude which was purified by column chromatography to provide 81.3 (0.25 g, 54.6%). MS(ES): m/z 255.12 $[M+H]^+$.

Synthesis of compound 81.4. The compound 1.3 (0.13 g, 0.51 mmol, 1.0 eq) was dissolved in DCM (1.0 mL) and TFA (0.5 mL) was added to the reaction mixture. The reaction was stirred at room temperature for 1 h. Upon completion of reaction, reaction mixture was transferred into water, basified with saturated bicarbonate solution and extracted with EtOAc. Organic layers were combined and dried over $Na_2SO_4$ and concentrated under reduced pressure to obtain crude 81.4. This was used in to next step without further purification. (0.07 g, 93%). MS(ES): m/z 147 $[M+H]^+$.

Synthesis of compound 81.5. Compound was prepared from 81.4 and 4.1 using the procedure described in Example 64.

Synthesis of I-81. (0.018 g, 34.1%). MS(ES): m/z 398.2 $[M+H]^+$; $^1H$ NMR (DMSO-$d_6$, 400 MHz): 9.6-9.59 (d, 1H), 9.36 (s. 1H), 8.32 (m, 1H), 7.95-7.93 (dd, 1H), 7.86-7.79 (m, 2H), 7.18-1.17 (d, 1H), 4.61 (s, 2H), 3.4 (s, 3H).

Example 82

Synthesis of 3-fluoro-2-(4-(3-(3-(2-methoxyethoxy) azetidin-1-yl)-1H-pyrazol-1-yl)-5-oxo-6,7-dihydro-5H-pyrrolo[3,4-b]pyridin-2-yl)benzonitrile, I-82

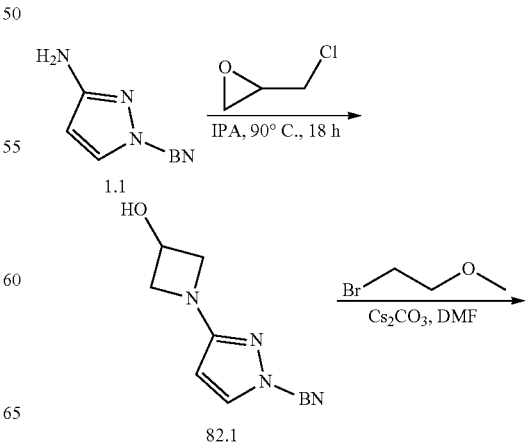

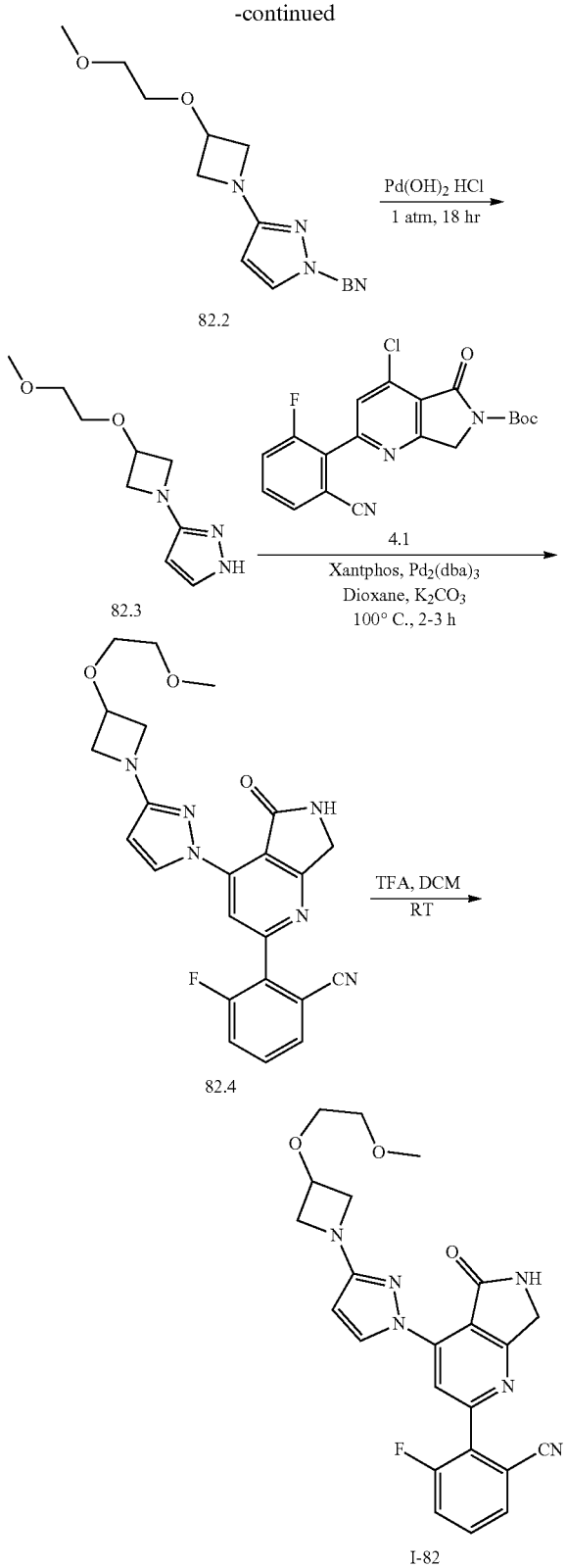

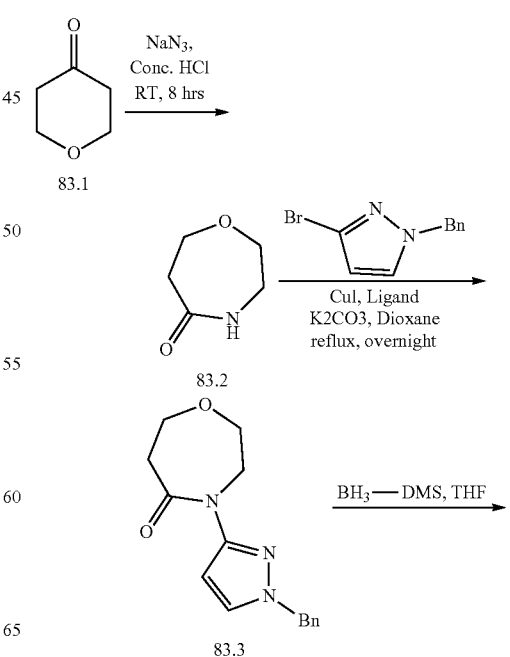

water and product was extracted with EtOAc. Organic layers were combined, washed with brine solution, dried over Na₂SO₄ and concentrated under reduced pressure to get crude which was purified by column chromatography to furnish 82.1 (0.8 g, 60.44%). MS(ES): m/z 230.5 [M+H]⁺.

Synthesis of compound 82.2. To 82.1 (0.8 g, 3.49 mmol, 1.0 eq) in DMF (5 mL) was added 1-bromo-2-methoxyethane (0.53 g, 3.84 mmol, 1.10 eq) and Cs₂CO₃ (1.7 g, 5.24 mmol, 1.5 eq.). Reaction mixture was stirred at 50° C. for 3 h. Upon completion of the reaction, reaction mixture was transferred into water and product was extracted with EtOAc. Organic layers were combined, washed with brine solution, dried over Na₂SO₄ and concentrated under reduced pressure to get pure 82.2 (0.45 g, 44.9%). MS(ES): m/z 288.4 [M+H]⁺.

Synthesis of compound 82.3. To the suspension of Pd(OH)₂ (0.25 g) in MeOH (5.0 mL) was added compound 82.2 (0.45 g, 1.57 mmol, 1.0 eq) followed by 1N HCl (catalytic) in hydrogenator and stirred under hydrogen pressure (1 atm) for 18 h. Reaction mixture filtered through celite and concentrated under reduced pressure to get crude which was purified by column chromatography to furnish 82.3 (0.21 g, %). MS(ES): m/z 139.9 [M+H]⁺.

Synthesis of compound 82.4. Compound 82.4 was prepared from compound 82.3 and 4.1 using the procedure from Example 64.

Synthesis of compound I-82. Compound I-82 was prepared from compound 82.4 using the procedure described in Example 64. MS(ES): m/z 449.28[M+H]⁺; ¹H NMR (MeOD, 400 MHz): 7.84-7.82 (m, 1H), 7.74-7.63 (m, 2H), 7.52 (s, 1H), 7.26 (s, 1H), 5.65 (s, 1H), 5.43 (s, 1H), 4.52 (s, 2H), 4.42-4.41 (m, 1H), 3.74-3.52 (m, 4H), 3.45-3.39 (m, 2H), 3.33-3.32 (m, 2H), 3.22 (s, 3H).

Example 83

Synthesis of 2-(4-(3-(1,4-oxazepan-4-yl)-1H-pyrazol-1-yl)-5-oxo-6,7-dihydro-5H-pyrrolo[3,4-b]pyridin-2-yl)-3-fluorobenzonitrile, I-83

Synthesis of compound 82.1. To a solution of 1.1 (1.0 g, 5.78 mmol, 1.0 eq) in 2-propanol (5.0 mL) was added 2-(chloromethyl) oxirane (0.7 g, 7.51 mmol, 1.3 eq). The reaction mixture was stirred at 90° C. for 18 h. Upon completion of the reaction, reaction mixture was poured into

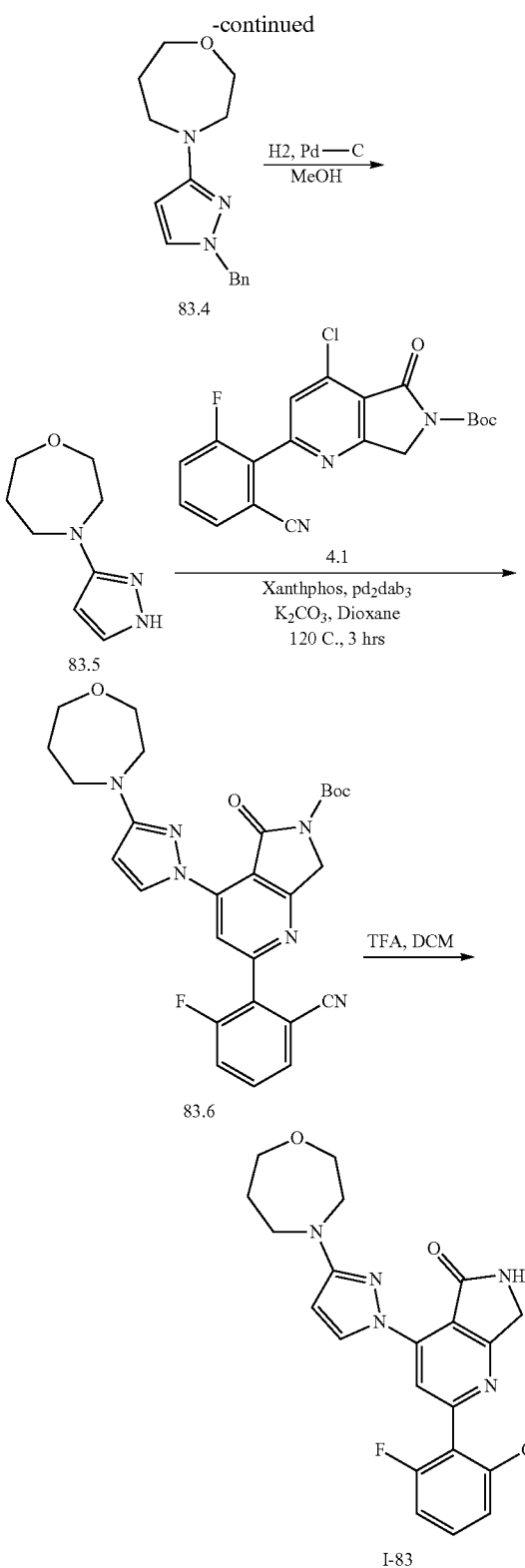

organic layers were washed with brine solution, dried over sodium sulphate and concentrated under reduced pressure to obtained crude. 83.2. (4.0 g, 34.8%). MS(ES): m/z 116.3 [M+H]⁻.

Synthesis of compound 83.3. To a solution of 1-benzyl-3-bromo-1H-pyrazole (0.5 g, 2.9 mmol, 1.0 eq) in 1,4 dioxane (10 ml) was added 83.2 (0.686 g, 4.3 mmol, 1.5 eq), CuI (0.027 g, 0.14 mmol, 0.05 eq), $K_2CO_3$ (0.8 g, 5.80 mmol, 2.0 eq) and trans-N,N'-Dimethylcyclohexane-1,2-diamine (0.02 g, 0.14 mmol, 0.05 eq) at room temperature and reaction mixture was stirred at 140° C. for 18 h. Upon completion of the reaction, mixture was transferred into water and product was extracted with EtOAc. Organic layers were combined, washed with brine, dried over sodium sulphate and concentrated under reduced pressure to obtain crude which was purified by column chromatography to get pure 83.3 (0.16 g, 20.4%). MS(ES): m/z 272.4 [M+H]⁺.

Synthesis of compound 83.4. To a solution of 83.2 (0.16 g, 0.58 mmol 1.0 eq) in THF (5 ml) was added Borane dimethyl sulfide (0.23 mL, 2.32 mmol, 4 eq) at 0° C. Reaction was stirred at room temperature for 2 h. Upon completion of the reaction, reaction mixture was concentrated under reduced pressure to obtain crude which was purified by column chromatography get pure 83.4 (0.1 g, 65.9%). MS(ES): m/z 258.4 [M+H]⁺.

Synthesis of compound 83.5. To a solution of 83.4 (0.1 g, 0.388 mmol, 1.0 eq) in MeOH (10 mL), 20% palladium hydroxide on charcoal (0.03 g) and 1N HCl (catalytic) were added. Reaction mixture was stirred under hydrogen at 40 psi for 24 h. Upon completion of the reaction, reaction mixture was filtered through celite and washed with methanol and concentrated under reduced pressure to obtain crude material. The crude was purified by column chromatography to get pure to get 83.5 (0.06 g, 92.34%). MS(ES): m/z 168.21 [M+H]⁺.

Synthesis of compound 83.6. Compound was prepared using the procedure described in Example 64.

Synthesis of compound I-83. Compound was prepared using the procedure described in Example 64. (0.020 g, 49.57%). MS(ES): m/z 419.28 [M+H]⁺; ¹H NMR (DMSO-d6, 400 MHz): 9.77-9.76 (d, 1H), 9.10 (s, 1H), 8.16 (s, 1H), 7.92-7.89 (m, 1H), 7.83-7.72 (m, 2H), 6.30-6.29 (d, 1H), 4.48 (s, 2H), 3.73-3.71 (m, 2H), 3.53-3.58 (m, 6H), 1.91-1.86 (m, 2H).

Example 84

Synthesis of 2-(4-(3-(3-amino-3-(trifluoromethyl) piperidin-1-yl)-1H-pyrazol-1-yl)-5-oxo-6,7-dihydro-5H-pyrrolo[3,4-b]pyridin-2-yl)-3-fluorobenzonitrile, I-84

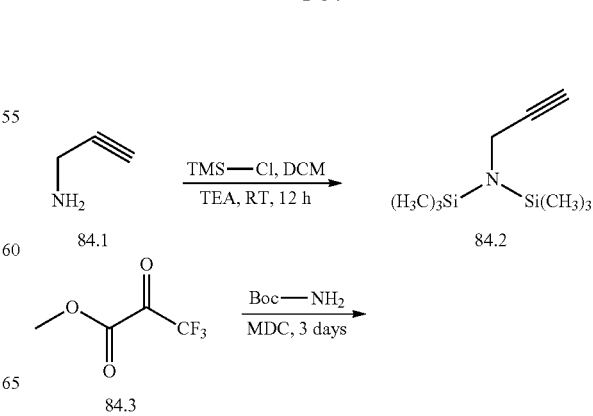

Synthesis of compound 83.2. To a cooled mixture of 83.1 (10.0 g, 99 mmol, 1.0 eq) in concentrated HCl (52 mL) at 0° C. was added sodium azide (11 g, 167 mmol, 1.69 eq) portion wise. Reaction mixture was stirred at room temperature for 8 h. Upon completion of the reaction, reaction mixture was transferred into water, basified to pH=9.0 by sodium carbonate and extracted with DCM. Combined

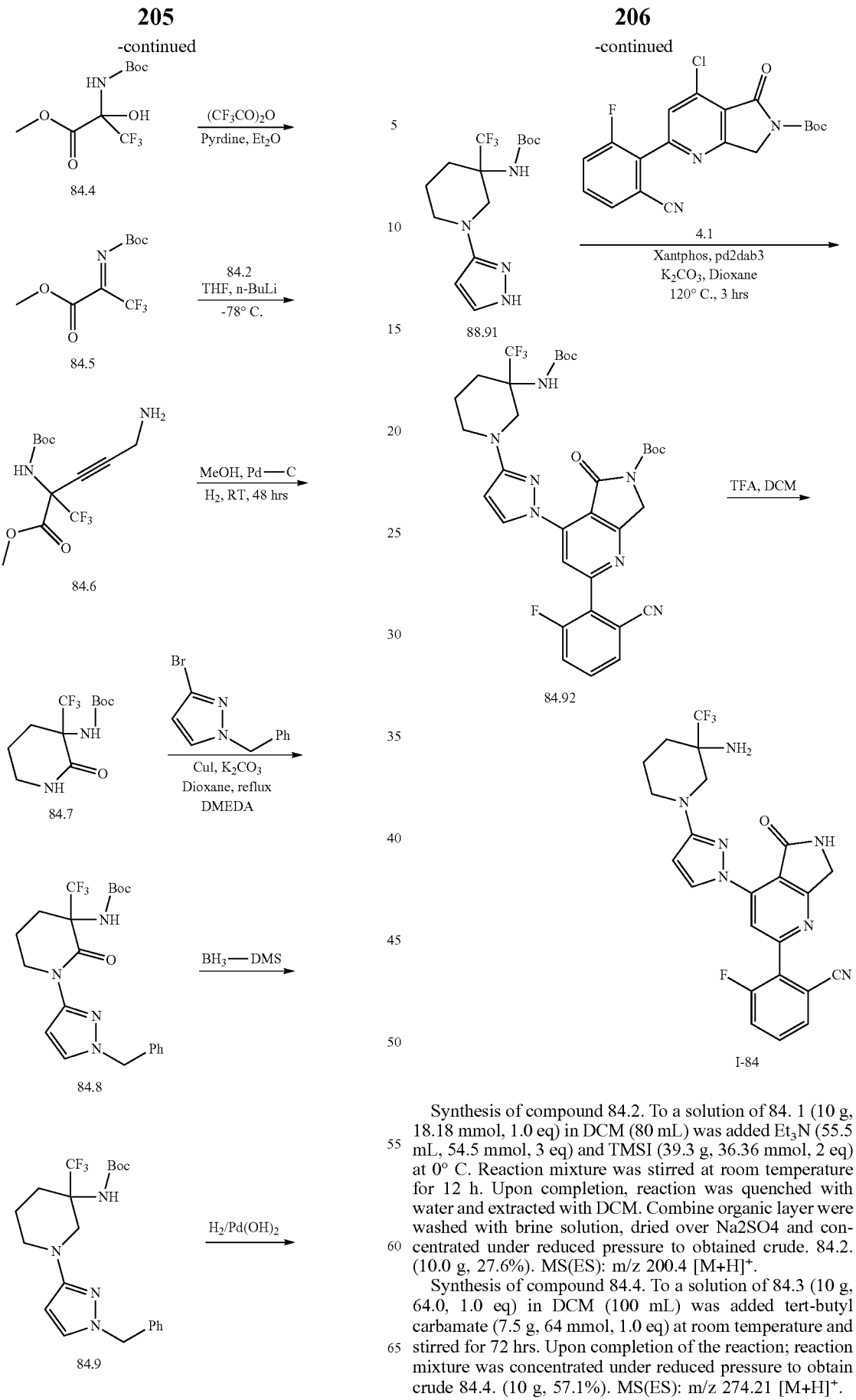

Synthesis of compound 84.2. To a solution of 84. 1 (10 g, 18.18 mmol, 1.0 eq) in DCM (80 mL) was added Et₃N (55.5 mL, 54.5 mmol, 3 eq) and TMSI (39.3 g, 36.36 mmol, 2 eq) at 0° C. Reaction mixture was stirred at room temperature for 12 h. Upon completion, reaction was quenched with water and extracted with DCM. Combine organic layer were washed with brine solution, dried over Na2SO4 and concentrated under reduced pressure to obtained crude. 84.2. (10.0 g, 27.6%). MS(ES): m/z 200.4 [M+H]⁺.

Synthesis of compound 84.4. To a solution of 84.3 (10 g, 64.0, 1.0 eq) in DCM (100 mL) was added tert-butyl carbamate (7.5 g, 64 mmol, 1.0 eq) at room temperature and stirred for 72 hrs. Upon completion of the reaction; reaction mixture was concentrated under reduced pressure to obtain crude 84.4. (10 g, 57.1%). MS(ES): m/z 274.21 [M+H]⁺.

Synthesis of compound 84.5. To a solution of 84.4 (7.7 g, 28 mmol, 1.0 eq) in Et₂O (100 ml) was added drop wise Triflic anhydride (6.0 g, 28 mmol, 1.02 eq) and pyridine (4.5 g, 57 mmol, 2.04 eq) at 0° C. for 90 min. Upon completion of reaction; reaction mixture was filtered and filtrate was concentrated under reduced pressure to obtained crude which was purified by trituration by get pure 84.5 (5.2 g, 72.3%). MS(ES): m/z 256.19 [M+H]⁺.

Synthesis of compound 84.6. To a solution of 84.2 (3.2 g, 16.4 mmol, 1.2 eq) in THF (20 ml) was added n-BuLi (2.4M in Hexane) (6.8 mL, 16.4 mmol, 1.2 eq) drop wise at −78° C. for 10 min. After 10 minutes a solution of 84.5 (3.5 g, 13.7 mmol, 1.0 eq) in THF (10 mL) was added drop wise at −78° C. for 30 min and reaction mixture was stirred at room temperature for 16 h. Upon completion of the reaction, reaction was quenched NH₄Cl and product was extracted with EtOAc. Organic layer was combined, washed with brine solution, dried over sodium sulphate and concentrated under reduced pressure to obtain crude material. 1.5 (3.7 g, 86.95%). MS(ES): m/z 311.36 [M+H]⁺.

Synthesis of compound 84.7. To a solution of 1.5 (3.2 g, 10.31 mmol, 1.0 eq) in Methanol (30 mL), 10% palladium hydroxide on charcoal (0.5 g) was added. Reaction mixture was stirred (under hydrogen) at 40 psi for 48 h. Upon completion of reaction, reaction mixture was filtered through celite and washed with methanol and concentrated under reduced pressure to obtain crude material. This is further purified by column chromatography and the compound was eluted in 40% ethyl acetate and Hexane to get pure to get 1.6. (1.2 g, 41.22%). MS(ES): m/z 283.21 [M+H]⁺.

Synthesis of compound 84.8. To a solution of 1-benzyl-3-bromo-1H-pyrazole (0.7 g, 2.9 mmol, 1.0 eq) in 1,4 dioxane (10 ml) was added 1.6 (0.1.2 g, 4.4 mmol, 1.5 eq), copper iodide (0.027 g, 0.14 mmol, 0.05 eq), potassium carbonate (0.8 g, 5.80 mmol, 2.0 eq) and trans-N,N'-Dimethylcyclohexane-1,2-diamine (0.02 g, 0.14 mmol, 0.05 eq) at room temperature and reaction mixture was stirred at 140° C. for 18 h. Upon completion of reaction, reaction mixture was transferred in water and product was extracted with ethyl acetate. Organic layer was combined, washed with brine solution, dried over sodium sulphate and concentrated under reduced pressure to obtain crude material. This is further purified by combi flash, the compound was eluted in 40% ethyl acetate and Hexane to get pure 1.6 (0.4 g, 21.2%). MS(ES): m/z 439.5 [M+H]⁺.

Synthesis of compound 84.9. To a solution of 1.6 (0.4 g, 0.91, 1.0 eq) in Tetrahydrofuran (5 ml) was added Borane dimethylsulfide (0.35 mL, 3.6 mmol, 4 eq) at 0° C. and stirred at room temperature for 2 h. Upon completion of reaction; reaction mixture methanol was added and concentrated under reduced pressure to obtain crude material. This is further purified by column chromatography and the compound was eluted 30% ethyl acetate and Hexane to get pure to get pure 1.8. (0.165 g, 42.6%). MS(ES): m/z 424.2 [M+H]⁺.

Synthesis of compound 84.91. To a solution of 1.7 (0.16 g, 0.388 mmol, 1.0 eq) in Methanol (10 mL), 20% palladium hydroxide on charcoal (0.03 g) and 1N HCl (catalytic) was added. Reaction mixture was stirred (under hydrogen) at 40 psi for 24 h. Upon completion of reaction, reaction mixture was filtered through celite and washed with methanol and concentrated under reduced pressure to obtain crude material. This is further purified by column chromatography and the compound was eluted in 5% Methanol in dichloromethane to get pure to get 1.8. (0.1 g, 79.35%). MS(ES): m/z 335.21 [M+H]⁻.

Synthesis of compound 84.92. The compound was prepared by the same method as 83.6.

Synthesis of compound I-84. The compound was prepared by treatment of 84.92 with TFA to remove the BOC group affording I-84 (0.011 g, 47.08%). MS(ES): m/z 486.33 [M+H]⁺. LCMS purity: 100%, HPLC purity: 98.40%, CHIRAL HPLC purity: 98.41. ¹H NMR (DMSO-d6, 400 MHZ): 9.75-9.74 (d, 1H), 9.12 (s, 1H), 8.16 (s, 1H), 7.92-7.90 (m, 1H), 7.83-7.76 (m, 2H), 6.41 (d, 1H), 4.40 (d, 1H), 3.83 (d, 1H), 3.62 (d, 1H), 3.55 (d, 1H), 2.83 (t, 1H), 1.97-1.96 (m, 3H), 1.70-1.67 (m, 2H), 1.61-1.58 (m, 1H).

Example 85

Synthesis of 3-fluoro-2-(4-(3-(4-hydroxy-2,6-dimethylpiperidin-1-yl)-1H-pyrazol-1-yl)-5-oxo-6,7-dihydro-5H-pyrrolo[3,4-b]pyridin-2-yl)benzonitrile, I-85

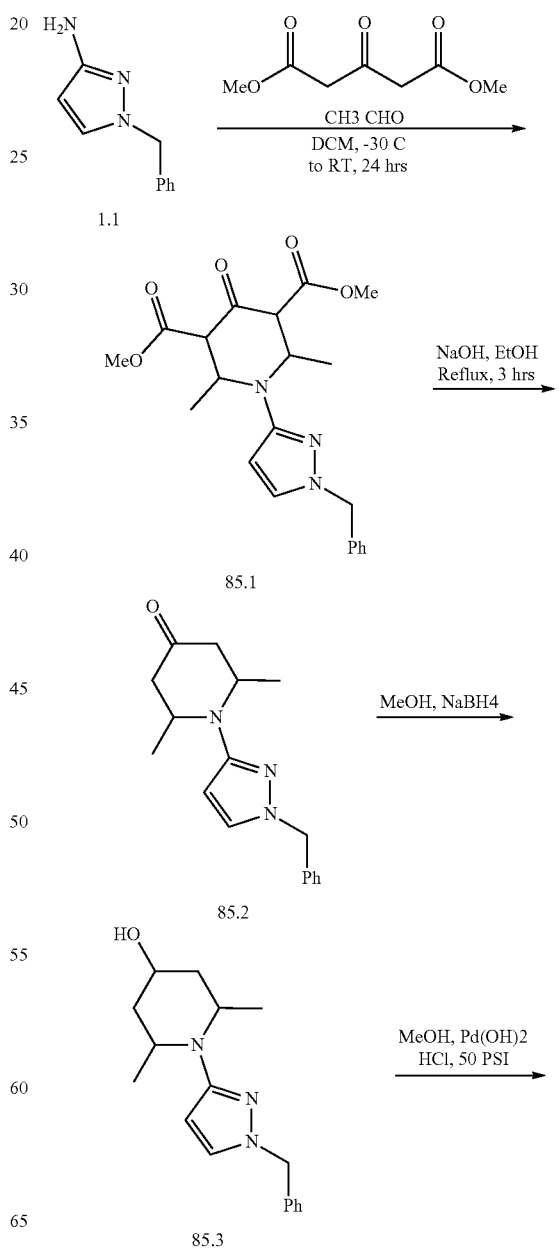

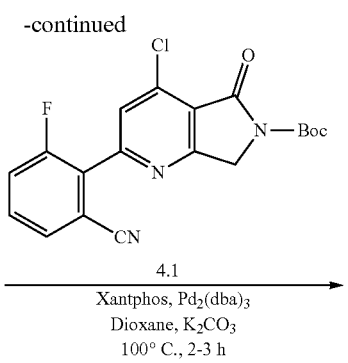

mixture was stirred at 80° C. for 24 h. Upon completion, of reaction was concentrated under reduced pressure to obtain crude which was purified by chromatography 85.2 (0.28 g, 39.16%). MS(ES): m/z 284.35 [M+H]⁺.

Synthesis of compound 85.3. To a solution of 1.2 (0.28 g, 0.98 mmol, 1.0 eq) in ethanol (10 ml) was added sodium borohydride (0.056 g, 1.5 mmol, 1.5 eq) at 0° C. Reaction mixture was stirred at room temperature for 16 h. Upon completion of the reaction, was transferred into water and extracted with dichloromethane, dried over sodium sulphate and concentrated under reduced pressure to obtain crude which was purified to obtain 85.3. (0.25 g, 88.68%). MS(ES): m/z 286.35 [M+H]⁺

Synthesis of compound 85.4. To a solution of 85.3 (0.23 g, 1.7 mmol, 1.0 eq) in Methanol (10 mL), 20% palladium hydroxide on charcoal (0.06 g) and 1N HCl (catalytic) was added. Reaction mixture was stirred under hydrogen at 40 psi for 24 h. Upon completion of the reaction, reaction mixture was filtered through celite and washed with methanol and concentrated under reduced pressure to obtain crude which was purified by column chromatography to provide 85.4. (0.12 g, 76.2%). MS(ES): m/z 196.21 [M+H]⁺.

Synthesis of compound 85.5. Compound was synthesized using the procedure described in Example 64.

Synthesis of compound I-85. Compound was synthesized using the procedure described in Example 64. (0.03 g, 45.9%). MS(ES): m/z 447.28 [M+H]⁺; ¹H NMR (DMSO-d6, 400 MHZ): 9.71 (d, 1H), 9.12 (s, 1H), 8.15 (s, 1H), 7.92-7.90 (m, 1H), 7.81-7.76 (m, 2H), 6.37 (d, 1H), 4.62 (s, 1H), 4.50 (s, 2H), 4.00-3.99 (m, 1H), 3.85-3.84 (m, 1H), 3.51-3.50 (m, 1H), 1.91-1.92 (m, 1H), 1.79-1.77 (m, 1H), 1.61-1.60 (m, 1H), 1.34 (d, 3H), 1.03 (d, 3H).

Example 86

Synthesis of 3-fluoro-2-(4-(3-(3-(hydroxymethyl)piperidin-1-yl)-1H-pyrazol-1-yl)-5-oxo-6,7-dihydro-5H-pyrrolo[3,4-b]pyridin-2-yl)benzonitrile, I-86

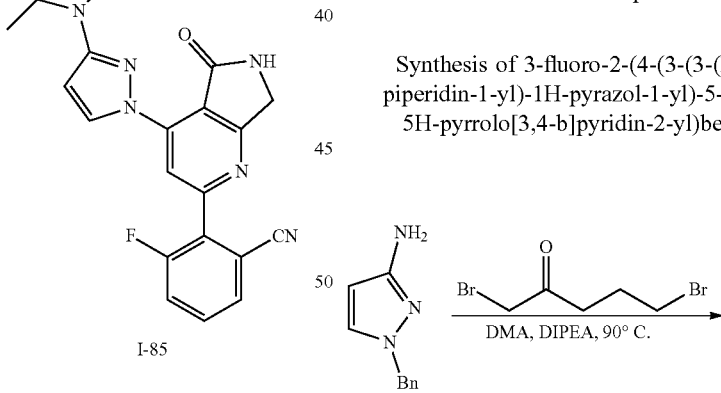

Synthesis of compound 85.1. To a solution of 1.1 (2.5 g, 14.3 mmol, 1.0 eq) in DCM (10 mL) was added dimethyl 3-oxopentanedioate (5 g, 28 mmol, 2 eq) and acetaldehyde (1.6 mL, 36.0 mmol, 2.1 eq) at −30° C. Reaction mixture was stirred at room temperature for 16 h. Upon completion of reaction; concentrated under reduced pressure to obtained crude material. This was purified by column chromatography and the compound was eluted in 5% ethyl acetate in hexane to get pure 85.1. (0.9 g, 15.6%). MS(ES): m/z 400.35 [M+H]⁺.

Synthesis of compound 85.2. To a solution of 85.1 (0.9 g, 2.2 mmol, 1.0 eq) in EtOH (5 mL), was added 2N NaOH (2.8 ml, 5.6 mmol, 2.5 eq) at room temperature. Reaction

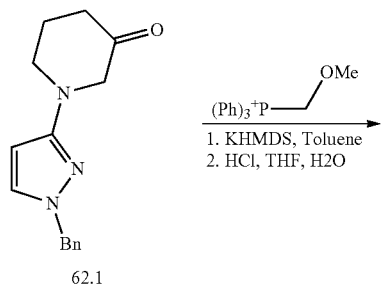

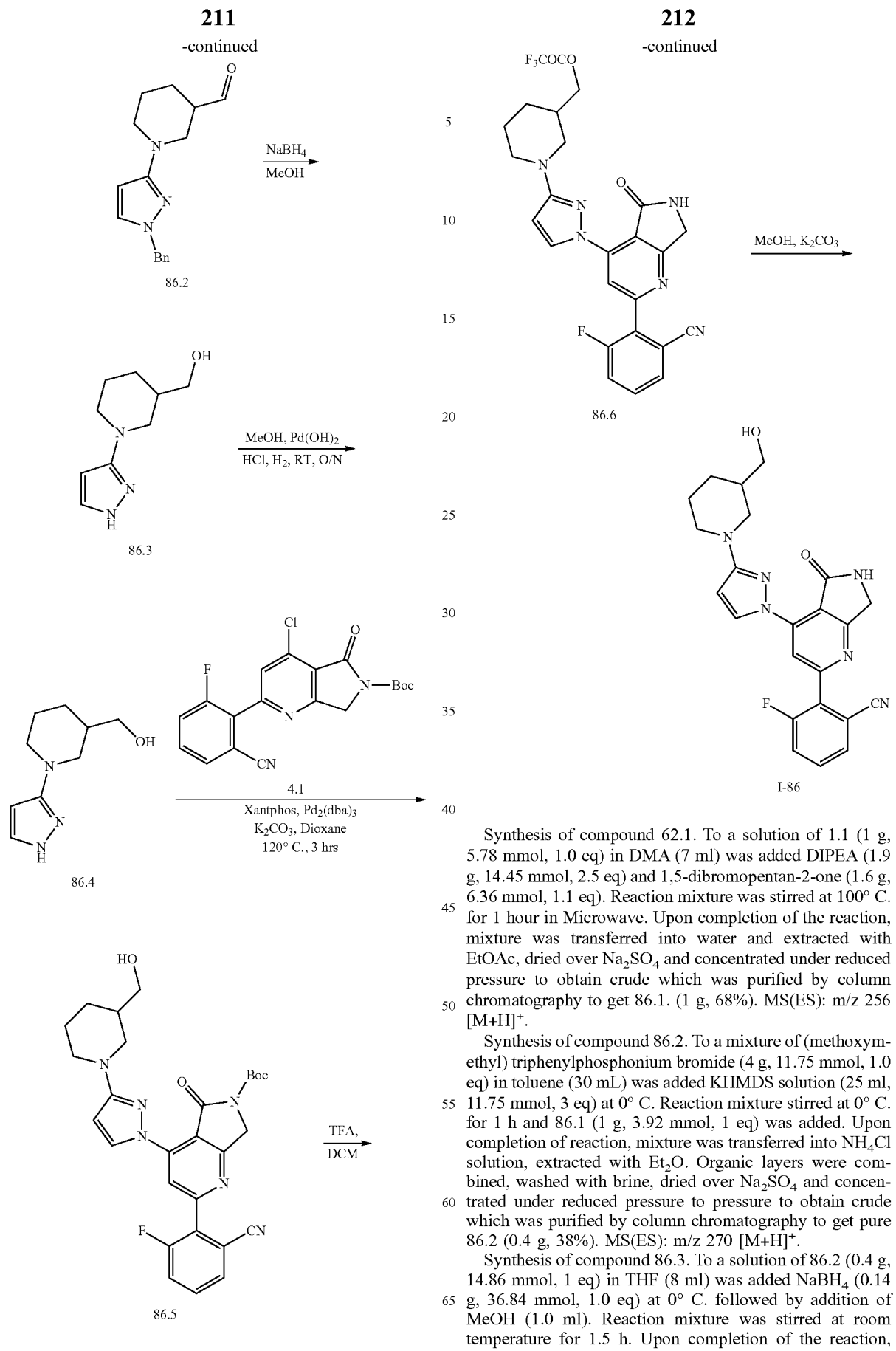

Synthesis of compound 62.1. To a solution of 1.1 (1 g, 5.78 mmol, 1.0 eq) in DMA (7 ml) was added DIPEA (1.9 g, 14.45 mmol, 2.5 eq) and 1,5-dibromopentan-2-one (1.6 g, 6.36 mmol, 1.1 eq). Reaction mixture was stirred at 100° C. for 1 hour in Microwave. Upon completion of the reaction, mixture was transferred into water and extracted with EtOAc, dried over Na$_2$SO$_4$ and concentrated under reduced pressure to obtain crude which was purified by column chromatography to get 86.1. (1 g, 68%). MS(ES): m/z 256 [M+H]$^+$.

Synthesis of compound 86.2. To a mixture of (methoxymethyl) triphenylphosphonium bromide (4 g, 11.75 mmol, 1.0 eq) in toluene (30 mL) was added KHMDS solution (25 ml, 11.75 mmol, 3 eq) at 0° C. Reaction mixture stirred at 0° C. for 1 h and 86.1 (1 g, 3.92 mmol, 1 eq) was added. Upon completion of reaction, mixture was transferred into NH$_4$Cl solution, extracted with Et$_2$O. Organic layers were combined, washed with brine, dried over Na$_2$SO$_4$ and concentrated under reduced pressure to pressure to obtain crude which was purified by column chromatography to get pure 86.2 (0.4 g, 38%). MS(ES): m/z 270 [M+H]$^+$.

Synthesis of compound 86.3. To a solution of 86.2 (0.4 g, 14.86 mmol, 1 eq) in THF (8 ml) was added NaBH$_4$ (0.14 g, 36.84 mmol, 1.0 eq) at 0° C. followed by addition of MeOH (1.0 ml). Reaction mixture was stirred at room temperature for 1.5 h. Upon completion of the reaction, mixture was transferred into water, then extracted with EtOAc. Organic layers were combined, washed with brine, dried over Na$_2$SO$_4$ and concentrated under reduced pressure to pressure to obtain crude which was purified by column chromatography to provide 86.3 (0.35 g, 87.5%). MS(ES): m/z 272 [M+H]$^+$.

Synthesis of compound 86.4. To a solution of 86.3 (0.25 g, 92.2 mmol, 1.0 eq) in Methanol (15.0 mL), 20% Pd(OH)$_2$/C (0.13 g) and 1.0 N HCl (catalytic) was added. Reaction mixture was stirred (under hydrogen) at 40 psi for 48 h. Upon completion of the reaction, reaction mixture was filtered through celite and washed with MeOH and concentrated under reduced pressure to obtain crude which was purified by column chromatography to provide (0.1 g, 60.24%). MS(ES): m/z 182 [M+H]$^+$.

Synthesis of compound 86.5. Compound 86.5 was prepared from compound 86.4 and 4.1 using the procedure described in Example 64.

Synthesis of compound 86.6. Compound 86.6 was prepared from 86.5 using the procedure described in Example 64.

Synthesis of compound I-86. To a solution of 86.6 (0.06 g, 0.11 mmol, 1 eq) in MeOH (3.0 ml) was added K$_2$CO$_3$ (0.15 g, 0.10 mmol, 4.0 eq). Reaction mixture was stirred at room temperature for 1 hour. Upon completion of the reaction, mixture was concentrated under reduced pressure. The crude was purified by column chromatography to provide I-86 (0.022 g, 44.9%). MS(ES): m/z 433 [M+H]$^+$; $^1$H NMR (MeOD, 400 MHz): 9.69-9.68 (d, 1H), 8.27 (s, 1H), 7.80-7.65 (m, 1H), 7.73-7.63 (m, 2H), 6.22-6.21 (d, 1H) 3.98-3.94 (m, 1H), 3.82-3.79 (m, 1H), 3.53-3.42 (m, 2H), 2.90-2.84 (m, 1H), 2.68-2.62 (m, 1H), 1.81-1.76 (m, 3H), 1.67-1.60 (m, 1H), 1.30-1.16 (m, 3H).

Example 87

Synthesis of 3-fluoro-2-(4-(3-(3-hydroxy-3-methyl-pyrrolidin-1-yl)-1H-pyrazol-1-yl)-5-oxo-6,7-di-hydro-5H-pyrrolo[3,4-b]pyridin-2-yl)benzonitrile, I-87

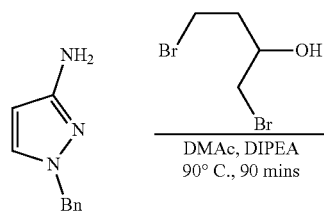

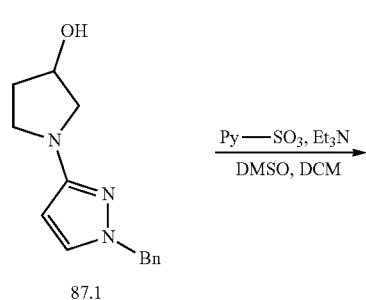

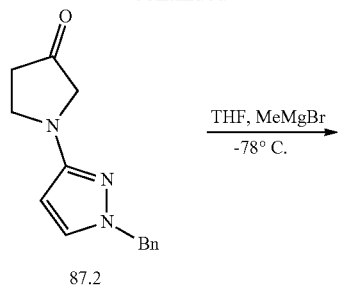

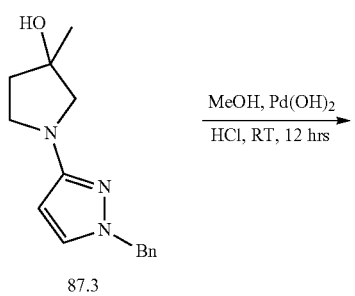

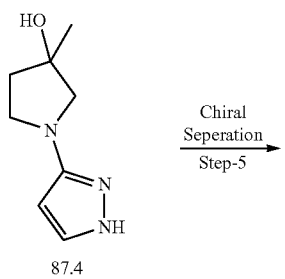

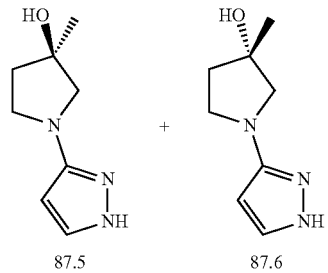

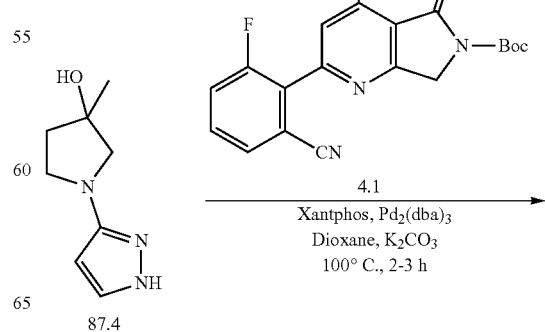

-continued

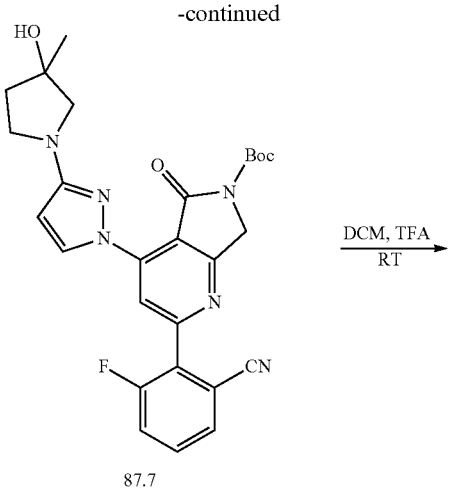

87.7

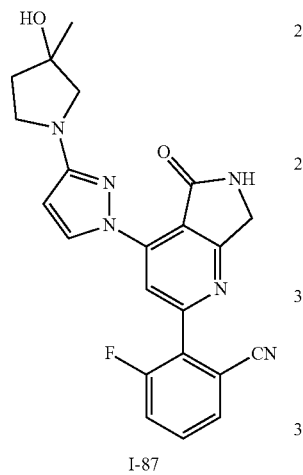

I-87

Synthesis of compound 87.1. A solution of 1.1 (2.0 g, 11.56 mmol, 1.0 eq) and 1,4-dibromobutan-2-ol (3 g, 12.93 mmol, 2.0 eq) in DMA (10.0 ml) reaction mixture was stirred at 100° C. for 1 hr in Microwave. Upon completion of the reaction, mixture was poured into water and extracted with EtOAc, dried over Na$_2$SO$_4$ and concentrated under reduced pressure to obtain crude which was purified by column chromatography to furnish 87.1. (1.2 g, 42.9%). MS(ES): m/z 244 [M+H]$^+$.

Synthesis of compound 87.2. To a mixture of 87.1 (0.9 g, 37.0 mmol, 1.0 eq) and Et$_3$N (2.24 g, 22.2 mmol, 6 eq) in DCM (10 mL), Sulfur trioxide pyridine complex (1.76 g, 11.1 mmol, 3 eq) was added slowly at room temperature. Reaction mixture was stirred at room temperature for 2 h. Upon completion of the reaction, mixture was transferred into NH$_4$Cl solution, extracted with DCM, dried over Na$_2$SO$_4$ and concentrated under reduced pressure to obtain crude which was purified by column chromatography to provide 87.2. (0.5 g, 50.50%). MS(ES): m/z 242 [M+H]$^+$.

Synthesis of compound 87.3. A mixture of 87.2 (0.5 g, 2.0 mmol, 1.0 eq) in THF (5 mL) was cooled to −78° C. and MeMgI (3M in THF) (1.38 ml, 4.1 mmol, 2 eq) was added. Reaction mixture was slowly warmed to room temperature and stirred for 1 h. Upon completion of the reaction, mixture was transferred into satd. NH$_4$Cl solution, extracted with EtOAc, dried over Na$_2$SO$_4$ and concentrated under reduced pressure at 36° C. to obtain 87.3 (0.4 g, 78.0%). MS(ES): m/z 258 [M+H]$^+$.

Synthesis of compound 87.4. To a solution of 87.2 (0.4 g, 1.5 mmol, 1.0 eq) in MeOH (5.0 mL), Pd(OH)$_2$/C (0.2 g) and 1N HCl (catalytic amount) was added. Reaction mixture was stirred under hydrogen pressure at 40 psi for 12 h. Upon completion of the reaction, reaction mixture was filtered through celite-bed and washed with methanol, concentrated under reduced pressure to obtain crude material. The crude was purified by column chromatography to furnish 87.4. (0.16 g, 61.5%). MS(ES): m/z 168 [M+H]$^+$.

Synthesis of compound 87.5. Compound 87.5 was prepared by chiral separation of compound 87.4.

Synthesis of compound 87.6. Compound 87.6 was prepared by chiral separation of compound 87.4.

Synthesis of compound 87.5. Compound 87.7 was prepared from compounds 87.4 and 4.1 using the procedure described in Example 64.

Synthesis of compound I-87. Compound I-87 was prepared from compound 87.7 using the procedure described in Example 64. MS(ES): m/z 419 [M+H]$^+$; $^1$H NMR (DMSO-d$_6$, 400 MHz): 9.79-9.78 (d, 1H), 9.09 (s, 1H), 8.16 (d, 1H), 7.92-7.90 (m, 1H), 7.83-7.73 (m, 2H), 6.12-6.11 (d, 1H), 4.78 (s, 1H), 4.48 (s, 2H), 3.49-3.38 (m, 2H), 3.33-3.22 (m, 2H), 1.89-1.83 (m, 2H), 1.32-1.31 (d, H).

Example 88

Synthesis of (R)-3-fluoro-2-(4-(3-(3-hydroxy-3-(trifluoromethyl)piperidin-1-yl)-1H-pyrazol-1-yl)-5-oxo-6,7-dihydro-5H-pyrrolo[3,4-b]pyridin-2-yl)benzonitrile, I-88

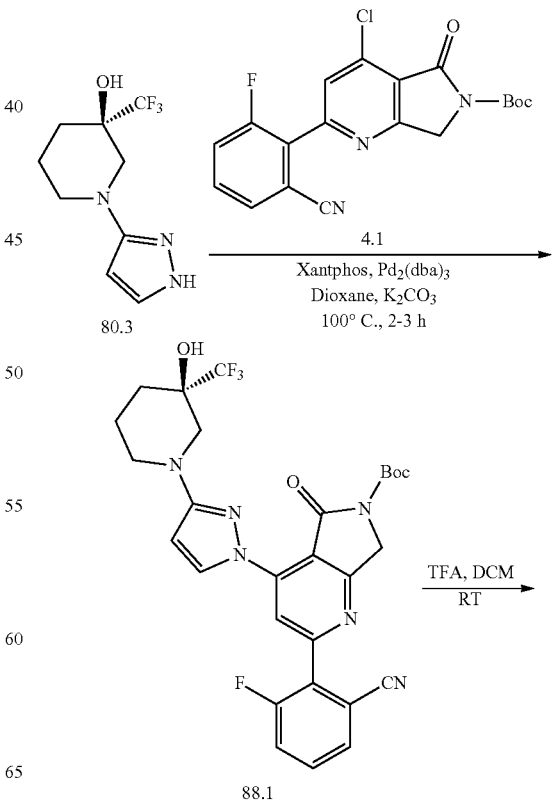

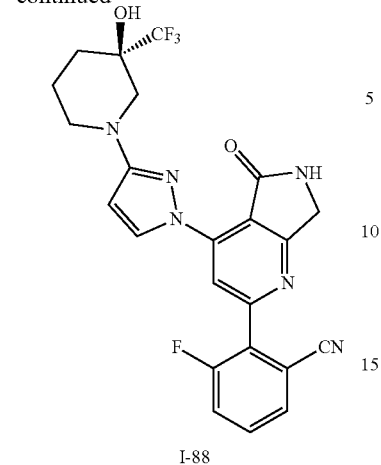

I-88

Compound I-88 was prepared from compounds 80.3 and 4.1 using the procedure described in Example 56. MS(ES): m/z 487 [M+H]+; 1H NMR (DMSO-$d_6$, 400 MHz): 9.75 (d, 1H), 9.11 (s, 1H), 8.15 (d, 1H), 7.92-7.90 (m, 1H), 7.83-7.73 (m, 2H), 6.38 (d, 1H), 6.02 (s, 1H), 4.49 (s, 2H), 3.85 (d, 1H), 3.75 (d, 1H), 3.08 (d, 1H), 2.88-2.82 (m, 1H), 1.90-1.79 (m, 2H), 1.73-1.70 (m, 1H), 1.66-1.60 (m, 1H).

Example 89

Synthesis of (S)-3-fluoro-2-(4-(3-(3-hydroxy-3-(trifluoromethyl)piperidin-1-yl)-1H-pyrazol-1-yl)-5-oxo-6,7-dihydro-5H-pyrrolo[3,4-b]pyridin-2-yl)benzonitrile, I-89

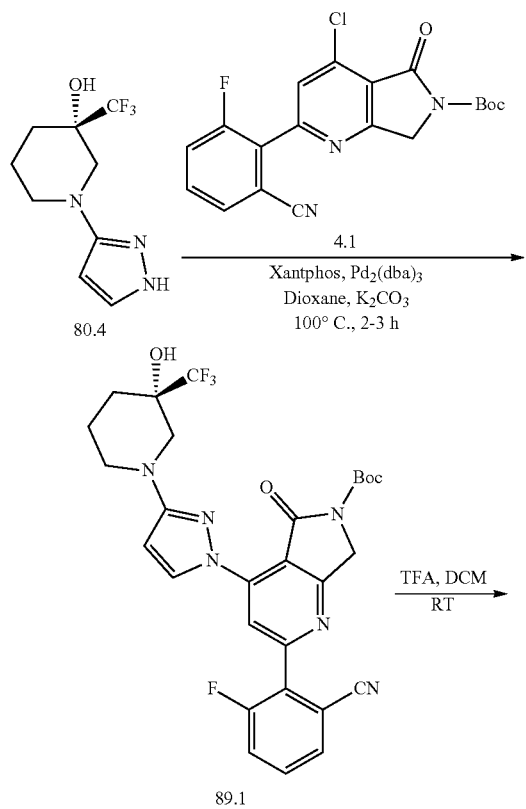

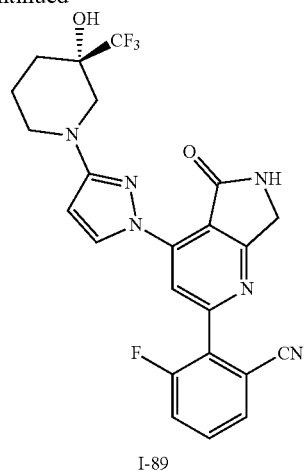

I-89

Compound I-89 was prepared from compounds 80.4 and 4.1 using the procedure described in Example 56. MS(ES): m/z 487 [M+H]+; 1H NMR (DMSO-$d_6$, 400 MHz): 9.75 (d, 1H), 9.11 (s, 1H), 8.15 (d, 1H), 7.92-7.90 (m, 1H), 7.83-7.73 (m, 2H), 6.38 (d, 1H), 6.02 (s, 1H), 4.49 (s, 2H), 3.85 (d, 1H), 3.75 (d, 1H), 3.08 (d, 1H), 2.88-2.82 (m, 1H), 1.90-1.79 (m, 2H), 1.73-1.70 (m, 1H), 1.66-1.60 (m, 1H).

Example 90

Synthesis of 2-(2,6-difluorophenyl)-4-(3-(3-(hydroxymethyl)morpholino)-1H-pyrazol-1-yl)-6,7-dihydro-5H-pyrrolo[3,4-b]pyridin-5-one, I-90

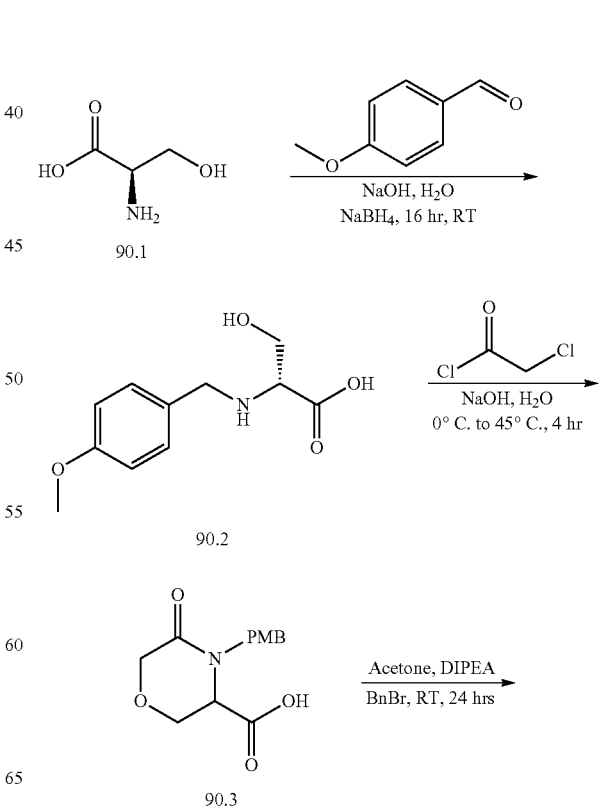

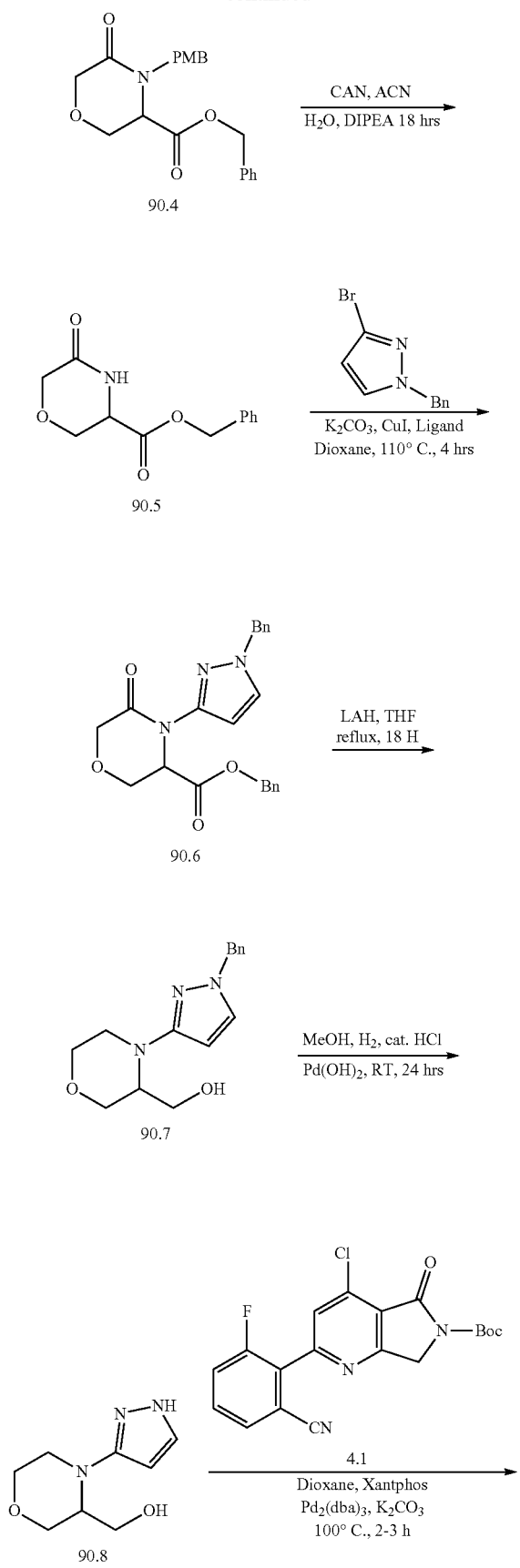

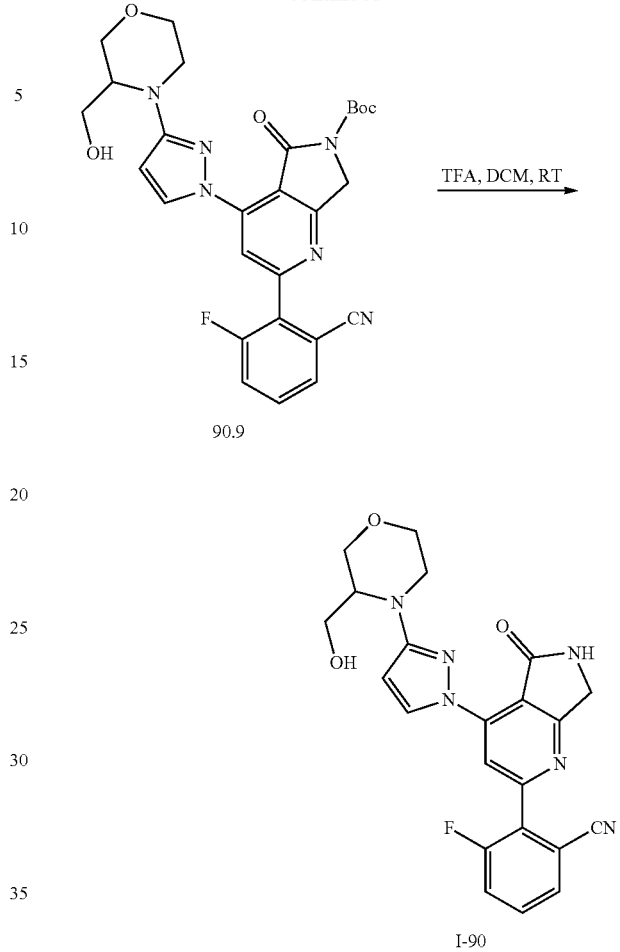

Synthesis of compound 90.2. To a solution of naOH (15.2 g, 0.38 mmol, 1 eq) in water (250 mL) was added 90.1 (40 g, 0.38 mmol, 1 eq) at 10° C. To this was added 4-methoxybenzaldehyde (92.1 g, 0.761 mmol, 2 eq) and stirred for 30 min. To this was added NaBH$_4$ (7.9 g, 0.20 mmol, 0.55 eq) portion wise in 20 min at 0° C. The reaction was stirred at room temperature for 16 h. Upon completion of the reaction, mixture was washed with Et$_2$O and aqueous was acidified by 2N HCl to Ph=4.5. The solids precipitated out were filtered and washed with Et$_2$O to get 90.2 (25.0 g, 29.2%). MS(ES): m/z 226.10 [M+H]$^+$.

Synthesis of compound 90.3. To a solution of NaOH (5.54 g, 138 mmol, 1 eq) in water (300 mL) was added 90.2 (24 g, 106 mmol, 1.0 eq) at 0° C. To this was added chloroacetyl chloride (24 g, 213 mmol, 2 eq) dropwise over a period of 20 min. To this mixture was added aq. NaOH to maintain pH=12. The reaction mass was stirred at 45° C. for 4 h. Upon completion of the reaction, mixture was cooled to 0° C. and acidified with dil. HCl till Ph=4. The product was extracted with EtOAc, dried over Na$_2$SO$_4$ and concentrated to get crude 90.3 The crude material was used for next step without further purification. (Crude Wt: 18.0 g, 63.7%). MS(ES): m/z 266.10 [M+H]$^+$.

Synthesis of compound 90.4. To a solution of 90.3 (18 g, 67.92 mmol, 1 eq) in acetone (500 mL) was added BnBr (17.4 mmol, 423.5 mmol, 1.5 eq), DIPEA (43 g, 339.6 mmol, 5 eq). The resulting mixture was stirred at room temperature for 18 h. Upon completion reaction was quenched with water and extracted with EtOAc. Organic layers were combined, washed with brine solution, dried over Na₂SO₄ and concentrated under reduced pressure to obtain crude which was purified by column chromatography to furnish 90.4 (8.0 g, 33.2%). MS(ES): m/z 356.15 [M+H]⁺.

Synthesis of compound 90.5. To a solution of 90.4 (8.0 g, 22.53 mmol, 1 eq) in acetonitrile (200 mL), water (200 mL) was added ceric ammonium nitrate (62 g, 112.67 mmol, 5 eq) at 0° C. for 1 h. To reaction was added DIPEA to adjust Ph=7 and stirred at room temperature overnight. Upon completion, reaction was quenched with water and extracted with EtOAc. Organic layers were combined, washed with brine solution, dried over Na₂SO₄ and concentrated under reduced pressure to obtain crude which was purified by trituration to provide 90.5 (2.0 g, 37.8%). MS(ES): m/z 236[M+H]⁺.

Synthesis of compound 90.6. To a solution of 90.5 (2 g, 8.43 mmol, 1.0 eq) in 1,4-dioxane (10 mL) was added 1-benzyl-3-bromo-1H-pyrazole (2.97 g, 12.65 mmol, 1.5 eq), CuI (1.62 g, 8.51 mmol, 1.0 eq), K₂CO₃ (2.34 g, 17.02 mmol, 2.0 eq) and trans-N,N'-Dimethylcyclohexane-1,2-diamine (1.2 g, 8.5 mmol, 1.0 eq) at room temperature and reaction mixture was stirred at 100° C. for 4 h. Upon completion of reaction, reaction mixture was transferred into water and product was extracted with EtOAc. Organic layers were combined, washed with brine solution, dried over Na₂SO₄ and concentrated under reduced pressure to obtain crude which was purified by column chromatography to furnish 90.6 (0.7 g, 21.2%). MS(ES): m/z 392.16 [M+H]⁺.

Synthesis of compound 90.7. To the suspension of LAH (0.226 g, 5.95 mmol, 2 eq) in TH (5 mL) was added a solution of 90.6 (0.7 g, 1.78 mmol, 1 eq) in THF (5.0 mL). The reaction mixture was heated to reflux for 18 h. Upon completion of reaction, mixture was cooled to room temperature and quenched in Na₂SO₄. The crude mixture was filtered through celite and washed with THF. Solvents were removed under reduced pressure to provide 90.7 (0.108 g, 22.0%). MS(ES): m/z 274.15 [M+H]⁺.

Synthesis of compound 90.8. To a solution of 90.7 (0.108 g, 0.395 mmol, 1.0 eq) in MeOH (5 mL). 20% Pd(OH)₂ (0.1 g) and 1N HCl (catalytic amount) were added. Reaction mixture was stirred (under hydrogen) at 30 psi for 24 h. Upon completion of the reaction, reaction mixture was filtered, solvents removed under reduced pressure and crude purified by column chromatography to furnish 90.8. (0.048 g, 66.3%). MS(ES): m/z 184.1 [M+H]⁺.

Synthesis of compound 90.9. Compound was prepared from 90.8 using the procedure described in Example 64.

Synthesis of compound I-90. Compound was prepared from 90.9 using the procedure described in Example 64. MS(ES): m/z 435 [M+H]⁺; ¹H NMR (DMSO-d₆, 400 MHz): 9.77-9.76 (d, 1H), 9.05 (s, 1H), 8.01 (s, 1H), 7.620-7.58 (m, 1H), 7.3-7.26 (m, 2H), 6.29-6.28 (d, 1H), 4.79-4.76 (m, 1H), 4.47 (s, 2H), 4-3.97 (s, 1H), 3.84-3.82 (m, 1H), 3.75-3.71 (m, 1H), 3.59-3.46 (m, 5H), 3.14-3.09 (m, 1H), Example 91

Synthesis of 1-(1-(2-(2-cyano-6-fluorophenyl)-5-oxo-6,7-dihydro-5H-pyrrolo[3,4-b]pyridin-4-yl)-1H-pyrazol-3-yl)piperidine-3-carboxylic acid, I-91

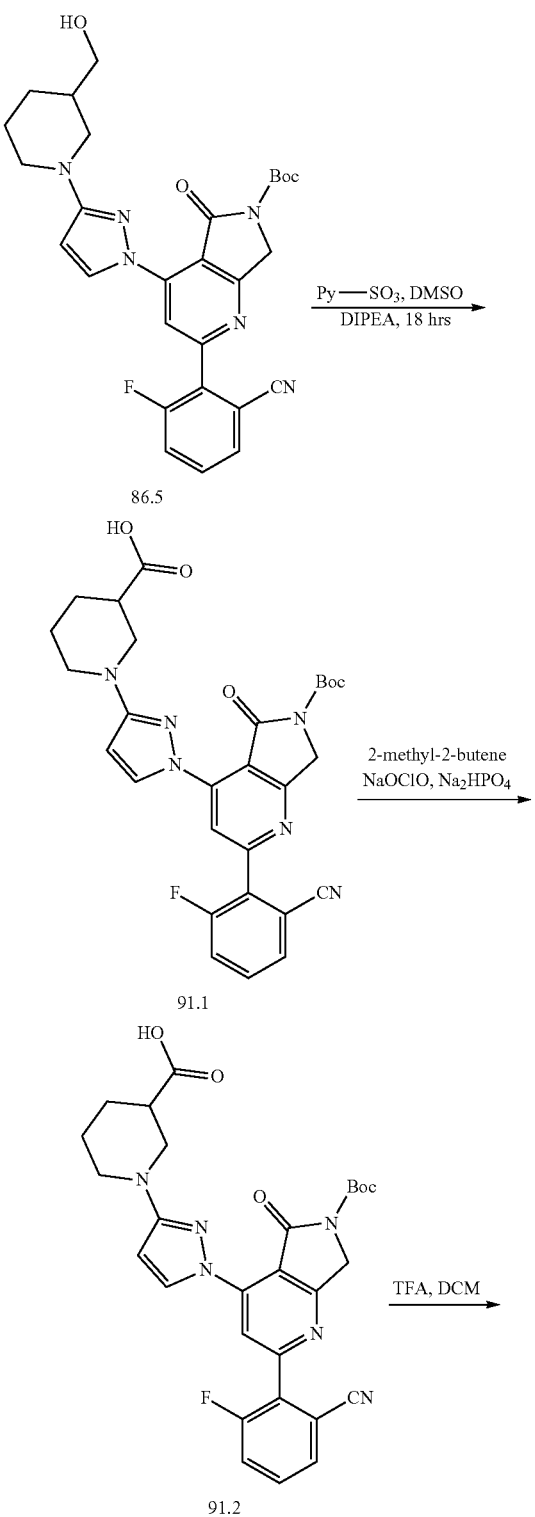

223

-continued

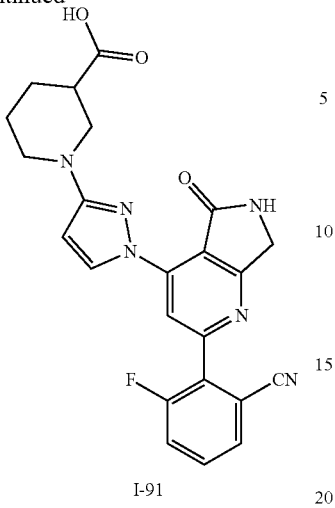

I-91

Synthesis of compound 91.1. To a solution of compound 86.5 (0.08 g, 0.015 mmol, 1.0 eq) in DCM (5.0 mL) was added Et3N (0.09 g, 0.90 mmol, 6.0 eq) and DMSO (0.117 g, 1.5 mmol, 10 eq) followed by addition of Sulfur trioxide pyridine complex (0.072 g, 0.45 mmol, 3 eq) portion wise. The reaction was stirred at room temperature for 18 h. Upon completion of the reaction; reaction mixture was transferred into NH$_4$Cl solution, extracted with EtOAc. Organic layers were combined, washed with brine solution, dried over Na$_2$SO$_4$ and concentrated under reduced pressure to pressure to obtain crude which was purified by column chromatography to furnish 91.1 (0.08 g, 90.0%). MS(ES): m/z 531 [M+H]$^+$.

Synthesis of compound 91.2. To a solution of 91.1 (0.080 g, 0.15 mmol, 1 eq) in t-butyl alcohol (1.0 ml) and 2-Methyl-2-buten (0.3 ml) was added Sodium chlorite (0.030 g, 0.34 mmol, 10 eq) followed by Sodium dihydrogen phosphate (20% w/v, 0.3 ml) at room temperature, Reaction mixture was stirred at room temperature for 1 h. Upon completion of reaction, mixture was extracted with EtOAc. Organic layers were combined, washed with brine, dried over Na$_2$SO$_4$ and concentrated under reduced pressure to pressure to obtain crude material 91.2 (0.048 g, 58.24%). MS(ES): m/z 547 [M+H]$^+$.

Synthesis of compound I-91. Compound I-91 was prepared from compound 91.2 suing procedure described in Example 64. MS(ES): m/z 447 [M+H]$^+$; $^1$H NMR (DMSO-d$_6$, 400 MHz): 12.38 (s, 1H), 9.75-9.75 (d, 1H), 9.11 (s, 1H), 8.11 (s, 1H), 7.91-7.89 (d, 1H), 7.82-7.75 (m, 2H), 6.38-6.37 (d, 1H), 4.49 (s, 2H), 3.86-3.83 (m, 1H), 3.68-3.65 (m, 1H), 3.04-2.88 (m, 3H), 1.93 (s, 1H), 1.71 (s, 1H), 1.55 (s, 2H).

Example 92

Synthesis of (R)-3-fluoro-2-(4-(3-(3-hydroxy-3-methylpyrrolidin-1-yl)-1H-pyrazol-1-yl)-5-oxo-6,7-dihydro-5H-pyrrolo[3,4-b]pyridin-2-yl)benzonitrile, I-92

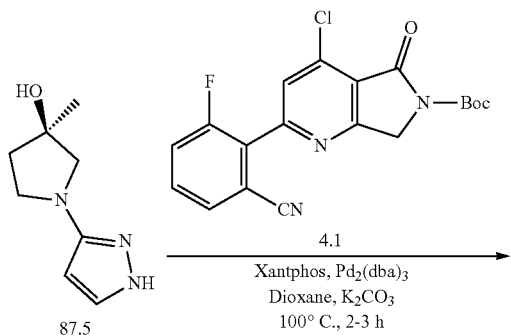

224

-continued

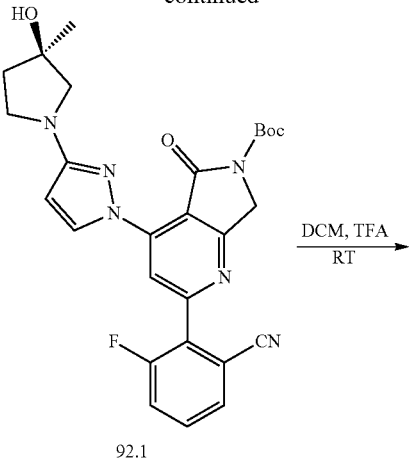

92.1

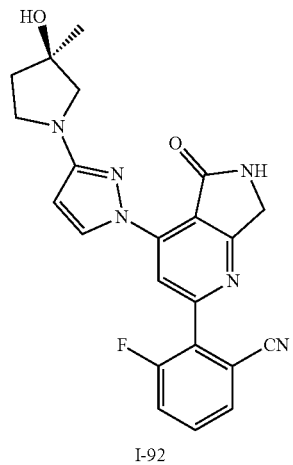

I-92

Compound I-92 was prepared from compounds 87.5 and 92.1 using the procedure described in Example 64. MS(ES): m/z 419 [M+H]$^+$; $^1$H NMR (DMSO-d$_6$, 400 MHz): 9.79-9.78 (d, 1H), 9.09 (s, 1H), 8.16 (d, 1H), 7.92-7.90 (m, 1H), 7.83-7.73 (m, 2H), 6.12-6.11 (d, 1H), 4.78 (s, 1H), 4.48 (s, 2H), 3.49-3.38 (m, 2H), 3.33-3.22 (m, 2H), 1.89-1.83 (m, 2H), 1.32-1.31 (d, 3H).

Example 93

Synthesis of (S)-3-fluoro-2-(4-(3-(3-hydroxy-3-methylpyrrolidin-1-yl)-1H-pyrazol-1-yl)-5-oxo-6,7-dihydro-5H-pyrrolo[3,4-b]pyridin-2-yl)benzonitrile, I-93

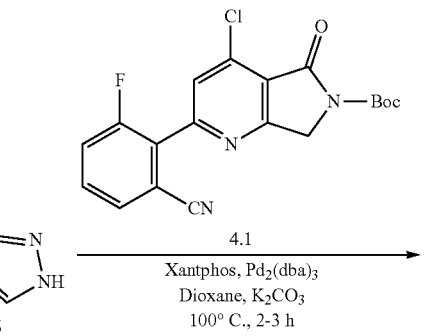

225

-continued

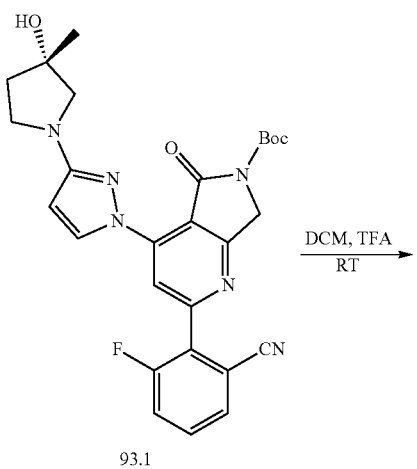

93.1

DCM, TFA
———————→
RT

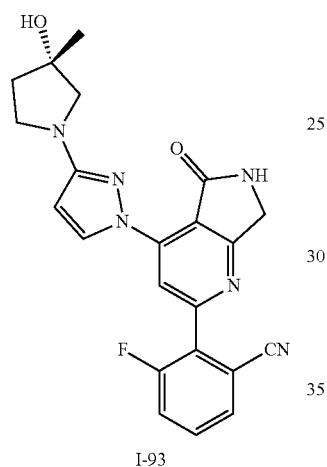

I-93

Compound I-93 was prepared from compound 87.6 and 4.1 using the procedure described in Example 64. MS(ES): m/z 419 [M+H]⁺; ¹H NMR (DMSO-d₆, 400 MHz): 9.79-9.78 (d, 1H), 9.08 (s, 1H), 8.16 (d, 1H), 7.92-7.90 (m, 1H), 7.83-7.73 (m, 2H), 6.12-6.11 (d, 1H), 4.77 (s, 1H), 4.48 (s, 2H), 3.49-3.38 (m, 2H), 3.33-3.22 (m, 2H), 1.88-1.84 (m, 2H), 1.32-1.31 (d, 3H).

Example 94

Synthesis of 3-fluoro-2-(4-(3-(2-hydroxyethyl)-1H-pyrazol-1-yl)-5-oxo-6,7-dihydro-5H-pyrrolo[3,4-b]pyridin-2-yl)benzonitrile, I-94

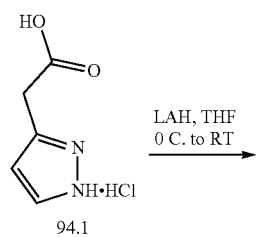

94.1

LAH, THF
———————→
0 C. to RT

226

-continued

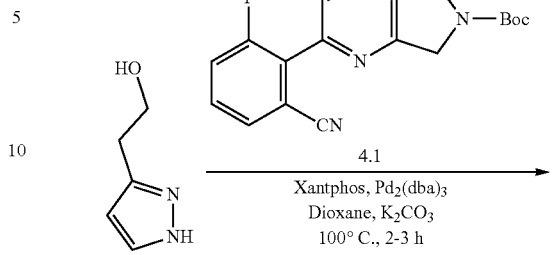

94.2

Xantphos, Pd₂(dba)₃
Dioxane, K₂CO₃
———————————→
100° C., 2-3 h

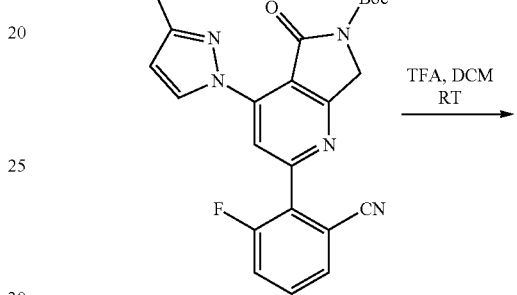

94.3

TFA, DCM
————————→
RT

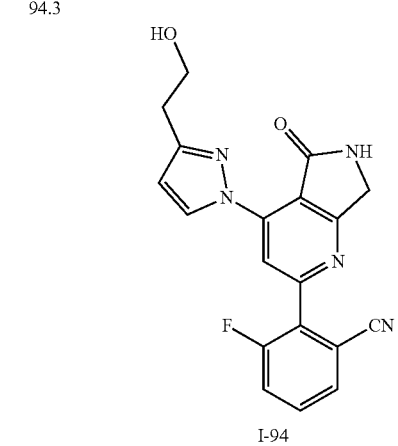

I-94

Synthesis of compound 94.2. To a solution of 94.1 (1 g, 6.1 mmol, 1.0 eq) in THF (10 mL) was added LAH (1 m) (24.6 g, 24.6 mmol, 4 eq) at 0° C. Reaction mixture was stirred at room temperature for 4 h. Upon completion of reaction, mixture was transferred into sodium sulphate decahydrate and filtered on celite bed the washed with ethyl acetate and filtrate was concentrated under reduced pressure to obtain crude, which was purified by column chromatography to furnish 94.2. (0.5 g, 72.49%). MS(ES): m/z 113.35 [M+H]⁻

Synthesis of compound 94.3. Compound was prepared from 94.2 and 4.1 using the procedure described in Example 64.

Synthesis of compound I-94. Compound was prepared using the procedure described in Example 64. (0.011 g, 56.1%). MS(ES): m/z 364.3 [M+H]⁺; ¹H NMR (DMSO-d6, 400 MHZ): 9.63 (d, 1H), 9.12 (s, 1H), 8.28 (s, 1H), 7.92-7.91 (m, 1H), 7.81-7.69 (m, 2H), 6.55 (d, 1H), 4.74 (d, 1H), 4.54 (s, 2H), 3.773-3.69 (m, 2H), 2.82-2.79 (m, 2H), Example 95

Synthesis of 1-(1-(2-(2-cyano-6-fluorophenyl)-5-oxo-6,7-dihydro-5H-pyrrolo[3,4-b]pyridin-4-yl)-1H-pyrazol-3-yl)piperidine-3-carbonitrile, I-95

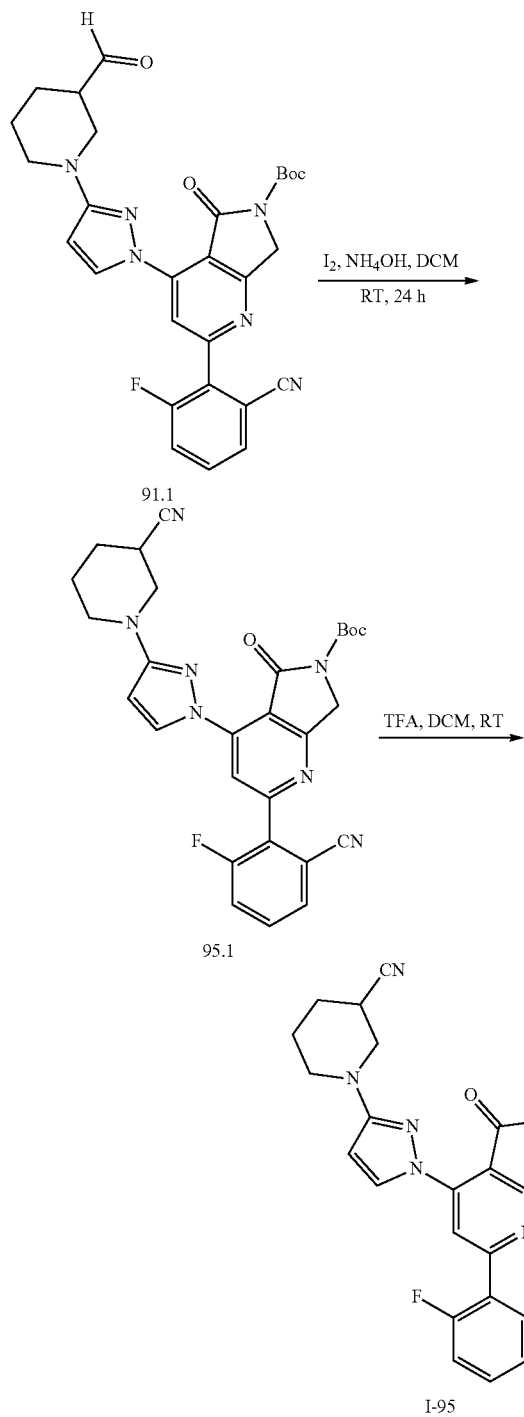

Synthesis of compound 95.1. To a mixture of 91.1 (0.07 g, 0.13 mmol, 1.0 eq) in DCM (2.0 ml) was added I$_2$ (0.05 g, 0.19 mmol, 1.5 eq) and NH$_4$OH (0.2 ml). Reaction was stirred at room temperature for 24 h. Upon completion of the reaction, reaction mixture was transferred into water, and extracted with EtOAc. Organic layers were combined, washed with brine, dried over Na$_2$SO$_4$ and concentrated under reduced pressure to obtain crude that was purified by column chromatography to provide 95.1 (0.06 g, 86.95%). MS(ES): m/z 528 [M+H]$^-$.

Synthesis of compound I-95. Compound was prepared from 95.1 using the procedure described in Example 64. (0.025 g, 52.1%). MS(ES): m/z 428 [M+H]$^+$; $^1$H NMR (DMSO-d$_6$, 400 MHz): 9.77 (d, 1H), 9.14 (s, 1H), 8.20 (s, 1H), 7.92-7.90 (m, 1H), 7.83-7.76 (m, 2H), 6.44 (d, 1H), 4.50 (s, 2H), 3.59-3.54 (m, 2H), 3.39-3.37 (m, 1H), 3.30-3.26 (m, 1H), 3.13-3.10 (m, 1H), 1.89-1.84 (m, 2H), 1.72-1.69 (m, 1H), 1.64-1.62 (m, 1H).

Example 96

Synthesis of 3-fluoro-2-(4-(3-(5-hydroxy-2-methyl-piperidin-1-yl)-1H-pyrazol-1-yl)-5-oxo-6,7-dihydro-5H-pyrrolo[3,4-b]pyridin-2-yl)benzonitrile, I-96

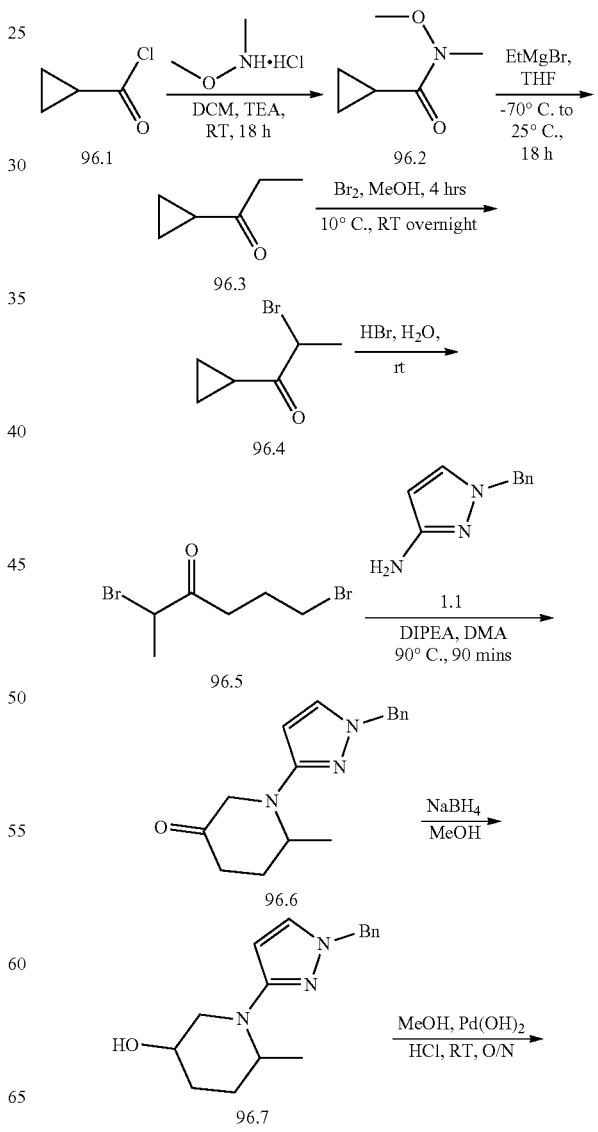

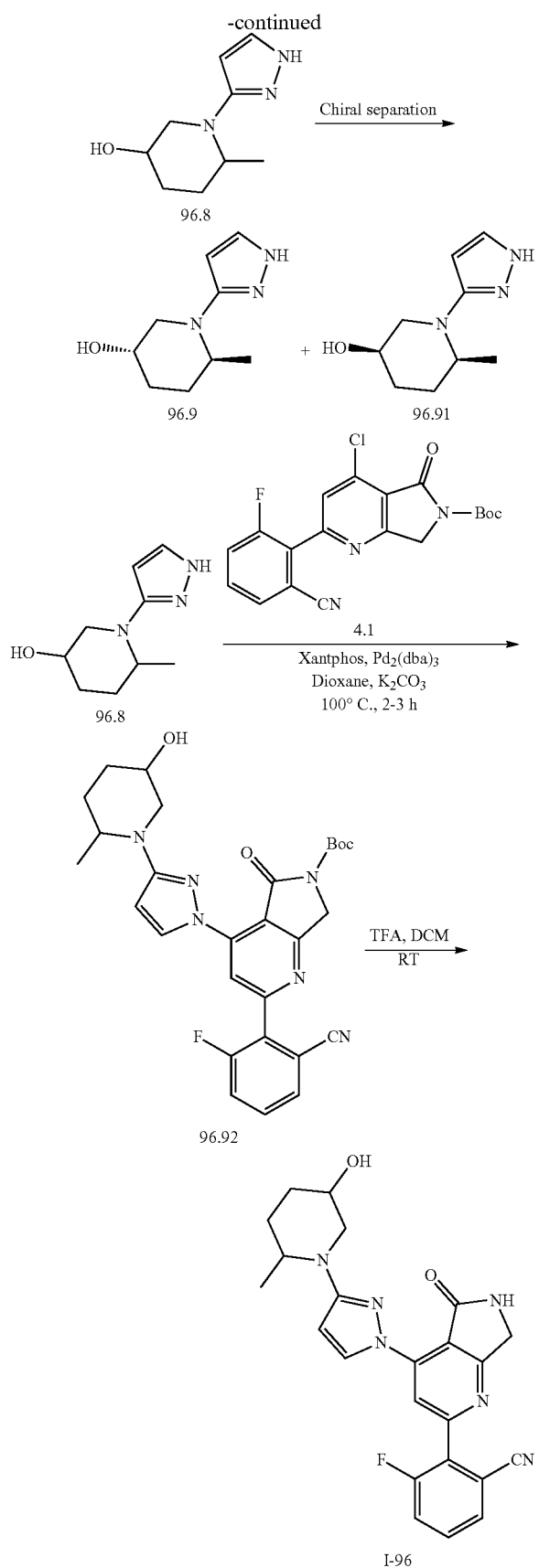

Synthesis of compound 96.2. To a solution of N,O-dimethylhydroxylamine HCl (10.0 g, 95.69 mmol, 1.0 eq) and Et$_3$N (19.36 g, 191.6 mmol, 2.0 eq) in CH$_2$Cl$_2$ (60 mL) reaction mixture was stirred at 0° C. for 30 min. Compound 96.1 was added at 0° C. Reaction mixture was stirred at room temperature for 15 h. Upon completion of the reaction, organic layer was washed with water, brine, sat NaHCO$_3$ solution and 1.0 N HCl, dried over Na$_2$SO$_4$ and concentrated under reduced pressure to pressure to obtain crude. Crude was purified by column chromatography to provide 96.2 (9.0 g, 72.9%).

Synthesis of compound 96.3. To a mixture of 96.2 (9.0 g, 69.76 mmol, 1.0 eq) in tetrahydrofuran (100.0 mL). Reaction mixture was cooled to −70° C. and EtMgBr (1M in THF) (72 ml, 73.25 mmol, 1.05 eq) was added. Reaction mixture was slowly warmed to room temperature and stirred for 18 h. Upon completion of the reaction; reaction mixture was transferred into satd. NH$_4$Cl, extracted with diethyl ether, dried over Na$_2$SO$_4$ and concentrated under reduced pressure to furnish 96.3 (6.0 g, 88.3%).

Synthesis of compound 96.4. To a solution of 96.3 (6.0 g, 71.42 mmol, 1.0 eq) in MeOH (70.0 mL). Reaction mixture was cooled to 0° C. and Br$_2$ (11.4 g, 71.42 mmol, 1.0 eq) was added. Reaction was stirred at 0° C. for 15 h. Upon completion of the reaction; mixture was transferred into water, extracted with CH$_2$Cl$_2$, dried over Na$_2$SO$_4$ and concentrated under reduced pressure to obtain crude which was purified by distillation to get pure 96.4 (1.0 g, 10%).

Synthesis of compound 96.5. To a solution of 96.4 (1.0 g, 5.6 mmol, 1.0 eq) was added HBr in water (47% in water) (10 mL). Reaction mixture was stirred at room temperature for 15 h. Upon completion of the reaction; mixture was transferred into water, and extracted with CH$_2$Cl$_2$ dried over Na$_2$SO$_4$ and concentrated under reduced pressure to obtain 96.5. (1.0 g, 68.96%).

Synthesis of compound 96.6. To a solution of 96.5 (1.0 g, 3.8 mmol, 1.0 eq) and 1.1 (0.67 g, 3.8 mmol, 1.0 eq) in DMA (6.0 ml) was added DIPEA (2.0 ml, 11.6 mmol, 3.0 eq) Reaction mixture was stirred at 100° C. in Microwave for 1 hour. Upon completion of the reaction, mixture was transferred into water and extracted with EtOAc, dried over Na$_2$SO$_4$ and concentrated under reduced pressure to obtain crude which was purified by column chromatography to provide 96.6 (0.7 g, 67.96%). MS(ES): m/z 269.6 [M+H]$^+$.

Synthesis of compound 96.7. To a solution of 96.6 (0.7 g, 2.6 mmol, 1.0 eq) in MeOH (10 mL). NaBH$_4$ (0.2 g, 5.2 mmol, 2.0 eq) was added at 0° C. Reaction mixture was stirred at 0° C. for 1 h. Upon completion of the reaction, mixture was transferred into NH$_4$Cl, extracted with EtOAc, dried over Na$_2$SO$_4$ and concentrated under reduced pressure to obtain crude which was purified by column chromatography to get 96.7 (0.7 g, 98.0%). MS(ES): m/z 272 [M+H]$^+$.

Synthesis of compound 96.8. To a solution of 96.7 (0.65 g, 2.39 mmol, 1.0 eq) in MeOH (10.0 mL), Pd(OH)$_2$ on charcoal (0.5 g) and 1N HCl (cat.) were added. Reaction mixture was stirred at 40 psi of H$_2$ pressure for 24 h. Upon completion of the reaction, mixture was filtered through celite-bed and washed with methanol, concentrated under reduced pressure to obtain crude material. The crude was purified by column chromatography to furnish 96.8. (0.2 g, 46.0%). MS(ES): m/z 182 [M+H]$^+$.

Synthesis of compound 96.9. Compound 96.9 was prepared by chiral separation of compound 96.8 (0.050 g), MS (ES): m/z 182 [M+H]$^+$, Synthesis of compound 96.91. Compound 96.91 was prepared by chiral purification of compound 96.8 MS (ES): m/z 182 [M+H]$^+$, Synthesis of compound 96.92. Compound 96.92 was prepared using the procedure described in Example 64.

Synthesis of compound I-96. Compound I-96 was prepared using the procedure described in Example 64. MS(ES): m/z 433 [M+H]+; 1H NMR (DMSO-d6, 400 MHz): 9.76 (s, 1H), 9.08 (s, 1H), 8.14 (s, 1H), 7.91-7.76 (m, 4H), 6.3 (s, 1H), 4.85 (s, 1H), 4.08-4.05 (m, 1H), 3.67-3.54 (m, 2H), 2.91-2.82 (m, 2H), 1.65-1.62 (m, 4H), 1.01-0.99 (d, 3H).

Example 97

Synthesis of (R)-3-fluoro-2-(4-(3-(3-(hydroxymethyl)piperidin-1-yl)-1H-pyrazol-1-yl)-5-oxo-6,7-dihydro-5H-pyrrolo[3,4-b]pyridin-2-yl)benzonitrile, I-97

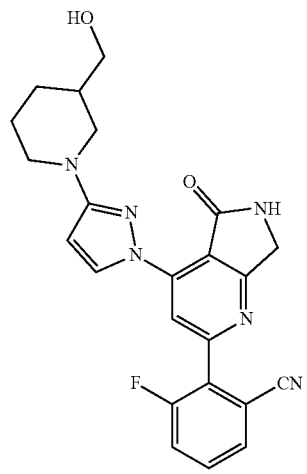

I-86

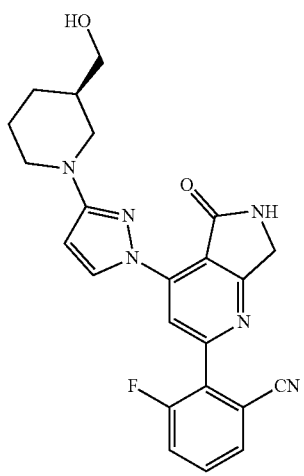

I-97

Compound I-97 was prepared by chiral purification of compound I-86. MS(ES): m/z 433 [M+H]+; 1H NMR (MeOD, 400 MHz): 9.69-9.68 (d, 1H), 8.28 (s, 1H), 7.79-7.72 (m, 1H), 7.71-7.62 (m, 2H), 6.23-6.22 (d, 1H) 3.98-3.95 (m, 1H), 3.83-3.80 (m, 1H), 3.53-3.43 (m, 2H), 2.91-2.85 (m, 1H), 2.68-2.62 (m, 1H), 1.85-1.76 (m, 3H), 1.70-1.64 (m, 1H), 1.23-1.17 (m, 3H).

Example 98

Synthesis of (S)-3-fluoro-2-(4-(3-(3-(hydroxymethyl)piperidin-1-yl)-1H-pyrazol-1-yl)-5-oxo-6,7-dihydro-5H-pyrrolo[3,4-b]pyridin-2-yl)benzonitrile, I-98

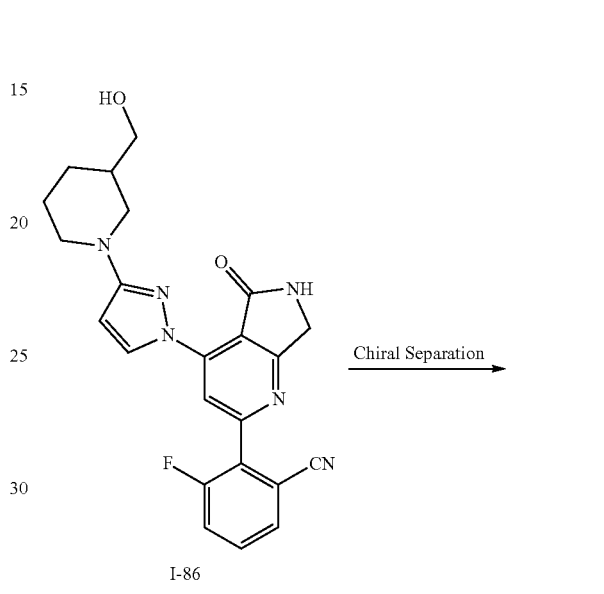

I-86

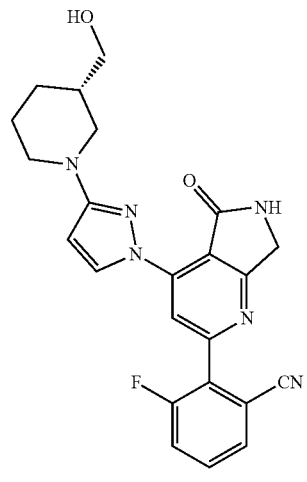

I-98

Compound I-98 was prepared by chiral purification of compound I-86. MS(ES): m/z 433 [M+H]+; 1H NMR (MeOD, 400 MHz): 9.69-9.68 (d, 1H), 8.27 (s, 1H), 7.78-7.71 (m, 1H), 7.69-7.62 (m, 2H), 6.23-6.22 (d, 1H) 3.98-3.95 (m, 1H), 3.82-3.79 (m, 1H), 3.53-3.43 (m, 2H), 2.90-2.84 (m, 1H), 2.68-2.64 (m, 1H), 1.81-1.76 (m, 3H), 1.71-1.60 (m, 1H), 1.30-1.17 (m, 3H).

Example 99
Synthesis of 3-fluoro-2-(4-(3-(4-((1-methylazetidin-3-yl)sulfonyl)piperazin-1-yl)-1H-pyrazol-1-yl)-5-oxo-6,7-dihydro-5H-pyrrolo[3,4-b]pyridin-2-yl)benzonitrile, I-99
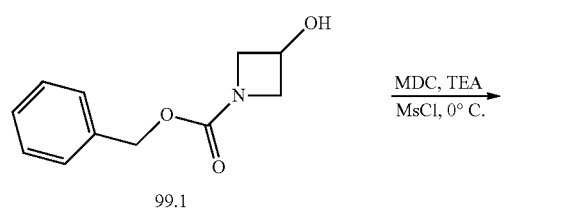
99.1
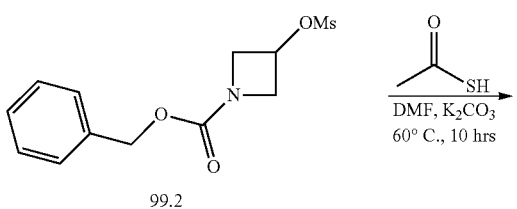
99.2
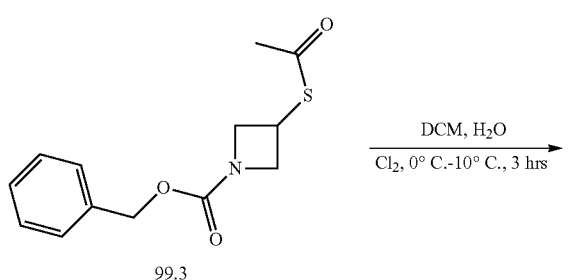
99.3
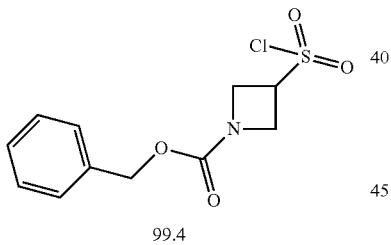
99.4
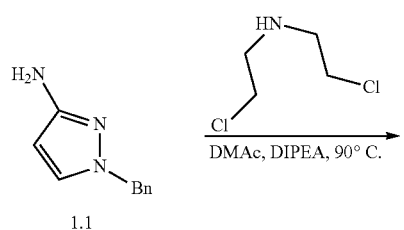
1.1
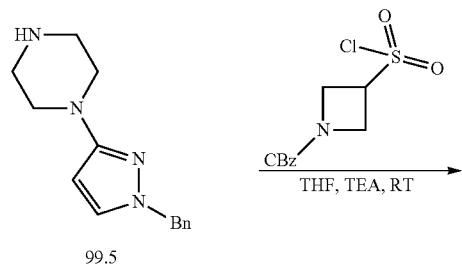
99.5
-continued
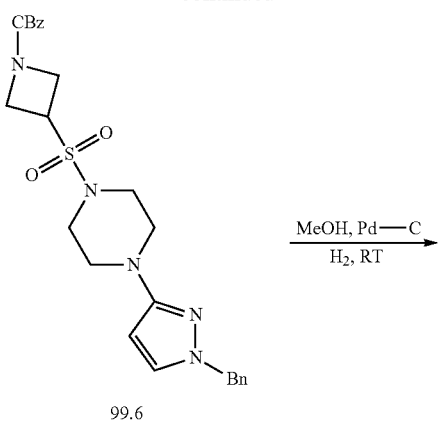
99.6
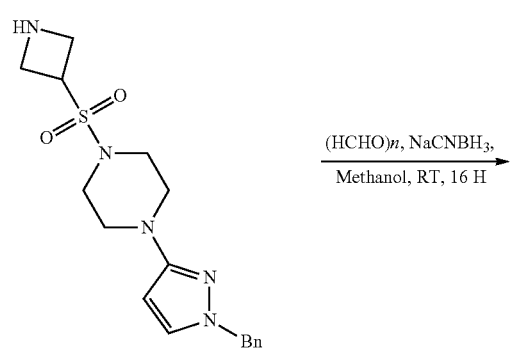
99.7
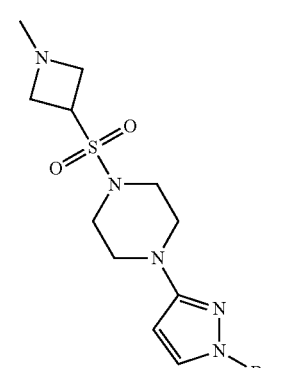
99.8
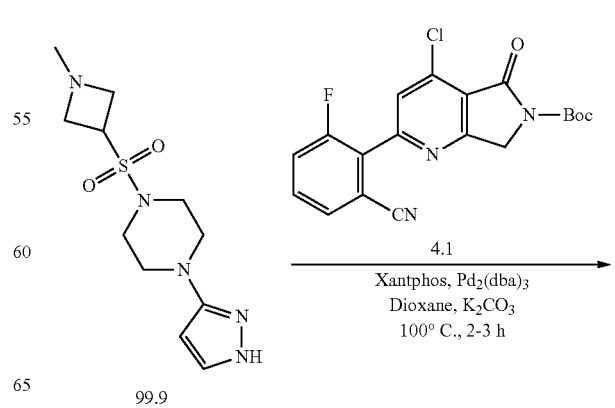
99.9    4.1

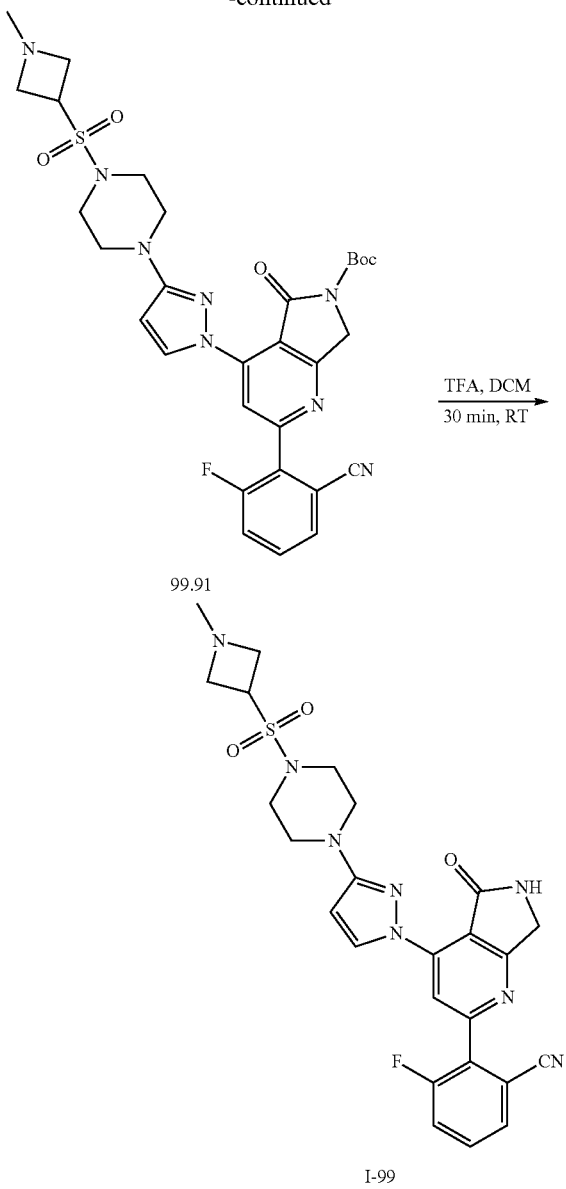

Synthesis of 99.2. To a solution of 99.1 (5.0 g, 24.15 mmol, 1 eq) in DCM (100 mL) was added Et₃N (5 g, 49.5 mmol, 2 eq). To this was added MsCl (2.89 g, 25.35 mmol, 1.05 eq) drop wise at 0° C. The reaction mixture was stirred at 0° C. for 30 min. Upon completion of the reaction, reaction was quenched with and extracted with DCM. Combined organic layers were washed with brine, dried over Na₂SO₄ and concentrated under reduced pressure to get crude which was purified by column chromatography to furnish 99.2 (5.0 g, 48%). MS(ES): m/z 285 [M+H]⁺.

Synthesis of 99.3. To a suspension of K₂CO₃ (3.63 g, 26.31 mmol, 1.5 eq) in DMF (100 mL) was added ethanethioic S-acid (1.99 g, 26.31 mmol, 1.5 eq) at 0° C. To this was added 99.2 (5 g, 17.54 mmol, 1 eq). The resulting mixture was heated to 60° C. for 6 h. Upon completion, the reaction was quenched with water then extracted with ethyl acetate. Organic layers were combined, washed with brine solution, dried over Na₂SO₄ and concentrated under reduced pressure to obtain crude which was purified by column chromatography to furnish 99.3 (2.1 g, 48.5%). MS(ES): m/z 266.12 [M+H]⁺.

Synthesis of 99.4. Through a solution of 99.3 (2.1 g, 7.92 mmol, 1 eq) in DCM (100 mL), water (30 mL) at 0° C., Cl₂ gas was bubbled for 1 h. Upon completion of the reaction; reaction mixture was poured into water, and extracted with EtOAc. Organic layers were combined, washed with brine, dried over Na₂SO₄ and concentrated under reduced pressure to pressure to obtain crude material which was purified by column chromatography to provide 99.4 (1.4 g, 29.96%). MS(ES): m/z 291.01 [M+H]⁺.

Synthesis of 99.5. To a solution of 1.1 (5.0 g, 28.9 mmol, 1 eq) in DMA (15 mL) was added bis(2-chloroethyl)amine (5.1 g, 28.65 mmol, 1 eq), DIPEA (11.15 g, 86.43 mmol, 3 eq). The resulting mixture was heated 90° C. in microwave for 2 h. Upon completion, the reaction was quenched with water and extracted with EtOAc, washed with brine, dried over Na₂SO₄ and concentrated under reduced pressure to get crude. The crude was purified by column chromatography to furnish 99.5 (0.5 g, 4.29%). MS(ES): m/z 243.16 [M+H]⁺.

Synthesis of 99.6. To a solution of 99.5 (0.5 g, 2.01 mmol, 1.0 eq) in DCM (20.0 mL) was added Et₃N (0.521 g, 5.16 mmol, 2.5 eq) at 0° C. To this was added 99.4 (0.716 g, 2.47 mmol, 1.2 eq). The reaction was stirred at room temperature for 1 h. Upon completion, the reaction was quenched with water and extracted with EtOAc, washed with brine, dried over Na₂SO₄ and concentrated under reduced pressure to get crude. The crude was purified by column chromatography to furnish 99.6 (0.45 g, 60.7%). MS(ES): m/z 359 [M+H]⁺.

Synthesis of 99.7. To a Solution of 99.6 (0.45 g, 0.909 mmol, 1.0 eq) in MoOH (3 mL) was added Pd(OH)₂ (0.15 g) and 1N HCl (0.5 mL). The mixture was stirred in hydrogenator under hydrogen (50 psi) at room temperature for 24 h. Upon completion of the reaction, reaction mixture was filtered through celite bed and washed with methanol (10 mL). Filtrate was concentrated under reduced pressure to obtain crude which was purified by column chromatography to provide 99.7 (0.2 g, 55.3%). MS(ES): m/z 266.25 [M+H]⁺.

Synthesis of 99.8. To a solution of 99.7 (0.3 g, 0.831 mmol, 1 eq) in MeOH (15 mL) was added paraformaldehyde (0.25 g, 8.31 mmol, 10 eq), NaCNBH₃ (0.06 g, 0.9141 mmol, 1.1 eq) at 0° C. The resulting reaction mass was stirred at room temperature for 16 h. Upon completion, the reaction was quenched with, extracted with ethyl acetate, washed with brine, then dried over Na₂SO₄. Solvents were removed under reduced pressure to provide crude which was purified by column chromatography to provide 99.8 (0.18 g, 57.8%). MS(ES): m/z 376.15 [M+H]⁺.

Synthesis of 99.9. To a Solution of 99.8 (0.18 g, 0.48 mmol, 1.0 eq) in MeOH (5.0 mL) was added Pd(OH)₂ (0.15 g) and 1N HCl (0.5 mL). The mixture was stirred in hydrogenator under hydrogen (50 psi) at room temperature for 24 h. Upon completion of the reaction, reaction mixture was filtered through celite bed and washed with methanol (10 mL). Filtrate was concentrated under reduced pressure to obtain crude which was purified by column chromatography to provide 99.9 (0.044 g, 32.2%). MS(ES): m/z 285.11 [M+H]⁻.

Synthesis of 99.91. Compound was prepared from 99.9 and 4.1 using the procedure described in Example 64.

Synthesis of I-99. Compound was prepared from 99.91 using the procedure described in Example 64. MS(ES): m/z 537.11 [M+H]⁺; ¹H NMR (DMSO-d₆, 400 MHz): 8.16 (s, 1H), 7.85-7.83 (d, 1H), 7.73-7.71 (m, 2H), 7.51 (s, 1H), 6.99 (s, 1H), 6.07 (s, 1H), 5.75 (m, 2H), 5.04 (m, 2H), 4.3 (m, 2H), 3.22-3.14 (m, 4H), 3.09-3.05 (m, 4H).

Example 100

Synthesis of 2-(4-(3-(1,4-dioxa-7-azaspiro[4.4]nonan-7-yl)-1H-pyrazol-1-yl)-5-oxo-6,7-dihydro-5H-pyrrolo[3,4-b]pyridin-2-yl)-3-fluorobenzonitrile, I-100

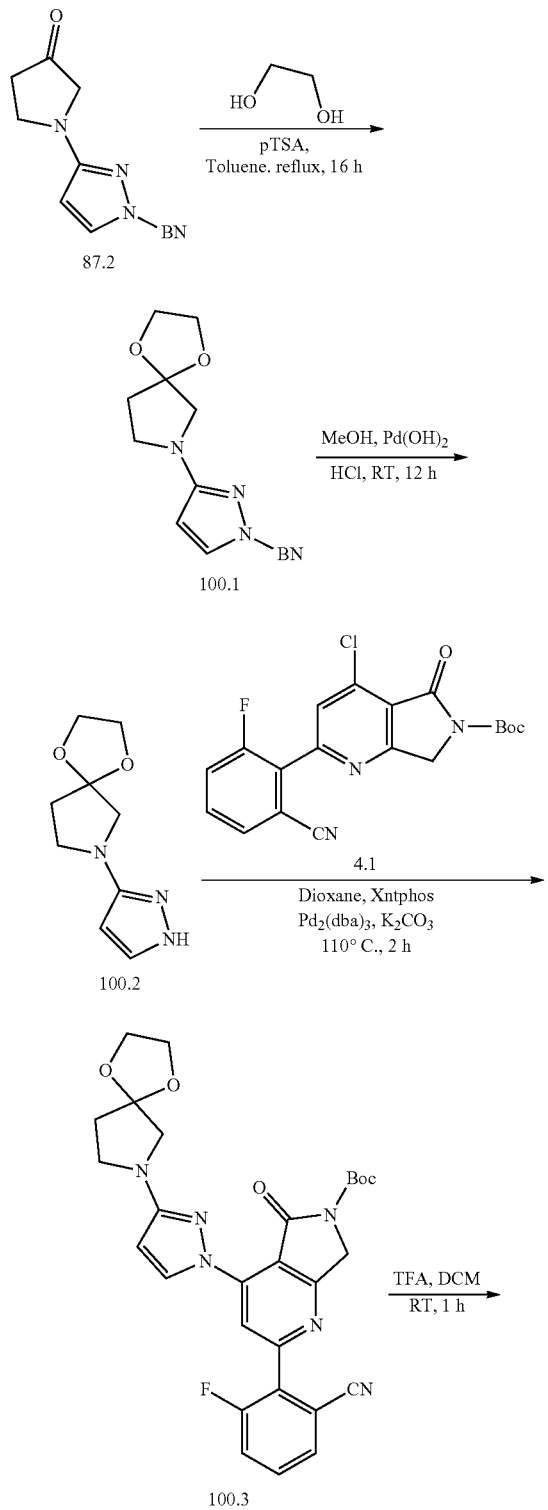

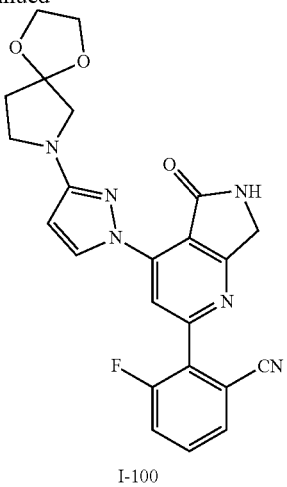

I-100

Synthesis of compound 100.1. To a solution of 100.1 (0.53 g, 2.19 mmol, 1.0 eq) in benzene (10.0 mL) were added Ethylene glycol (0.817 g, 13.2 mmol, 6.0 eq), p-TsOH (0.037 g, 0.21 mmol, 0.1 eq). Reaction was stirred at 90° C. for 16 h in Dean-Stark apparatus. Upon completion of the reaction, mixture was transferred into water, and then extracted with EtOAc. Organic layers were combined, washed with brine, dried over $Na_2SO_4$ and concentrated under reduced pressure to obtain crude which was purified by column chromatography to provide 100.1 (0.41 g, 65.5%). MS(ES): m/z 286 [M+H]$^+$.

Synthesis of compound 100.2. To a solution of 100.1 (0.4 g, 1.40 mmol, 1.0 eq) in MeOH (10.0 mL). 20% Pd(OH)$_2$ (0.1 g) and 1N HCl (catalytic amount) were added. Reaction mixture was stirred (under hydrogen) at 40 psi for 12 h. Upon completion of the reaction, reaction mixture was filtered and solvents removed under reduced pressure to obtain crude which was purified by column chromatography to furnish 100.2 (0.13 g, 47.6%). MS(ES): m/z 196 [M+H]$^+$.

Synthesis of compound 100.3. Compound was prepared from 100.2 and 4.1 using the procedure described in Example 64.

Synthesis of compound I-100. Compound was prepared from 100.3 using the procedure described in Example 64. MS(ES): m/z 447 [M+H]$^+$; $^1$H NMR (DMSO-d$_6$, 400 MHz): 9.78 (s, 1H), 9.10 (s, 1H), 8.10 (s, 1H), 7.91 (d, 1H), 7.83-7.75 (m, 2H), 6.16 (d, 1H), 4.49 (s, 2H), 3.92 (s, 4H), 3.44 (t, 2H), 3.39 (s, 2H), 2.10 (t, 2H).

Example 101

Synthesis of 3-fluoro-2-(5-oxo-4-(3-(tetrahydrofuran-2-yl)-1H-pyrazol-1-yl)-6,7-dihydro-5H-pyrrolo[3,4-b]pyridin-2-yl)benzonitrile, I-101

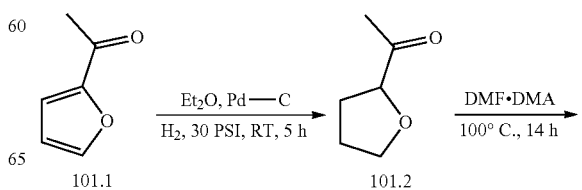

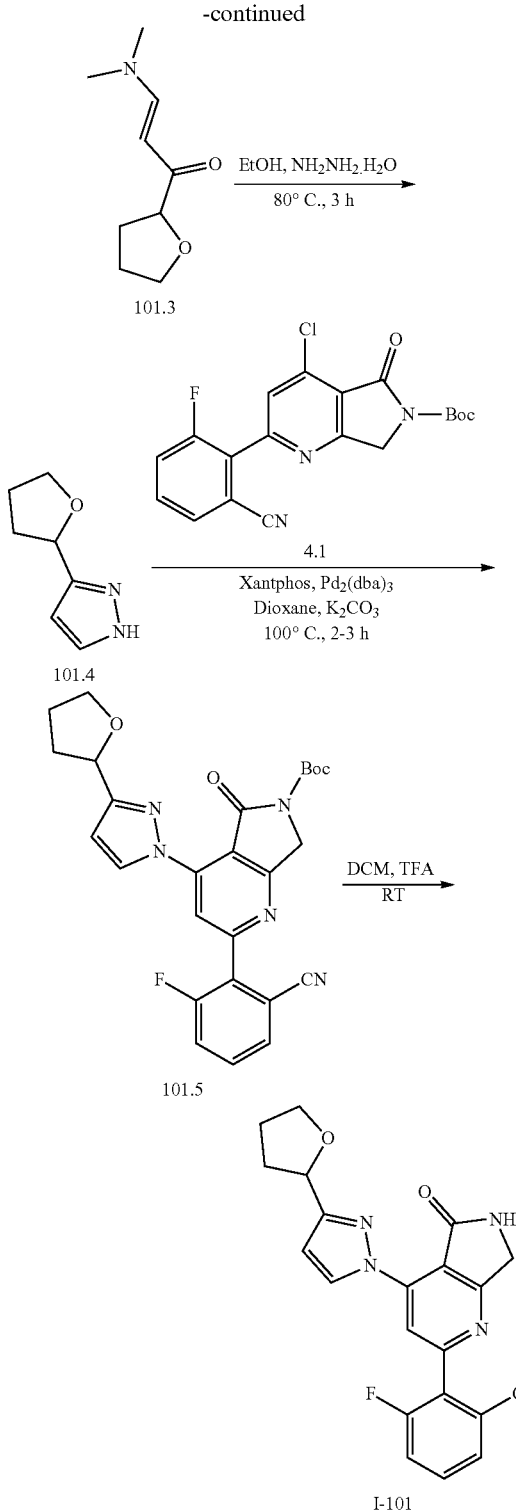

Synthesis of compound 101.3. A mixture of 101.2 (2.4 g, 21.0 mmol, 1.0 eq) and 1,1-dimethoxy-N,N-dimethylmethanamine (5.0 g, 42.1 mmol, 2.0 eq) in sealed tube was stirred at 100° C. for 12 h. Upon completion of the reaction, mixture was concentrated under reduced pressure to obtain the crude which was purified by column chromatography to provide 101.3 (2.5 g, 70.4%). MS(ES): m/z 170 [M+H]+.

Synthesis of compound 101.4. To a solution of 101.3 (2.0 g, 11.8 mmol, 1.0 eq) in EtOH (20 ml) was added Hydrazine monohydrate (0.7 g, 14.2 mmol, 1.2 eq). Reaction mixture was stirred at 80° C. for 3 hours. Upon completion, reaction mixture was concentrated to obtain crude which was purified by column chromatography to provide 101.4 (0.9 g, 55.2%). MS(ES): m/z 139 [M+H]+.

Synthesis of compound 101.5. Compound was prepared from 101.4 and 4.1 using the procedure described in Example 64.

Synthesis of compound I-101. Compound was prepared from 101.5 using the procedure described in Example 64. (0.1 g, 31.4%). MS(ES): m/z 390 [M+H]+; 1H NMR (CDCl3, 400 MHz): 9.65 (d, 1H), 8.48 (d, 1H), 7.69 (d, 1H), 7.60-7.55 (m, 1H), 7.51-7.47 (m, 1H), 6.68 (s, 1H), 6.54 (d, 1H), 5.07 (t, 1H), 4.66 (s, 2H), 4.10-4.05 (m, 1H), 3.97-3.92 (m, 1H), 2.37-2.33 (m, 1H), 2.17-2.03 (m, 3H).

Example 102

Synthesis of 2-(1-(2-(2-cyano-6-fluorophenyl)-5-oxo-6,7-dihydro-5H-pyrrolo[3,4-b]pyridin-4-yl)-1H-pyrazol-3-yl)acetic acid, I-102

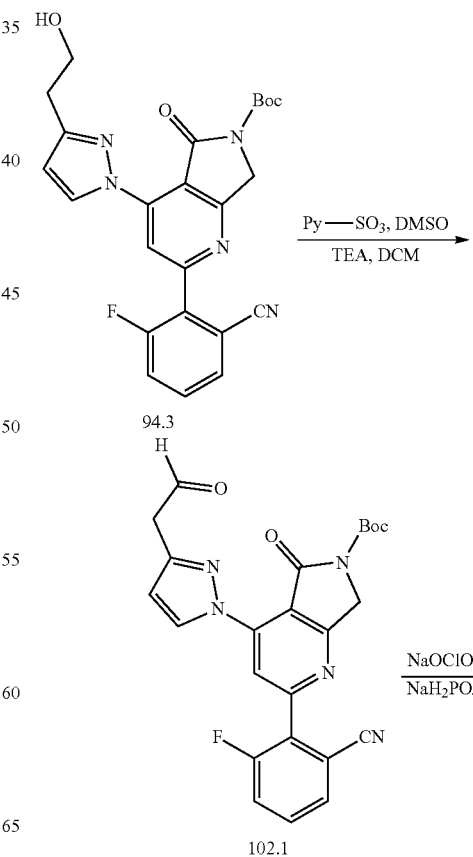

Synthesis of compound 101.2. To a solution of 101.1 (4 g, 36.3 mmol, 1.0 eq) in Et2O (20 mL) was added 10% Pd/C (0.25 g). Reaction mixture was stirred at room temperature under H2 at 30 psi for 5 h. Upon completion of the reaction, mixture was filtered. Filtrate was concentrated under reduced pressure to obtain crude which was purified by column chromatography to get 101.1. (2.8 g, 67.6%). MS(ES): m/z 115 [M+H]+.

241

-continued

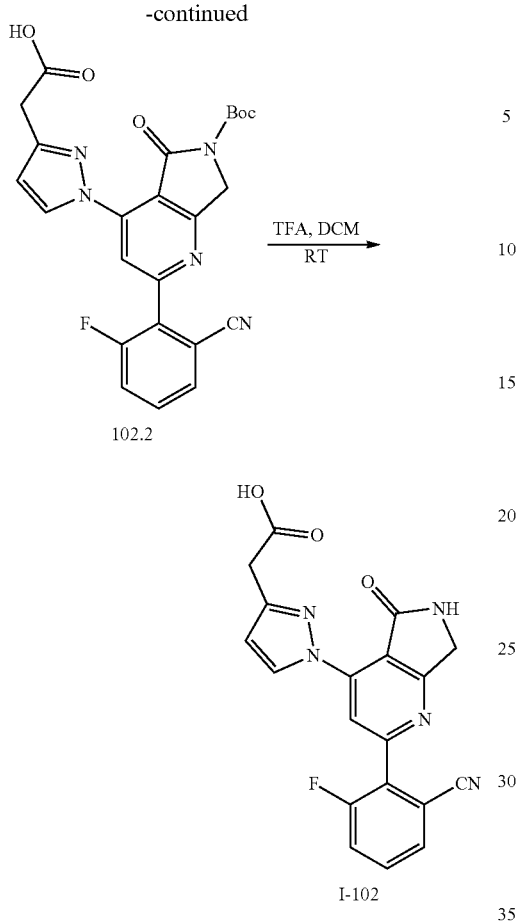

Example 103

Synthesis of (R)-3-fluoro-2-(5-oxo-4-(3-(tetrahydrofuran-2-yl)-1H-pyrazol-1-yl)-6,7-dihydro-5H-pyrrolo[3,4-b]pyridin-2-yl)benzonitrile, I-103

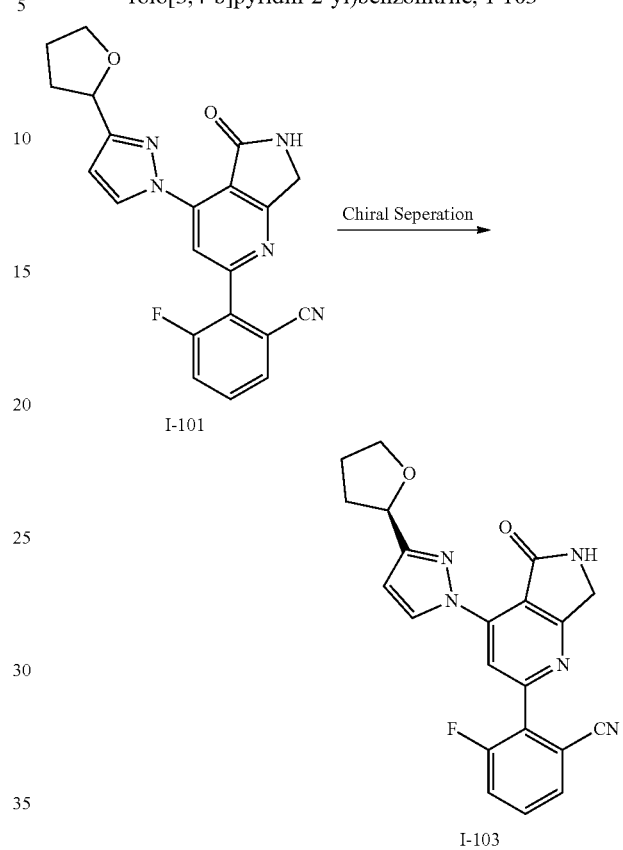

Synthesis of compound 102.1. To a solution of 94.3 (0.4 g, 0.86 mmol, 1.0 eq) in DMSO (0.067 g, 8.6 mmol, 10.0 eq) and DCM (5.0 mL) was added Et₃N (0.7 mL, 24.6 mmol, 6 eq) and Sulfur trioxide pyridine complex (0.4 mL, 2.5 mmol, 3 eq) at 0° C. Reaction mixture was stirred at room temperature for 1 h. Upon completion of the reaction, reaction mixture was transferred into water and product was extracted with DCM. Organic layers were combined, washed with brine solution, dried over Na₂SO₄ and concentrated under reduced pressure to obtain crude 120.1. (0.12 g, 29.0%). MS(ES): m/z 464.68 [M+H]⁺. Crude was used for next step without purification.

Synthesis of compound 102.2. To a solution of 120.1 (0.1 g, 0.21 mmol, 1.0 eq) in t-butanol was added sodium chlorite (0.29 g, 2.1 mmol, 10 eq) and di-sodium hydrogen phosphate dihydrate (1.5 mL) followed by 2-methyl-2-butene (1.5 mL). Reaction mixture was stirred at room temperature for 4 h. Upon completion of the reaction, reaction mixture was transferred into water and product was extracted with EtOAc. Organic layers were combined, washed with brine solution, dried over Na₂SO₄ and concentrated under reduced pressure to obtain crude which was purified by preparative HPLC to obtain 20.2. (0.02 g, 16.1%). MS(ES): m/z 478.5 [M+H]⁺.

Synthesis of compound I-102. Compound was prepared using the procedure described in Example 64. (0.010 g, 63.27%). MS(ES): m/z 378.18 [M+H]⁺; ¹H NMR (MeOD, 400 MHz): 9.62 (s, 1H), 8.42 (s, 1H), 7.82-7.80 (m, 1H), 7.76-7.65 (m, 3H), 6.59 (s, 1H), 4.62 (s, 2H), 3.68 (s, 2H).

Compound I-103 was prepared by chiral purification of compound I-101. MS(ES): m/z 390 [M+H]⁺; ¹H NMR (CDCl₃, 400 MHz): 9.65 (d, 1H), 8.48 (d, 1H), 7.69 (d, 1H), 7.60-7.55 (m, 1H), 7.51-7.47 (m, 1H), 6.68 (s, 1H), 6.54 (d, 1H), 5.07 (t, 1H), 4.66 (s, 2H), 4.10-4.05 (m, 1H), 3.97-3.92 (m, 1H), 2.37-2.33 (m, 1H), 2.17-2.03 (m, 3H).

Example 104

Synthesis of (S)-3-fluoro-2-(5-oxo-4-(3-(tetrahydrofuran-2-yl)-1H-pyrazol-1-yl)-6,7-dihydro-5H-pyrrolo[3,4-b]pyridin-2-yl)benzonitrile, I-104

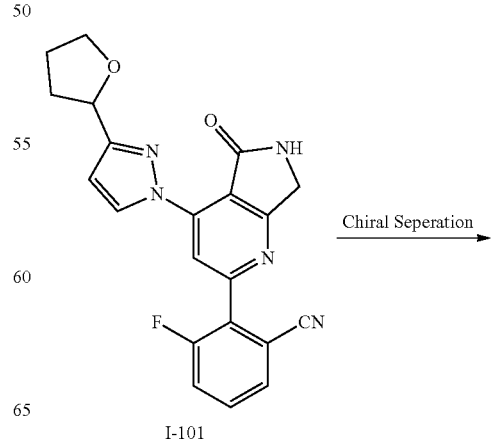

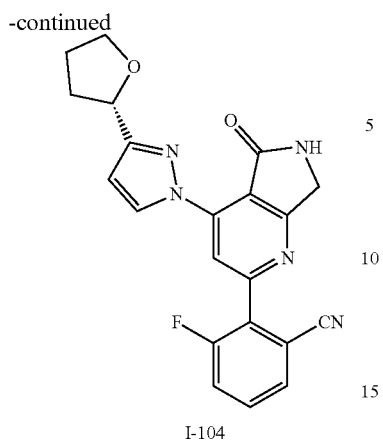

I-104

Compound I-103 was prepared by chiral purification of compound I-101. MS(ES): m/z 390 [M+H]$^+$; $^1$H NMR (CDCl$_3$, 400 MHz): 9.65 (d, 1H), 8.48 (d, 1H), 7.69 (d, 1H), 7.60-7.55 (m, 1H), 7.51-7.47 (m, 1H), 6.68 (s, 1H), 6.54 (d, 1H), 5.07 (t, 1H), 4.66 (s, 2H), 4.10-4.05 (m, 1H), 3.97-3.92 (m, 1H), 2.37-2.33 (m, 1H), 2.17-2.03 (m, 3H).

Example 105

Synthesis of 2-(4-(3-((3S,4R)-3,4-dihydroxypiperidin-1-yl)-1H-pyrazol-1-yl)-5-oxo-6,7-dihydro-5H-pyrrolo[3,4-b]pyridin-2-yl)-3-fluorobenzonitrile, I-105

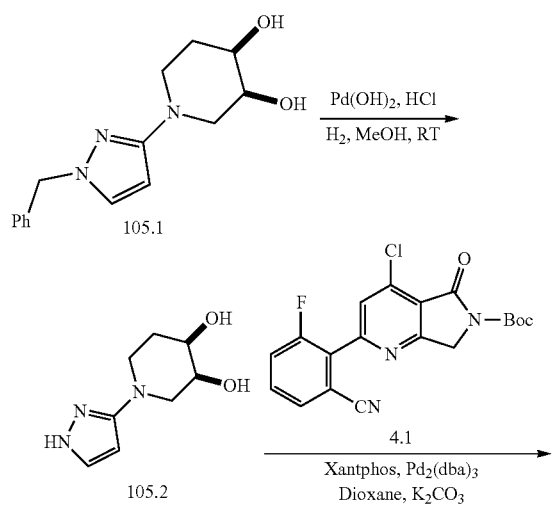

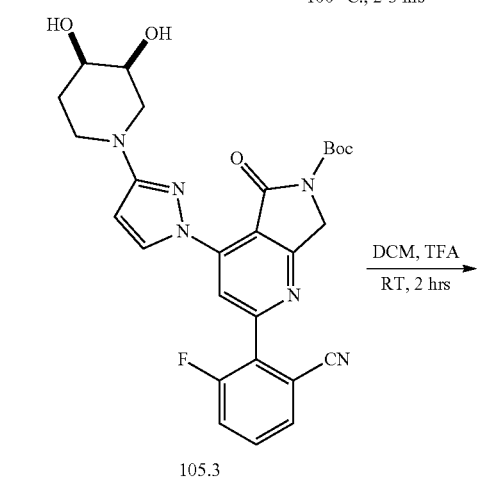

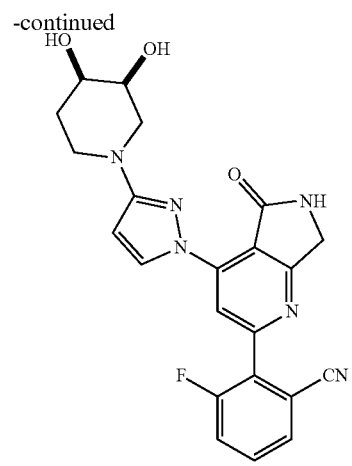

I-105

Synthesis of compound 105.2. To a solution of 105.1 (0.4 g, 1.46 mmol, 1.0 eq) in MeOH (20 mL) was added Pd(OH)$_2$ (0.45 g), dil. HCl (0.1 mL) in 50 mL autoclave. The hydrogen was purged to 50 psi. The reaction was stirred at room temperature overnight. Upon completion of the reaction, mixture was filtered. The mother liquor was evaporated to furnish 105.2 (0.15 g, 55.9%). Crude compound was used for next step without any purification. LCMS (ES): m/z 184.21 [M+H]$^+$.

Synthesis of compound 105.3. Compound 105.3 was prepared from 105.2 and 4.1 as described in Example 64

Synthesis of compound I-105. Compound I-105 was prepared from 105.3 as described in example 64. MS(ES): m/z 435.15 [M+H]$^+$; $^1$H NMR (MeOD, 400 MHz): 9.71-9.70 (d, 1H), 8.29 (s, 1H), 7.8-7.78 (m, 1H), 7.75-7.64 (m, 2H), 6.25 (s, 1H), 4.54-4.12 (s, 2H), 3.9-3.83 (m, 1H), 3.82-3.8 (m, 1H), 3.54-3.45 (m, 3H), 3.43-3.42 (m, 1H), 1.97-1.91 (m, 1H), 1.83-1.77 (m, 1H).

Example 106

Synthesis of 3-fluoro-2-(4-(3-((2R,6R)-4-hydroxy-2,6-dimethylpiperidin-1-yl)-1H-pyrazol-1-yl)-5-oxo-6,7-dihydro-5H-pyrrolo[3,4-b]pyridin-2-yl)benzonitrile, I-106

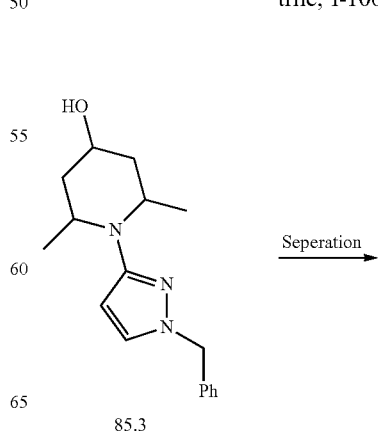

-continued

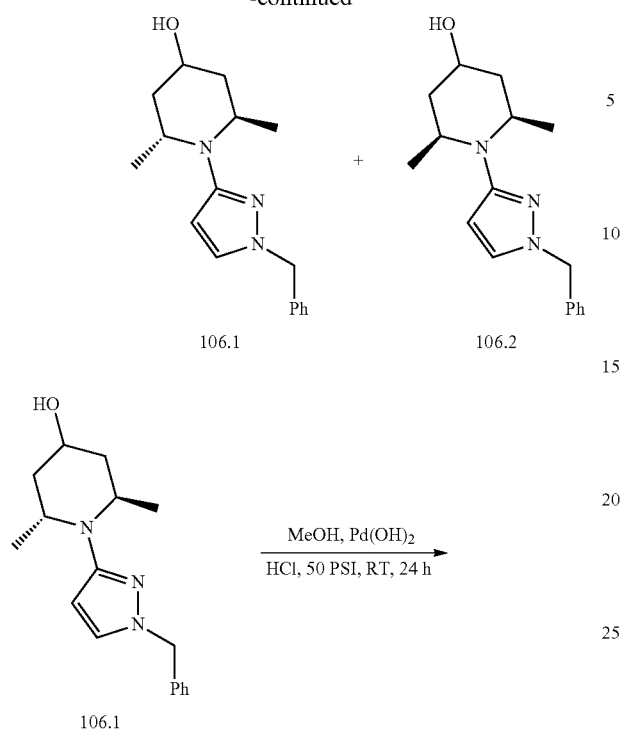

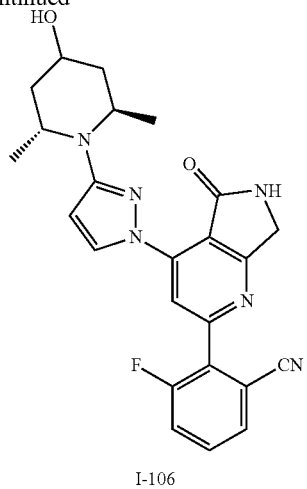

I-106

Synthesis of compound 106.1 and 106.2. Compounds were prepared by chiral purification of compound 85.3.

Synthesis of compound 106.3. To a solution of 106.1 (0.24 g, 0.77 mmol, 1.0 eq) in MeOH (10 mL), 20% palladium hydroxide on charcoal (0.06 g) and 1N HCl (catalytic) were added. Reaction mixture was stirred under hydrogen at 40 psi for 24 h. Upon completion of the reaction, reaction mixture was filtered through celite, and concentrated under reduced pressure to obtain crude material. The crude was purified by column chromatography to get pure to get 106.3 (0.105 g, 69.7%). MS(ES): m/z 195.3 [M+H]$^+$.

Synthesis of compound 106.4. Compound was prepared using the procedure described in Example 64.

Synthesis of compound I-106. Compound was prepared using the procedure described in Example 64. (0.015 g, 47.09%). MS(ES): m/z 447.28 [M+H]$^+$; $^1$H NMR (DMSO-$d_6$, 400 MHz): 9.71 (d, 1H), 9.13 (s, 1H), 8.18 (s, 1H), 7.92-7.90 (m, 1H), 7.83-7.75 (m, 2H), 6.34 (d, 1H), 4.69 (s, 1H), 4.50 (s, 2H), 3.78-3.77 (bs, 1H), 3.56-3.52 (m, 2H), 1.93-1.89 (m, 2H), 1.47-1.41 (m, 1H), 1.26-1.20 (m, 1H), 1.13-1.11 (d, 6H).

Example 107

Synthesis of 3-fluoro-2-(4-(3-((2S,6R)-4-hydroxy-2,6-dimethylpiperidin-1-yl)-1H-pyrazol-1-yl)-5-oxo-6,7-dihydro-5H-pyrrolo[3,4-b]pyridin-2-yl)benzonitrile, I-107

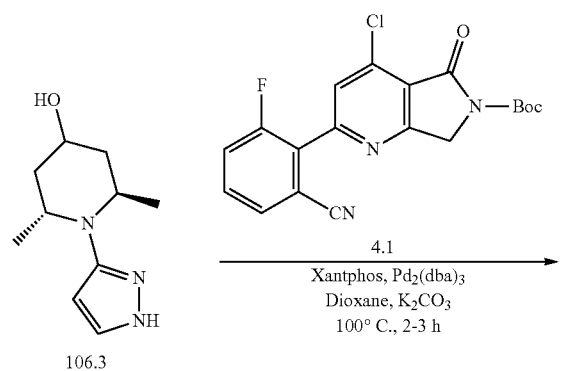

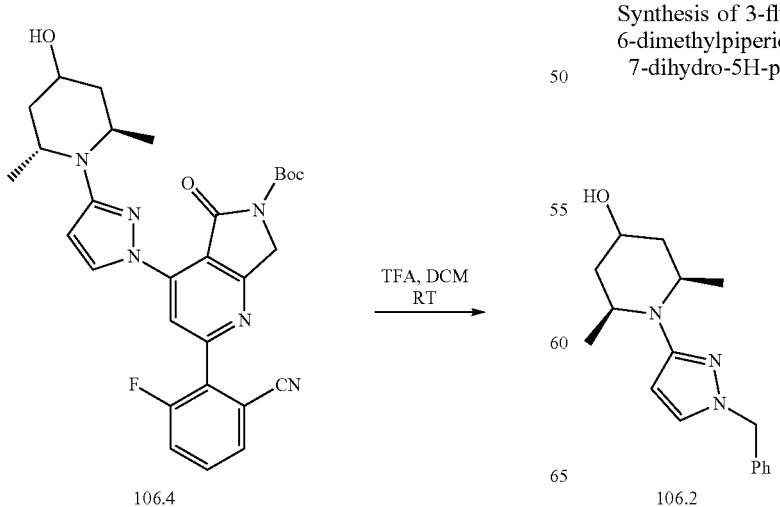

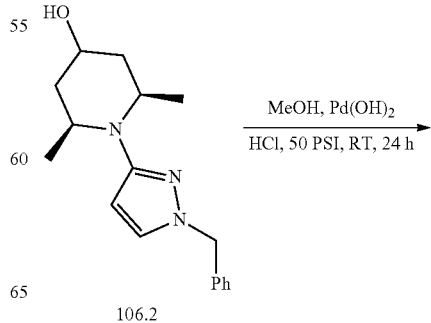

247
-continued
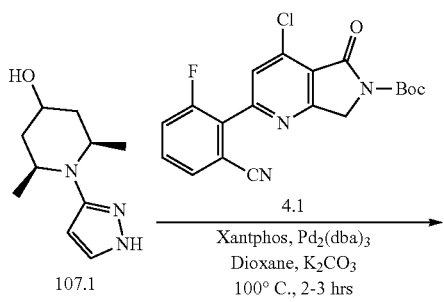
Compound I-107 was prepared using the procedures referred in Example 106. (0.017 g, 50.76%). MS(ES): m/z 447.28 [M+H]$^+$; $^1$H NMR (DMSO-d$_6$, 400 MHz): 9.71 (d, 1H), 9.12 (s, 1H), 8.15 (s, 1H), 7.92-7.90 (m, 1H), 7.84-7.73 (m, 2H), 6.36 (d, 1H), 4.62-4.60 (d, 1H), 4.50 (s, 2H), 3.99 (bs, 1H), 3.86-3.83 (m, 1H), 3.53-3.51 (m, 1H), 1.95-1.93 (m, 1H), 1.81-1.78 (m, 1H), 1.64-1.57 (m, 1H), 1.34 (d, 3H), 1.03 (d, 3H).
248
Example 108
Synthesis of 2-(4-(3-((4R)-3,4-dihydroxy-3-methyl-piperidin-1-yl)-1H-pyrazol-1-yl)-5-oxo-6,7-dihydro-5H-pyrrolo[3,4-b]pyridin-2-yl)-3-fluorobenzonitrile, I-108
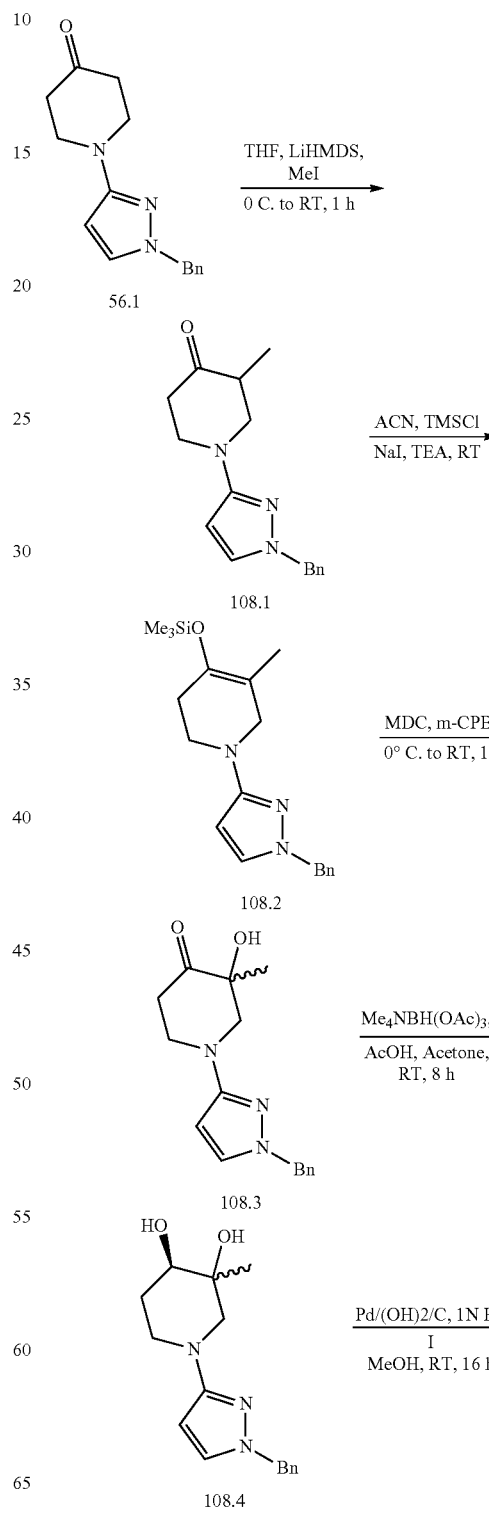

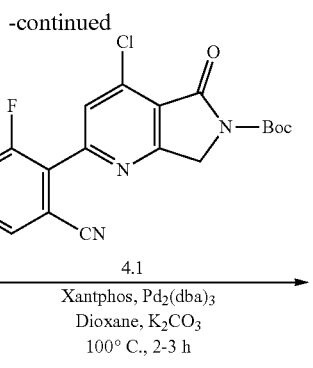

under reduced pressure. The crude was purified by column chromatography to furnish 108.1 (0.78 g, 28.05%). MS(ES): m/z 270 [M+H]$^+$.

Synthesis of compound 108.2. To a solution of 108.1 (0.780 g, 2.89 mmol, 1.0 eq) in acetonitrile (12.0 mL) was added NaI (0.868 g, 5.79 mmol, 3.0 eq) followed by Et$_3$N (0.586 g, 5.79 mmol, 2.0 eq) at 0° C. and reaction mixture was stirred at room temperature for 1 h. Reaction mixture was cooled to 0° C. and TMSCl (0.629 g, 5.79 mmol, 2.0 eq) was added dropwise. Reaction was stirred at room temperature for 15 h. Upon completion of reaction, reaction mixture was transferred into ice. Resulting mixture was extracted with EtOAc. Organic layers were combined, washed with brine, dried over Na$_2$SO$_4$ and concentrated under reduced pressure. The crude was purified by column chromatography to furnish 108.2 (0.78 g, 79.6%). MS(ES): m/z 342 [M+H]$^+$.

Synthesis of compound 108.3. To a mixture of 108.2 (0.780 g, 2.28 mmol, 1.0 eq) in DCM (15.0 mL) was added metachloroperoxybenzoic acid (0.786 g, 4.56 mmol, 0.1 eq) at 0° C. Reaction mixture stirred at room temperature for 1 h. Upon completion of the reaction; reaction mixture was transferred into water, then extracted with EtOAc. Organic layer was combined, washed with NaHCO$_3$, dried over Na$_2$SO$_4$ and concentrated under reduced pressure to pressure to obtain crude which was purified by column chromatography to provide 108.3 (0.68 g, 85.1%). MS(ES): m/z 286 [M+H]$^+$.

Synthesis of compound 108.4. To a solution of NH$_4$BH (OAc)$_3$ (2.72 g, 17.9 mmol, 8 eq) in acetone (50 mL) and HOAc (2.15 g, 35.4 mmol, 16 eq), was added 108.3 (0.640 g, 2.24 mmol, 1.0 eq) at 0° C. Reaction was stirred at room temperature for 8 h. Upon completion of the reaction; reaction mixture was transferred into water, then extracted with EtOAc. Organic layers were combined, washed with brine, dried over Na$_2$SO$_4$ and concentrated under reduced pressure to pressure to obtain crude which was purified by column chromatography 108.4 (0.15 g, 23.0%). MS(ES): m/z 288 [M+H]$^+$.

Synthesis of compound 108.5. To a solution of 108.4 (0.150 g, 0.52 mmol, 1.0 eq) in MeOH (5 mL). 20% Pd(OH)$_2$ (0.03 g) and 1N HCl (catalytic amount) was added. Reaction mixture was stirred (under hydrogen) at 40 psi for 16 h. Upon completion of the reaction, reaction mixture was filtered through celite-bed and washed with MeOH. Filtrate was concentrated under reduced pressure to obtain crude, which was purified by column chromatography to provide 108.5. (0.095 g, 93.13%). MS(ES): m/z 198 [M+H]$^+$.

Synthesis of compound 108.6. Compound was prepared from 108.5 and 4.1 using the procedure described in Example 64.

Synthesis of compound I-108. Compound was prepared from 108.6 using the procedure described in Example 64 MS(ES): m/z 449 [M+H]$^+$; $^1$H NMR (MeOD, 400 MHz): 9.75 (d, 1H), 9.10 (s, 1H), 8.15 (s, 1H), 7.92-7.90 (m, 1H), 7.83-7.75 (m, 2H), 6.34 (d, 1H), 4.73 (d, 1H), 4.50 (d, 3H), 3.50-3.48 (m, 1H), 3.41-3.39 (m, 1H), 3.13-3.08 (m, 1H), 2.91 (d, 1H), 1.92-1.87 (m, 1H), 1.46-1.42 (m, 1H), 1.08 (s, 3H).

Synthesis of compound 108.1. To a solution of 56.1 (2.6 g, 10.18 mmol, 1.0 eq) in THF (34.0 mL) was added LHMDS (2.55 g, 15.2 mmol, 1.5 eq) at 0° C. and reaction mixture was stirred at room temperature for 1 h. Reaction mixture was cooled to 0° C. and MeI (2.17 g, 15.2 mmol, 1.5 eq) was added dropwise, over 1 hour. Upon completion of the reaction, reaction mixture was transferred into ice, then extracted with EtOAc. Organic layers were combined, washed with brine, dried over Na$_2$SO$_4$ and concentrated

Example 109

Synthesis of 2-(4-(3-((3S,4R)-3,4-dihydroxypyrrolidin-1-yl)-1H-pyrazol-1-yl)-5-oxo-6,7-dihydro-5H-pyrrolo[3,4-b]pyridin-2-yl)-3-fluorobenzonitrile, I-109

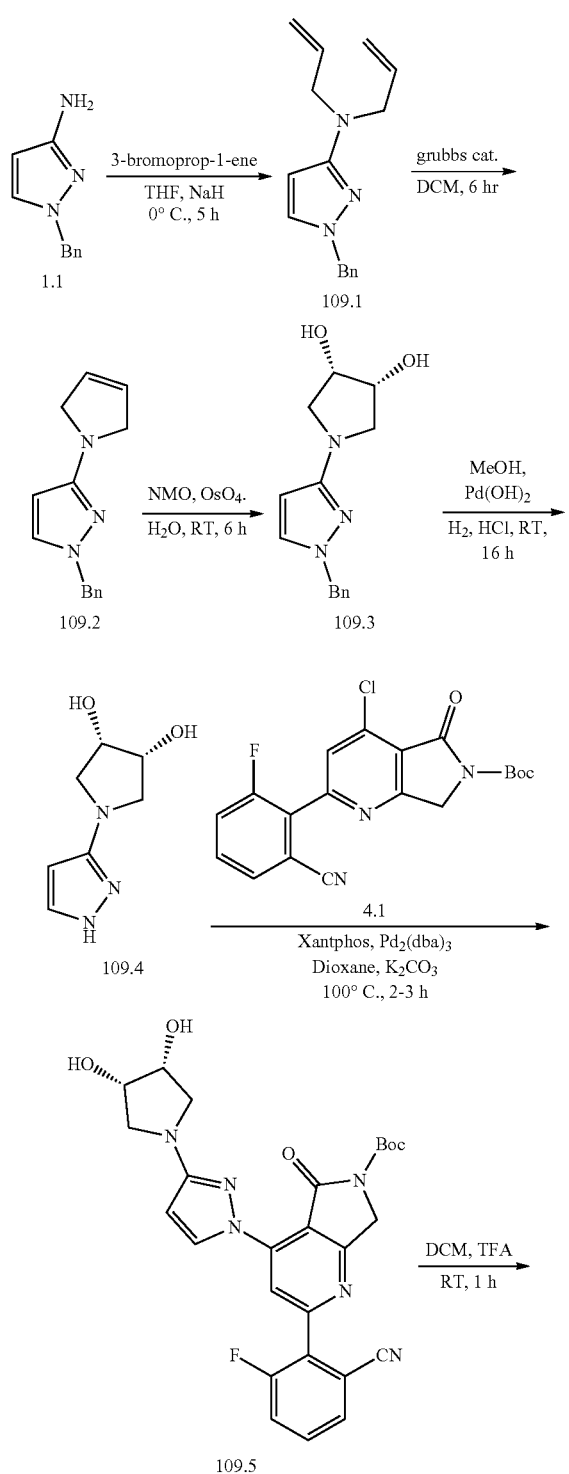

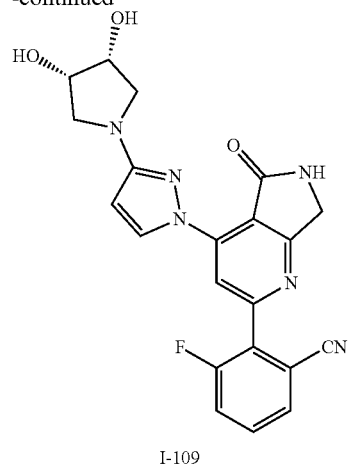

I-109

Synthesis of compound 109.1. To a solution of 1.1 (1.0 g, 5.7 mmol, 1.0 eq) in DMF 10 mL) was added NaH (0.7 g, 17.3 mmol, 3 eq) at 0° C. and reaction mixture was stirred at room temperature for 1 h. Reaction mixture was cooled to 0° C. and 3-bromopropane-1-ene (1.1 ml, 13.2 mmol, 2.3 eq) was added dropwise, stirred at room temperature for 3 h. Upon completion of the reaction, reaction mixture was transferred into ice. Resulting mixture was extracted with EtOAc. Organic layer were combined, washed with brine, dried over $Na_2SO_4$ and concentrated under reduced pressure to obtain crude compound. The crude was purified by column chromatography to furnish 109.1 (1.2 g, 82.19%). MS(ES): m/z 254 [M+H]$^+$.

Synthesis of compound 109.2. To a mixture of 109.1 (0.5 g, 1.9 mmol, 1.0 eq) in DCM (10.0 mL) was added Benzylidene-bis(tricyclohexylphosphino)-dichlororuthenium (0.162 g, 0.19 mmol, 0.1 eq). Reaction mixture stirred at room temperature for 6 h. Upon completion of the reaction; reaction mixture was transferred into water, extracted with EtOAc. Organic layers were combined, washed with brine, dried over $Na_2SO_4$ and concentrated under reduced pressure to obtain crude which was purified by column chromatography to provide 109.2 (0.25 g, 56.3%). MS(ES): m/z 226 [M+H]$^+$.

Synthesis of compound 109.3. To a solution of $OsO_4$ catalyst (2% in water) (0.01 eq) in water (2.0 mL) was added N-Methylmorpholine N-oxide (0.13 g, 11.1 mmol, 1.0 eq) at 0° C. then 109.2 (0.13 g, 11.1 mmol, 2.3 eq) in acetone (2.0 ml) was added dropwise at 0° C. reaction mixture was stirred at room temperature for 6 h. Upon completion of the reaction; reaction mixture was transferred into water, extracted with EtOAc. Organic layer were combined, washed with brine solution, dried over $Na_2SO_4$ and concentrated under reduced pressure to obtain crude material. This is further purified by column chromatography to get pure 109.3 (0.15 g, 52.26%). MS(ES): m/z 260 [M+H]$^+$.

Synthesis of compound 109.4. To a solution of 109.3 (0.15 g, 0.57 mmol, 1.0 eq) in MeOH (15.0 mL) was added 20% $Pd(OH)_2$ on charcoal (0.15 g) and 1N HCl (catalytic amount). Reaction mixture was stirred (under hydrogen) at 40 psi for 24 h. Upon completion of the reaction, reaction mixture was filtered through celite-bed and washed with methanol and concentrated under reduced pressure to obtain crude material. The crude was purified by column chromatography to furnish 109.4 (0.1 g, 82%). MS(ES): m/z 170 [M+H]$^+$.

Synthesis of compound 109.5. Compound 109.5 was prepared as described in Example 64.
Synthesis of compound I-109. Compound I-109 was prepared as described in Example 64. MS(ES): m/z 421 [M+H]+; 1H NMR (DMSO-d6, 400 MHz): 9.78-9.77 (d, 1H), 9.10 (s, H), 8.16 (s, 1H), 7.91-7.90 (d, 1H), 7.83-7.73 (m, 2H), 6.13-6.12 (d, 1H), 4.93 (s, 2H), 4.48 (s, 2H), 4.11 (s, 2H), 3.51-3.47 (m, 2H), 3.23-3.19 (m, 2H).
Example 110
Synthesis of 3-fluoro-2-(4-(3-(2-methyl-2,7-diazaspiro[3.5]nonan-7-yl)-1H-pyrazol-1-yl)-5-oxo-6,7-dihydro-5H-pyrrolo[3,4-b]pyridin-2-yl)benzonitrile, I-110
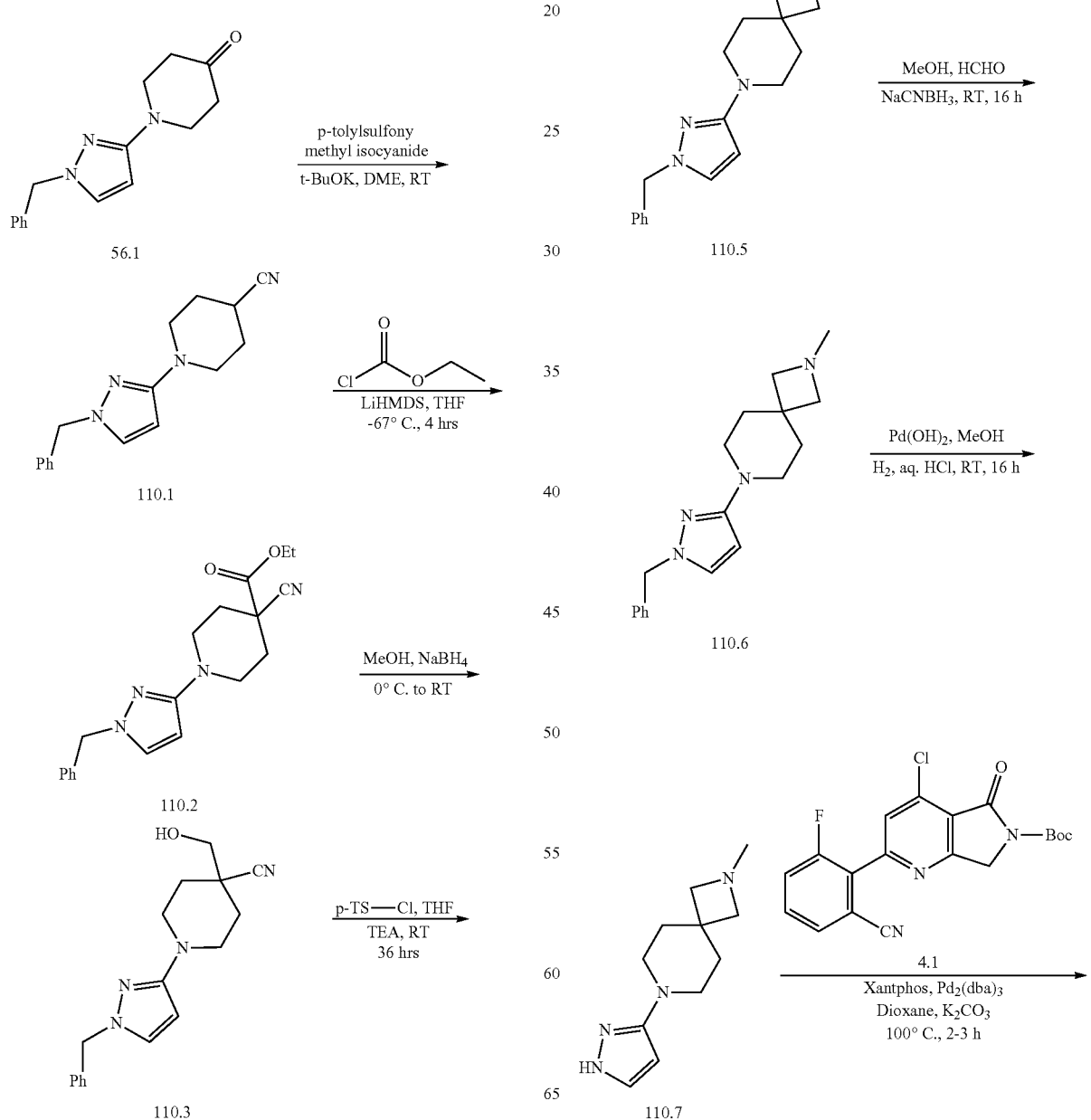

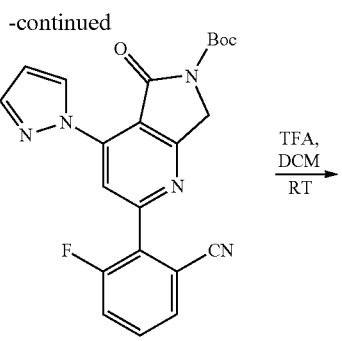

110.8

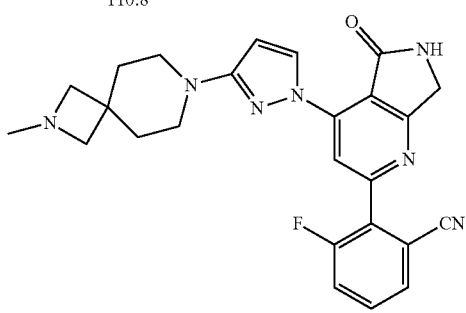

I-110

Synthesis of compound 110.1. A solution of 56.1 (2.4 g, 10.6 mmol, 1.0 eq) in DME (25.0 ml) was stirred at −10° C. for 30 min. Potassium tert-butoxide (3.08 g, 27.5 mmol, 2.6 eq) and Toluenesulfonylmethyl isocyanide (2.31 g, 11.84 mmol, 1.12 eq) were added at 0° C. Reaction mixture was stirred at room temperature for 15 h. Upon completion, mixture was extracted with EtOAc. Organic layers were combined, washed with brine, sat NaHCO$_3$ solution, dried over sodium sulphate and concentrated under reduced pressure to pressure to obtain crude material. The crude was purified by column chromatography to provide 110.1 (1.2 g, 48%). MS(ES): m/z 267 [M+H]$^+$.

Synthesis of compound 110.2. To a mixture of 110.1 (1.2 g, 4.39 mmol, 1.0 eq) in THF (20 mL) was added LHMDS (2.20 g, 13.1 mmol, 3.1 eq) at −78° C. followed by Ethyl chloroformate (1.90 g, 17.1 mmol, 4.0 eq). Reaction mixture was slowly warmed to room temperature and stirred for 4 h. Upon completion of the reaction; reaction mixture was transferred into ice, and extracted with EtOAc. Organic layers were combined, washed with brine, dried over Na$_2$SO$_4$ and concentrated under reduced pressure to obtain crude which was purified by column chromatography to provide 110.2 (1.2 g, 68.6%). MS(ES): m/z 389 [M+H]$^+$.

Synthesis of compound 110.3. To a solution of 110.2 (1.2 g, 2.21 mmol, 1.0 eq) in MeOH (10.0 mL) was added NaBH$_4$ (0.167 g, 4.40 mmol, 1.5 eq) at 0° C. and stirred at room temperature for 2 h. Upon completion of the reaction, mixture was transferred into ice, extracted with EtOAc. Organic layers were combined, washed with brine solution, dried over Na$_2$SO$_4$ and concentrated under reduced to pressure to obtain crude which was purified by column chromatography to provide 110.3 (1.05 g, 92.1%). MS(ES): m/z 297 [M+H]$^-$.

Synthesis of compound 110.4. To solution of 110.3 (1.0 g, 0.33 mmol, 1.0 eq) in DCM (10 mL) was added Et$_3$N (1.0 g, 10.1 mmol, 3 eq) and p-Toluenesulfonyl chloride (1.25 g, 6.75 mmol, 2.0 eq). Reaction mixture was stirred at room temperature for 36 h. Upon completion of the reaction, mixture was transferred into ice, and then extracted with EtOAc. Organic layers were combined, washed with brine solution, dried over Na$_2$SO$_4$ and concentrated under reduced pressure to pressure to obtain crude which was purified by column chromatography to provide 110.4 (1.0 g, 66.66%). MS(ES): m/z 451 [M+H]$^+$.

Synthesis of compound 110.5. To a solution of 110.4 (1.0 g, 2.22 mmol, 1.0 eq) in THF (15 mL) was added LAH (0.2 g, 5.33 mmol, 2 eq) at 0° C. and stirred at room temperature for 16 h. Upon completion of the reaction; reaction mixture was transferred into ice, extracted with EtOAc. Organic layers were combined, washed with brine solution, dried over Na$_2$SO$_4$ and concentrated under reduced pressure to pressure to obtain crude which was purified by column chromatography to provide 110.5 (0.55 g, 88.7%). MS(ES): m/z 283 [M+H]$^-$.

Synthesis of compound 110.6. To a solution of 110.5 (0.55 g, 1.94 mmol, 1.0 eq) in MeOH (10 ml) was added para-formaldehyde (0.35 g, 11.69 mmol, 6.0 eq), NaCHBH$_3$ (0.146 g, 2.32 mmol, 1.2 eq) and HOAc (0.582 g, 9.7 mmol, 5 eq) at 0° C. Reaction mixture was stirred at room temperature for 15 h. Upon completion of the reaction, mixture was extracted with EtOAc. Organic layers were combined, washed with brine, saturated NaHCO$_3$, dried over Na$_2$SO$_4$ and concentrated under reduced pressure to obtain crude which was purified by chromatography to provide 110.6 (0.295 g, 51.8%). MS(ES): m/z 297 [M+H]$^+$.

Synthesis of compound 110.7. To a solution of 110.6 (0.29 g, 0.97 mmol, 1.0 eq) in MeOH (10.0 mL) were added 20% Pd(OH)$_2$ (0.06 g) and 1N HCl (catalytic amount). Reaction mixture was stirred (under hydrogen) at 20 psi for 16 h. Upon completion of the reaction, mixture was filtered through celite. Solvents were removed under reduced pressure to obtain crude which was purified by column chromatography to furnish 110.7. (0.19 g, 95.0%). MS(ES): m/z 207 [M+H]$^+$.

Synthesis of compound 110.8. Compound was prepared from 110.7 and 4.1 using the procedure described in Example 64.

Synthesis of compound I-110. Compound was prepared from 110.8 using the procedure described in Example 64. MS(ES): m/z 458 [M+H]$^+$; $^1$H NMR (DMSO, 400 MHz): 8.58 (S, 1H), 7.86 (d, 2H), 7.75-7.70 (m, 2H), 7.00 (s, 1H), 6.57 (s, 1H), 4.66 (s, 2H), 3.66 (t, 4H), 3.22 (s, 4H), 2.18 (s, 3H), 1.38 (t, 4H).

Example 111

Synthesis of (R)-3-fluoro-2-(4-(3-(3-hydroxy-3-methylpiperidin-1-yl)-1H-pyrazol-1-yl)-5-oxo-6,7-dihydro-5H-pyrrolo[3,4-b]pyridin-2-yl-7,7-d2)benzonitrile, I-111

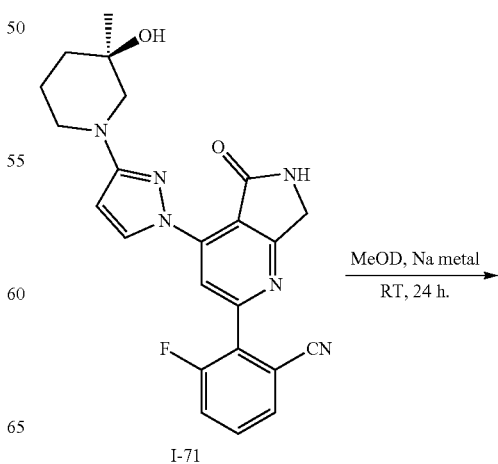

I-71

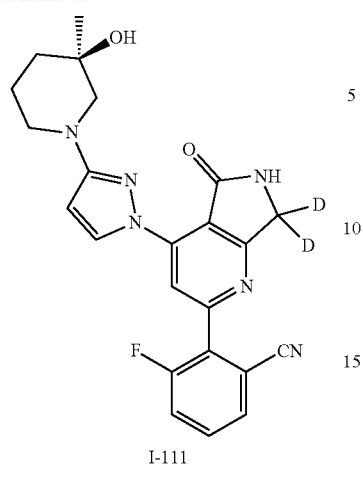

I-111

Sodium metal (0.026 g, 1.15 mmol, 10 eq) was added slowly in deuterated methanol (2 mL) at 0° C. and solution of I-71 (0.050 g, 1.15 mmol, 1.0 eq) in deuterated chloroform (1 ml) was added. The reaction was stirred at room temperature for 24 h. Upon completion of the reaction, mixture was transferred into water, extracted with EtOAc. Organic layers were combined, washed with brine solution, dried over $Na_2SO_4$ and concentrated under reduced pressure to pressure to obtain crude which was purified by column chromatography to furnish I-111 (0.030 g, 60%). MS(ES): m/z 435 [M+H]$^+$; $^1$H NMR (DMSO-d$_6$, 400 MHz): 9.76 (d, 1H), 9.08 (s, 1H), 8.15 (s, 1H), 7.93-7.90 (m, 1H), 7.83-7.75 (m, 2H), 6.33 (d, 1H), 3.31-3.28 (m, 1H), 3.22-3.20 (m, 1H), 3.11 (s, 2H), 1.77-1.75 (m, 1H), 1.51-149 (m, 3H), 1.13 (s, 3H).

Example 112

Synthesis of 3-fluoro-2-(4-(3-((2S,5S)-5-hydroxy-2-methylpiperidin-1-yl)-1H-pyrazol-1-yl)-5-oxo-6,7-dihydro-5H-pyrrolo[3,4-b]pyridin-2-yl)benzonitrile, I-112

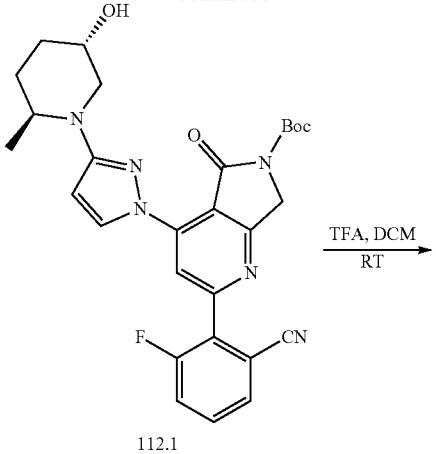

112.1

I-112

Compound I-112 was prepared from compounds 96.9 and 112.1 using the procedure described in Example 64. MS(ES): m/z 433.43 [M+H]$^+$ $^1$H NMR (DMSO-d$_6$, 400 MHz): 9.76 (s, 1H), 9.11 (s, 1H), 8.15 (s, 1H), 7.92-7.90 (d, 1H), 7.83-7.73 (m, 2H), 6.32 (s, 1H), 4.88 (s, 1H), 4.49 (s, 2H), 4.10-4.02 (m, 1H), 3.67-3.58 (m, 2H), 2.85-2.75 (m, 1H), 1.65-1.62 (m, 2H), 1.48-1.43 (m, 2H), 1.01-0.99 (d, 3H).

Example 113

Synthesis of 3-fluoro-2-(4-(3-((2S,5R)-5-hydroxy-2-methylpiperidin-1-yl)-1H-pyrazol-1-yl)-5-oxo-6,7-dihydro-5H-pyrrolo[3,4-b]pyridin-2-yl)benzonitrile, I-113

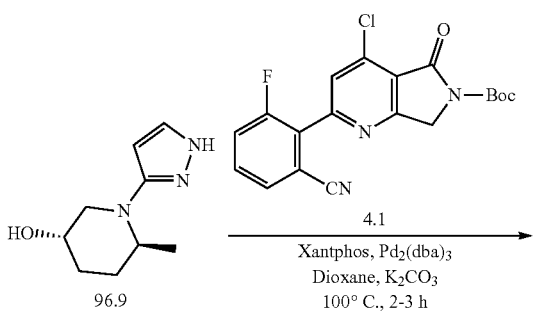

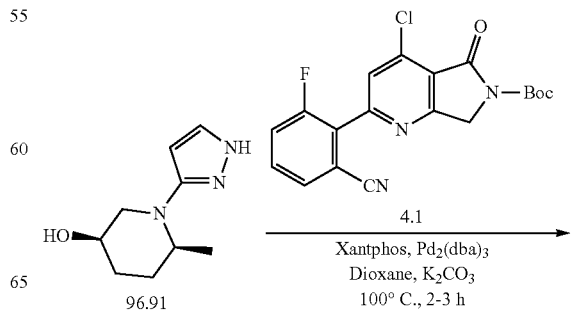

259

-continued

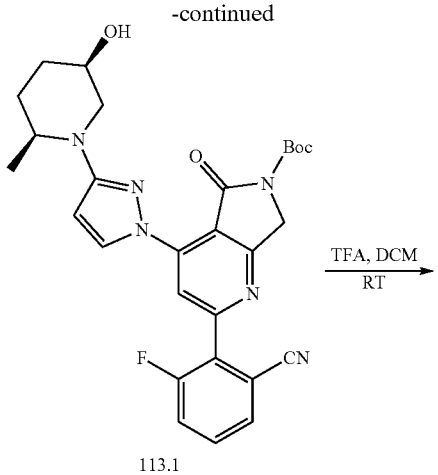

113.1

TFA, DCM
RT
→

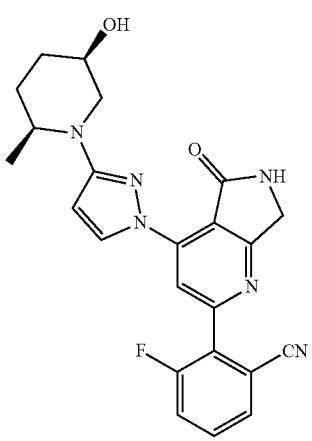

I-113

Compound I-113 was prepared from compounds 96.91 and 113.1 using the procedure described in Example 64. MS(ES): m/z 433.43 [M+H]+; $^1$H NMR (DMSO-d$_6$, 400 MHz): 9.77 (s, 1H), 9.11 (s, 1H), 8.14 (s, 1H), 7.92-7.90 (d, 1H), 7.83-7.73 (m, 2H), 6.31 (s, 1H), 4.88 (s, 1H), 4.49 (s, 2H), 4.10-4.02 (m, 1H), 3.67-3.58 (m, 2H), 2.82 (m, 1H), 1.65-1.62 (m, 2H), 1.48-1.43 (m, 2H), 1.01-0.99 (d, 3H).

Example 114

Synthesis of (R)-3-fluoro-2-(4-(3-(3-hydroxypyrrolidin-1-yl)-1H-pyrazol-1-yl)-5-oxo-6,7-dihydro-5H-pyrrolo[3,4-b]pyridin-2-yl-7,7-d2)benzonitrile, I-114

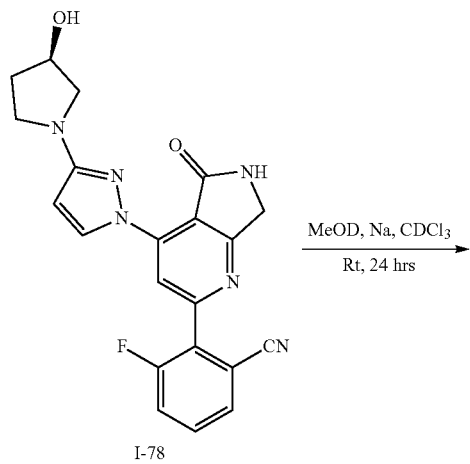

I-78

MeOD, Na, CDCl$_3$
Rt, 24 hrs
→

260

-continued

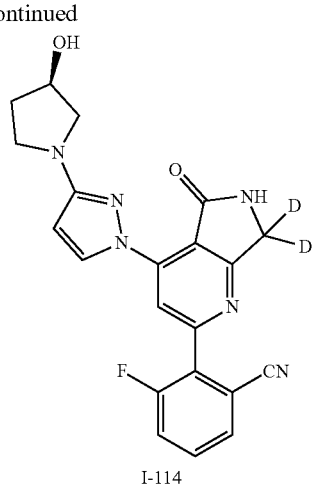

I-114

Compound I-114 was prepared from compound I-78 using the procedure described in Example 111. MS(ES): m/z 407.16 [M+H]+; $^1$H NMR (DMSO-d$_6$, 400 MHz): 9.79 (s, 1H), 9.07 (s, 1H), 8.17-8.11 (m, 1H), 7.92-7.9 (d, 1H), 7.83-7.73 (m, 2H), 6.14 (s, 1H), 4.49 (s, 1H), 4.36 (s, 1H), 3.48-3.32 (m, 3H), 3.17 (m, 1H), 2.02-2 (m, 1H), 1.99-1.95 (m, 1H).

Example 115

Synthesis of 2-(4-(3-((3R,4S)-3,4-dihydroxyazepan-1-yl)-1H-pyrazol-1-yl)-5-oxo-6,7-dihydro-5H-pyrrolo[3,4-b]pyridin-2-yl)-3-fluorobenzonitrile, I-115

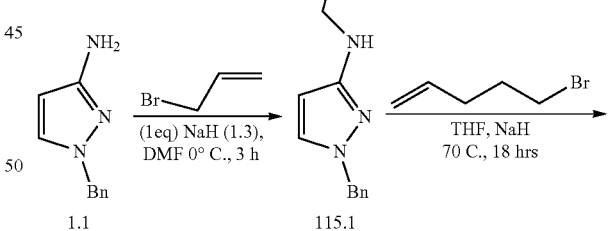

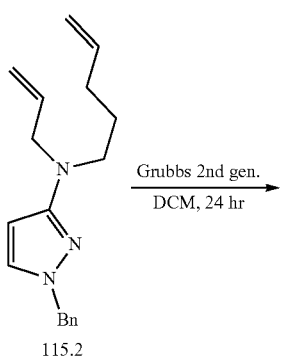

115.2

Grubbs 2nd gen.
DCM, 24 hr
→

-continued

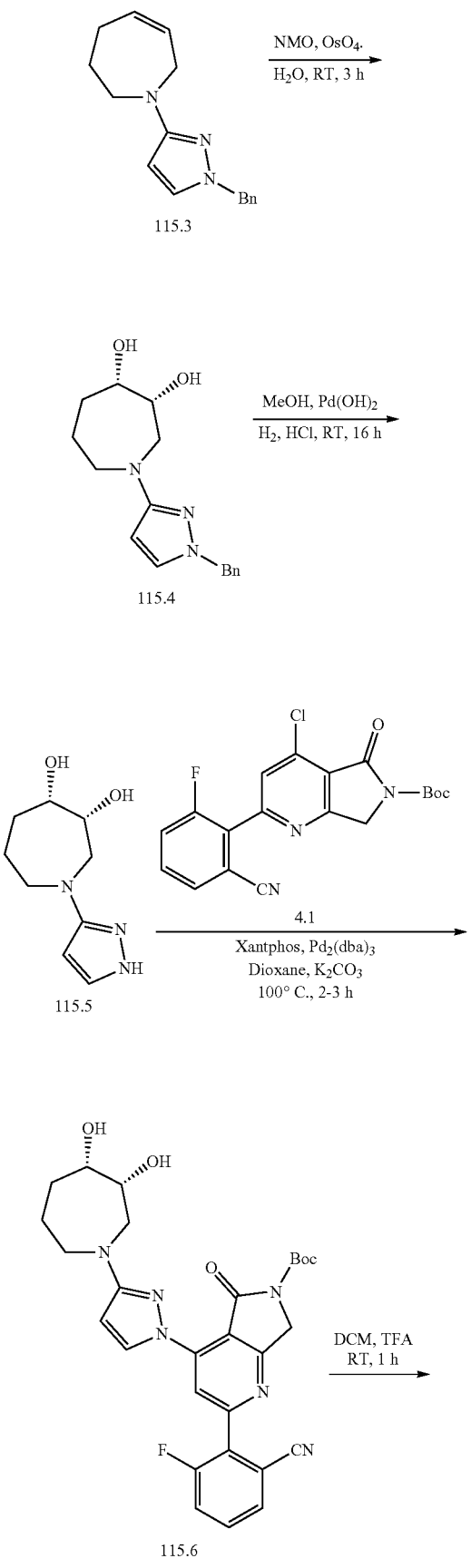

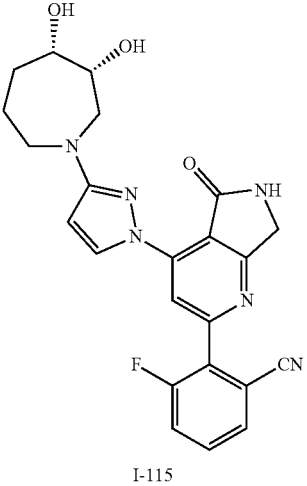

I-115

Synthesis of compound 115.1. To a solution of 1.1 (5.0 g, 28.9 mmol, 1.0 eq) in DMF (15 mL) was added NaH (1.5 g, 37.5 mmol, 1.3 eq) at 0° C. and reaction mixture was stirred at room temperature for 1 h. Reaction mixture was cooled to 0° C. and 3-bromopropane-1-ene (2.5 ml, 28.9 mmol, 1 eq) was added dropwise, stirred at room temperature for 3 h. Upon completion of the reaction, reaction mixture was transferred into ice. Resulting mixture was extracted with EtOAc. Organic layers were combined, washed with brine, dried over $Na_2SO_4$ and concentrated under reduced pressure. Resulting crude was purified by column chromatography to furnish 115.1 (3 g, 48.8%). MS(ES): m/z 214 [M+H]$^+$.

Synthesis of compound 115.2. To a solution of 115.1 (3.0 g, 14.0 mmol, 1.0 eq) in THF (30.0 mL) was added NaH (1.7 g, 42.2 mmol, 3 eq) at 0° C. and reaction mixture was stirred at room temperature for 1 h. Reaction mixture was cooled to 0° C. and 5-bromo-1-pentene (4.19 g, 28.1 mmol, 2 eq) was added dropwise, stirred at 60-70° C. for 15 h. Upon completion of the reaction, reaction mixture was poured into ice. Resulting mixture was extracted with EtOAc. Organic layers were combined, washed with brine solution, dried over $Na_2SO_4$ and concentrated under reduced pressure. The crude was purified by column chromatography to provide 115.2 (3.0 g, 75.6%). MS(ES): m/z 282 [M+H]+.

Synthesis of compound 115.3. To a mixture of 115.2 (1.5 g, 5.3 mmol, 1.0 eq) in DCM (15 mL) was added Benzylidene-bis (tricyclohexylphosphino)-dichlororuthenium (0.43 g, 0.53 mmol, 0.1 eq). Reaction mixture stirred at room temperature for 18 h. Upon completion of the reaction; reaction mixture was poured into water, and then extracted with EtOAc. Organic layers were combined, washed with brine, dried over $Na_2SO_4$ and concentrated under reduced pressure to obtain crude material. The crude was purified by column chromatography to furnish 115.3 (0.2 g, 14.8%). MS(ES): m/z 254 [M+H]$^+$.

Synthesis of compound 115.4. To a solution of OsO$_4$ (catalytic) (2% in water) (0.01 eq) in water (1.0 mL) was added N-Methylmorpholine N-oxide (0.092 g, 0.79 mmol, 1.0 eq) at 0° C. then 115.3 (0.2 g, 0.79 mmol, 1 eq) in acetone (1.0 ml) was added dropwise at 0° C. and stirred at room temperature for 3 h. Upon completion of the reaction, mixture was transferred into water, and extracted with EtOAc. Organic layers were combined, washed with brine, dried over $Na_2SO_4$ and concentrated under reduced pressure to pressure to obtain crude which was purified by column chromatography to furnish 115.4 (0.13 g, 57.5%). MS (ES): m/z 288 [M+H]$^+$.

Synthesis of compound 115.5. To a solution of 115.5 (0.12 g, 0.41 mmol, 1.0 eq) in MeOH (5.0 mL), 20% Pd(OH)$_2$ (0.15 g) and 1N HCl (catalytic amount) were added into reaction. Reaction mixture was stirred under 40 psi of H$_2$ gas for 24 h. Upon completion of reaction, mixture was filtered through celite-bed and washed with methanol, concentrated under reduced pressure to obtain crude material. The crude was purified by column chromatography to furnish 115.5. (0.020 g, 24.4%). MS(ES): m/z 198 [M+H]$^-$.

Synthesis of compound 115.6. Compound 115.6 was prepared as described in Example 64.

Synthesis of compound I-115. Compound I-115 was prepared from compound 115.6 as described in Example 64. MS(ES): m/z 449 [M+H]$^+$; $^1$H NMR (DMSO-d$_6$, 400 MHz): 9.76-9.75 (d, 1H), 9.08 (s, 1H), 8.15 (s, 1H), 7.92-7.90 (m, 1H), 7.83-7.73 (m, 2H), 6.24 (d, 1H), 4.67-4.66 (d, 1H), 4.48 (s, 2H), 4.43-4.42 (d, 1H), 3.69-3.68 (m, 2H), 3.59-3.51 (m, 2H), 3.31-3.34 (m, 2H), 1.89-1.80 (m, 2H), 1.65-1.64 (m, 1H), 1.38-1.33 (m, 1H), Example 116

Synthesis of 1-(1-(2-(2-cyano-6-fluorophenyl)-5-oxo-6,7-dihydro-5H-pyrrolo[3,4-b]pyridin-4-yl)-1H-pyrazol-3-yl)pyrrolidine-3-carbonitrile, I-116

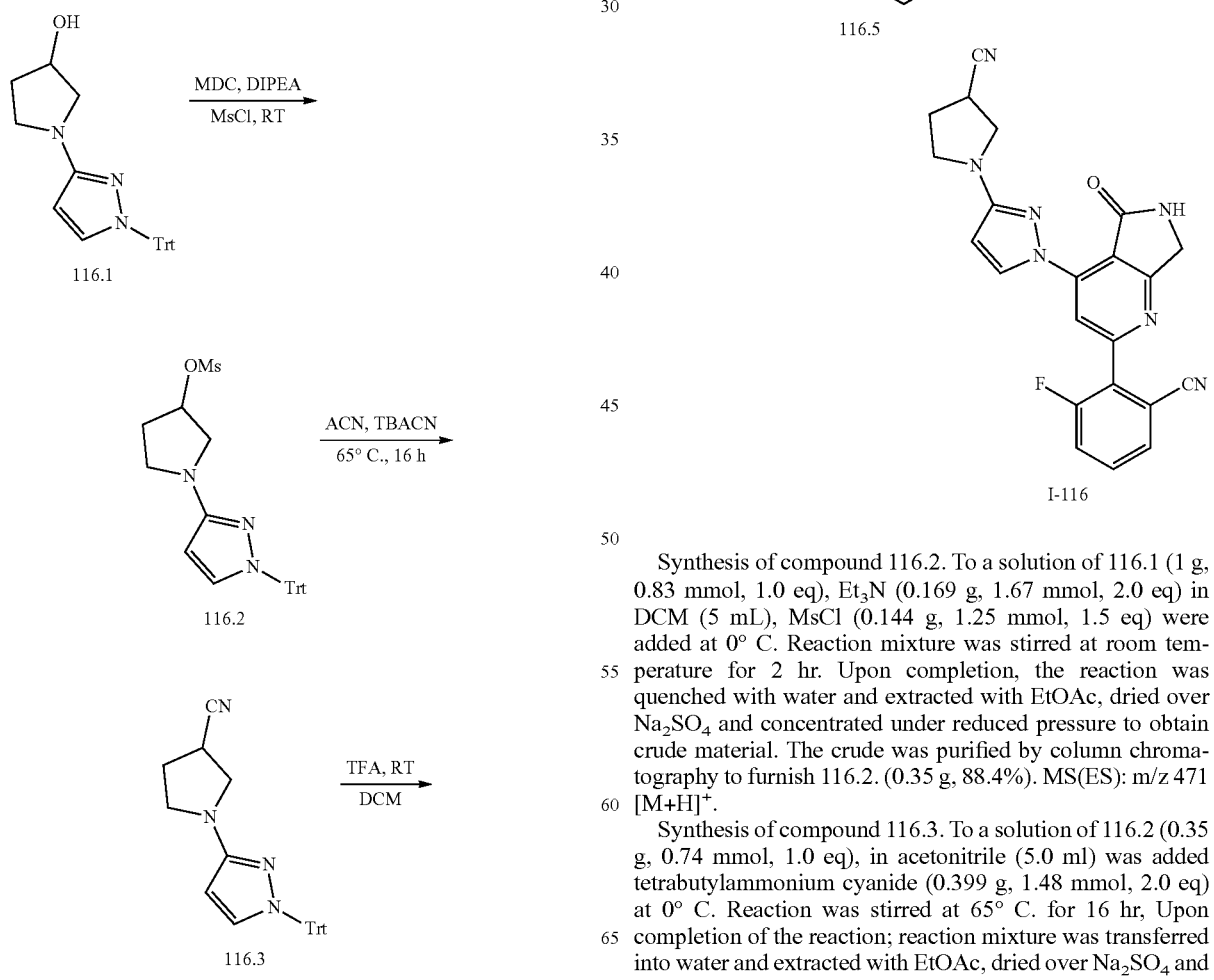

Synthesis of compound 116.2. To a solution of 116.1 (1 g, 0.83 mmol, 1.0 eq), Et$_3$N (0.169 g, 1.67 mmol, 2.0 eq) in DCM (5 mL), MsCl (0.144 g, 1.25 mmol, 1.5 eq) were added at 0° C. Reaction mixture was stirred at room temperature for 2 hr. Upon completion, the reaction was quenched with water and extracted with EtOAc, dried over Na$_2$SO$_4$ and concentrated under reduced pressure to obtain crude material. The crude was purified by column chromatography to furnish 116.2. (0.35 g, 88.4%). MS(ES): m/z 471 [M+H]$^+$.

Synthesis of compound 116.3. To a solution of 116.2 (0.35 g, 0.74 mmol, 1.0 eq), in acetonitrile (5.0 ml) was added tetrabutylammonium cyanide (0.399 g, 1.48 mmol, 2.0 eq) at 0° C. Reaction was stirred at 65° C. for 16 hr, Upon completion of the reaction; reaction mixture was transferred into water and extracted with EtOAc, dried over Na$_2$SO$_4$ and concentrated under reduced pressure to obtain crude which was purified by column chromatography to provide 116.3 (0.16 g, 53.3%). MS(ES): m/z 405 [M+H]+.

Synthesis of compound 116.4. The compound 116.3 (0.15 g, 0.094 mmol, 1.0 eq) was dissolved in DCM (1.0 mL) and TFA (0.5 mL) was added to the reaction mixture. The reaction was stirred at room temperature for 3 h. Upon completion of the reaction, mixture was transferred in water and product was extracted with EtOAc. Organic layers were combined, washed with NaHCO3, dried over Na2SO4 and concentrated under reduced pressure to obtain crude which was purified by column chromatography to provide 116.5 (0.04 g, 66.7%). MS(ES): m/z 163 [M+H]+.

Synthesis of compound 116.5. Compound was prepared from 116.4 and 4.1 using the procedure described in Example 64.

Synthesis of compound I-116. Compound was prepared from 116.5 using the procedure described in Example 64. MS(ES): m/z 414 [M+H]+; $^1$H NMR (CDCl3, 400 MHz): 9.79 (d, 1H), 8.36 (d, 1H), 7.69 (d, 1H), 7.60-7.54 (m, 1H), 7.52-7.47 (m, 1H), 6.28 (s, 1H), 5.96 (d, 1H), 4.60 (s, 2H), 3.85-3.81 (m, 1H), 3.73-3.63 (m, 2H), 3.56-3.52 (m, 1H), 3.28-3.21 (m, 1H), 2.74-2.34 (m, 2H).

Example 117

Synthesis of 2-(4-(3-(((1r,4r)-4-(dimethylamino) cyclohexyl)oxy)-1H-pyrazol-1-yl)-5-oxo-6,7-di-hydro-5H-pyrrolo[3,4-b]pyridin-2-yl)-3-fluoroben-zonitrile, I-117

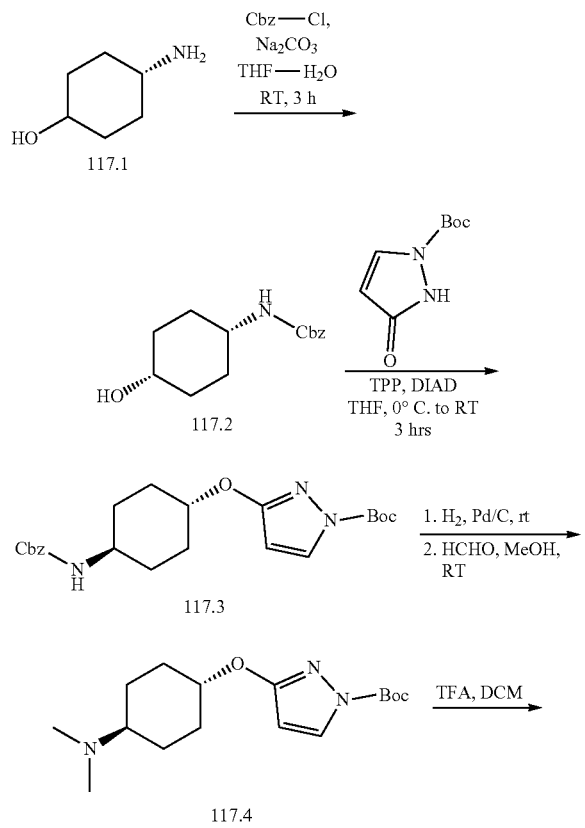

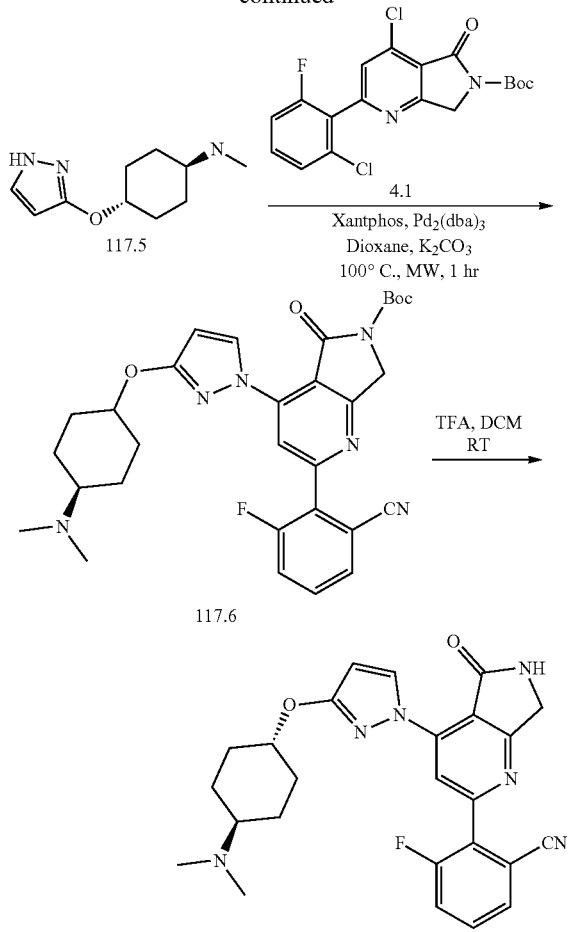

Synthesis of compound 117.2. To a solution of 117.1 (5.0 g, 33.1 mmol, 1.0 eq) in THF (50 mL) and water (15 ml) was added Sodium carbonate (7.6 g, 72.8 mmol, 2.2 eq) at 0° C. and reaction mixture was stirred at room temperature for 1 h. Benzyl Chloroformate (6.1 g, 36.4 mmol, 2.3 eq) was added dropwise at 0° C., stirred at room temperature for 3 h. Upon completion of the reaction, reaction mixture was transferred into ice. Resulting mixture was extracted with EtOAc. Organic layers were combined, washed with brine, dried over sodium sulphate and concentrated under reduced pressure to obtain crude which was purified by column chromatography to provide 1.1 (5.0 g, 60.7%). MS(ES): m/z 250 [M+H]+.

Synthesis of compound 117.3. To a mixture of 117.2 (0.5 g, 2.0 mmol, 1.0 eq) in THF (2.5 mL) was added tert-butyl 3-oxo-2,3-dihydro-1H-pyrazole-1-carboxylate (0.505 g, 2.5 mmol, 0.1 eq) and PPh (0.655 g, 2.5 mmol, 0.1 eq) Reaction mixture stirred at room temperature for 3 h. Upon completion of the reaction, reaction mixture was transferred into water, extracted with EtOAc. Organic layers were combined, washed with brine solution, dried over sodium sulphate and concentrated under reduced pressure to pressure to obtain crude that was purified by column chromatography to provide 117.3 (0.25 g, 30.01%). MS(ES): m/z 416 [M+H]+.

Synthesis of compound 117.4. To a solution of 117.3 (0.250 g, 0.60 mmol, 1.0 eq) in Methanol (10 mL) was added 10% palladium on charcoal (0.07 g). Reaction mixture was stirred under hydrogen at 40 psi for 2 h. Formaldehyde (0.108 g, 36.1 mmol, 6.0 eq) was added and reaction mixture stirred at room temperature for 3 h. Upon completion of the reaction, reaction mixture was filtered through celite, concentrated under reduced pressure to obtain crude that was purified by column chromatography to provide 117.4. (0.184 g, 95.12%). MS(ES): m/z 310[M+H]⁻.

Synthesis of compound 117.5. To a solution of 117.4 (0.184 g, 0.59 mmol, 1.0 eq) in DCM (3 mL) was added TFA (0.9 ml). Reaction mixture was stirred at room temperature for 2 h. Upon completion of the reaction, mixture was poured into water, basified with saturated bicarbonate solution and product was extracted with EtOAc. Organic layers were combined, dried over sodium sulphate and concentrated under reduced pressure to obtain crude which was purified by column chromatography to yield 117.5 (0.1 g, 80.64%). MS(ES): m/z 210 [M+H]⁺.

Synthesis of compound 117.6. Compound was prepared using the procedure described in Example 64.

Synthesis of compound I-117. Compound was prepared using the procedure described in Example 64. (0.050 g, 47.16%). MS(ES): m/z 461 [M+H]⁺; ¹H NMR (DMSO-$d_6$, 400 MHz): 9.66 (d, 1H), 9.18 (s, 1H), 8.15 (s, 1H), 7.93-7.90 (d, 1H), 7.84-7.74 (m, 2H), 6.24 (d, 1H), 4.57-4.52 (m, 3H), 3.17-3.16 (m, 1H), 2.23 (s, 6H), 2.18 (s, 1H), 1.86-1.83 (m, 2H), 1.44-1.35 (m, 5H).

Example 118

Synthesis of (S)-2-(4-(3-(3-amino-3-(trifluoromethyl)piperidin-1-yl)-1H-pyrazol-1-yl)-5-oxo-6,7-dihydro-5H-pyrrolo[3,4-b]pyridin-2-yl)-3-fluorobenzonitrile, I-118

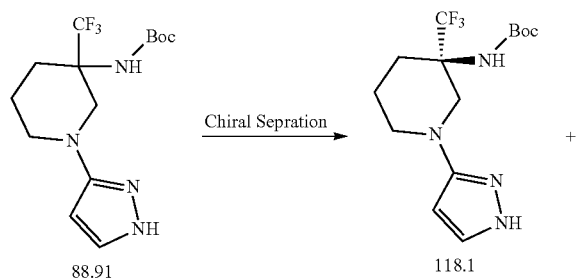

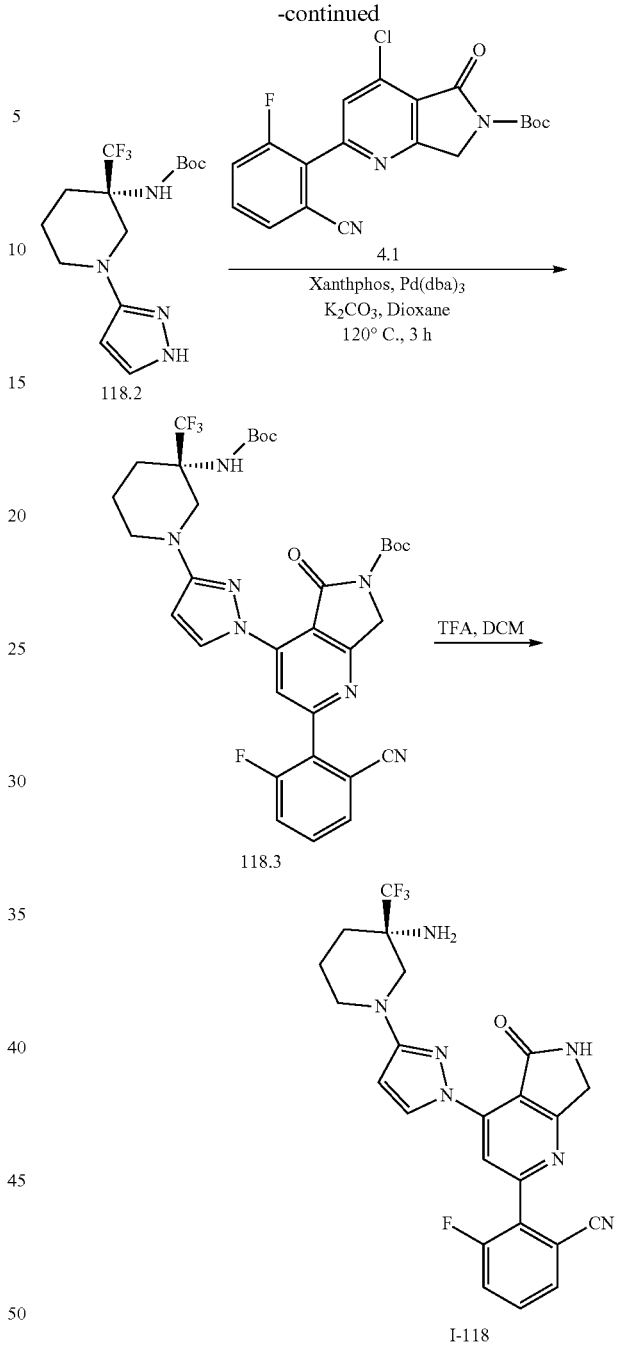

Synthesis of compound 118.1 and 118.2. Compounds were prepared by chiral purification of 88.91

Synthesis of compound 118.3. Compound was prepared from 4.1 and 118.2 using the procedure described in Example 64.

Synthesis of compound I-118. Compound was prepared from 118.3 using the procedure described in Example 64 (0.015 g, 70.6%). MS(ES): m/z 486.18 [M+H]⁻; ¹H NMR (DMSO-$d_6$, 400 MHz): 9.75-9.74 (d, 1H), 9.12 (s, 1H), 8.16 (s, 1H), 7.92-7.90 (m, 1H), 7.83-7.76 (m, 2H), 6.41 (d, 1H), 4.49 (s, 2H), 3.84 (d, 1H), 3.64-3.61 (m, 1H), 3.06-2.86 (m, 1H), 2.86-2.79 (m, 1H), 1.97-1.91 (m, 3H), 1.70-1.61 (m, 2H), 1.61-1.57 (m, 1H).

Example 119

Synthesis of (R)-2-(4-(3-(3-amino-3-(trifluoromethyl)piperidin-1-yl)-1H-pyrazol-1-yl)-5-oxo-6,7-dihydro-5H-pyrrolo[3,4-b]pyridin-2-yl)-3-fluorobenzonitrile, I-119

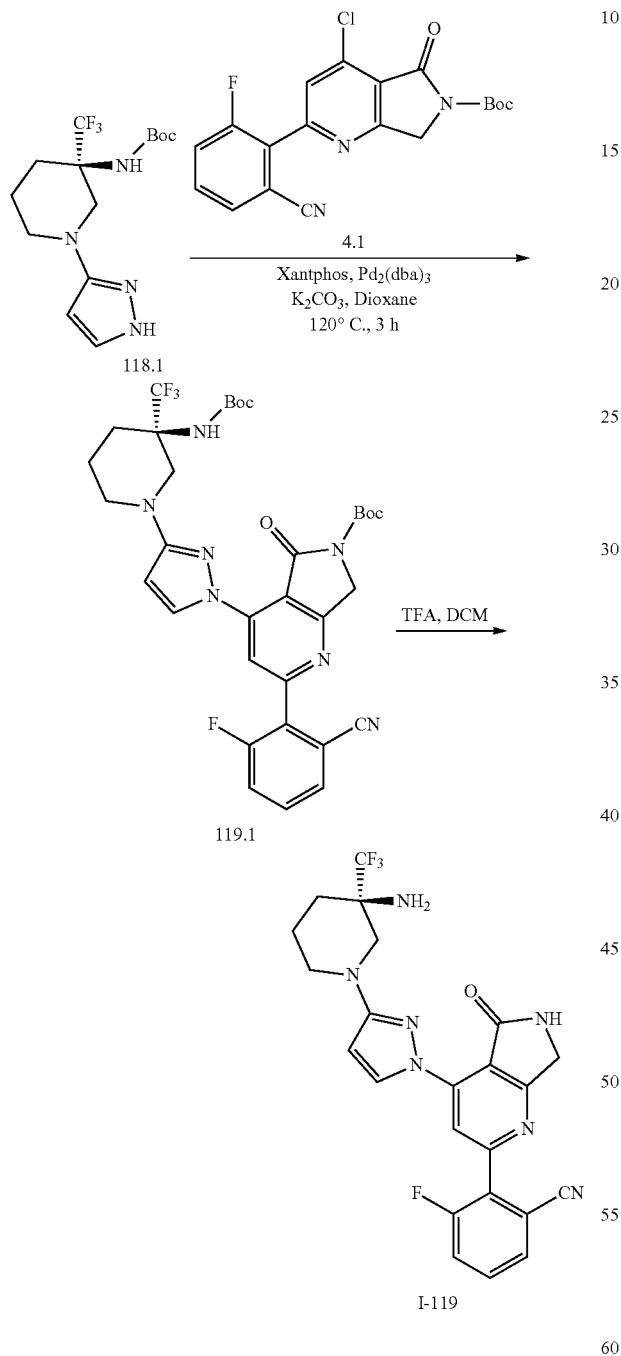

Compound I-119 was prepared from 118.1 and 4.1 using the procedure referred to in Example I-118. MS(ES): m/z 486.18 [M+H]+; ¹H NMR (DMSO-d₆, 400 MHz): 9.75-9.74 (d, 1H), 9.12 (s, 1H), 8.16 (s, 1H), 7.92-7.90 (m, 1H), 7.83-7.76 (m, 2H), 6.41 (d, 1H), 4.49 (s, 2H), 3.84 (d, 1H), 3.64-3.61 (m, 1H), 3.06-2.86 (m, 1H), 2.86-2.79 (m, 1H), 1.97-1.91 (m, 3H), 1.70-1.61 (m, 2H), 1.61-1.57 (m, 1H).

Example 120

Synthesis of N-(1-(1-(2-(2-cyano-6-fluorophenyl)-5-oxo-6,7-dihydro-5H-pyrrolo[3,4-b]pyridin-4-yl)-1H-pyrazol-3-yl)pyrrolidin-3-yl)methanesulfonamide, I-120

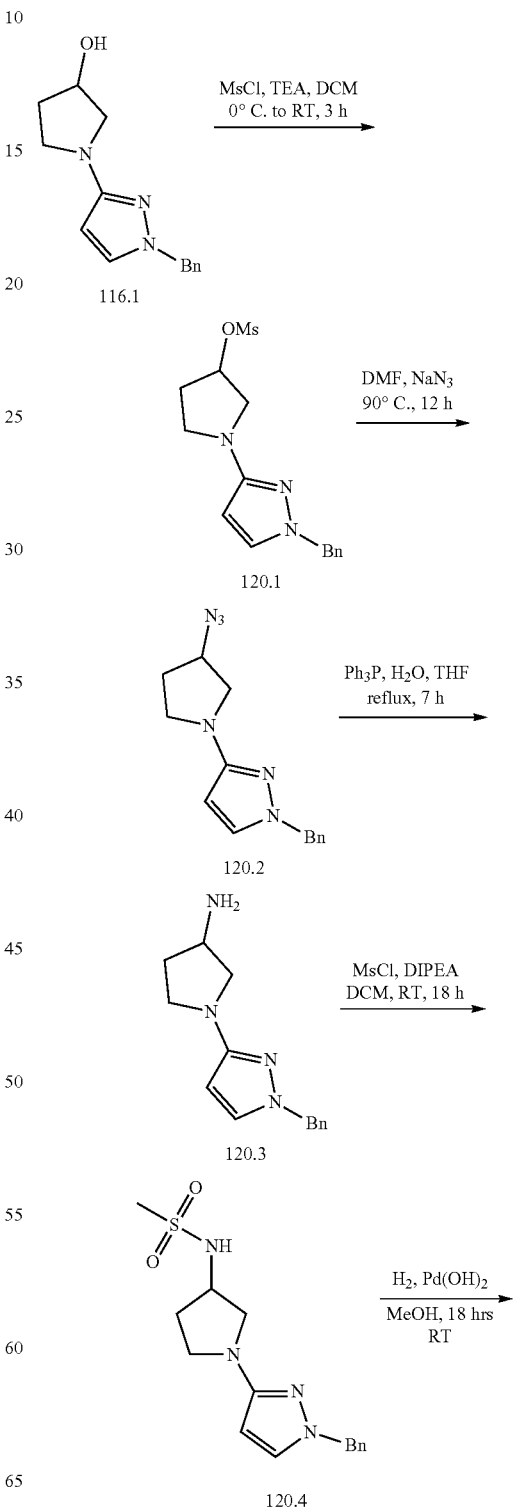

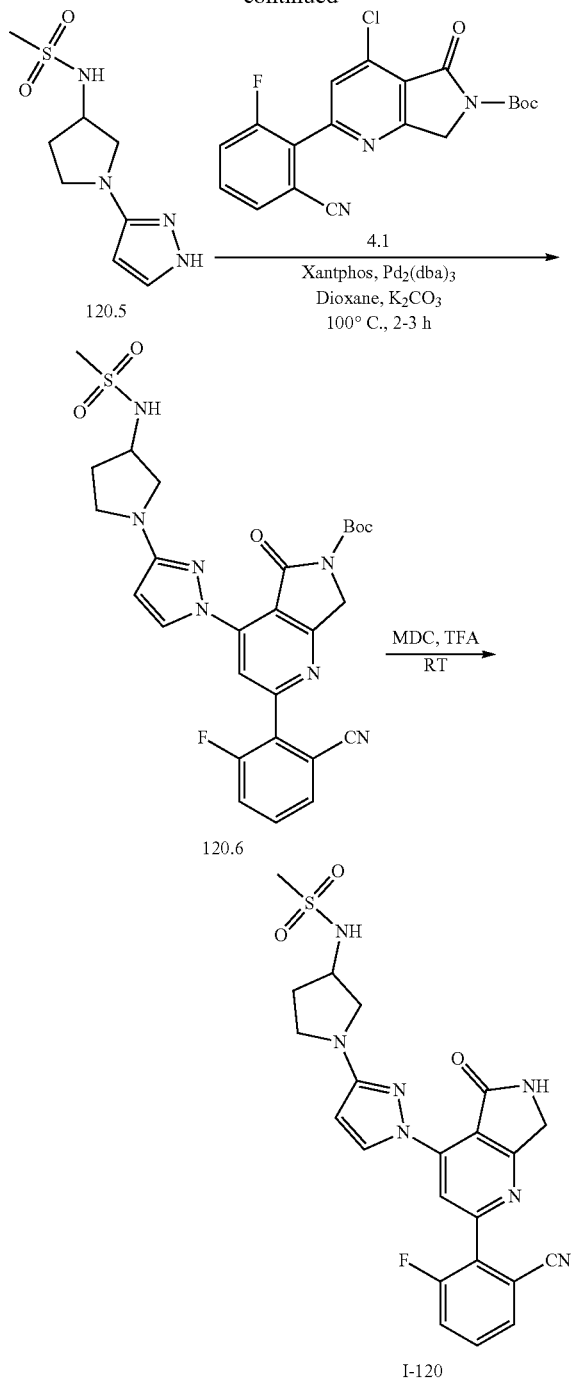

Synthesis of compound 120.2. To a solution of 120.1 (1.2 g, 3.73 mmol, 1.0 eq) in DMF (20 mL) was added sodium azide (0.970 g, 14.9 mmol, 4 eq) at 0° C. under nitrogen. Reaction mixture stirred at 100° C. for 12 h. Upon completion of the reaction, reaction mixture was transferred into ice. Resulting mixture was extracted with EtOAc. Organic layers were combined, washed with brine solution, dried over sodium sulphate and concentrated under reduced pressure. Crude was purified by column chromatography to get pure 120.2 (1.0 g, 98.02%). MS(ES): m/z 269 [M+H]$^+$.

Synthesis of compound 120.3. To a mixture of 120.2 (1 g, 3.73 mmol, 1.0 eq) in THF (50 mL) and water (8 ml) was added PPh$_3$ (1.91 g, 7.29 mmol, 2.0 eq) at 0° C. Reaction was mixture stirred at 70° C. for 7 h. Upon completion of reaction; reaction mixture was transferred into water, extracted with EtOAc. Organic layers were combined, washed with sodium bicarbonate solution, dried over Na$_2$SO$_4$ and concentrated under reduced pressure to pressure to obtain crude which was purified by column chromatography to provide 120.3 (0.8 g, 88.88%). MS(ES): m/z 243 [M+H]$^+$.

Synthesis of compound 120.4. To a solution of 120.3 (0.8 g, 3.30 mmol, 1 eq) in DCM (10 mL) was added Et$_3$N (1.2 ml, 8.36 mmol, 2.53 eq) at 0° C. and stirred at room temperature for 1 h followed by addition of MsCl (0.54 ml, 6.84 mmol, 2.0 eq) at 0° C. Reaction mixture was stirred at room temperature for 18 h. Upon completion of the reaction; reaction mixture was transferred into water, extracted with EtOAc. Organic layers were combined, washed with brine solution, dried over sodium sulphate and concentrated under reduced pressure to pressure to obtain crude material. The crude was purified by column chromatography to furnish 120.4 (1.0 g, 94.33%). MS(ES): m/z 321 [M+H]$^+$.

Synthesis of compound 120.5. To a solution of 120.4 (0.350 g, 1.09 mmol, 1.0 eq) in methanol (5 ml) 20% palladium hydroxide on charcoal (0.270 g) and 1N HCl (catalytic amount) were added into reaction. Reaction mixture was stirred under hydrogen at 30 psi for 15 h. Upon completion of the reaction, reaction mixture was filtered through celite-bed and washed with methanol. Filtrate was concentrated under reduced pressure to obtain crude which was purified by column chromatography to get 120.5. (0.280 g, 72%). MS(ES): m/z 231 [M+H]$^+$.

Synthesis of compound 120.6. Compound was prepared using the procedure described in Example 64.

Synthesis of compound I-120. Compound was prepared using the procedure described in Example 64. (0.02 g, 30.3%). MS(ES): m/z 482 [M+H]$^+$; $^1$H NMR (DMSO-d$_6$, 400 MHz): 9.79 (d, 1H), 9.11 (s, 1H), 8.17 (s, 1H), 7.92-7.90 (m, 1H), 7.83-7.74 (m, 2H), 7.44 (d, 1H), 6.17 (d, 1H), 4.49 (d, 2H), 4.05-4.00 (m, 1H), 3.66-3.62 (m, 1H), 3.50-3.44 (m, 1H), 3.37-3.35 (m, 1H), 3.24-3.20 (m, 1H), 2.97 (s, 3H), 2.24-2.18 (m, 1H), 1.99-1.92 (m, 1H).

Synthesis of compound 120.1. To a solution of 116.1 (1.0 g, 4.11 mmol, 1.0 eq) in DCM (20 mL) was added triethylamine (1.44 ml, 10.3 mmol, 2.5 eq) at 0° C. under nitrogen, and mixture was stirred at room temperature for 1 h. Reaction mixture was cooled to 0° C. and MsCl (0.66 ml, 8.50 mmol, 2.0 eq) was added dropwise, stirred at room temperature for 3 h. Upon completion of reaction, reaction mixture was transferred into ice. Resulting mixture was extracted with EtOAc. Organic layers were combined, washed with brine solution, dried over sodium sulphate and concentrated under reduced pressure to get 120.1 (1.2 g, 90.90%). MS(ES): m/z 322 [M+H]$^+$.

Example 121

Synthesis of 3-fluoro-2-(4-(3-(6-hydroxy-1,4-oxazepan-4-yl)-1H-pyrazol-1-yl)-5-oxo-6,7-dihydro-5H-pyrrolo[3,4-b]pyridin-2-yl)benzonitrile, I-121

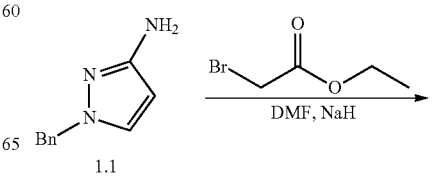

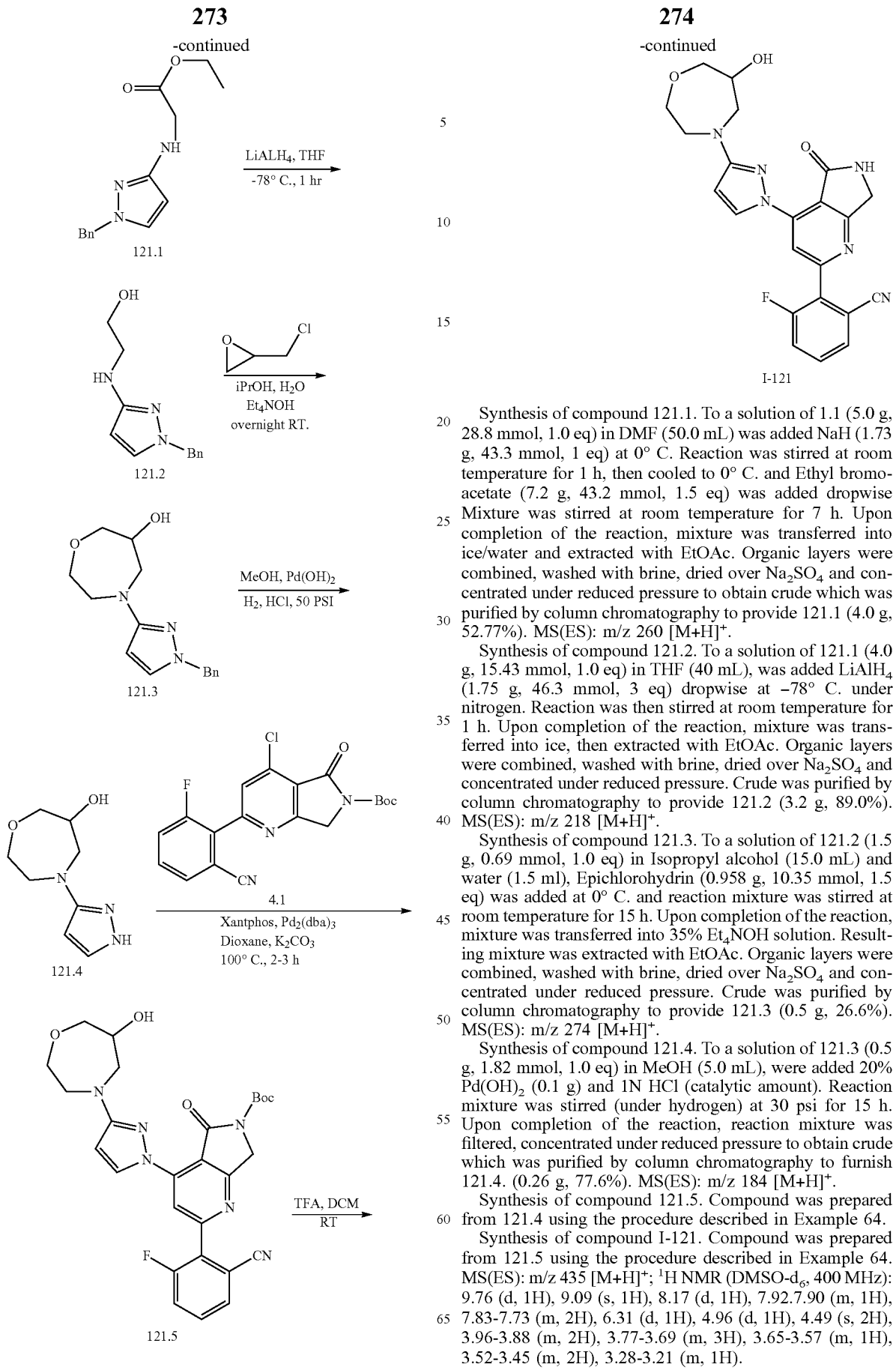

Synthesis of compound 121.1. To a solution of 1.1 (5.0 g, 28.8 mmol, 1.0 eq) in DMF (50.0 mL) was added NaH (1.73 g, 43.3 mmol, 1 eq) at 0° C. Reaction was stirred at room temperature for 1 h, then cooled to 0° C. and Ethyl bromoacetate (7.2 g, 43.2 mmol, 1.5 eq) was added dropwise Mixture was stirred at room temperature for 7 h. Upon completion of the reaction, mixture was transferred into ice/water and extracted with EtOAc. Organic layers were combined, washed with brine, dried over $Na_2SO_4$ and concentrated under reduced pressure to obtain crude which was purified by column chromatography to provide 121.1 (4.0 g, 52.77%). MS(ES): m/z 260 [M+H]$^+$.

Synthesis of compound 121.2. To a solution of 121.1 (4.0 g, 15.43 mmol, 1.0 eq) in THF (40 mL), was added LiAlH$_4$ (1.75 g, 46.3 mmol, 3 eq) dropwise at −78° C. under nitrogen. Reaction was then stirred at room temperature for 1 h. Upon completion of the reaction, mixture was transferred into ice, then extracted with EtOAc. Organic layers were combined, washed with brine, dried over $Na_2SO_4$ and concentrated under reduced pressure. Crude was purified by column chromatography to provide 121.2 (3.2 g, 89.0%). MS(ES): m/z 218 [M+H]$^+$.

Synthesis of compound 121.3. To a solution of 121.2 (1.5 g, 0.69 mmol, 1.0 eq) in Isopropyl alcohol (15.0 mL) and water (1.5 ml), Epichlorohydrin (0.958 g, 10.35 mmol, 1.5 eq) was added at 0° C. and reaction mixture was stirred at room temperature for 15 h. Upon completion of the reaction, mixture was transferred into 35% Et$_4$NOH solution. Resulting mixture was extracted with EtOAc. Organic layers were combined, washed with brine, dried over $Na_2SO_4$ and concentrated under reduced pressure. Crude was purified by column chromatography to provide 121.3 (0.5 g, 26.6%). MS(ES): m/z 274 [M+H]$^+$.

Synthesis of compound 121.4. To a solution of 121.3 (0.5 g, 1.82 mmol, 1.0 eq) in MeOH (5.0 mL), were added 20% Pd(OH)$_2$ (0.1 g) and 1N HCl (catalytic amount). Reaction mixture was stirred (under hydrogen) at 30 psi for 15 h. Upon completion of the reaction, reaction mixture was filtered, concentrated under reduced pressure to obtain crude which was purified by column chromatography to furnish 121.4. (0.26 g, 77.6%). MS(ES): m/z 184 [M+H]$^+$.

Synthesis of compound 121.5. Compound was prepared from 121.4 using the procedure described in Example 64.

Synthesis of compound I-121. Compound was prepared from 121.5 using the procedure described in Example 64. MS(ES): m/z 435 [M+H]$^+$; $^1$H NMR (DMSO-d$_6$, 400 MHz): 9.76 (d, 1H), 9.09 (s, 1H), 8.17 (d, 1H), 7.92-7.90 (m, 1H), 7.83-7.73 (m, 2H), 6.31 (d, 1H), 4.96 (d, 1H), 4.49 (s, 2H), 3.96-3.88 (m, 2H), 3.77-3.69 (m, 3H), 3.65-3.57 (m, 1H), 3.52-3.45 (m, 2H), 3.28-3.21 (m, 1H).

Example 122

Synthesis of 1-(1-(2-(2-cyano-6-fluorophenyl)-5-oxo-6,7-dihydro-5H-pyrrolo[3,4-b]pyridin-4-yl)-1H-pyrazol-3-yl)piperidine-3-carboxamide, I-122

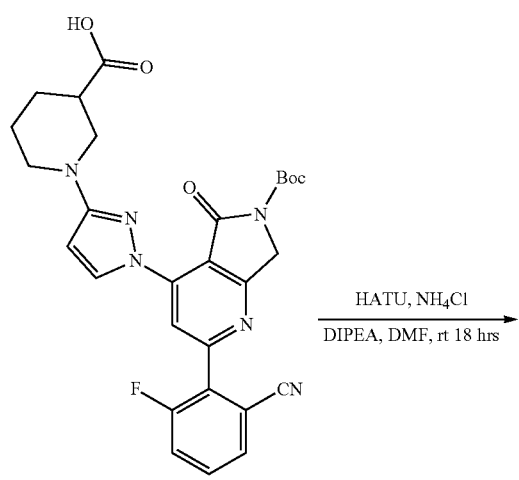

Synthesis of compound 122.1. Compound 91.2 (0.07 g, 0.012 mmol, 1.0 eq) was dissolved in DMF (1.0 mL) and HATU (0.09 g, 0.022 mmol, 1.2 eq) was added at 0° C. followed by NH$_4$Cl (0.009 g, 0.15 mmol, 1.2 eq) and DIPEA (0.033 g, 0.25 mmol, 2 eq). The reaction was stirred at room temperature for 16 h. Upon completion of the reaction, reaction mixture was transferred into water and then extracted with EtOAc. Organic layers were combined, washed with brine, dried over Na$_2$SO$_4$ and concentrated under reduced to pressure to obtain crude which was purified by column chromatography to provide 122.1 (0.07 g, 90.0%). MS(ES): m/z 546 [M+H]$^+$.

Synthesis of compound I-122. Compound I-122 was prepared from compound 122.1 using the procedure described in Example 64. MS(ES): m/z 446 [M+H]$^+$; $^1$H NMR (MeOD, 400 MHz): 9.71-9.70 (d, 1H), 8.30-8.29 (d, 1H), 7.80-7.78 (m, 1H), 7.74-7.64 (m, 2H), 6.27-6.26 (d, 1H), 4.62-4.56 (m, 2H), 4.04-4.01 (m, 1H), 3.88-3.85 (m, 1H), 3.05-2.99 (m, 1H), 2.93-2.83 (m, 1H), 2.61-2.58 (m, 1H), 1.99-1.97 (m, 1H), 1.80-1.76 (m, 1H), 1.72-1.62 (m, 2H).

Example 123

Synthesis of N-(1-(1-(2-(2-cyano-6-fluorophenyl)-5-oxo-6,7-dihydro-5H-pyrrolo[3,4-b]pyridin-4-yl)-1H-pyrazol-3-yl)piperidin-3-yl)acetamide, I-123

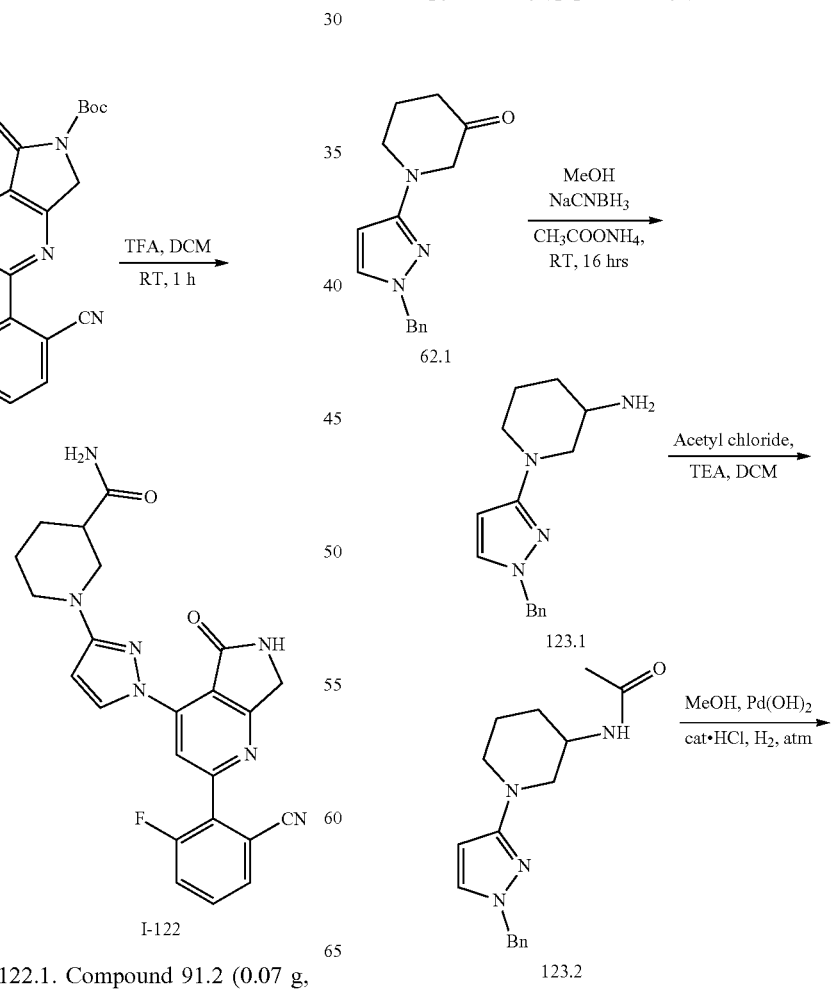

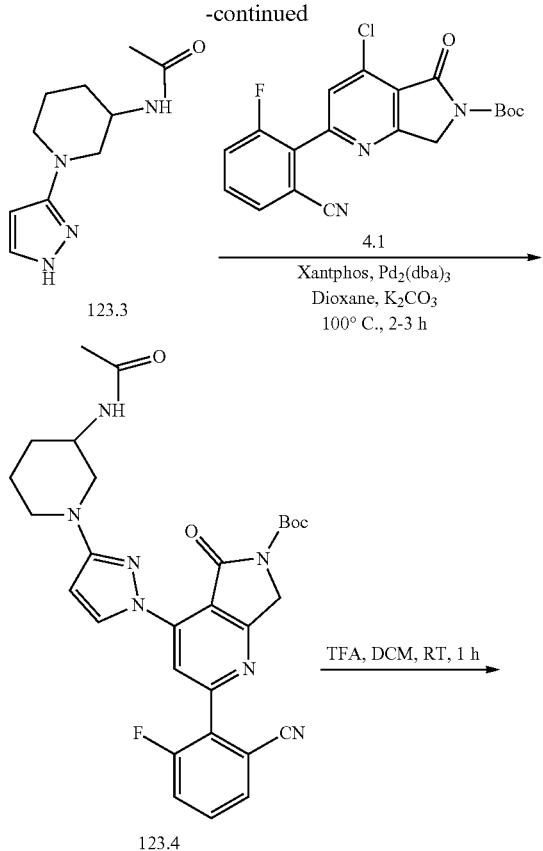

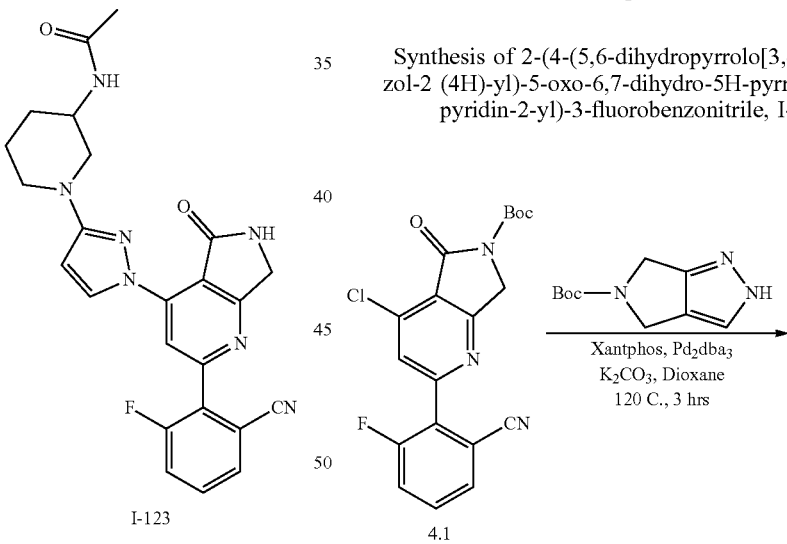

Et₃N (0.17 g, 1.77 mmol, 2 eq) and AcCl (0.84 g, 1.08 mmol, 1.2 eq) at 0° C. Reaction mixture was stirred at room temperature for 1 h. Upon completion of the reaction, mixture was transferred into water and extracted with DCM, dried over Na₂SO₄ and concentrated under reduced pressure to obtain crude which was purified by column chromatography to provide 123.2 (0.13 g, 48.6%). MS(ES): m/z 299.32 [M+H]⁺.

Synthesis of compound 123.3. To a solution of 123.2 (0.13 g, 0.435 mmol, 1.0 eq) in MeOH (5.0 mL), 20% Pd(OH)₂ (0.06 g) and 1 N HCl (catalytic) were added. Reaction mixture was stirred under 40 psi of hydrogen gas 24 h. Upon completion of the reaction, reaction mixture was filtered. Solvent were removed under reduced pressure to obtain crude which was purified by column chromatography to obtain 123.3. (0.075 g, 82.6%). MS(ES): m/z 209.21 [M+H]⁺.

Synthesis of compound 123.4. Compound was prepared from 123.3 and 4.1 using the procedure described in example 64.

Synthesis of compound I-123. Compound was prepared from 123.4 using the procedure described in Example 64. MS(ES): m/z 419.3 [M+H]⁺; ¹H NMR (DMSO-d₆, 400 MHz): 9.75-9.74 (d, 1H), 9.12 (s, 1H), 8.16 (s, 1H), 7.92-7.87 (m, 2H), 7.83-7.75 (m, 2H), 6.35 (d, 1H), 4.48 (s, 2H), 3.76-3.74 (m, 1H), 3.70-3.60 (m, 2H), 2.92-2.87 (m, 1H), 2.75-2.67 (m, 1H), 1.80 (s, 3H), 1.75-1.74 (m, 2H), 1.57-1.54 (m, 1H), 1.37-1.35 (m, 1H).

Example 124

Synthesis of 2-(4-(5,6-dihydropyrrolo[3,4-c]pyrazol-2 (4H)-yl)-5-oxo-6,7-dihydro-5H-pyrrolo[3,4-b]pyridin-2-yl)-3-fluorobenzonitrile, I-124

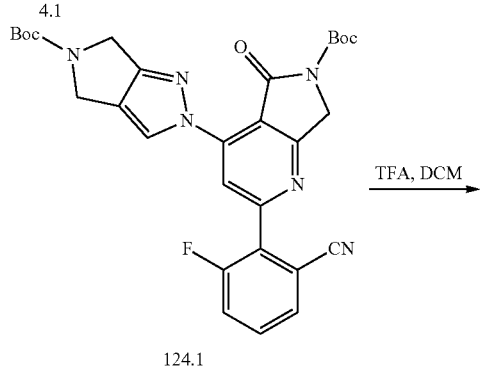

Synthesis of compound 123.1. To a solution of 62.1 (2 g, 7.8 mmol, 1.0 eq) in MeOH (10.0 mL) was added NH₄OAc (6.0 g, 78.0 mmol, 10 eq) and NaCNBH₃ (1.0 g, 15 mmol, 2.0 eq) at 0° C. Reaction mixture was stirred at room temperature for 16 h. Upon completion of the reaction, mixture was transferred into water and extracted with DCM, combined organic layers were washed brine dried over Na₂SO₄ and concentrated under reduced pressure to obtained crude. The crude was purified by column chromatography to provide 123.1 (0.25 g, 12.45%). MS(ES): m/z 257.35 [M+H]⁺.

Synthesis of compound 123.2. To a solution of 123.1 (0.25 g, 0.889 mmol, 1.0 eq) in DCM (10 ml) was added -continued

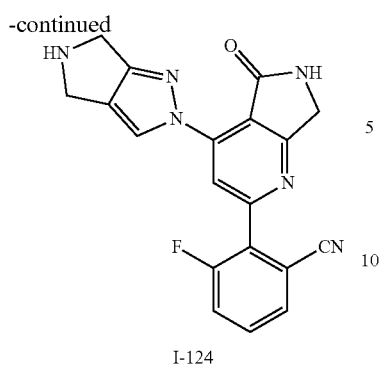

I-124

Compound I-124 was prepared from 4.1 and tert-butyl 2,6-dihydropyrrolo[3,4-c]pyrazole-5(4H)-carboxylate using the procedure described in Example 64. MS(ES): m/z 461 [M+H]$^+$, LCMS purity: 100%, HPLC purity: 99.14%, $^1$H NMR (DMSO-d$_6$, 400 MHz): 9.79 (s, 1H), 9.57 (s, 1H), 9.30 (s, 1H), 8.29 (d, 1H), 7.94-7.92 (m, 1H), 7.84-7.78 (m, 2H), 4.57 (d, 2H), 4.46-4.42 (m, 4H).

Example 125

Synthesis of (R)-1-(1-(2-(2-cyano-6-fluorophenyl)-5-oxo-6,7-dihydro-5H-pyrrolo[3,4-b]pyridin-4-yl)-1H-pyrazol-3-yl)piperidine-3-carboxamide, I-125

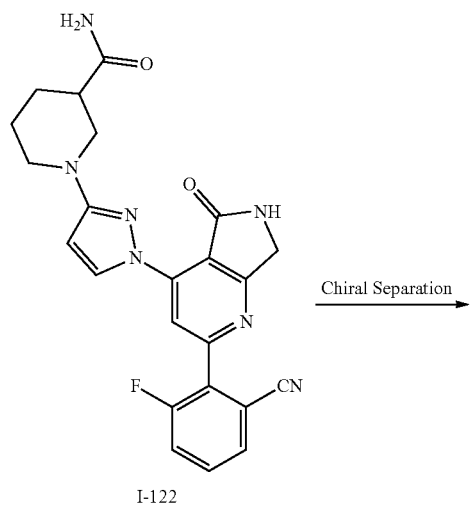

Compound I-125 was prepared by chiral purification of compound I-122. MS(ES): m/z 446 [M+H]$^+$; 1H NMR (DMSO, 400 MHz): 9.76-9.75 (d, 1H), 9.11 (s, 1H), 8.17 (s, 1H), 7.91-7.81 (m, 1H), 7.83-7.75 (m, 2H), 7.36 (s, 1H), 6.85 (s, 1H), 6.40-6.39 (d, 1H), 4.49 (s, 2H), 3.89-3.80 (m, 2H), 2.86-2.72 (m, 2H), 2.38-2.32 (m, 1H), 1.86-1.84 (m, 1H), 1.70-1.68 (m, 1H), 1.53-1.48 (m, 2H).

Example 126

Synthesis of (S)-1-(1-(2-(2-cyano-6-fluorophenyl)-5-oxo-6,7-dihydro-5H-pyrrolo[3,4-b]pyridin-4-yl)-1H-pyrazol-3-yl)piperidine-3-carboxamide, I-126

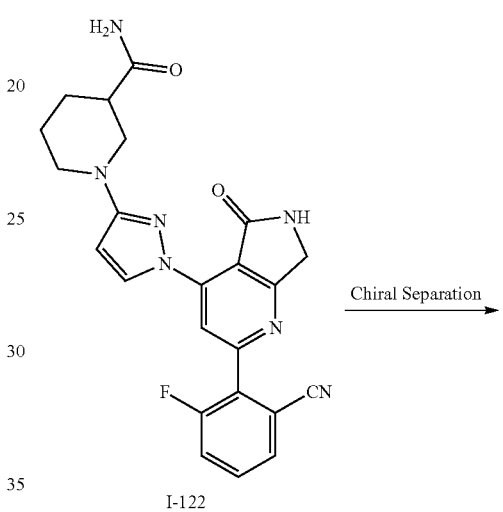

I-122

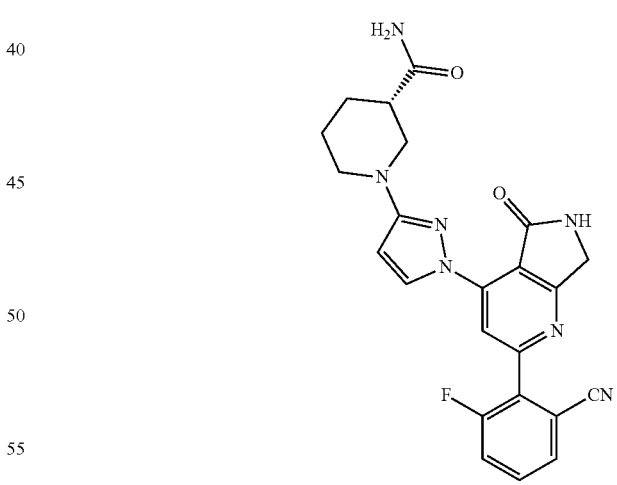

I-126

Compound I-126 was prepared by chiral purification of compound I-122. MS(ES): m/z 446 [M+H]$^+$; $^1$H NMR (DMSO, 400 MHz): 9.76-9.75 (d, 1H), 9.11 (s, 1H), 8.17 (s, 1H), 7.91-7.89 (m, 1H), 7.82-7.74 (m, 2H), 7.36 (s, 1H), 6.85 (s, 1H), 6.40-6.39 (d, 1H), 4.49 (s, 2H), 3.88-3.80 (m, 2H), 2.86-2.66 (m, 2H), 2.39-2.32 (m, 1H), 1.88-1.85 (m, 1H), 1.70-1.68 (m, 1H), 1.53-1.48 (m, 2H).

Example 127

Synthesis of (R)-1-(1-(2-(2-cyano-6-fluorophenyl)-5-oxo-6,7-dihydro-5H-pyrrolo[3,4-b]pyridin-4-yl)-1H-pyrazol-3-yl)pyrrolidine-3-carbonitrile, I-127

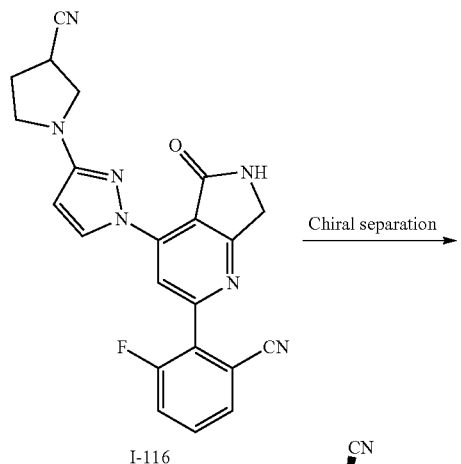

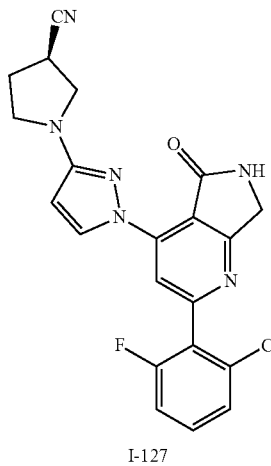

Compound I-127 was prepared by chiral purification of I-116. MS(ES): m/z 414 [M+H]$^+$; $^1$H NMR (MeOD, 400 MHz): 9.79 (d, 1H), 9.13 (s, 1H), 7.92-7.90 (m, 1H), 7.83-7.75 (m, 2H), 6.23 (d, 1H), 4.50 (s, 2H), 3.85-3.81 (m, 1H), 3.73-3.63 (m, 2H), 3.56-3.52 (m, 1H), 3.28-3.21 (m, 1H), 2.74-2.34 (m, 2H).

Example 128

Synthesis of (S)-1-(1-(2-(2-cyano-6-fluorophenyl)-5-oxo-6,7-dihydro-5H-pyrrolo[3,4-b]pyridin-4-yl)-1H-pyrazol-3-yl)pyrrolidine-3-carbonitrile, I-128

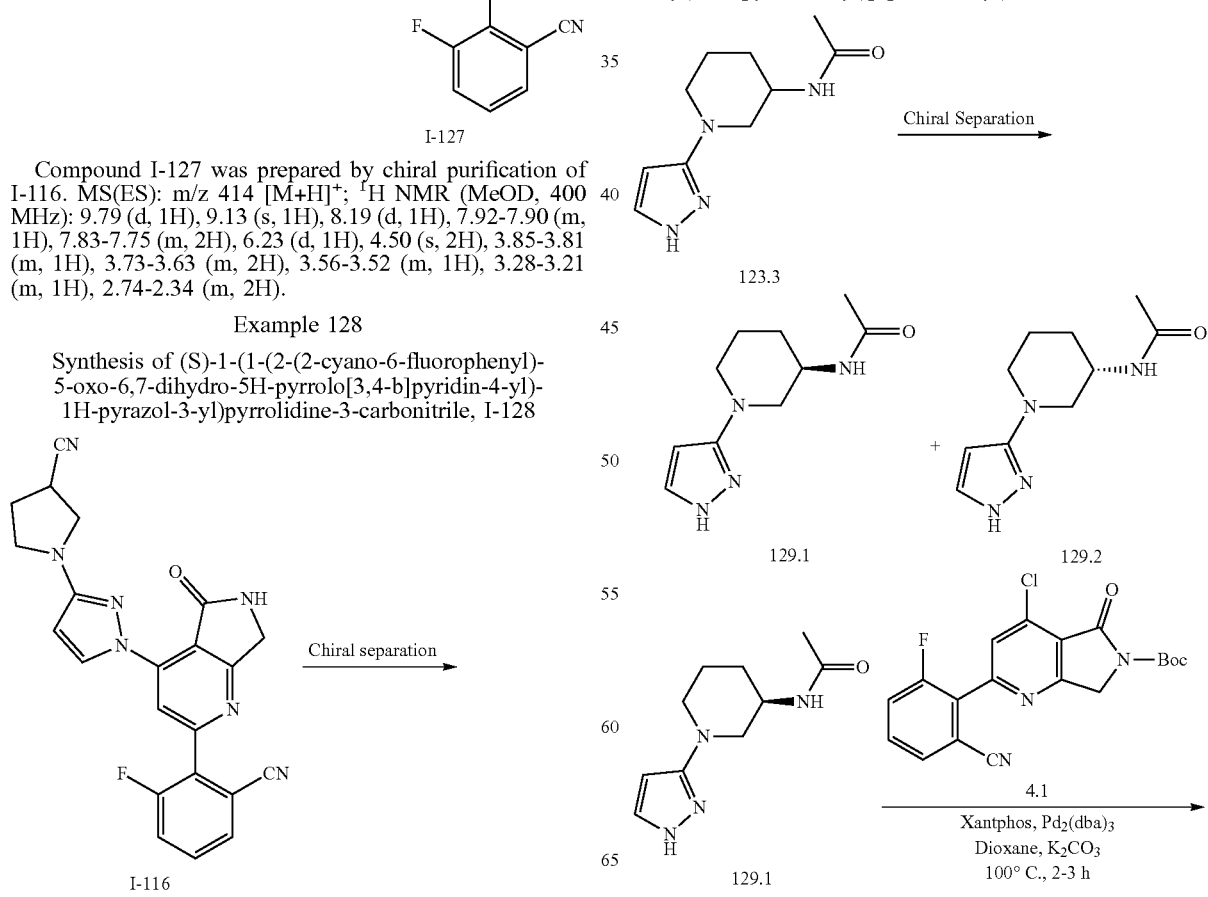

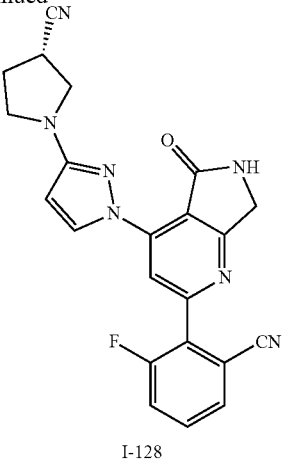

Compound I-128 was prepared by chiral purification of I-116. MS(ES): m/z 414 [M+H]$^+$; $^1$H NMR (MeOD, 400 MHz): 9.79 (d, 1H), 9.13 (s, 1H), 8.19 (d, 1H), 7.92-7.90 (m, 1H), 7.83-7.75 (m, 2H), 6.23 (d, 1H), 4.50 (s, 2H), 3.85-3.81 (m, 1H), 3.73-3.63 (m, 2H), 3.56-3.52 (m, 1H), 3.28-3.21 (m, 1H), 2.74-2.34 (m, 2H).

Example 129

Synthesis of (R)-N-(1-(1-(2-(2-cyano-6-fluorophenyl)-5-oxo-6,7-dihydro-5H-pyrrolo[3,4-b]pyridin-4-yl)-1H-pyrazol-3-yl)piperidin-3-yl)acetamide, I-129

283
-continued

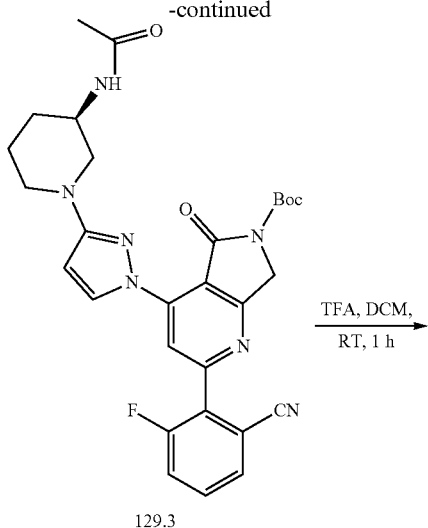

129.3

↓ TFA, DCM, RT, 1 h

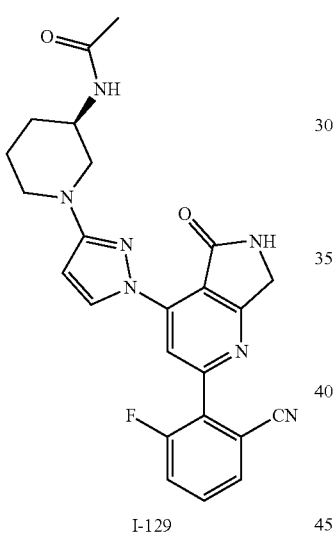

I-129

Synthesis of compounds 129.1. and 129.2. Compound 129.1 and 129.2 were prepared by chiral purification of compound 123.3.

Synthesis of compound 129.3. Compound was prepared from 129.1 and 4.1 using the procedure described in Example 64.

Synthesis of compound I-129. Compound was prepared from 129.3 using the procedure described in Example 64. MS(ES): m/z 460.2 [M+H]$^+$; $^1$H NMR (DMSO-d$_6$, 400 MHz): 9.75-9.74 (d, 1H), 9.12 (s, 1H), 8.16 (s, 1H), 7.92-7.87 (m, 2H), 7.83-7.75 (m, 2H), 6.35 (d, 1H), 4.49 (s, 2H), 3.76-3.74 (m, 1H), 3.70-3.60 (m, 2H), 2.93-2.87 (m, 1H), 2.72-2.67 (m, 1H), 1.80 (s, 3H), 1.75-1.74 (m, 2H), 1.57-1.54 (m, 1H), 1.37-1.35 (m, 1H).

284

Example 130

Synthesis of (S)-N-(1-(1-(2-(2-cyano-6-fluorophenyl)-5-oxo-6,7-dihydro-5H-pyrrolo[3,4-b]pyridin-4-yl)-1H-pyrazol-3-yl)piperidin-3-yl)acetamide, I-130

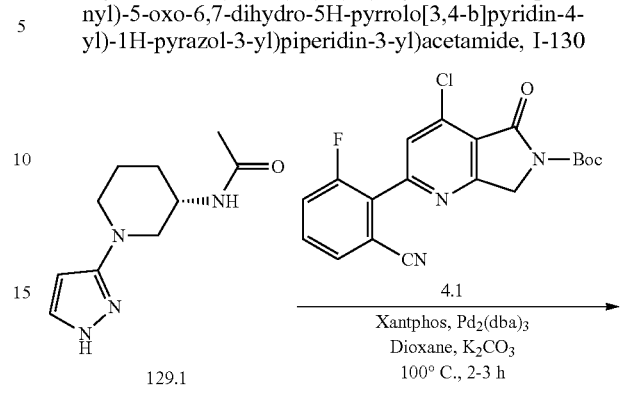

129.1    4.1

Xantphos, Pd$_2$(dba)$_3$
Dioxane, K$_2$CO$_3$
100° C., 2-3 h

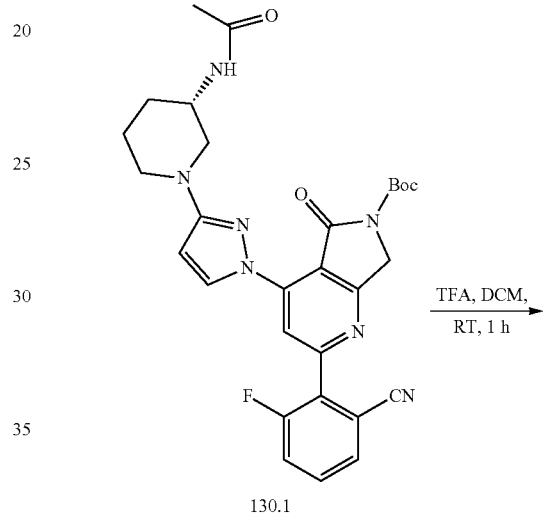

130.1

↓ TFA, DCM, RT, 1 h

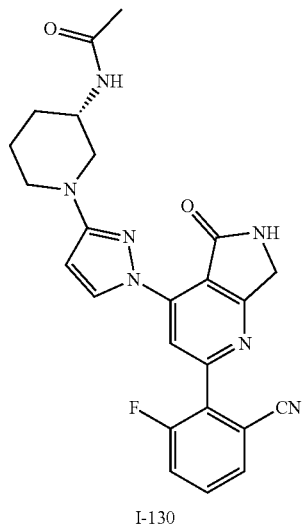 [SMILES: CC(=O)N[C@@H]1CCCN(c2ccn(-c3cc(-c4c(F)cccc4C#N)nc4c3C(=O)NC4)n2)C1]

I-130

Compound I-130 was prepared from 129.2 and 4.1 using the procedures referred in Example 129. MS(ES): m/z 460.2 [M+H]$^+$; $^1$H NMR (DMSO-d$_6$, 400 MHz): 9.75-9.74 (d, 1H), 9.12 (s, 1H), 8.16 (s, 1H), 7.92-7.87 (m, 2H), 7.83-7.75 (m, 2H), 6.35 (d, 1H), 4.49 (s, 2H), 3.76-3.74 (m, 1H), 3.70-3.60 (m, 2H), 2.93-2.87 (m, 1H), 2.72-2.67 (m, 1H), 1.80 (s, 3H), 1.75-1.74 (m, 2H), 1.57-1.54 (m, 1H), 1.37-1.35 (m, 1H).

Example 131

Synthesis of (S)-3-fluoro-2-(4-(3-(6-hydroxy-1,4-oxazepan-4-yl)-1H-pyrazol-1-yl)-5-oxo-6,7-dihydro-5H-pyrrolo[3,4-b]pyridin-2-yl)benzonitrile, I-131

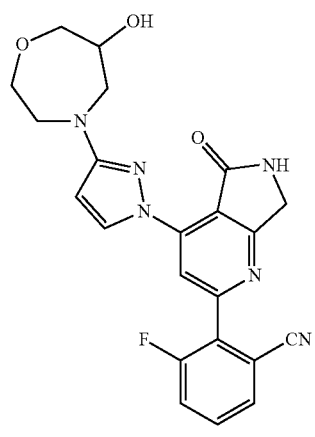

I-121

→ Chiral Separation →

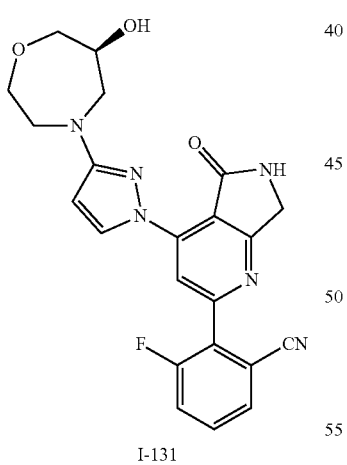

I-131

Compound I-131 was prepared by chiral purification of compound I-121. MS(ES): m/z 435 [M+H]$^+$; $^1$H NMR (DMSO-d$_6$, 400 MHz): 9.76 (d, 1H), 9.10 (s, 1H), 8.15 (d, 1H), 7.92.7.90 (m, 1H), 7.81-7.75 (m, 2H), 6.31 (d, 1H), 4.96 (d, 1H), 4.49 (s, 2H), 3.96-3.88 (m, 2H), 3.77-3.69 (m, 3H), 3.65-3.57 (m, 1H), 3.52-3.45 (m, 2H), 3.28-3.21 (m, 1H).

Example 132

Synthesis of (R)-3-fluoro-2-(4-(3-(6-hydroxy-1,4-oxazepan-4-yl)-1H-pyrazol-1-yl)-5-oxo-6,7-dihydro-5H-pyrrolo[3,4-b]pyridin-2-yl)benzonitrile, I-132

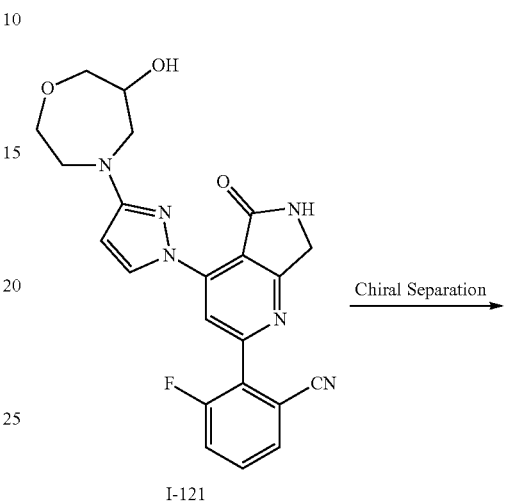

I-121

→ Chiral Separation →

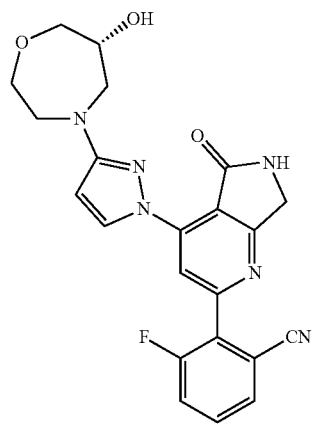

I-132

Compound I-132 was prepared by chiral purification of compound I-121. MS(ES): m/z 435 [M+H]$^+$; $^1$H NMR (DMSO-d$_6$, 400 MHz): 9.76 (d, 1H), 9.10 (s, 1H), 8.15 (d, 1H), 7.92.7.90 (m, 1H), 7.81-7.75 (m, 2H), 6.31 (d, 1H), 4.96 (d, 1H), 4.49 (s, 2H), 3.96-3.88 (m, 2H), 3.77-3.69 (m, 3H), 3.65-3.57 (m, 1H), 3.52-3.45 (m, 2H), 3.28-3.21 (m, 1H).

Example 133

Synthesis of 1-(1-(2-(2-cyano-6-fluorophenyl)-5-oxo-6,7-dihydro-5H-pyrrolo[3,4-b]pyridin-4-yl)-1H-pyrazol-3-yl)-3-methylpiperidine-3-carbonitrile, I-133

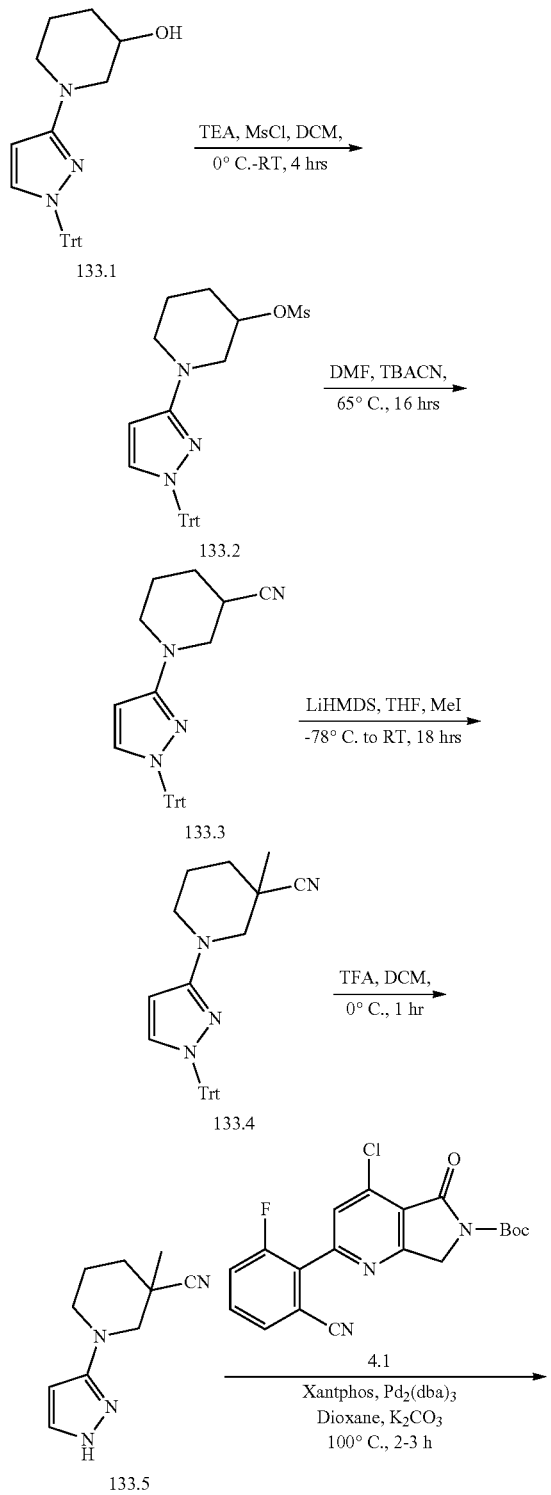

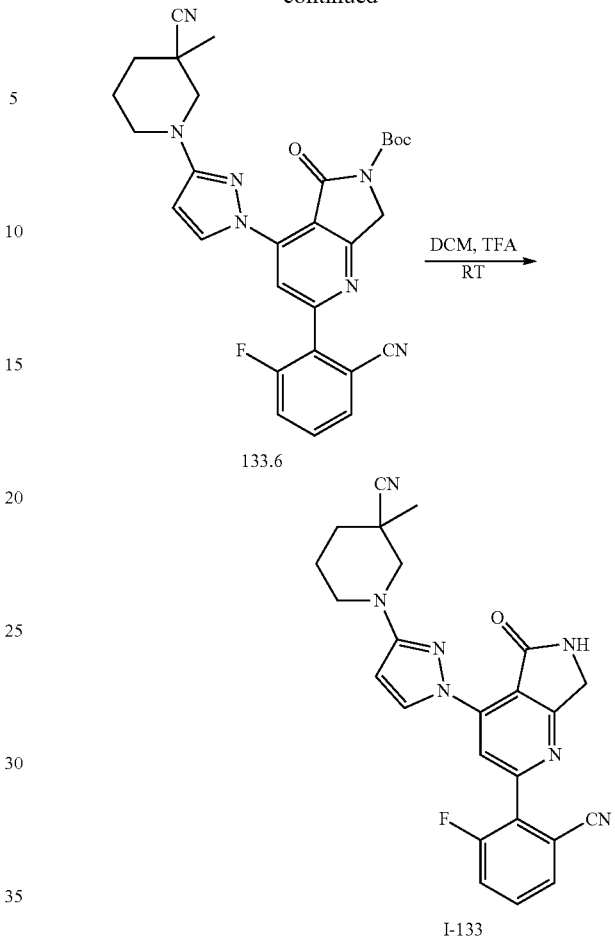

Synthesis of compound 133.2. To a solution of 133.1 (0.82 g, 2.0 mmol, 1.0 eq) and Et$_3$N (0.406 g, 4.02 mmol, 2 eq) in DCM (15.0 ml), MsCl was added at 0° C. Reaction mixture was stirred at room temperature for 4 hr. Upon completion of the reaction; reaction mixture was transferred into water and extracted with EtOAc, dried over Na$_2$SO$_4$ and concentrated under reduced pressure to obtain crude which was purified by column chromatography to provide 133.2 (0.790 g, 81.4%). MS(ES): m/z 488 [M+H]$^+$.

Synthesis of compound 133.3. A mixture of 133.2 (0.79 g, 1.62 mmol, 1.0 eq) and tetrabutylammonium cyanide (0.872 g, 3.24 mmol, 2.0 eq) in CH$_3$CN (3.0 mL) was stirred at 65° C. for 14 h. Upon completion of the reaction, mixture was transferred into water solution, then extracted with EtOAc. Organic layers were combined, washed with brine, dried over Na$_2$SO$_4$ and concentrated under reduced pressure to pressure to obtain crude which was purified by column chromatography to get pure 133.3 (0.47 g, 69.3%). MS(ES): m/z 419 [M+H]$^+$.

Synthesis of compound 133.4. To a solution of 133.3 (0.2 g, 0.478 mmol, 1 eq) in THF (2.0 ml), LHMDS (1.2 ml, 1.2 mmol, 2.5 eq) was added at −78° C. MeI (0.82 g, 0.57 mmol, 1.2 eq) was added dropwise at 0° C. Reaction mixture was stirred at room temperature for 15 h. Upon completion of reaction, mixture was transferred into water, then extracted with EtOAc. Organic layers were combined, washed with brine solution, dried over Na$_2$SO$_4$ and concentrated under reduced pressure to pressure to obtain crude which was purified by column chromatography to provide 133.4 (0.12 g, 60.0%). MS(ES): m/z 433 [M+H]$^+$.

Synthesis of compound 133.5. To a solution of 133.54 (0.12 g, 0.27 mmol, 1.0 eq) in DCM (1 mL), TFA (0.1 ml)

was added. Reaction mixture was stirred at 0° C. for 2 hours. Upon completion of the reaction, mixture was transferred into water and product was extracted with EtOAc. Organic layers were combined, washed with brine solution and concentrated under reduced pressure to obtain crude which was purified by column chromatography to get 133.5. (0.01 g, 20.0%). MS(ES): m/z 191 [M+H]$^+$.

Synthesis of compound 133.6. Compound 133.6 was prepared from compound 133.5 and 4.1 using the procedure described in Example 64.

Synthesis of compound I-133. Compound I-133 was prepared from compound 133.6 using the procedure described in Example 64. MS(ES): m/z 442 [M+H]$^+$; $^1$H NMR (DMSO-d$_6$, 400 MHz): 9.73-9.72 (d, 1H), 9.12 (s, 1H), 8.23-8.21 (d, 1H), 7.92-7.90 (m, 1H), 7.83-7.75 (m, 2H), 6.28-6.26 (m, 1H), 4.49 (s, 2H), 3.80-3.77 (m, 1H), 3.65-3.62 (m, 1H), 3.54-3.44 (m, 1H), 2.18-2.06 (m, 2H), 1.99-1.90 (m, 3H), 1.27-1.17 (m, 3H).

Example 134

Synthesis of (R)-N-(1-(1-(2-(2-cyano-6-fluorophenyl)-5-oxo-6,7-dihydro-5H-pyrrolo[3,4-b]pyridin-4-yl)-1H-pyrazol-3-yl)pyrrolidin-3-yl)methanesulfonamide, I-134

Compound was prepared by chiral purification of compound I-120. MS(ES): m/z 482 [M+H]$^+$, $^1$H NMR (DMSO-d$_6$, 400 MHz): 9.79 (d, 1H), 9.11 (s, 1H), 8.17 (s, 1H), 7.92-7.90 (m, 1H), 7.83-7.74 (m, 2H), 7.43 (d, 1H), 6.17 (d, 1H), 4.49 (d, 2H), 4.05-4.00 (m, 1H), 3.66-3.62 (m, 1H), 3.50-3.44 (m, 1H), 3.37-3.35 (m, 1H), 3.24-3.20 (m, 1H), 2.97 (s, 3H), 2.24-2.18 (m, 1H), 1.99-1.92 (m, 1H).

Example 135

Synthesis of (S)-N-(1-(1-(2-(2-cyano-6-fluorophenyl)-5-oxo-6,7-dihydro-5H-pyrrolo[3,4-b]pyridin-4-yl)-1H-pyrazol-3-yl)pyrrolidin-3-yl)methanesulfonamide, I-135

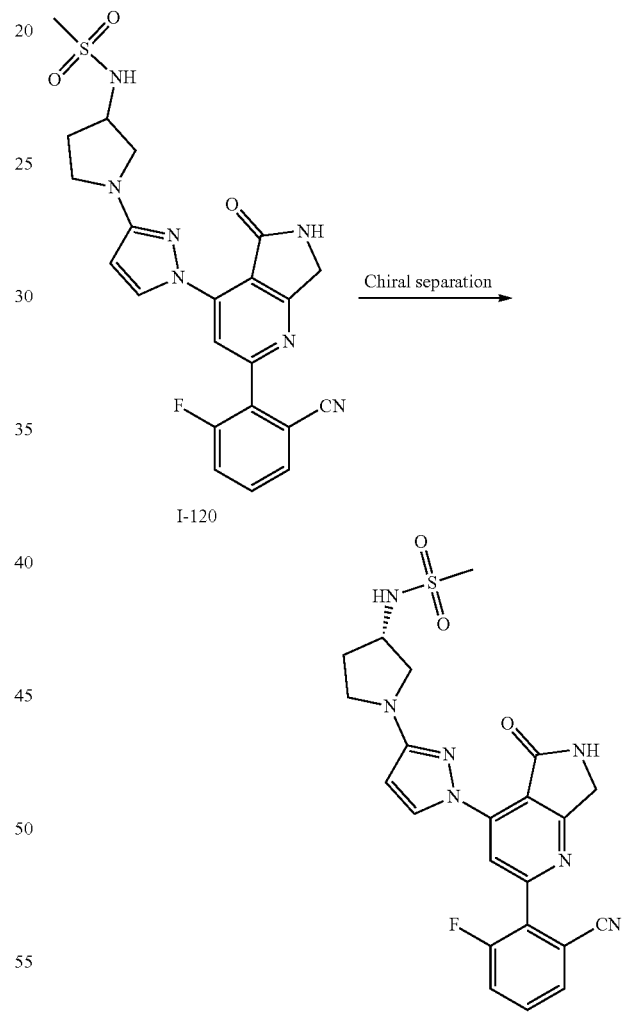

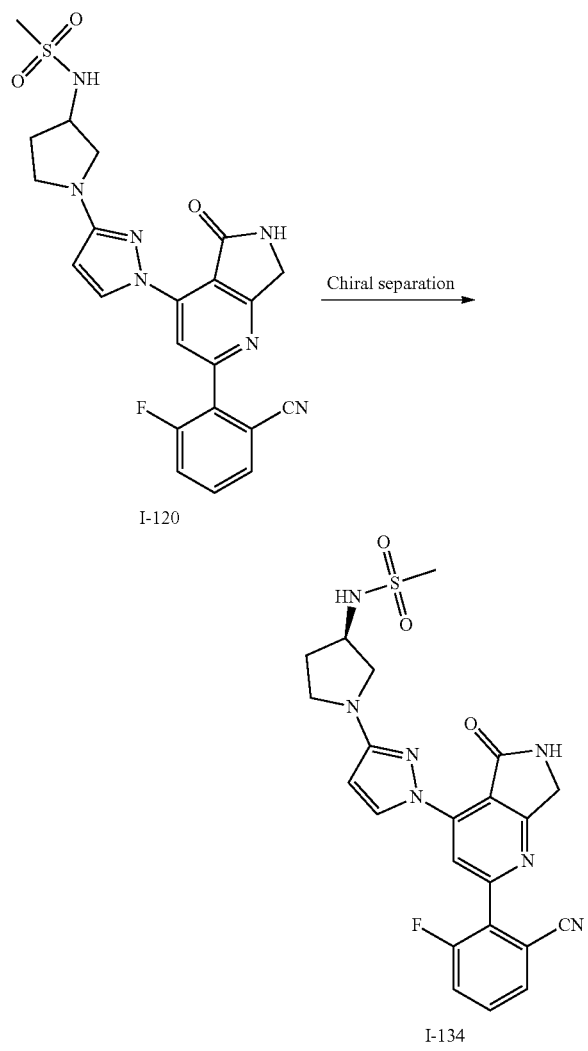

Compound was prepared by chiral purification of compound I-120. MS(ES): m/z 482 [M+H]$^+$; $^1$H NMR (DMSO-d$_6$, 400 MHz): 9.78 (d, 1H), 9.11 (s, 1H), 8.16 (s, 1H), 7.91-7.90 (m, 1H), 7.81-7.77 (m, 2H), 7.43 (d, 1H), 6.17 (d, 1H), 4.48 (d, 2H), 4.05-4.00 (m, 1H), 3.66-3.62 (m, 1H), 3.50-3.44 (m, 1H), 3.37-3.35 (m, 1H), 3.24-3.20 (m, 1H), 2.97 (s, 3H), 2.24-2.18 (m, 1H), 1.99-1.92 (m, 1H).

Example 136

Synthesis of 2-(4-(3-((3R,4S)-3,4-dihydroxypiperidin-1-yl)-1H-pyrazol-1-yl)-5-oxo-6,7-dihydro-5H-pyrrolo[3,4-b]pyridin-2-yl)-3-fluorobenzonitrile, I-136

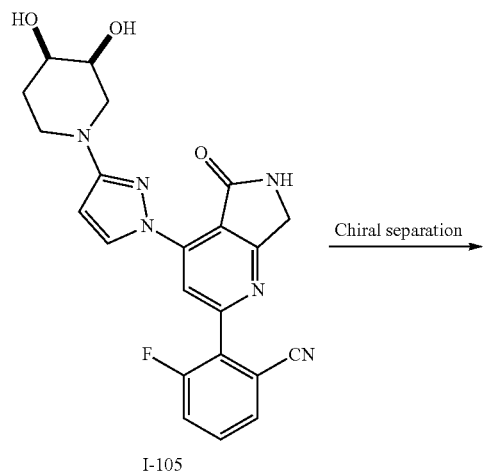

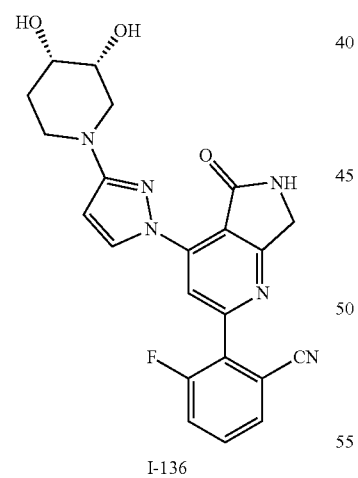

Compound I-136 was prepared by chiral separation of compound I-105. MS(ES): m/z 435.33 [M+H]$^+$; $^1$H NMR (DMSO-d$_6$, 400 MHz): 9.76 (s, 1H), 9.10 (s, 1H), 8.16 (s, 1H), 7.92-7.90 (m, 1H), 7.83-7.73 (m, 2H), 6.347-6.34 (d, 1H), 4.63-4.62 (d, 1H), 4.53-4.52 (d, 1H), 4.49 (s, 2H), 3.74-3.73 (m, 1H), 3.58 (m, 1H), 3.28-3.21 (m, 4H), 1.76-1.73 (m, 1H), 1.62 (m, 1H).

Example 137

Synthesis of 2-(4-(3-((3S,4R)-3,4-dihydroxypiperidin-1-yl)-1H-pyrazol-1-yl)-5-oxo-6,7-dihydro-5H-pyrrolo[3,4-b]pyridin-2-yl)-3-fluorobenzonitrile, I-137

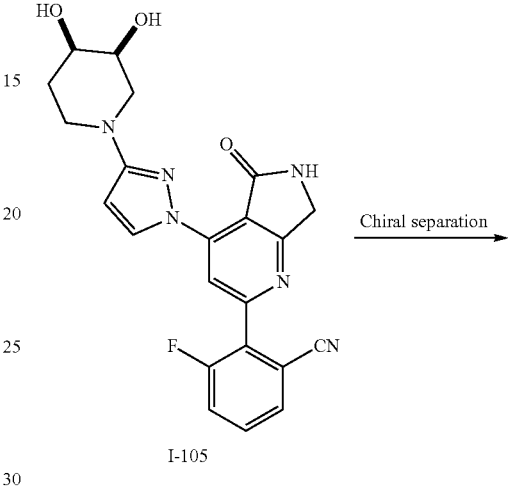

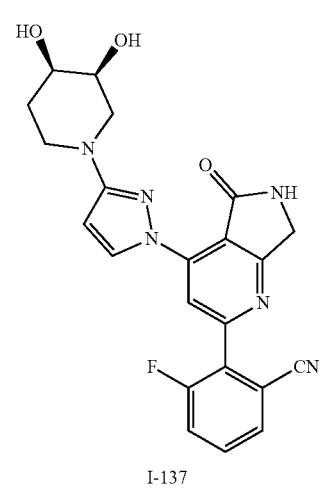

Compound I-137 was prepared by chiral purification of I-105. MS(ES): m/z 435.38 [M+H]$^+$; $^1$H NMR (DMSO-d$_6$, 400 MHz): 9.76-9.75 (d, 1H), 8.16 (s, 1H), 7.91-7.89 (m, 1H), 7.83-7.33 (m, 2H), 4.65-4.64 (d, 1H), 40.55-4.54 (d, 1H), 4.49 (s, 2H), 4.36-4.35 (d, 1H), 3.79-3.73 (m, 2H), 3.59 (m, 1H), 3.31-3.16 (m, 3H), 1.78-1.74 (m, 1H), 1.64-1.59 (m, 1H).

Example 138

Synthesis of 3-fluoro-2-(5-oxo-4-(3-(3-oxomorpholino)-1H-pyrazol-1-yl)-6,7-dihydro-5H-pyrrolo[3,4-b]pyridin-2-yl)benzonitrile, I-138

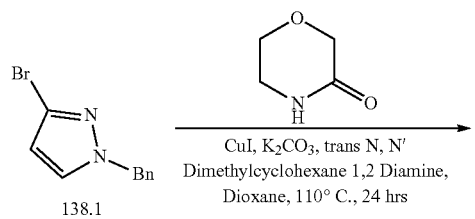

138.1

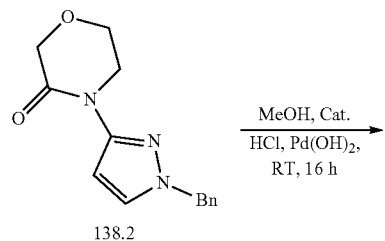

138.2

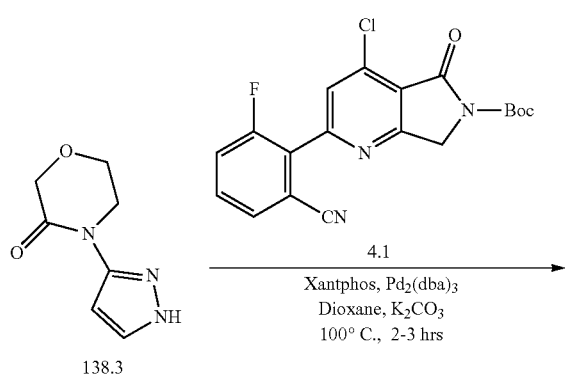

138.3

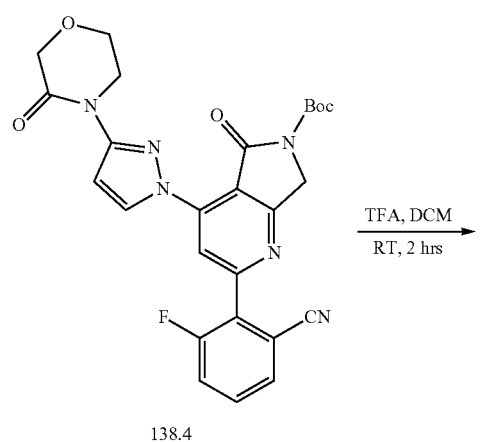

138.4

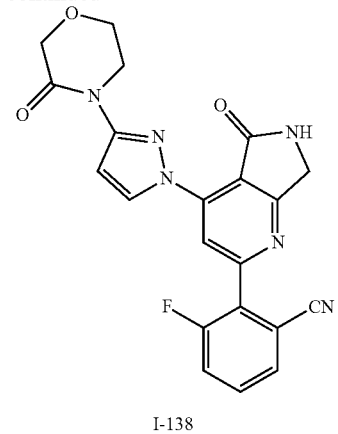 [SMILES: N#Cc1cccc(F)c1-c1cc(-n2ccc(N3CCOCC3=O)n2)c2c(n1)CNC2=O]

I-138

Synthesis of compound 138.2. To a solution of 138.1 (0.5 g, 1.76 mmol, 1.0 eq) in DMSO (5.0 ml) was added Morpholin-3-one (0.266 g, 2.63 mmol, 1.5 eq), CuI (0.033 g, 0.17 mmol, 0.1 eq), K$_2$CO$_3$ (0.6 g, 4.40 mmol, 2.5 eq) and trans-N,N'-Dimethylcyclohexane-1,2-diamine (0.012 g, 0.81 mmol, 0.05 eq) at room temperature. Reaction mixture was stirred at 110° C. for 18 hours. Upon completion of the reaction, mixture was poured into water and product was extracted with EtOAc. Organic layers were combined, washed with brine, dried over Na$_2$SO$_4$ and concentrated under reduced pressure to obtain crude which was purified by column chromatography to furnish 138.2 (0.55 g, 74.1%). MS(ES): m/z 258 [M+H]$^+$.

Synthesis of compound 138.3. To a solution of 138.2 (0.5 g, 1.94 mmol, 1.0 eq) in MeOH (5.0 mL) were added 20% Pd(OH)$_2$/C (0.75 g) and 1.0 N HCl (catalytic amount). Reaction mixture was stirred (under hydrogen) at 40 psi for 3 h. Upon completion of the reaction, reaction mixture was filtered then concentrated under reduced pressure to obtain crude which was purified by column chromatography to provide 138.2. (0.15 g, 46.29%). MS(ES): m/z 168 [M+H]$^+$.

Synthesis of compound 138.4. Compound was prepared from 138.3 and 4.1 using the procedure described in Example 64.

Synthesis of compound I-138. Compound was prepared from 138.4 using the procedure described in Example 64. MS(ES): m/z 419 [M+H]$^+$; $^1$H NMR (DMSO-d$_6$, 400 MHz): 9.76 (s, 1H), 9.29 (s, 1H), 8.29 (s, 1H), 7.94-7.92 (m, 1H), 7.85-7.75 (m, 2H), 7.14 (t, 1H), 4.55 (s, 2H), 4.28 (s, 2H), 4.03-3.99 (m, 4H).

Example 139

Synthesis of 3-fluoro-2-(5-oxo-4-(3-(2-oxopyrrolidin-1-yl)-1H-pyrazol-1-yl)-6,7-dihydro-5H-pyrrolo[3,4-b]pyridin-2-yl)benzonitrile I-139

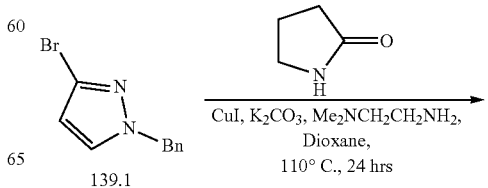

139.1

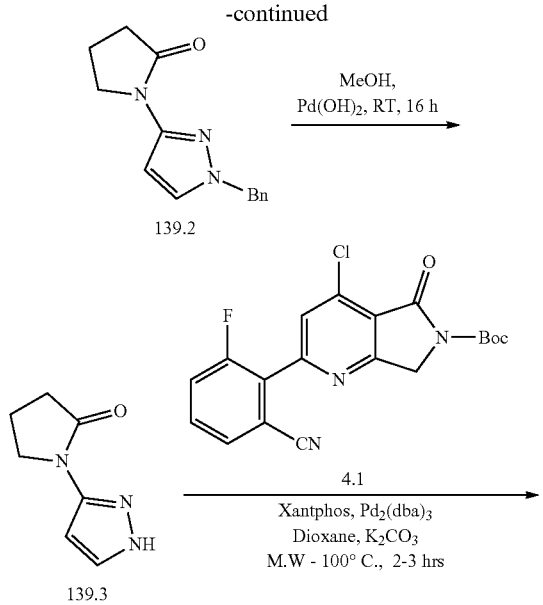
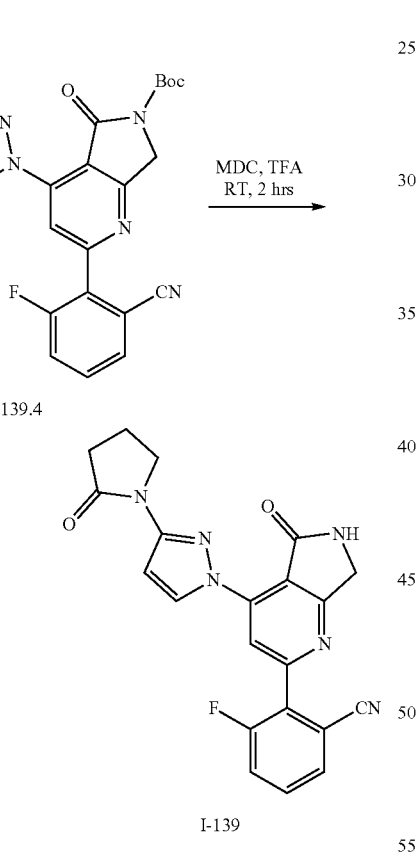

which was purified by column chromatography to provide 139.2 (0.250 g, 59.38%). MS(ES): m/z 242 [M+H]⁻.

Synthesis of compound 139.3. To a solution of 139.2 (0.250 g, 1.03 mmol, 1.0 eq) in MeOH (5 mL). 20% palladium hydroxide on charcoal (0.75 g) and 1N HCl (catalytic amount) were added into reaction. Reaction mixture was stirred under hydrogen at 40 psi for 3 h. Upon completion of the reaction, reaction mixture was filtered. Filtrate was concentrated under reduced pressure to obtain crude which was purified by column chromatography to provide 139.2 (0.090 g, 57.69%). MS(ES): m/z 152 [M+H]⁺.

Synthesis of compound 139.4. Compound was prepared using the procedure described in Example 64.

Synthesis of compound I-139. Compound was from 139.4 prepared using the procedure described in Example 64. (0.035 g, 35.35%). MS(ES): m/z 403 [M+H]⁺; ¹H NMR (DMSO-d₆, 400 MHZ): 9.78 (s, 1H), 9.25 (s, 1H), 8.26 (s, 1H), 7.94-7.92 (m, 1H), 7.85-7.75 (m, 2H), 7.10 (d, 1H), 4.54 (d, 2H), 4.05-3.90 (m, 2H), 2.67-2.53 (m, 2H), 2.13-2.08 (m, 2H).

Example 140

Synthesis of 3-fluoro-2-(5-oxo-4-(3-(3-oxo-1,4-diazepan-1-yl)-1H-pyrazol-1-yl)-6,7-dihydro-5H-pyrrolo[3,4-b]pyridin-2-yl)benzonitrile, I-140

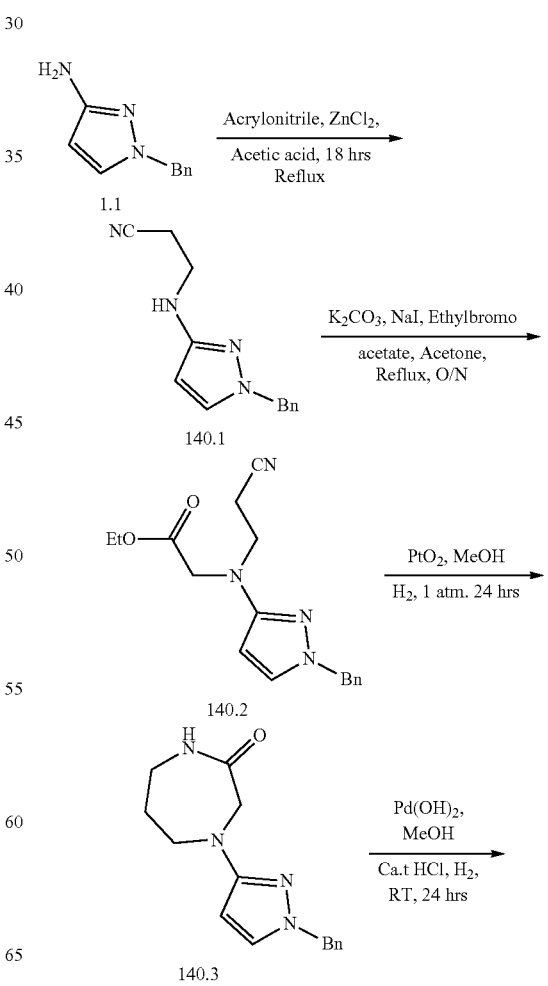

Synthesis of compound 139.2. To a solution of 139.1 (0.5 g, 1.75 mmol, 1.0 eq) in dioxane (5 ml) was added pyrrolidin-2-one (0.178 g, 2.09 mmol, 1.2 eq), CuI (0.016 g, 0.08 mmol, 0.05 eq), K₂CO₃ (0.723 g, 5.20 mmol, 4.4 eq) and trans-N,N'-Dimethylcyclohexane-1,2-diamine (0.007 g, 0.08 mmol, 0.05 eq) at room temperature and reaction mixture was stirred at 110° C. for 24 h. Upon completion of the reaction, reaction mixture was transferred into water and product was extracted with EtOAc. Organic layers were combined, washed with brine, dried over sodium sulphate and concentrated under reduced pressure to obtain crude

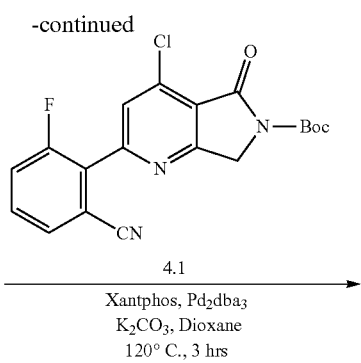

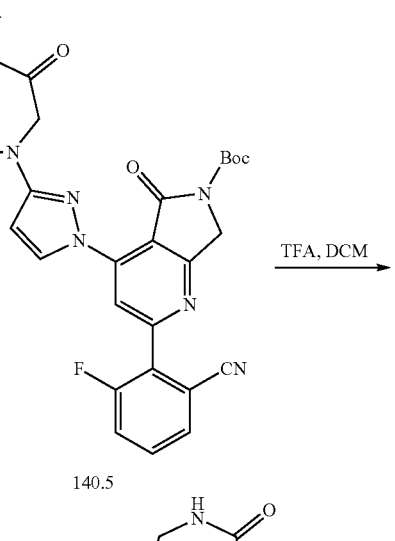

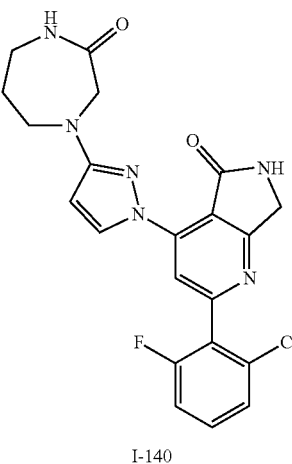

1.5 eq) was added slowly at 0° C., The reaction was stirred at 56° C. for 15 h Upon completion of the reaction, reaction mixture was transferred into water, then extracted with EtOAc. Organic layers were combined, washed with brine, dried over $Na_2SO_4$ and concentrated under reduced pressure to pressure to obtain crude which was purified by column chromatography to furnish 140.2 (1.0 g, 45.7%). MS(ES): m/z 313 [M+H]$^+$.

Synthesis of compound 140.3. To a solution of 140.2. (1.0 g, 3.20 mmol, 1.0 eq) in MeOH (12.0 mL), $PtO_2$ (0.4 g) was added. Reaction mixture was stirred under hydrogen at 40 psi for 15 h. Upon completion of the reaction, mixture was filtered. Filtrate was concentrated under reduced pressure to obtain crude which was purified by column chromatography to provide 140.3. (0.45 g, 52.02%). MS(ES): m/z 271 [M+H]$^+$.

Synthesis of compound 140.4. To a solution of 140.3. (0.4 g, 1.48 mmol, 1.0 eq) in Methanol (3.0 mL) was added 20% $Pd(OH)_2$ on charcoal (0.6 g) and 1N HCl (catalytic amount). Reaction mixture was stirred under hydrogen at 30 psi for 15 h. Upon completion of the reaction, reaction mixture was filtered. Filtrate was concentrated under reduced pressure to obtain crude which was purified by column chromatography to provide 140.4. (0.1 g, 37.6%). MS(ES): m/z 181 [M+H]$^+$.

Synthesis of compound 140.5. Compound was prepared from 140.4 and 4.1 using the procedure described in Example 64.

Synthesis of compound I-140. Compound was prepared from 140.5 using the procedure described in Example 64 (0.03 g, 37.0%). MS(ES): m/z 432 [M+H]$^+$; $^1$H NMR (DMSO-$d_6$, 400 MHz): 9.72 (d, 1H), 9.11 (s, 1H), 8.14 (d, 1H), 7.92-7.90 (m, 1H), 7.82-7.76 (m, 2H), 7.45 (t, 3H), 6.14 (s, 1H), 6.25 (d, 1H), 4.49 (d, 2H), 4.04 (d, 2H), 3.68 (t, 2H), 3.19 (d, 2H), 1.72 (d, 2H).

Example 141

Synthesis of 3-fluoro-2-(5-oxo-4-(3-(5-oxo-1,4-diazepan-1-yl)-1H-pyrazol-1-yl)-6,7-dihydro-5H-pyrrolo[3,4-b]pyridin-2-yl)benzonitrile, I-141

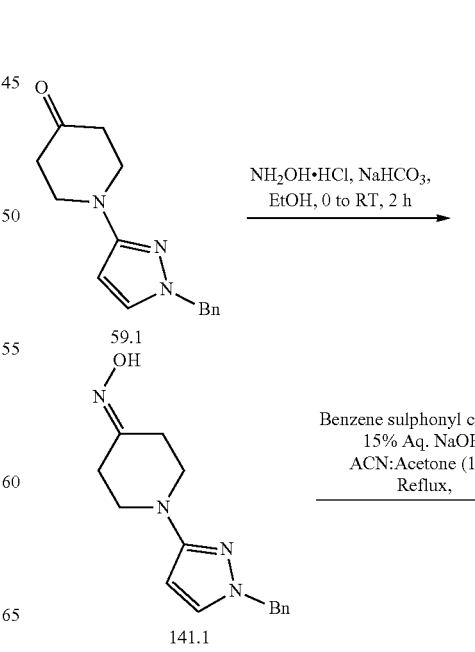

Synthesis of compound 140.1. To a solution of 1.1 (5.0 g, 28.9 mmol, 1.0 eq) and $ZnCl_2$ (0.393 g, 2.8 mmol, 0.1 eq) in water (10.0 mL) was added acrylonitrile (2.29 g, 43.3 mmol, 1.5 eq) at 0° C. The reaction was stirred at 110° C. for 18 h. Upon completion of reaction; reaction mixture was poured into water, then extracted with EtOAc. Organic layers were combined, washed with brine, dried over $Na_2SO_4$ and concentrated under reduced pressure to pressure to obtain crude material. The crude was purified by column chromatography to furnish 140.1 (1.6 g, 24.4%). MS(ES): m/z 228 [M+H]$^+$.

Synthesis of compound 140.2. To a solution of 140.1 (1.6 g, 7.04 mmol, 1.0 eq) in acetone (12 mL). NaI (0.211 g, 1.40 mmol, 0.2 eq) and $K_2CO_3$ (1.9 g, 13.7 mmol, 2.0 eq) were added into at 0° C. Ethyl bromoacetate (1.7 g, 10.57 mmol,

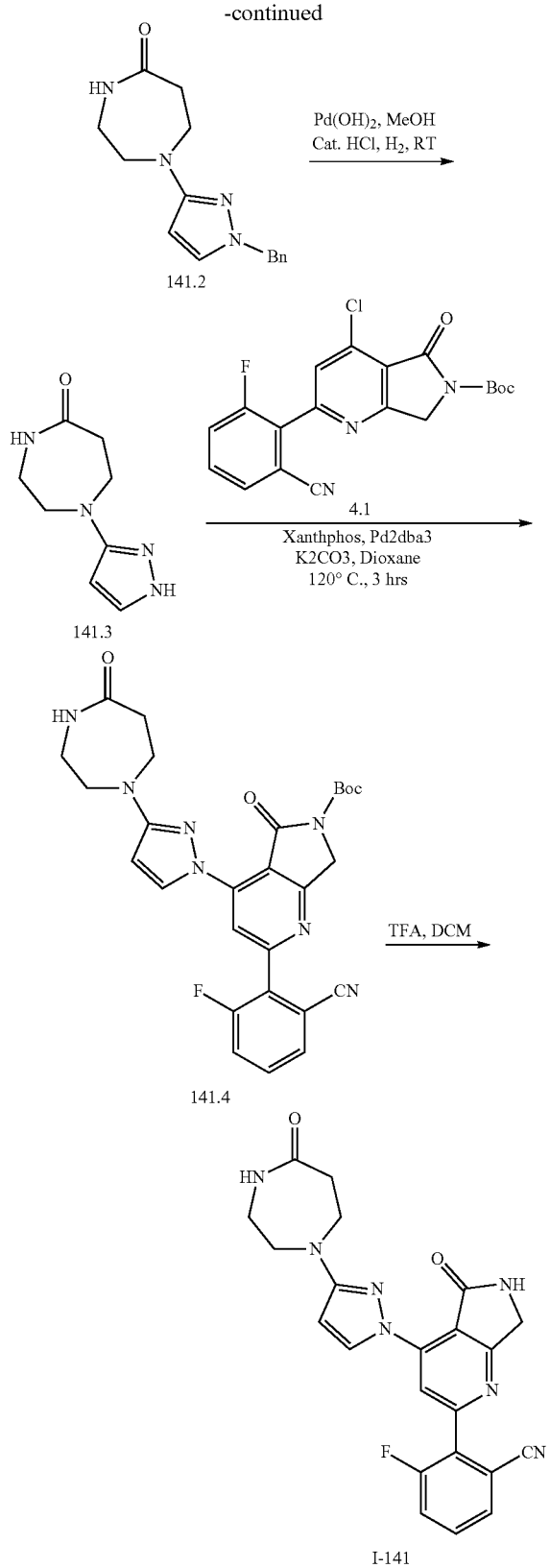

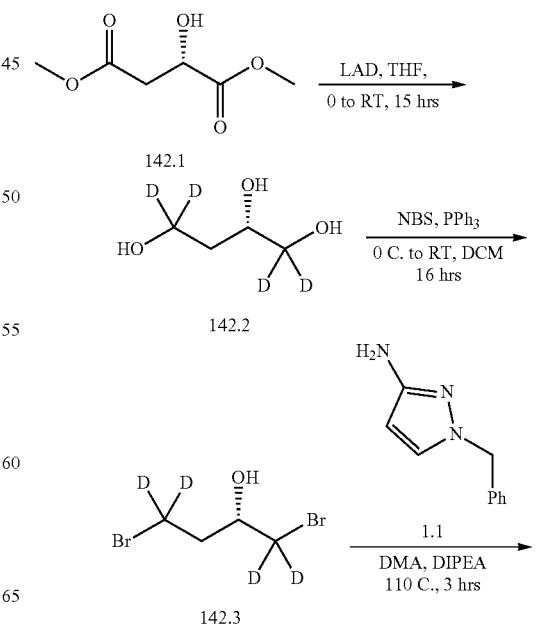

Synthesis of compound 141.1. Solution of 59.1 (1.0 g, 3.9 mmol, 1.0 eq.) was added drop wise in to a stirring solution of Hydroxylamine hydrochloride (0.272 g, 3.9 mmol, 1.0 eq.) and Sodium bicarbonate (0.990 g, 10.7 mmol, 2.75 eq.) in EtOH (10 mL) at 0° C. The reaction mixture was stirred at room temperature for 2 h. Upon completion of reaction, mixture was transferred into water and product was extracted with EtOAc. Organic layers were combined, washed with brine solution, dried over $Na_2SO_4$ and concentrated under reduced pressure to obtain crude which was purified by column chromatography to provide 141.1 (0.6 g, 25.27%). MS(ES): m/z 271.19 $[M+H]^+$, Synthesis of compound 141.2. To a solution 141.1 (0.5 g, 1.85 mmol, 1.0 eq.) in acetone (15 mL) was added $Na_2CO_3$ (0.589 g, 5.55 mmol, 1.0 eq.) and p-TsCl (0.530 g, 2.77 mmol, 1.5 eq.) at room temperature. The reaction mixture was stirred at room temperature for 3 h. Upon completion of reaction, mixture was transferred into water and product was extracted with EtOAc. Organic layers were combined, washed with brine solution, dried over sodium sulphate and concentrated under reduced pressure to obtain crude material. The crude was purified by column chromatography to provide 141.2 (0.220 g, 44.12%). MS(ES): m/z 271.19 $[M+H]^+$ Synthesis of compound 141.3. To a solution of 141.2 (0.22 g, 0.85 mmol, 1.0 eq) in MeOH (5 mL) was added palladium hydroxide (0.05 g), dil. HCl (catalyst) in 20 mL autoclave. The hydrogen was purged to 50 psi. The mixture was stirred at room temperature overnight. Upon completion of reaction was filtered and concentrated to provide 141.3 (0.12 g, 78.2%). LCMS(ES): m/z 153.3 $[M+H]^+$.

Synthesis of compound 141.4. Compound was synthesized using the procedure in Example 64.

Synthesis of compound I-141. Compound was synthesized using the procedure in Example 64. (0.04 g, 61.60%). MS(ES): m/z 440 $[M+H]^-$; $^1H$ NMR (DMSO-$d_6$, 400 MHz): 9.77-9.76 (d, 1H), 9.15 (s, 1H), 8.17 (s, 1H), 7.92-7.90 (m, 1H), 7.83-7.75 (m, 2H), 7.64 (t, 1H), 6.38 (d, 1H), 4.49 (s, 2H), 3.58-3.52 (m, 4H), 3.21-3.20 (m, 2H), 2.50-2.49 (m, 2H).

Example 142

Synthesis of (S)-3-fluoro-2-(4-(3-(3-hydroxypyrrolidin-1-yl-2,2,5,5-d4)-1H-pyrazol-1-yl)-5-oxo-6,7-dihydro-5H-pyrrolo[3,4-b]pyridin-2-yl)benzonitrile I-142

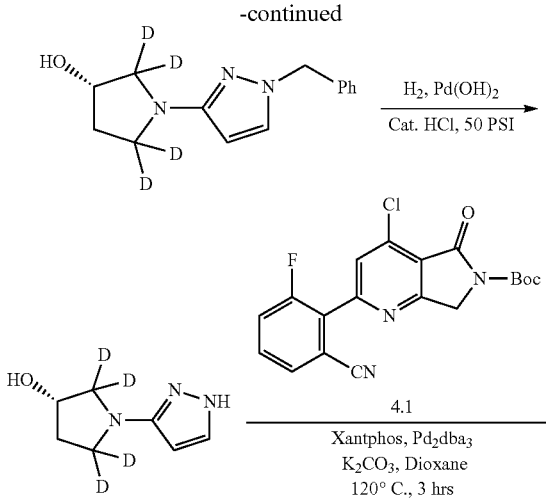

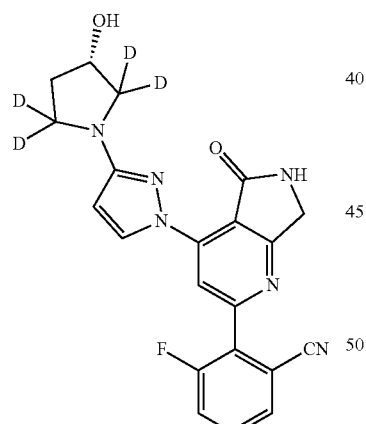

141.6

TFA, DCM

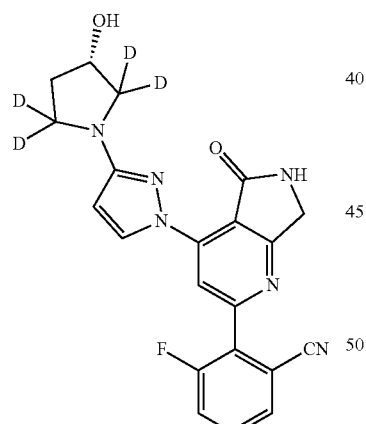

I-142

Synthesis of compound 142.2. To a solution of 142.1 (1.0 g, 6.16 mmol, 1.0 eq) in THF (5.0 mL) was added Lithium Aluminum Deuteride (0.906 g, 21.5 mmol, 3.5 eq) at 0° C. and the reaction was stirred at room temperature for 15 h. Upon completion of reaction, reaction mixture was transferred into water, and extracted with EtOAc. Organic layers were combined, washed with brine, dried over $Na_2SO_4$ and concentrated under reduced pressure to pressure to obtain crude which was purified by column chromatography to provide 142.2 (0.617 g, 90.9%). $^1$H NMR (CDCl$_3$, 400 MHZ): 3.50 (t, 1H), 1.60 (d, 2H).

Synthesis of compound 142.3. To a solution of 142.2. (0.610 g, 5.53 mmol, 1.0 eq) in DCM (15.0 mL) was added PPh$_3$ (2.88 g, 11.0 mmol, 2.0 eq) 0° C. followed by NBS (1.97 g, 11.0 mmol, 2.0 eq). The reaction was stirred at room temperature for 15 h. Upon completion of reaction, reaction mixture was transferred into water, and extracted with EtOAc. Organic layers were combined, washed with brine, dried over $Na_2SO_4$ and concentrated under reduced pressure to pressure to obtain crude which was purified by column chromatography to furnish 142.3 (0.35 g, 26.9%). $^1$H NMR (CDCl$_3$, 400 MHZ): 3.90 (t, 1H), 1.90 (d, 2H).

Synthesis of compound 142.4. To a solution of 142.3 (0.125 g, 0.52 mmol, 1.0 eq) in DMA (3.0 mL) was added 1.1 (0.91 g, 0.52 mmol, 1.0 eq) and DIPEA (0.170 g, 1.32 mmol, 2.5 eq). Reaction mixture was stirred at 110° C. for 3 h in Microwave. Upon completion of the reaction; reaction mixture was transferred into water, then extracted with EtOAc. Organic layers were combined, washed with brine, dried over $Na_2SO_4$ and concentrated under reduced pressure to pressure to obtain crude which was purified by column chromatography to furnish 142.4 (0.065 g, 66.3%). MS(ES): m/z 248 [M+H]$^+$.

Synthesis of compound 142.5. To a solution of 142.4 (0.065 g, 0.26 mmol, 1.0 eq) in MeOH (2 mL) was added 20% Pd(OH)$_2$ (0.030 g) and 1N HCl (catalytic amount). Reaction mixture was stirred (under hydrogen) at 50 psi for 15 h. Upon completion of the reaction, reaction mixture was filtered through celite bed and washed with methanol. Filtrate was concentrated under reduced pressure to obtain crude which was purified by column chromatography to furnish 142.5 (0.035 g, 85.36%). MS(ES): m/z 158 [M+H]$^+$.

Synthesis of compound 142.6. Compound was prepared from 142.5 and 4.1 using the procedure described in Example 64.

Synthesis of compound I-142. MS(ES): m/z 409 [M+H]$^+$; $^1$H NMR (DMSO-d$_6$, 400 MHZ): 9.79 (d, 1H), 9.08 (s, 1H), 8.17 (d, 1H), 7.92-7.89 (m, 1H), 7.83-7.73 (m, 2H), 6.14 (s, 1H), 4.92 (d, 1H), 4.48 (s, 2H), 4.36-4.33 (m, 1H), 2.07-1.96 (m, 1H), 1.85-1.81 (m, 1H).

Example 143

Synthesis of 3-fluoro-2-(4-(3-((3R,4S)-3-hydroxy-4-methoxypyrrolidin-1-yl)-1H-pyrazol-1-yl)-5-oxo-6,7-dihydro-5H-pyrrolo[3,4-b]pyridin-2-yl)benzonitrile, I-143

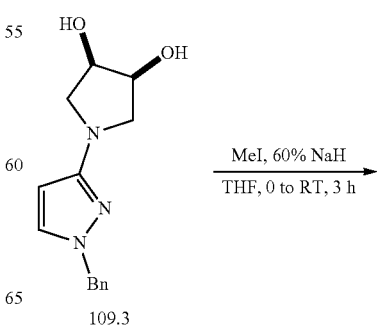

109.3

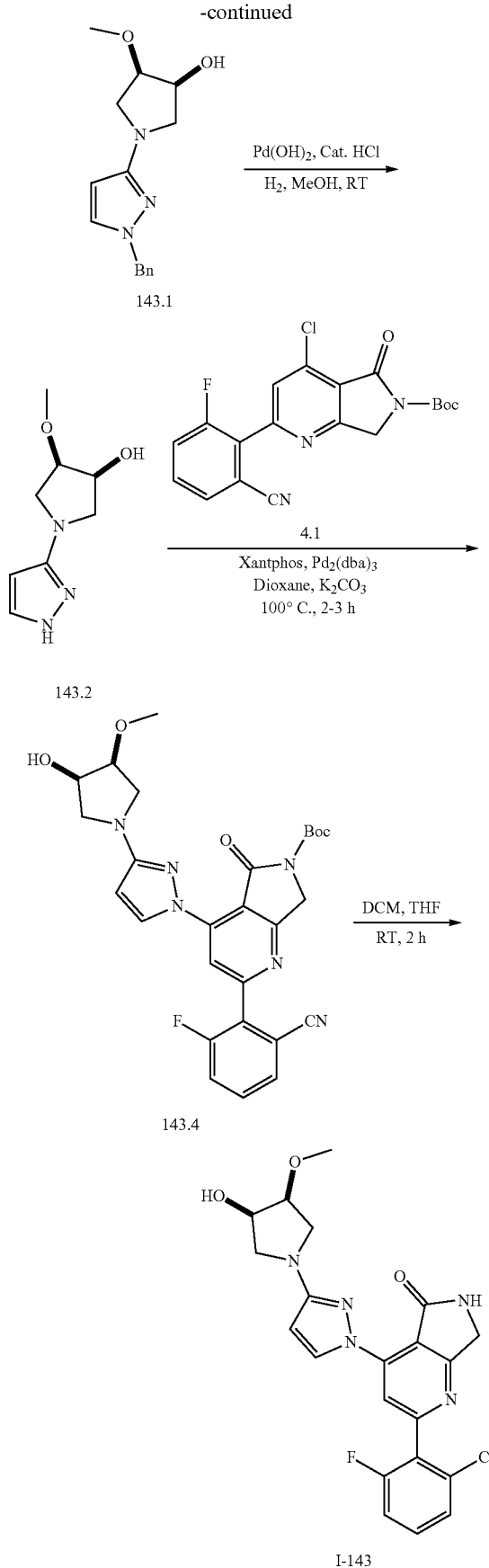

Synthesis of compound 143.1. To a solution of 109.3 (1.0 g, 3.8 mmol, 1.0 eq) in THF (10 mL) was added NaH (0.15 g, 3.8 mmol, 1 eq) at 0° C. and reaction mixture was stirred at room temperature for 1 h. Reaction mixture was cooled to 0° C. and MeI (0.43 g, 3.0 mmol, 0.8 eq) was added dropwise, stirred at room temperature for 3 h. Upon completion of the reaction, mixture was poured into ice. Resulting mixture was extracted with EtOAc. Organic layers were combined, washed with brine solution, dried over $Na_2SO_4$ and concentrated under reduced pressure. The crude was purified by column chromatography to furnish 109.3 (0.25 g, 95.0%). MS(ES): m/z 274 [M+H]+.

Synthesis of compound 143.2. To a solution of 109.3 (0.25 g, 0.91 mmol, 1.0 eq) in MeOH (10.0 mL), 20% Pd(OH)$_2$ on charcoal (0.2 g) and 1N HCl (catalytic) were added. Reaction mixture was stirred (under hydrogen) at 40 psi for 15 h. Upon completion of the reaction, mixture was filtered through celite-bed, washed with MeOH and concentrated under reduced pressure to obtain crude. The crude was further purified by column chromatography to provide 143.2. (0.06 g, 92.0%). MS(ES): m/z 184 [M+H]+.

Synthesis of compound 143.4. Compound 143.4 was prepared using the procedure described in Example 64.

Synthesis of compound I-143. Compound I-143 was prepared from compound 143.4 using the procedure in Example 64. MS(ES): m/z 435 [M+H]+; $^1$H NMR (DMSO-d$_6$, 400 MHz): 9.70 (d, 1H), 8.27 (s, 1H), 7.77 (d, 1H), 7.64-7.74 (m, 2H), 6.06 (s, 1H), 4.53 (s, 2H), 4.40-4.44 (m, 1H), 3.95-3.99 (m, 1H), 3.61-3.67 (m, 2H), 3.33-3.48 (m, 5H).

Example 144

Synthesis of 2-(4-(3-((3S,5R)-3,5-dihydroxy-3,5-dimethylpiperidin-1-yl)-1H-pyrazol-1-yl)-5-oxo-6,7-dihydro-5H-pyrrolo[3,4-b]pyridin-2-yl)-3-fluorobenzonitrile, I-144

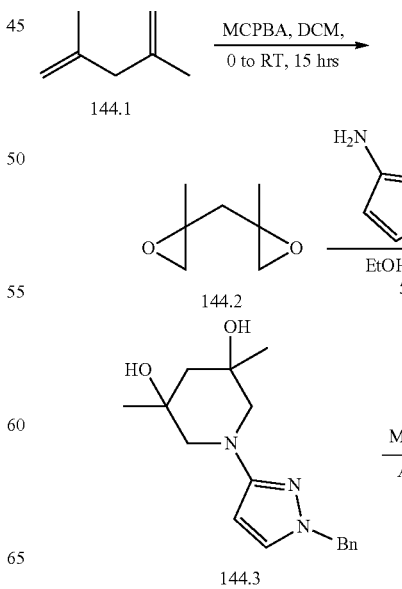

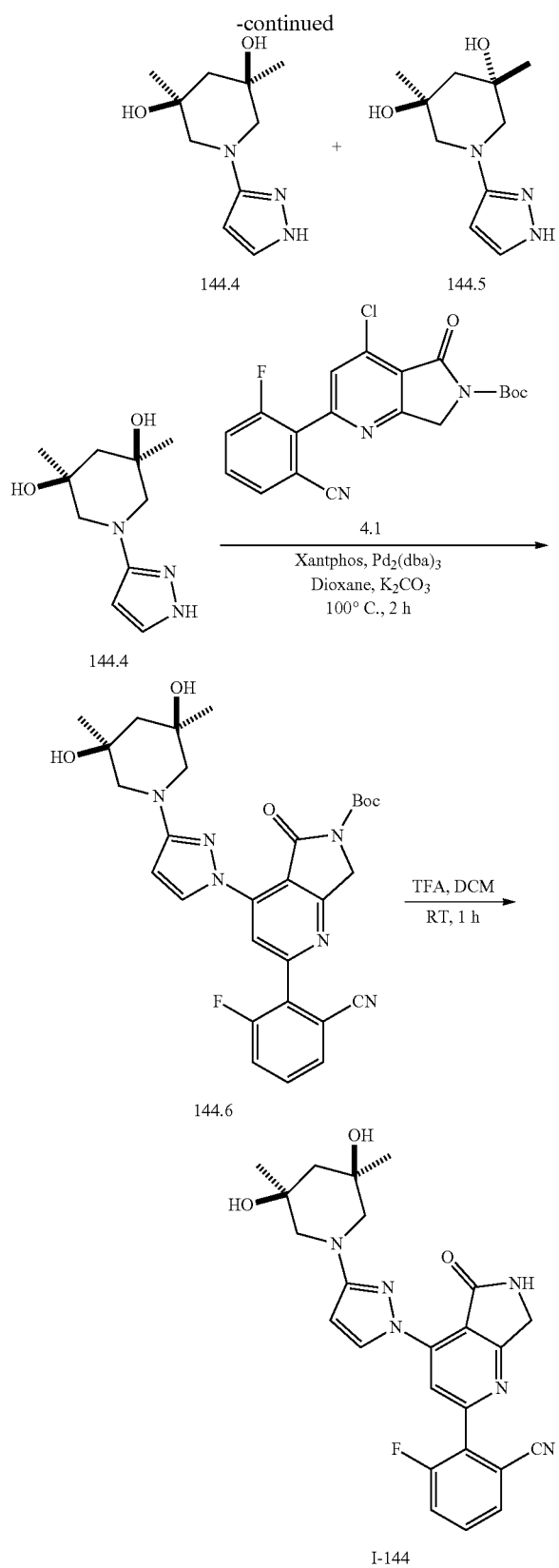

portionwise. Reaction mixture stirred at room temperature for 15 h. Upon completion of the reaction; reaction mixture was transferred into water and extracted with DCM, washed with 5.0 N NaOH, dried over $Na_2SO_4$ and concentrated under reduced pressure to obtain crude 144.2 (1.1 g, 82.5%). MS(ES): m/z 129.2 $[M+H]^+$. Crude material was used for next step without purification.

Synthesis of compound 144.3. To a solution of 144.2 (1.0 g, 7.8 mmol, 1.0 eq) in EtOH (10.0 mL) was added 1.1 (0.69 g, 3.9 mmol, 0.5 eq). Reaction was stirred at 50° C. for 5 h. Upon completion of the reaction solvents were removed under reduced pressure to furnish crude that was purified by reverse phase chromatography to yield 144.3. (0.13 g, 5.53%). MS(ES): m/z 302.5 $[M+H]^-$.

Synthesis of compounds 144.4 and 144.5. To a solution of 144.3 (0.13 g, 0.43 mmol, 1.0 eq) in MeOH (2.0 mL), were added $Pd(OH)_2/C$ (0.05 g) and 1N HCl (catalytic amount). Reaction mixture was stirred under hydrogen pressure at 40 psi for 12 h. Upon completion of the reaction, mixture was filtered and concentrated under reduced pressure to obtain crude material. This is further purified by column chromatography to provide 144.4 (0.020 g), MS (ES): m/z 212.4 $[M+H]^+$, and 144.5 (0.035 g), MS (ES): m/z 212.3$[M+H]^+$ Synthesis of compound 144.6. Compound was prepared from compounds 144.4 and 4.1 using the procedure described in Example 64.

Synthesis of compound I-144. Compound was prepared from compound 144.6 using the procedure described in Example 64. MS(ES): m/z 463.43 $[M+H]^+$; $^1H$ NMR (MeOD, 400 MHz): 9.73-9.72 (d, 1H), 8.27 (s, 1H), 7.81-7.80 (m, 1H), 7.73-7.67 (m, 2H), 6.12-6.11 (d, 1H), 4.63 (s, 1H), 4.56 (s, 2H), 4.42 (m, 1H), 3.53-3.33 (m, 2H), 3.18-3.15 (m, 1H), 2.28-2.15 (m, 1H), 2.09-2.06 (m, 1H), 1.47 (s, 3H), 1.21 (s, 3H).

Example 145

Synthesis of 2-(4-(3-((3S,5S)-3,5-dihydroxy-3,5-dimethylpiperidin-1-yl)-1H-pyrazol-1-yl)-5-oxo-6,7-dihydro-5H-pyrrolo[3,4-b]pyridin-2-yl)-3-fluorobenzonitrile, I-145

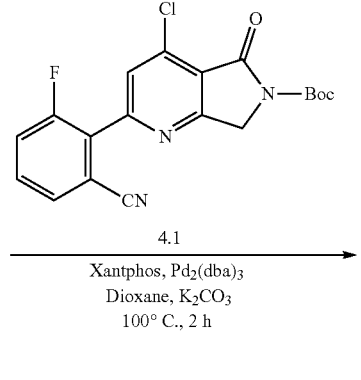

Synthesis of compound 144.2. To a solution of 144.1 (1 g, 10.18 mmol, 1.0 eq) in DCM (10.0 ml) was added m-chloroperbenzoic acid (3.51 g, 20.36 mmol, 2.0 eq) at 0° C.

307
-continued
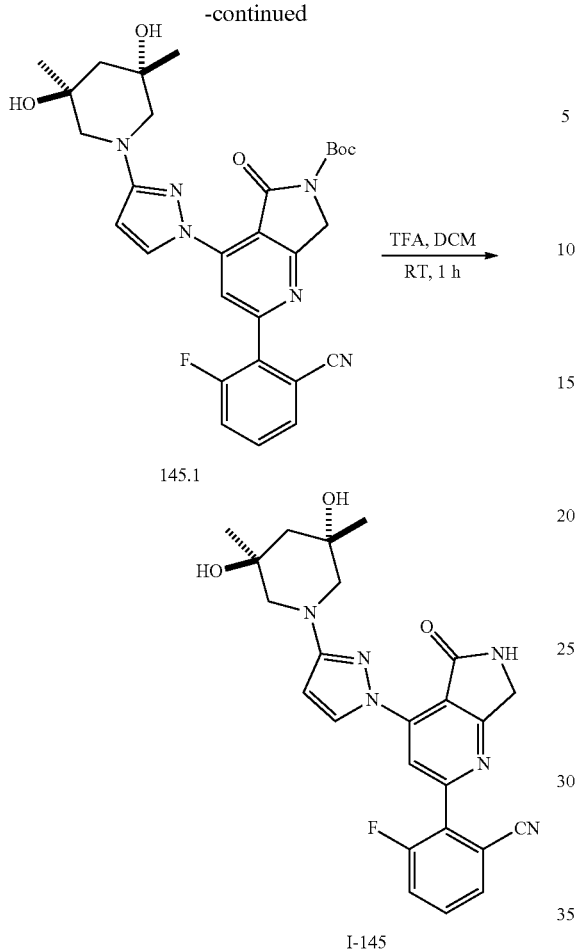
145.1
I-145
Compound I-145 was prepared from compounds 144.5 and 4.1 using the procedure described in Example 64. MS(ES): m/z 463.38 [M+H]−; $^1$H NMR (MeOD, 400 MHz): 9.72-9.71 (d, 1H), 8.23-8.22 (d, 1H), 7.81-7.79 (m, 1H), 7.73-7.64 (m, 3H), 6.10-6.09 (d, 1H), 4.55 (s, 2H), 4.18-4.15 (m, 1H), 3.55-3.49 (m, 2H), 2.34-2.31 (m, 2H), 1.57 (s, 3H), 1.39 (s, 3H).
Example 146
Synthesis of 3-fluoro-2-(5-oxo-4-(3-(6-oxo-2,7-diazaspiro[4.4]nonan-2-yl)-1H-pyrazol-1-yl)-6,7-dihydro-5H-pyrrolo[3,4-b]pyridin-2-yl)benzonitrile I-146
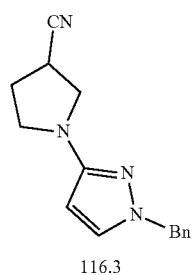
116.3
308
-continued
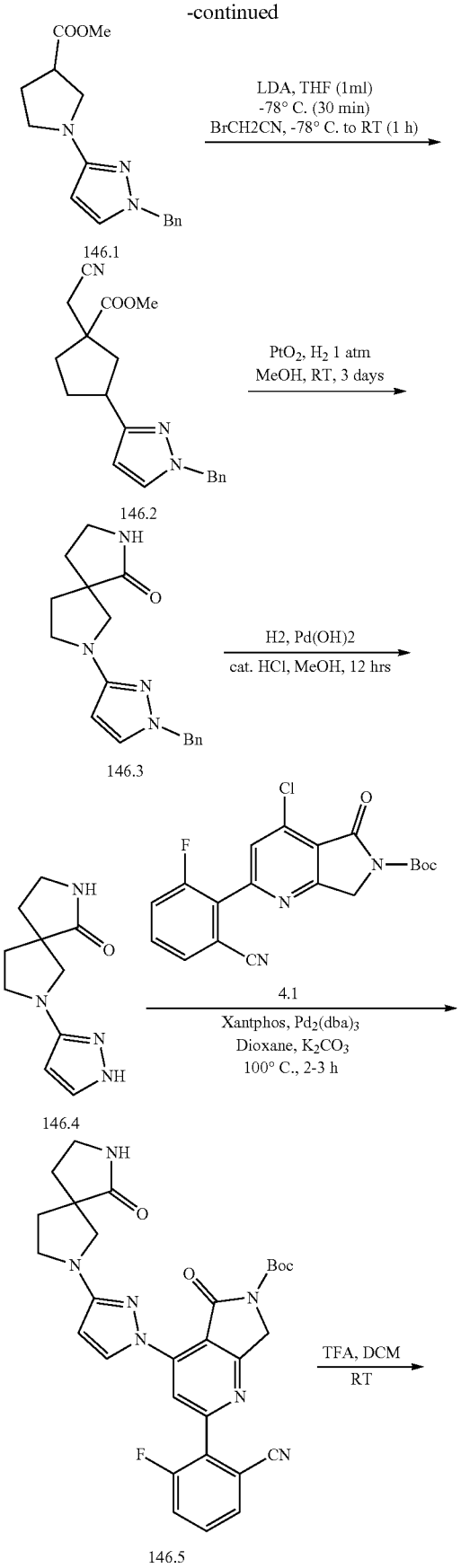

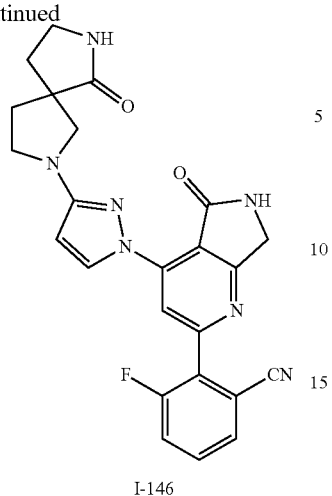

I-146

Synthesis of compound 146.1. To a solution of 116.3 (1.3 g, 5.10 mmol, 1.0 eq) in MeOH (24 mL) was added 4.0 M HCl in dioxane (13 ml) at 0° C. under nitrogen, and mixture was stirred at room temperature for 18 h. Upon completion of reaction, mixture was transferred into ice. Resulting mixture was extracted with EtOAc. Organic layers were combined, washed with brine solution, dried over sodium sulphate and concentrated under reduced pressure to get 146.1 (1.0 g, 68.02%). MS(ES): m/z 286 [M+H]$^+$.

Synthesis of compound 146.2. To a solution of 146.1 (1.0 g, 3.50 mmol, 1.0 eq) in THF (7 mL) was added LDA (2M) (2.8 ml, 4.80 mmol, 1.6 eq) at −78° C. under nitrogen. Reaction mixture stirred at −78° C. for 1 h. Bromoacetonitrile (0.5 g, 4.20 mmol, 1.2 eq) was added at −78° C. and reaction mixture was stirred at room temperature for 1 h. Upon completion of the reaction, reaction mixture was transferred into ice. Resulting mixture was extracted with EtOAc. Organic layers were combined, washed with brine, dried over sodium sulphate and concentrated under reduced pressure. The crude was purified by column chromatography to get pure 146.2 (0.7 g, 61.94%). MS(ES): m/z 325 [M+H]$^+$.

Synthesis of compound 146.3. To a mixture of 146.2 (0.7 g, 2.16 mmol, 1.0 eq) in MeOH (15 mL) was added PtO$_2$ (0.245 g, 1.08 mmol, 0.5 eq) at 0° C. Reaction mixture was stirred under hydrogen for 72 h. Upon completion of reaction, reaction mixture was filtered through celite-bed and washed with methanol. Filtrate was concentrated under reduced pressure to obtain crude which was purified by column chromatography to provide 146.3 (0.4 g, 62.5%). MS(ES): m/z 297 [M+H]$^+$.

Synthesis of compound 146.4. To a solution of 146.3 (0.4 g, 1.35 mmol, 1.0 eq) in MeOH (5 ml) 20% palladium hydroxide on charcoal (0.340 g) and 1N HCl (catalytic amount) was added into reaction. Reaction mixture was stirred (under hydrogen) at 30 psi for 12 h. Upon completion of the reaction, reaction mixture was filtered through celite-bed and washed with methanol. Filtrate was concentrated under reduced pressure to obtain crude material. The crude was purified by column chromatography to provide 146.4. (0.280 g, 71.94%). MS(ES): m/z 207 [M+H]$^+$.

Synthesis of compound 146.5. Compound was prepared using the procedure described in Example 64.

Synthesis of compound I-146. Compound was prepared using the procedure described in Example 64 (0.08 g, 76.9%). MS(ES): m/z 458 [M+H]$^+$; $^1$H NMR (DMSO-d$_6$, 400 MHz): 9.79 (d, 1H), 9.11 (s, 1H), 8.17 (s, 1H), 7.92-7.90 (m, 1H), 7.83-7.75 (m, 3H), 6.17 (d, 1H), 4.49 (d, 2H), 3.56-3.49 (m, 1H), 3.45-3.35 (m, 4H), 3.30-3.20 (m, 2H), 2.12-2.04 (m, 2H), 1.92-1.86 (m, 1H).

Example 147

Synthesis of 3-fluoro-2-(4-(3-(3-(4-methylpiperazin-1-yl)piperidin-1-yl)-1H-pyrazol-1-yl)-5-oxo-6,7-dihydro-5H-pyrrolo[3,4-b]pyridin-2-yl)benzonitrile, I-147

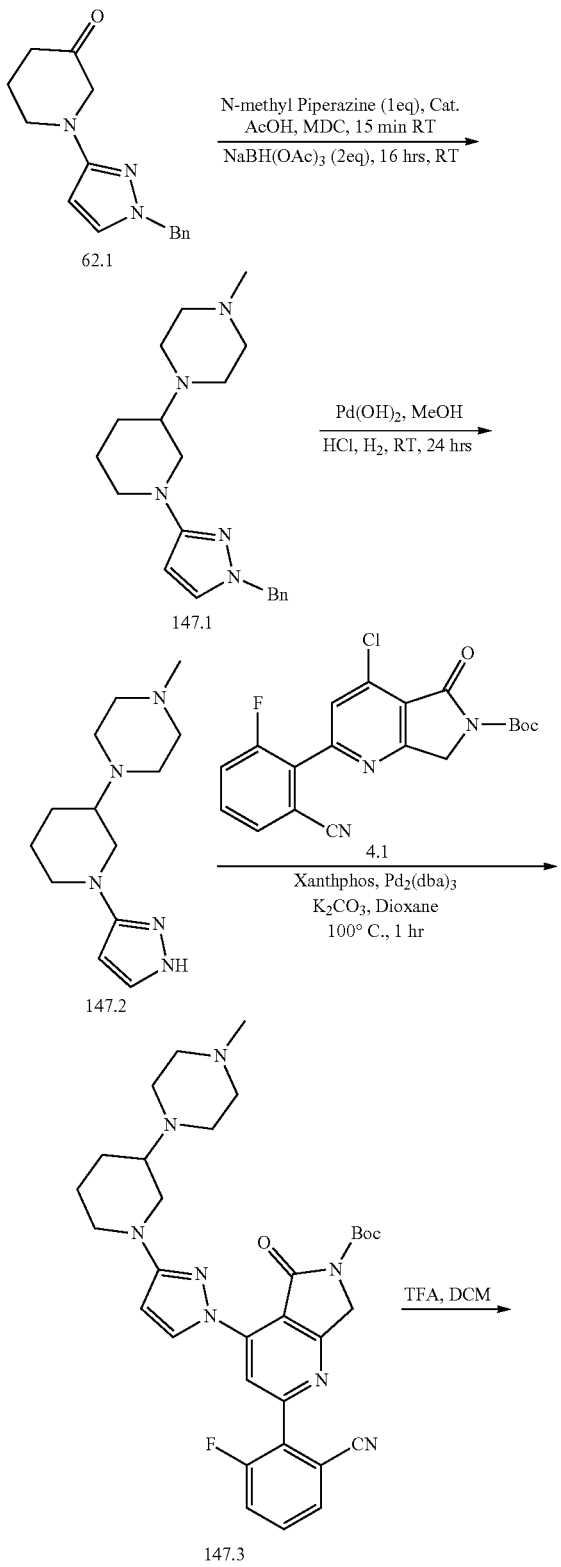

311
-continued

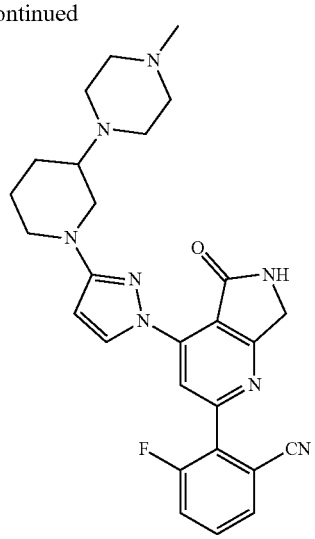

I-147

Synthesis of compound 147.1. To a solution of 62.1 (0.7 g, 2.7 mmol, 1.0 eq) in DCM (10 ml) was added N-methyl piperazine (0.3 g, 3.0 mmol, 1.1 eq), HOAc (0.016 g, 0.027 mmol, 0.1 eq). Mixture was stirred for 15 min followed by the addition of NaBH(OAC)$_3$ (1.1 g, 5.4 mmol, 2.0 eq) Reaction mixture was stirred at room temperature for 16 h. Upon completion of the reaction, reaction mixture was transferred into aqueous NaHCO$_2$ solution and extracted with DCM, dried over Na$_2$SO$_4$ and concentrated under reduced pressure to obtain crude which was purified by column chromatography to provide 147.1. (0.2 g, 21.5%). MS(ES): m/z 340.5 [M+H]$^+$.

Synthesis of compound 147.2. To a solution of 147.1 (0.2 g, 0.589 mmol, 1.0 eq) in MeOH (10.0 mL), 20% Pd (OH)$_2$/C (0.1 g) and 1N HCl (catalytic) was added. Reaction mixture was stirred (under hydrogen) at 40 psi for 24 h. Upon completion of the reaction, reaction mixture was filtered through celite and washed with methanol. Solution was concentrated under reduced pressure to obtain crude material. This is further purified by column chromatography to provide 147.2. (0.08 g, 54.5%). MS(ES): m/z 250.4 [M+H]$^+$.

Synthesis of compound 147.3. Compound 147.3 was prepared from compounds 147.2 and 4.1 using the procedure described in Example 64.

Synthesis of compound I-147. Compound I-147 was prepared from compound 147.3 using the procedure described in Example 64. MS(ES): m/z 501.48 [M+H]$^+$; $^1$H NMR (DMSO-d$_6$, 400 MHz): 9.74-9.73 (d, 1H), 9.11 (s, 1H), 8.11 (s, 1H), 7.92-7.90 (m, 1H), 7.77-7.73 (m, 2H), 7.39-7.36 (m, 1H), 6.39 (d, 1H), 4.49 (s, 2H), 3.91-3.88 (m, 1H), 3.78-3.75 (m, 1H), 2.76-2.67 (m, 2H), 2.57 (bs, 4H), 2.40 (bs, 4H), 2.20 (s, 3H), 1.90-1.88 (m, 1H), 1.72-1.65 (m, 1H), 1.53-1.49 (m, 1H), 1.32-1.25 (m, 1H).

312

Example 148

Synthesis of (S)-3-fluoro-2-(4-(3-(3-hydroxy-2-oxopyrrolidin-1-yl)-1H-pyrazol-1-yl)-5-oxo-6,7-dihydro-5H-pyrrolo[3,4-b]pyridin-2-yl)benzonitrile, I-148

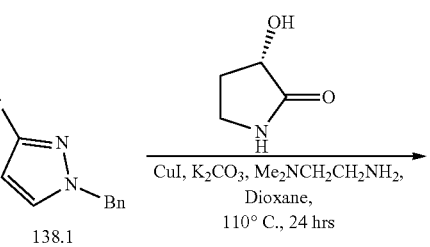

138.1

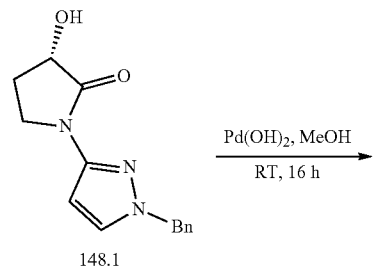

148.1

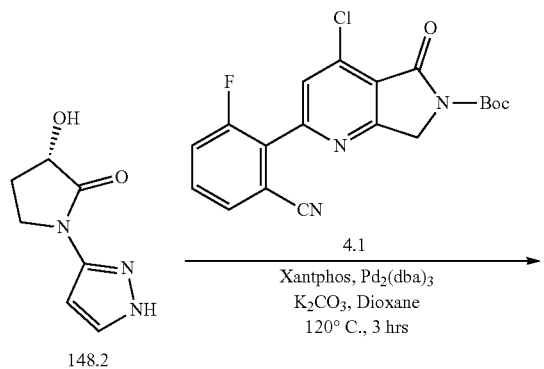

148.2

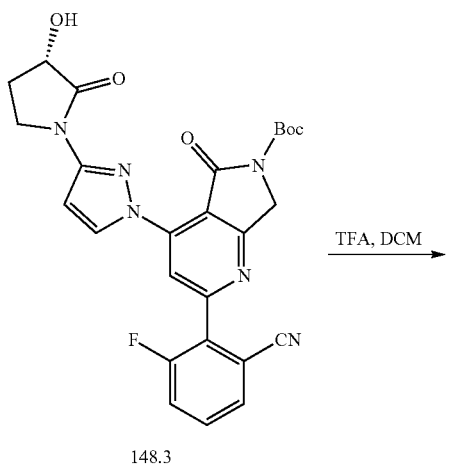

148.3

-continued

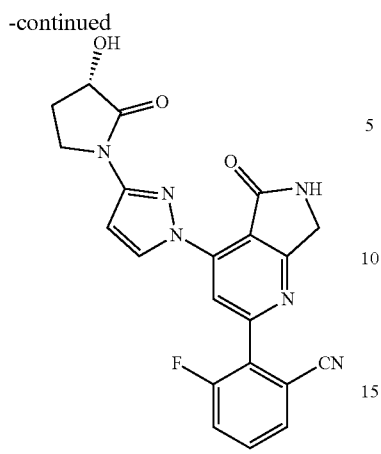

I-148

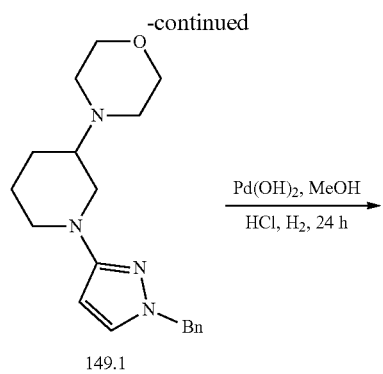

149.1

Synthesis of compound 148.1. To a solution of 138.1 (0.5 g, 1.75 mmol, 1.0 eq) in Dioxane (5.0 ml) was added (S)-3-Hydroxypyrrolidine (0.266 g, 2.63 mmol, 1.5 eq), CuI (0.016 g, 0.08 mmol, 0.05 eq), $K_2CO_3$ (0.728 g, 5.27 mmol, 3.0 eq) and trans-N,N'-Dimethylcyclohexane-1,2-diamine (0.012 g, 0.81 mmol, 0.05 eq) at room temperature and reaction mixture was stirred at 110° C. for 24 h. Upon completion of the reaction, mixture was poured into water and product was extracted with EtOAc. Organic layers were combined, washed with brine, dried over $Na_2SO_4$ and concentrated under reduced pressure to obtain crude which was purified by column chromatography to provide 148.1 (0.34 g, 75.55%). MS(ES): m/z 258 [M+H]$^+$.

Synthesis of compound 148.2. Compound was prepared from compound 148.1 using the procedure described in Example 138.

Synthesis of compound 148.3. Compound was prepared from compounds 148.2 and 4.1 using the procedure described in Example 64.

Synthesis of compound I-148. Compound was prepared from 148.3 using the procedure described in Example 64. MS(ES): m/z 419 [M+H]$^+$; $^1$H NMR (DMSO-$d_6$, 400 MHz): 9.76 (d, 1H), 8.37 (s, 1H), 7.81-7.79 (m, 1H), 7.73-7.66 (m, 2H), 7.16 (s, 1H), 4.60 (s, 2H), 4.53-4.47 (m, 2H), 4.13-4.08 (m, 2H), 3.84-3.78 (m, 1H), Example 149

Synthesis of 3-fluoro-2-(4-(3-(3-morpholinopiperidin-1-yl)-1H-pyrazol-1-yl)-5-oxo-6,7-dihydro-5H-pyrrolo[3,4-b]pyridin-2-yl)benzonitrile, I-149

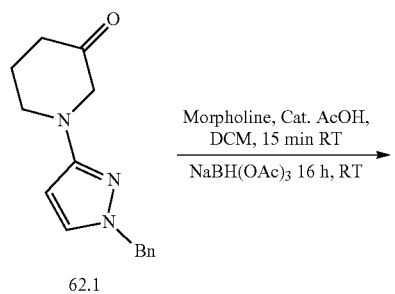

62.1

Morpholine, Cat. AcOH,
DCM, 15 min RT
―――――――――――→
NaBH(OAc)$_3$ 16 h, RT

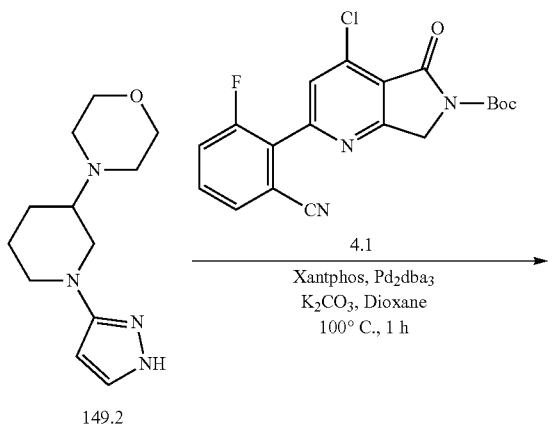

149.2

Xantphos, Pd$_2$dba$_3$
K$_2$CO$_3$, Dioxane
100° C., 1 h
―――――――――――→

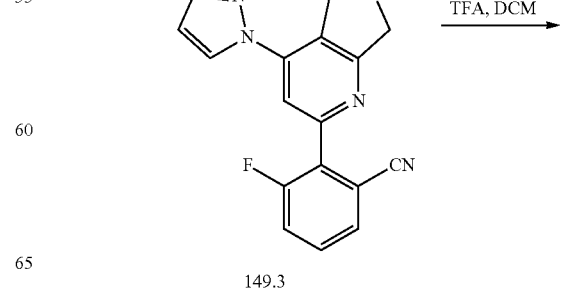

149.3

TFA, DCM
―――――――→

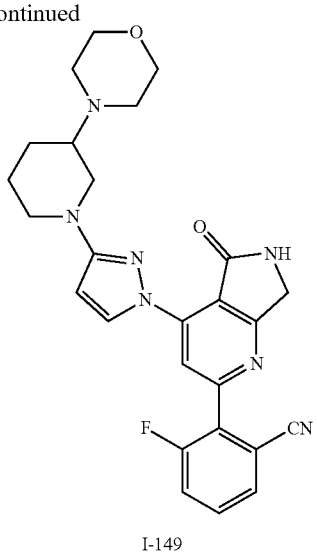

I-149

Synthesis of compound 149.1. To a solution of 62.1 (2.0 g, 7.8 mmol, 1.0 eq) in DCM (20.0 ml) was added morpholine (0.74 g, 8.6 mmol, 1.1 eq), HOAc (0.04 g, 0.078 mmol, 0.1 eq) and stirred for 15 min followed by addition of NaBH(OAc)$_3$ (3.3 g, 15.6 mmol, 2.0 eq) Reaction mixture was stirred at room temperature for 16 h. Upon completion of reaction, mixture was transferred into aq. NaHCO$_3$ solution and extracted with DCM, dried over Na$_2$SO$_4$ and concentrated under reduced pressure to obtain crude which was purified by column chromatography to furnish 149.1. (0.9 g, 35.2%). MS(ES): m/z 327.5 [M+H]$^+$.

Synthesis of compound 149.2. To a solution of 149.1 (0.9 g, 2.76 mmol, 1.0 eq) in MeOH (10 mL), 20% Pd(OH)$_2$/C (0.2 g) and 1N HCl (catalytic) were added. Reaction mixture was stirred (under hydrogen) at 40 psi for 24 h. Upon completion of the reaction, reaction mixture was filtered and concentrated under reduced pressure to obtain crude which was purified by column chromatography to get 149.2. (0.5 g, 76.74%). MS(ES): m/z 237.35 [M+H]$^+$.

Synthesis of compound 149.3. Compound was prepared from compounds 149.2 and 4.1 using the procedure described in Example 64.

Synthesis of compound I-149. Compounds was prepared from compound 149.3 using the procedure in Example 64. MS(ES): m/z 488.53 [M+H]$^+$; $^1$H NMR (DMSO-d$_6$, 400 MHz): 9.74-9.73 (d, 1H), 9.11 (s, 1H), 8.18 (s, 1H), 7.91 (m, 1H), 7.82-7.72 (m, 2H), 6.39 (d, 1H), 4.49 (s, 2H), 3.93-3.90 (m, 1H), 3.77-3.74 (m, 1H), 3.55 (s, 4H), 2.74-2.67 (m, 2H), 2.57 (bs, 4H), 2.36-2.32 (m, 1H), 1.92-1.82 (m, 1H), 1.52-1.34 (m, 3H).

Example 150

Synthesis of 3-fluoro-2-(4-(3-((2S,3R)-3-hydroxy-2-methylpyrrolidin-1-yl)-1H-pyrazol-1-yl)-5-oxo-6,7-dihydro-5H-pyrrolo[3,4-b]pyridin-2-yl)benzonitrile, I-150

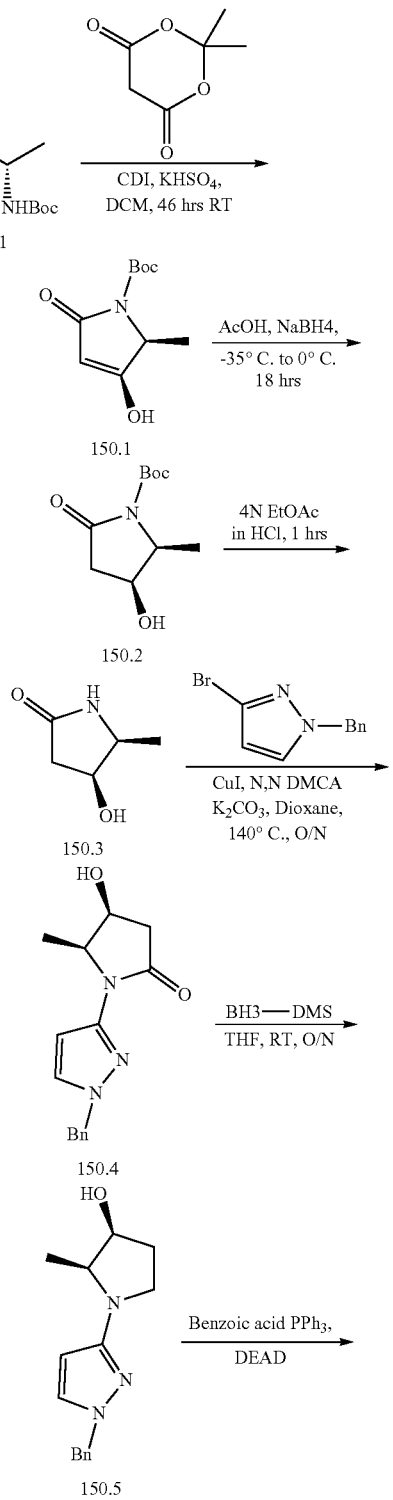

-continued

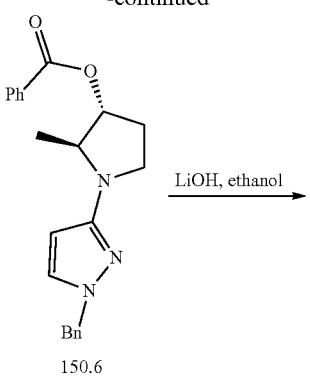
150.6

LiOH, ethanol →

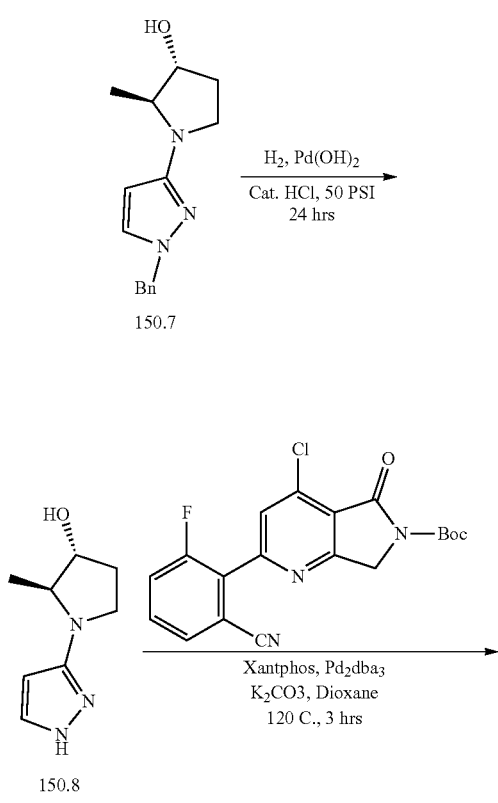

-continued

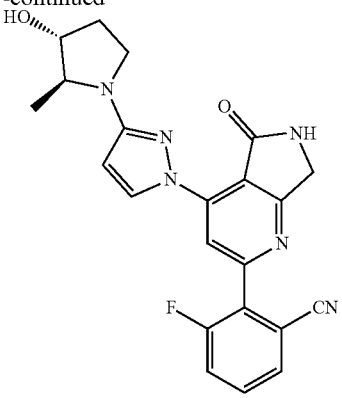
I-150

Synthesis of compound 150.1. To a solution of 150.1 (25.0 g, 132 mmol, 1.0 eq) in DCM (250 ml) was added 2,2-dimethyl-1,3-dioxane-4,6-dione (20 g, 138 mmol, 1.05 eq) and CDI (25.6 g, 0158 mmol, 1.2 eq) at 0° C. Reaction mixture was stirred at room temperature for 72 h. Upon completion of reaction, mixture was transferred into aqueous 5% KHSO$_4$ and extracted with DCM. Combined organic layers were washed with aq. NaHCO$_3$. Aqueous layer was acidified with citric acid and extracted with DCM, dried over Na$_2$SO$_4$ and concentrated under reduced pressure to obtain crude 150.1. (15.0 g, 53.24%). MS(ES): m/z 214.20 [M+H]$^+$.

Synthesis of compound 150.2. To a solution of 150.1 (15 g, 132.6 mmol, 1.0 eq) in DCM (150 ml) was added HOAc (6.8 g, 113.5 mmol, 8.6 eq) and NaBH$_4$ (0.35 g, 0.94 mmol, 0.07 eq) at 0° C. for 18 hrs. Upon completion of the reaction, mixture was transferred into water and extracted with DCM, dried over Na$_2$SO$_4$ and concentrated under reduced pressure to obtain crude 1.2. (7.5 g, 26.20%). MS(ES): m/z 216.5 [M+H]$^+$.

Synthesis of compound 150.3. To a solution of 150.2 (7.5 g, 132.6 mmol, 1.0 eq) in DCM (150.0 ml) was added 4N HCl solution in Dioxane (10 mL) at 0° C. and stirred at room temperature for 2 hours. Upon completion of reaction, mixture was concentrated under reduced pressure to obtain crude which was purified by column chromatography to furnish 150.3 (2.2 g, 54.84%). MS(ES): m/z 116.5 [M+H]$^+$.

Synthesis of compound 150.4. To a solution of 1-benzyl-3-bromo-1H-pyrazole (2.7 g, 0.84 mmol, 1.0 eq) in 1,4 Dioxane (20 ml) was added 150.3 (1.97 g, 11.39 mmol, 1.5 eq), CuI (0.216 g, 1.139 mmol, 0.1 eq), K$_2$CO$_3$ (3.14 g, 22.78 mmol, 2.0 eq) and trans-N,N'-Dimethylcyclohexane-1,2-diamine (0.197 g, 1.139 mmol, 0.1 eq) reaction mixture was stirred at 140° C. for 18 h. Upon completion of the reaction, mixture was transferred into water and product was extracted with EtOAc. Organic layers were combined, washed with brine, dried over Na$_2$SO$_4$ and concentrated under reduced pressure to obtain crude which was purified by column chromatography to provide 150.4 (0.36 g, 11.6%). MS(ES): m/z 272.32 [M+H]$^+$.

Synthesis of compound 150.5. To a solution of 150.4 (0.36 g, 1.32, 1.0 eq) in THF (5.0 ml) was added Borane dimethyl sulfide (0.5 g, 6.64, 5 eq) at 0° C. and stirred at room temperature for 2 h. Upon completion of the reaction, MeOH was added and concentrated under reduced pressure to obtain crude which was purified by column chromatography to provide 150.5. (0.30 g, 87.3%). MS(ES): m/z 258.3 [M+H]$^+$.

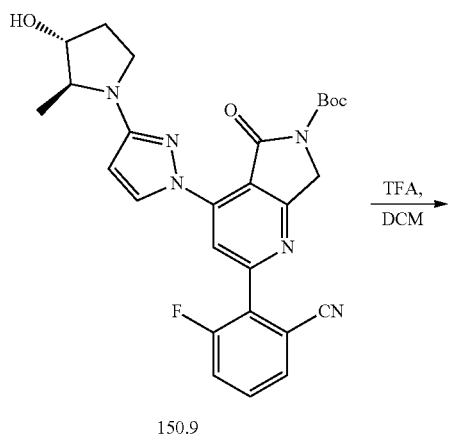
150.9

TFA, DCM →

Synthesis of compound 150.6. To a solution of 150.5 (0.3 g, 1.16 mmol, 1.0 eq) in THF (10 ml) were added benzoic acid (0.17 g, 1.4 mmol, 1.2 eq), PPh₃ (0.073 g, 1.4 mmol, 1.2 eq), and DEAD (0.22 g, 1.28 mmol, 1.1 eq) at room temperature. Reaction mixture was stirred at room temperature for 18 h. Upon completion of the reaction, mixture was transferred into water and product was extracted with EtOAc. Organic layers were combined, washed with brine solution, dried over Na₂SO₄ and concentrated under reduced pressure to obtain crude which was purified by column to provide 150.6 (0.21 g, 49.1%). MS(ES): m/z 362.12 [M+H]⁺.

Synthesis of compound 150.7. To a solution of 150.6 (0.21 g, 0.58 mmol, 1.0 eq) in MeOH:H₂O (8:2) (5 ml) was added LiOH (0.03 g, 0.69 mmol, 1.2 eq) at room temperature and reaction mixture was stirred at 50° C. for 2 h. Upon completion of the reaction, reaction mixture was concentrated under reduced pressure, water was added and product was extracted with EtOAc. Organic layers were combined, washed with brine solution, dried over Na₂SO₄ and concentrated under reduced pressure to obtain crude which was purified by column chromatography to provide 150.7 (0.14 g, 93.1%). MS(ES): m/z 258.32 [M+H]⁺.

Synthesis of compound 150.8. To a solution of 150.7 (0.14 g, 0.54 mmol, 1.0 eq) in MeOH (10 mL), 20% Pd(OH)₂/C (0.06 g) and 1.0 N HCl (catalytic) was added. Reaction mixture was stirred (under H₂) at 40 psi for 24 h. Upon completion of the reaction, mixture was filtered through celite, washed with MeOH and concentrated under reduced pressure to obtain crude which was purified by column chromatography to provide 150.8. (0.065 g, 71.5%). MS(ES): m/z 168.21 [M+H]⁺.

Synthesis of compound 150.9. Compound was prepared from compounds 150.8 and 4.1 using the procedure described in example 60.4. (0.08 g, 46.0%). MS(ES): m/z 519.5 [M+H]⁺.

Synthesis of compound I-150. Compound was prepared from 150.9 using procedure described in Example 64. (MS(ES): m/z 419.3 [M+H]⁺; ¹H NMR (DMSO-d₆, 400 MHz): 9.75-9.74 (d, 1H), 9.09 (s, 1H), 8.17 (s, 1H), 7.91 (m, 1H), 7.82-7.72 (m, 2H), 6.14 (d, 1H), 4.92 (d, 1H), 4.48 (s, 2H), 3.93-3.90 (m, 1H), 3.64-3.59 (m, 1H), 3.46-3.33 (m, 2H), 2.11-2.06 (m, 1H), 1.81-1.76 (m, 1H), 1.34 (d, 3H).

Example 151

Synthesis of 3-fluoro-2-(4-(3-isopropyl-1H-pyrazol-1-yl)-5-oxo-6,7-dihydro-5H-pyrrolo[3,4-b]pyridin-2-yl)benzonitrile, I-151

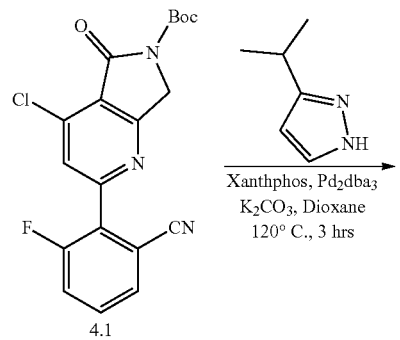

4.1

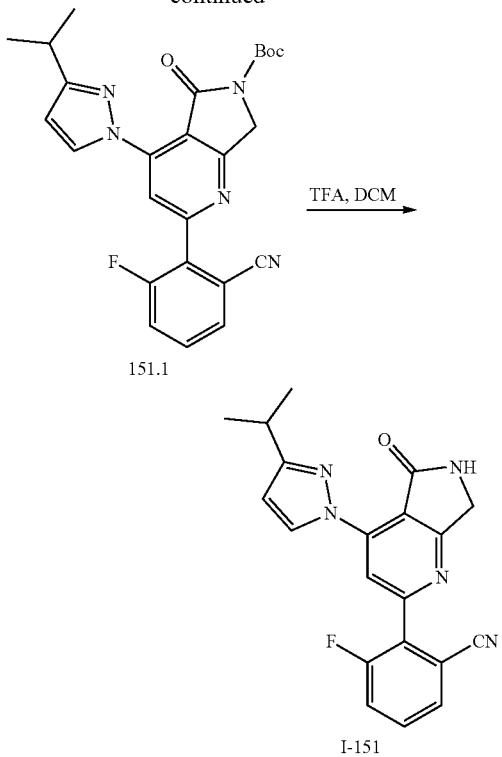

151.1

I-151

Compound I-151 was prepared from 4.1 and 3-isopropyl-1H-pyrazole using the procedures described in Example 64. (0.025 g, 54.3%). MS(ES): m/z 362[M+H]⁺; ¹H NMR (DMSO-d₆, 400 MHz): 9.63 (d, 1H), 9.21 (s, 1H), 8.28 (s, 1H), 7.98-7.96 (m, 1H), 7.84-7.74 (m, 2H), 5.27 (s, 1H), 4.54 (m, 2H), 3.05-2.98 (m, 1H), 1.31-1.16 (m, 6H).

Example 152

Synthesis of 3-fluoro-2-(5-oxo-4-(3-(3-(pyrrolidine-1-carbonyl)piperidin-1-yl)-1H-pyrazol-1-yl)-6,7-dihydro-5H-pyrrolo[3,4-b]pyridin-2-yl)benzonitrile, I-152

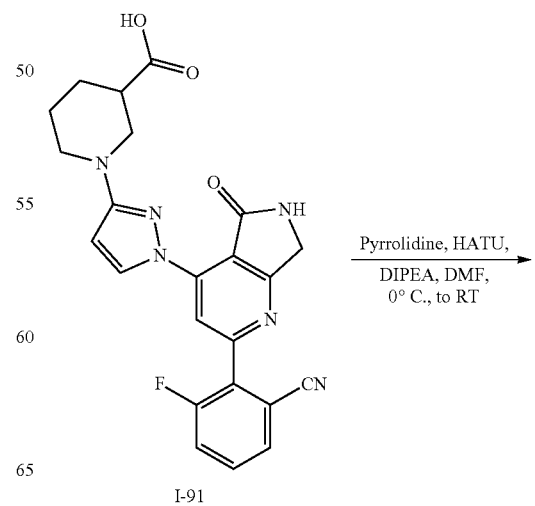

I-91

-continued

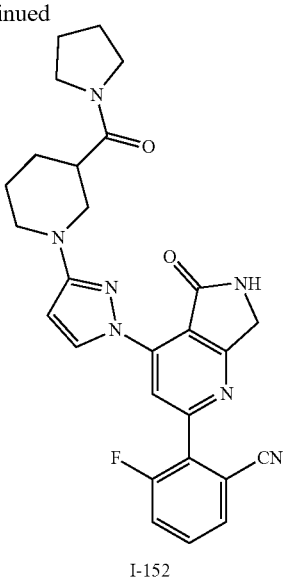

I-152

Compound I-91 (0.04 g, 0.089 mmol, 1.0 eq) was dissolved in DMF (1.5 mL) and HATU (0.041 g, 0.10 mmol, 1.2 eq) was added at 0° C. followed by pyrrolidine (0.008 g, 0.10 mmol, 1.2 eq) and DIPEA (0.023 g, 0.17 mmol, 2 eq). The reaction was stirred at room temperature for 16 hours. Upon completion, reaction mixture was transferred into water solution, extracted with EtOAc. Organic layers were combined, washed with brine, dried over $Na_2SO_4$ and concentrated under reduced pressure to pressure to obtain crude which was purified by column chromatography to provide I-152 (0.025 g, 56.8%). MS(ES): m/z 500 [M+H]$^+$; $^1$H NMR (DMSO-$d_6$, 400 MHz): 9.79-9.78 (d, 1H), 9.13 (s, 1H), 8.15 (s, 1H), 7.93-7.90 (m, 1H), 7.83-7.75 (m, 2H), 6.42-6.41 (d, 1H), 4.49 (s, 2H), 3.97-3.94 (m, 1H), 3.86-3.83 (m, 1H), 3.59-3.56 (m, 1H), 3.46-3.41 (m, 1H), 3.25-3.24 (d, 2H), 2.88-2.82 (t, 2H), 2.72-2.67 (m, 1H), 1.82-1.79 (m, 1H), 1.74-1.70 (m, 3H), 1.67-1.60 (m, 2H), 1.56-1.46 (m, 2H).

Example 153

Synthesis of 3-fluoro-2-(4-(3-((3R,4S)-3-hydroxy-4-methoxypyrrolidin-1-yl)-1H-pyrazol-1-yl)-5-oxo-6,7-dihydro-5H-pyrrolo[3,4-b]pyridin-2-yl)benzonitrile, I-153

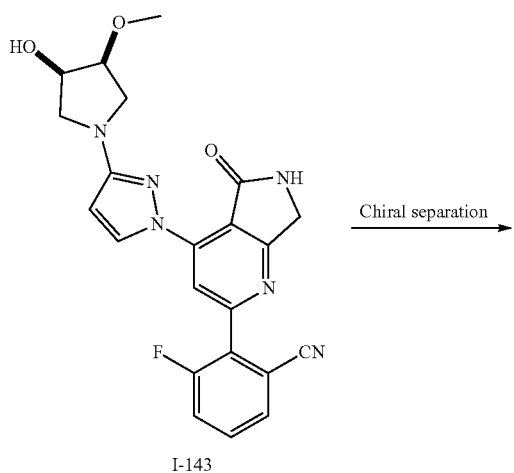

I-143

-continued

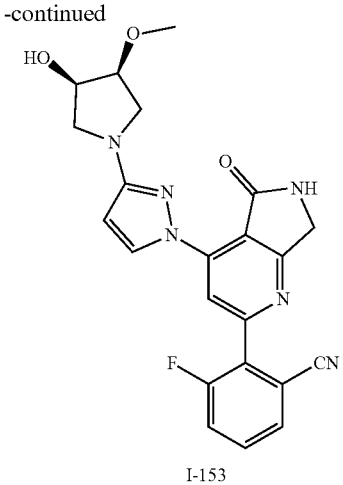

I-153

Compound I-153 was prepared by chiral purification of compound I-143. MS(ES): m/z 434 [M+H]$^-$; $^1$H NMR (DMSO-$d_6$, 400 MHz): 9.70 (d, 1H), 8.27 (s, 1H), 7.77 (d, 1H), 7.63-7.74 (m, 2H), 6.07 (s, 1H), 4.53 (s, 2H), 4.40-4.44 (m, 1H), 3.94-3.98 (m, 1H), 3.60-3.68 (m, 2H), 3.33-3.48 (m, 5H).

Example 154

Synthesis of 3-fluoro-2-(4-(3-((3S,4R)-3-hydroxy-4-methoxypyrrolidin-1-yl)-1H-pyrazol-1-yl)-5-oxo-6,7-dihydro-5H-pyrrolo[3,4-b]pyridin-2-yl)benzonitrile, I-154

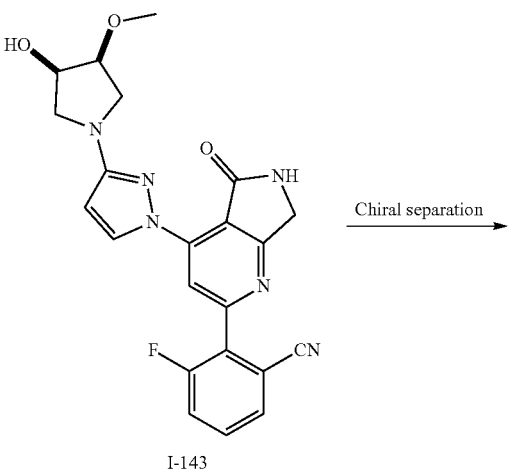

I-143

Chiral separation →

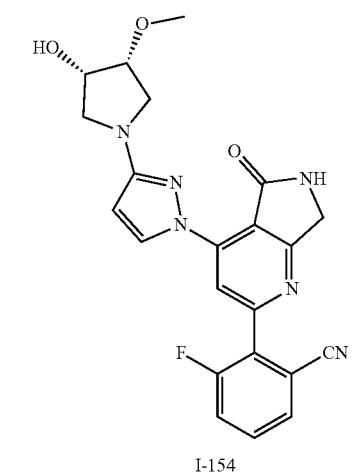

I-154

Compound I-154 was prepared by chiral separation of compound I-143. MS(ES): m/z 434 [M+H]⁻; ¹H NMR (DMSO-d₆, 400 MHz): 9.70 (d, 1H), 8.27 (s, 1H), 7.77 (d, 1H), 7.63-7.74 (m, 2H), 6.07 (s, 1H), 4.53 (s, 2H), 4.40-4.44 (m, 1H), 3.94-3.98 (m, 1H), 3.60-3.68 (m, 2H), 3.33-3.48 (m, 5H).

Example 155

Synthesis of (S)-3-fluoro-2-(4-(3-(3-(4-methylpiperazin-1-yl)piperidin-1-yl)-1H-pyrazol-1-yl)-5-oxo-6,7-dihydro-5H-pyrrolo[3,4-b]pyridin-2-yl)benzonitrile, I-155

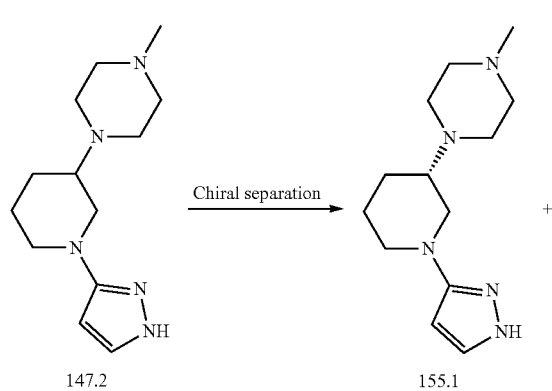

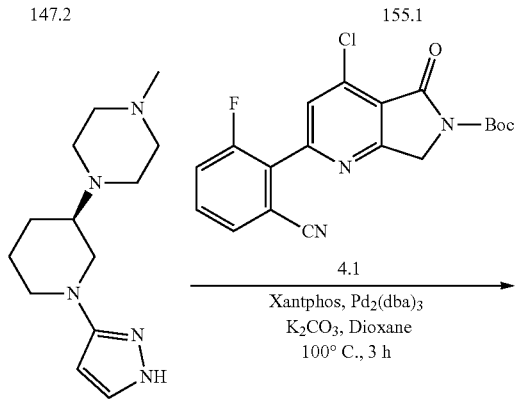

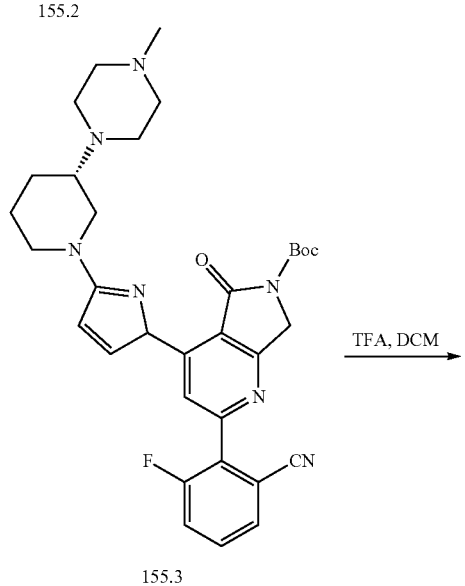

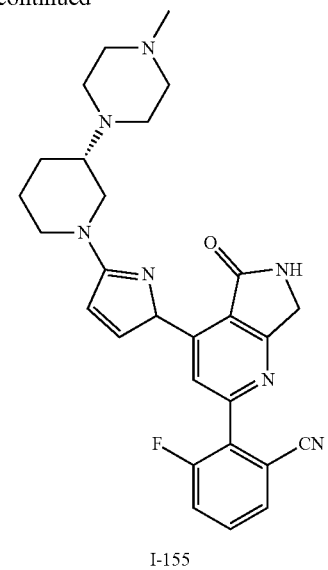

I-155

Synthesis of compounds 155.1 and 155.2. Compounds 155.1 and 155.2 were prepared by chiral purification of compound 147.2

Synthesis of compound 155.3. Compound 155.3 was prepared from compounds 155.1 and 4.1 using the procedure described in Example 64.

Synthesis of compound I-155. Compound I-155 was prepared from compound 155.3 using the procedure described in Example 64. MS(ES): m/z 501.65 [M+H]⁺; ¹H NMR (DMSO-d₆, 400 MHz): 9.74-9.73 (d, 1H), 9.11 (s, 1H), 8.11 (s, 1H), 7.92-7.90 (m, 1H), 7.77-7.73 (m, 2H), 7.39-7.36 (m, 1H), 6.39 (d, 1H), 4.49 (s, 2H), 3.91-3.88 (m, 1H), 3.78-3.75 (m, 1H), 2.76-2.67 (m, 2H), 2.57 (bs, 4H), 2.40 (bs, 4H), 2.20 (s, 3H), 1.90-1.88 (m, 1H), 1.72-1.65 (m, 1H), 1.53-1.49 (m, 1H), 1.32-1.25 (m, 1H).

Example 156

Synthesis of (R)-3-fluoro-2-(4-(3-(3-(4-methylpiperazin-1-yl)piperidin-1-yl)-1H-pyrazol-1-yl)-5-oxo-6,7-dihydro-5H-pyrrolo[3,4-b]pyridin-2-yl)benzonitrile, I-156

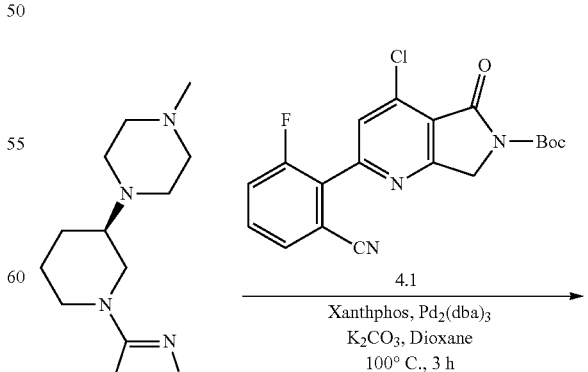

325
-continued

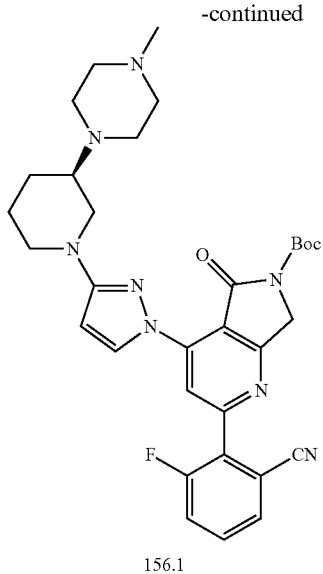  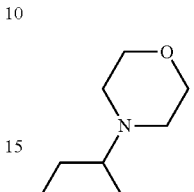

156.1

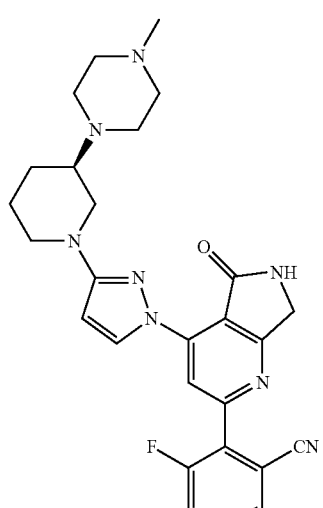

I-156

Synthesis of compound 156.1. Compound 156.1 was prepared from compounds 155.2 and 4.1 using the procedure described in Example 64.

Synthesis of compound I-156. Compound I-156 was prepared from compound 156.1 using the procedure described in Example 64. MS(ES): m/z 501.65 [M+H]⁺; ¹H NMR (DMSO-d₆, 400 MHz): 9.74-9.73 (d, 1H), 9.11 (s, 1H), 8.11 (s, 1H), 7.92-7.90 (m, 1H), 7.77-7.73 (m, 2H), 7.39-7.36 (m, 1H), 6.39 (d, 1H), 4.49 (s, 2H), 3.91-3.88 (m, 1H), 3.78-3.75 (m, 1H), 2.76-2.67 (m, 2H), 2.57 (bs, 4H), 2.40 (bs, 4H), 2.20 (s, 3H), 1.90-1.88 (m, 1H), 1.72-1.65 (m, 1H), 1.53-1.49 (m, 1H), 1.32-1.25 (m, 1H).

326
Example 157

Synthesis of (S)-3-fluoro-2-(4-(3-(3-morpholinopiperidin-1-yl)-1H-pyrazol-1-yl)-5-oxo-6,7-dihydro-5H-pyrrolo[3,4-b]pyridin-2-yl)benzonitrile, I-157

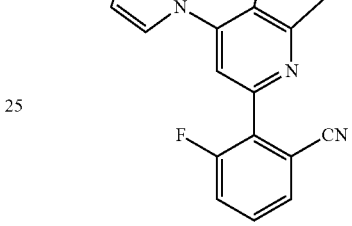

I-149

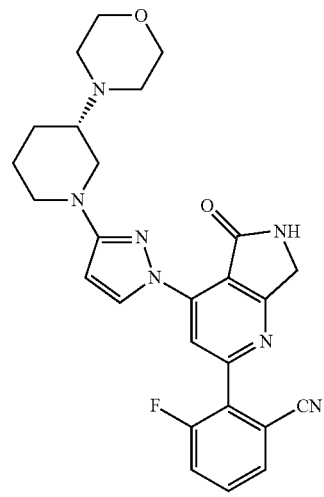

I-157

Compound I-157 was prepared by chiral purification of compound I-149. MS(ES): m/z 488.33 [M+H]⁺; ¹H NMR (DMSO, 400 MHz): 9.74-9.73 (d, 1H), 9.11 (s, 1H), 8.18 (s, 1H), 7.91 (m, 1H), 7.82-7.72 (m, 2H), 6.39 (d, 1H), 4.49 (s, 2H), 3.93-3.90 (m, 1H), 3.77-3.74 (m, 1H), 3.55 (s, 4H), 2.74-2.67 (m, 2H), 2.57 (bs, 4H), 2.36-2.32 (m, 1H), 1.92-1.82 (m, 1H), 1.52-1.34 (m, 3H).

327
Example 158

Synthesis of (R)-3-fluoro-2-(4-(3-(3-morpholinopiperidin-1-yl)-1H-pyrazol-1-yl)-5-oxo-6,7-dihydro-5H-pyrrolo[3,4-b]pyridin-2-yl)benzonitrile, I-158

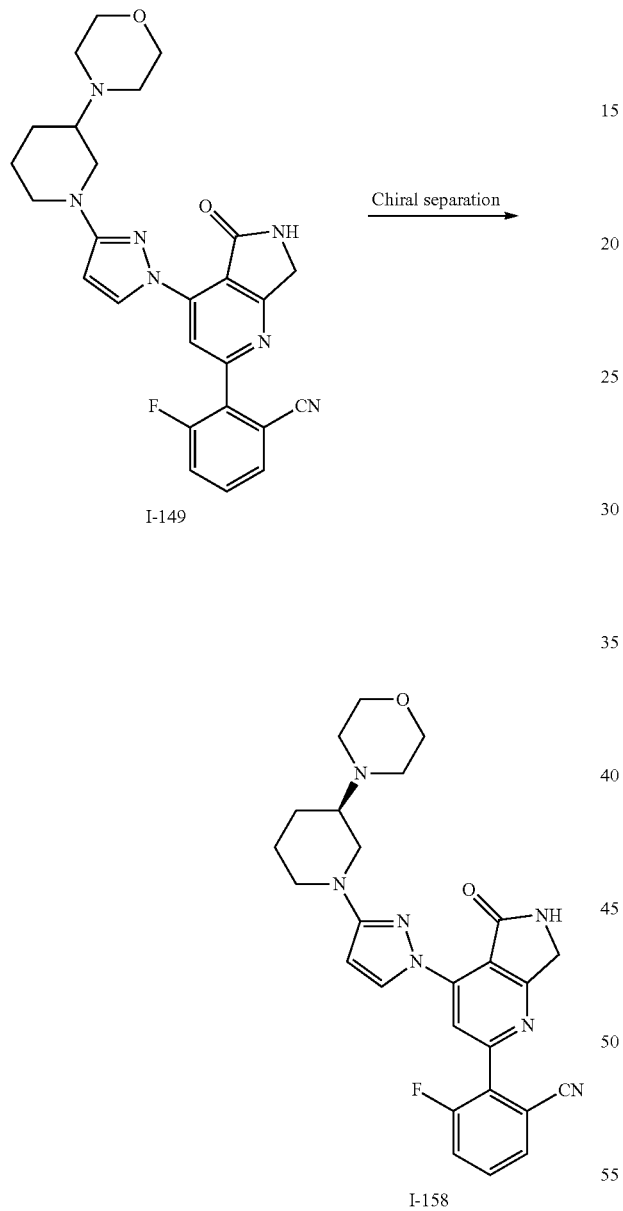

Compound I-158 was prepared by chiral purification of compound I-149. MS(ES): m/z 488.38 [M+H]$^+$; $^1$H NMR (DMSO, 400 MHz): 9.74-9.73 (d, 1H), 9.11 (s, 1H), 8.18 (s, 1H), 7.91 (m, 1H), 7.82-7.72 (m, 2H), 6.39 (d, 1H), 4.49 (s, 2H), 3.93-3.90 (m, 1H), 3.77-3.74 (m, 1H), 3.55 (s, 4H), 2.74-2.67 (m, 2H), 2.57 (bs, 4H), 2.36-2.32 (m, 1H), 1.92-1.82 (m, 1H), 1.52-1.34 (m, 3H).

328
Example 159

Synthesis of 1-(1-(2-(2-cyano-6-fluorophenyl)-5-oxo-6,7-dihydro-5H-pyrrolo[3,4-b]pyridin-4-yl)-1H-pyrazol-3-yl)-N-ethylpiperidine-3-carboxamide, I-159

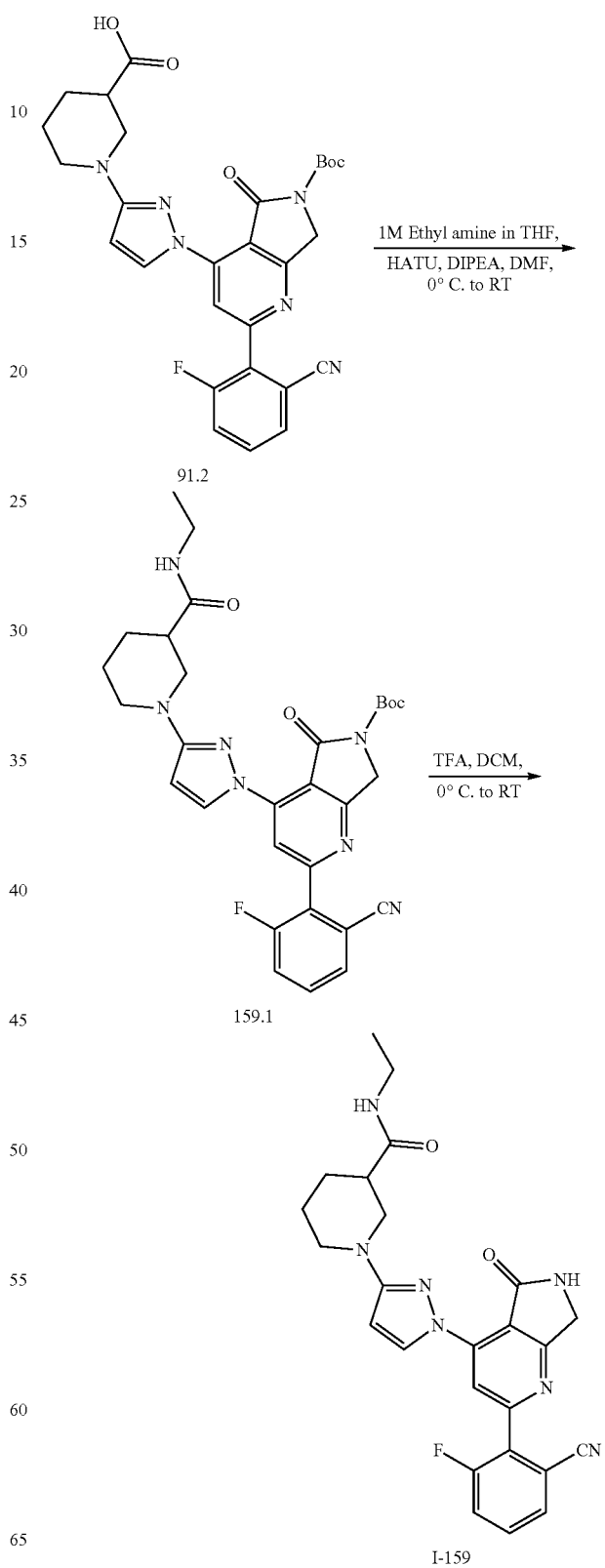

Synthesis of compound 159.1. Compound 159.1 was prepared from ethylamine and compound 91.2 using the procedure described in Example 152.

Synthesis of compound I-159. Compound I-159 was prepared from compound 159.1 using the procedure described in Example 64. MS (ES): m/z 474 [M+H]$^+$; $^1$H NMR (DMSO, 400 MHz): 9.75-9.74 (d, 1H), 9.12 (s, 1H), 8.17 (d, 1H), 7.92-7.87 (m, 2H), 7.82-7.73 (m, 2H), 6.40-6.39 (d, 1H), 4.49 (s, 2H), 3.85-3.82 (m, 2H), 3.09-3.01 (m, 2H), 2.88-2.82 (m, 1H), 2.78-2.72 (m, 1H), 2.40-2.33 (m, 1H), 1.81-1.80 (m, 1H), 1.71-1.69 (m, 1H), 1.55-1.51 (m, 2H), 1.01-1.00 (m, 3H).

Example 160

Synthesis of 3-fluoro-2-(4-(3-(4-fluoro-3-hydroxypiperidin-1-yl)-1H-pyrazol-1-yl)-5-oxo-6,7-dihydro-5H-pyrrolo[3,4-b]pyridin-2-yl)benzonitrile, I-160

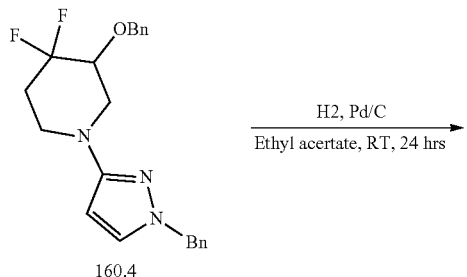

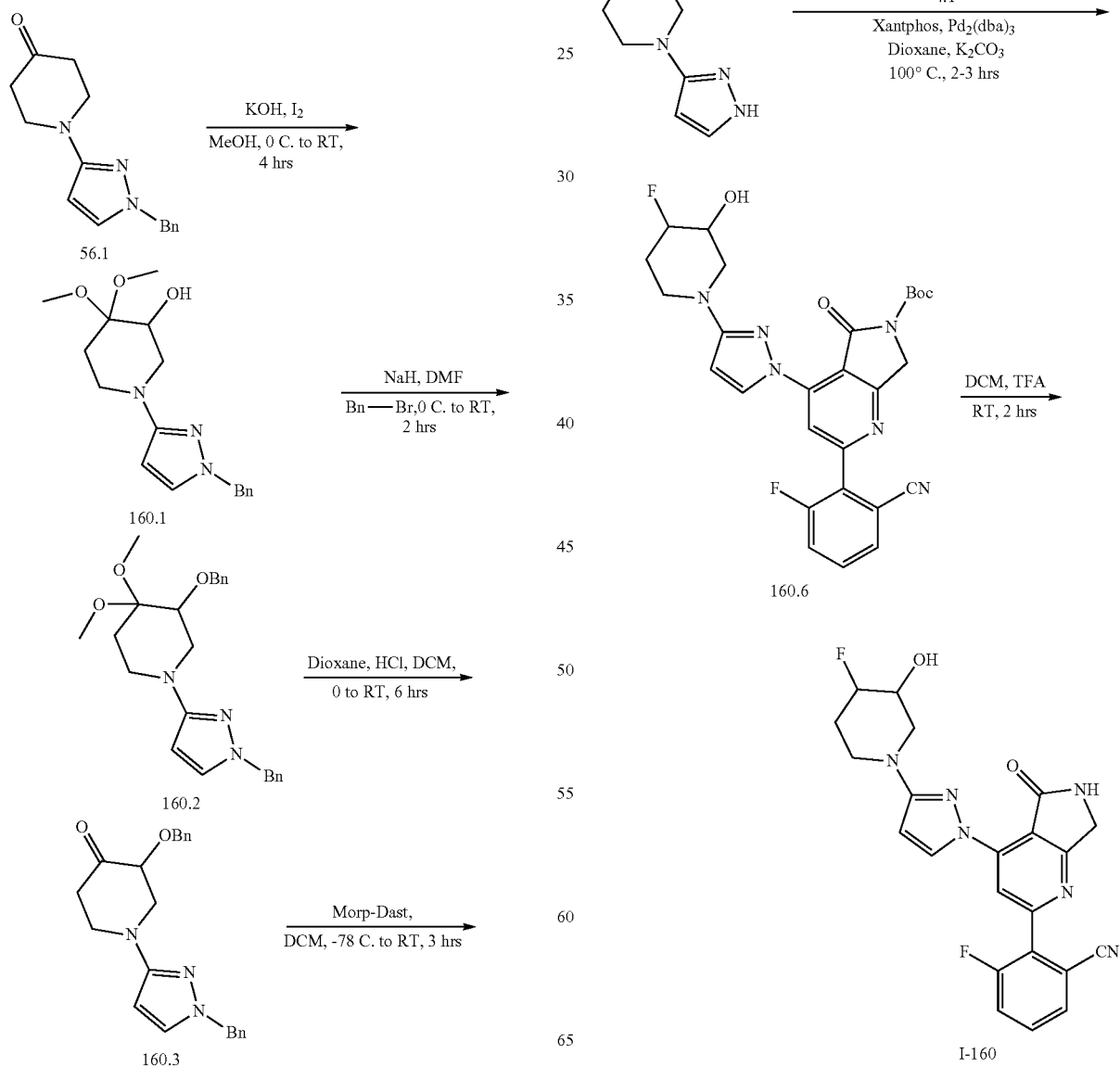

Synthesis of compound 160.1. To a solution of KOH (2.5 g, 44.6 mmol, 2.4 eq) in MeOH (50 mL) was added 56.1 (2.6 g, 18.0 mmol, 1.0 eq) followed by I$_2$ (5.0 g, 19.0 mmol, 1.1 eq) at 0° C. Reaction was stirred at room temperature for 4 h. Upon completion of the reaction, reaction mixture was concentrated under reduced pressure. Residue was triturated with toluene, filtered and washed with toluene. Filtrate was concentrated under reduced pressure to obtain crude which was purified by column chromatography to provide 160.1 (12 g, 50.0%). MS(ES): m/z 318 [M+H]$^+$.

Synthesis of compound 160.2. To a solution of 160.1 (12 g, 37.8 mmol, 1.0 eq) in DMF (120 mL) was added NaH (1.36 g, 56.7 mmol, 1.5 eq) at 0° C. under nitrogen, and mixture was stirred at room temperature for 1 h. Reaction mixture was cooled to 0° C. and BnBr (7.11 g, 41.5 mmol, 1.1 eq) was added dropwise. Reaction was stirred at room temperature for 2 h. Upon completion of the reaction, reaction mixture was transferred into ice, then extracted with EtOAc. Organic layers were combined, washed with brine, dried over Na$_2$SO$_4$ and concentrated under reduced pressure. The crude was purified by column chromatography to provide 160.2 (12.3 g, 79.87%). MS(ES): m/z 408 [M+H]$^+$.

Synthesis of compound 160.3. To a mixture of 160.2 (12.3 g, 2.28 mmol, 1.0 eq) in DCM (25 mL) was added 4M HCl in dioxane (36 ml) at 0° C. Reaction mixture was stirred at room temperature for 6 h. Upon completion of the reaction; reaction mixture was transferred into water, then extracted with EtOAc. Organic layers were combined, washed with NaHCO$_3$ solution, dried over Na$_2$SO$_4$ and concentrated under reduced pressure to pressure to obtain crude material. This was further purified by column chromatography and the compound was eluted in 20% ethyl acetate in hexane to get pure 160.3 (4.5 g, 31.7%). MS(ES): m/z 362 [M+H]$^+$.

Synthesis of compound 160.4. To a solution of 160.3 (3.2 g, 8.85 mmol, 1 eq) in DCM (30 mL) was added Morpholinosulfur Trifluoride (4.65 g, 26.5 mmol, 3.0 eq) at −78° C. Reaction was stirred at room temperature for 3 hours. Upon completion of the reaction; reaction mixture was transferred into water, then extracted with EtOAc. Organic layers were combined, washed with brine solution, dried over Na$_2$SO$_4$ and concentrated under reduced pressure to pressure to obtain crude which was purified by column chromatography to provide 160.4 (0.18 g, 5.3%). MS(ES): m/z 384 [M+H]$^+$.

Synthesis of compound 160.5. To a solution of 160.4 (0.150 g, 0.39 mmol, 1.0 eq) in EtOAc (5 mL) and water (0.5 ml) were added 20% Pd(OH)$_2$ (0.03 g) and 1N HCl (catalytic amount). Reaction mixture was stirred (under hydrogen) at 30 psi for 15 h. Upon completion of the reaction, mixture was filtered through celite-bed and washed with methanol. Filtrate was concentrated under reduced pressure to obtain crude which was purified by column chromatography to provide 160.5. (0.06 g, 83.33%). MS(ES): m/z 198 [M+H]$^+$.

Synthesis of compound 160.6. Compound was prepared from 160.5 and 4.1 using the procedure described in Example 64

Synthesis of compound I-160. Compound was prepared from 160.5 using the procedure described in Example 64. MS(ES): m/z 437 [M+H]$^+$; $^1$H NMR (DMSO-d$_6$, 400 MHz): 9.79 (d, 1H), 9.11 (s, 1H), 8.18 (s, 1H), 7.92-7.90 (m, 1H), 7.83-7.73 (m, 2H), 6.19 (d, 1H), 4.49 (d, 2H), 3.72-3.62 (m, 2H), 3.58-3.43 (m, 4H), 2.19-2.11 (m 2H).

Example 161

Synthesis of 3-fluoro-2-(4-(3-((3aR,6aS)-2-methyl-tetrahydro-5H-[1,3]dioxolo-[4,5-c]pyrrol-5-yl)-1H-pyrazol-1-yl)-5-oxo-6,7-dihydro-5H-pyrrolo[3,4-b]pyridin-2-yl)benzonitrile, I-161

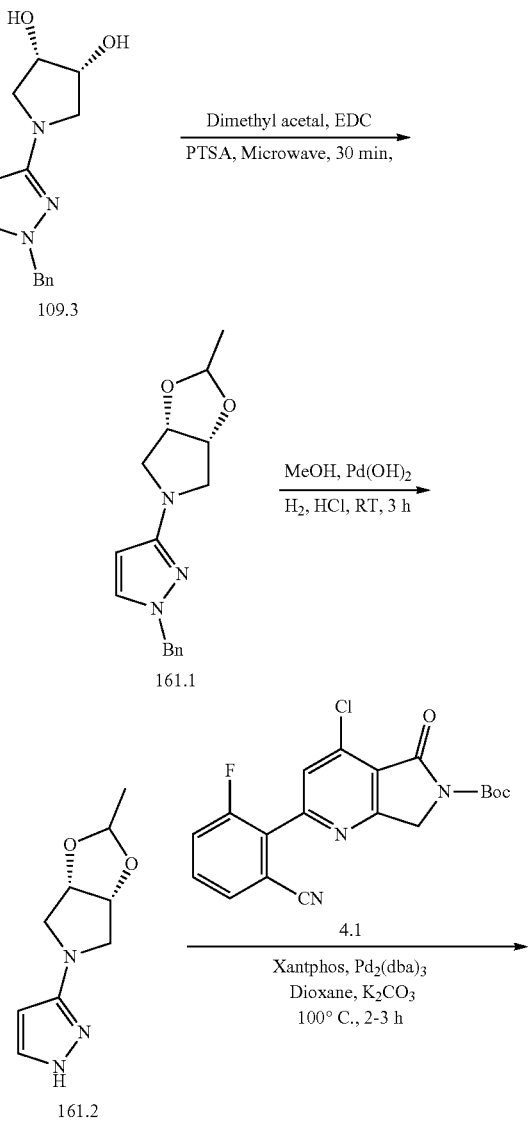

-continued

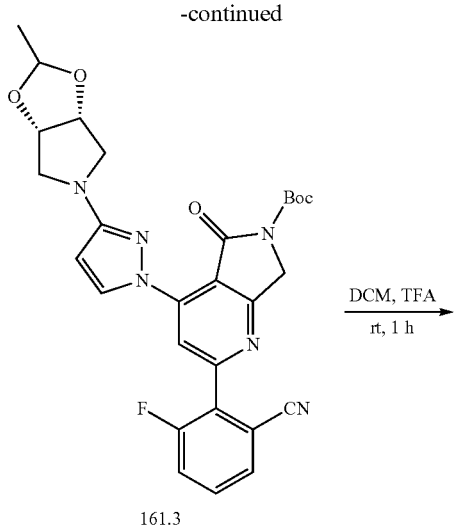

161.3

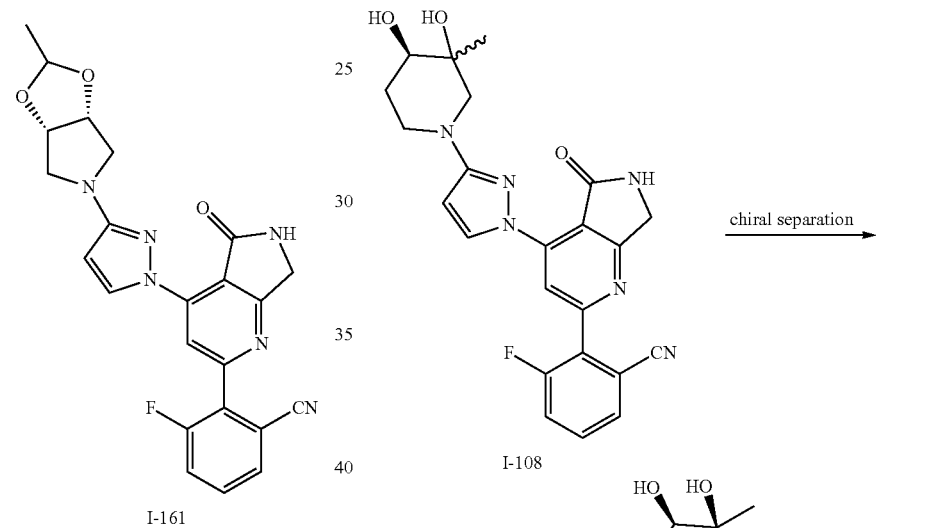

Synthesis of compound 161.1. To a solution of 109.3 (0.3 g, 1.15 mmol, 1.0 eq) in 1,2-Dichloroethane (8 mL) was added dimethyl acetal (0.5 g, 57.9 mmol, 1.0 eq) and p-Toluenesulphonic acid (0.002 g, 0.01 mmol, 1.0 eq). Suspension was stirred at 90° C. for 1 h in Microwave. Upon completion of the reaction; mixture was transferred into water, extracted with EtOAc. Organic layers were combined, washed with brine, dried over $Na_2SO_4$ and concentrated under reduced pressure to obtain crude which was purified by column chromatography to furnish 161.1 (0.085 g, 25.75%). MS(ES): m/z 286 [M+H]$^+$.

Synthesis of compound 161.2. To a solution of 161.1 (0.080 g, 0.28 mmol, 1.0 eq) in MeOH (5.0 mL) were added 20% $Pd(OH)_2/C$ (0.1 g) and 1N HCl (catalytic). Reaction mixture was stirred (under hydrogen) at 40 psi for 3 h. Upon completion of the reaction, reaction mixture was filtered through celite-bed and washed with methanol, concentrated under reduced pressure to obtain crude material. The crude was purified by column chromatography to provide 161.2 (0.065 g, 82.0%). MS(ES): m/z 196 [M+H]$^+$.

Synthesis of compound 161.3. Compound 161.3 was prepared from compound 161.2 and 4.1 using the procedure described in Example 64.

Synthesis of compound 161.4. Compound 161.4 was prepared from 161.3 using the procedure described in Example 64. MS(ES): m/z 447 [M+H]$^+$; $^1$H NMR (DMSO-$d_6$, 400 MHz): 9.70 (s, 1H), 8.30 (s, 1H), 7.64-7.80 (m, 3H), 6.16 (s, 1H), 4.91 (s, 2H), 4.84 (s, 2H), 4.56 (s, 1H), 3.75 (d, 2H), 3.18 (m, 2H), 1.36 (d, 3H).

Example 162

Synthesis of 2-(4-(3-((3S,4R)-3,4-dihydroxy-3-methylpiperidin-1-yl)-1H-pyrazol-1-yl)-5-oxo-6,7-dihydro-5H-pyrrolo[3,4-b]pyridin-2-yl)-3-fluorobenzonitrile, I-162

Compound I-162 was prepared by chiral purification of I-108. MS(ES): m/z 449 [M+H]$^+$; $^1$H NMR (DMSO-$d_6$, 400 MHz): 9.75 (d, 1H), 9.10 (s, 1H), 8.15 (s, 1H), 7.92-7.90 (m, 1H), 7.83-7.75 (m, 2H), 6.34 (d, 1H), 4.73 (d, 1H), 4.50 (d, 3H), 3.50-3.48 (m, 1H), 3.41-3.39 (m, 1H), 3.13-3.08 (m, 1H), 2.91 (d, 1H), 1.92-1.87 (m, 1H), 1.46-1.42 (m, 1H), 1.08 (s, 3H).

Example 163

Synthesis of (S)-3-fluoro-2-(4-(3-(3-(hydroxymethyl)morpholino)-1H-pyrazol-1-yl)-5-oxo-6,7-dihydro-5H-pyrrolo[3,4-b]pyridin-2-yl)benzonitrile, I-163

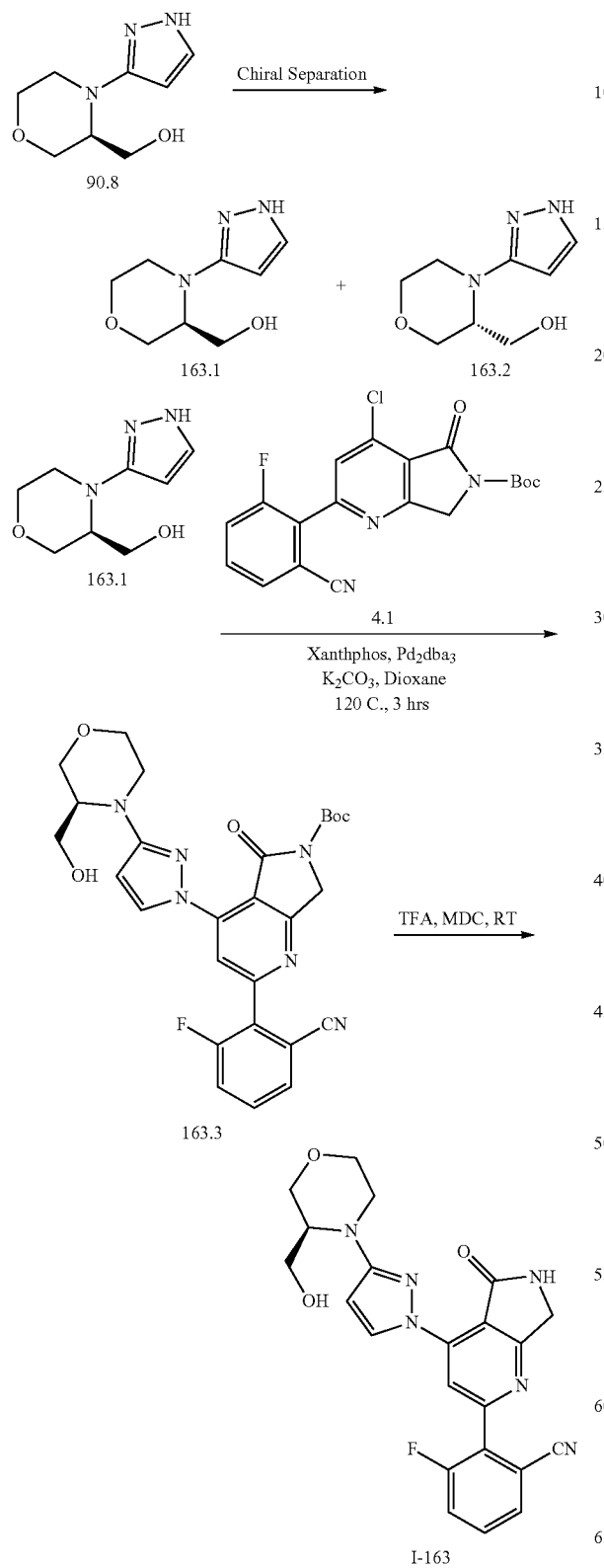

Synthesis of compounds 163.1 and 163.2. Compounds 163.1 and 163.2 were prepared by chiral purification of compound 90.8.

Synthesis of compound 163.3. Compound was prepared from 163.1 and 4.1 using the procedure described in Example 64.

Synthesis of compound I-163. Compound was prepared from 163.3 using the procedure described in Example 64. MS(ES): m/z 428.15 [M+H]$^-$; $^1$H NMR (DMSO-d$_6$, 400 MHz): 9.78 (d, 1H), 9.11 (s, 1H), 8.16 (s, 1H), 7.91-7.89 (dd, 1H), 7.83-7.74 (m, 2H), 6.31 (d 1H), 4.78 (t, 1H), 4.49 (s, 2H), 4.01-3.98 (d, 1H), 3.86-3.83 (m, 1H), 3.76-3.7 (m, 1H), 3.6-3.53 (m, 3H), 3.49-3.43 (m, 2H), 3.17-3.13 (m, 1H).

Example 164

Synthesis of (R)-3-fluoro-2-(4-(3-(3-(hydroxymethyl)morpholino)-1H-pyrazol-1-yl)-5-oxo-6,7-dihydro-5H-pyrrolo[3,4-b]pyridin-2-yl)benzonitrile, I-164

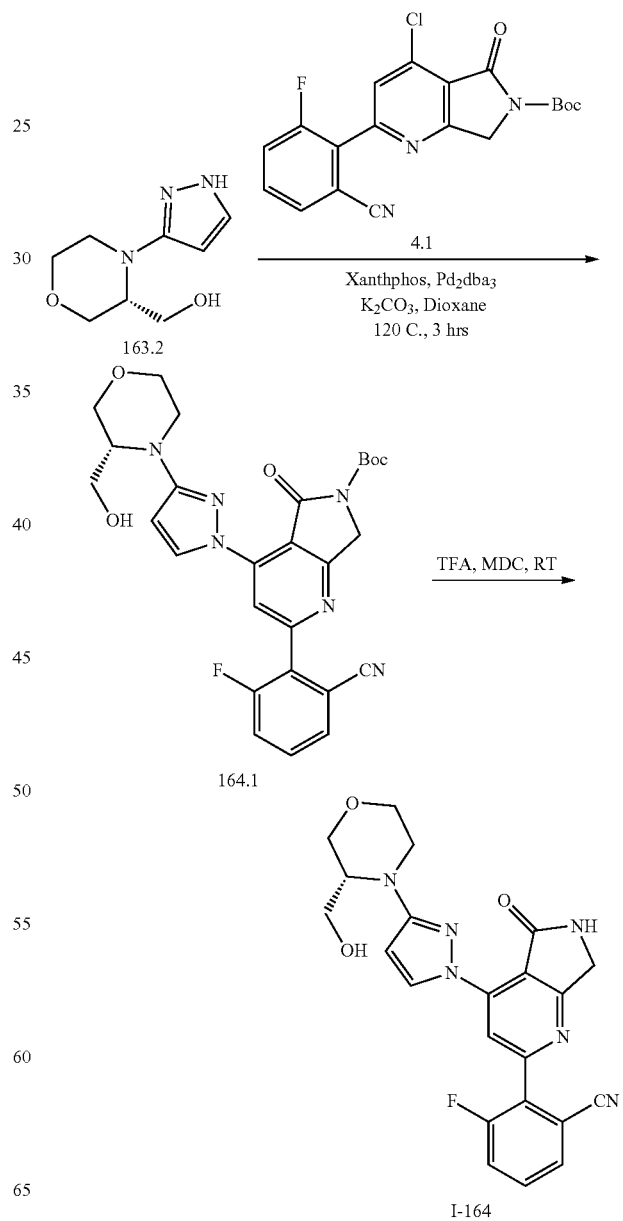

Compound I-164 was prepared from 163.2 and 4.1 using the procedures referred to in Example 163. MS(ES): m/z 428.15 [M+H]⁻; ¹H NMR (DMSO-d$_6$, 400 MHz): 9.78 (d, 1H), 9.11 (s, 1H), 8.16 (s, 1H), 7.9-7.89 (dd, 1H), 7.83-7.73 (m, 2H), 6.31 (d, 1H), 4.78 (t, 1H), 4.49 (s, 2H), 4-3.99 (d, 1H), 3.86-3.83 (m, 1H), 3.76-3.7 (m, 1H), 3.6-3.53 (m, 3H), 3.49-3.43 (m, 2H), 3.17-3.13 (m, 1H).

Example 165

Synthesis of (R)-3-fluoro-2-(5-oxo-4-(3-(6-oxo-2,7-diazaspiro[4.4]nonan-2-yl)-1H-pyrazol-1-yl)-6,7-dihydro-5H-pyrrolo[3,4-b]pyridin-2-yl)benzonitrile, I-165

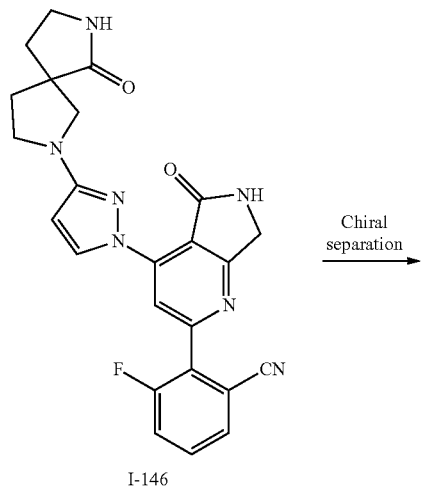

I-146

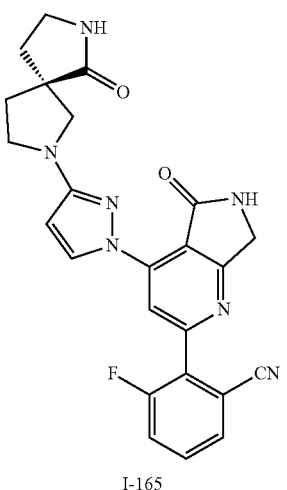

I-165

Compound was prepared by chiral purification of I-165. MS(ES): m/z 458 [M+H]⁺; ¹H NMR (CDCl$_3$, 400 MHz): 9.73 (S, 1H), 8.35 (d, 1H), 7.67 (d, 1H), 7.58-7.53 (m, 1H), 7.50-7.46 (m, 1H), 6.46 (s, 1H), 5.96 (d, 1H), 5.81 (s, 1H), 4.61 (d, 2H), 3.71-3.61 (m, 2H), 3.57-3.50 (m, 1H), 2.43-2.40 (m, 1H), 2.27-2.16 (m, 2H), 1.97-1.92 (m, 1H), 1.31-1.27 (m, 3H).

Example 166

Synthesis of (S)-3-fluoro-2-(5-oxo-4-(3-(6-oxo-2,7-diazaspiro[4.4]nonan-2-yl)-1H-pyrazol-1-yl)-6,7-dihydro-5H-pyrrolo[3,4-b]pyridin-2-yl)benzonitrile, I-166

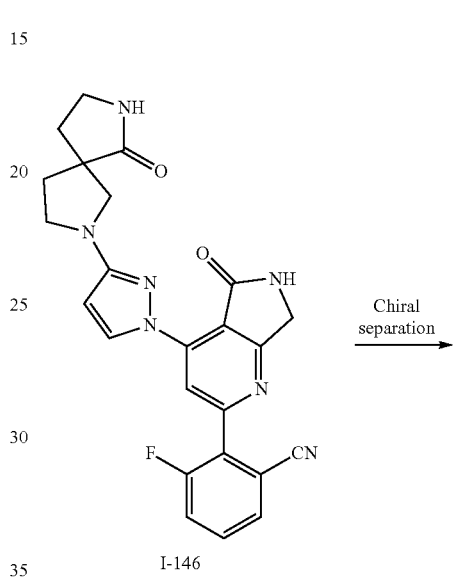

I-146

I-166

Compound was prepared by chiral purification of I-165. MS(ES): m/z 458 [M+H]⁺; ¹H NMR (CDCl$_3$, 400 MHz): 9.73 (s, 1H), 8.35 (d, 1H), 7.67 (d, 1H), 7.58-7.53 (m, 1H), 7.50-7.46 (m, 1H), 6.46 (s, 1H), 5.96 (d, 1H), 5.81 (s, 1H), 4.61 (d, 2H), 3.71-3.61 (m, 2H), 3.57-3.50 (m, 1H), 2.43-2.40 (m, 1H), 2.27-2.16 (m 2H), 1.97-1.92 (m, 1H), 1.31-1.27 (m, 3H).

339

Example 167

Synthesis of (R)-3-fluoro-2-(5-oxo-4-(3-(3-(pyrrolidine-1-carbonyl)piperidin-1-yl)-1H-pyrazol-1-yl)-6,7-dihydro-5H-pyrrolo[3,4-b]pyridin-2-yl)benzonitrile, I-167

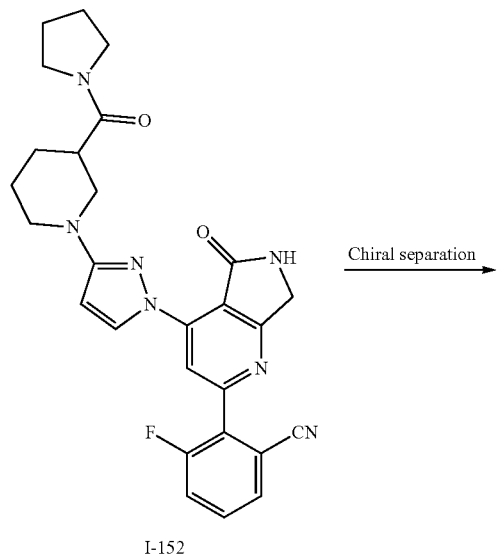

I-152

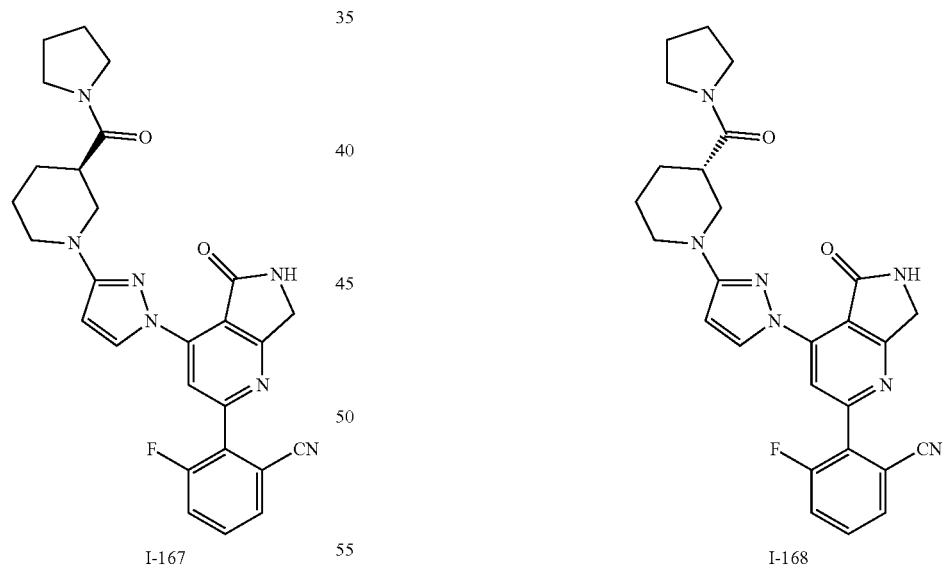

I-167

Compound I-167 was prepared by chiral purification of compound I-152. MS(ES): m/z 500 [M+H]$^-$; $^1$H NMR (DMSO-d$_6$, 400 MHz): 9.79-9.78 (d, 1H), 9.12 (s, 1H), 8.15 (s, 1H), 7.93-7.90 (m, 1H), 7.83-7.75 (M, 2H), 6.41-6.40 (d, 1H), 4.49 (s, 2H), 3.97-3.94 (m, 1H), 3.85-3.83 (m, 1H), 3.58-3.56 (m, 1H), 3.47-3.41 (m, 1H), 3.25-3.23 (d, 2H), 2.88-2.82 (t, 2H), 2.71-2.67 (m, 1H), 1.82-1.79 (m, 1H), 1.74-1.70 (m, 3H), 1.67-1.60 (m, 2H), 1.56-1.46 (m, 2H).

340

Example 168

Synthesis of (S)-3-fluoro-2-(5-oxo-4-(3-(3-(pyrrolidine-1-carbonyl)piperidin-1-yl)-1H-pyrazol-1-yl)-6,7-dihydro-5H-pyrrolo[3,4-b]pyridin-2-yl)benzonitrile, I-168

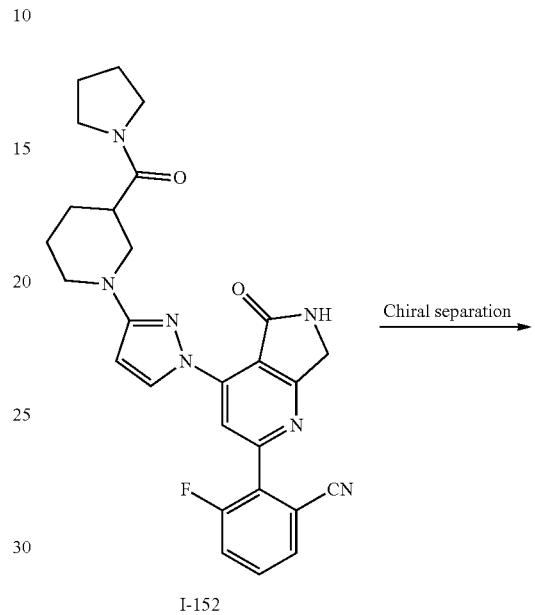

I-152

I-168

Compound I-168 was prepared by chiral purification of compound I-152. MS(ES): m/z 500 [M+H]$^-$; $^1$H NMR (DMSO-d$_6$, 400 MHz): 9.79-9.78 (d, 1H), 9.13 (s, 1H), 8.15 (s, 1H), 7.93-7.90 (m, 1H), 7.83-7.75 (M, 2H), 6.42-6.41 (d, 1H), 4.49 (s, 2H), 3.97-3.94 (m, 1H), 3.86-3.83 (m, 1H), 3.59-3.56 (m, 1H), 3.46-3.41 (m, 1H), 3.25-3.23 (d, 2H), 2.88-2.82 (t, 2H), 2.72-2.66 (m, 1H), 1.82-1.79 (m, 1H), 1.74-1.70 (m, 3H), 1.67-1.60 (m, 2H), 1.56-1.46 (m, 2H).

Example 169

Synthesis of 3-fluoro-2-(4-(3-((4aR,7aS)-hexahydro-6H-[1,4]dioxino[2,3-c]pyrrol-6-yl)-1H-pyrazol-1-yl)-5-oxo-6,7-dihydro-5H-pyrrolo[3,4-b]pyridin-2-yl)benzonitrile, I-169

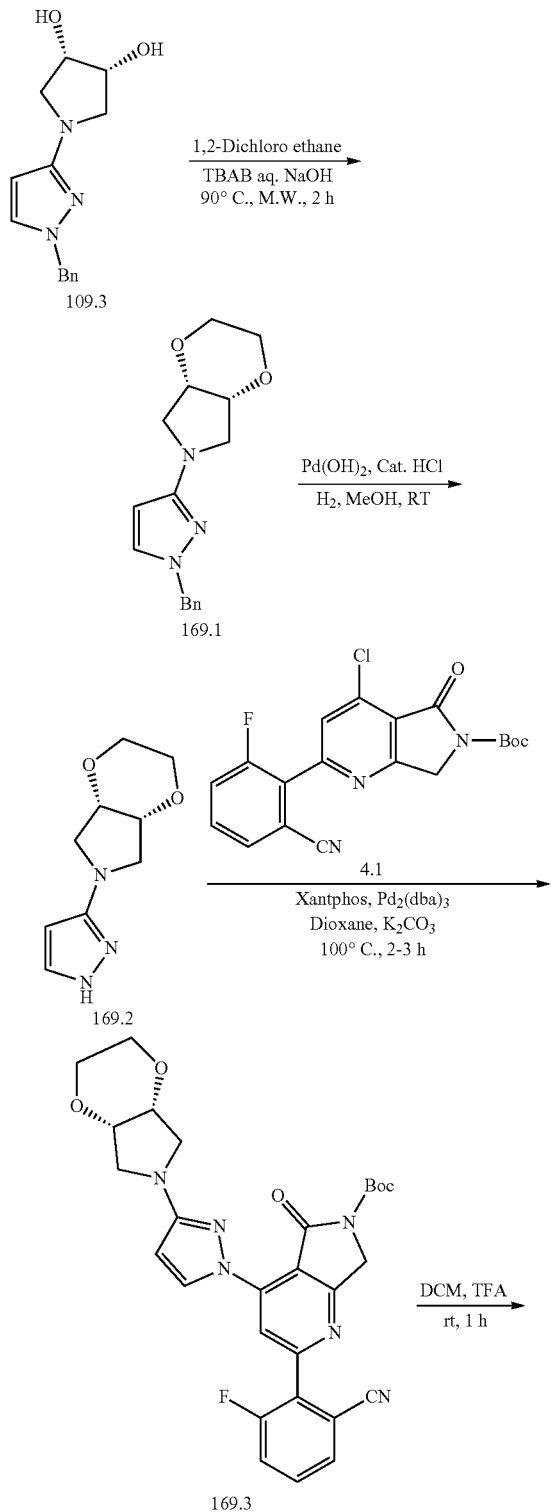

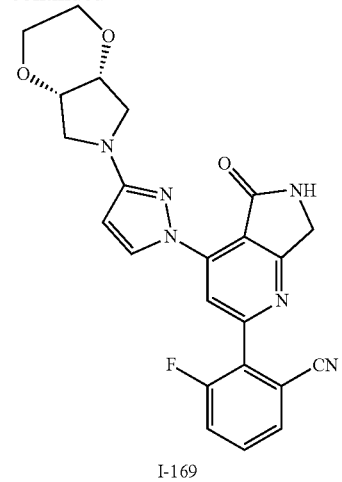 [SMILES: N#Cc1cccc(F)c1-c1cc(-n2ccc(N3C[C@@H]4OCCO[C@@H]4C3)n2)c2c(n1)CNC2=O]

I-169

Synthesis of compound 169.1. To a solution of 109.3 (0.7 g, 2.70 mmol, 1.0 eq) in 1,2-Dichloroethane (14.0 mL) was added TBAB (0.174 g, 0.54 mmol, 1.0 eq) and 35% NaOH (14 ml) stirred at 90° C. for 1 hour in Microwave. Upon completion of the reaction; mixture was transferred into water, extracted with EtOAc. Organic layers were combined, washed with brine, dried over $Na_2SO_4$ and concentrated under reduced pressure to pressure to obtain crude which was purified by column chromatography to furnish 169.1 (0.125 g, 16.23%). MS(ES): m/z 286 $[M+H]^+$.

Synthesis of compound 169.2. Compound 169.2 was prepared from 169.1 using the procedure described in Example 161.

Synthesis of compound 169.3. Compound 169.3 was prepared from compound 169.2 and 4.1 using the procedure described in Example 64.

Synthesis of compound I-169. Compound I-169 was prepared from compound 169.3 using the procedure described in Example 64. MS(ES): m/z 447 $[M+H]^+$; $^1H$ NMR (DMSO-$d_6$, 400 MHz): 9.78 (s, 1H), 9.10 (s, 1H), 8.17 (s, 1H), 7.69-7.90 (m, 3H), 6.16 (s, 1H), 4.48 (s, 2H), 4.25 (s, 2H), 3.56-3.79 (m, 2H), 3.46-3.56 (m, 6H).

Example 170

Synthesis of 3-fluoro-2-(4-(3-(3-hydroxy-3-(methyl-d3)pyrrolidin-1-yl-2,2,5,5-d4)-1H-pyrazol-1-yl)-5-oxo-6,7-dihydro-5H-pyrrolo[3,4-b]pyridin-2-yl)benzonitrile, I-170

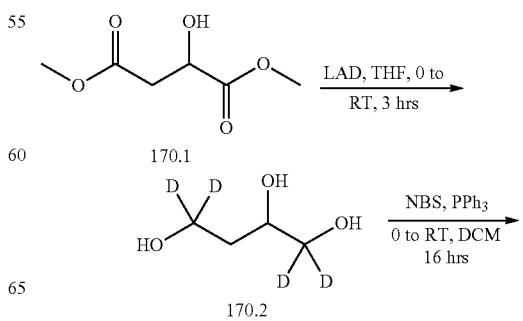

-continued

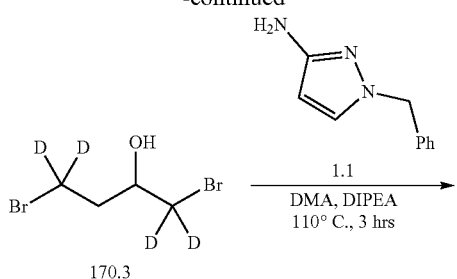

170.3

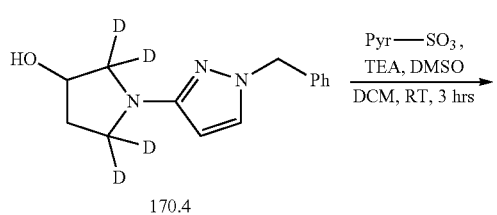

170.4

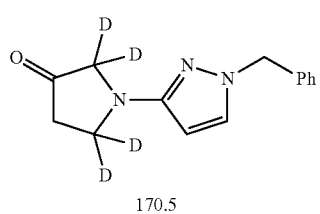

170.5

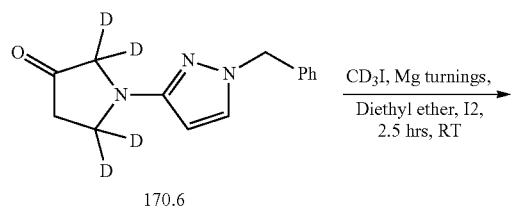

170.6

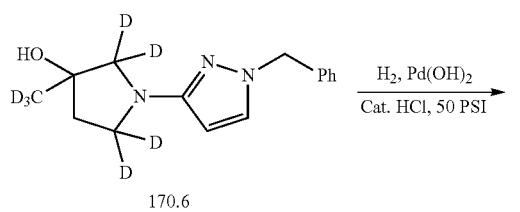

170.6

170.7

-continued

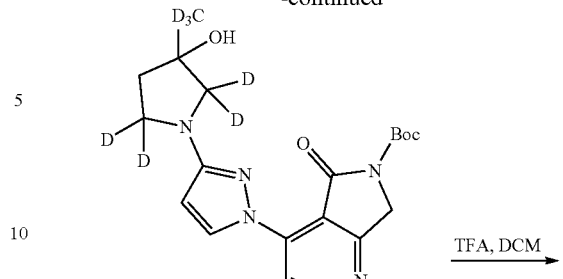

170.8

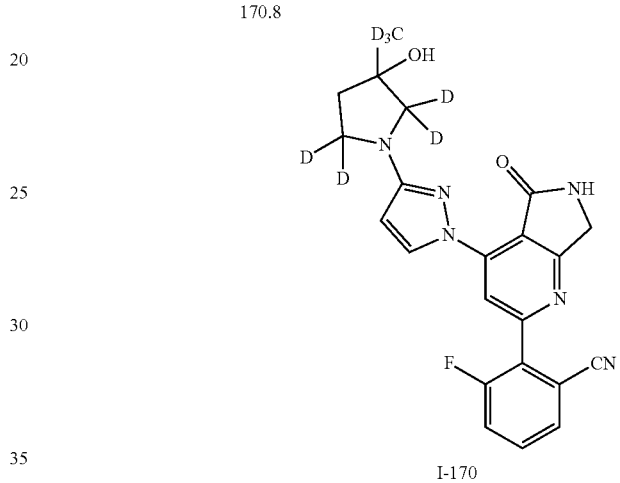

I-170

Synthesis of compound 170.2. To a suspension of LAD (1.8 g, 43 mmol, 3.5 eq) in THF (20 mL) was added solution of 170.1 (2 g, 13.3 mmol, 1 eq) in THF (3 mL) at 0° C. The reaction was stirred at room temperature for 18 h. Upon completion, reaction was quenched with $D_2O$ and 10% sulphuric acid, extracted with EtOAc, washed with brine, dried over $Na_2SO_4$ and concentrated under reduced pressure to get crude. Crude was purified by column chromatography to provide 170.2. (1.45 g, 95.7%). MS(ES): m/z 111.09 [M+H]$^+$.

Synthesis of compound 170.3. To a solution of 170.2 (1.44 g, 13.3 mmol, 1 eq) in DCM (3.0 mL) was added PPh$_3$ (6.97 g, 5.99 mmol, 2.0 eq) followed by NBS (1.06 g, 5.99 mmol, 2.0 eq). Reaction mixture was stirred at room temperature for 15 h. Upon completion of the reaction, reaction mixture was poured into water and extracted with EtOAc. Organic layers were combined, washed with brine solution, dried over $Na_2SO_4$ and concentrated under reduced pressure to pressure to obtain crude which was purified by column chromatography to provide 170.3 (0.6 g, 20.0%). MS(ES): m/z 236 [M+H]$^+$.

Synthesis of compound 170.4. To a solution of 170.3 (0.6 g, 2.4 mmol, 1.0 eq) and 1.12 (0.4 g, 2.4 mmol, 2.0 eq) in DMA (5.0 ml), DIPEA (0.799 g, 1.98 mmol, 2.5 eq) was added. Reaction mixture was stirred at 90° C. for 1 h in Microwave. Upon completion of the reaction, mixture was transferred into water and extracted with EtOAc, dried over $Na_2SO_4$ and concentrated under reduced pressure to obtain crude which was purified by column chromatography to yield 170.4 (0.4 g, 63.53%). MS(ES): m/z 248 [M+H]$^+$.

Synthesis of compound 170.5. To a solution of 170.4 (0.4 g, 0.9 mmol, 1.0 eq) in DCM (5 ml) was added Et$_3$N (0.578 g, 5.4 mmol, 6.0 eq) and DMSO (0.7 g, 9 mmol, 10.0 eq) at 0° C. Reaction mixture was stirred at 0° C. for 10 min. To this reaction mixture Sulfur trioxide pyridine complex (0.438 g, 2.7 mmol, 3.0 eq) was added portionwise at 0° C. Reaction mixture was stirred at room temperature for 3 h. Upon completion of the reaction; reaction mixture was quenched by saturated NH$_4$Cl solution and extracted with DCM. Combined organic layers were washed with brine, dried over Na$_2$SO$_4$ and concentrated under reduced pressure to obtain crude that was purified by column chromatography to furnish 170.5. (0.09 g, 50.6%). MS(ES): m/z 246.15 [M+H]$^+$ Synthesis of compound 170.6. To a stirred suspension of Mg turnings (0.039 g, 1.61 mmol, 3.6 eq) in Et$_2$O (2.0 mL) was added I$_2$ (catalytic) and stirred for 10 min. Reaction mixture was cooled to 0° C. and deuterated iodomethane (0.195 g, 1.34 mmol, 3.0 eq) was added slowly. Reaction mixture was stirred at room temperature for 2.5 h. This suspension was added to a solution of 170.5 (0.11 g, 0.044 mmol, 1.0 eq) in THF (2.0 mL) at −78° C. Reaction mixture was stirred at room temperature for 16 h. Upon completion of the reaction, reaction mixture was transferred in satd. NH$_4$Cl and extracted with EtOAc. Organic layers were combined, washed with brine solution, dried over Na$_2$SO$_4$ and concentrated under reduced pressure to obtain crude which was purified by column chromatography to provide 170.6 (0.039 g, 32.9%). MS(ES): m/z 267.4 [M+H]$^+$ Synthesis of compound 170.7. To a solution of 170.7 (0.039 g, 0.146 mmol, 1.0 eq) in methanol (3.0 mL) was added Pd(OH)$_2$ (0.02 g), 1N HCl (catalytic). Reaction was stirred at room temperature under hydrogen pressure for 16 h. Upon completion, reaction was filtered. Filtrate was concentrated under reduced pressure to obtain 170.7 (0.016 g, 62.0%). LCMS(ES): m/z 177.3 [M+H]$^+$.

Synthesis of compound 170.8. Compound was prepared from 170.7 and 4.1 using the procedure described in Example 64.

Synthesis of compound I-170. Compound was prepared from 170.8 using the procedure described in Example 64 (0.013 g, 53.48%). MS(ES): m/z 426 [M+H]$^+$; $^1$H NMR (DMSO, 400 MHz): 9.79-9.78 (d, 1H), 9.10 (s, 1H), 8.16 (s, 1H), 7.92-7.90 (m, 1H), 7.81-7.74 (m, 2H), 6.12 (d, 1H), 4.77 (s, 1H), 4.48 (s, 2H), 1.88-1.81 (m, 2H).

Example 171

Synthesis of (S)-1-(1-(2-(2-cyano-6-fluorophenyl)-5-oxo-6,7-dihydro-5H-pyrrolo[3,4-b]pyridin-4-yl)-1H-pyrazol-3-yl)-N-ethylpiperidine-3-carboxamide, I-171

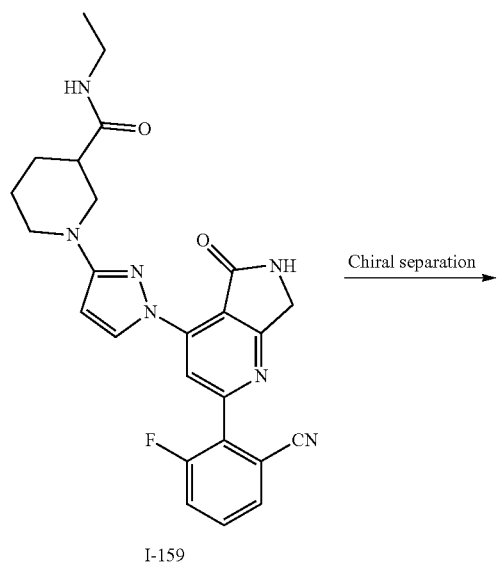

I-159

Chiral separation →

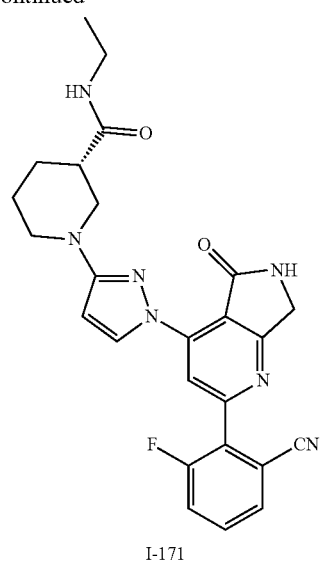

I-171

Compound I-171 was prepared by chiral purification of compound I-159. MS(ES): m/z 474 [M+H]$^+$; $^1$H NMR (DMSO, 400 MHz): 9.75-9.74 (d, 1H), 9.12 (s, 1H), 8.17 (d, 1H), 7.92-7.87 (m, 2H), 7.82-7.73 (m, 2H), 6.40-6.39 (d, 1H), 4.49 (s, 2H), 3.85-3.82 (m, 2H), 3.09-3.01 (m, 2H), 2.88-2.82 (m, 1H), 2.78-2.72 (m, 1H), 2.40-2.33 (m, 1H), 1.81-1.80 (m, 1H), 1.71-1.69 (m, 1H), 1.55-1.51 (m, 2H), 1.01-1.00 (m, 3H).

Example 172

Synthesis of (R)-1-(1-(2-(2-cyano-6-fluorophenyl)-5-oxo-6,7-dihydro-5H-pyrrolo[3,4-b]pyridin-4-yl)-1H-pyrazol-3-yl)-N-ethylpiperidine-3-carboxamide, I-172

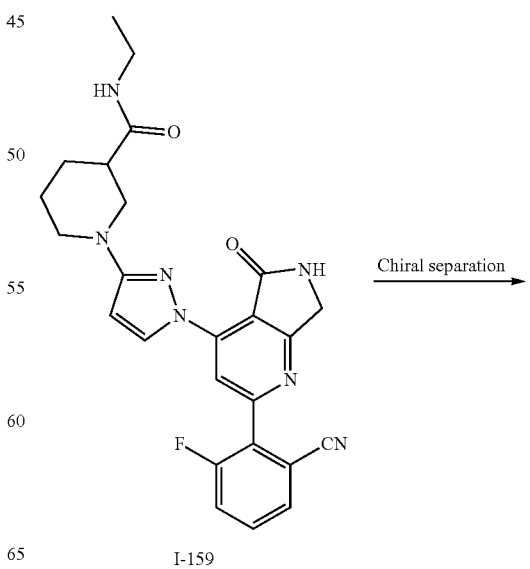

I-159

Chiral separation →

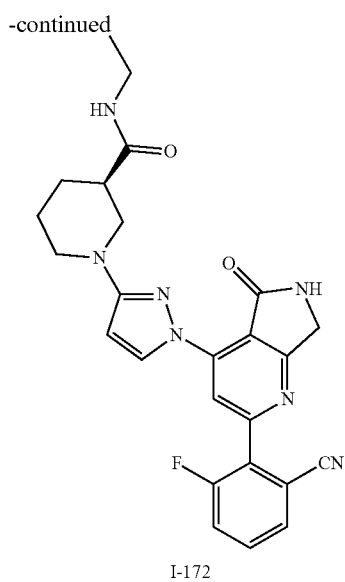

I-172

Compound I-171 was prepared by chiral purification of compound I-159. MS(ES): m/z 474 [M+H]+; 1H NMR (DMSO, 400 MHz): 9.75-9.74 (d, 1H), 9.12 (s, 1H), 8.17 (d, 1H), 7.92-7.87 (m, 2H), 7.82-7.73 (m, 2H), 6.40-6.39 (d, 1H), 4.49 (s, 2H), 3.85-3.82 (m, 2H), 3.09-3.01 (m, 2H), 2.88-2.82 (m, 1H), 2.78-2.72 (m, 1H), 2.40-2.33 (m, 1H), 1.81-1.80 (m, 1H), 1.71-1.69 (m, 1H), 1.55-1.51 (m, 2H), 1.01-0.98 (m, 3H).

Example 173

Synthesis of 3-fluoro-2-(4-(3-((3S,4R)-4-fluoro-3-hydroxypiperidin-1-yl)-1H-pyrazol-1-yl)-5-oxo-6,7-dihydro-5H-pyrrolo[3,4-b]pyridin-2-yl)benzonitrile, I-173

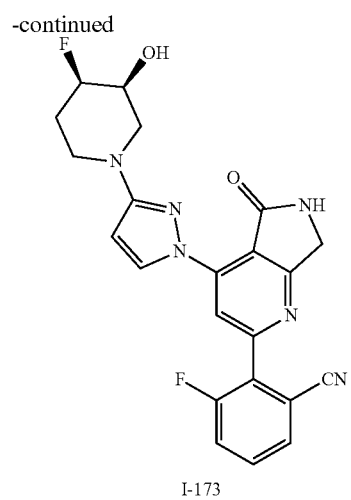

I-173

Compound I-173 was prepared by chiral purification of compound I-160. MS(ES): m/z 437 [M+H]+; 1H NMR (DMSO-d6, 400 MHz): 9.79 (d, 1H), 9.11 (s, 1H), 8.17 (s, 1H), 7.91-7.89 (m, 1H), 7.83-7.75 (m, 2H), 6.19 (d, 1H), 4.49 (d, 2H), 3.72-3.62 (m, 2H), 3.58-3.43 (m, 4H), 2.18-2.11 (m, 2H).

Example 174

Synthesis of 3-fluoro-2-(4-(3-((3R,4S)-4-fluoro-3-hydroxypiperidin-1-yl)-1H-pyrazol-1-yl)-5-oxo-6,7-dihydro-5H-pyrrolo[3,4-b]pyridin-2-yl)benzonitrile, I-174

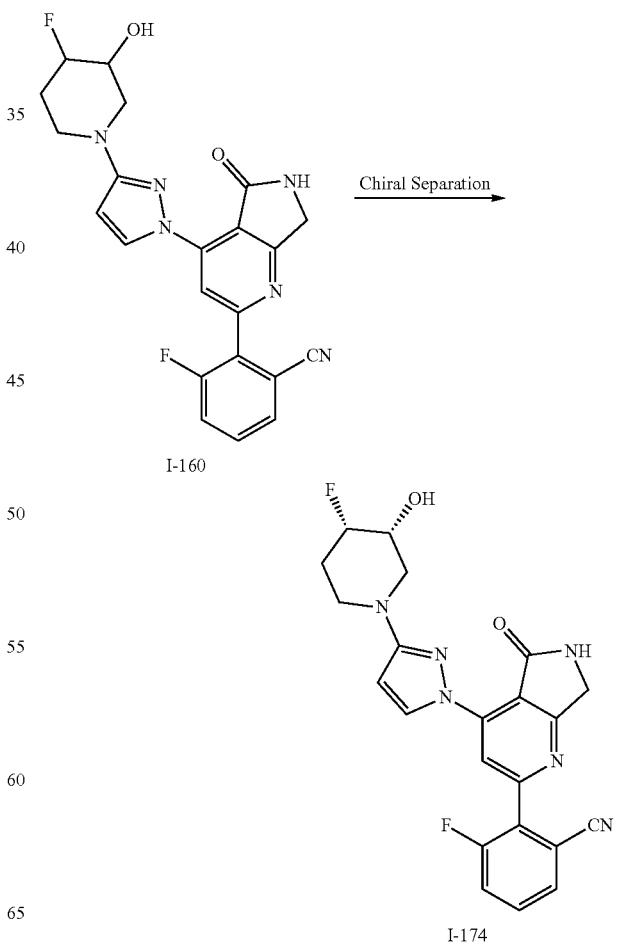

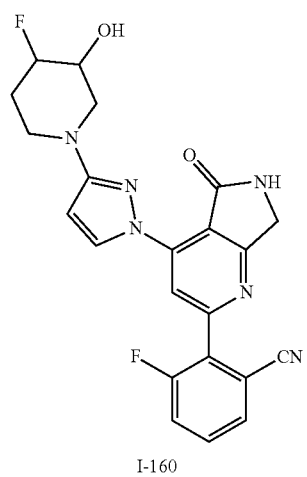

Compound I-174 was prepared by chiral purification of compound I-160. MS(ES): m/z 437 [M+H]$^+$; $^1$H NMR (DMSO-d$_6$, 400 MHz): 9.79 (d, 1H), 9.11 (s, 1H), 8.17 (s, 1H), 7.91-7.89 (m, 1H), 7.83-7.75 (m, 2H), 6.19 (d, 1H), 4.49 (d, 2H), 3.72-3.62 (m, 2H), 3.58-3.43 (m, 4H), 2.17-2.10 (m, 2H).

Example 175

Synthesis of 3-fluoro-2-(5-oxo-4-(3-(3-oxopiperazin-1-yl)-1H-pyrazol-1-yl)-6,7-dihydro-5H-pyrrolo[3,4-b]pyridin-2-yl)benzonitrile, I-175

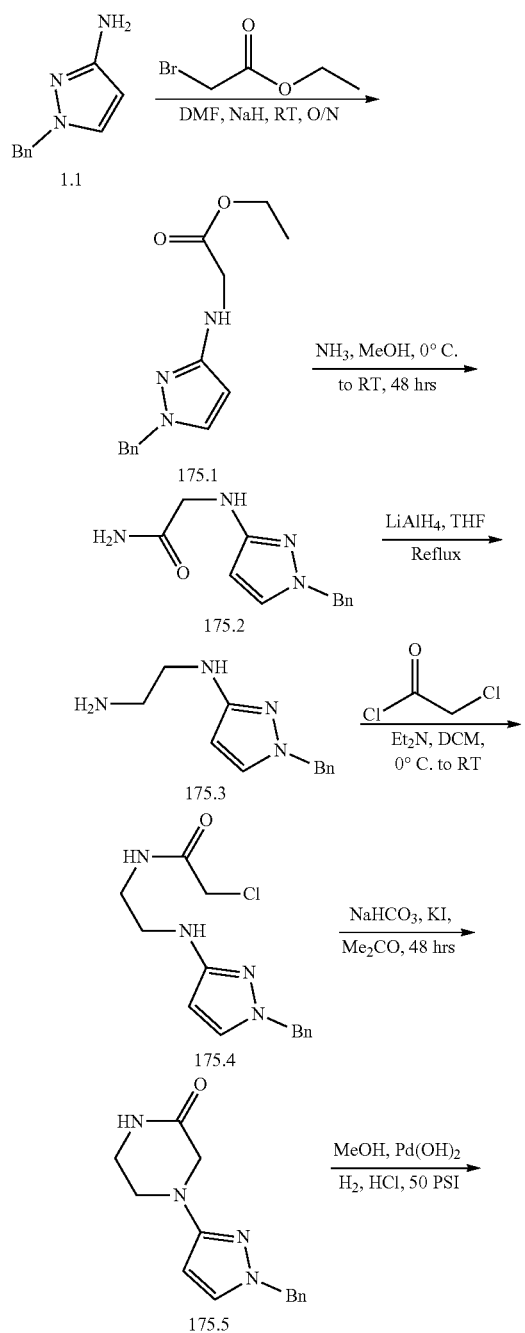

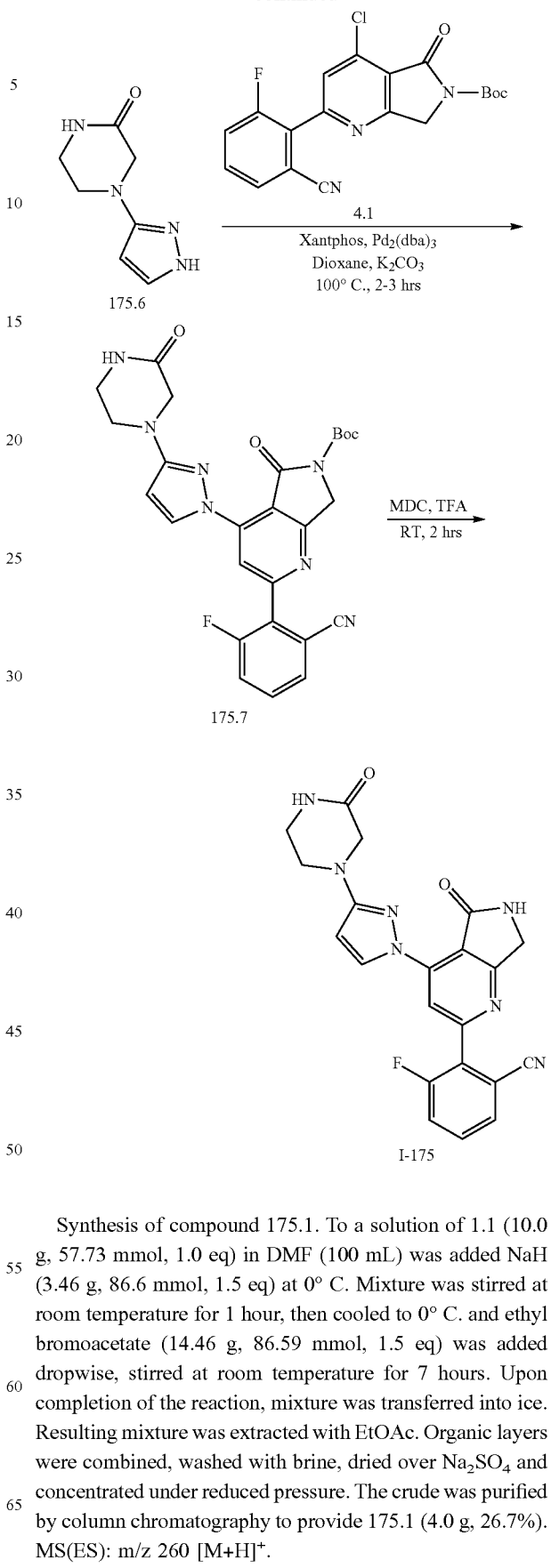

Synthesis of compound 175.1. To a solution of 1.1 (10.0 g, 57.73 mmol, 1.0 eq) in DMF (100 mL) was added NaH (3.46 g, 86.6 mmol, 1.5 eq) at 0° C. Mixture was stirred at room temperature for 1 hour, then cooled to 0° C. and ethyl bromoacetate (14.46 g, 86.59 mmol, 1.5 eq) was added dropwise, stirred at room temperature for 7 hours. Upon completion of the reaction, mixture was transferred into ice. Resulting mixture was extracted with EtOAc. Organic layers were combined, washed with brine, dried over Na$_2$SO$_4$ and concentrated under reduced pressure. The crude was purified by column chromatography to provide 175.1 (4.0 g, 26.7%). MS(ES): m/z 260 [M+H]$^+$.

Synthesis of compound 175.2. A solution of 175.2 (4.0 g, 15.4 mmol, 1.0 eq) in MeOH (40.0 mL), was purged with $NH_3$ gas for 48 h. Upon completion of the reaction, mixture concentrated under reduced pressure and triturated with ether to get 175.2 (3.0 g, 84.55%). MS (ES): m/z 231 $[M+H]^+$.

Synthesis of compound 175.3. To a solution of 175.2 (3.0 g, 13.04 mmol, 1.0 eq) in THF (60 mL), $LiAlH_4$ (39 ml, 40.43 mmol, 3.1 eq) was added at 0° C. Reaction mixture was stirred at 70-80° C. for 3 h. Upon completion of the reaction, mixture was transferred into ice-water solution. Resulting mixture was extracted with EtOAc. Organic layers were combined, washed with brine, dried over $Na_2SO_4$ and concentrated under reduced pressure. Resulting crude was purified by column chromatography to provide pure 175.3 (1.5 g, 53.4%). MS(ES): m/z 218 $[M+H]^+$.

Synthesis of compound 175.4. To a solution of 175.3 (1.5 g, 6.91 mmol, 1.0 eq) in DCM (40 mL) was added $Et_3N$ (2.09 g, 20.69 mmol, 3 eq) at 0° C. Reaction mixture was stirred at room temperature for 1 hour. Reaction mixture was then cooled to 0° C. and Chloroacetyl chloride (1.17 g, 10.3 mmol, 1.5 eq) was added dropwise, stirred at room temperature for 2 h. Upon completion of the reaction, mixture was transferred into ice. Resulting mixture was extracted with EtOAc. Organic layers were combined, washed with brine, dried over $Na_2SO_4$ and concentrated under reduced pressure to provide crude which was purified by column chromatography to provide 175.4 (0.5 g, 25%). MS(ES): m/z 294 $[M+H]^+$.

Synthesis of compound 175.5. To a solution of 175.4 (0.39 g, 1.33 mmol, 1.0 eq) in acetone (30 mL), KI (0.228 g, 1.37 mmol, 1.03 eq) and $NaHCO_3$ (0.458 g, 5.50 mmol, 4.1 eq) were added. Reaction mixture was stirred at 60° C. for 48 h. Upon completion of the reaction, reaction mixture was transferred into ice-water solution. Resulting mixture was extracted with EtOAc Organic layers were combined, washed with brine, dried over $Na_2SO_4$ and concentrated under reduced pressure. Resulting crude was purified by column chromatography to provide 175.5 (0.17 g, 50%). MS(ES): m/z 257 $[M+H]^+$.

Synthesis of compound 175.6. To a solution of 175.5 (0.15 g, 0.58 mmol, 1.0 eq) in MeOH (5 mL). 20% $Pd(OH)_2$ (0.225 g) and 1 N HCl (catalytic amount) were added Reaction mixture was stirred (under hydrogen) at 50 psi for 15 h. Upon completion of the reaction, mixture was filtered through celite-bed and washed with MeOH, concentrated under reduced pressure to obtain crude which was purified by column chromatography to furnish 175.6. (0.09 g, 92.8%). MS(ES): m/z 168 $[M+H]^+$.

Synthesis of compound 175.7. Compound was prepared from 175.6 and 4.1 using the procedure in Example 64.

Synthesis of compound I-175. Compound was prepared from 175.7 using the procedure described in Example 64. MS(ES): m/z 419 $[M+H]^+$; 1H NMR (DMSO-$d_6$, 400 MHz): 9.78 (d, 1H), 9.15 (s, 1H), 8.22 (d, 1H), 8.04 (s, 1H), 7.92-7.90 (m, 1H), 7.83-7.73 (m, 2H), 6.44 (d, 1H), 4.50 (s, 2H), 3.87 (s, 2H), 3.57-3.51 (m, 2H), 3.39-3.29 (m, 2H).

Example 176

Synthesis of 2-(4-(3-((3S,4R)-3,4-dimethoxypiperidin-1-yl)-1H-pyrazol-1-yl)-5-oxo-6,7-dihydro-5H-pyrrolo[3,4-b]pyridin-2-yl)-3-fluorobenzonitrile, I-176

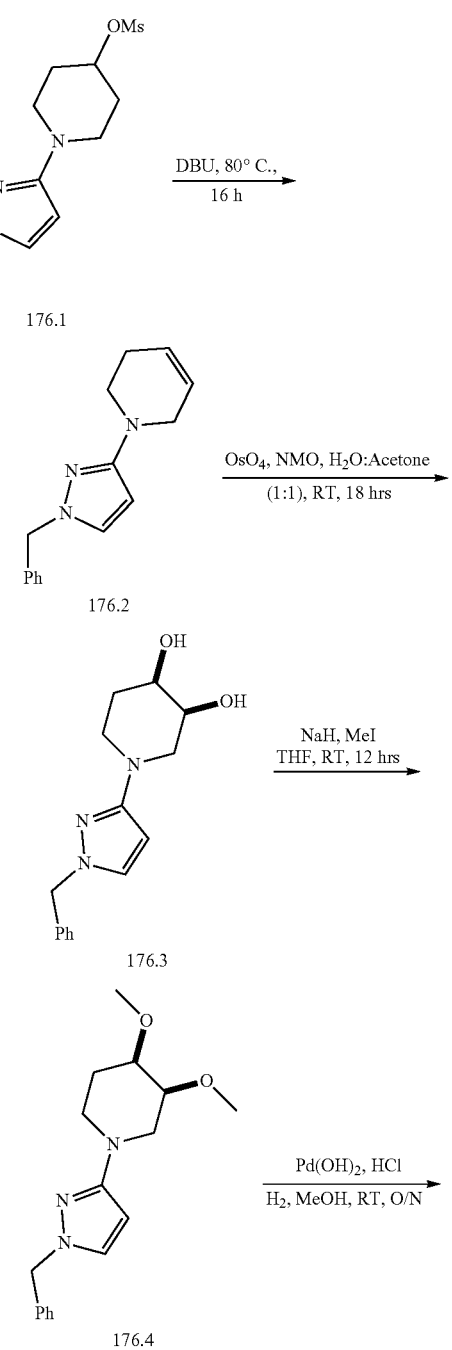

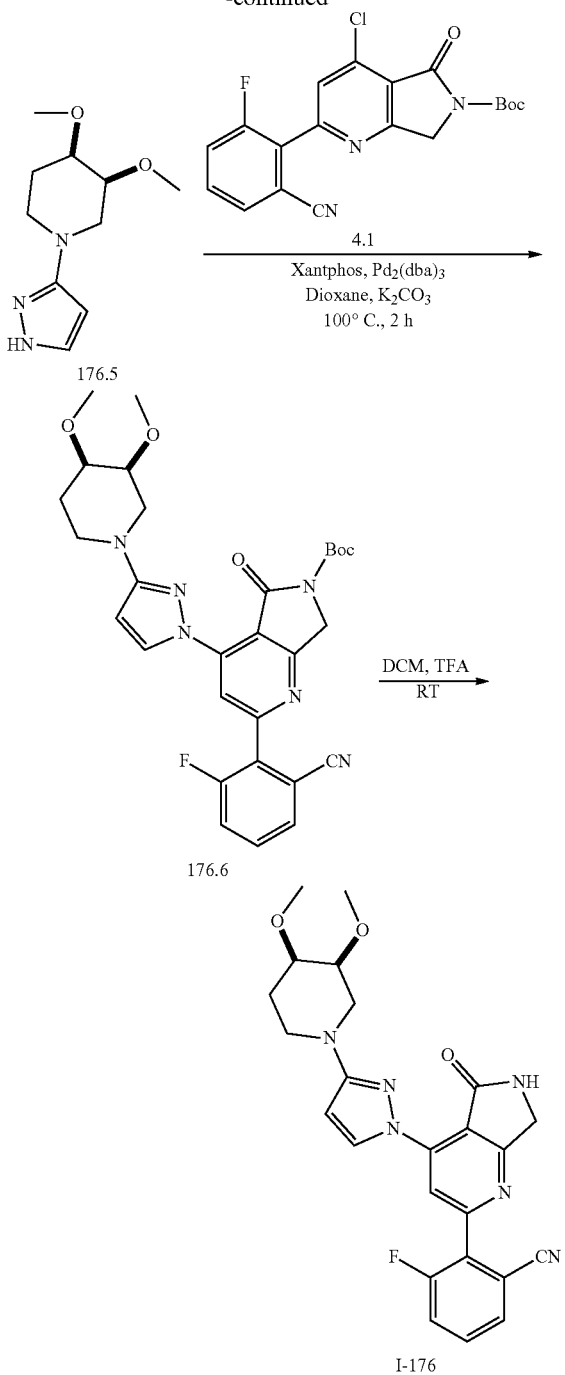

mmol, 2.3 eq) in acetone (31 ml) was added dropwise at 0° C. Reaction mixture was stirred at room temperature for 18 h. Upon completion of the reaction, reaction mixture was transferred into water, extracted with EtOAc. Organic layers were combined, washed with brine, dried over sodium sulphate and concentrated under reduced pressure to pressure to obtain crude which was purified by column chromatography to provide 176.3. (1.6 g, 40%). MS(ES): m/z 274 [M+H]+.

Synthesis of compound 176.4. To a mixture of 176.3 (0.6 g, 2.19 mmol, 1.0 eq) in THF (5.0 mL) was added sodium NaH (0.105 g, 2.6 mmol, 1.2 eq) at 0° C. Methyl iodide was added (0.5 g, 3.2 mmol, 1.5 eq) at 0° C. Reaction mixture was stirred under nitrogen for 12 h. Upon completion of the reaction, reaction mixture was transferred into ice, the extracted with EtOAc. Organic layers were combined, washed with brine, dried over sodium sulphate and concentrated under reduced pressure to pressure to obtain crude which was purified by column chromatography to provide 176.4 (0.120 g, 18.18%). MS(ES): m/z 302 [M+H]+.

Synthesis of compound 176.5. To a solution of 176.4 (0.110 g, 0.36 mmol, 1.0 eq) in methanol (5 ml) 20% Pd(OH)$_2$ on charcoal (0.1 g) and 1N HCl (catalytic amount) were added into reaction. Reaction mixture was stirred under hydrogen at 50 psi for 12 h. Upon completion of the reaction, reaction mixture was filtered. Filtrate was concentrated under reduced pressure to obtain crude which was purified by column chromatography to provide 176.5. (0.040 g, 57.14%). MS(ES): m/z 212 [M+H]+.

Synthesis of compound 176.6. Compound was prepared using the procedure described in Example 64.

Synthesis of compound I-176. Compound was prepared using the procedure described in Example 64. (0.025 g, 60.97%). MS(ES): m/z 463 [M+H]−; 1H NMR (DMSO-d6, 400 MHz): 9.72 (d, H), 8.30 (d, 1H), 7.81-7.78 (m, 1H), 7.74-7.64 (m, 3H), 6.26 (d, 1H), 4.56 (d, 2H), 3.69-3.62 (m, 2H), 3.61-3.59 (m, 2H), 3.54-3.49 (m, 2H), 3.45 (s, 6H), 1.70-1.80 (m, H).

Example 177

Synthesis of N-(1-(2-(2-cyano-6-fluorophenyl)-5-oxo-6,7-dihydro-5H-pyrrolo[3,4-b]pyridin-4-yl)-1H-pyrazol-4-yl)acetamide, I-177

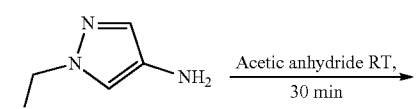

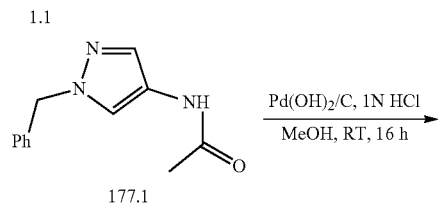

Synthesis of compound 176.2. To a solution of 176.1 (6.0 g, 17.9 mmol, 1.0 eq) in DBU (30 mL) was added at 0° C. under nitrogen, and mixture was stirred at 80° C. for 16 hours. Upon completion of the reaction, reaction mixture was transferred into ice. Resulting mixture was extracted with EtOAc. Organic layers were combined, washed with brine solution, dried over Na$_2$SO$_4$ and concentrated under reduced pressure to get 176.2 (3.3 g, 77.1%). MS(ES): m/z 240 [M+H]+.

Synthesis of compound 176.3. To a solution of Osmium tetroxide (2.6 ml, 0.1 mmol, 0.01 eq) (2% in water) (0.01 eq) in water (31.0 mL) was added N-Methylmorpholine N-oxide (1.7 g, 14.6 mmol, 1.0 eq) at 0° C. then 176.2 (3.5 g, 14.6

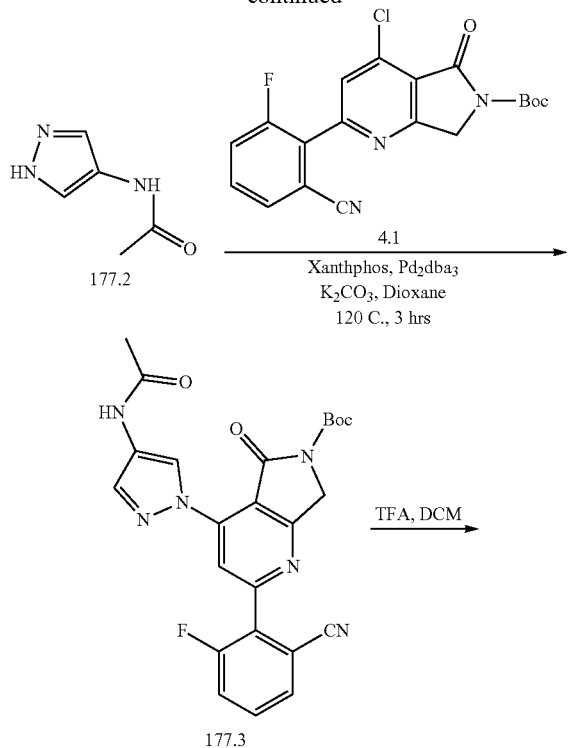

Synthesis of compound I-177. A mixture of 1.1 (0.3 g, 1.73 mmol, 1.0 eq) and acetic anhydride (0.5 mL, 1.73 mmol, 1.0 eq) was stirred at 25° C. for 0.5 h. Upon completion of the reaction; reaction mixture was transferred into water, and extracted with EtOAc. Organic layers were combined, washed with brine, dried over $Na_2SO_4$ and concentrated under reduced pressure to obtain crude which was purified by column chromatography to provide 177.1 (0.34 g, 91.9%). MS(ES): m/z 216 $[M+H]^+$.

Synthesis of compound 177.2. To a solution of 177.1. (0.16 g, 0.74 mmol, 1.0 eq) in MeOH (5 mL) were added 20% $Pd(OH)_2$ on charcoal (0.25 g) and 1N HCl (catalytic amount). Reaction mixture was stirred (under hydrogen) at 40 psi for 16 h. Upon completion of the reaction, reaction mixture was filtered through celite-bed and washed with methanol. Filtrate was concentrated under reduced pressure to obtain crude which was purified by column chromatography to furnish 177.2. (0.04 g, 44.4%). MS(ES): m/z 126 $[M+H]^+$.

Synthesis of compound 177.3. Compound 177.3 was prepared from 177.2 and 4.1 using the procedure described in Example 64.

Synthesis of compound I-177. Compound was prepared from 177.3 using the procedure described in Example 64. MS(ES): m/z 377 $[M+H]^+$; $^1$H NMR (DMSO-$d_6$, 400 MHz): 10.31 (s, 1H), 9.85 (s, 1H), 8.31 (s, 1H), 8.02 (s, 1H), 7.92-7.90 (m, 1H), 7.81-7.76 (m, 2H), 4.53 (s, 2H), 2.03 (s, 3H).

Example 178

Synthesis of 2-(4-(3-((3R,4S)-3,4-dihydroxyazepan-1-yl)-1H-pyrazol-1-yl)-5-oxo-6,7-dihydro-5H-pyrrolo[3,4-b]pyridin-2-yl)-3-fluorobenzonitrile, I-178

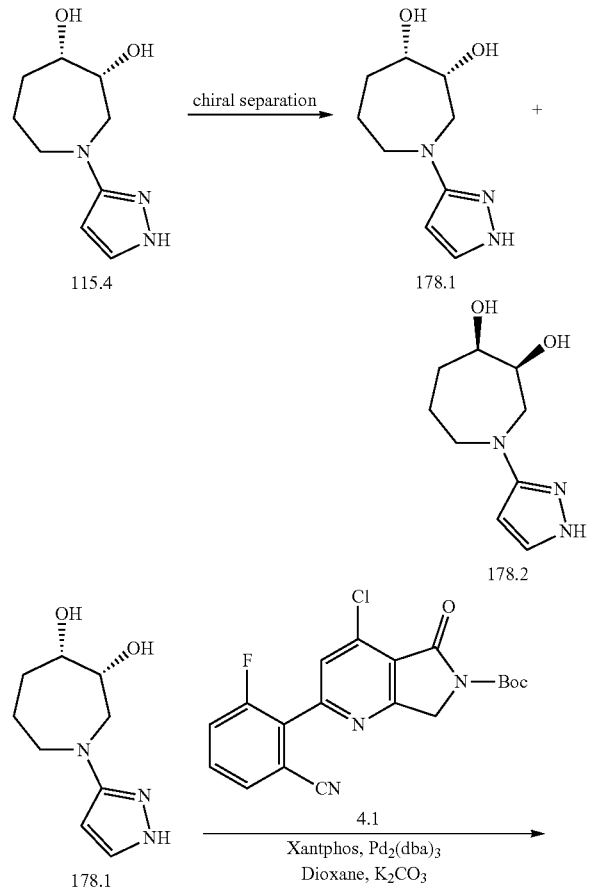

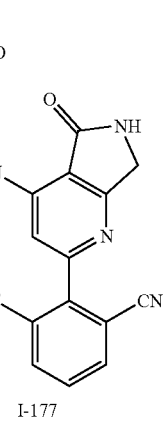

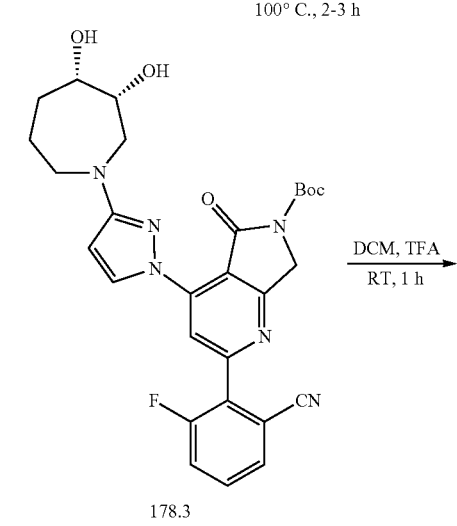

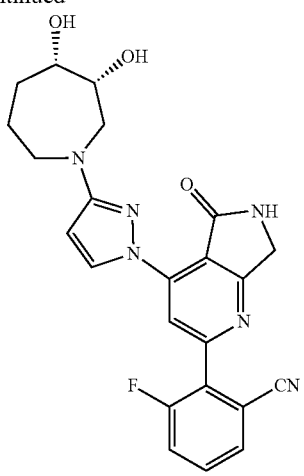

I-178

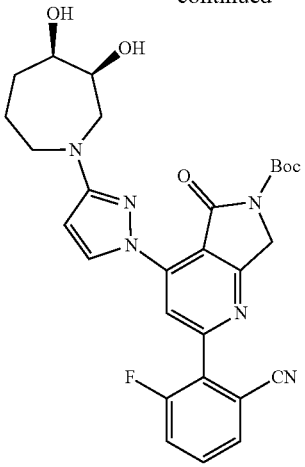

179.1

Synthesis of compounds 171.1 and 178.2. Compounds 171.1 and 178.2 were prepared by chiral separation of compound 115.4.

Synthesis of compound 178.3. Compound 178.3 was prepared from compounds 178.1 and 4.1 using the procedure described in Example 64.

Synthesis of compound I-178. Compound I-178 was prepared from compound 178.3 using the procedure described in Example 64. MS(ES): m/z 449 [M+H]$^+$; $^1$H NMR (CDCl$_3$, 400 MHz): 9.73-9.74 (d, 1H), 8.30 (s, 1H), 7.66 (d, 1H), 7.56-7.60 (m, 1H), 7.47-7.53 (m, 1H), 6.34 (s, 1H), 6.03 (d, 1H), 4.60 (s, 2H), 4.07 (s, 1H), 3.80-3.89 (m, 2H), 3.42-3.50 (m, 4H), 3.28 (d, 1H), 2.45 (d, 1H), 2.05-2.09 (m, 1H), 1.65-1.64 (m, 1H), 1.38-1.33 (m, 1H).

Example 179

Synthesis of 2-(4-(3-((3S,4R)-3,4-dihydroxyazepan-1-yl)-1H-pyrazol-1-yl)-5-oxo-6,7-dihydro-5H-pyrrolo[3,4-b]pyridin-2-yl)-3-fluorobenzonitrile, I-179

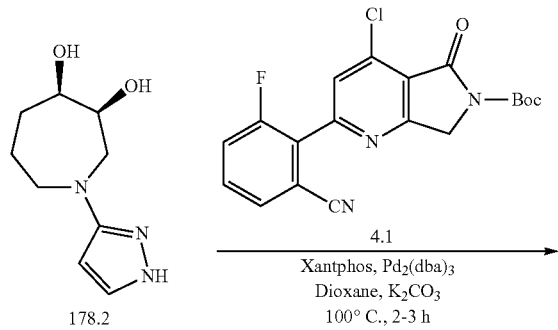

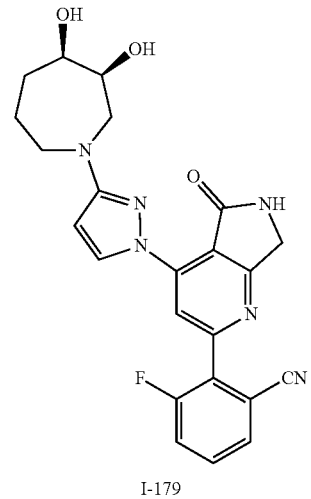

I-179

Compound I-179 was synthesized using the procedure described in Example 64. MS(ES): m/z 449 [M+H]$^-$; $^1$H NMR (DMSO-d$_6$, 400 MHz): 9.76-9.75 (d, 1H), 9.08 (s, 1H), 8.15 (s, 1H), 7.92-7.90 (m, 1H), 7.83-7.73 (m, 2H), 6.24 (d, 1H), 4.67-4.66 (d, 1H), 4.48 (s, 2H), 4.43-4.42 (d, 1H), 3.69-3.68 (m, 2H), 3.59-3.51 (m, 2H), 3.31-3.34 (m, 2H), 1.89-1.80 (m, 2H), 1.65-1.64 (m, 1H), 1.38-1.33 (m, 1H).

Example 180

Synthesis of 2-(2-(2-cyano-6-fluorophenyl)-5-oxo-6,7-dihydro-5H-pyrrolo-[3,4-b]pyridin-4-yl)-4,5,6,7-tetrahydro-2H-pyrazolo[4,3-b]pyridine-6-carboxamide, I-180

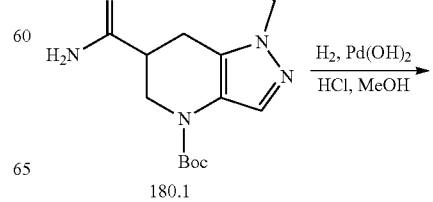

180.1

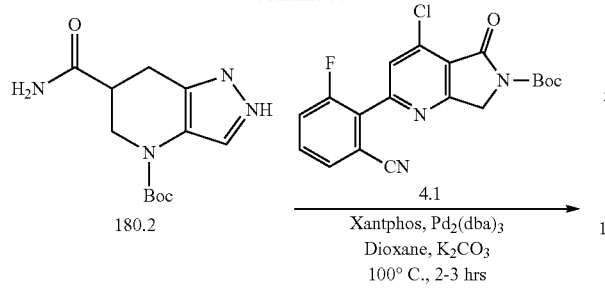

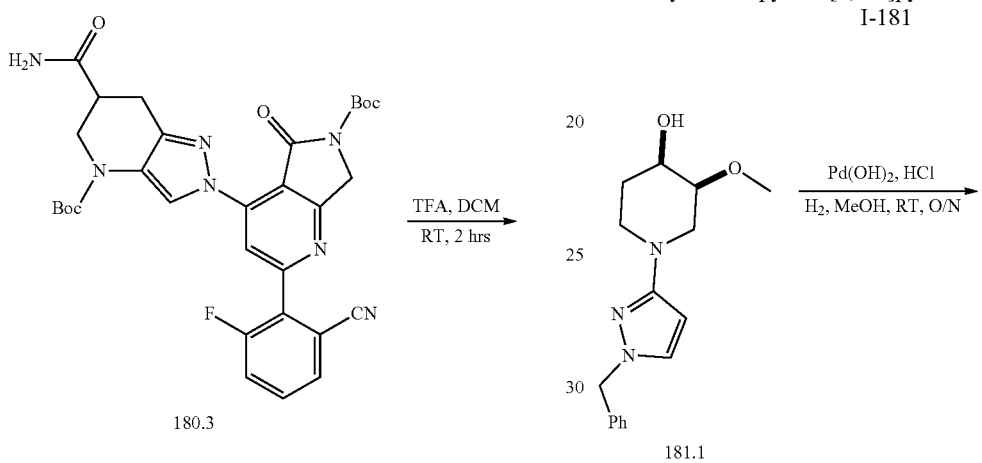

Synthesis of compound I-180. Compound I-180 was prepared from compound 180.3 using the procedure described in Example 64. MS(ES): m/z 418.14 [M+H]$^+$; NMR (MeOD, 400 MHz): 9.18 (s, 1H), 8.33 (s, 1H), 7.8-7.71 (s, 1H), 7.7-7.66 (m, 3H), 5.5 (m, 4H), 4.94 (s, 2H), 3.69-3.58 (m, 1H), 3.02-3.01 (m, 2H), 2.86 (m, 1H).

Example 181

Synthesis of 3-fluoro-2-(4-(3-((3S,4R)-4-hydroxy-3-methoxypiperidin-1-yl)-1H-pyrazol-1-yl)-5-oxo-6,7-dihydro-5H-pyrrolo[3,4-b]pyridin-2-yl)benzonitrile I-181

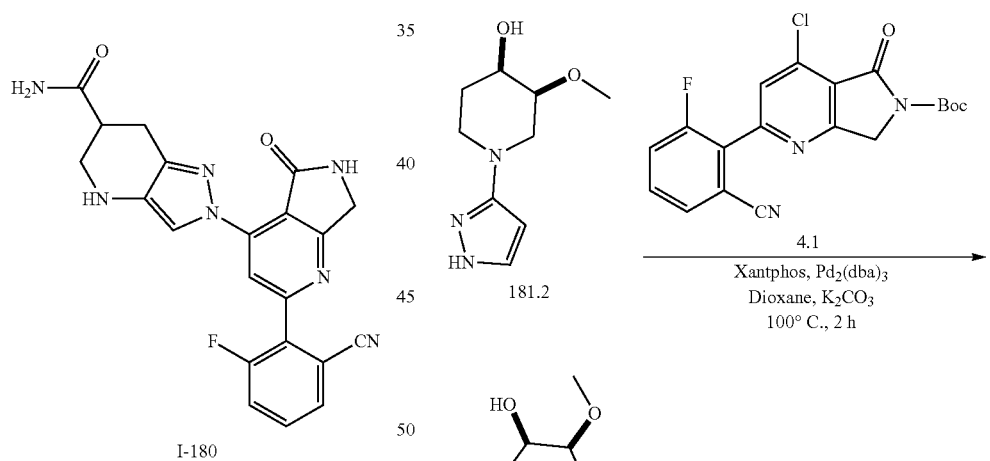

Synthesis of compound 180.2. To a solution of 180.1 (0.06 g, 0.0168 mmol, 1.0 eq) in MeOH (5 mL) was added Pd(OH)$_2$ (0.07 g), dil. HCl (0.1 mL) in 20.0 mL autoclave. The hydrogen was purged to 50 psi. Reaction was stirred at room temperature overnight. Upon completion of the reaction solids were filtered off. The mother liquor was evaporated to obtain crude 180.2 (0.035 g, 78.1%), which was used for next step without purification. LCMS(ES): m/z 267.14 [M+H]$^+$.

Synthesis of compound 180.3. Compound 180.3 was prepared from compounds 180.2 and 4.1 using the procedure described in Example 64,

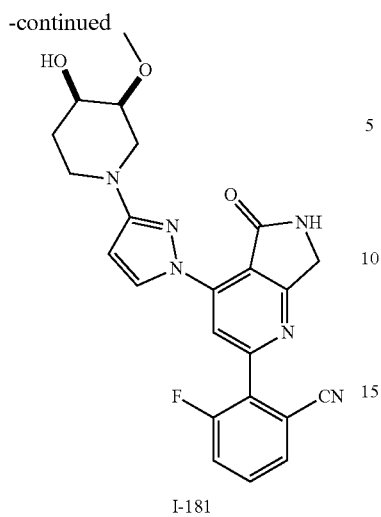

I-181

Synthesis of compound 181.2. To a solution of 181 (0.080 g, 0.27 mmol, 1.0 eq) in MeOH (10 ml) 20% Pd(OH)₂ on charcoal (0.080 g) and 1N HCl (catalytic amount) was added into reaction. Reaction mixture was stirred under hydrogen at 50 psi for 12 h. Upon completion of the reaction, reaction mixture was filtered. Filtrate was concentrated under reduced pressure to obtain crude which was purified by column chromatography to provide 182.2. (0.040 g, 74.07%). MS(ES): m/z 198 [M+H]⁺.

Synthesis of compound 181.3. Compound was prepared using the procedure described in Example 64.

Synthesis of compound I-181. Compound was prepared using the procedure described in Example 64. (0.012 g, 54.5%). MS(ES): m/z 449 [M+H]⁺; ¹H NMR (DMSO-d₆, 400 MHZ): 9.73 (d, 1H), 9.11 (s, 1H), 8.18 (d, 1H), 7.92 (d, 1H), 7.83-7.75 (m, 2H), 6.39 (d, 1H), 4.61 (d, 1H), 4.49 (d, 2H), 3.90 (d, 1H), 3.40-3.25 (m, 8H), 1.75-1.72 (m, 1H), 1.62-1.57 (m, 1H).

Example 182

Synthesis of 2-(4-(3-((3R,4R)-3,4-dihydroxy-3-methylpiperidin-1-yl)-1H-pyrazol-1-yl)-5-oxo-6,7-dihydro-5H-pyrrolo[3,4-b]pyridin-2-yl)-3-fluorobenzonitrile, I-182

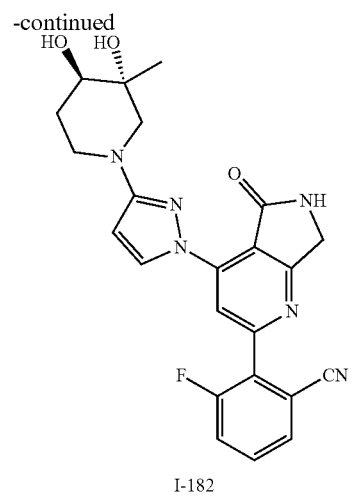

I-182

Compound I-182 was prepared by chiral purification of compound I-108. MS(ES): m/z 449 [M+H]⁺; ¹H NMR (DMSO-d₆, 400 MHz): 9.75 (d, 1H), 9.10 (s, 1H), 8.15 (s, 1H), 7.92-7.90 (m, 1H), 7.83-7.75 (m, 2H), 6.34 (d, 1H), 4.73 (d, 1H), 4.50 (d, 3H), 3.50-3.48 (m, 1H), 3.41-3.39 (m, 1H), 3.13-3.08 (m, 1H), 2.91 (d, 1H), 1.92-1.87 (m, 1H), 1.46-1.42 (m, 1H), 1.08 (s, 3H).

Example 183

Synthesis of (S)-3-fluoro-2-(4-(3-(3-hydroxy-3-(methyl-d3)pyrrolidin-1-yl-2,2,5,5-d4)-1H-pyrazol-1-yl)-5-oxo-6,7-dihydro-5H-pyrrolo[3,4-b]pyridin-2-yl)benzonitrile, I-183

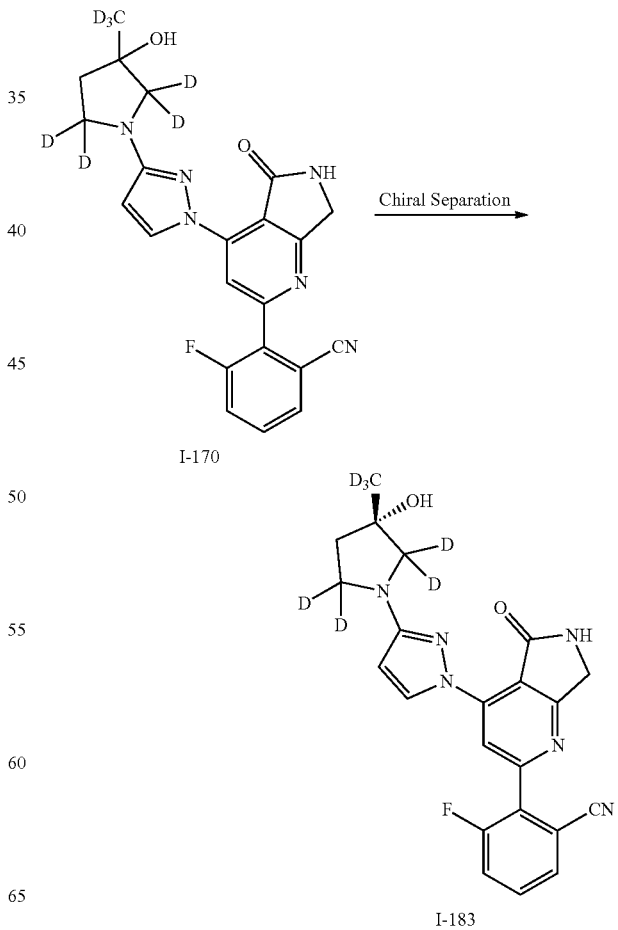

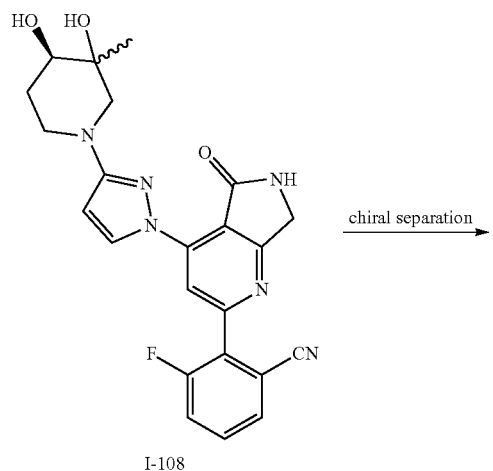

363

Compound I-183 was prepared by purification of compound I-170. MS(ES): m/z 426.48 [M+H]⁺; ¹H NMR (DMSO, 400 MHz): 9.79-9.78 (d, 1H), 9.10 (s, 1H), 8.16 (s, 1H), 7.92-7.90 (m, 1H), 7.81-7.74 (m, 2H), 6.12 (d, 1H), 4.77 (s, 1H), 4.48 (s, 2H), 1.88-1.81 (m, 2H).

Example 184

Synthesis of (R)-3-fluoro-2-(4-(3-(3-hydroxy-3-(methyl-d3)pyrrolidin-1-yl-2,2,5,5-d4)-1H-pyrazol-1-yl)-5-oxo-6,7-dihydro-5H-pyrrolo[3,4-b]pyridin-2-yl)benzonitrile, I-184

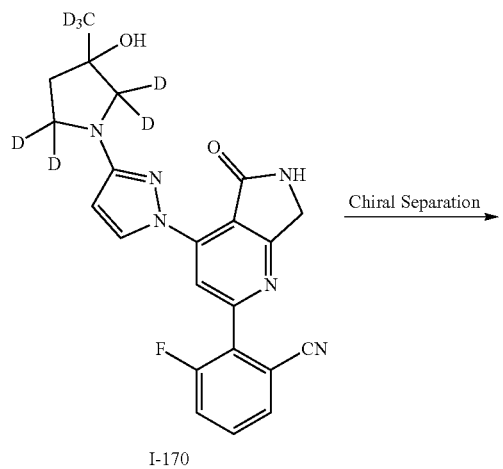

I-170

↓ Chiral Separation

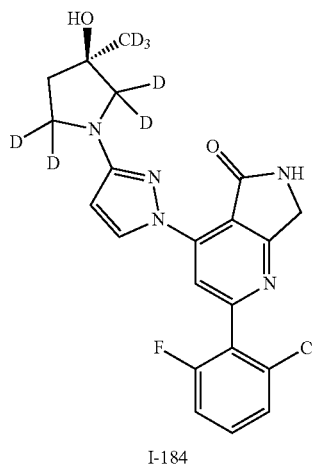

I-184

Compound I-183 was prepared by purification of compound I-170. MS(ES): m/z 426.48 [M+H]+; 1H NMR (DMSO, 400 MHz): 9.79-9.78 (d, 1H), 9.10 (s, 1H), 8.16 (s, 1H), 7.92-7.90 (m, 1H), 7.81-7.74 (m, 2H), 6.12 (d, 1H), 4.77 (s, 1H), 4.48 (s, 2H), 1.88-1.81 (m, 2H).

364

Example 185

Synthesis of 3-fluoro-2-(4-(4-fluoro-3-(3-hydroxy-pyrrolidin-1-yl)-1H-pyrazol-1-yl)-5-oxo-6,7-dihydro-5H-pyrrolo[3,4-b]pyridin-2-yl)benzonitrile, I-185

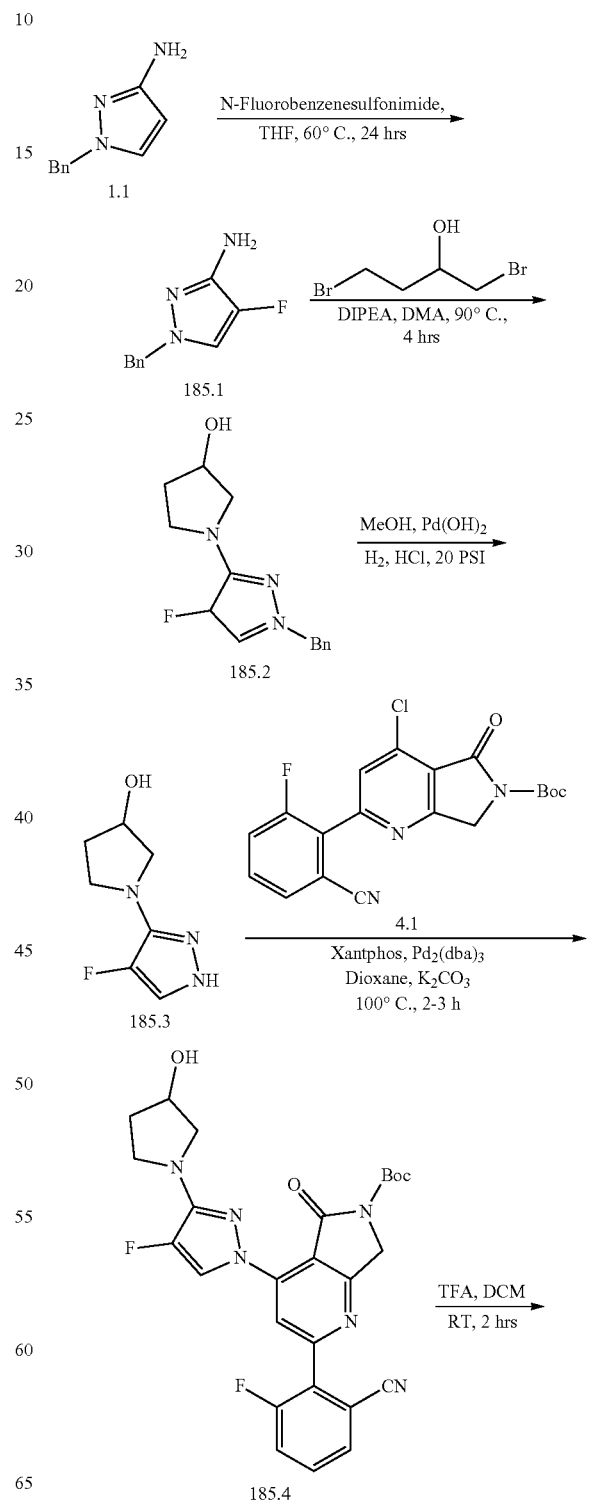

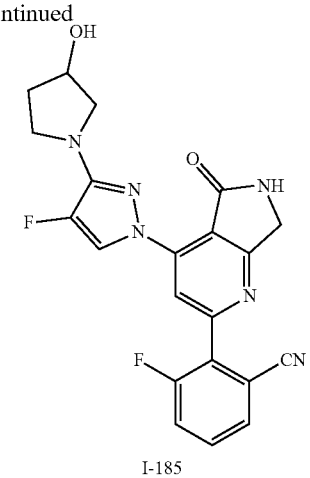

I-185

Synthesis of compound 185.1. To a solution of 1.1 (4.0 g, 23.12 mmole) in dioxane (50 mL) was added N-Fluorobenzenesulfonimide (7.86 g, 24.25 mmole). The resulting mixture was heated to 110° C. for 2 h. Upon completion, the reaction was cooled to room temperature and poured in to water. The product was extracted with EtOAc, washed with brine solution, dried over Na₂SO₄ and concentrated under reduced pressure to obtain crude which was purified by column chromatography to furnish 185.1 (0.3 g, 6.0%). MS(ES): m/z 192.09 [M+H]⁺.

Synthesis of compound 185.2. To a solution of 185.1 (0.3 g, 1.57 mmole) in DMA (5.0 mL) was added 1,4-dibromobutan-2-ol (0.473 g, 2.03 mmole), and DIPEA (1.02 g, 7.85 mmole). The resulting mixture was irradiated under microwave at 100° C. for 80 min. Upon completion of the reaction was cooled to room temperature and poured into water. The product was extracted with EtOAc and combined washed with brine, dried over Na₂SO₄ and concentrated under reduced pressure to obtain crude which was purified by column chromatography to furnish 1.2 (0.15 g, 76.3%). MS(ES): m/z 262.13 [M+H]⁺.

Synthesis of compound 185.3. To a solution of 185.2 (0.15 g, 0.574 mmol, 1.0 eq) in MeOH (3 mL) was added Pd(OH)₂ (0.075 g), dil. HCl (0.05 mL) in a 20 mL autoclave. Hydrogen gas was purged to 50 psi. Reaction was stirred at room temperature overnight. Upon completion of the reaction solids were filtered off. Mother liquor was evaporated to obtain crude which was purified by preparative HPLC to afford 185.3 (0.055 g, 55.97%). LCMS(ES): m/z 172.05 [M+H]⁺.

Synthesis of compound 185.4. Compound 185.4 was prepared from compounds 185.3 and 4.1 using the procedure described in Example 64.

Synthesis of compound I-185. Compound I-185 was prepared from compound 185.3 using the procedure described in Example 64. MS(ES): m/z 423.13 [M+H]⁺; ¹H NMR (DMSO-d₆, 400 MHz): 10.02-10.01 (d, 1H), 9.16 (s, 1H), 8.13 (s, 1H), 7.91-7.89 (dd, 1H), 7.82-7.73 (m, 2H), 4.49 (m, 2H), 4.37-4.35 (m, 1H), 3.55-3.49 (m, 4H), 3.37-3.31 (m, 2H), 2.02-1.94 (m, 1H), 1.86-1.83 (m, 1H).

Example 186

Synthesis of 3-fluoro-2-(4-(3-(3-hydroxy-3-methyl-piperidin-1-yl-2,2,4,4,5,5,6,6-d8)-1H-pyrazol-1-yl)-5-oxo-6,7-dihydro-5H-pyrrolo[3,4-b]pyridin-2-yl)benzonitrile, I-186

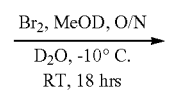

186.1

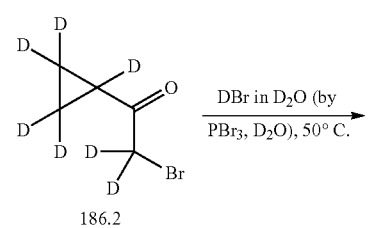

186.2

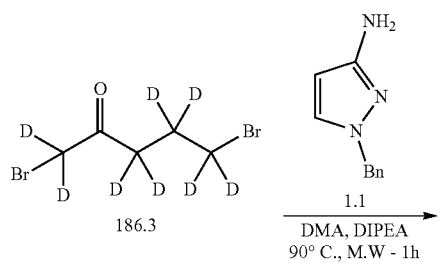

186.3

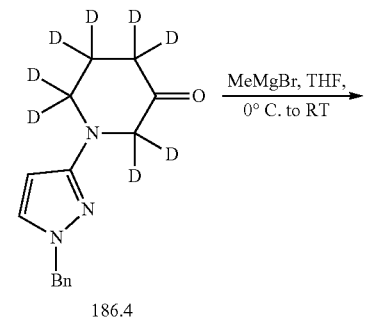

186.4

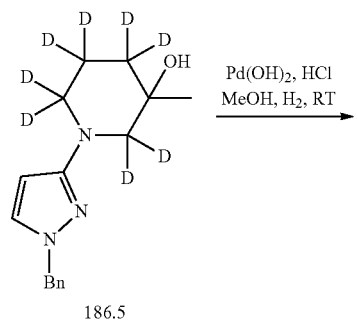

186.5

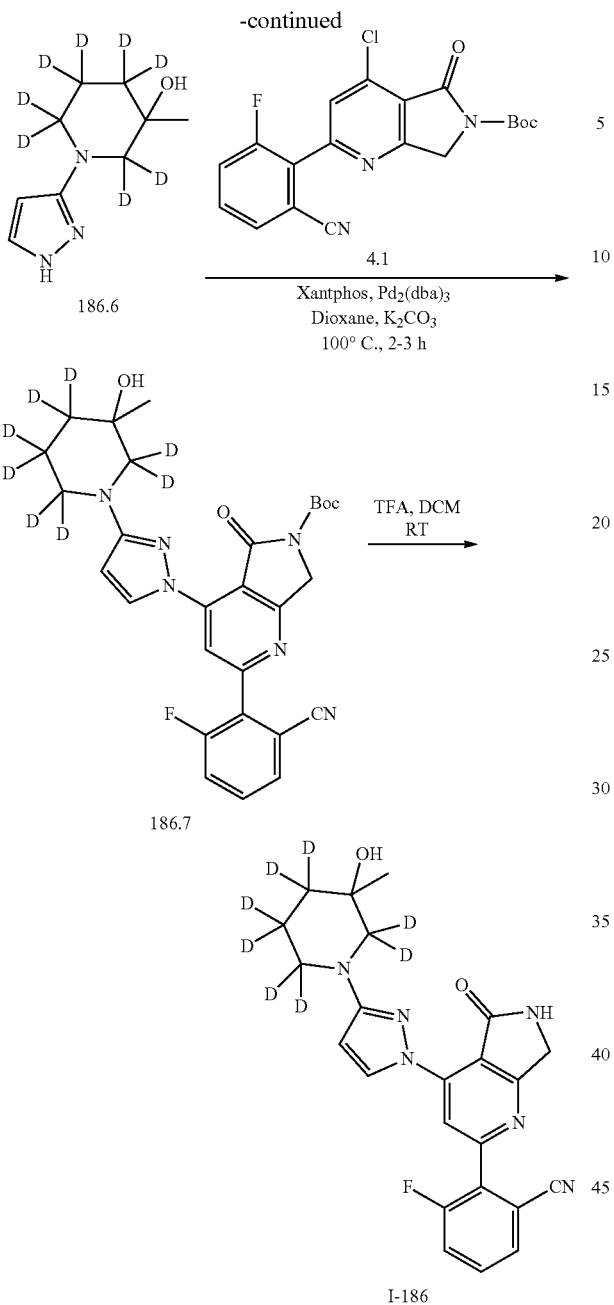

combined, washed with brine, dried over Na₂SO₄ and concentrated under reduced pressure to obtain crude 186.3 which was used as such for next step. (0.37 g, 10.86%). MS(ES): m/z 252.19 [M+H]⁺.

Synthesis of compound 186.4. To a solution of 186.3 (0.37 g, 0.14 mmol, 1.0 eq.) in DMA (5 mL) was added 1.1 (0.25 g, 0.14 mmol, 1.0 eq.) and DIPEA (0.6 ml, 3.5 mmol, 2.5 eq). The reaction mixture was heated to 120° C. for 4 h. Upon completion of the reaction, reaction mixture was transferred into D₂O and product was extracted with EtOAc. Organic layers were combined, washed with brine, dried over Na₂SO₄ and concentrated under reduced pressure to obtain crude which was purified by column chromatography to furnish 186.4 (0.1 g, 25.3%). MS(ES): m/z 264.19 [M+H]⁺, Synthesis of compound 186.5. To a solution of 186.4 (0.1 g, 0.38 mmol, 1.0 eq) in THF (3 mL) was added 1M MeMgBr solution in THF (0.3 mL, 1.1 mmol, 3.0 eq) at 0° C. The reaction mixture was stirred at room temperature for 16 h. Upon completion of the reaction, reaction mixture was transferred into D₂O and product was extracted with DCM. Organic layers were combined, washed with brine, dried over Na₂SO₄ and concentrated under reduced pressure to obtain crude material 186.5. (0.1 g, 94.0%). MS(ES): m/z 280.21 [M+H]⁺.

Synthesis of compound 186.6. To a solution of 186.5 (0.1 g, 0.35 mmol, 1.0 eq) in methanol-d4 (3.0 mL) was added Pd(OH)₂ (0.025 g), dil. HCl (catalyst) in 20 mL autoclave. Autoclave was placed at 50 psi of H₂ gas. The mixture was stirred at room temperature for overnight. Upon completion of the reaction was filtered and solvents removed under reduced pressure to provide 186.6 (0.045 g, 64.0%). LCMS(ES): m/z 190.15 [M+H]⁺.

Synthesis of compound 186.7. Compound was prepared from compound 186.6 using the procedure described in Example 64.

Synthesis of compound I-186. Compound was prepared from 186.7 and 4.1 using the procedure described in Example 64. MS(ES): m/z 440 [M+H]⁺; ¹H NMR (DMSO-d₆, 400 MHz): 9.76-9.75 (d, 1H), 9.09 (s, 1H), 8.15 (s, 1H), 7.92-7.89 (m, 1H), 7.83-7.75 (m, 2H), 6.32 (d, 1H), 4.65 (s, 1H), 4.49 (s, 2H), 1.12 (s, 3H).

Example 187

Synthesis of 3-fluoro-2-(4-(3-(3-hydroxy-2,2-dimethylpyrrolidin-1-yl)-1H-pyrazol-1-yl)-5-oxo-6,7-dihydro-5H-pyrrolo[3,4-b]pyridin-2-yl)benzonitrile I-187

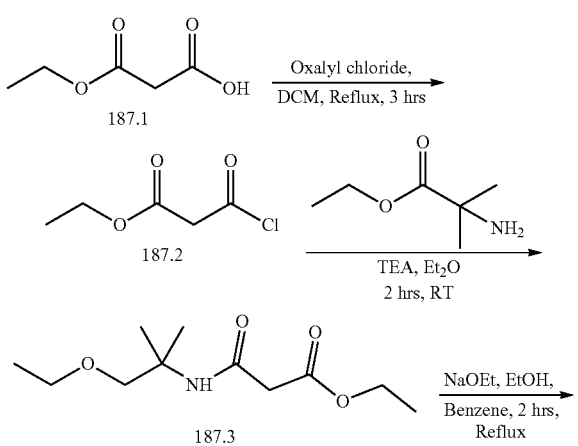

Synthesis of compound 186.2. To a solution of 16.1 (2.3 g, 25.2 mmol, 1.0 eq.) in Methanol-d4 (10 mL) was added Br₂ (1.3 mL, 25.2 mmol, 2.0 eq.), and stirred at 0° C. for 2 h. After 2 h D₂O (5.0 mL) was added and the resulting mixture stirred at room temperature for 16 h. Upon completion of the reaction, reaction mixture was transferred in D₂O and product was extracted with Et₂O. Organic layers were combined, washed with brine, dried over Na₂SO₄ and concentrated under reduced pressure to obtain crude 186.2 which was used as such for next step. 1.1 (2.3 g, 54.20%). MS(ES): m/z 172.19 [M+H]⁺, Synthesis of compound 186.3. A solution 186.2 (2.3 g, 13.5 mmol, 1.0 eq.) in Deuterium bromide solution in deuterium oxide (15 mL) was heated at 60° C. for 5 h. Upon completion of the reaction, mixture was poured into D₂O and product was extracted with Et₂O. Organic layers were -continued

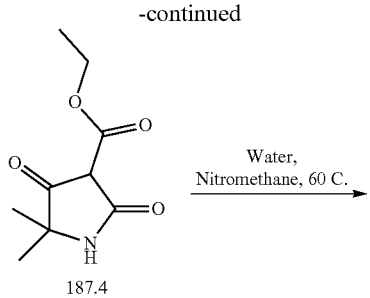
187.4

Water, Nitromethane, 60 C.

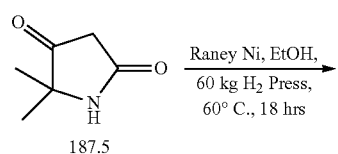
187.5

Raney Ni, EtOH, 60 kg H₂ Press, 60° C., 18 hrs

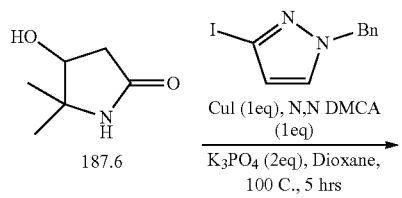
187.6

CuI (1eq), N,N DMCA (1eq)
K₃PO₄ (2eq), Dioxane, 100 C., 5 hrs

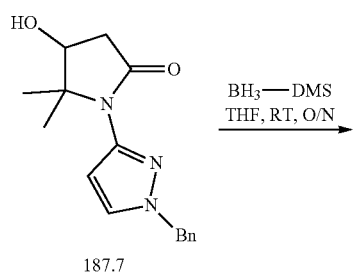
187.7

BH₃—DMS
THF, RT, O/N

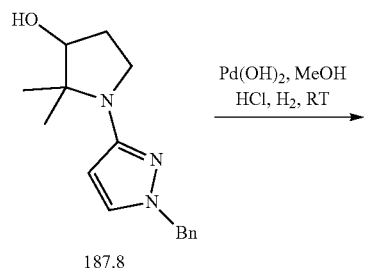
187.8

Pd(OH)₂, MeOH
HCl, H₂, RT

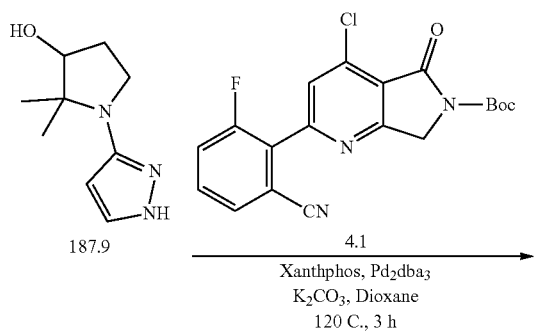
187.9    4.1

Xanthphos, Pd₂dba₃
K₂CO₃, Dioxane
120 C., 3 h

-continued

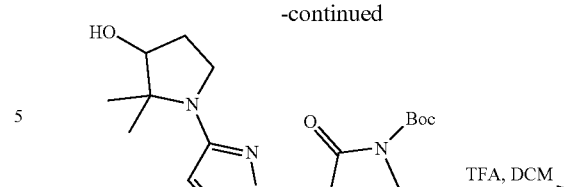
187.91

TFA, DCM

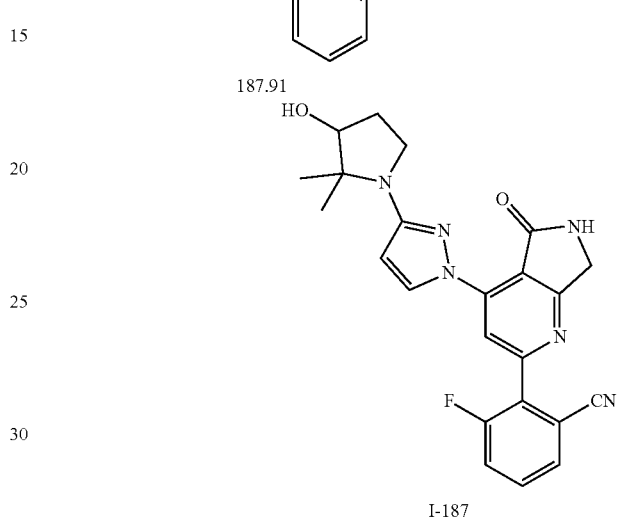
I-187

Synthesis of compound 187.2. To a solution of 187.1 (50 g, 378 mmol, 1 eq) in DCM (500 mL) was added oxalyl chloride (96.01 g, 756 mmol, 2 eq) drop wise at 0° C. over a period of 30 min. The resulting mixture was heated to reflux for 3 h. Upon completion of the reaction solvents were removed to provide crude 1.1 (16.2 g) which was used for next step as such.

Synthesis of compound 187.3. To a solution of 187.2 (18.8 g, 88.88 mmol, 1 eq) in Et₂O (105 mL) was added Et₃N (19.8 g, 196 mmol, 2.2 eq) at 0° C. To this was added ethyl 2-amino-2-methylpropanoate (16.0 g, 106 mmol, 1.2 eq) dropwise over 20 min. The resulting mixture was stirred at room temperature for 2 hours. Upon completion of the reaction, reaction was transferred into ice cold water extracted with Et₂O. Combined organic layers were washed with saturated NaHCO₃, dried over Na₂SO₄. Solvent was concentrated under reduced pressure to get crude 187.3 (10.0 g, 38.4%). MS(ES): m/z 246.11 [M+H]⁺ which was used for next step without further purification.

Synthesis of compound 187.4. To a solution of NaOEt (prepared from Na metal 1.4 g, 1.54 eq in ethyl acetate 26 mL at room temperature) was added benzene (40 mL). The mixture was heated to reflux for 20 min. To this was added 187.3 (10 g, 40.81 mmol, 1 eq) and resulting mixture was stirred at reflux temperature for 2 h. Upon completion of the reaction, mixture was concentrated under reduced pressure to get crude. To crude compound was added 3 N hydrochloric acid and mixture was extracted with DCM, washed with brine, dried over Na₂SO₄ and concentrated under reduced pressure to get crude compound 187.4 (7.5 g, 92.3%). MS(ES): m/z 200.01 [M+H]⁺.

Synthesis of compound 187.5. To a solution of 187.4 (4.6 g, 23.11 mmol, 1 eq) in nitromethane (80 mL) was added water (1.0 mL). The mixture was heated to 125° C. for 45 min. Upon completion of reaction, solvents were removed to obtain crude which was purified by trituration to get pure 187.5. (1.2 g, 41.8%). MS(ES): m/z 128.07 [M+H]+.

Synthesis of compound 187.6. To a solution of 187.5 (700 mg, 5.51 mmol, 1 eq) in ethanol (70 mL) was added Raney Ni (400 mg). The resulting mixture was purged hydrogen (50 psi) and heated to 60° C. for 18 h. Upon completion of the reaction was filtered. Filtrate was concentrated under reduced pressure to get crude which was purified by trituration to provide 187.6. (0.55 g, 77%). MS(ES): m/z 130.25 [M+H]+.

Synthesis of compound 187.7. To a solution of 187.6 (1.4 g, 10.85 mmol, 1.0 eq) in 1,4-dioxane (20 mL) was added 1-benzyl-3-iodo-1H-pyrazole (4 g, 14.1 mmol, 1.5 eq), CuI (2.06 g, 10.87 mmol, 1 eq), potassium phosphate (4.60 g, 21.7 mmol, 2.0 eq) and trans-N,N'-Dimethylcyclohexane-1, 2-diamine (1.54 g, 10.8 mmol, 1 eq) at room temperature and reaction mixture was stirred at 100° C. for 5 h. Upon completion of reaction, reaction mixture was transferred into water and product was extracted with EtOAc. Organic layers were combined, washed with brine, dried over Na$_2$SO$_4$ and concentrated under reduced pressure to obtain crude which was purified by column chromatography to provide 187.7 (0.3 g, 10.2%). MS(ES): 286.15 m/z [M+H]+.

Synthesis of compound 187.8. To a solution of 187.7 (0.05 g, 0.176 mmol, 1 eq) in THF (4.0 mL) was added Borane dimethyl sulfide complex (0.04 g, 0.528 mmol, 3 eq) at room temperature. The resulting mixture was stirred at room temperature for overnight. To this reaction was added methanol (3 mL) at 0° C. The resulting mixture was heated to 80° C. for 1.5 h. Upon completion, the reaction mixture was concentrated under reduced pressure to get crude which was purified by column chromatography to provide 187.8 (0.03 g, 63.09%). MS(ES): 272.17 m/z [M+H]+.

Synthesis of compound 187.9. To a solution of 187.9 (0.03 g, 110.7 mmol, 1.0 eq) in MeOH (3 mL) was added Pd(OH)$_2$ (0.075 g), 1N HCl (0.05 mL) in 20 mL hydrogenator. Reaction mixture was kept under hydrogen pressure (50 psi). The mixture was stirred at room temperature for 16 hours. Upon completion of the reaction, mixture was filtered The filtrate was concentrated under reduced pressure to obtain crude which was purified using prep HPLC to afford 187.9 (0.015 g, 74.86%). LCMS(ES): m/z 182.12 [M+H]+.

Synthesis of compound 187.91. Compound was prepared from 187.9 and 4.1 using the procedure described in Example 64.

Synthesis of compound I-187. Compound was prepared from 187.91 using the procedure described in Example 64. MS(ES): m/z 433.17 [M+H]−; $^1$H NMR (DMSO-d$_6$, 400 MHz): 9.76 (s, 1H), 9.08 (s, 1H), 8.17 (s, 1H), 7.93-7.91 (dd, 1H), 7.7-7.73 (m, 2H), 6.2-6.19 (d, 1H), 5.11-5.1 (d, 1H), 4.48 (s, 2H), 3.83-3.78 (m, 1H), 3.43-3.37 (m, 1H), 2.09-2.04 (m, 1H), 1.38 (s, 3H), 1.22 (s, 3H).

Example 188

Synthesis of 2-(4-(3-((1R,5S)-8-oxa-3-azabicyclo[3.2.1]octan-3-yl)-1H-pyrazol-1-yl)-5-oxo-6,7-dihydro-5H-pyrrolo[3,4-b]pyridin-2-yl)-3-fluorobenzonitrile, I-188

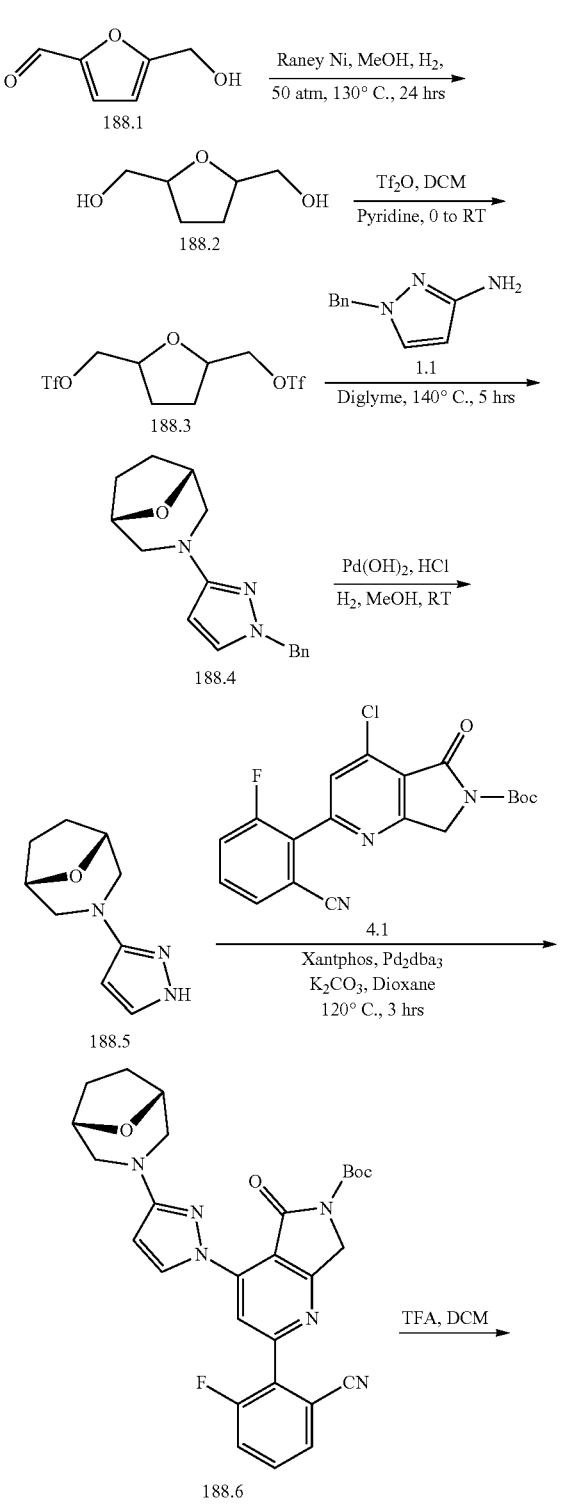

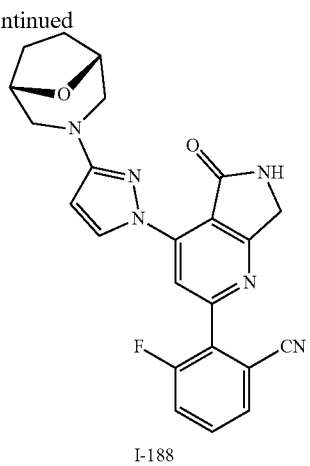

I-188

Synthesis of compound 188.2. To a solution of 188.1 (2 g, 15.87 mmol, 1 eq) in MeOH (80 mL) was added Raney Nickel (1.0 g). The resulting mixture was stirred at 130° C. under 50 atm of $H_2$ pressure for 24 h. Upon completion of the reaction, reaction mixture was filtered. Filtrate was concentrated under reduced pressure to obtain crude which was purified by column chromatography to provide 182.2 (1.3 g, 62.03%). MS(ES): m/z 133.2 [M+H]+.

Synthesis of compound 188.3. To a solution of 182.2 (0.1 g, 0.75 mmol, 1 eq) in DCM (5 mL) was added pyridine (0.18 g, 2.27 mmol, 3.0 eq). Reaction mixture was cooled to 0° C. and $Tf_2O$ (0.42 g, 1.51 mmol, 2.0 eq) was added dropwise. The reaction was stirred at room temperature for 4 h. Upon completion of the reaction, reaction was poured into water and extracted with DCM. Combined organic layers were washed with brine, dried over $Na_2SO_4$ and concentrated under reduced pressure to get crude 188.3 (0.12 g, 40.0%). MS(ES): m/z 397.3 [M+H]+. Crude compound was used in next step without further purification.

Synthesis of compound 188.4. To a solution of 188.3 (0.12 g, 0.303 mmol, 1 eq), in Diglyme (0.5 mL) was added 1.1 (0.157 g, 0.909 mmol, 1.1 eq). The reaction was stirred at 140° C. for 5 h. Upon completion of the reaction, mixture was transferred into water and extracted with EtOAc. Combined organic layers were washed with brine, dried over $Na_2SO_4$ and concentrated under reduced pressure to get crude which was purified by column chromatography to provide 184.4 (0.05 g, 61.3%). MS(ES): m/z 270.4 [M+H]+.

Synthesis of compound 188.5. To a solution of 184.4 (0.050 g, 0.186 mmol, 1.0 eq) in MeOH (10 mL) was added Pd(OH)$_2$ (0.05 g), 1N HCl (catalytic), in hydrogenator. Reaction mixture was stirred under hydrogen (50 psi) at room temperature for 18 h. Upon completion of the reaction, reaction mixture was filtered. Filtrate was concentrated under reduced pressure to obtain crude which was purified by column chromatography to provide 188.5 (0.025 g, 75.11%). MS(ES): m/z 180.3 [M+H]+.

Synthesis of compound 188.6. Compound was prepared from 188.5 and 4.1 using the procedure described in Example 64.

Synthesis of compound I-188. Compound was prepared from 188.6 using the procedure described in Example 64. (0.020 g, 61.63%). MS(ES): m/z 431.38 [M+H]+; $^1$H NMR (DMSO-d$_6$, 400 MHz): 9.77-9.76 (d, 1H), 9.13 (s, 1H), 8.16 (s, 1H), 7.92-7.9 (dd, 1H), 7.84-7.74 (m, 2H), 6.30-6.29 (d, 1H), 4.50 (s, 2H), 4.39 (s, 2H), 3.46-3.43 (m, 2H), 3.01-2.98 (m, 2H), 1.82 (bs, 4H).

Example 189

Synthesis of (R)-3-fluoro-2-(4-(4-fluoro-3-(3-hydroxypyrrolidin-1-yl)-1H-pyrazol-1-yl)-5-oxo-6,7-dihydro-5H-pyrrolo[3,4-b]pyridin-2-yl)benzonitrile, I-189

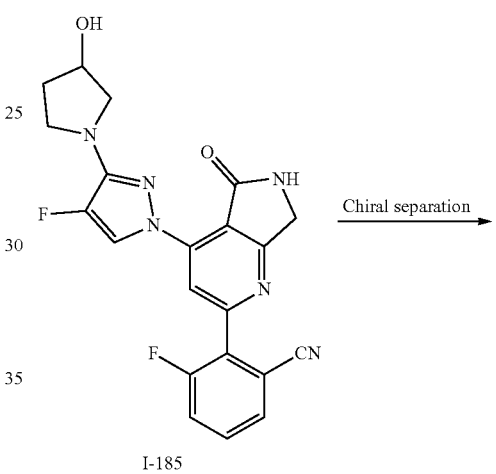

I-185

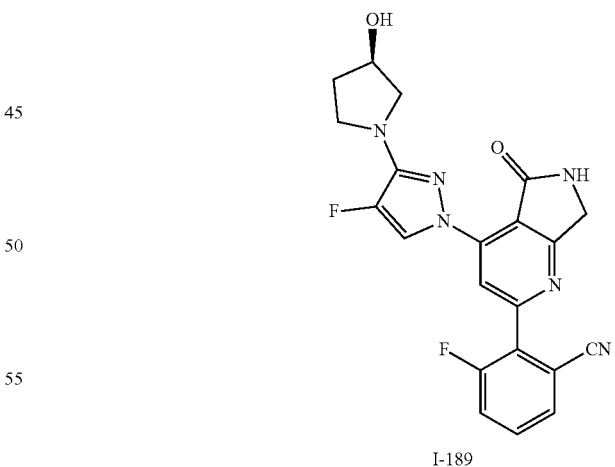

I-189

Compound I-189 was prepared by chiral separation of compound I-189. MS(ES): m/z 423.38 [M+H]+; $^1$H NMR (DMSO-d6, 400 MHz): 10.03-10.02 (d, 1H), 9.17 (s, 1H), 8.13 (s, 1H), 7.92-7.9 (m, 1H), 7.83-7.73 (m, 2H), 4.98-4.97 (m, 1H), 4.49 (s, 2H), 4.36 (s, 1H), 3.55-3.49 (m, 3H), 2.93-2.91 (m, 2H), 2-1.96 (m, 1H), 1.98-1.84 (m, 1H).

Example 190

Synthesis of (S)-3-fluoro-2-(4-(4-fluoro-3-(3-hydroxypyrrolidin-1-yl)-1H-pyrazol-1-yl)-5-oxo-6,7-dihydro-5H-pyrrolo[3,4-b]pyridin-2-yl)benzonitrile, I-190

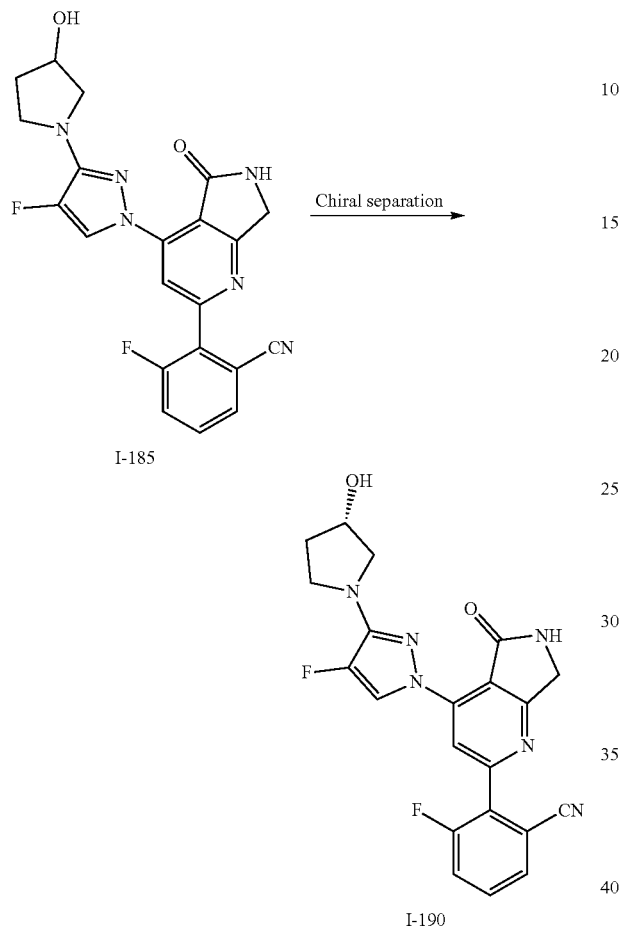

Compound I-190 was prepared by chiral purification of compound I-185. MS(ES): m/z 423.33 [M+H]$^+$; $^1$H NMR (DMSO-d$_6$, 400 MHz): 10.03-10.02 (d, 1H), 9.17 (s, 1H), 8.12 (s, 1H), 7.9-7.89 (m, 1H), 7.82-7.73 (m, 2H), 4.98-4.97 (s, 1H), 4.49 (s, 2H), 4.36 (s, 1H), 3.55-3.48 (m, 3H), 2-1.98 (m, 1H), 1.86-1.83 (m, 1H).

Example 191

Synthesis of 3-fluoro-2-(4-(3-(3-hydroxy-3-(pyrrolidine-1-carbonyl)-pyrrolidin-1-yl)-1H-pyrazol-1-yl)-5-oxo-6,7-dihydro-5H-pyrrolo[3,4-b]pyridin-2-yl)benzonitrile, I-191

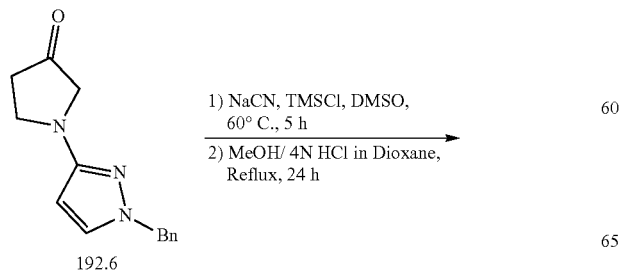

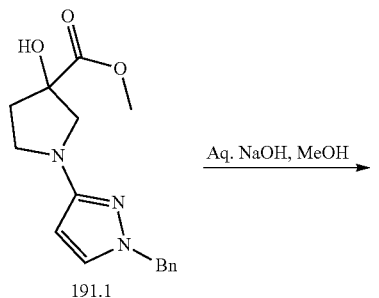

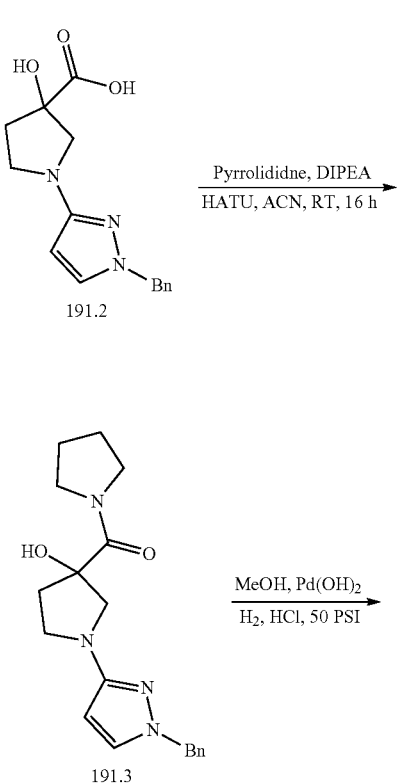

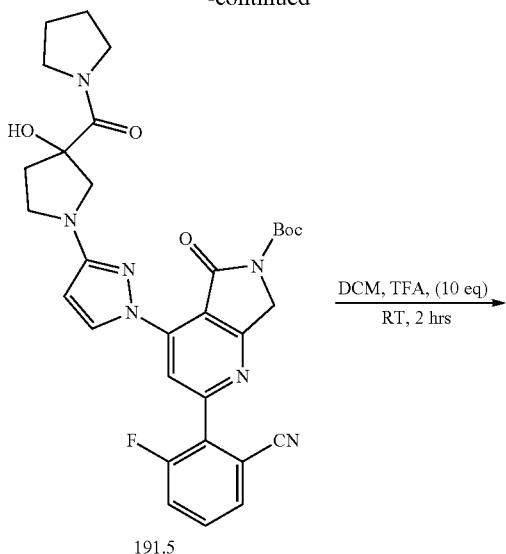

191.5

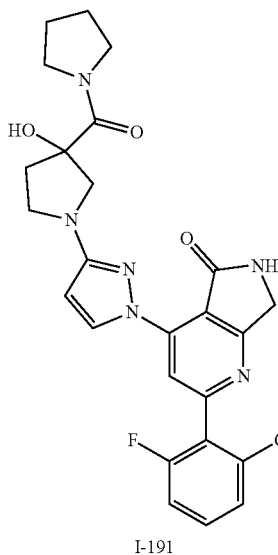

I-191

Synthesis of compound 191.1. To a mixture of 192.6 (2.4 g, 9.95 mmol, 1.0 eq) in DMSO (25 mL) was added NaCN (0.976 g, 19.91 mmol, 2 eq) and trimethylsilyl cyanide (1.6 g, 14.93 mmol, 1.5 eq) at room temperature. Reaction mixture stirred at 65° C. for 30 min. Upon completion of the reaction; reaction mixture was transferred into water, and extracted with EtOAc. Organic layers were combined, washed with brine, dried over Na$_2$SO$_4$ and concentrated under reduced pressure to obtain crude which was was refluxed in MeOH (30.0 ml) for 30 min. Reaction mixture was concentrated under reduced pressure to get crude material 191.1. (1.9 g, 65.0%). MS(ES): m/z 302 [M+H]$^+$.

Synthesis of compound 191.2. To a solution of 191.1 (1.9 g, 6.31 mmol, 1 eq) in THF:MeOH (2:1, 30 ml) was added LiOH (0.795 g, 18.93 mmol, 3.0 eq) in water (5.0 ml) at room temperature. Reaction mixture was stirred at room temperature for 3 h. Upon completion of the reaction, mixture was concentrated under reduced pressure, acidified by 10% citric acid aqueous solution and extracted with EtOAc. Organic layers were combined, washed with brine, dried over Na$_2$SO$_4$ and concentrated under reduced pressure to pressure to obtain crude material 191.2 (1.5 g, 83.3%). MS(ES): m/z 28s [M+H]$^+$.

Synthesis of compound 191.3. To a solution of 191.2 (1.5 g, 5.22 mmol, 1.0 eq) in DMF (15 mL) was added HATU (3.0 g, 7.83 mmol, 1.5 eq) at 0° C. and stirred at this temperature for 30 min followed by addition of pyrrolidine (0.48 ml, 5.74 mmol, 1.1 eq) and DIPEA (2.8 ml, 15.67 mmol, 3.0 eq). Reaction mixture was stirred at room temperature for 16 h. Upon completion of the reaction, reaction mixture was poured into water, and extracted with EtOAc. Organic layers were combined, washed with brine, dried over Na$_2$SO$_4$ and concentrated under reduced pressure to obtain crude which was purified by column chromatography to provide 191.3 (1.6 g, 90.0%). MS(ES): m/z 341 [M+H]$^+$.

Synthesis of compound 191.4. To a solution of 191.3 (1.6 g, 4.70 mmol, 1.0 eq) in MeOH (30 mL) was added 20% Pd(OH)$_2$ on charcoal (0.3 g) and 1N HCl (catalytic). Reaction mixture was stirred under hydrogen for 16 h. Upon completion of the reaction, reaction mixture was filtered through celite and washed with methanol and concentrated under reduced pressure to obtain crude material. This is further treated with polymer bound tetra-alkyl ammonium carbonate in methanol to neutral pH=7, then filtered through celite and filtrate was concentrated under reduced pressure to get 191.4. (1.15 g, 98.1%). MS(ES): m/z 251 [M+H]$^+$.

Synthesis of compound 191.5. Compound was prepared from 191.4 and 4.1 using the procedure described in Example 64.

Synthesis of compound I-191. Compound was prepared from 191.5 using the procedure described in Example 64. MS(ES): m/z 502 [M+H]$^+$; $^1$H NMR (DMSO-d$_6$, 400 MHz): 9.78-9.77 (d, 1H), 9.10 (s, 1H), 8.16 (s, 1H), 7.91 (d, 1H), 7.83-7.76 (m, 2H), 6.17-6.16 (d, 1H), 5.80-5.75 (m, 2H), 4.49 (s, 2H), 3.80-3.72 (m, 4H), 3.48-3.45 (m, 4H), 2.38-2.33 (m, 1H), 2.08 (s, 1H), 1.86-1.83 (m, 2H), 1.75-1.72 (m, 2H).

Example 192

Synthesis of 3-fluoro-2-(4-(3-(8-hydroxy-6,10-di-oxa-2-azaspiro[4.5]decan-2-yl)-1H-pyrazol-1-yl)-5-oxo-6,7-dihydro-5H-pyrrolo[3,4-b]pyridin-2-yl)ben-zonitrile I-192

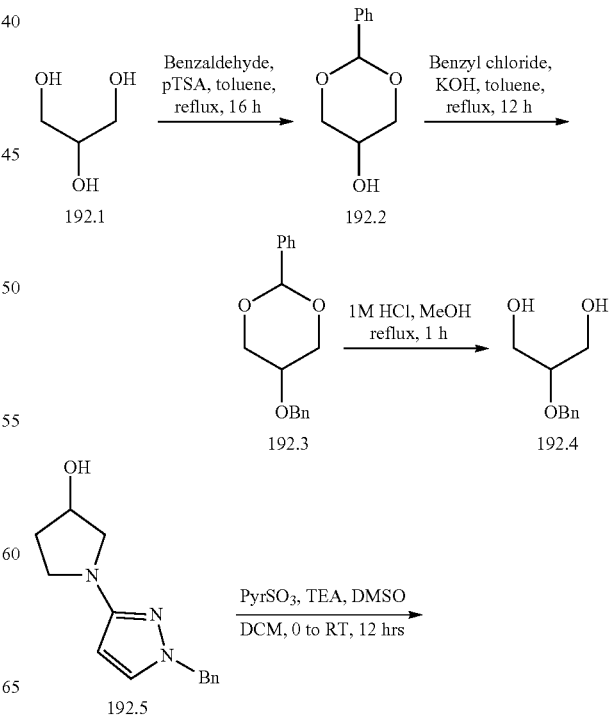

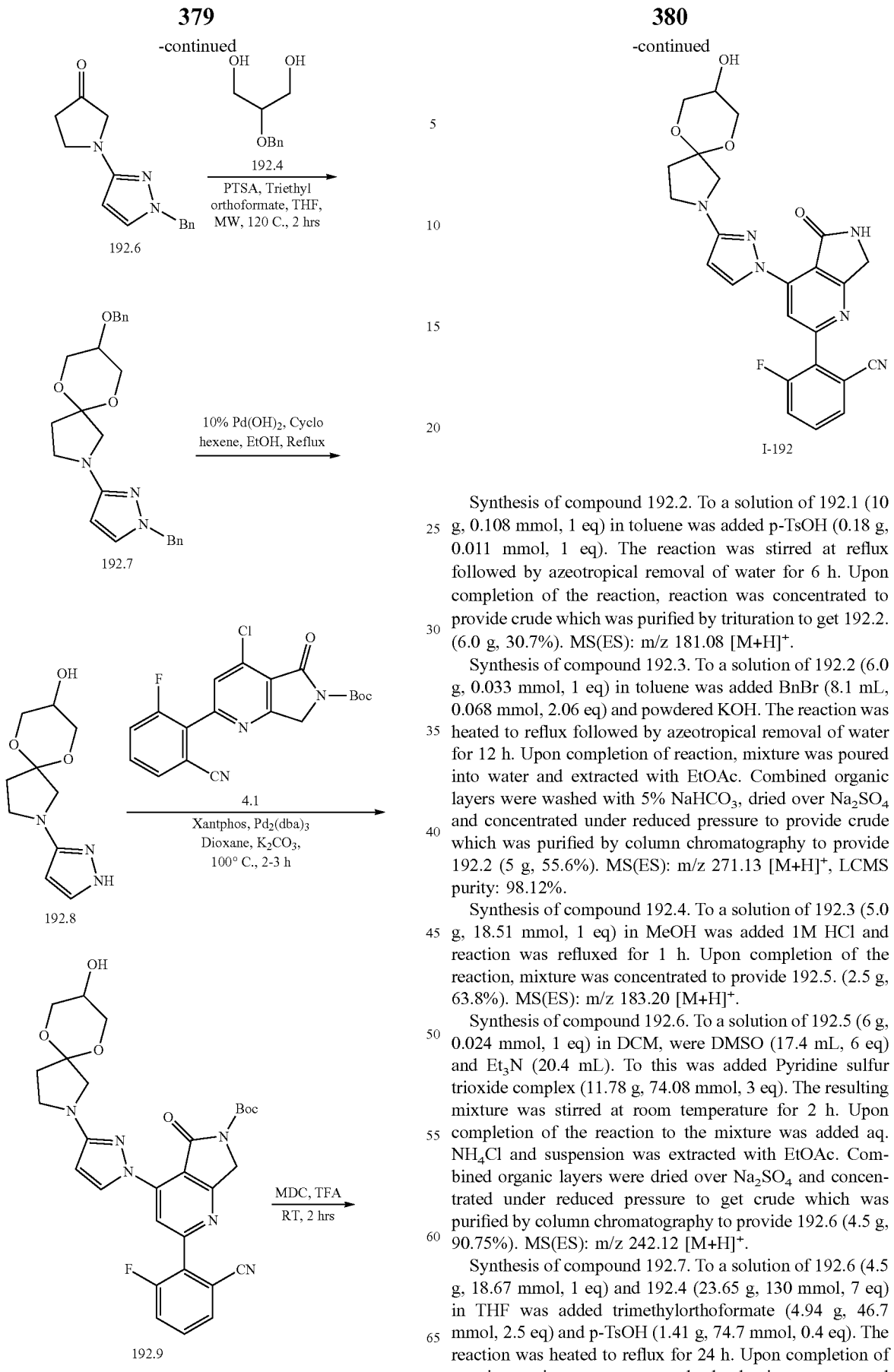

Synthesis of compound 192.2. To a solution of 192.1 (10 g, 0.108 mmol, 1 eq) in toluene was added p-TsOH (0.18 g, 0.011 mmol, 1 eq). The reaction was stirred at reflux followed by azeotropical removal of water for 6 h. Upon completion of the reaction, reaction was concentrated to provide crude which was purified by trituration to get 192.2. (6.0 g, 30.7%). MS(ES): m/z 181.08 [M+H]$^+$.

Synthesis of compound 192.3. To a solution of 192.2 (6.0 g, 0.033 mmol, 1 eq) in toluene was added BnBr (8.1 mL, 0.068 mmol, 2.06 eq) and powdered KOH. The reaction was heated to reflux followed by azeotropical removal of water for 12 h. Upon completion of reaction, mixture was poured into water and extracted with EtOAc. Combined organic layers were washed with 5% NaHCO$_3$, dried over Na$_2$SO$_4$ and concentrated under reduced pressure to provide crude which was purified by column chromatography to provide 192.2 (5 g, 55.6%). MS(ES): m/z 271.13 [M+H]$^+$, LCMS purity: 98.12%.

Synthesis of compound 192.4. To a solution of 192.3 (5.0 g, 18.51 mmol, 1 eq) in MeOH was added 1M HCl and reaction was refluxed for 1 h. Upon completion of the reaction, mixture was concentrated to provide 192.5. (2.5 g, 63.8%). MS(ES): m/z 183.20 [M+H]$^+$.

Synthesis of compound 192.6. To a solution of 192.5 (6 g, 0.024 mmol, 1 eq) in DCM, were DMSO (17.4 mL, 6 eq) and Et$_3$N (20.4 mL). To this was added Pyridine sulfur trioxide complex (11.78 g, 74.08 mmol, 3 eq). The resulting mixture was stirred at room temperature for 2 h. Upon completion of the reaction to the mixture was added aq. NH$_4$Cl and suspension was extracted with EtOAc. Combined organic layers were dried over Na$_2$SO$_4$ and concentrated under reduced pressure to get crude which was purified by column chromatography to provide 192.6 (4.5 g, 90.75%). MS(ES): m/z 242.12 [M+H]$^+$.

Synthesis of compound 192.7. To a solution of 192.6 (4.5 g, 18.67 mmol, 1 eq) and 192.4 (23.65 g, 130 mmol, 7 eq) in THF was added trimethylorthoformate (4.94 g, 46.7 mmol, 2.5 eq) and p-TsOH (1.41 g, 74.7 mmol, 0.4 eq). The reaction was heated to reflux for 24 h. Upon completion of reaction, mixture was poured slowly into water and extracted with EtOAc. Combined organic layers was washed with 5% NaHCO$_3$, dried over Na$_2$SO$_4$ and concentrated under reduced pressure to get crude which was purified by column chromatography to furnish 192.7 (1.4 g, 18.5%). MS(ES): m/z 406.21 [M+H]$^+$.

Synthesis of compound 192.8. To a solution of 192.7 (1.4 g, 3.45 mmol, 1.0 eq) in cyclohexane, ethanol was added Pd(OH)$_2$ (0.5 g) in 20 mL hydrogenator and the resulting mixture was heated to reflux under hydrogen pressure for 3 hours then at temperature overnight. Upon completion of the reaction was filtered and mother liquor was concentrated to obtain crude which was purified by column chromatography to provide 192.8 (0.4 g, 51.5%). MS(ES): m/z 226.11 [M+H]$^+$, LCMS purity: 98.12%.

Synthesis of compound 192.9. Compound was prepared from 192.8 and 4.1 using the procedure described in Example 64.

Synthesis of compound I-192. Compound was prepared from 192.9 using the procedure described in Example 64. MS(ES): m/z 477.2 [M+H]$^+$; $^1$H NMR (DMSO-d$_6$, 400 MHz): 9.77-9.76 (m, 1H), 9.11 (s, 1H), 8.17 (m, 1H), 7.92-7.90 (m, 1H), 7.79-7.76 (m, 2H), 6.2-6.17 (dd, 1H), 5.10-5.09 (d, 1H), 4.49 (s, 2H), 3.94-3.89 (m, 2H), 3.60-3.56 (m, 2H), 3.52-3.51 (m, 2H), 3.43-3.41 (m, 2H), 2.33-2.25 (t, 1H), 2.18-2.17 (t, 1H).

Example 193

Synthesis of 3-fluoro-2-(4-(3-((3R,4R)-3-hydroxy-4-methoxypiperidin-1-yl)-1H-pyrazol-1-yl)-5-oxo-6,7-dihydro-5H-pyrrolo[3,4-b]pyridin-2-yl)benzonitrile, I-193

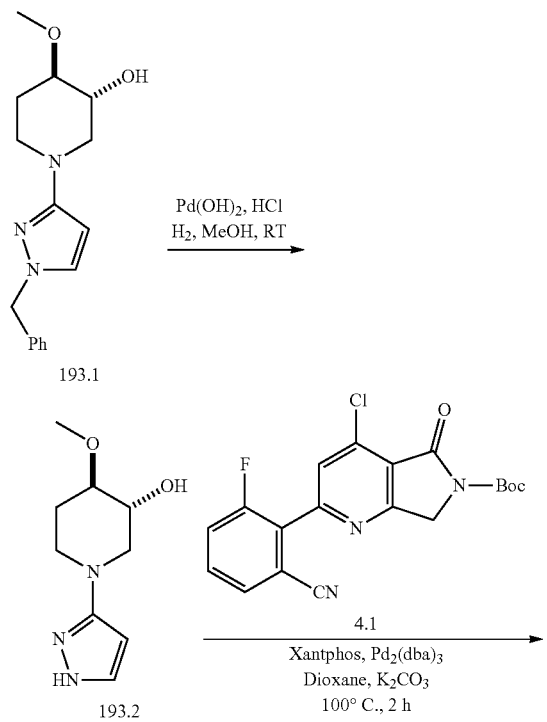

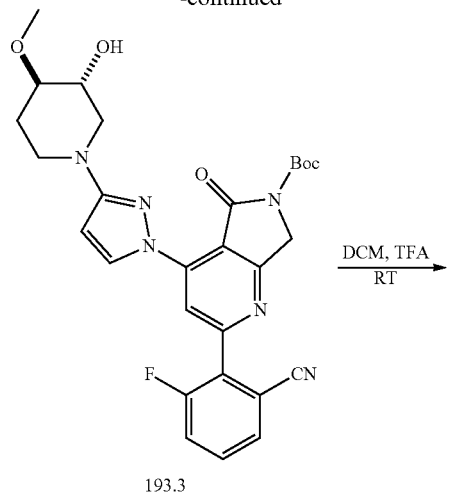

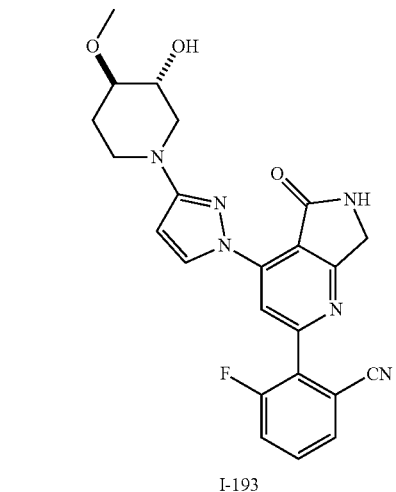

Synthesis of compound 193.2. To a solution of 193.1 (0.2 g, 0.696 mmol, 1.0 eq) in MeOH (3 mL) was added Pd(OH)$_2$ (0.5 g) and 1N HCl (0.5 mL) in hydrogenator. The reaction mixture was stirred at room temperature under hydrogen pressure of 40 psi for 16 h. Upon completion of the reaction, mixture was filtered. Filtrate was concentrated under reduced pressure to obtain crude which was purified by column chromatography to provide 193.2 (0.12 g, 87.4%). MS(ES): m/z 198.23 [M+H]$^+$.

Synthesis of compound 193.3. Compound was prepared from 4.1 and 193.3 using the procedure described in Example 64.

Synthesis of compound I-193. Compound was prepared using the procedure described in Example 64. (0.12 g, 49.9%). MS(ES): m/z 449.17 [M+H]$^+$; $^1$H NMR (DMSO-d$_6$, 400 MHz): 9.75 (s, 1H), 9.12 (s, 1H), 8.16 (s, 1H), 7.96-7.9 (dd, 1H), 7.83-7.73 (m, 2H), 6.36-6.35 (d, 1H), 5.08-5.07 (d, 1H), 4.49 (s, 2H), 3.7-3.67 (m, 1H), 3.64-3.47 (m, 1H), 3.46-3.39 (m, 1H), 3.12-3.07 (m, 1H), 2.96-2.91 (m, 1H), 2.79-2.67 (s, 1H), 2.08-1.99 (m, 1H), 1.42-1.33 (m, 1H).

Example 194

Synthesis of 3-fluoro-2-(4-(3-(3-hydroxypyrrolidin-1-yl-2,2,3,4,4,5,5-d7)-1H-pyrazol-1-yl)-5-oxo-6,7-dihydro-5H-pyrrolo[3,4-b]pyridin-2-yl)benzonitrile, I-194

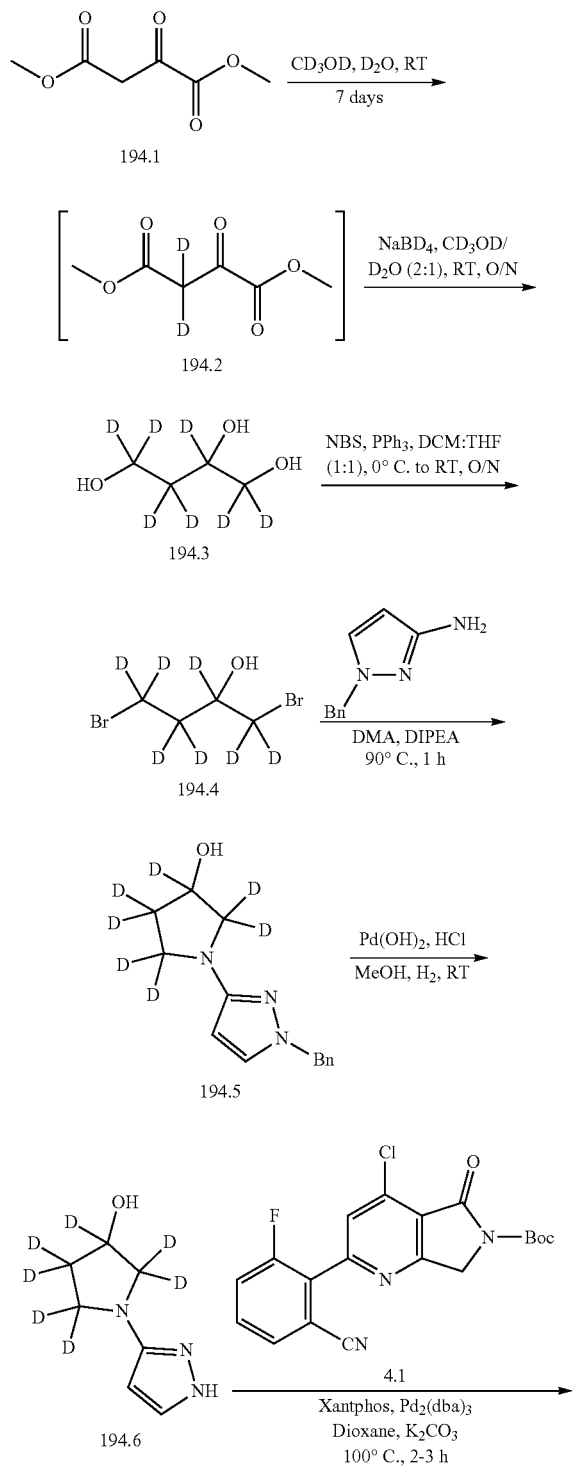

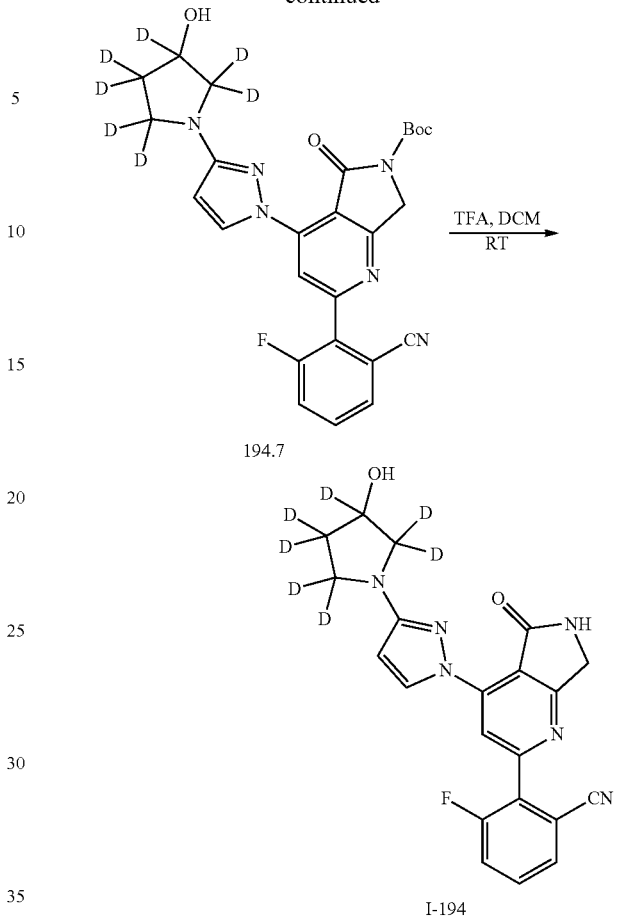

Synthesis of compound 194.2. To a solution of 194.1 (1.7 g, 10.6 mmol, 1.0 eq) in deuterated methanol (5.1 ml) was added D₂O (2.55 mL). Reaction mixture was stirred at room temperature for 7 days. Upon completion of reaction, reaction mixture was concentrated under reduced pressure to obtain crude which was purified by column chromatography to provide 194.2. (0.630 g, 36.6%). ¹H NMR (CDCl₃, 400 MHZ): 3.61 (s, 3H), 3.66 (s, 3H).

Synthesis of compound 194.3. To a mixture 194.2 (0.630 g, 3.61 mmol, 1.0 eq) in deuterated methanol (2 mL) was added solution of NaBD₄ (0.453 g, 10.8 mmol, 3.0 eq) in D₂O (1 ml) at 0° C. Reaction mixture was stirred at room temperature for 15 h. Upon completion of the reaction, mixture was transferred into 6 N hydrochloric acid solution, extracted with DCM. Organic layers were combined, washed with brine solution, dried over Na₂SO₄ and concentrated under reduced pressure to pressure to obtain crude which was purified by column chromatography to get pure 1.2 (0.33 g, 80.7%). ¹H NMR (CDCl₃, 400 MHz): 5.22 (s, 2H), 4.52 (s, 1H).

Synthesis of compound 194.4. To a solution of 194.3 (0.33 g, 2.99 mmol, 1 eq) in THF (1.5 ml) was added PPh₃ (1.57 g, 5.99 mmol, 2.0 eq) and DCM (3.0 mL) at 0° C. then NBS (1.06 g, 5.99 mmol, 2.0 eq) was added dropwise at 0° C. Reaction mixture was stirred at room temperature for 15 h. Upon completion of the reaction, mixture was transferred into water, extracted with EtOAc. Organic layers were combined, washed with brine, dried over Na₂SO₄ and concentrated under reduced pressure to pressure to obtain crude which was purified by column chromatography to provide get pure 194.4 (0.19 g, 29.5%). MS(ES): m/z 240 [M+H]+.

Synthesis of compound 194.5. To a solution of 194.4 (0.19 g, 0.79 mmol, 1.0 eq) and 1-benzyl-1H-pyrazol-3-amine (0.137 g, 0.79 mmol, 2.0 eq) in DMA (5 ml), DIPEA was added (0.250 g, 1.98 mmol, 2.5 eq). Reaction was stirred at 90° C. for 1 hr in Microwave. Upon completion of reaction, reaction mixture was transferred into water and extracted with EtOAc, dried over Na2SO4 and concentrated under reduced pressure to obtain crude which was purified by column chromatography to furnish 194.5. (1.2 g, 61.53%). MS(ES): m/z 251 [M+H]+.

Synthesis of compound 194.6. To a solution of 194.5 (0.1 g, 0.4 mmol, 1.0 eq) in MeOH (5 mL). 20% Pd(OH)2 on charcoal (0.02 g) and 1N HCl (catalytic amount) was added. Reaction mixture was stirred(under hydrogen at 40 psi for 15 h. Upon completion of the reaction, reaction mixture was filtered. Filtrate was concentrated under reduced pressure to obtain crude which was purified by column chromatography to get 194.6. (0.052 g, 83.9%). MS(ES): m/z 161 [M+H]+.

Synthesis of compound 194.7. Compound was prepared from 194.6 and 4.1 using the procedure described in Example 64

Synthesis of compound I-194. Compound was prepared using the procedure described in Example 64. (0.075 g, 78.94%). MS(ES): m/z 412 [M+H]+; 1H NMR (DMSO, 400 MHz): 9.79-9.78 (d, 1H), 9.09 (s, 1H), 8.17 (s, 1H), 7.92-7.90 (m, 1H), 7.83-7.73 (m, 2H), 6.14 (d, 1H), 4.90 (s, 1H), 4.48 (s, 2H).

Example 195

Synthesis of 3-fluoro-2-(4-(3-((3R,4R)-4-hydroxy-3-methoxypiperidin-1-yl)-1H-pyrazol-1-yl)-5-oxo-6,7-dihydro-5H-pyrrolo[3,4-b]pyridin-2-yl)benzonitrile, I-195

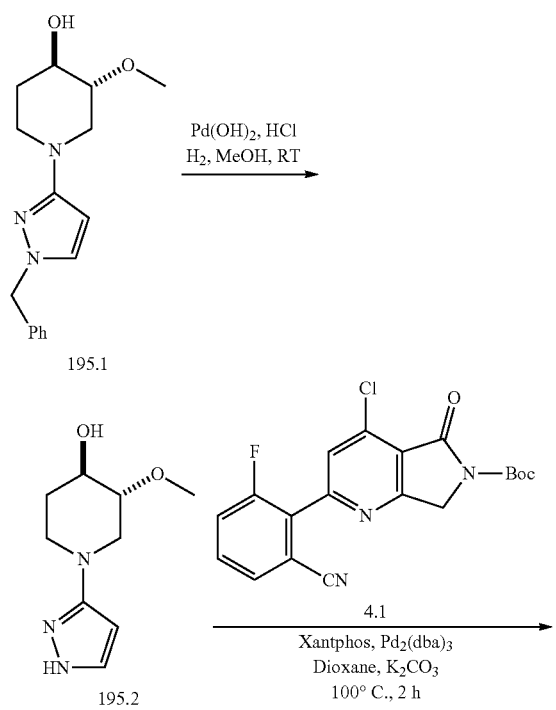

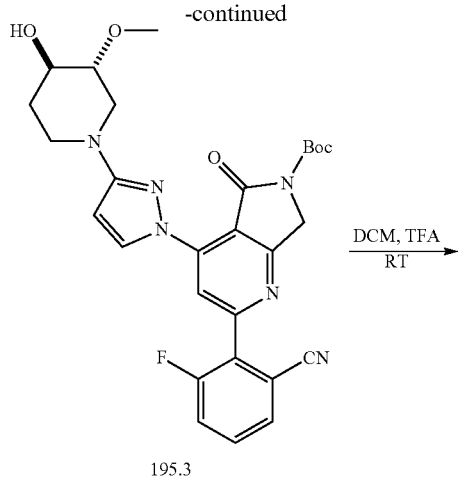

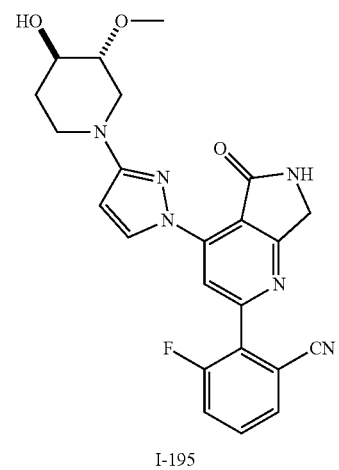

Synthesis of compound 195.2. To a solution of 195.1 (0.1 g, 0.348 mmol, 1.0 eq) in MeOH (3 mL) was added Pd(OH)2 (0.5 g) and 1N HCl (0.5 mL) in hydrogenator. The reaction mixture was stirred at room temperature under 40 psi H2 gas pressure for 16 h. Upon completion of the reaction, suspension was filtered. The mother liquor was concentrated under reduced pressure to obtain crude which was purified by column chromatography to provide 195.2 (0.075 g, 78.0%). MS(ES): m/z 198.23 [M+H]+.

Synthesis of compound 195.3. Compound was prepared from 195.2 and 4.1 using the procedure described in Example 64.

Synthesis of compound I-195. Compound was prepared from 195.3 using the procedure described in Example 64. (0.09 g, 78.6%). MS(ES): m/z 449.17 [M+H]+; 1H NMR (DMSO-d6, 400 MHz): 9.75 (s, 1H), 9.12 (s, 1H), 8.18 (s, 1H), 7.92-7.9 (d, 1H), 7.83-7.73 (m, 2H), 6.41-6.4 (d, 1H), 4.95-4.94 (d, 1H), 4.49 (s, 1H), 3.83-3.8 (m, 1H), 3.62-3.59 (m, 1H), 3.5-3.48 (m, 1H), 3.07-3.05 (m, 3H), 3.05-3 (m, 3H), 2.97-2.84 (m, 1H), 1.86-0.82 (m, 1H), 1.47-1.4 (m, 1H).

Example 196

Synthesis of 3-fluoro-2-(4-(3-(3-hydroxy-3-(methyl-d3)pyrrolidin-1-yl-2,2,4,4,5,5-d6)-1H-pyrazol-1-yl)-5-oxo-6,7-dihydro-5H-pyrrolo[3,4-b]pyridin-2-yl)benzonitrile, I-196

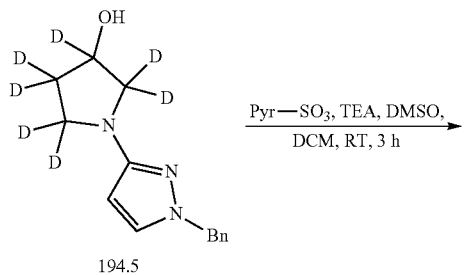

194.5

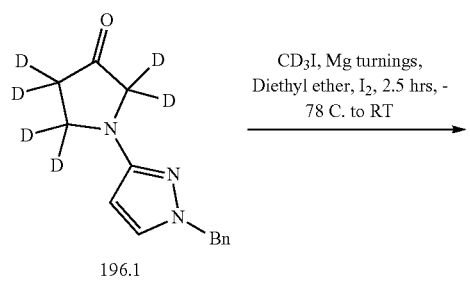

196.1

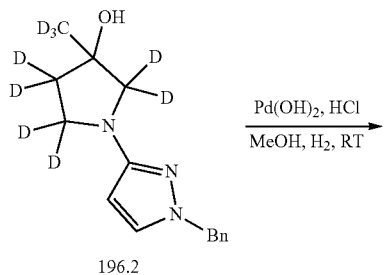

196.2

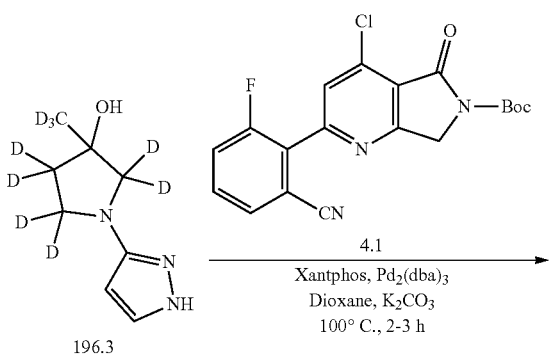

196.3

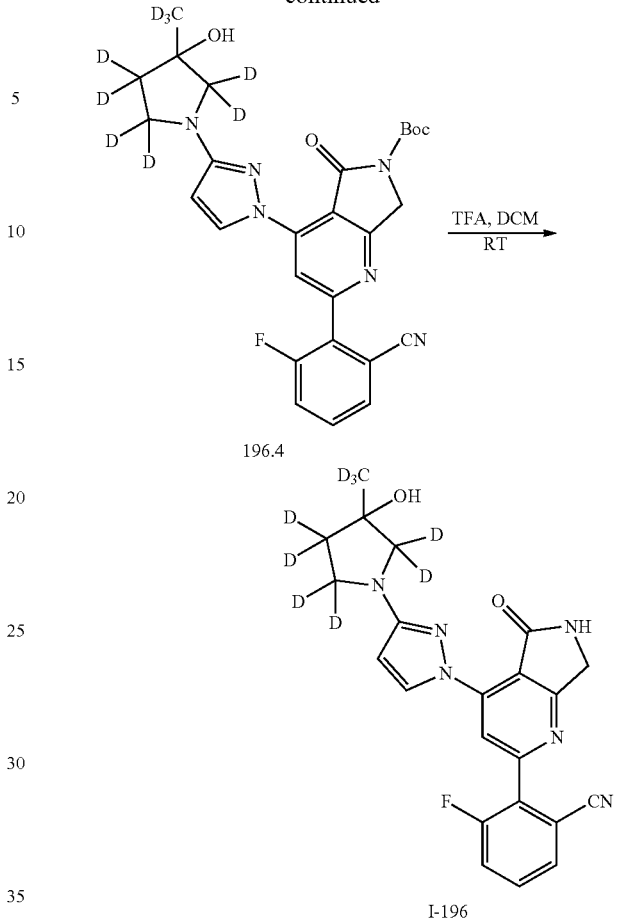

Synthesis of compound 196.1. To a solution of 194.5 (0.23 g, 0.9 mmol, 1.0 eq) in DCM (5 ml) was added Et₃N (0.578 g, 5.4 mmol, 6.0 eq) and DMSO (0.7 g, 9 mmol, 10.0 eq) at 0° C. Reaction mixture was stirred at 0° C. for 10 min. To this reaction mixture Sulfur trioxide pyridine complex (0.438 g, 2.7 mmol, 3.0 eq) was added portionwise at 0° C. Reaction mixture was stirred at room temperature for 3 h. Upon completion, reaction mixture was quenched by saturated NH₄Cl solution and extracted with DCM. Combined organic layers were washed with brine, dried over Na₂SO₄ and concentrated under reduced pressure to obtain crude which was purified by column chromatography to provide 196.1 (0.11 g, 50.6%). MS(ES): m/z 248.3 [M+H]⁺

Synthesis of compound 196.2. To a stirred suspension of Mg turnings (0.039 g, 1.61 mmol, 3.6 eq) in Et₂O (2 mL) was added I₂ crystal (catalytic) and stirred for 10 min. Reaction mixture was cooled to 0° C. and deuterated iodomethane (0.195 g, 1.34 mmol, 3.0 eq) was added slowly. Reaction mixture was stirred at room temperature for 2.5 h. This suspension was added to a solution of 196.1 (0.11 g, 0.044 mmol, 1.0 eq) in THF (2.0 mL) at −78° C. Reaction mixture was stirred at room temperature for 16 h. Upon completion of the reaction, mixture was transferred in satd. NH₄Cl solution and product was extracted with EtOAc. Organic layers were combined, washed with brine solution, dried over Na₂SO₄ and concentrated under reduced pressure to obtain crude which was purified by column chromatography to provide 196.2 (0.039 g, 32.9%). MS(ES): m/z 267.4 [M+H]⁺.

Synthesis of compound 196.3. To a solution of 196.3 (0.039 g, 0.146 mmol, 1.0 eq) in MeOH (3.0 mL) was added Pd(OH)₂ (0.020 g), 1N HCl (catalytic). Reaction mixture was stirred at room temperature under hydrogen pressure for 16 h. Upon completion, reaction was filtered and solvents removed under reduced pressure to obtain 196.3 (0.016 g, 62%). LCMS(ES): m/z 177.3 [M+H]+.

Synthesis of compound 196.4. Compound was prepared from 196.3 and 4.1 using the procedure described in Example 64.

Synthesis of compound I-196. Compound was prepared from 196.4 using the procedure described in Example 64. (0.013 g, 53.48%). MS(ES): m/z 428.43 [M+H]+; 1H NMR (DMSO-d6, 400 MHz): 9.79-9.78 (d, 1H), 9.09 (s, 1H), 8.16 (s, 1H), 7.92-7.90 (m, 1H), 7.83-7.73 (m, 2H), 6.12 (d, 1H), 4.75 (s, 1H), 4.48 (s, 2H).

Example 197

Synthesis of (S)-3-fluoro-2-(4-(3-(3-hydroxy-3-(pyrrolidine-1-carbonyl)-pyrrolidin-1-yl)-1H-pyrazol-1-yl)-5-oxo-6,7-dihydro-5H-pyrrolo[3,4-b]pyridin-2-yl)benzonitrile, I-197

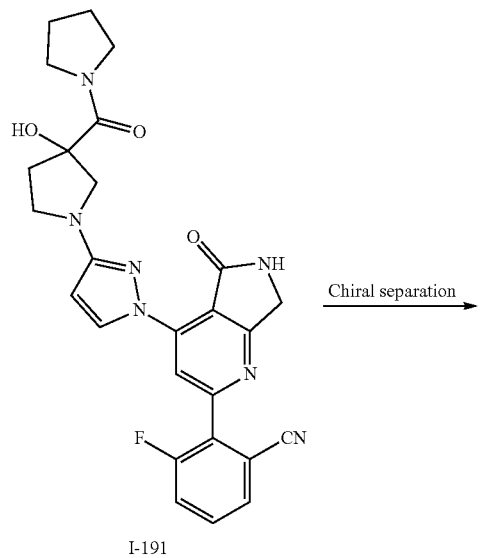

I-191

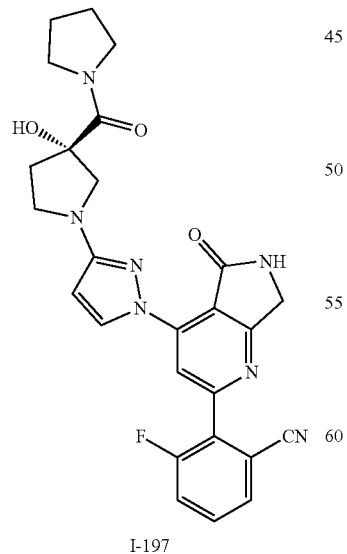

I-197

Compound I-197 was prepared by chiral purification compound I-191. MS(ES): m/z 502 [M+H]+; 1H NMR (DMSO-d6, 400 MHz): 9.78-9.77 (d, 1H), 9.10 (s, 1H), 8.16 (s, 1H), 7.91 (d, 1H), 7.83-7.76 (m, 2H), 6.17-6.16 (d, 1H), 5.80-5.75 (m, 2H), 4.49 (s, 2H), 3.80-3.72 (m, 4H), 3.48-3.45 (m, 4H), 2.38-2.33 (m, 1H), 2.08 (s, 1H), 1.86-1.83 (m, 2H), 1.75-1.72 (m, 2H).

Example 198

Synthesis of (R)-3-fluoro-2-(4-(3-(3-hydroxy-3-(pyrrolidine-1-carbonyl)-pyrrolidin-1-yl)-1H-pyrazol-1-yl)-5-oxo-6,7-dihydro-5H-pyrrolo[3,4-b]pyridin-2-yl)benzonitrile, I-198

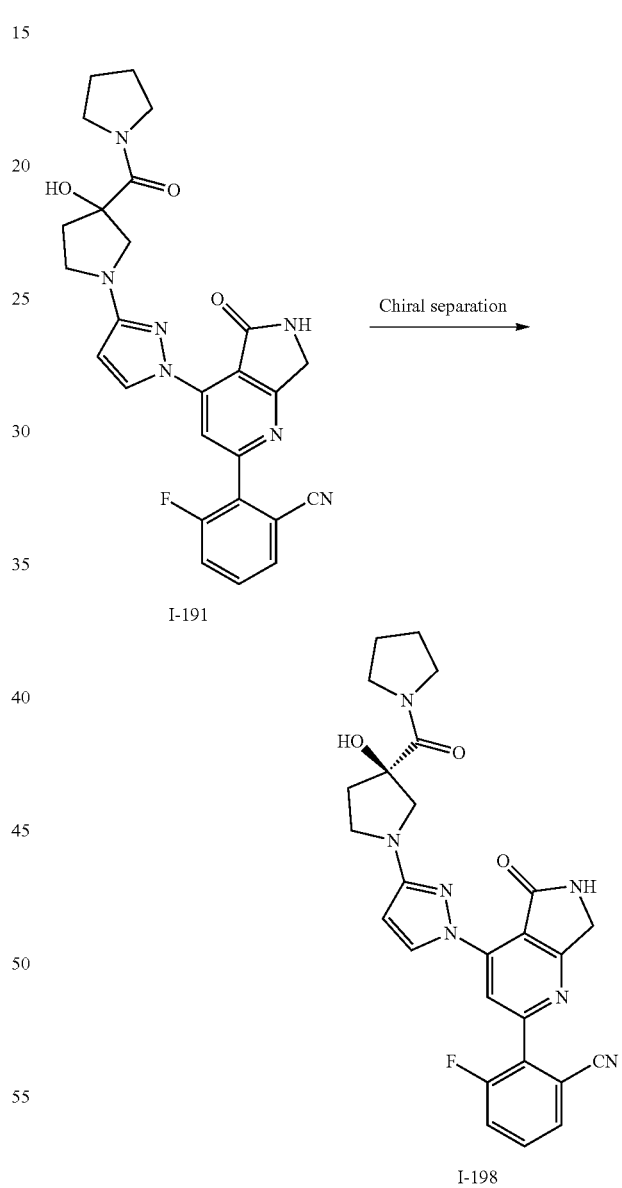

Compound I-198 was prepared by chiral purification compound I-191. MS(ES): m/z 502 [M+H]+; 1H NMR (DMSO-d6, 400 MHz): 9.78-9.77 (d, 1H), 9.10 (s, 1H), 8.16 (s, 1H), 7.91 (d, 1H), 7.83-7.76 (m, 2H), 6.17-6.16 (d, 1H), 5.80-5.75 (m, 2H), 4.49 (s, 2H), 3.80-3.72 (m, 4H), 3.48-3.45 (m, 4H), 2.38-2.33 (m, 1H), 2.08 (s, 1H), 1.86-1.83 (m, 2H), 1.75-1.72 (m, 2H).

Example 199

Synthesis of 3-fluoro-2-(4-(3-((3R,4S)-3-hydroxy-4-(methoxy-d3)pyrrolidin-1-yl)-1H-pyrazol-1-yl)-5-oxo-6,7-dihydro-5H-pyrrolo[3,4-b]pyridin-2-yl)benzonitrile, I-199

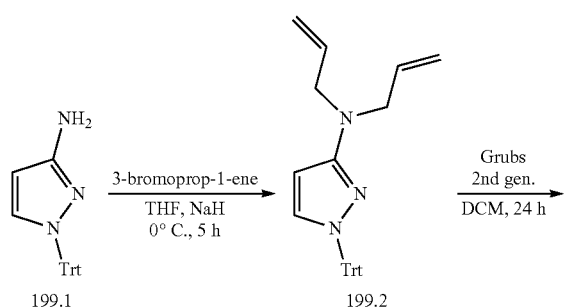

Synthesis of compound 199.4. Compound 199.4 was synthesized from trityl protected 199.1 using the procedure described in Example 109.

Synthesis of compound 199.5. To a solution of 199.4 (1.0 g, 3.8 mmol, 1.0 eq) in THF (20 mL) was added NaH (0.2 g, 4.86 mmol, 1 eq) at 0° C. Reaction mixture was stirred at room temperature for 1 h. Reaction mixture was cooled to 0° C. and Methyl-d3 Iodide (0.56 g, 3.89 mmol, 0.8 eq) was added dropwise. Reaction was stirred at room temperature for 3 hours. Upon completion of the reaction, reaction mixture was transferred into ice. Resulting mixture was extracted with EtOAc. Organic layers were combined, washed with brine solution, dried over $Na_2SO_4$ and concentrated under reduced pressure. The crude was purified by column chromatography to furnish 199.5 (0.45 g, 22.5%). MS(ES): m/z 429 [M+H]$^+$.

Synthesis of compound 199.6. To a solution of 199.5 (0.45 g, 1.05 mmol, 1.0 eq) in DCM (5.0 mL) was added TFA (5.0 ml). Reaction was stirred at room temperature for 6 hours. Upon completion of the reaction, mixture was poured into water, basified with satd. $NaHCO_3$ solution and extracted with EtOAc. Organic layers were combined, dried over $Na_2SO_4$ and concentrated under reduced pressure to obtain crude which was purified by column chromatography to furnish 199.6 (0.19 g, 90.0%). MS(ES): m/z 187 [M+H]$^+$.

Synthesis of compound 199.7. Compound 199.7 was prepared from compound 199.6 using the procedure described in Example 64.

Synthesis of compound I-199. Compound I-199 was prepared from compound 199.7 using the procedure described in Example 64. MS(ES): m/z 438 [M+H]$^+$; $^1$H NMR (DMSO-d$_6$, 400 MHz): 9.78-9.77 (d, 1H), 9.10 (s, 1H), 8.17-8.16 (s, 1H), 7.92-7.90 (m, 1H), 7.83-7.75 (m, 2H), 6.14-6.13 (d, 1H), 4.92-4.90 (d, 1H), 4.48 (s, 2H), 4.30-4.25 (m, 1H), 3.85-3.81 (m, 1H), 3.55-3.47 (m, 2H), 3.37-3.31 (m, 2H).

Example 200

Synthesis of 3-fluoro-2-(4-(3-(3-hydroxy-3-(methyl-d3)pyrrolidin-1-yl-2,2,5,5-d4)-1H-pyrazol-1-yl)-5-oxo-6,7-dihydro-5H-pyrrolo[3,4-b]pyridin-2-yl-7,7-d2)benzonitrile, I-200

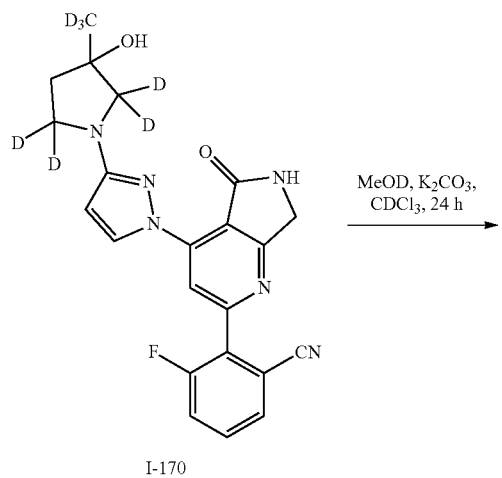

I-170

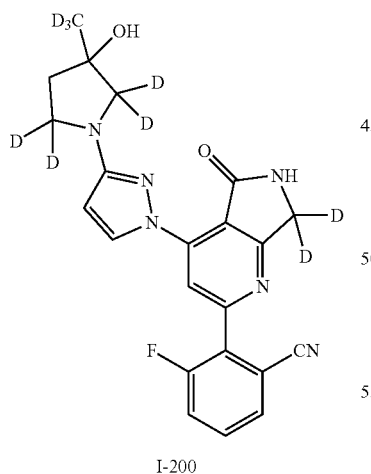

I-200

To a solution of I-170 (0.07 g, 0.164 mmol, 1 eq) in deuterated methanol (5 mL) and deuterated chloroform (2.5 mL) was added K$_2$CO$_3$ (0.045 g, 0.32 mmol, 2.0 eq). The reaction was stirred at room temperature for 24 h. Upon completion of the reaction; reaction mixture was poured into water, extracted with EtOAc. Organic layers were combined, washed with brine, dried over Na$_2$SO$_4$ and concentrated under reduced pressure to pressure to obtain crude which was purified by column chromatography to furnish I-200 (0.05 g, 71.1%). MS(ES): m/z 428.48 [M+H]$^+$; $^1$H NMR (DMSO-d$_6$, 400 MHz): 9.79 (d, 1H), 9.06 (s, 1H), 8.16 (s, 1H), 7.92-7.90 (m, 1H), 7.83-7.75 (m, 2H), 6.11-6.10 (d, 1H), 4.75 (s, 1H), 1.88-1.81 (m, 2H).

Example 201

Synthesis of 3-fluoro-2-(4-(3-((3R,4R)-4-hydroxy-3-methoxypiperidin-1-yl)-1H-pyrazol-1-yl)-5-oxo-6,7-dihydro-5H-pyrrolo[3,4-b]pyridin-2-yl)benzonitrile, I-201

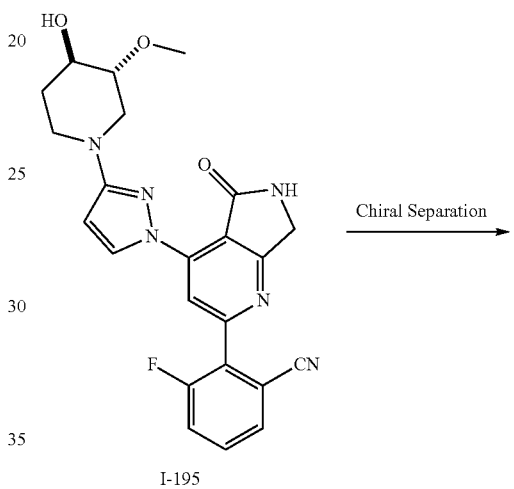

I-195

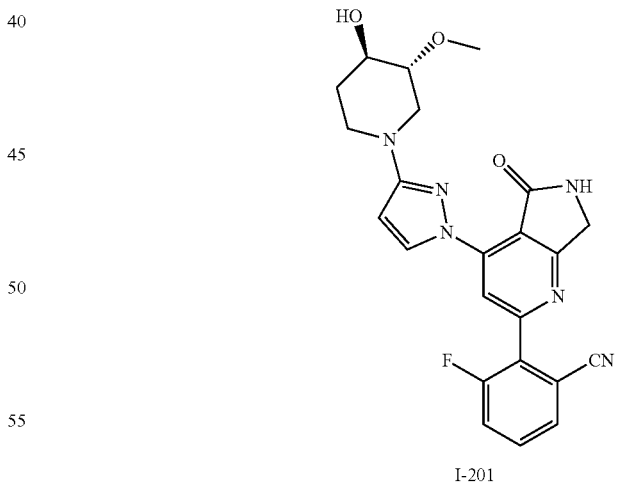

I-201

Compound I-201 was prepared by chiral purification of compound I-195. MS(ES): m/z 449.38 [M+H]$^+$; $^1$H NMR (DMSO-d$_6$, 400 MHz): 9.75 (s, 1H), 9.12 (s, 1H), 8.18 (s, 1H), 7.92-7.9 (d, 1H), 7.83-7.73 (m, 2H), 6.41-6.4 (d, 1H), 4.95-4.94 (d, 1H), 4.49 (s, 1H), 3.83-3.8 (m, 1H), 3.62-3.59 (m, 1H), 3.5-3.48 (m, 1H), 3.07-3.05 (m, 3H), 3.05-3 (m, 3H), 2.97-2.84 (m, 1H), 1.86-0.82 (m, 1H), 1.47-1.4 (m, 1H).

Example 202

Synthesis of 3-fluoro-2-(4-(3-((3S,4S)-4-hydroxy-3-methoxypiperidin-1-yl)-1H-pyrazol-1-yl)-5-oxo-6,7-dihydro-5H-pyrrolo[3,4-b]pyridin-2-yl)benzonitrile, I-202

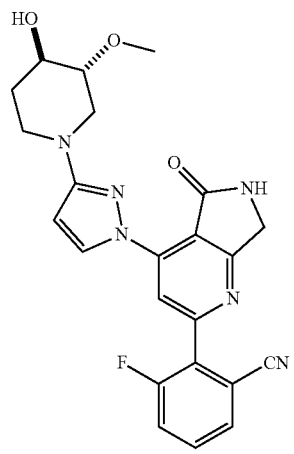

I-195

Chiral Separation →

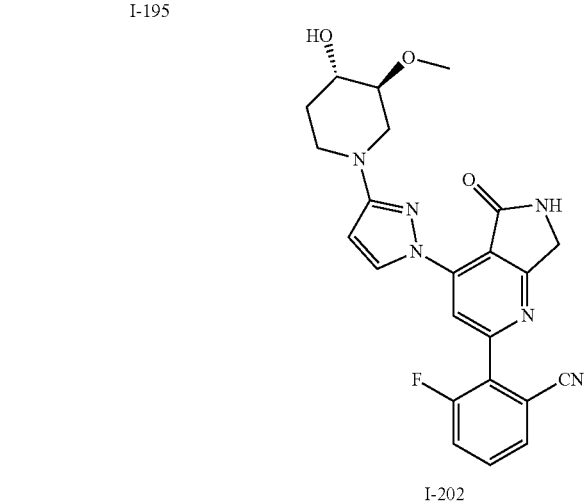

I-202

Compound I-202 was prepared by chiral purification of compound I-195. MS(ES): m/z 449.38 [M+H]$^+$; $^1$H NMR (DMSO-d$_6$, 400 MHz): 9.75 (s, 1H), 9.12 (s, 1H), 8.18 (s, 1H), 7.92-7.9 (d, 1H), 7.83-7.73 (m, 2H), 6.41-6.4 (d, 1H), 4.95-4.94 (d, 1H), 4.49 (s, 1H), 3.83-3.8 (m, 1H), 3.62-3.59 (m, 1H), 3.5-3.48 (m, 1H), 3.07-3.05 (m, 3H), 3.05-3 (m, 3H), 2.97-2.84 (m, 1H), 1.86-0.82 (m, 1H), 1.47-1.4 (m, 1H).

Example 203

Synthesis of 3-fluoro-2-(4-(3-(4-hydroxypiperidin-1-yl-2,2,3,3,4,5,5,6,6-d9)-1H-pyrazol-1-yl)-5-oxo-6,7-dihydro-5H-pyrrolo[3,4-b]pyridin-2-yl)benzonitrile, I-203

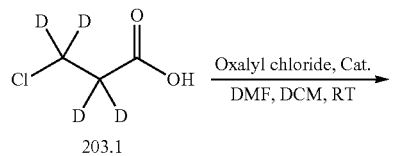

203.1

Oxalyl chloride, Cat.
DMF, DCM, RT →

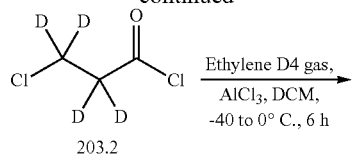

203.2

Ethylene D4 gas,
AlCl$_3$, DCM,
-40 to 0° C., 6 h →

203.3

1) DIPEA, DMA, 120° C., 2 h
2) MeOD/D$_2$O, K$_2$CO$_3$ for 24 h →

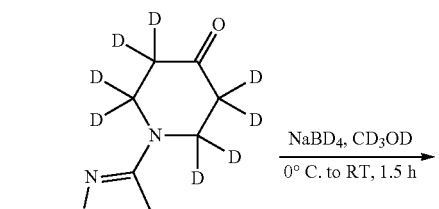

203.4

NaBD$_4$, CD$_3$OD
0° C. to RT, 1.5 h →

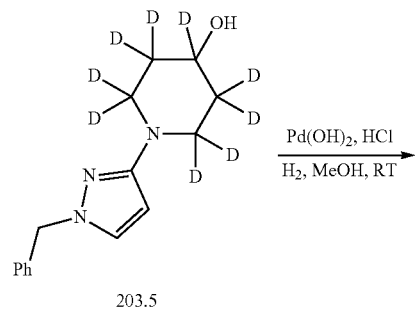

203.5

Pd(OH)$_2$, HCl
H$_2$, MeOH, RT →

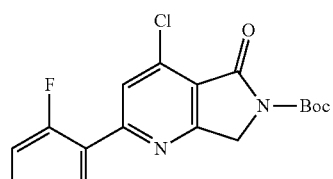

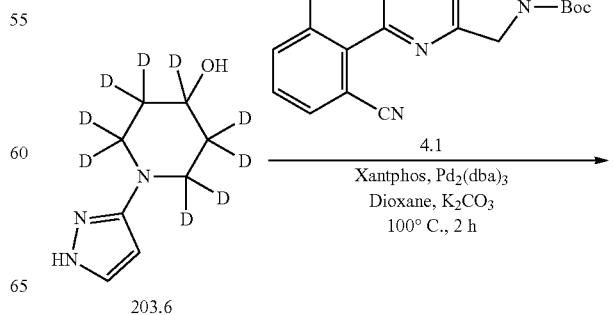

203.6

4.1
Xantphos, Pd$_2$(dba)$_3$
Dioxane, K$_2$CO$_3$
100° C., 2 h →

397

-continued

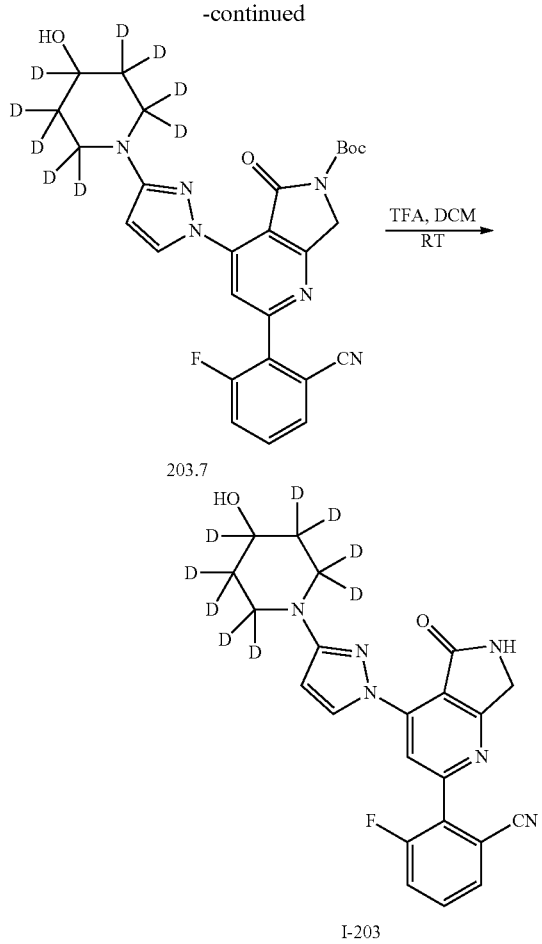

Synthesis of compound 203.2. To a solution of 203.1 (2.0 g, 17.85 mmol, 1.0 eq.) in DCM (10 mL) was added Oxalyl chloride (2.7 mL, 35.71 mmol, 2.0 eq.), cat. DMF (0.1 mL). The resulting mixture was stirred at room temperature for 6 h. Upon completion of the reaction solvent was evaporated to furnish 203.1. (2.1 g, 90.37%). $^1$D-NMR (CDCl$_3$, 61 MHz): 4.30 (s, 2D), 3.89 (s, 2D).

Synthesis of compound 203.3. To a solution 203.2 (2.1 g, 16.15 mmol, 1.0 eq.) in DCM (25 mL) was added portion wise AlCl$_3$ (2.57 g, 19.38 mmol, 1.2 eq.) at −40° C. Mixture was purged with ethylene gas for 6 h. Upon completion of the reaction, 1N HCl was added and mixture was extracted with DCM. Organic layers were combined, washed with brine solution, dried over Na$_2$SO$_4$ and concentrated under reduced pressure to obtain crude which was purified by column chromatography to furnish 203.3 (1.0 g, 38.0%), $^1$D-NMR (CDCl3, 61 MHz): 3.75 (s, 4D), 3.33 (s, 4D).

Synthesis of compound 203.4 To a solution of 203.3 (0.884 g, 5.11 mmol, 1.0 eq.) in dimethylacetamide (10 mL) was added 203.31 (1 g, 5.78 mmol, 1.2 eq.) and DIPEA (5.34 g, 41.09 mmol, 3.0 eq). The reaction was stirred at 120° C. for 4 h. Upon completion of reaction, reaction mixture was transferred in D$_2$O and product was extracted with EtOAc. Organic layers were combined, washed with brine, dried over Na$_2$SO$_4$ and concentrated under reduced pressure to obtain crude which was purified by column chromatography to furnish 203.4 (0.25 g, 15.48%). MS(ES): m/z 264.19 [M+H]$^+$, Synthesis of compound 203.5. To a solution of 203.4 (0.25 g, 0.95 mmol, 1.0 eq) in CD$_3$OD (3 mL) was added

398

NaBD$_4$ (0.119 g, 2.85 mmol, 3.0 eq) at 0° C. The reaction mixture was stirred at room temperature for 30 min. Upon completion of the reaction, reaction mixture was transferred into 1N HCl in D$_2$O and product was extracted with DCM. Organic layers was combined, washed with brine, dried over Na$_2$SO$_4$ and concentrated under reduced pressure to obtain crude 203.5 (0.16 g, 63.3%). MS(ES): m/z 267.21 [M+H]$^+$.

Synthesis of compound 203.6. To a solution of 203.6 (0.15 g, 0.6015 mmol, 1.0 eq) in MeOH (3 mL) was added Pd(OH)$_2$ (0.2 g), dil. HCl (0.05 mL) in 20 mL autoclave. The hydrogen was purged to 50 psi. The reaction was stirred at room temperature overnight. Upon completion of the reaction solids were filtered off. Mother liquor was concentrated under reduced pressure to obtain 203.6 (0.1 g, 94.16%). LCMS(ES): m/z 177.15 [M+H]$^-$.

Synthesis of compound 203.7. Compound 203.7 was prepared from compounds 203.6 and 4.1 using the procedure described in Example 64.

Synthesis of compound I-203. Compound I-203 was prepared from compound 203.7 using the procedure from Example 64. MS(ES): m/z 427 [M+H]$^+$, LCMS purity: 100%, HPLC purity: 99.43%, $^1$H NMR (DMSO-d$_6$, 400 MHZ): 9.76-9.75 (d, J=2.8 Hz, 1H), 9.11 (s, 1H), 8.17 (s, 1H), 9.92-7.9 (m, 1H), 7.83-7.75 (m, 2H), 6.35 (d, J=2.8 Hz, 1H), 4.65 (s, 1H), 4.49 (s, 2H), 1.36 (s, 2H).

Example 204

Synthesis of (R)-3-fluoro-2-(4-(3-(3-hydroxy-2,2-dimethylpyrrolidin-1-yl)-1H-pyrazol-1-yl)-5-oxo-6,7-dihydro-5H-pyrrolo[3,4-b]pyridin-2-yl)benzonitrile, I-204

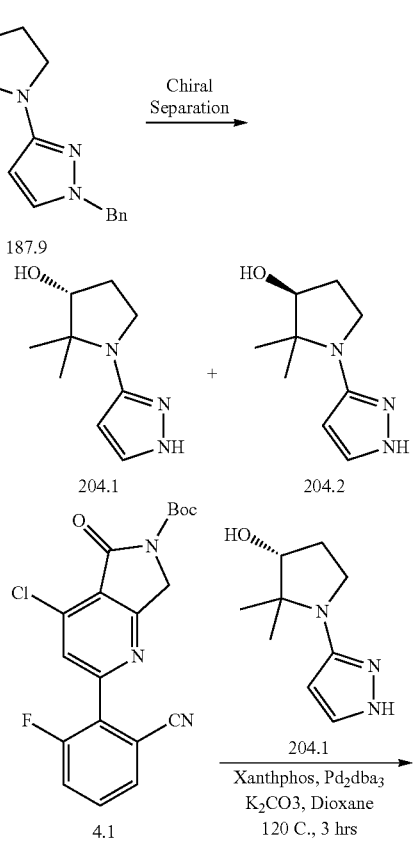

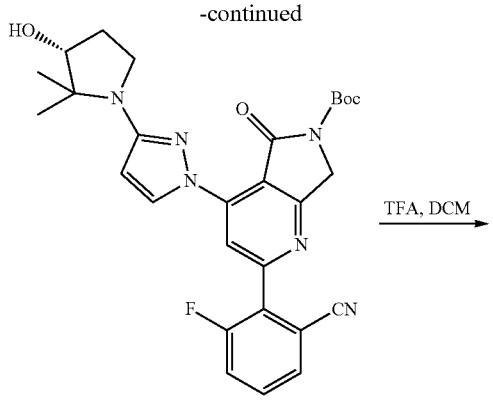

204.3

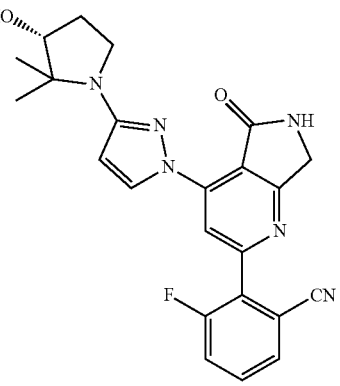

I-204

Synthesis of compound 204.1 and 204.2. Compounds 204.1 and 204.2 were prepared by chiral purification of 187.9.

Synthesis of compound 204.3. Compound was prepared from 4.1 and 204.1 using the procedure in Example 64.

Synthesis of compound I-204. Compound was prepared from 204.3 using the procedure described in Example 64. MS(ES): m/z 433.17 [M+H]−; ¹H NMR (DMSO-d₆, 400 MHz): 9.758-9.751 (d, 1H), 9.07 (s, 1H), 8.17 (s, 1H), 7.93-7.91 (dd, 1H), 7.7-7.73 (m, 2H), 6.2-6.19 (d, 1H), 5.10-5.09 (d, 1H), 4.48 (s, 2H), 3.83-3.76 (m, 2H), 3.4-3.37 (m, 2H), 2.09-2.07 (m, 1H), 1.38 (s, 3H), 1.22 (s, 3H).

Example 205

Synthesis of (S)-3-fluoro-2-(4-(3-(3-hydroxy-2,2-dimethylpyrrolidin-1-yl)-1H-pyrazol-1-yl)-5-oxo-6,7-dihydro-5H-pyrrolo[3,4-b]pyridin-2-yl)benzonitrile I-205

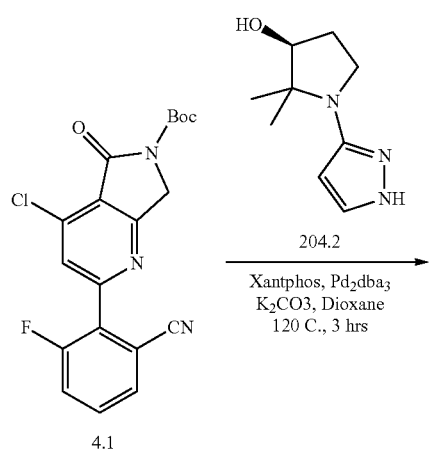

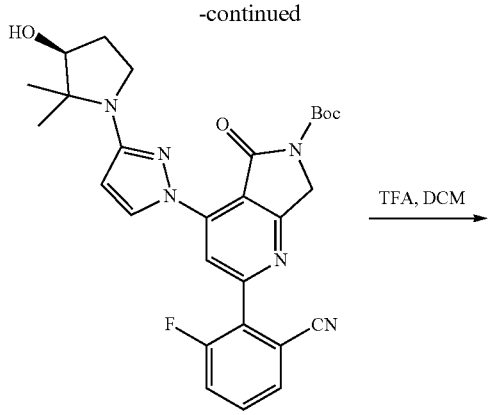

205.1

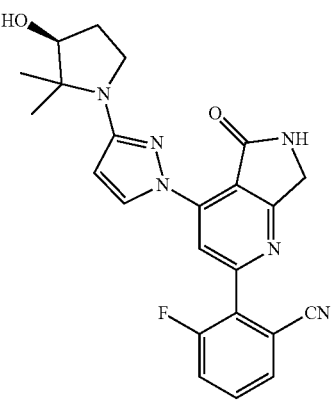

I-205

Compound I-205 was synthesized from 4.1 and 204.2 using the procedures referred in example 204. MS(ES): m/z 433.17 [M+H]+; 1H NMR (DMSO-d₆, 400 MHz): 9.758-9.751 (d, 1H), 9.07 (s, 1H), 8.17 (s, 1H), 7.93-7.91 (dd, 1H), 7.7-7.73 (m, 2H), 6.2-6.19 (d, 1H), 5.10-5.09 (d, 1H), 4.48 (s, 2H), 3.83-3.76 (m, 2H), 3.4-3.37 (m, 2H), 2.09-2.07 (m, 1H), 1.38 (s, 3H), 1.22 (s, 3H).

Example 206

Synthesis of (S)-3-fluoro-2-(4-(3-(3-hydroxy-3-(methyl-d3)pyrrolidin-1-yl-2,2,5,5-d4)-1H-pyrazol-1-yl)-5-oxo-6,7-dihydro-5H-pyrrolo[3,4-b]pyridin-2-yl-7,7-d2)benzonitrile, I-206

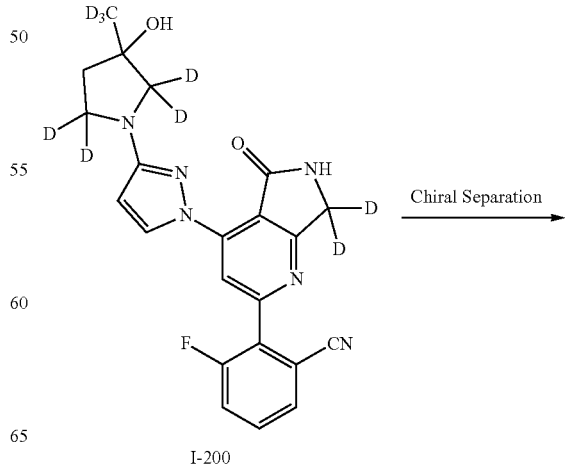

I-200

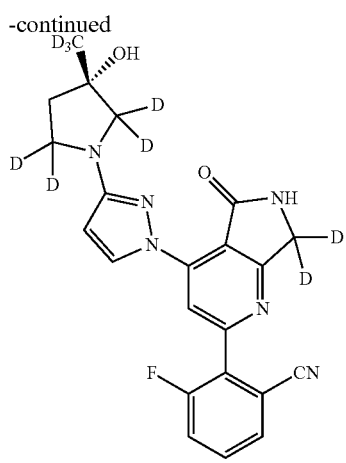

I-206

Compound I-206 was prepared by chiral purification of I-200. MS(ES): m/z 428.38 [M+H]⁺; ¹H NMR (DMSO-d₆, 400 MHz): 9.79 (d, 1H), 9.07 (s, 1H), 8.16 (s, 1H), 7.92-7.90 (m, 1H), 7.83-7.75 (m, 2H), 6.11-6.10 (d, 1H), 4.76 (s, 1H), 1.88-1.81 (m, 2H).

Example 207

Synthesis of (R)-3-fluoro-2-(4-(3-(3-hydroxy-3-(methyl-d3)pyrrolidin-1-yl-2,2,5,5-d4)-1H-pyrazol-1-yl)-5-oxo-6,7-dihydro-5H-pyrrolo[3,4-b]pyridin-2-yl-7,7-d2)benzonitrile, I-207

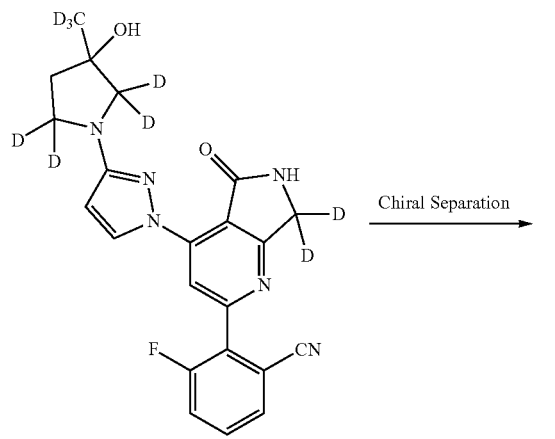

I-207

Compound I-207 was prepared by chiral purification of I-200. MS(ES): m/z 428.38 [M+H]⁺; ¹H NMR (DMSO-d₆, 400 MHz): 9.79 (d, 1H), 9.07 (s, 1H), 8.16 (s, 1H), 7.92-7.90 (m, 1H), 7.83-7.75 (m, 2H), 6.11-6.10 (d, 1H), 4.76 (s, 1H), 1.88-1.81 (m, 2H).

Example 208

Synthesis of (R)-3-fluoro-2-(4-(3-(3-hydroxypyrrolidin-1-yl-2,2,3,4,4,5,5-d7)-1H-pyrazol-1-yl)-5-oxo-6,7-dihydro-5H-pyrrolo[3,4-b]pyridin-2-yl)benzonitrile, I-208

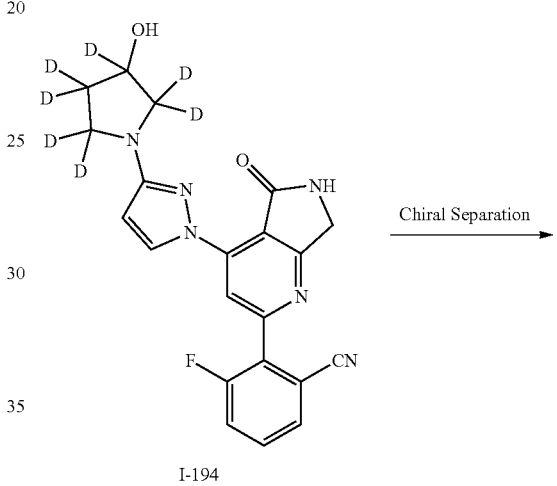

I-194

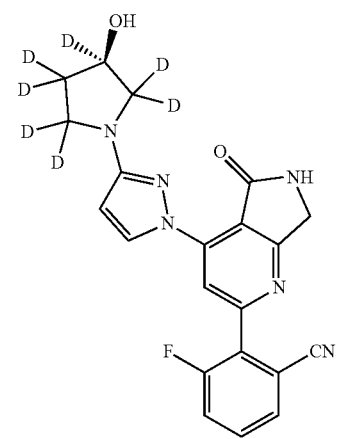

I-208

Compound I-208 was prepared by chiral purification of compound I-194. MS(ES): m/z 412.48 [M+H]⁺; ¹H NMR (DMSO, 400 MHz): 9.79-9.78 (d, 1H), 9.09 (s, 1H), 8.17 (s, 1H), 7.92-7.90 (m, 1H), 7.83-7.73 (m, 2H), 6.14 (d, 1H), 4.90 (s, 1H), 4.48 (s, 2H).

Example 209

Synthesis of (S)-3-fluoro-2-(4-(3-(3-hydroxypyrrolidin-1-yl-2,2,3,4,4,5,5-d7)-1H-pyrazol-1-yl)-5-oxo-6,7-dihydro-5H-pyrrolo[3,4-b]pyridin-2-yl)benzonitrile, I-209

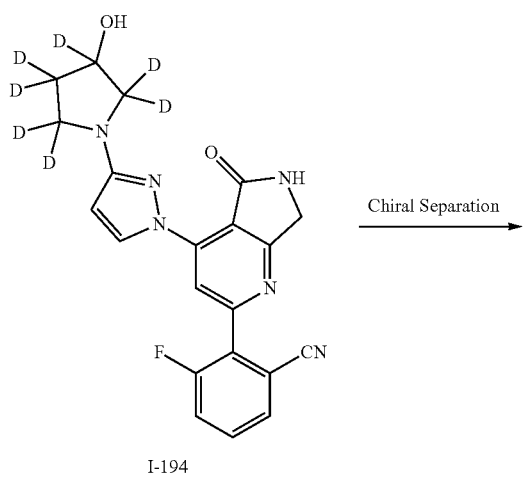

I-194

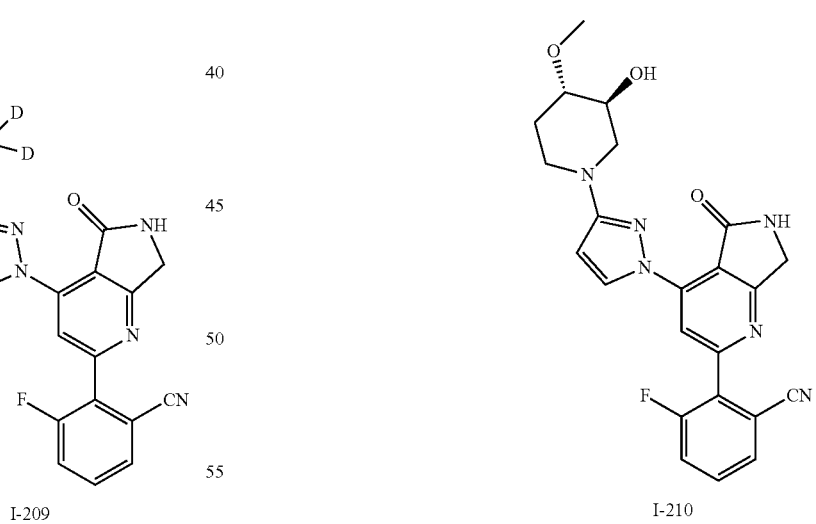

I-209

Compound I-209 was prepared by chiral purification of compound I-194. MS(ES): m/z 412.48 [M+H]$^+$; $^1$H NMR (DMSO, 400 MHz): 9.79-9.78 (d, 1H), 9.09 (s, 1H), 8.17 (s, 1H), 7.92-7.90 (m, 1H), 7.83-7.73 (m, 2H), 6.14 (d, 1H), 4.90 (s, 1H), 4.48 (s, 2H).

Example 210

Synthesis of 3-fluoro-2-(4-(3-((3S,4S)-3-hydroxy-4-methoxypiperidin-1-yl)-1H-pyrazol-1-yl)-5-oxo-6,7-dihydro-5H-pyrrolo[3,4-b]pyridin-2-yl)benzonitrile, I-210

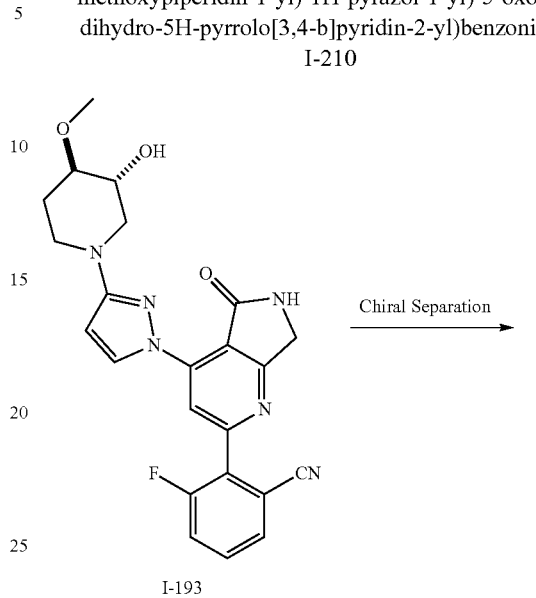

I-193

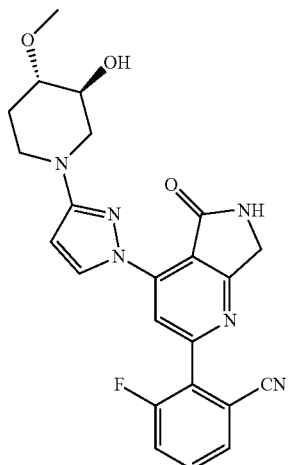

I-210

Compound I-210 was prepared by chiral purification of compound I-210. MS(ES): m/z 449.38 [M+H]$^+$; $^1$H NMR (DMSO-d$_6$, 400 MHz): 9.75 (s, 1H), 9.11 (s, 1H), 8.17-8.16 (d, 1H), 7.92-7.9 (dd, 1H), 7.83-7.73 (m, 2H), 6.36-6.35 (d, 1H), 5.08-5.07 (d, 1H), 4.49 (s, 2H), 3.7-3.67 (m, 1H), 3.64-3.47 (m, 1H), 3.46-3.39 (m, 1H), 3.12-3.07 (m, 1H), 2.96-2.91 (m, 1H), 2.79-2.67 (s, 1H), 2.08-1.99 (m, 1H), 1.42-1.33 (m, 1H).

Example 211

Synthesis of 3-fluoro-2-(4-(3-((3R,4R)-3-hydroxy-4-methoxypiperidin-1-yl)-1H-pyrazol-1-yl)-5-oxo-6,7-dihydro-5H-pyrrolo[3,4-b]pyridin-2-yl)benzonitrile, I-211

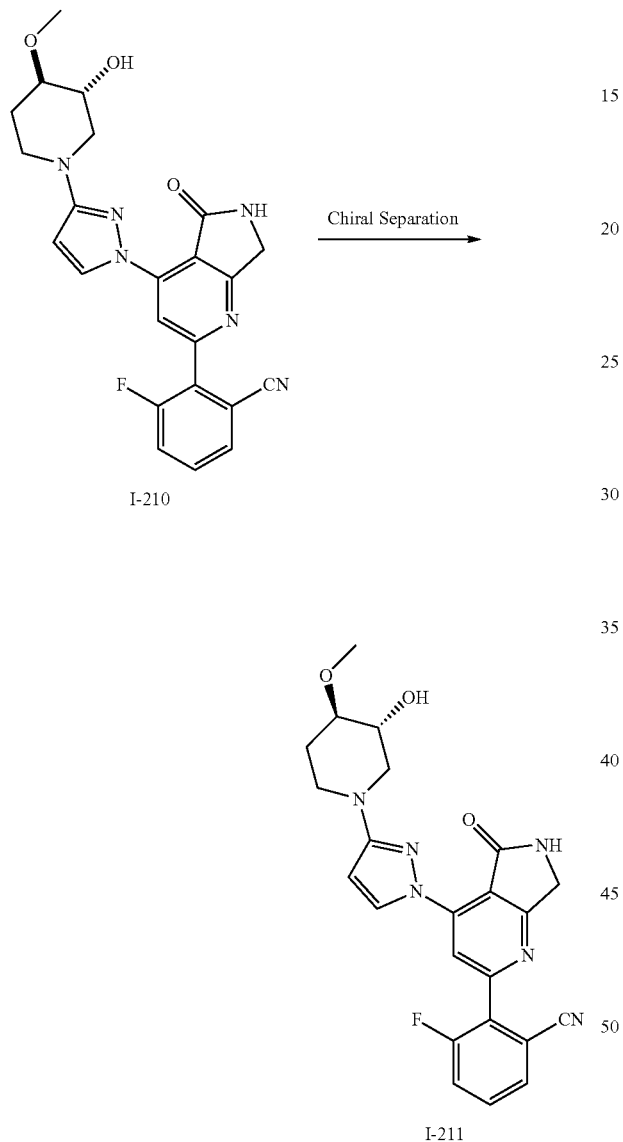

Compound I-211 was prepared by chiral purification of compound I-210. MS(ES): m/z 449.38 [M+H]$^+$; $^1$H NMR (DMSO-d$_6$, 400 MHz): 9.75 (s, 1H), 9.12 (s, 1H), 8.16 (s, 1H), 7.96-7.9 (dd, 1H), 7.83-7.73 (m, 2H), 6.36-6.35 (d, 1H), 5.08-5.07 (d, 1H), 4.49 (s, 2H), 3.7-3.67 (m, 1H), 3.64-3.47 (m, 1H), 3.46-3.39 (m, 1H), 3.12-3.07 (m, 1H), 2.96-2.91 (m, 1H), 2.79-2.67 (s, 1H), 2.08-1.99 (m, 1H), 1.42-1.33 (m, 1H).

Example 212

Synthesis of N-(1-(2-(2-cyano-6-fluorophenyl)-5-oxo-6,7-dihydro-5H-pyrrolo[3,4-b]pyridin-4-yl)-1H-pyrazol-3-yl)acetamide, I-212

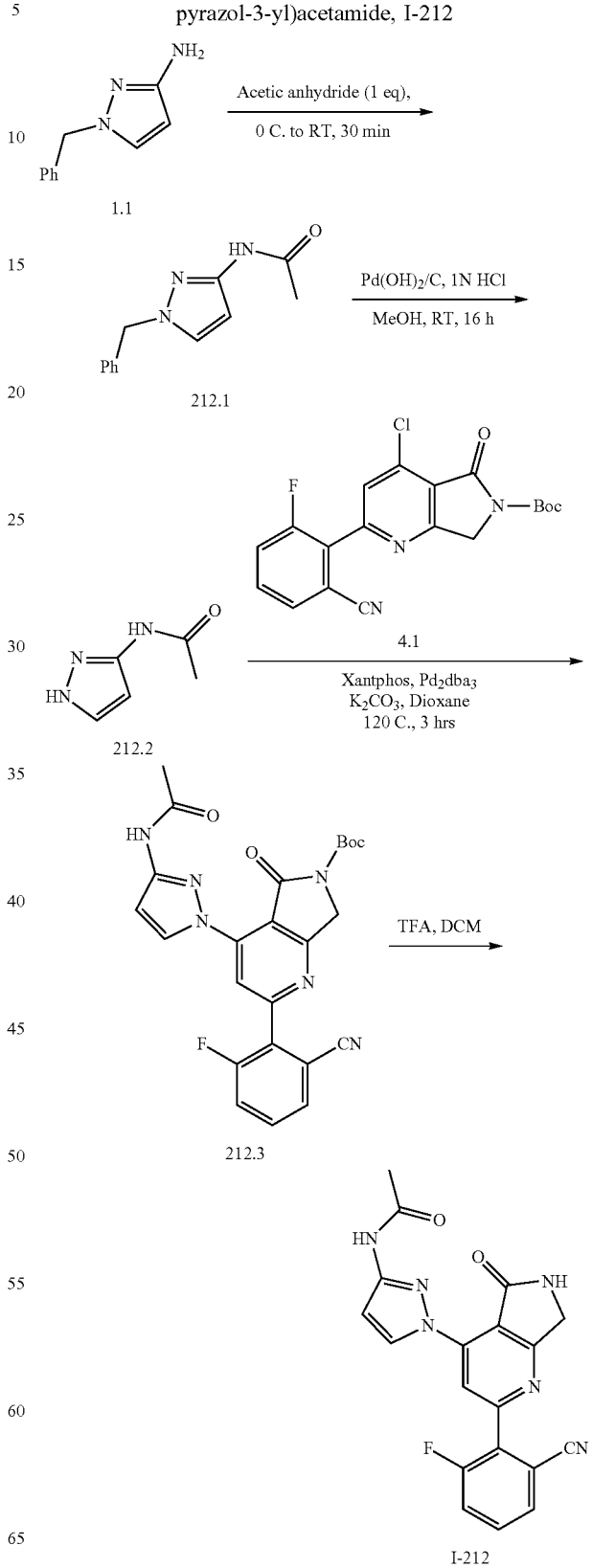

Synthesis of compound 212.1. A mixture of 1.1 (1.0 g, 5.77 mmol, 1.0 eq) and acetic anhydride (1.5 ml, 5.7 mmol, 1.0 eq) was stirred at 25° C. for 0.5 h. Upon completion of reaction; reaction mixture was transferred into water, extracted with EtOAc. Organic layers were combined, washed with brine solution, dried over sodium sulphate and concentrated under reduced pressure to obtain crude which was purified by column chromatography to provide 212.1 (1.0 g, 83.33%). MS(ES): m/z 216 [M+H]$^+$.

Synthesis of compound 212.2. To a solution of 212.1. (0.5 g, 2.32 mmol, 1.0 eq) in MeOH (20 mL) was added 20% palladium hydroxide on charcoal (0.5 g) and 1N HCl (catalytic amount). Reaction mixture was stirred under hydrogen at 40 psi for 16 h. Upon completion of the reaction, reaction mixture was filtered through Celite bed and washed with methanol. Filtrate was concentrated under reduced pressure to obtain crude which was purified by column chromatography to furnish 212.2. (0.2 g, 68.96%). MS(ES): m/z 126 [M+H]$^+$.

Synthesis of compound 212.3. Compound was prepared using the procedure described in Example 64.

Synthesis of compound I-212. Compound was prepared using the procedure described in Example 64. (0.050 g, 25.47%). MS(ES): m/z 377 [M+H]$^+$; $^1$H NMR (DMSO-d$_6$, 400 MHZ): 10.88 (s, 1H), 9.72 (s, 1H), 9.23 (s, 1H), 8.19 (s, 1H), 7.94-7.92 (m, 1H), 7.85-7.77 (m, 2H), 6.94 (d, 1H), 4.54 (s, 2H), 2.06 (s, 3H).

Example 213

Synthesis of 3-fluoro-2-(4-(3-((3S,4R)-3-hydroxy-4-methoxy-3-methylpiperidin-1-yl)-1H-pyrazol-1-yl)-5-oxo-6,7-dihydro-5H-pyrrolo[3,4-b]pyridin-2-yl)benzonitrile, I-213

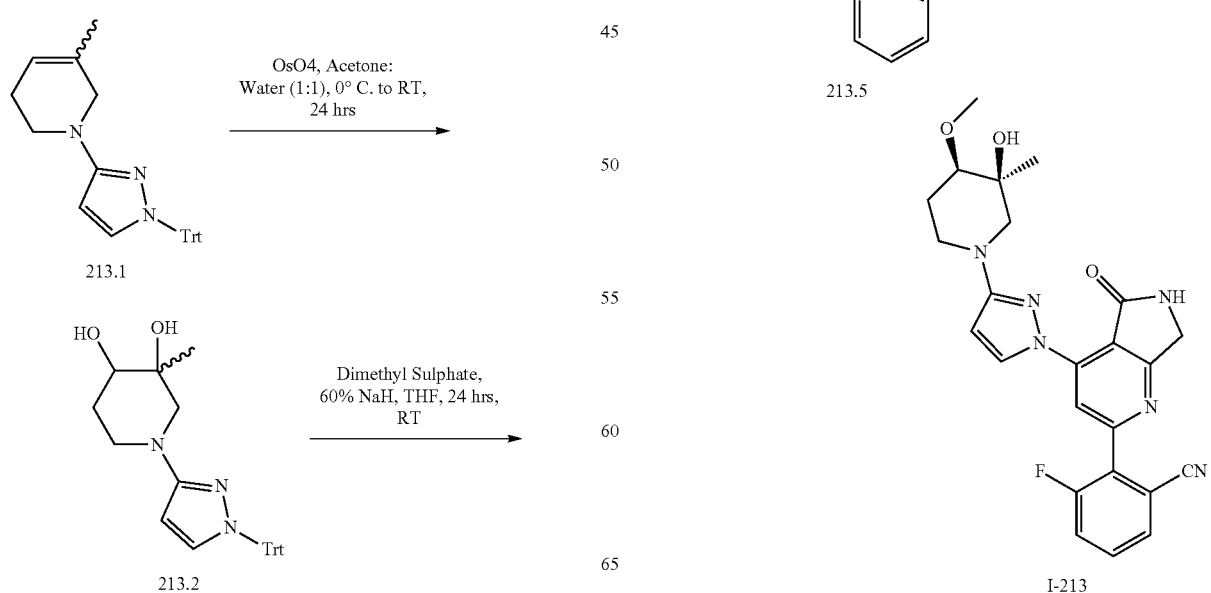

Synthesis of compound 213.2. To a solution of Osmium tetroxide (2% in water) (0.52 ml, 0.044 mmol, 0.01 eq) in water (20 ml) was added N-Methylmorpholine N-oxide (0.52 g, 4.4 mmol, 1.0 eq) at 0° C. then 1 (1.8 g, 4.4 mmol, 1 eq) in acetone (20 ml) was added dropwise at 0° C. Reaction mixture was stirred at room temperature for 24 h. Upon completion of the reaction; reaction mixture was transferred into water, extracted with EtOAc. Organic layers were combined, washed with brine solution, dried over sodium sulphate and concentrated under reduced pressure to pressure to obtain crude which was purified by column chromatography to provide 213.2 (1.1 g, 56.38%). MS(ES): m/z 440.56 [M+H]$^+$.

Synthesis of compound 213.3. To a solution of 213.2 (0.6 g, 1.3 mmol, 1.0 eq) THF (20 mL) was added NaH (0.06 g, 1.5 mmol, 1.1 eq) at 0° C. and reaction mixture was stirred at 0° C. for 10 min. Reaction mixture was cooled to 0° C. and dimethyl sulfate (0.162 g, 1.2 mmol, 0.98 eq) was added dropwise, stirred at room temperature for 16 h. Upon completion of the reaction, reaction mixture was transferred into ice and extracted ethyl acetate. Organic layers were combined, washed with brine, dried over sodium sulphate and concentrated under reduced pressure. Crude was purified by column chromatography to furnish 213.3 (0.12 g, 19.38%). MS(ES): m/z 454.5 [M+H]$^+$.

Synthesis of compound 213.4. To a solution of 213.3 (0.12 g, 0.26 mmol, 1.0 eq) in DCM (5 mL) was added TFA (5 ml) and stirred at room temperature for 6 h. Upon completion of reaction, reaction mixture was transferred in water, basified with saturated bicarbonate solution and product was extracted with EtOAc. Organic layers were combined, dried over sodium sulphate and concentrated under reduced pressure to obtain crude which was purified by column chromatography to provide 213.4. (0.04 g, 71.57%). MS(ES): m/z 212.17 [M+H]$^+$.

Synthesis of compound 213.5. Compound was prepared using the procedure described in example 64.

Synthesis of compound I-213. Compound was prepared using the procedure described in example 64 (0.04 g, 69.51%). MS(ES): m/z 438 [M+H]$^+$; $^1$H NMR (DMSO-d$_6$, 400 MHz): 9.75-9.74 (d, 1H), 9.10 (s, 1H), 8.15 (s, 1H), 7.91-7.90 (d, 1H), 7.81-7.73 (m, 2H), 6.35-6.34 (d, 1H), 4.48 (s, 2H), 4.23 (m, 1H), 3.57-3.51 (m, 1H), 3.31 (s, 3H), 3.17-3.16 (d, 1H), 3.12-3.05 (m, 2H), 2.98-2.95 (d, 1H), 1.81-1.76 (q, 1H), 1.15 (s, 3H).

Example 214

Synthesis of 3-fluoro-2-(4-(3-((2S,4R)-4-hydroxy-2-(hydroxymethyl)pyro-lidin-1-yl)-1H-pyrazol-1-yl)-5-oxo-6,7-dihydro-5H-pyrrolo[3,4-b]pyridin-2-yl) benzonitrile, I-214

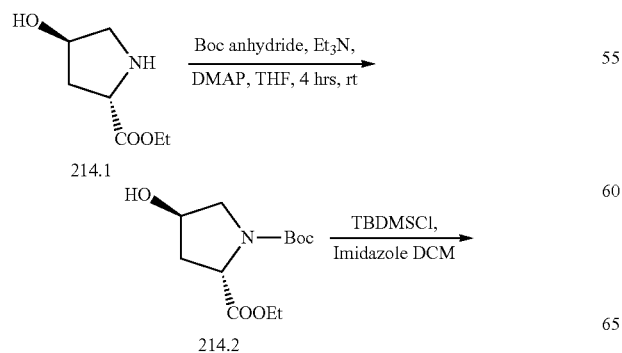

214.1

214.2

-continued

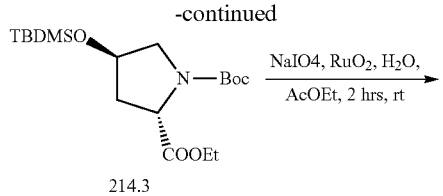

214.3

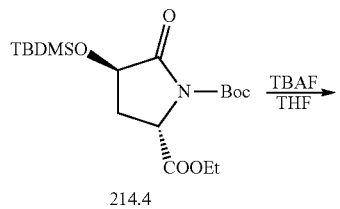

214.4

214.5

214.6

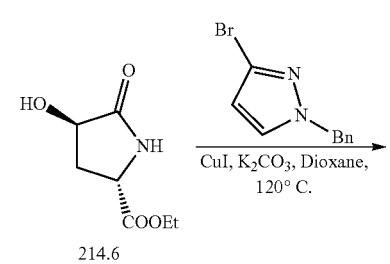

214.7

214.8

-continued

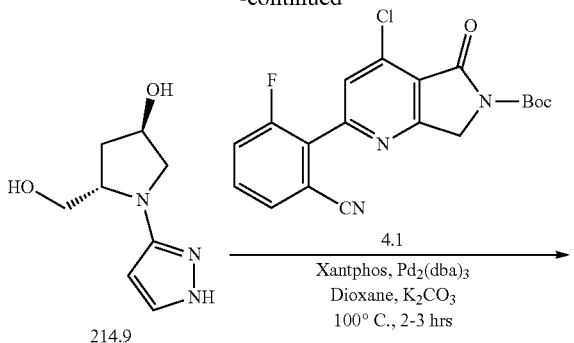

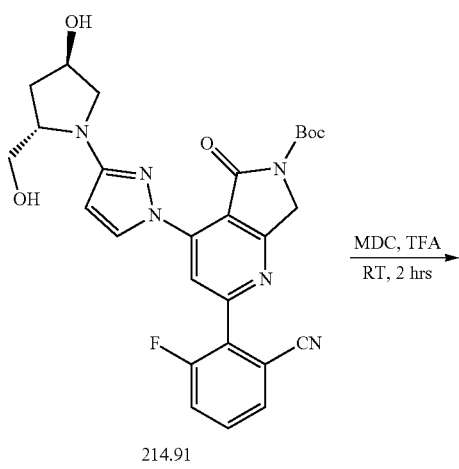

Synthesis of compound 214.2. To a solution of 214.1 (5.0 g, 25.6 mmol, 1.0 eq) in DCM (50 mL) and ethanol (10 mL) was added Et₃N (5.2 mL, 0.038 mmol, 1.5 eq) di-tert.butyl dicarbonate (032 mmol, 1.2 eq) at 0° C. Reaction mixture was stirred at room temperature for 16 h. Upon completion of the reaction, mixture was transferred into water and extracted with DCM, combined organic layers were washed with brine, dried over Na₂SO₄ and concentrated under reduced pressure to obtained crude which was purified by column chromatography to furnish 214.2. (6.1 g, 74.9%). MS(ES): m/z 260.12 [M+H]⁻.

Synthesis of compound 214.3. To a solution of 214.2 (6.1 g, 23.5 mmol, 1.0 eq) in DCM (150 mL) was added imidazole (3.2 g, 47.1 mmol, 1.88 eq) and TDDMSCl (3.7 g, 24.9 mmol, 1.06 eq) at room temperature and stirred for 18 hrs. Upon completion of the reaction, mixture was transferred into 0.5N HCl solution, extracted with DCM, dried over Na₂SO₄ and concentrated under reduced pressure to obtain crude 214.3. (8.5 g, 96.7%). MS(ES): m/z 374.2 [M+H]⁺.

Synthesis of compound 214.4. Solution of 214.3 (8.5 g, 22.7 mmol, 1.0 eq) in EtOAc (40 ml) was added in to a solution of Sodium periodate (8.5 g, 56.0 mmol, 2.5 eq) and Ruthenium(IV) oxide hydrate (0.6 g, 4.5 mmol, 0.2 eq) in water (50 mL) at 0° C. and stirred at room temperature for 16 h. Upon completion of the reaction, mixture was transferred into water and extracted with EtOAc, combined organic layers were washed with brine, dried over Na₂SO₄ and concentrated under reduced pressure to obtained crude which was purified by column chromatography to provide 214.4 (6.0 g, 68.04%). MS(ES): m/z 388.12 [M+H]⁺.

Synthesis of compound 214.5. To a solution of 214.4 (6.0 g, 16.8 mmol, 1.0 eq) in THF (60 ml) was added TBAF (6.0 mL), at room temperature and reaction mixture was stirred at room temperature for 6 h. Upon completion of the reaction, reaction mixture was concentrated under reduced pressure to obtain crude which was purified by column chromatography to provide 214.5 (3.0 g, 70.9%). MS(ES): m/z 274.2 [M+H]⁺.

Synthesis of compound 214.6. To a solution of 214.5 (3.0 g, 10.98 mmol, 1.0 eq) in DCM (30.0 ml) was added TFA (2.0 mL) at room temperature and reaction mixture was stirred at room temperature for 6 h. Upon completion of reaction, reaction mixture was concentrated under reduced to obtain crude which was purified by column chromatography to provide 214.6 (0.14 g, 93.10%). MS(ES): m/z 258.32 [M+H]⁺.

Synthesis of compound 214.7. To a solution of 1-benzyl-3-bromo-1H-pyrazole (1 g, 4.22 mmol, 1.0 eq) in 1,4 Dioxane (00 ml) was added 214.6 (0.94 g, 5.48 mmol, 1.3 eq), CuI (0.08 g, 0.422 mmol, 0.1 eq), K₂CO₃ (1.16 g, 8.44 mmol, 2.0 eq) and trans-N,N'-Dimethylcyclohexane-1,2-diamine (0.060 g, 0.422 mmol, 0.1 eq). Reaction was stirred at 140° C. for 18 h. Upon completion of the reaction, reaction mixture was transferred into water and product was extracted with EtOAc. Organic layers were combined, washed with brine, dried over Na₂SO₄ and concentrated under reduced pressure to obtain crude which was purified by column chromatography to provide 214.7 (0.26 g, 18.7%). MS(ES): m/z 330.36 [M+H]⁺.

Synthesis of compound 214.8. To a solution of 214.7 (0.26 g, 0.79 mmol, 1.0 eq) in THF (5.0 ml) was added Borane dimethyl sulfide (0.3 g, 3.9 mmol, 5 eq) at 0° C. and stirred at room temperature for 16 h. Upon completion reaction was quenched with methanol, solvents removed under reduced pressure to provide crude which was purified by column chromatography to furnish 214.8 (0.075 g, 34.7%). MS(ES): m/z 274.3 [M+H]⁺.

Synthesis of compound 214.9. To a solution of 214.8 (0.075 g, 0.274 mmol, 1.0 eq) in MeOH (10.0 mL), were added 20% Pd(OH)₂ (0.03 g) and 1N HCl (catalytic). Reaction mixture was stirred (under hydrogen) at 40 psi for 24 h. Upon completion of reaction, reaction mixture was filtered and solvent removed under reduced pressure to provide crude which was purified by column chromatography to get 214.9. (0.03 g, 59.7%). MS(ES): m/z 184.21 [M+H]⁺.

Synthesis of compound 214.91. Compound was prepared from 214.9 and 4.1 using the procedure described in Example 64.

Synthesis of compound I-214. Compound was prepared from 214.91 using procedure described in Example 64. MS(ES): m/z 435.4 [M+H]+; ¹H NMR (DMSO-d₆, 400 MHz): 9.75-9.74 (d, 1H), 9.10 (s, 1H), 8.15 (s, 1H), 7.92 (m, 1H), 7.84-7.74 (m, 2H), 6.18 (d, 1H), 4.90 (d, 1H), 4.71-4.68 (m, 1H), 4.49 (s, 2H), 4.43-4.34 (m, 1H) 3.8-3.82 (m, 1H), 3.64-3.59 (m, 3H), 3.25-3.23 (m, 1H), 2.11-2.06 (m, 1H), 1.81-1.76 (m, 1H).

Example 215

Synthesis of (3R,4R)-1-(1-(2-(2-cyano-6-fluorophenyl)-5-oxo-6,7-dihydro-5H-pyrrolo[3,4-b]pyridin-4-yl)-1H-pyrazol-3-yl)-3-hydroxypiperidine-4-carbonitrile, I-215

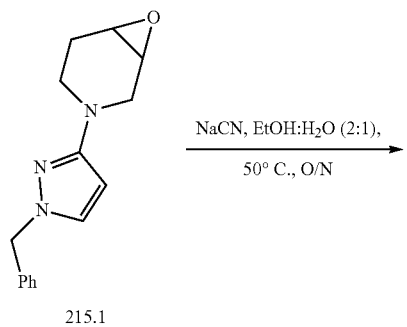

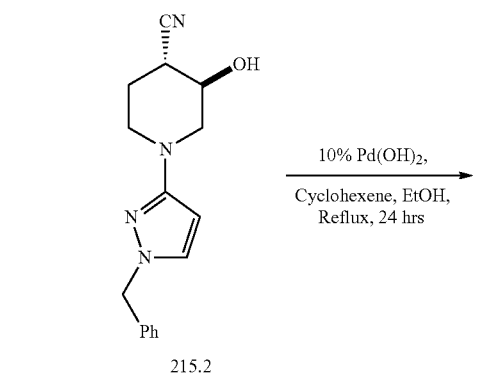

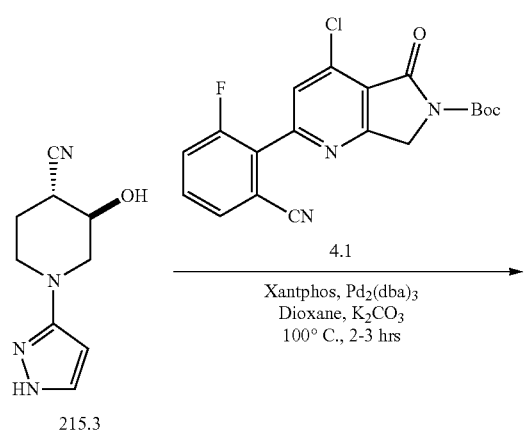

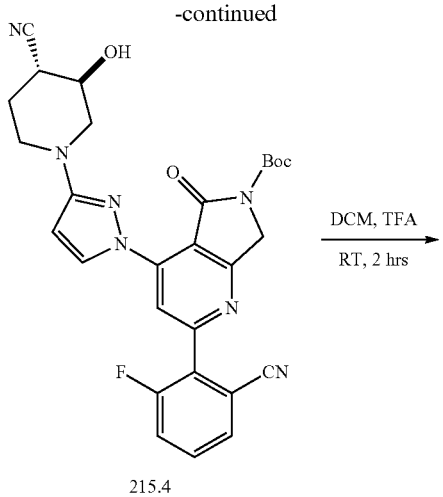

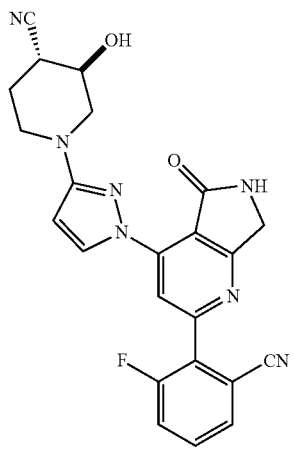

Synthesis of compound 215.2. To a solution of 215.1 (1 g, 3.92 mmol, 1 eq) in EtOH (20 mL), and water (10 mL) was added NaCN (0.23 g, 0.0047 mmol, 1.2 eq). The reaction was stirred at 50° C. for 18 h. Upon completion of the reaction, solvent was removed under reduced pressure. Residues was dissolved in water and extract with EtOAc. Combined organic layers were washed with brine, dried over Na₂SO₄ and concentrated under reduced pressure to get crude which was purified by preparative HPLC to provide 215.2 (0.5 g, 73.4%), MS(ES): m/z 283.15 [M+H]+.

Synthesis of compound 215.3. A solution of 1. (0.4 g, 1.41 mmol, 1.0 eq) in EtOH (5.0 mL) and cyclohexene (5 mL) was added Pd(OH)² (0.2 g). Reaction mixture was refluxed for 24 h. Upon completion of the reaction, mixture was concentrated under reduced pressure to obtain crude. Which was purified by column chromatography to furnish 215.3 (0.125 g, 36.7%). MS(ES): m/z 193.12 [M+H]+.

Synthesis of compound 215.4. Compound was prepared from 215.4 and 4.1 using the procedure described in Example 64

Synthesis of compound I-215. Compound was prepared from 215.4 using the procedure described in Example 64. (0.095 g, 93.2%). MS(ES): m/z 444.02 [M+H]+, ¹H NMR (DMSO-d$_6$, 400 MHz): 9.76-9.75 (d, 1H), 9.14 (s, 1H), 8.21-8.17 (m, 1H), 7.95-7.9 (m, 1H), 7.84-7.74 (m, 1H), 5.8-5.78 (d, 1H), 4.5 (s, 2H), 3.96-3.79 (m, 1H), 3.75-3.68 (m, 1H), 3.67-3.61 (m, 1H), 3.44-3.29 (m, 2H), 2.89-2.74 (m, 2H), 2.73-2.71 (m, 2H), 2.63-2.61 (m, 1H), 2.11-2.1 (m, 1H).

Example 216

Synthesis of (3R,4R)-1-(1-(2-(2-cyano-6-fluorophenyl)-5-oxo-6,7-dihydro-5H-pyrrolo[3,4-b]pyridin-4-yl)-1H-pyrazol-3-yl)-3-hydroxypiperidine-4-carbonitrile, I-216

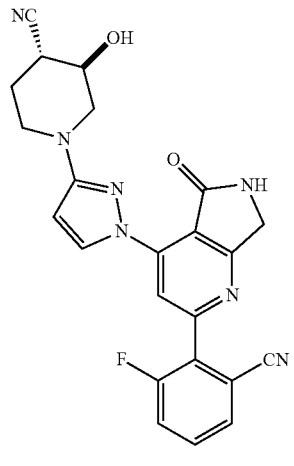

I-215

→ Chiral Separation

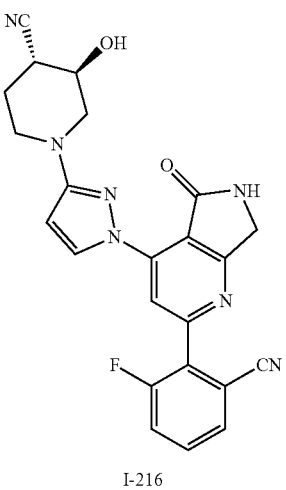 [SMILES: N#Cc1cccc(F)c1-c1cc(-n2ccc(N3CC[C@H](C#N)[C@@H](O)C3)n2)c2c(n1)CNC2=O]

I-216

Compound I-216 was prepared by chiral purification of compound I-215. MS(ES): m/z 444.12 [M+H]$^+$; $^1$H NMR (DMSO-d$_6$, 400 MHz): 9.76-9.75 (d, 1H), 9.14 (s, 1H), 8.21-8.17 (m, 1H), 7.95-7.9 (m, 1H), 7.84-7.74 (m, 1H), 5.8-5.78 (d, 1H), 4.5 (s, 2H), 3.96-3.79 (m, 1H), 3.75-3.68 (m, 1H), 3.67-3.61 (m, 1H), 3.44-3.29 (m, 2H), 2.89-2.74 (m, 2H), 2.73-2.71 (m, 2H), 2.63-2.61 (m, 1H), 2.11-2.1 (m, 1H).

Example 217

Synthesis of (3S,4S)-1-(1-(2-(2-cyano-6-fluorophenyl)-5-oxo-6,7-dihydro-5H-pyrrolo[3,4-b]pyridin-4-yl)-1H-pyrazol-3-yl)-3-hydroxypiperidine-4-carbonitrile, I-217

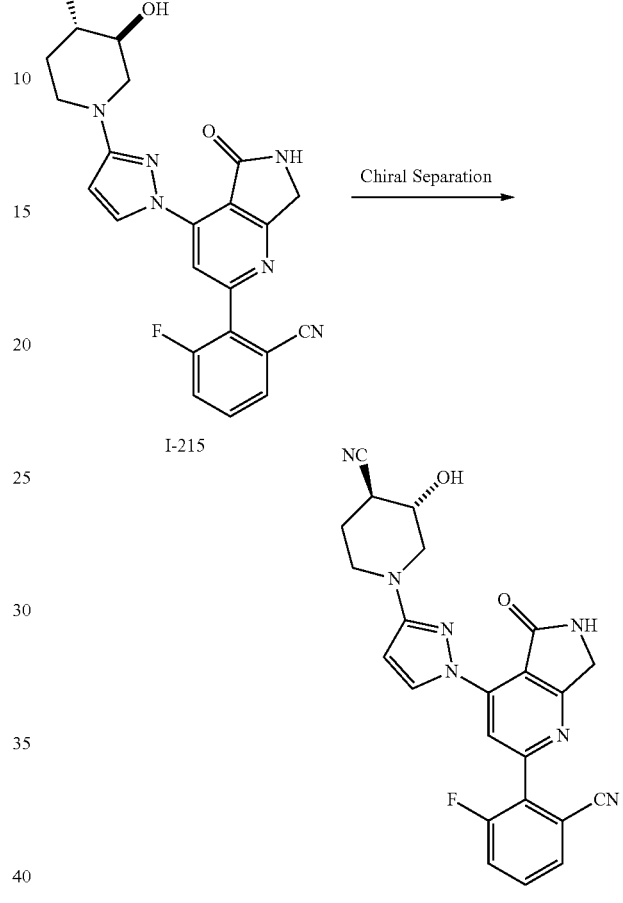

Compound I-217 was prepared by chiral purification of compound I-215. MS(ES): m/z 444.12 [M+H]$^+$; $^1$H NMR (DMSO-d$_6$, 400 MHz): 9.76-9.75 (d, 1H), 9.14 (s, 1H), 8.21-8.17 (m, 1H), 7.95-7.9 (m, 1H), 7.84-7.74 (m, 1H), 5.8-5.78 (d, 1H), 4.5 (s, 2H), 3.96-3.79 (m, 1H), 3.75-3.68 (m, 1H), 3.67-3.61 (m, 1H), 3.44-3.29 (m, 2H), 2.89-2.74 (m, 2H), 2.73-2.71 (m, 2H), 2.63-2.61 (m, 1H), 2.11-2.1 (m, 1H).

Example 218

Synthesis of 3-fluoro-2-(4-(3-((3S,4R)-4-hydroxy-3-morpholinopiperidin-1-yl)-1H-pyrazol-1-yl)-5-oxo-6,7-dihydro-5H-pyrrolo[3,4-b]pyridin-2-yl)benzonitrile, I-218

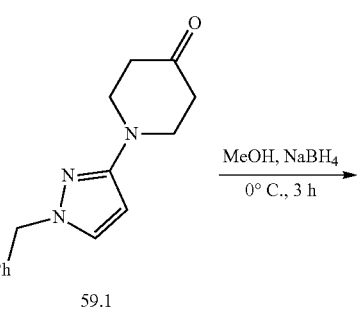

59.1 →MeOH, NaBH$_4$ / 0° C., 3 h

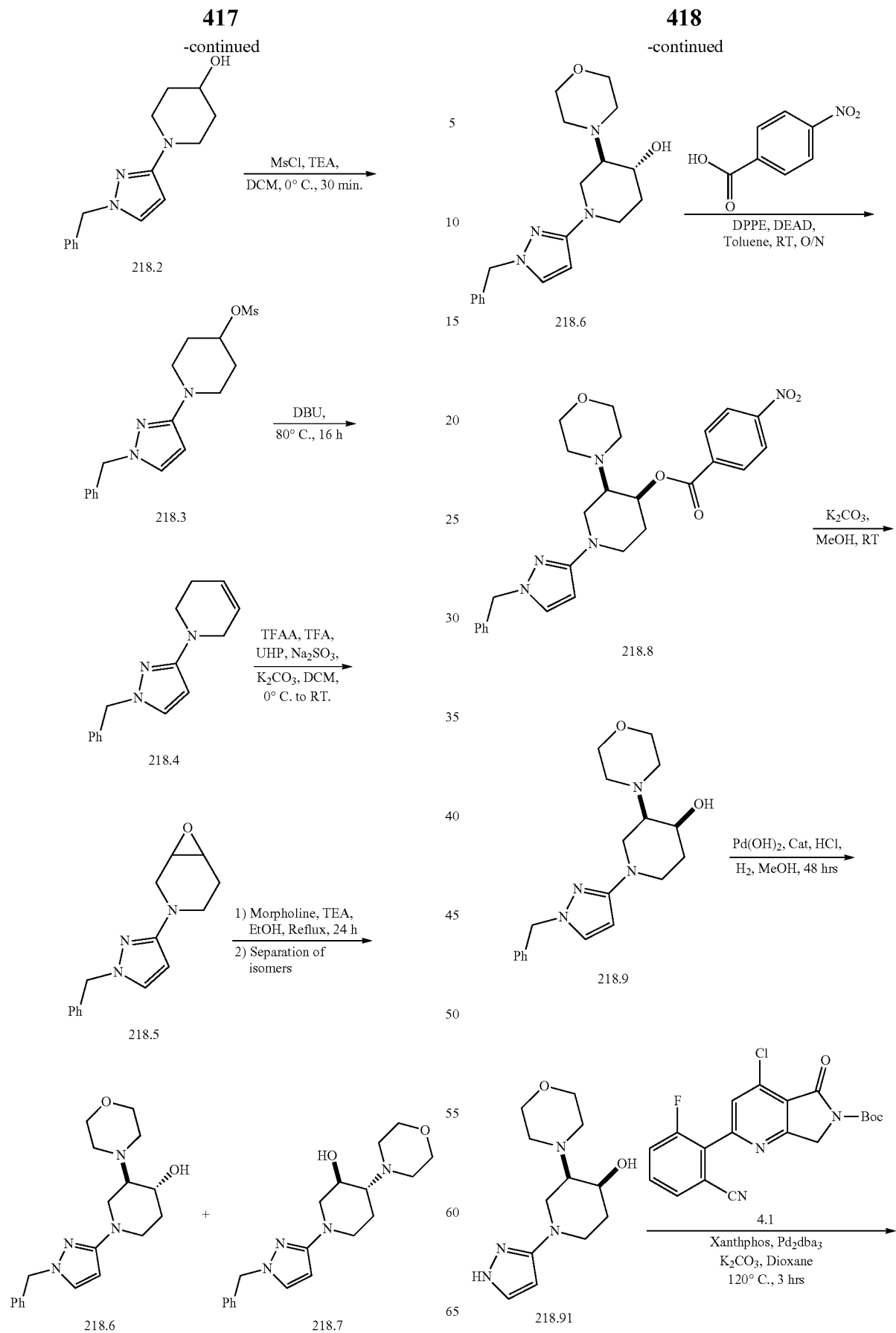

-continued

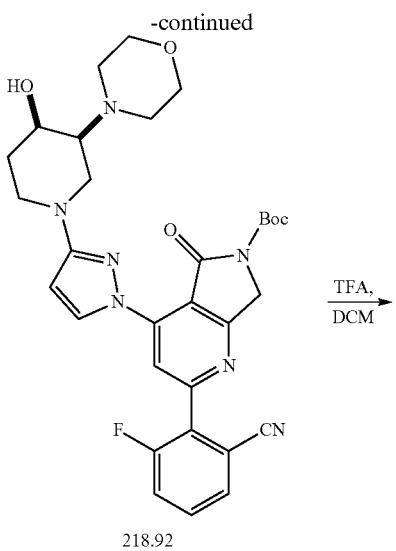

218.92

→ TFA, DCM

I-218

Synthesis of compound 218.2. To a solution of 59.1 (10.0 g, 39.2 mmol, 1 eq.) in MeOH (200 mL) was added NaBH₄ (7.45 g, 196.05 mmol, 5 eq.) at 0° C. in 6 portions over a period of 20 min. The reaction was stirred at 0° C. for 2 hours. Upon completion of the reaction, mixture was poured into 2N HCl and extracted with EtOAc. Organic layers we combined then washed with brine, dried over Na₂SO₄ and concentrated under reduced pressure to obtain crude which was purified by column chromatography to get pure 218.2 (8.0 g, 79.4%). MS(ES): m/z 258.16 [M+H]⁺.

Synthesis of compound 218.3. To a solution of 218.2 (6.4 g, 29.9 mmol, 1 eq.) in DCM (100 mL) was added Et₃N (5 g, 49.5 mmol, 2 eq.), MsCl (4.25 g, 37.35 mmol, 1.5 eq.) at 0° C. Upon completion of the reaction, mixture was poured into water and extracted with EtOAc. Combined EtOAc was washed with brine, dried over Na₂SO₄ and concentrated under reduced pressure to obtain crude 218.3 which was used for next step without purification. (5.0 g, 59.9%). MS(ES): m/z 336.13 [M+H]⁺.

Synthesis of compound 218.4. To a solution of 218.3 (5.0 g, 14.92 mmol, 1 eq.) was added DBU (20 mL). The reaction was refluxed for 16 h. Upon completion of the reaction, mixture was poured into water and extracted with EtOAc. Organic layers were combined and washed with brine, dried over Na₂SO₄ and concentrated under reduced pressure to obtain crude which was purified by column chromatography to provide 218.4 (3 g, 84.09%). MS(ES): m/z 240.15 [M+H]⁺.

Synthesis of compound 218.5. To a solution of Urea hydrogen peroxide (4.92 g, 52.3 mmol, 5 eq.) in DCM (42 mL) was added TFA (11 g, 52.3 mol, 5 eq.) drop wise at 0° C. Mixture was stirred at 0° C. for 1 h. To this mixture was added 218.4 (2.5 g, 10.48 mmol, 1 eq.) and TFA (6 g, 52 mmol, 5.0 eq.). The reaction was stirred at room temperature for 2 h. Upon completion of the reaction Na₂CO₃ (5.43 g, 51.8 mmol, 5 eq.) and K₂CO₃ (7.21 g, 52.3 mmol, 5.0 eq.) were added at −10° C. Mixture was extracted with DCM and back washed with aq. NaHCO₃ then dried over Na₂SO₄ and concentrated under reduced pressure to obtain crude 218.5 which was directly used for next step without purification. (Crude: 1.2 g, 44.99%). MS(ES): m/z 256.13 [M+H]⁺.

Synthesis of compound 218.6 and 218.7. To a solution of 218.5 (1.2 g, 4.7 mmol, 1.0 eq.) in EtOH (10 mL) was added morpholine (1.22 g, 14.11 mmole, 3.0 eq) and Et₃N (4.75 g, 47.05 mmol, 10 eq). The reaction mixture was heated to reflux for 3 h. Upon completion, reaction was cooled to room temperature and poured into water. The product was extracted with EtOAc, organic layers were combined, washed with brine solution, dried over Na₂SO₄ and concentrated under reduced pressure to obtain crude which was purified by reverse phase chromatography, to get pure 218.6 (0.35 g, 32.62%), 218.7 (0.15 g, 13.98%). MS(ES): m/z 343.21 [M+H]⁺.

Synthesis of compound 218.8. To a solution of 218.6 (0.35 g, 1.02 mmole) in toluene (15 mL) at 0° C. was added 4-nitrobenzoic acid (0.341 mg, 2.04 mmole) and 1,2-Bis (diphenylphosphino)-ethane (0.814 g, 2.04 mmole). To this mixture DEAD (0.712 g, 4.09 mmole) was added drop wise over 5 min. The reaction was stirred at room temperature for overnight. Upon completion, reaction was cooled to room temperature and poured into satd. NaHCO₃ solution. Mixture was extracted with EtOAc, then washed with brine solution, dried over Na₂SO₄ and concentrated under reduced pressure to obtain crude which was purified by column chromatography to furnish 218.8. (0.2 g, 39.8%). MS(ES): m/z 492.22 [M+H]⁺.

Synthesis of compound 219.9. To a solution of 219.9 (0.2 g, 0.407 mmole) in MeOH (6.0 mL) was added K₂CO₃ (168 mg, 1.22 mmole). The reaction mixture was stirred at room temperature overnight. Upon completion, the reaction was cooled to room temperature and poured into water. The product was extracted with EtOAc then washed with brine, dried over Na₂SO₄ and concentrated under reduced pressure to obtain crude material. The crude was purified by column chromatography to provide 219.9 (0.13 g, 93.3%). MS(ES): m/z 343.21 [M+H]⁺.

Synthesis of compound 218.91. To a solution of 219.9 (0.13 g, 0.3801 mmol, 1.0 eq) in MeOH (3.0 mL) was added Pd(OH)₂ (0.15 g), and dil. HCl (0.05 mL). Reaction was stirred under H₂ gas overnight. Upon completion, the reaction was filtered, and washed with methanol (10 mL). Mother liquor was evaporated to obtain crude which was purified by column chromatography, to provide 218.91 (0.08 g, 72.4%). LCMS(ES): m/z 253.16 [M+H]⁺.

Synthesis of compound 218.92. Compound 218.92 was prepared from compounds 218.91 and 4.1 using the procedure described in Example 64.

Synthesis of compound I-218. Compound I-218 was prepared from compound 218.92 using the procedure described in Example 64. MS(ES): m/z 504.15 [M+H]⁺; ¹H NMR (DMSO-d₆, 400 MHz): 9.75-9.74 (d, 1H), 9.11 (s, 1H), 8.17 (s, 1H), 7.92-7.9 (dd, 1H), 7.83-7.73 (m, 2H), 6.39 (s, 1H), 4.49 (m, 3H), 3.92-3.66 (m, 3H), 3.55-3.5 (m, 4H), 2.85-2.78 (m, 2H), 2.75-2.66 (m, 4H), 2.51-2.39 (m, 2H), 1.99-1.91 (m, 1H).

Example 219

Synthesis of 3-fluoro-2-(4-(3-(4-fluoro-3-hydroxy-3-methylpiperidin-1-yl)-1H-pyrazol-1-yl)-5-oxo-6,7-dihydro-5H-pyrrolo[3,4-b]pyridin-2-yl)benzonitrile, I-219

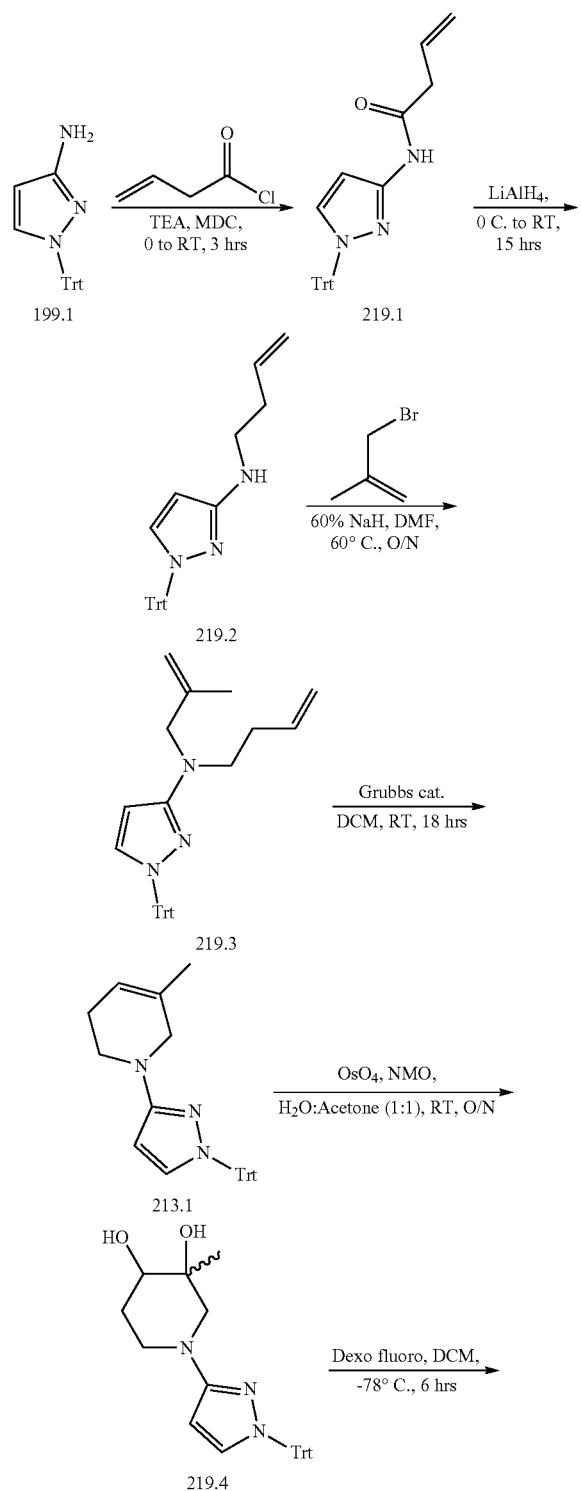

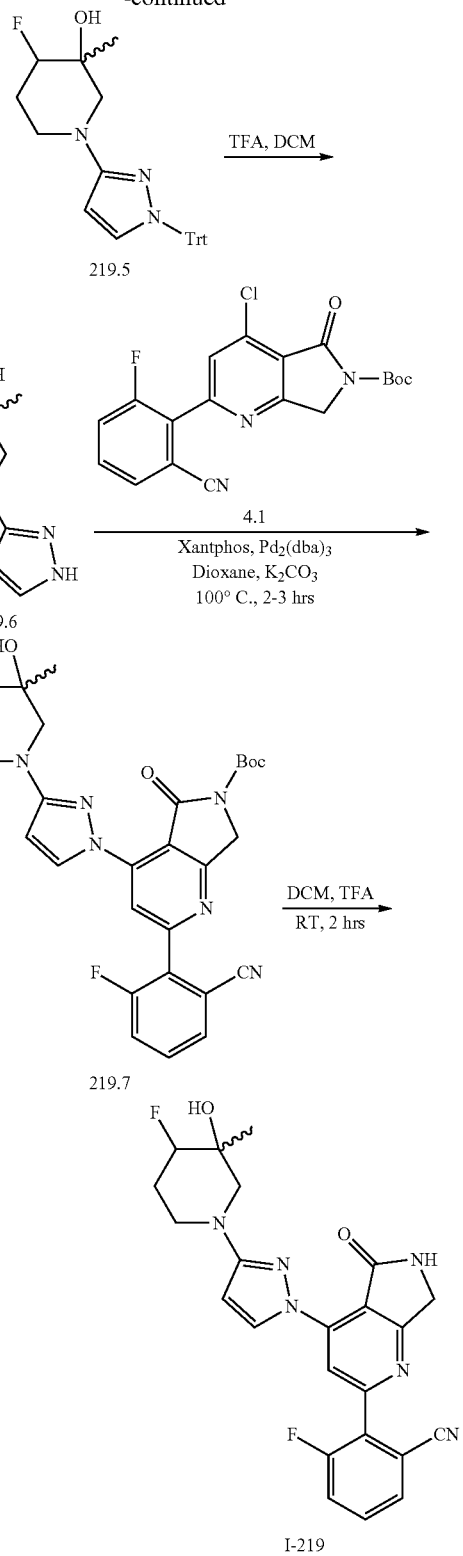

Synthesis of compound 219.1. To a solution of 199.1 (20 g, 61.53 mmol, 1.0 eq) and Et₃N (22 ml, 123.0 mmol, 2.0 eq) in DCM (100 mL) was added but-3-enoyl chloride (8.2 g, 61.53 mmol, 1.0 eq) at 0° C. Reaction mixture was stirred at 0° C. for 30 minutes. The reaction mixture was stirred at room temperature for 3 h. Upon completion of the reaction, mixture was poured into water, and extracted with EtOAc.

Organic layers were combined, washed with brine, dried over $Na_2SO_4$ and concentrated under reduced pressure to pressure to obtain crude which was purified by column chromatography to provide 219.1 (14.0 g, 60.79%). MS(ES): m/z 394 [M+H]+.

Synthesis of compound 219.2. To a solution of 219.1 (14 g, 35.6 mmol, 1.0 eq) in THF (300 mL) was added $LiAlH_4$ (7 g, 184.0 mmol, 3.0 eq) slowly at 0° C. Reaction mixture was stirred at 0° C. for 30 minutes, the warmed up to ambient temperature and stirred for 15 hours. Upon completion of the reaction, mixture was transferred into $Na_2SO_4$ very slowly and filtered through celite then concentrated under reduced pressure to pressure to obtain crude material. Solvents were removed under a reduced pressure and crude purified by column chromatography to furnish 219.2 (3.94 g, 29.12%). MS(ES): m/z 380 [M+H]+.

Synthesis of compound 219.3. To a solution of 219.2 (3.8 g, 2.63 mmol, 1.0 eq) in DMF (40 mL) was added 60% NaH (0.8 g, 20.0 mmol, 2.0 eq) slowly at 0° C. Reaction mixture was stirred at 0° C. for 30 minutes. 3-bromo-2-methylprop-1-ene (2.0 g, 15.0 mmol, 1.5 eq) was added The reaction mixture was stirred at 70° C. for 15 h. Upon completion of the reaction; reaction mixture was transferred into ice, then DCM. Organic layers were combined, washed with brine solution, dried over $Na_2SO_4$ and concentrated under reduced pressure to pressure to obtain crude which was purified by column chromatography to provide 219.3 (3.5 g, 80.8%). MS(ES): m/z 434 [M+H]+.

Synthesis of compound 213.1. To a solution of 1.3 (3.5 g, 8.04 mmol, 1.0 eq) in DCM (30 mL) was added [1,3-bis-(2,4,6-trimethylphenyl)-2-imidazolidinylidene]dichloro-(phenylmethy-lene)(tricyclehexylphosphino)ruthenium (0.355 g, 0.40 mmol, 0.05 eq) and stirred at room temperature for 18 h. Upon completion of the reaction; reaction mixture was transferred into water, and extracted with DCM. Organic layers were combined, washed with brine solution, dried over Na2SO4 and concentrated under reduced pressure to pressure to obtain crude which was purified by column chromatography to furnish 213.1 (2.8 g, 86.15%). MS(ES): m/z 406 [M+H]−.

Synthesis of compound 219.4. To a solution of $OsO_4$ (1 ml, 0.69 mmol, 0.1 eq) (2% in water) in water (15 mL) was added N-Methylmorpholine N-oxide (0.808 g, 6.9 mmol, 1.0 eq) at 0° C. then 213.1 (2.8 g, 6.9 mmol, 1.0 eq) in acetone (15 ml) was added dropwise at 0° C. Reaction mixture was stirred at room temperature for 15 h. Upon completion of the reaction, mixture was poured into water, extracted with EtOAc. Organic layers were combined, washed with brine, dried over $Na_2SO_4$ and concentrated under reduced pressure to pressure to obtain crude which was purified by column chromatography to provide 219.4. (1.8 g, 59.4%). MS(ES): m/z 440 [M+H]+.

Synthesis of compound 219.5. To a solution of 219.4 (0.3 g, 0.6 mmol, 1.0 eq) in DCM (6.0 mL) was added Bis(2-methoxyethyl)aminosulfur trifluoride (0.090 g, 0.4 mmol, 1.0 eq) at −78° C. Reaction mixture was stirred at 0° C. for 30 minutes, then warmed up to ambient temperature and stirred for 6 h. Upon completion of the reaction, mixture was transferred into water, extracted with EtOAc. Organic layers were combined, washed with brine, dried over $Na_2SO_4$ and concentrated under reduced pressure to obtain crude which was purified by column chromatography to provide 219.5 (0.14 g, 46.7%). MS(ES): m/z 442 [M+H]−.

Synthesis of compound 219.6. The compound 219.5 (0.140 g, 0.31 mmol, 1.0 eq) was dissolved in DCM (5 mL) and TFA (1 mL) was added to the reaction mixture. The reaction was stirred at room temperature for 15 h. Upon completion of the reaction, reaction mixture was poured into water, basified with satd. $NaHCO_3$ solution and extracted with EtOAc. Organic layers were combined and dried over $Na_2SO_4$ and concentrated under reduced pressure to obtain crude which was purified by column chromatography to furnish 219.6 (0.05 g, 79.36%). MS(ES): m/z 200 [M+H]+.

Synthesis of compound 219.7. Compound was prepared from 219.6 and 4.1 using the procedure described in Example 64

Synthesis of compound I-219. Compound was prepared from 219.7 using the procedure described in Example 64. (0.026 g, 49.05%). MS(ES): m/z 451 [M+H]−; 1H NMR ($CDCl_3$, 400 MHz): 9.74 (d, 1H), 8.34 (s, 1H), 7.69-7.67 (m, 1H), 7.60-7.55 (m, 1H), 7.52-7.47 (m, 1H), 6.39 (s, 1H), 6.09 (d, 1H), 4.61 (d, 2H), 3.89-3.84 (m, 1H), 3.81-3.75 (m, 1H), 3.70-3.65 (m, 1H), 3.19-3.13 (m, 2H), 1.54 (s, 3H), 1.35-1.24 (m, 1H), 0.92 (t, 1H).

Example 220

Synthesis of (R)-3-fluoro-2-(4-(3-(3-hydroxy-3-methylpiperidin-1-yl-2,2,4,4,5,5,6,6-d8)-1H-pyrazol-1-yl)-5-oxo-6,7-dihydro-5H-pyrrolo[3,4-b]pyridin-2-yl)benzonitrile, I-220

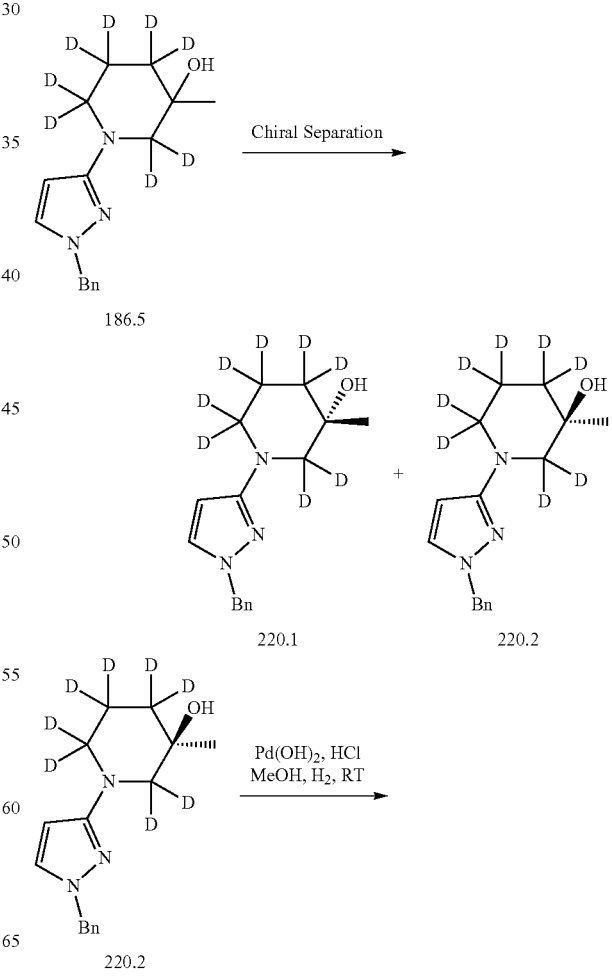

425

-continued

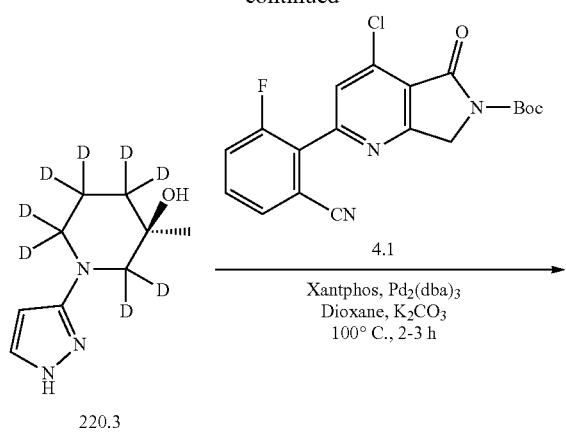

Synthesis of compounds 220.1 and 220.2. Compounds were prepared by chiral purification of compound 186.5

Synthesis of compound 220.3. To a solution of 220.2 (0.070 g, 0.25 mmol, 1.0 eq) in MeOH (10 mL) was added Pd(OH)$_2$ (0.020 g), 1N HCl (catalyst) in hydrogenator. Reaction mixture was stirred under hydrogen pressure (50 psi) at room temperature for 16 h. Upon completion of the reaction was filtered and solvents removed under reduced pressure to provide 220.3 (0.022 g, 46.4%). LCMS(ES): m/z 190.3 [M+H]$^+$.

Synthesis of compound 220.4. Compound was prepared from 220.3 and 4.1 using the procedure described in Example 64.

Synthesis of compound I-220. Compound was prepared from 220.4 using the procedure described in Example 64. (0.012 g, 85.1%). MS(ES): m/z 440.5 [M+H]$^+$; $^1$H NMR (MeOD, 400 MHz): 9.70 (d, 1H), 8.28 (s, 1H), 7.80-7.79 (m, 1H), 7.73-7.66 (m, 3H), 6.24-6.23 (d, 1H), 4.5 (s, 2H), 1.16 (s, 3H).

426

Example 221

Synthesis of 3-fluoro-2-(4-(3-((5r,8r)-8-hydroxy-6,10-dioxa-2-azaspiro-[4.5]decan-2-yl)-1H-pyrazol-1-yl)-5-oxo-6,7-dihydro-5H-pyrrolo[3,4-b]pyridin-2-yl)benzonitrile, I-221

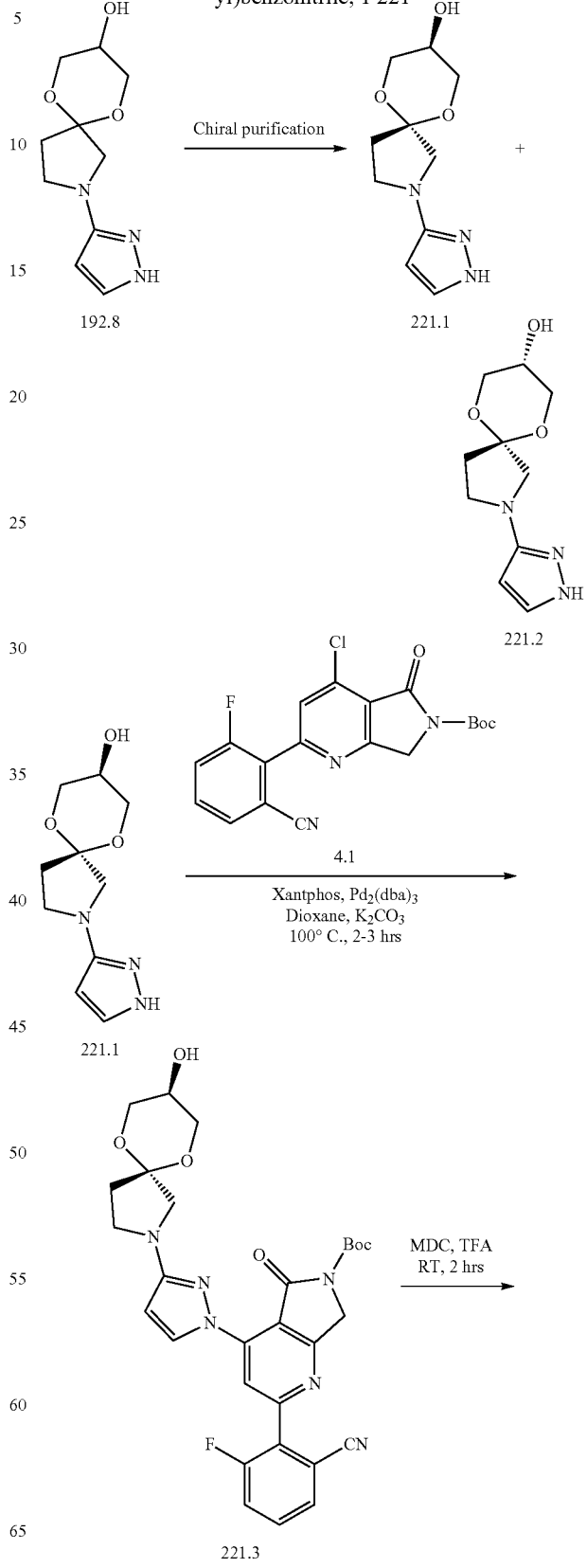

427
-continued

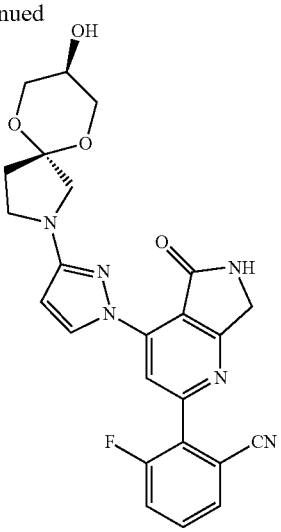

I-221

428
-continued

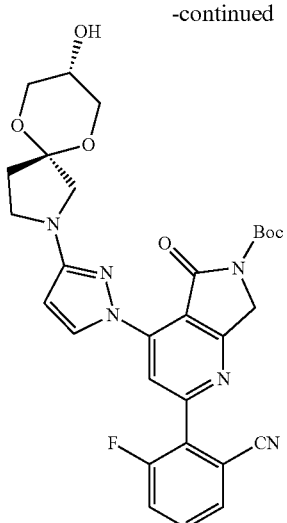

222.1

Synthesis of compounds 221.2 and 221.2. Compound 221.2 and 221.1 were prepared by chiral purification of 192.8.

Synthesis of compound 221.3. Compound was prepared from 221.1 and 4.1 using the procedure described in Example 64.

Synthesis of compound I-221. Compound was prepared from 221.3 using the procedure described in example 64. MS(ES): m/z 477.2 [M+H]$^+$; $^1$H NMR (DMSO-d$_6$, 400 MHz): 9.76 (d, 1H), 9.11 (s, 1H), 8.17 (s, 1H), 7.92-7.90 (m, 1H), 7.79-7.75 (m, 2H), 6.16 (d, 1H), 5.10 (s, 1H), 4.49 (s, 2H), 4.12-4.08 (m, 1H), 3.90-3.88 (m, 2H), 3.57-3.51 (m, 4H), 3.43-3.38 (m, 2H), 2.27-2.23 (t, 2H)

Example 222

Synthesis of 3-fluoro-2-(4-(3-((5s,8s)-8-hydroxy-6,10-dioxa-2-azaspiro[4.5]decan-2-yl)-1H-pyrazol-1-yl)-5-oxo-6,7-dihydro-5H-pyrrolo[3,4-b]pyridin-2-yl)benzonitrile, I-222

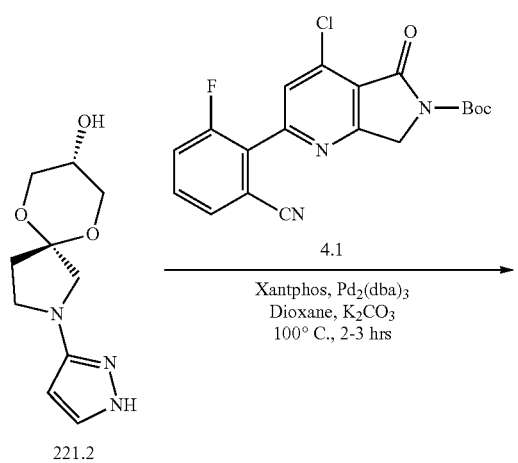

221.2

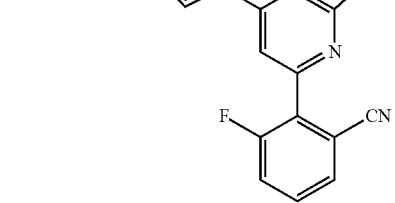

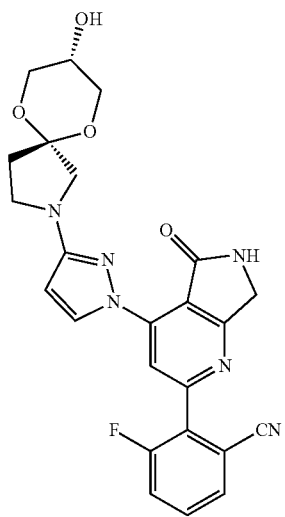

I-222

Compound I-222 was prepared from 221.2 and 4.1 using the procedure referred to in Example 221. MS(ES): m/z 477.2 [M+H]$^+$; $^1$H NMR (DMSO-d$_6$, 400 MHz): 9.76 (d, 1H), 9.11 (s, 1H), 8.17 (s, 1H), 7.92-7.90 (m, 1H), 7.79-7.75 (m, 2H), 6.16 (d, 1H), 5.10 (s, 1H), 4.49 (s, 2H), 4.12-4.08 (m, 1H), 3.90-3.88 (m, 2H), 3.57-3.51 (m, 4H), 3.43-3.38 (m, 2H), 2.27-2.23 (t, 2H)

429

Example 223

Synthesis of 3-fluoro-2-(4-(3-((3S,4R)-3-hydroxy-4-(methoxy-d3)pyrrolidin-1-yl)-1H-pyrazol-1-yl)-5-oxo-6,7-dihydro-5H-pyrrolo[3,4-b]pyridin-2-yl)benzonitrile, I-223

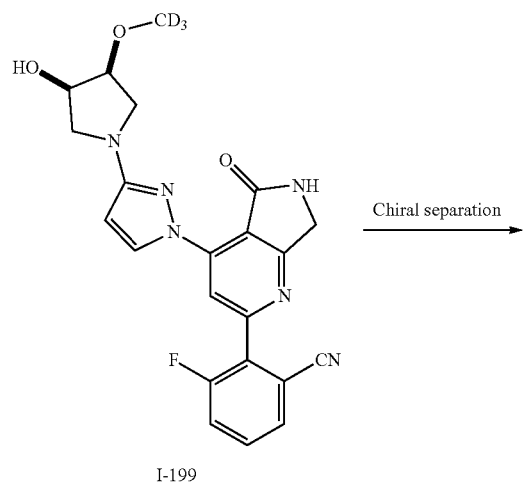

I-199

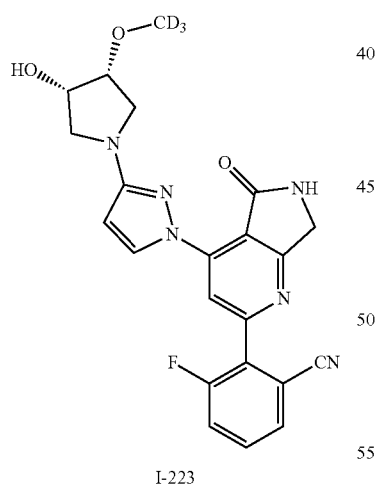

I-223

Compound I-223 was prepared by chiral purification of compound I-199. MS(ES): m/z 438 [M+H]+; %. ¹H NMR (MeOD, 400 MHz): 9.70-9.69 (d, 1H), 8.27 (s, 1H), 7.80-70-0.65 (m, 3H), 6.07-6.06 (d, 1H), 4.42 (s, 2H), 4.41-4.40 (m, 1H), 3.99-3.95 (m, 1H), 3.66-3.61 (m, 2H), 3.48-3.33 (m, 2H).

430

Example 224

Synthesis of 3-fluoro-2-(4-(3-((3R,4S)-3-hydroxy-4-(methoxy-d3)pyrrolidin-1-yl)-1H-pyrazol-1-yl)-5-oxo-6,7-dihydro-5H-pyrrolo[3,4-b]pyridin-2-yl)benzonitrile, I-224

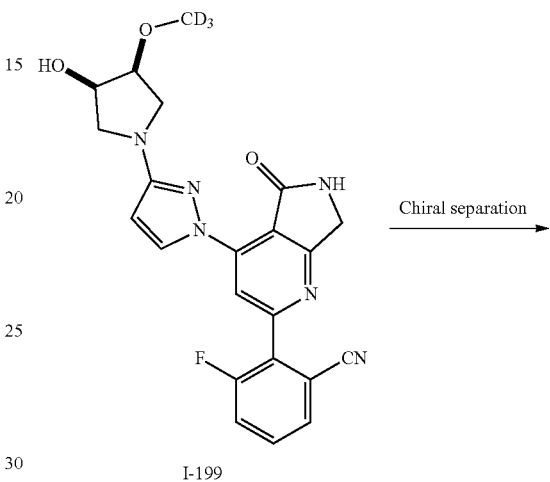

I-199

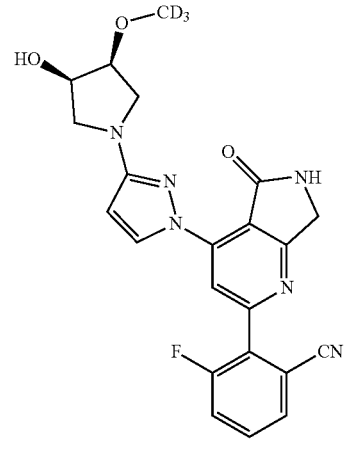

I-224

Compound I-224 was prepared by chiral purification of compound I-199. MS(ES): m/z 438 [M+H]+; ¹H NMR (MeOD, 400 MHz): 9.70-9.69 (d, 1H), 8.27 (s 1H), 7.80-70-0.65 (m, 3H), 6.07-6.06 (d, 1H), 4.42 (s, 2H), 4.41-4.40 (m, 1H), 3.99-3.95 (m, 1H), 3.66-3.61 (m, 2H), 3.48-3.33 (m, 2H).

Example 225

Synthesis of 3-fluoro-2-(4-(3-((4aS,7aR)-4-methyl-hexahydropyrrolo[3,4-b][1,4]oxazin-6 (2H)-yl)-1H-pyrazol-1-yl)-5-oxo-6,7-dihydro-5H-pyrrolo[3,4-b]pyridin-2-yl)benzonitrile, I-225

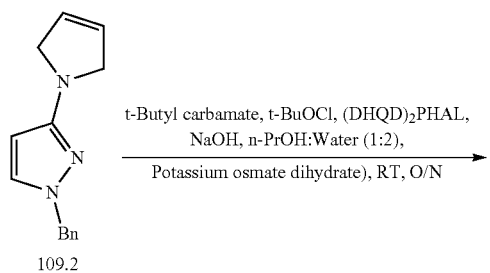

109.2 t-Butyl carbamate, t-BuOCl, (DHQD)$_2$PHAL, NaOH, n-PrOH:Water (1:2), Potassium osmate dihydrate), RT, O/N

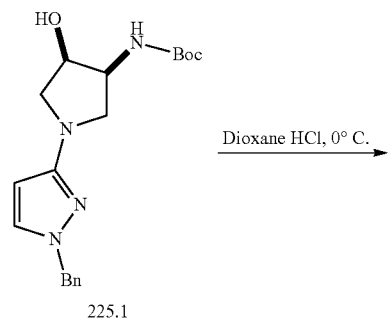

225.1

Dioxane HCl, 0° C.

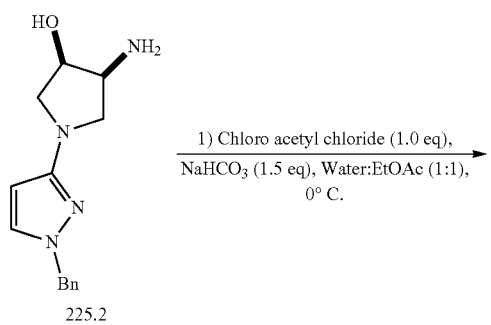

225.2

1) Chloro acetyl chloride (1.0 eq), NaHCO$_3$ (1.5 eq), Water:EtOAc (1:1), 0° C.

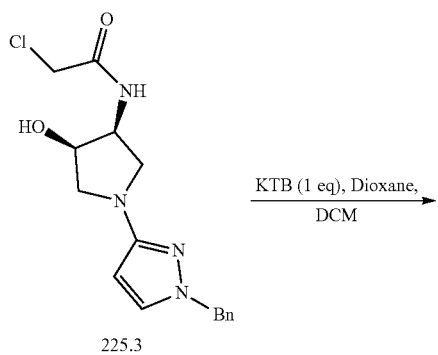

225.3

KTB (1 eq), Dioxane, DCM

-continued

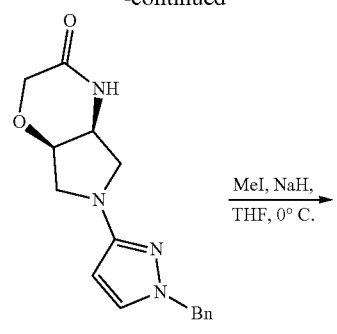

225.4

MeI, NaH, THF, 0° C.

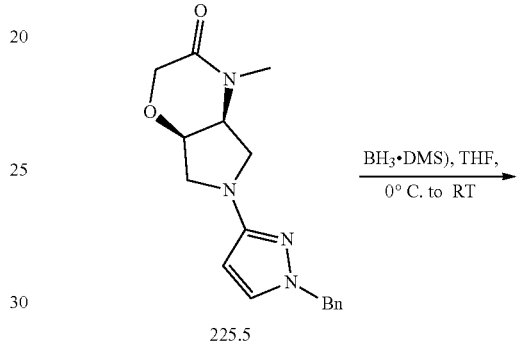

225.5

BH$_3$·DMS), THF, 0° C. to RT

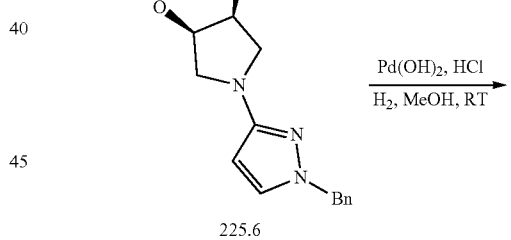

225.6

Pd(OH)$_2$, HCl H$_2$, MeOH, RT

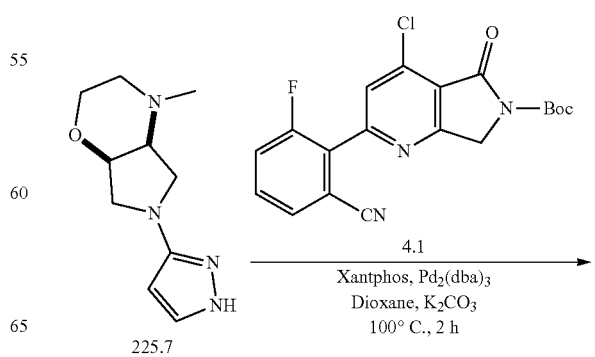

225.7

4.1

Xantphos, Pd$_2$(dba)$_3$
Dioxane, K$_2$CO$_3$
100° C., 2 h

-continued

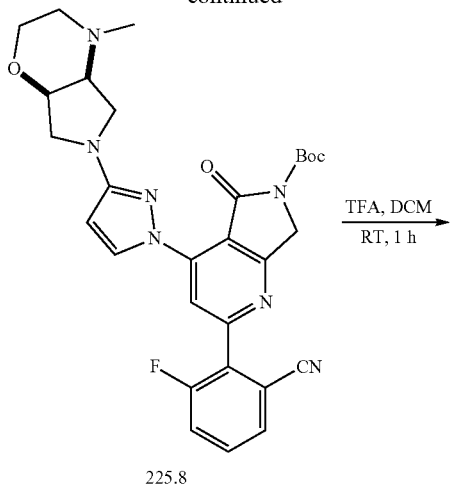

225.8

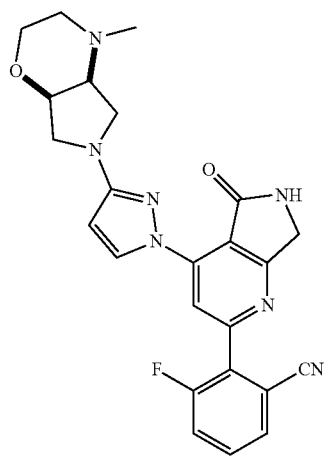

I-225

Synthesis of compound 225.1. To a solution of tert-butyl carbamate (0.780 g, 6.6 mmol, 3 eq.) in propanol (7.0 mL) was added solution of NaOH (0.266 g, 6.6 mmol, 3 eq) in water (1.0 mL), t-Butyl Hypochlorite (0.616 g, 6.6 mmol, 3 eq.), Hydroquinidine 1,4-phthalazinediyl diether (0.086 g, 0.11 mmol, 0.05 eq) in propanol (3 mL) and stirred at room temperature for 20 min. To this was added compound 109.2 (0.5 g, 2.2 mmol, 1 eq) and potassium osmate dihydrate (0.041 g, 0.11 mmol, 0.05 eq). The reaction was stirred at room temperature for 24 h. Upon completion of the reaction, mixture was poured into water and extracted with EtOAc. Organic layers were combined, washed with brine, dried over $Na_2SO_4$ and concentrated under reduced pressure to obtain crude which was purified by preparative HPLC to provide 225.1. (0.3 g, 37.7%), MS(ES): m/z 359.20 [M+H]⁺.

Synthesis of compound 225.2. To a solution of compound 225.1 (0.3 g, 0.837 mmol, 1 eq) in dioxane (1 mL) was added dioxane: HCl (2.0 mL) at 0° C. The reaction was stirred at room temperature for 1 h. Upon completion, reaction mixture was concentrated under reduced pressure to obtain crude which was dissolved in MeOH and neutralized with polymer supported tetra alkyl ammonium carbonate, filtered and concentrated under reduced pressure to obtain 225.2. (0.1 g, 46.25%). MS(ES): m/z 259.15 [M+H]⁺

Synthesis of compound 225.3. To a solution of compound 225.3 (0.1 g, 0.386 mmol, 1.0 eq) in EtOAc:water (1:1) (2 mL) was added $NaHCO_3$ (0.048 g, 0.579 mmol, 1.5 eq) at 0° C. Suspension was stirred for 10 minutes followed by drop wise addition of chloroacetyl chloride (0.042 g, 0.386 mmol, 1.0 eq). Reaction was stirred at room temperature for 1 h. Upon completion of the reaction, reaction mixture was pored into water and product was extracted with EtOAc. Organic layers were combined, washed with brine, dried over $Na_2SO_4$ and concentrated under reduced pressure to obtain crude which was purified by column chromatography to provide 225.3. (0.1 g, 77.2%). MS(ES): m/z 335.8 [M+H]⁺

Synthesis of compound 225.4. To a solution of compound 225.3 (0.1 g, 0.299 mmol, 1.0 eq) in 1,4-dioxane (3.0 mL) and DCM (3 mL) was added potassium tert-butoxide (0.035 g, 0.299 mmol, 1.0 eq) at 0° C. Reaction mixture stirred at room temperature for 24 h. Upon completion of the reaction, reaction mixture was poured into water and product was extracted with DCM. Organic layers were combined, washed with brine solution, dried over $Na_2SO_4$ and concentrated under reduced pressure to obtain 225.4. (0.085 g, 95.39%). MS(ES): m/z 299.5 [M+H]⁺

Synthesis of compound 225.5. To the suspension of NaH (0.017 g, 0.427 mmol, 1.5 eq) in DMF (3 mL) at 0° C. was added compound 225.4 (0.085 g, 0.285 mmol, 1.0 eq). Reaction mixture stirred at room temperature for 3 h. Upon completion of the reaction, reaction mixture was transferred into ice/water and product was extracted with EtOAc. Organic layers were combined, washed with brine, dried over $Na_2SO_4$ and concentrated under reduced pressure to obtain crude which was purified by column chromatography to furnish 225.5 (0.057 g, 64%). MS(ES): m/z 313.5 [M+H]⁺.

Synthesis of compound 225.6. To a solution of compound 225.5 (0.050 g, 0.160 mmol, 1.0 eq) in THF (2.0 mL) was added $BH_3$-DMS (0.060 g, 0.801 mmol, 5.0 eq) dropwise at 0° C. Reaction mixture stirred at room temperature for 24 h. Upon completion of the reaction, MeOH was added and stirred for 1 hour. Reaction mixture was concentrated under reduced pressure to obtain crude which was purified by column chromatography to provide 225.6. (0.03 g, 62.8%). MS(ES): m/z 299.5 [M+H]⁺

Synthesis of compound 225.7. To the suspension of $Pd(OH)_2$ (0.060 g) in MeOH (5.0 mL) was added compound 225.6 (0.030 g, 0.1 mmol, 1.0 eq) followed by 1.0 N HCl (catalytic). Reaction was stirred under hydrogen pressure for 24 h, then filtered through celite and concentrated under reduced pressure to get 225.7 (0.015 g, 71.6%). MS(ES): m/z 209.4 [M+H]⁺.

Synthesis of compound 225.8. Compound 225.8 was prepared from compounds 225.7 and 4.1 using the procedure described in Example 64.

Synthesis of compound I-225. MS(ES): m/z 460.5[M+H]⁺, LCMS purity: 96.7%, HPLC purity: 99.5%, ¹H NMR (DMSO, 400 MHz): 9.78 (s, 1H), 9.1 (s, 1H), 7.92-7.90 (m, 1H), 7.81-7.76 (m, 2H), 6.16 (d, 1H), 4.48 (s, 2H), 4.07 (s, 2H), 3.77-3.75 (m, 2H), 3.52-3.48 (m, 3H), 2.60-2.58 (m, 2H), 2.39-2.32 (m, 4H).

Example 226

Synthesis of 3-fluoro-2-(4-(3-((3R,4S)-3-hydroxy-4-methoxy-3-methyl-pyrrolidin-1-yl)-1H-pyrazol-1-yl)-5-oxo-6,7-dihydro-5H-pyrrolo[3,4-b]pyridin-2-yl)benzonitrile, I-226

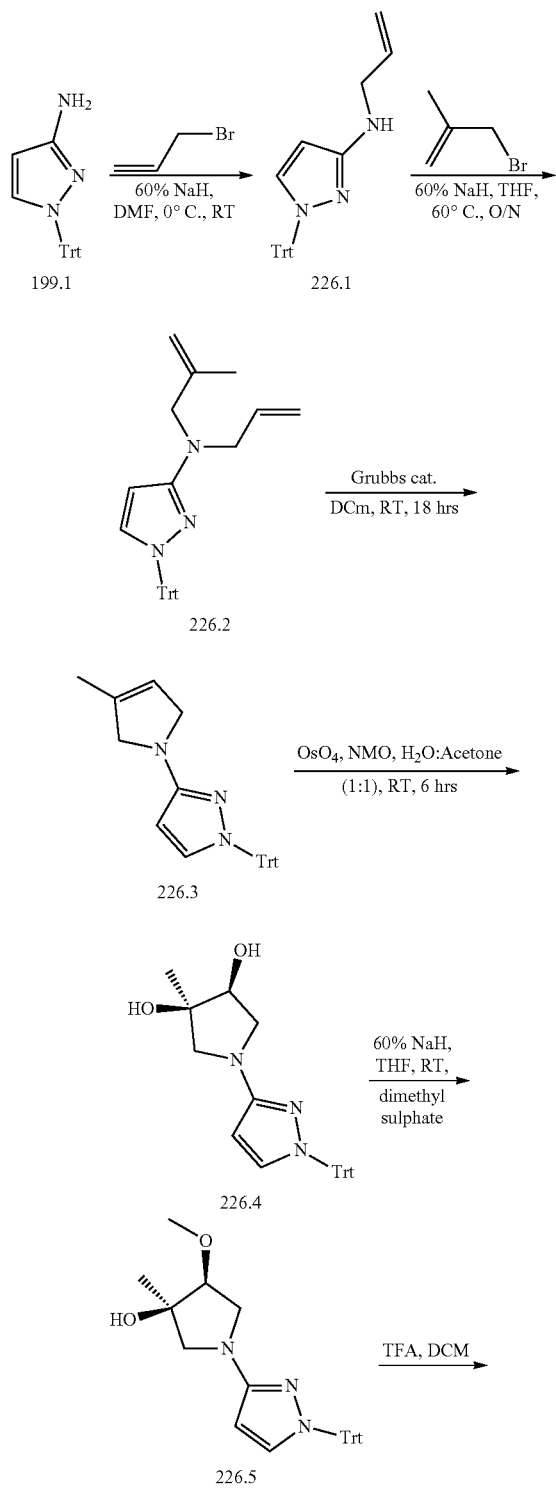

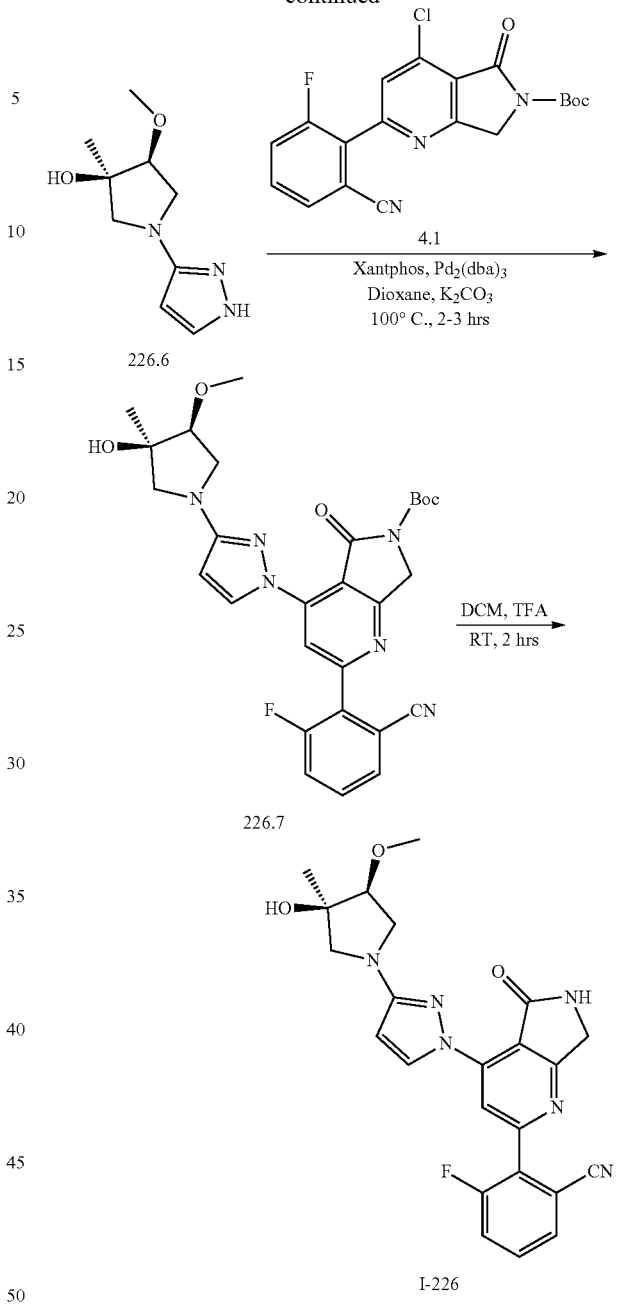

Synthesis of compound 226.1. To a solution of 199.1 (20 g, 61.53 mmol, 1.0 eq) in DMF (200 mL) was added 60% NaH (2.46 g, 61.53 mmol, 1.0 eq) at 0° C. Reaction mixture was stirred at 0° C. for 30 minutes and to it allyl bromide (7.44 g, 61.53 mmol, 1.0 eq) was added. The reaction mixture was stirred at room temperature for 3 h. Upon completion of the reaction, mixture was poured into water, and extracted with EtOAc. Organic layers were combined, washed with brine solution, dried over $Na_2SO_4$ and concentrated under reduced pressure to pressure to obtain crude which was purified by column chromatography to furnish 226.1 (14 g, 63.63%). MS(ES): m/z 366.4 [M+H]⁺.

Synthesis of compound 226.2. To a solution of 226.1 (14 g, 38.30 mmol, 1.0 eq) in THF (140 mL) was added 60% NaH (4.60 g, 115.0 mmol, 1.0 eq) at 0° C. Reaction mixture was stirred at 0° C. for 30 minutes and to it 3-bromo-2- methylprop-1-ene (10.34 g, 76.6 mmol, 2.0 eq) was added. The reaction was stirred at 60° C. for 15 h. Upon completion of the reaction, mixture was poured into water, extracted with EtOAc. Organic layers were combined, washed with brine solution, dried over Na$_2$SO$_4$ and concentrated under reduced pressure to obtain crude which was purified by column chromatography to provide 226.2 (10 g, 62.5%). MS(ES): m/z 420 [M+H]$^+$.

Synthesis of compound 226.3. To a solution of 226.2 (6.0 g, 14.3 mmol, 1.0 eq) in DCM (30 mL) was added Benzylidene-bis(tricyclohexylphosphino)-dichlororuthenium (0.6 g, 0.70 mmol, 0.05 eq). Reaction was stirred at room temperature for 18 h. Upon completion of the reaction; reaction mixture was transferred into water, and extracted with DCM. Organic layers were combined, washed with brine, dried over Na$_2$SO$_4$ and concentrated under reduced pressure to pressure to obtain crude which was purified by column chromatography to obtain 226.3 (2.14 g, 38.28%). MS(ES): m/z 392 [M+H]$^+$.

Synthesis of compound 226.4. To a solution of OsO$_4$ (0.68 ml, 0.05 mmol, 0.01 eq) (2% in water) in water (21 mL) was added N-Methylmorpholine N-oxide (0.628 g, 5.36 mmol, 1.0 eq) at 0° C. then 226.3 (2.1 g, 5.36 mmol, 1.0 eq) in acetone (21 ml) was added dropwise at 0° C. Reaction mixture was stirred at room temperature for 6 h. Upon completion of the reaction, mixture was transferred into water, extracted with EtOAc. Organic layers were combined, washed with brine solution, dried over Na$_2$SO$_4$ and concentrated under reduced pressure to pressure to obtain crude which was purified by column chromatography to provide 226.4 (1.0 g, 43.8%). MS(ES): m/z 426 [M+H]$^+$.

Synthesis of compound 226.5. To a solution of 226.4 (1 g, 2.35 mmol, 1.0 eq) in THF (10 mL) was added 60% NaH (0.094 g, 2.35 mmol, 1.0 eq) at 0° C. Reaction mixture was stirred at 0° C. for 30 minutes and to it dimethyl sulphate (0.218 ml, 2.30 mmol, 1.0 eq) was added at same temperature. The reaction mixture was stirred at room temperature for 3 h. Upon completion of reaction, reaction mixture was transferred into water, and extracted with EtOAc. Organic layers were combined, washed with brine, dried over Na$_2$SO$_4$ and concentrated under reduced pressure to pressure to obtain crude which was purified by column chromatography 226.5 (0.5 g, 48.54%). MS(ES): m/z 440 [M+H]$^+$.

Synthesis of compound 226.6. The compound 226.5 (0.5 g, 1.13 mmol, 1.0 eq) was dissolved in DCM (5.0 mL) and TFA (1.0 mL) was added to the reaction mixture. Reaction was stirred at room temperature for 1.5 h. Upon completion of the reaction, mixture was poured in water, basified with saturated bicarbonate solution and extracted with EtOAc. Organic layers were combined, dried over Na$_2$SO$_4$ and concentrated under reduced pressure to obtain crude which was purified by column chromatography to provide 226.6 (0.1 g, 44.64%). MS(ES): m/z 198 [M+H]$^+$.

Synthesis of compound 226.7. Compound was prepared from 226.6 and 4.1 using the procedure described in Example 64.

Synthesis of compound I-227. Compound was prepared from 226.7 using the procedure described in Example 64. (0.030 g, 49.2%). MS(ES): m/z 449 [M+H]$^+$; $^1$H NMR (DMSO, 400 MHz): 9.78 (d, 1H), 9.09 (s, 1H), 8.16 (s, 1H), 7.92-7.90 (m, 1H), 7.83-7.73 (m, 2H), 6.13 (t, 1H), 4.65 (s, 1H), 4.48 (d, 2H), 3.65-3.61 (m. 1H), 3.57-3.54 (m, 1H), 3.38 (s, 3H), 3.24-3.16 (m, 3H), 1.25 (t, 3H).

Example 227

Synthesis of 3-fluoro-2-(4-(3-(4-methyl-5-oxo-2,5-dihydro-1H-pyrrol-3-yl)-1H-pyrazol-1-yl)-5-oxo-6,7-dihydro-5H-pyrrolo[3,4-b]pyridin-2-yl)benzonitrile, I-227

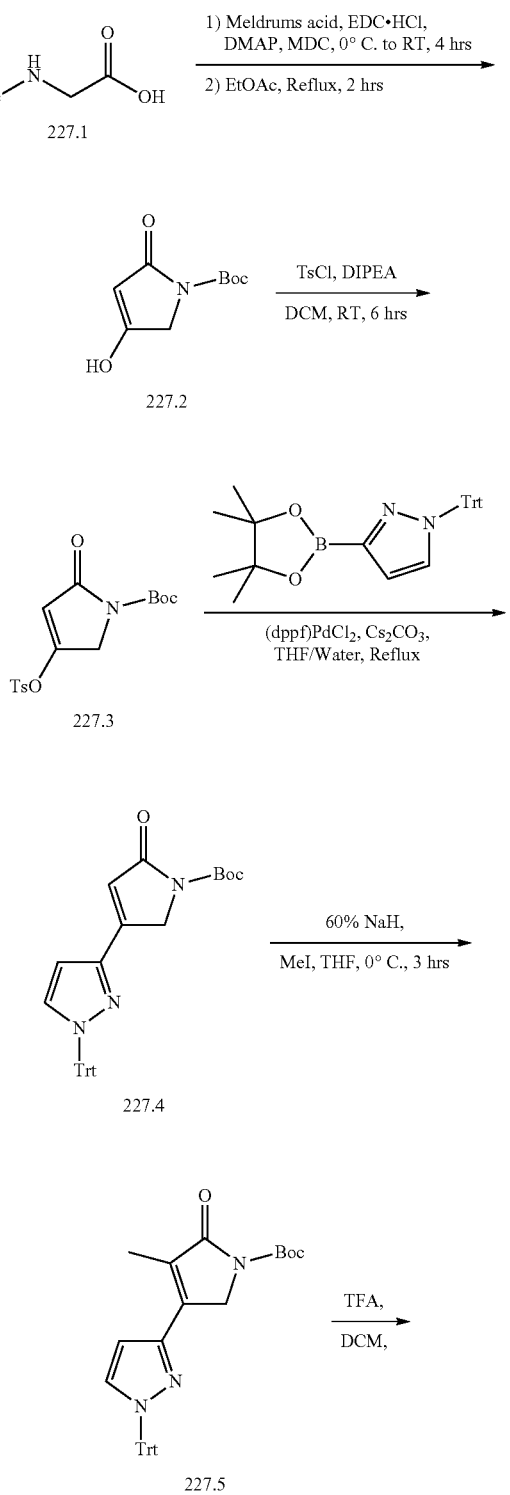

-continued

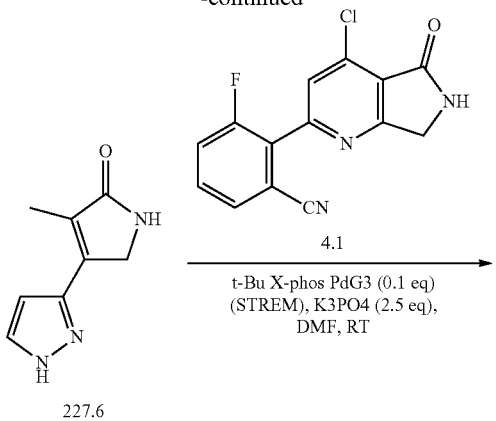

was purified by column chromatography to furnish 227.3 (6.0 g, 26.08%). MS(ES): m/z 356 [M+H]⁺.

Synthesis of compound 227.4. To a mixture of 227.3 (2.33 g, 6.57 mmol, 1.0 eq) in THF (60 ml) and water (6 mL) was added 3-(4,4,5,5-tetramethyl-1,3,2-dioxaborolan-2-yl)-1-trityl-1H-pyrazole (4.3 g, 9.86 mmol, 1.5 eq). The reaction mixture was degassed for 10 min. under argon atmosphere, and Cs$_2$CO$_3$ (5.93 g, 16.4 mmol, 2.5 eq) was added. The reaction mixture was degassed for 10 minutes using argon, then dppfPdCl$_2$ (0.240 g, 0.32 mmol, 0.05 eq) was added, and again degassed for 5 min. The reaction was then heated at 100° C. for 6 h. Upon completion of the reaction, reaction mixture was poured into water and extracted with EtOAc. Organic layers were combined, washed with brine, dried over Na$_2$SO$_4$ and concentrated under reduced pressure to obtain crude which was purified by column chromatography to furnish 227.4 (2.7 g, 83.85%). MS(ES): m/z 492 [M+H]⁺.

Synthesis of compound 227.5. To a solution of 227.4 (2.0 g, 4.24 mmol, 1.0 eq) in THF (50 mL) was added 60% NaH (0.170 g, 4.24 mmol, 1.0 eq) at 0° C. Reaction mixture was stirred at 0° C. for 30 minutes and to it MeI (0.664 g, 4.67 mmol, 1.1 eq) was added. The reaction mixture was stirred at room temperature for 3 h. Upon completion of the reaction, mixture was transferred into water, and extracted with EtOAc. Organic layers were combined, washed with brine, dried over Na$_2$SO$_4$ and concentrated under reduced pressure to pressure to obtain crude which was purified by column chromatography to furnish 227.6 (0.7 g, 34.14%). MS(ES): m/z 506 [M+H]⁺.

Synthesis of compound 227.6. The compound 227.5 (0.7 g, 1.38 mmol, 1.0 eq) was dissolved in DCM (10 mL) and TFA (1.5 mL) was added to the reaction mixture. The reaction was stirred at room temperature for 15 h. Upon completion of the reaction, mixture was poured into water, basified with satd. NaHCO$_3$ and extracted with EtOAc. Organic layers were combined and dried over Na$_2$SO$_4$ and concentrated under reduced pressure to obtain crude which was purified by column chromatography to provide 227.6 (0.12 g, 52.9%). MS(ES): m/z 164 [M+H]⁺.

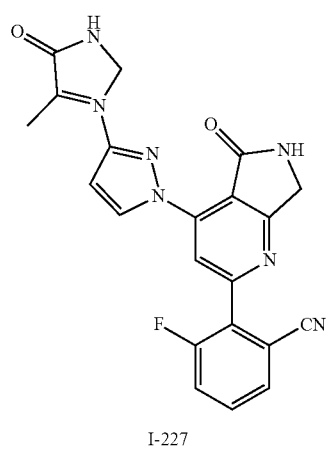

Synthesis of compound I-227. To a mixture of 227.6 (0.075 g, 0.45 mmol, 1.0 eq) in DMF (2 ml) was added 4.1 (0.132 g, 0.45 mmol, 1.0 eq). The reaction mixture was degassed for 10 min. under argon atmosphere, K$_3$PO$_4$ (0.246 g, 1.43 mmol, 2.5 eq). Reaction mixture was degassed for 10 min. under argon atmosphere, then tBuXPhos-Pd-G3, [(2-Di-tert-butylphosphino-2',4',6'-triisopropyl-1,1'-biphenyl)-2-(2'-amino-1,1'-biphenyl)] palladium(II) methanesulfonate (0.037 g, 0.04 mmol, 0.1 eq) were added, again degassed for 5 min. The reaction was stirred at room temperature for 1 h. Upon completion of the reaction, reaction mixture was transferred in water and extracted with EtOAc. Organic layers were combined, washed with brine, dried over Na$_2$SO$_4$ and concentrated under reduced pressure to obtain crude which was purified by column chromatography to provide I-227 (0.030 g, 15.87%). MS(ES): m/z 415 [M+H]⁻; ¹H NMR (DMSO, 400 MHz): 9.73 (d, 1H), 9.28 (s, 1H), 8.37 (d, 2H), 7.95 (d, 1H), 7.86-7.78 (m, 2H), 7.00 (d, 1H), 4.58 (d, 2H), 4.25 (s, 2H), 2.08 (s, 3H).

Synthesis of compound 227.2. To a solution of 227.1 (25 g, 142.8 mmol, 1.0 eq) in DCM (1250 mL) was added 2,2-dimethyl-1,3-dioxane-4,6-dione (12 g, 214.2 mmol, 1.5 eq) and DMAP (26.14 g, 214.2 mmol, 1.5 eq) at 0° C. Reaction mixture was stirred at 0° C. and to it EDCI-HCl (41 g, 214.2 mmol, 1.5 eq) was added at same temperature. The reaction mixture was stirred at room temperature for 4 h. Upon completion of the reaction, reaction mixture was transferred into water, extracted with DCM. Organic layers were combined, washed with 15% Potassium sulfate solution, brine solution, citric acid solution, dried over Na$_2$SO$_4$ and concentrated under reduced pressure to obtain crude which was purified by crystallization to afford 227.2 (16 g, 56.14%). MS(ES): m/z 201 [M+H]⁺.

Synthesis of compound 227.3. To a solution of 227.2 (13 g, 65.0 mmol, 1.0 eq) in DCM (500 mL) was added DIPEA (16.6 g, 130.0 mmol, 2.0 eq) at 0° C. Reaction mixture was stirred at 0° C. for 30 minutes and to it TsCl (12.4 g, 65.0 mmol, 1.0 eq) was added at same temperature. The reaction mixture was stirred at room temperature for 6 h. Upon completion of the reaction, reaction mixture was transferred into water, and extracted with ethyl acetate. Organic layers were combined, washed with brine, dried over Na$_2$SO$_4$ and concentrated under reduced pressure to obtain crude which

441

Example 228

Synthesis of 3-fluoro-2-(4-(3-((3S,4R)-3-hydroxy-4-methoxy-3-methylpiperidin-1-yl)-1H-pyrazol-1-yl)-5-oxo-6,7-dihydro-5H-pyrrolo[3,4-b]pyridin-2-yl)benzonitrile I-228

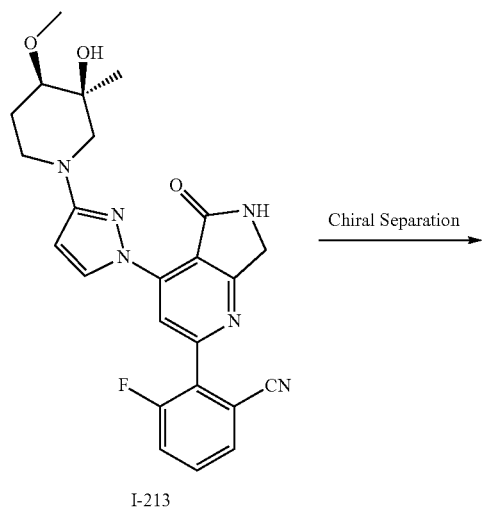

I-213

→ Chiral Separation →

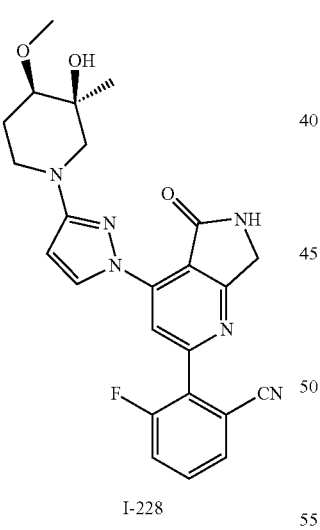

I-228

Compound I-228 was prepared by chiral separation of compound I-213. (0.04 g, 69.51%). MS(ES): m/z 438 [M+H]+; 1H MS(ES): m/z 438 [M+H]+; 1H NMR (CDCl3, 400 MHz): 9.74-9.73 (d, 1H), 8.34 (s, 1H), 7.68-7.66 (d, 1H), 7.60-7.47 (m, 2H), 6.25 (s, 1H), 6.08 (d, 1H), 4.60 (s, 2H), 3.45 (s, 3H), 3.36 (d, 1H), 3.33-3.28 (m, 1H), 3.22-3.19 (m, 1H), 2.83 (s, 1H). 2.19 (s1H) 1.96-1.95 (m, 2H), 1.37 (s, 3H).

442

Example 229

Synthesis of 3-fluoro-2-(4-(3-((3R,4S)-3-hydroxy-4-methoxy-3-methylpiperi-din-1-yl)-1H-pyrazol-1-yl)-5-oxo-6,7-dihydro-5H-pyrrolo[3,4-b]pyridin-2-yl)benzonitrile, I-229

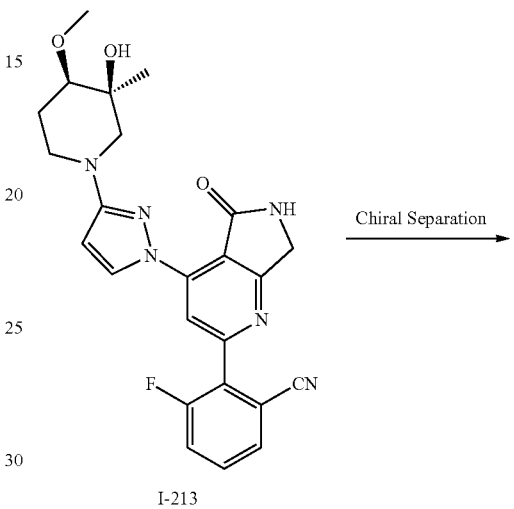

I-213

→ Chiral Separation →

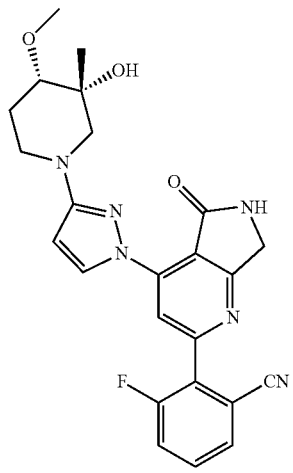

I-229

Compound I-229 was prepared by chiral separation of compound I-213. (0.04 g, 69.5%). MS(ES): m/z 438 [M+H]+; 1H NMR (CDCl3, 400 MHZ): 9.74-9.73 (d, 1H), 8.34 (s, 1H), 7.68-7.66 (m, 3H), 7.60-7.47 (m, 2H), 6.26 (s, 1H), 6.08 (d, 1H), 4.60 (s, 2H), 3.45 (s, 3H), 3.36 (d, 1H), 3.33-3.28 (m, 1H), 3.22-3.19 (m, 1H), 2.83 (s, 1H). 2.19 (s1H) 1.96-1.95 (m, 2H), 1.33 (S, 3H).

Example 230

Synthesis of 2-(4-(3-((3R,4S)-3,4-dimethoxy-3-methylpyrrolidin-1-yl)-1H-pyrazol-1-yl)-5-oxo-6,7-dihydro-5H-pyrrolo[3,4-b]pyridin-2-yl)-3-fluorobenzonitrile, I-230

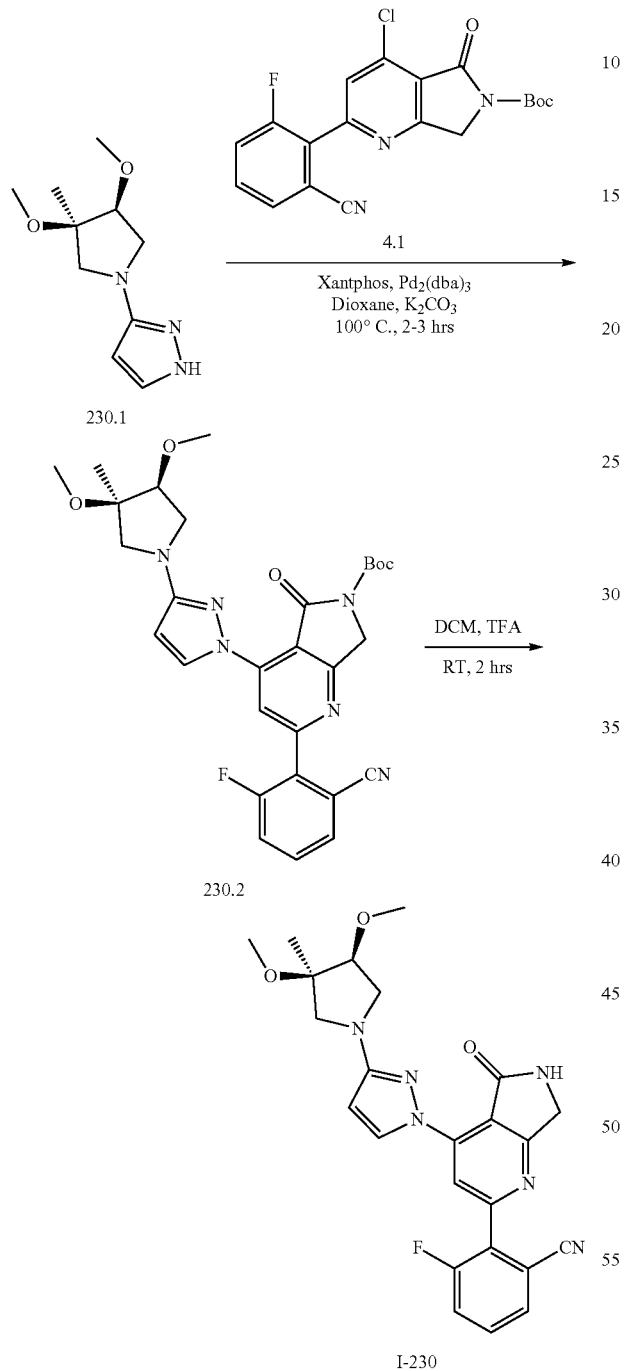

Compound I-230 was prepared from compounds 230.21 and 4.1 using the procedures described in Example 64. (0.035 g, 71.4%). MS(ES): m/z 463 [M+H]+; ¹H NMR (DMSO, 400 MHz): 9.78 (d, 1H), 9.09 (s, 1H), 8.16 (s, 1H), 7.92-7.90 (m, 1H), 7.83-7.75 (m, 2H), 6.14 (d, 1H), 4.48 (d, 2H), 3.71 (t, 1H), 3.60-3.56 (m, 1H), 3.42 (s, 3H), 3.38-3.33 (m, 3H), 3.21 (s, 3H), 1.27 (s, 3H).

Example 231

Synthesis of 3-fluoro-2-(4-(1-(morpholine-4-carbonyl)-1H-pyrazol-3-yl)-5-oxo-6,7-dihydro-5H-pyrrolo[3,4-b]pyridin-2-yl)benzonitrile, I-231

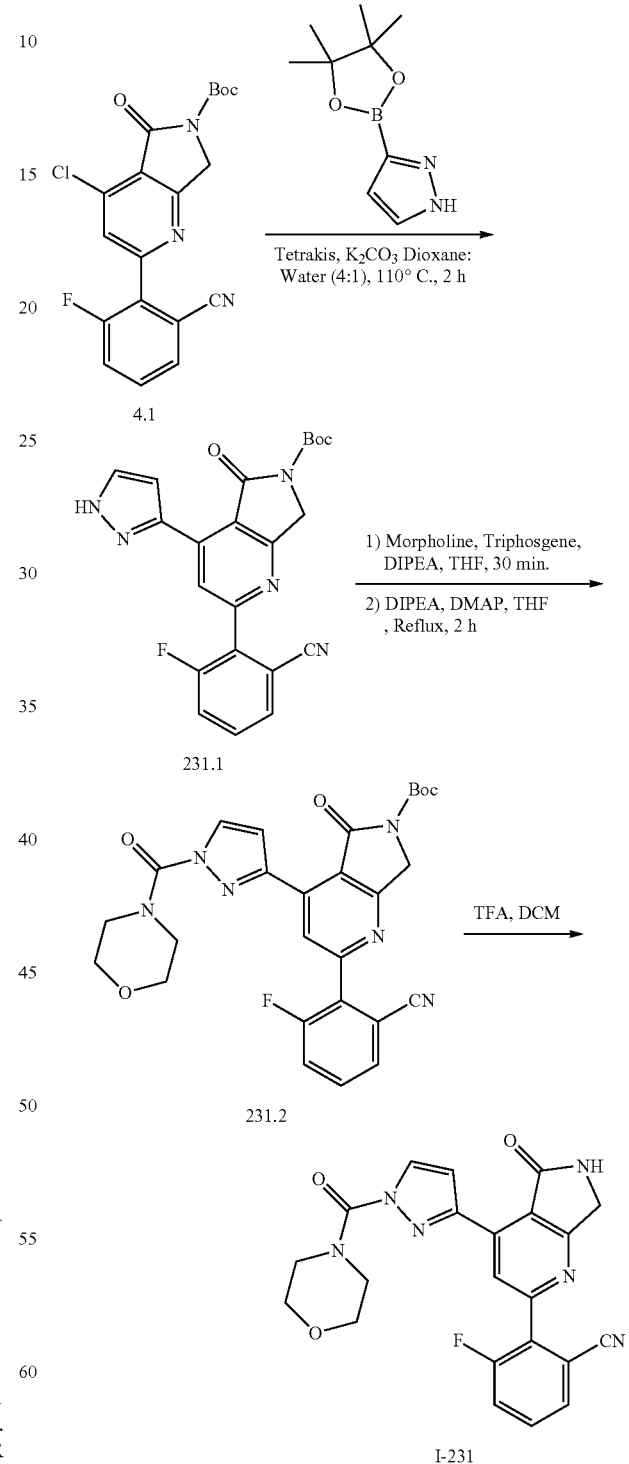

Synthesis of compound 231.1. o a mixture of 4.1 (0.200 g, 0.516 mmol, 1.0 eq) in 1,4-dioxane (3.2 ml) and water (0.8 mL) was added 3-(4,4,5,5-tetramethyl-1,3,2-dioxaborolan-2-yl)-1H-pyrazole (0.12 g, 0.62 mmol, 1.2 eq) and K₂CO₃ (0.216 g, 1.55 mmol, 3.0 eq). The reaction mixture was degassed for 10 min. under argon atmosphere, then Pd(PPh₃)₄ (0.060 g, 0.0516 mmol, 0.1 eq) added, again degassed for 5 min. The reaction was then heated at 110° C. for 2 h. Upon completion of the reaction, mixture was transferred into water and product was extracted with EtOAc. Organic layers were combined, washed with brine dried over Na₂SO₄ and concentrated under reduced pressure to obtain crude which was purified by column chromatography to furnish 231.1 (0.105 g, 46.2%). MS(ES): m/z 420.4 [M+H]⁺.

Synthesis of compound 231.2. To a solution of morpholine (0.020 g, 0.238, 1.0 eq) in THF (3 mL) was added DIPEA (0.105 g, 0.715 mmol, 3.0 eq). Reaction mixture was cooled to 0° C. and triphosgene (0.035 g, 0.119 mmol, 0.5 eq) was added and stirred at room temperature for 30 min. Reaction mixture again cooled to 0° C. and DMAP (0.028 g, 0.238 mmol, 1.0 eq) was added and stirred for 10 min followed by addition of compound 231.1 (0.100 g, 0.238 mmol, 1.0 eq) in THF (1 mL). Reaction mixture stirred at room temperature for 2 h. Upon completion of the reaction, reaction mixture was transferred into water and product was extracted with EtOAc. Organic layers were combined, washed with brine, dried over Na₂SO₄ and concentrated under reduced pressure to obtain crude which was purified by column chromatography to provide 232.2 (0.065 g, 51.2%). MS(ES): m/z 533.5 [M+H]⁺.

Synthesis of compound I-231. Compound was prepared using the procedure described in example 64. (0.027 g, 51.16%). MS(ES): m/z 433.33 [M+H]⁺; ¹H NMR (DMSO-d₆, 400 MHz): 9.1 (s, 1H), 8.35-8.34 (d, 1H), 8.27 (s, 1H), 7.94-7.93 (d, 1H), 7.85-7.77 (m, 3H), 4.64-4.58 (m, 1H), 4.54 (s, 2H), 3.77 (s, 4H), 3.69 (s 4H).

Example 232

Synthesis of Compound 3-fluoro-2-(4-(3-isopropyl-1H-1,2,4-triazol-1-yl)-5-oxo-6,7-dihydro-5H-pyrrolo[3,4-b]pyridin-2-yl)benzonitrile, I-232

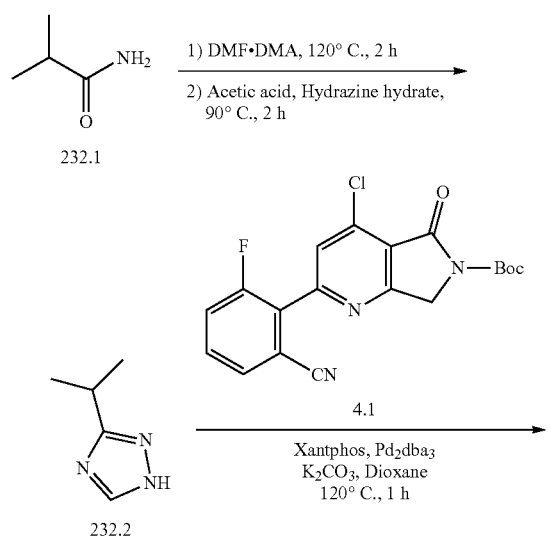

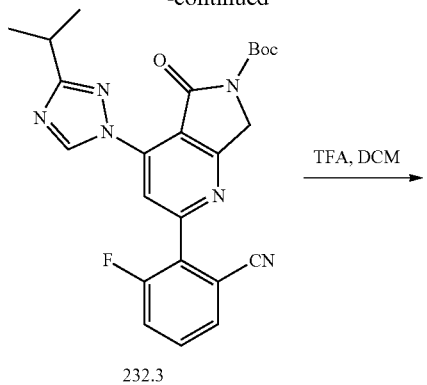

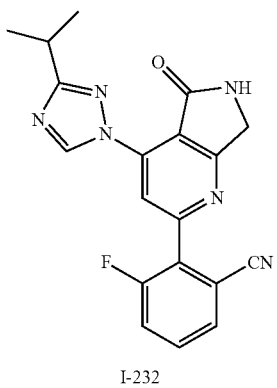

Synthesis of compound 232.2. A solution of 232.1 (5.0 g, mmol, 1.0 eq) in DMF-DMA (140 mL) was stirred at 120° C. for 2 h. Upon completion of the reaction, reaction mixture was concentrated under reduced pressure to obtain crude oil. The oil was dissolved in acetic acid (100 mL) and hydrazine hydrate (10 mL) was added dropwise. The reaction mixture was heated at 90° C. for 2 h and then cooled to room temperature. The mixture was concentrated under reduced pressure and the residue was treated with saturated potassium carbonate solution (pH=8), then extracted with DCM. Organic layers were combined, washed with brine, dried over Na₂SO₄ and concentrated under reduced pressure. The crude was purified by column chromatography to furnish 232.2 (2.0 g, 31.35%). MS(ES): m/z 112.08 [M+H]⁺.

Synthesis of compound 232.3. Compound was prepared from 232.2 and 4.1 using the procedure described in Example 64.

Synthesis of compound I-232. Compound was prepared from 232.3 using the procedure described in Example 64. (0.025 g, 53.2%). MS(ES): m/z 363.44 [M+H]⁺; ¹H NMR (DMSO-d₆, 400 MHz): 10.03 (s, 1H), 9.34 (s, 1H), 8.22 (s, 1H), 8.21-7.92 (m, 1H), 7.85-7.76 (m, 2H), 4.60 (s, 2H), 3.14-3.07 (m, 1H), 1.32-1.30 (d, 6H).

Example 233

Synthesis of 2-(2,6-difluorophenyl)-4-(4-isopropylthiazol-2-yl)-6,7-dihydro-5H-pyrrolo[3,4-b]pyridin-5-one, I-233

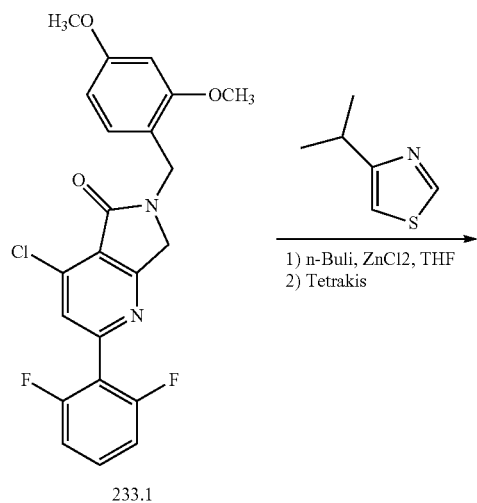

Synthesis of compound 233.2. To a solution of 4-isopropylthiazole (0.177 g, 1.39 mmol, 2.0 eq) in THF (3 mL) was added n-BuLi (2.18 mL, 3.485 mmol, 5.0 eq) at −78° C. and stirred for 1 h. To this added ZnCl$_2$ (0.759 g, 5.58 mmol, 8.0 eq) at −78° C. and stirred for 30 min. Reaction mixture then stirred at 0° C. for 30 min followed by addition of Pd(PPh3)$_4$ (0.040 g, 0.034 mmol, 0.005 eq) and 233.1 (0.3 g, 0.697 mmol, 1.0 eq). The reaction mixture was stirred at 60° C. for 12 h. Upon completion of the reaction, reaction mixture was transferred into saturated NH$_4$Cl solution and product was extracted with EtOAc. Organic layers were combined, washed with brine, dried over Na$_2$SO$_4$ and concentrated under reduced pressure to obtain crude which purified by prep HPLC to get pure 232.2 (0.10 g, 27.53%). MS(ES): m/z 522.5 [M+H]$^+$ Synthesis of compound I-233. Compound 232.2 (0.100 g, 0.191 mmol, 1.0 eq) was dissolved in DCM (5.0 mL) and TFA (5 mL) was added to the reaction mixture. The reaction was stirred at 50° C. for 5 h. Upon completion of reaction, reaction mixture was poured into water, basified with satd. NaHCO$_3$ and extracted with EtOAc. Organic layers were combined and dried over Na2SO4 and concentrated under reduced pressure to obtain crude which was purified by column chromatography to provide I-233 (0.025 g, 35.1%). MS(ES): m/z 372.2 [M+H]$^-$; $^1$H NMR (DMSO-d$_6$, 400 MHz): 9.08 (s, 1H), 8.35 (s, 1H), 7.68 (s, 1H), 7.66-7.59 (m, 1H), 7.33-7.28 (m, 2H), 4.54 (s, 2H), 3.16-3.10 (m, 1H), 1.30-1.28 (d 6H).

Example 234

Synthesis of 3-fluoro-2-(4-(1-((3R,4R)-4-hydroxytetrahydrofuran-3-yl)-1H-pyrazol-3-yl)-5-oxo-6,7-dihydro-5H-pyrrolo[3,4-b]pyridin-2-yl)benzonitrile, I-234

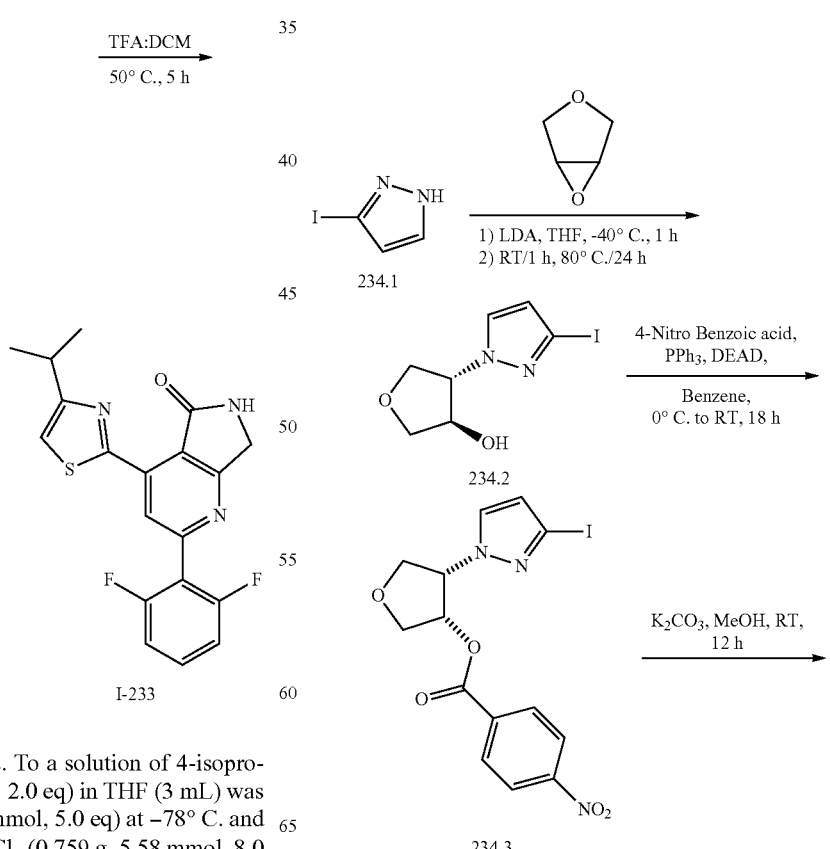

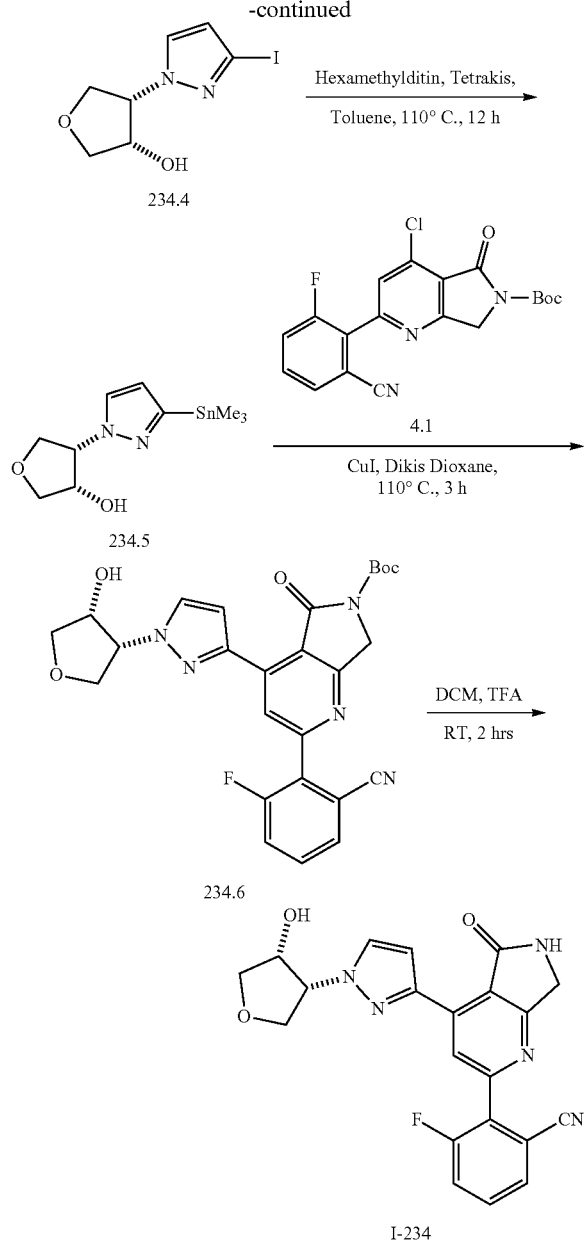

mixture slowly warmed to room temperature and stirred for 18 h. Upon completion of the reaction; reaction mixture was transferred into water, and extracted with EtOAc. Organic layers were combined, washed with brine, dried over Na₂SO₄ and concentrated under reduced pressure to pressure to obtain crude which was purified by column chromatography to furnish 234.3 (3.0 g, 78.31%). MS(ES): m/z 430.2 [M+H]⁺.

Synthesis of compound 234.4. To a solution of 234.3 (3.0 g, 6.99 mmol, 1.0 eq) in MeOH (150 mL) was added K₂CO₃ (1.44 g, 10.48 mmol, 1.5 eq). Reaction was stirred at room temperature for 12 h. Upon completion of the reaction, mixture was concentrated under reduced pressure. Residue was dissolved in EtOAc and washed with aqueous sodium bicarbonate solution followed by brine, dried over Na₂SO₄ and concentrated under reduced pressure to pressure to obtain crude which was purified by column chromatography to provide 234.4 (1.0 g, 51.08%). MS(ES): m/z 281.2 [M+H]⁺.

Synthesis of compound 234.5. A mixture of 234.4 (0.2 g, 0.714 mmol, 1.0 eq) in toluene (5 mL) was degassed with argon for 10 min followed by addition of hexamethylditin (0.701 g, 2.142 mmol, 3 eq) and Pd(PPh₃)₄ (0.082 g, 0.0714 mmol, 0.1 eq). Reaction mixture was again degassed for 10 min and heated to 110° C. for 12 h. Upon completion of the reaction, mixture was filtered through celite and concentrated under reduced pressure to obtain crude 234.5 (0.23 g, 97%). MS(ES): m/z 318 [M+H]⁺. Crude compound was directly used for next step without further purification.

Synthesis of compound 234.6. To a mixture of 4.1 (0.080 g, 0.206 mmol, 1.0 eq) in 1,4-dioxane (2.0 ml) was added 234.5 (0.131 g, 0.412 mmol, 2.0 eq). The reaction mixture was degassed for 10 min. under argon atmosphere, then CuI (0.015 g, 0.082 mmol, 0.2 eq) was added followed by Pd(PPh₃)₂Cl₂ (0.028 g, 0.0412 mmol, 0.1 eq) added, again degassed for 5 min. The reaction was then heated at 110° C. for 3 h. Upon completion of the reaction, mixture filtered, concentrated under reduced pressure to obtain crude which was purified by column chromatography to provide 234.6 (0.085 g, 36.5%). MS(ES): m/z 506.5 [M+H]⁺.

Synthesis of compound I-234. Compound was prepared using the procedure described in Example 64. (0.025 g, 36.6%). MS(ES): m/z 406.38 [M+H]⁺; ¹H NMR (CDCl₃, 400 MHz): 8.13 (d, 1H), 7.70-7.68 (d, 1H), 7.63-7.45 (m, 4H), 6.72 (s, 1H), 4.92-4.87 (m, 1H), 4.77-4.72 (m, 1H), 4.65 (s, 2H), 4.35-4.27 (m, 3H), 4.22-4.18 (m, 1H), 4.08-4.02 (m, 1H).

Synthesis of compound 234.2. To a solution of 234.1 (5.0 g, 25.77 mmol, 1.0 eq) in THF (15 mL) was added LDA (2M in THF) (14 mL, 28.33 mmol, 1.1 eq) at −78° C. Reaction mixture was stirred at −40° C. for 1 h. To this added solution of 3,6-dioxabicyclo[3.1.0]hexane (1.77 g, 20.61 mmol, 0.8 eq) in THF (10 mL). Reaction mixture was stirred at room temperature for 1 h and heated at 80° C. for 24 h. Upon completion of the reaction, mixture was transferred into water, and extracted with EtOAc. Organic layers were combined, washed with brine, dried over Na₂SO₄ and concentrated under reduced pressure to pressure to obtain crude which was purified by column chromatography to furnish 234.2 (2.5 g, 34.63%). MS(ES): m/z 281.2 [M+H]⁺.

Synthesis of compound 234.3. To a mixture of 234.2 (2.5 g, 8.92 mmol, 1.0 eq) in benzene (30 mL) was added 4-nitro benzoic acid (6.56 g, 39.28 mmol, 4.4 eq) and PPh₃ (11.45 g, 43.7 mmol, 4.9 eq). Reaction mixture was cooled to 0° C. and DEAD (7.6 g, 43.7 mmol, 4.9 eq) was added. Reaction Example 235

Synthesis of 3-fluoro-2-(4-(6-hydroxy-4,5,6,7-tetrahydropyrazolo[1,5-a]pyrimidin-2-yl)-5-oxo-6,7-dihydro-5H-pyrrolo[3,4-b]pyridin-2-yl)benzonitrile I-235

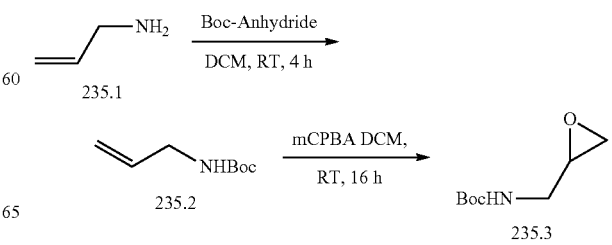

451

-continued

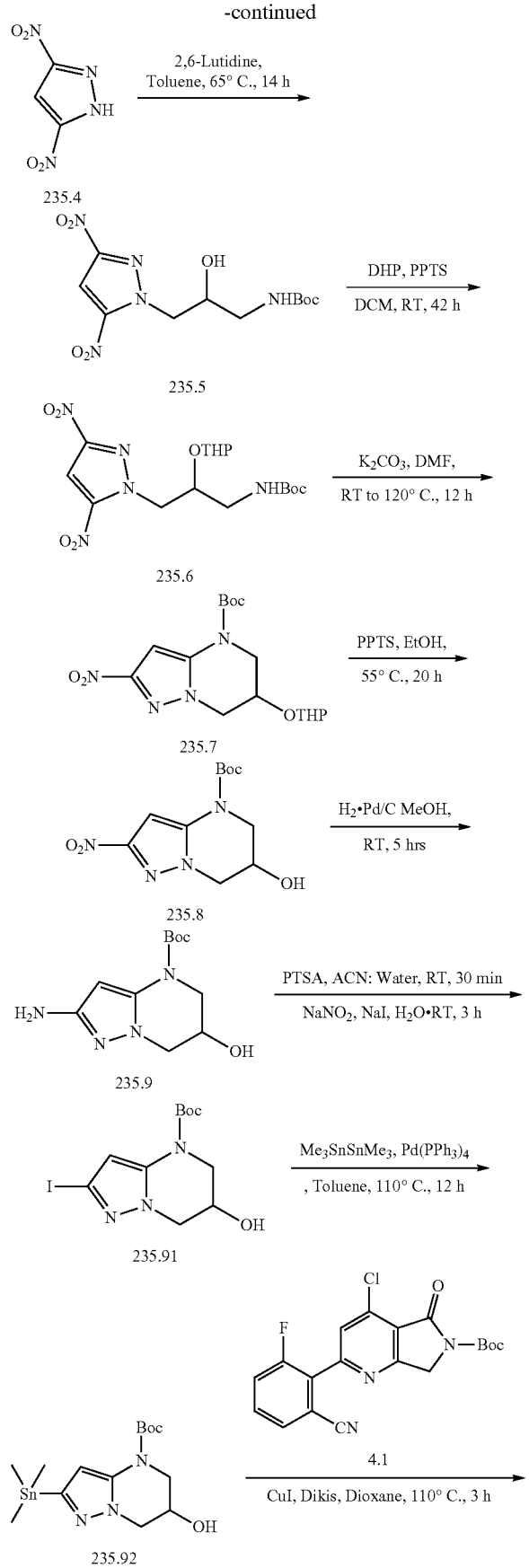

452

-continued

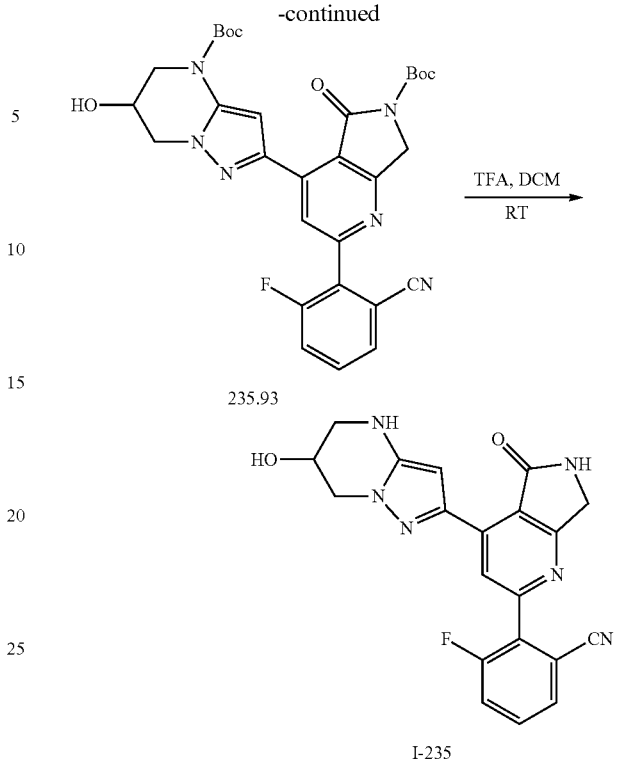

Synthesis of compound 235.2. To a solution of prop-2-en-1-amine (15.0 g, 263 mmol, 1.0 eq) in DCM (300 mL) was added di-tert-butyl dicarbonate (57.3 g, 263 mmol, 1.0 eq) at 0° C. Reaction mixture was stirred at room temperature for 4 h. Upon completion of reaction; reaction mixture was washed with 5% citric acid solution followed by brine. Organic layer was dried over $Na_2SO_4$ and concentrated under reduced pressure to pressure to obtain pure 235.2 (35 g, 84.74%).

Synthesis of compound 235.3. To a solution of compound 235.2 (35.0 g, 222 mmol, 1.0 eq) in DCM (600 mL) was added 3-chloroperbenzoic acid (72.85 g, 423.5 mmol, 1.9 eq) at 0° C. portionwise. Reaction mixture was stirred at room temperature for 16 h. Upon completion of reaction, mixture was washed with 10% sodium sulfite solution followed by washing with saturated $NaHCO_3$ solution and brine. Organic layers were dried over $Na_2SO_4$ and concentrated under reduced pressure to pressure to obtain crude 235.3 (37 g, 95%). This was directly used for next step without any purification.

Synthesis of compound 235.5. To a mixture of 235.3 (10.0 g, 63.29 mmol, 1.0 eq) and compound 235.4 (16.4 g, 94.9 mmol, 1.5 eq) in toluene (100 mL) was added 2,6-Lutidine (1.2 mL, 9.49 mmol, 0.15 eq). Reaction mixture was stirred at 65° C. for 14 h. Upon completion of the reaction, mixture was transferred into aqueous sodium bicarbonate solution, extracted with dichloromethane. Organic layer was combined, washed with brine solution, dried over $Na_2SO_4$ and concentrated under reduced pressure to pressure to obtain crude which was purified by column chromatography to yield 235.5 (12.5 g, 59.6%). MS(ES): m/z 332.3 $[M+H]^+$.

Synthesis of compound 235.6. To a mixture of 235.5 (12.4 g, 37.5 mmol, 1.0 eq) and dihydropyran (13.8 g, 150 mmol, 4.0 eq) in DCM (600 mL) was added Pyridinium p-toluenesulfonate (5.65 g, 22.5 mmol, 0.6 eq). Reaction mixture was stirred at room temperature for 42 h. Upon completion of the reaction; reaction mixture was poured into aq. NaHCO₃ solution, extracted with DCM. Organic layers were combined, washed with brine, dried over Na₂SO₄ and concentrated under reduced pressure to pressure to obtain crude which was purified by column chromatography to provide 235.6 (14.4 g, 92.61%). MS(ES): m/z 416.4 [M+H]⁺.

Synthesis of compound 235.7. To a solution of 235.6 (3.6 g, 8.64 mmol 1.0 eq) in DMF (90 mL) was added K₂CO₃ (3.6 g, 25.98 mmol, 3.0 eq) in a sealed tube and stirred at 120° C. for 12 h. Upon completion of the reaction, mixture was transferred into ice cold water, extracted with EtOAc. Organic layers were combined, washed with brine, dried over Na₂SO₄ and concentrated under reduced pressure to pressure to obtain crude which was purified by column chromatography to provide 235.7 (0.8 g, 25%). MS(ES): m/z 369.4 [M+H]⁺.

Synthesis of compound 235.8. To a solution of 235.7 (2.9 g, 7.88 mmol, 1.0 eq) in EtOH (50 mL) was added Pyridinium p-toluenesulfonate (0.98 g, 3.94 mmol, 0.5 eq). Reaction mixture was heated to 55° C. for 20 h. Upon completion of the reaction, mixture was concentrated under reduced pressure to obtain residue. To this added water and extracted with EtOAc. Organic layers were combined, washed with brine, dried over Na₂SO₄ and concentrated under reduced pressure to pressure to obtain crude that was purified by column chromatography to provide 235.8 (1.6 g, 71.3%). MS(ES): m/z 285.3 [M+H]⁺.

Synthesis of compound 235.9. To the suspension of 10% Pd/C (0.2 g) in MeOH (20 mL) was added compound 235.8 (1.6 g, 5.63 mmol, 1.0 eq) and hydrogen gas was bubbled through it for 5 h. Reaction mixture was filtered and concentrated under reduced pressure to obtain 235.9 (1.4 g, 97.8%). MS(ES): m/z 255.3 [M+H]⁺.

Synthesis of compound 235.91. To a solution of 235.9 (0.4 g, 1.57 mmol, 1.0 eq) in acetonitrile (4 mL) was added solution of p-TsOH (0.812 g, 4.72 mmol, 3.0 eq) in water (4 mL). Reaction mixture stirred at room temperature for 30 min and solution of NaNO₂ (0.272 g, 3.93 mmol, 2.5 eq) and NaI (0.591 g, 3.93 mmol, 2.5 eq) in water (4 mL) was added to it. Reaction mixture was stirred at room temperature for 3 h. Upon completion of reaction, reaction mixture was transferred into ice cold water, and extracted with ethyl acetate. Organic layers were combined, washed with brine solution, dried over Na₂SO₄ and concentrated under reduced pressure to pressure to obtain crude which was purified by column chromatography to provide 235.91 (0.28 g, 45.8%). MS(ES): m/z 366.2 [M+H]⁺.

Synthesis of compound 235.92. A solution of 235.91 (0.28 g, 0.767 mmol, 1.0 eq) in toluene (5 mL) was degassed for 10 min. under argon atmosphere, then Pd(PPh3)₄ (0.089 g, 0.0767 mmol, 0.1 eq) was added, and again degassed for 5 min followed by addition of hexamethylditin (0.754 g, 2.3 mmol, 3.0 eq). The reaction was then heated at 110° C. for 12 h. Upon completion of the reaction, reaction mixture was transferred into water and product was extracted with EtOAc. Organic layers were combined, washed with brine, dried over Na₂SO₄ and concentrated under reduced pressure to obtain crude which was purified by column chromatography to provide 235.92 (0.27 g, 87.6%). MS(ES): m/z 403.2 [M+H]⁺.

Synthesis of compound 235.93. Compound was prepared from 235.92 and 4.1 using the procedure described in Example 64.

Synthesis of compound I-235. Compound was prepared from 235.93 using the procedure described in Example 64. (0.01 g, 75%). MS(ES): m/z 391.38 [M+H]⁺; ¹H NMR (DMSO-d₆, 400 MHz): 8.90 (s, 1H), 8.23 (s, 1H), 7.91-7.89 (d, 1H), 7.81-7.74 (m, 2H), 6.94 (s, 1H), 6.30 (s, 1H), 4.46 (s, 2H), 4.21-4.17 (m, 2H), 3.92-3.91 (m, 1H), 3.24-3.16 (m, 2H), 3.10 (bs, 1).

Example 236

Tyk2 & JAK2 Radioactive Kinase Assay

Peptide substrate, [KKSRGDYMTMQIG], (20 μM) is prepared in reaction buffer (20 mM Hepes pH 7.5, 10 mM MgCl₂, 1 mM EGTA, 0.02% Brij35, 0.02 mg/mL BSA, 0.1 mM Na₃PO₄, 2 mM DTT, 1% DMSO. TYK2 (Invitrogen) kinase is added, followed by compounds in DMSO. ³³PATP is added to initiate the reaction with ATP at 10 μM. Kinase reaction is incubated for 120 min at room temp and reactions are spotted onto P81 ion exchange paper (Whatman #3698-915), and then washed extensively in 0.75% phosphoric acid, prior to reading the radioactivity counts. For JAK2 (Invitrogen) kinase assay the peptide substrate poly[Glu:Tyr] (4:1), 0.2 mg/ml is used, in the reaction carried out the same as for TYK2.

Example 237

Tyk2 & JAK2 Caliper Assay

The caliper machine employs an off chip mobility shift assay to detect phosphorylated peptide substrates from kinase assays, using microfluidics technology. The assays are carried out at ATP concentration equivalent to the ATP $K_m$, and at 1 mM ATP. Compounds are serially diluted in DMSO then further diluted in assay buffer (25 mM HEPES, pH 7.5, 0.01% Brij-35, 0.01% Triton, 0.5 mM EGTA). 5 ul of diluted compound was added into wells first, then 10 ul of enzyme mix was added into wells, followed by 10 uL of substrate mix (peptide and ATP in 10 mM MgCl₂) to start reaction. Reaction was incubated at 28° C. for 25 min and then added 25 ul stop buffer (100 mM HEPES, 0.015% Brij-35, 50 mM EDTA), followed by reading with Caliper. JAK2 at 1 nM final concentration and TYK2 at 9.75 nM are from Carna, and substrates used are ATP at 20 and 16 uM, respectively. JAK2 assay uses peptide 22 and TYK2 uses peptide 30 (Caliper), each at 3 uM.

Table 2 shows the activity of selected compounds of this invention in the Tyk2 and JAK2 radioactive kinase assay. The compound numbers correspond to the compound numbers in Table 1. Compounds having an activity designated as "AA" provided a Ki between 0.000009-0.0001 μM. Compounds having an activity designated as "A" provided an Ki 0.0001-0.01 μM; compounds having an activity designated as "B" provided an Ki of 0.01-0.1 μM; compounds having an activity designated as "C" provided an Ki of 0.1-1.0 μM; and compounds having an activity designated as "D" provided an Ki≥1.0 μM.

TABLE 2

Tyk2 & JAK2 Radioactive Kinase Inhibition Data

| Compound | Tyk2 Ki | JAK2 Ki |
| --- | --- | --- |
| I-1 | A | C |
| I-2 | B | D |
| I-3 | A | C |
| I-4 | A | B |
| I-5 | A | C |
| I-6 | A | A |

TABLE 2-continued

Tyk2 & JAK2 Radioactive Kinase Inhibition Data

| Compound | Tyk2 Ki | JAK2 Ki |
|---|---|---|
| I-7 | A | C |
| I-9 | A | C |
| I-16 | A | C |
| I-56 | A | B |
| I-57 | A | C |
| I-58 | B | C |
| I-59 | A | A |
| I-60 | A | B |
| I-61 | A | B |
| I-62 | AA | B |
| I-63 | A | B |
| I-64 | A | B |
| I-65 | A | B |
| I-66 | A | B |
| I-67 | A | B |
| I-68 | A | B |
| I-69 | A | B |
| I-70 | A | A |
| I-71 | AA | B |
| I-72 | A | A |
| I-73 | A | A |
| I-74 | A | B |
| I-75 | A | A |
| I-76 | AA | A |
| I-77 | A | B |
| I-78 | A | B |
| I-79 | A | B |
| I-80 | A | B |
| I-81 | B | D |
| I-82 | D | D |
| I-83 | A | B |
| I-84 | AA | A |
| I-85 | B | D |
| I-86 | A | B |
| I-87 | A | B |
| I-88 | AA | B |
| I-89 | A | B |
| I-90 | A | C |
| I-91 | A | B |
| I-92 | A | B |
| I-93 | A | B |
| I-94 | B | C |
| I-95 | A | B |
| I-96 | A | B |
| I-97 | A | B |
| I-98 | A | B |
| I-99 | D | D |
| I-100 | AA | A |
| I-101 | A | B |
| I-102 | B | D |
| I-103 | A | B |
| I-104 | A | C |
| I-105 | A | B |
| I-106 | B | C |
| I-107 | B | C |
| I-108 | A | A |
| I-109 | A | A |
| I-110 | D | D |
| I-111 | A | B |
| I-112 | A | B |
| I-113 | A | B |
| I-114 | A | A |
| I-115 | A | B |
| I-116 | A | A |
| I-117 | A | B |
| I-118 | AA | A |
| I-119 | AA | A |
| I-120 | A | A |
| I-121 | A | B |
| I-122 | A | B |
| I-123 | A | A |
| I-124 | B | C |
| I-125 | A | B |
| I-126 | A | B |
| I-127 | A | B |
| I-128 | A | B |
| I-129 | A | B |
| I-130 | A | B |
| I-131 | A | B |
| I-132 | A | B |
| I-133 | A | A |
| I-134 | A | A |
| I-135 | A | A |
| I-136 | AA | A |
| I-137 | A | A |
| I-138 | A | C |
| I-139 | A | B |
| I-140 | A | A |
| I-141 | AA | A |
| I-142 | AA | A |
| I-143 | A | A |
| I-144 | B | C |
| I-145 | A | B |
| I-146 | A | B |
| I-147 | A | B |
| I-148 | B | D |
| I-149 | AA | A |
| I-150 | AA | A |
| I-151 | A | C |
| I-152 | A | A |
| I-153 | A | A |
| I-154 | A | A |
| I-155 | A | B |
| I-156 | A | B |
| I-157 | A | B |
| I-158 | A | B |
| I-159 | A | B |
| I-160 | AA | A |
| I-161 | A | B |
| I-162 | AA | A |
| I-163 | A | A |
| I-164 | A | A |
| I-165 | A | A |
| I-166 | AA | A |
| I-167 | A | A |
| I-168 | A | A |
| I-169 | A | A |
| I-170 | A | A |
| I-171 | A | B |
| I-172 | A | B |
| I-173 | AA | A |
| I-174 | A | B |
| I-175 | A | C |
| I-176 | A | B |
| I-177 | D | D |
| I-178 | A | B |
| I-179 | A | B |
| I-180 | A | B |
| I-181 | A | B |
| I-182 | A | A |
| I-183 | A | A |
| I-184 | A | A |
| I-185 | A | B |
| I-186 | A | B |
| I-187 | AA | A |
| I-188 | AA | A |
| I-189 | A | B |
| I-190 | A | B |
| I-191 | A | A |
| I-192 | A | A |
| I-193 | A | A |
| I-194 | A | A |
| I-195 | A | A |
| I-196 | A | A |
| I-197 | A | B |
| I-198 | A | B |
| I-199 | A | B |
| I-200 | A | B |
| I-201 | A | B |
| I-202 | A | B |
| I-203 | A | B |
| I-204 | A | B |

TABLE 2-continued

Tyk2 & JAK2 Radioactive Kinase Inhibition Data

| Compound | Tyk2 Ki | JAK2 Ki |
|---|---|---|
| I-205 | A | B |
| I-206 | A | B |
| I-207 | A | B |
| I-208 | A | B |
| I-209 | A | B |
| I-210 | A | B |
| I-211 | A | B |
| I-212 | A | C |
| I-213 | AA | B |
| I-214 | A | B |
| I-215 | A | B |
| I-216 | A | A |
| I-217 | A | A |
| I-218 | A | B |
| I-219 | A | B |
| I-220 | A | B |
| I-221 | A | A |
| I-222 | A | B |
| I-223 | A | B |
| I-224 | A | B |
| I-225 | A | A |
| I-226 | A | A |
| I-227 | A | B |
| I-228 | A | B |
| I-229 | AA | B |
| I-230 | A | A |
| I-231 | B | C |
| I-232 | D | D |
| I-233 | B | D |
| I-234 | B | C |
| I-235 | A | A |

Example 238

IL-12 Induced pSTAT4 in Human PBMC

Human PBMC are isolated from buffy coat and are stored frozen for assays as needed. Cells for assay are thawed and resuspended in complete media containing serum, then cells are diluted to 1.67 E6 cells/ml so that 120 ul per well is 200,000 cells. 15 ul of compound or DMSO is added to the well at the desired concentrations and incubated at 1 hr at 37 C. 15 ul of stimulus (final concentration of 1.7 ng/mL IL-12) is added for 30 minutes prior to pSTAT4 and total STAT4 analysis using cell lysates prepared and analyzed by MSD reagents as per manufacturer protocol. The final DMSO concentration of compound in the assay is 0.1%.

Example 239

GM-CSF Induced pSTAT5 in Human PBMC

Cells are prepared for analysis as in the above procedure and 15 ul of GM-CSF (final concentration 5 ng/mL) is added for 20 minutes prior to pSTAT5 and total STAT5 analysis using cell lysates prepared and analyzed by MSD reagents as per manufacturer protocol. The final DMSO concentration of compound in the assay is 0.1%.

Table 3 shows the activity of selected compounds of this invention in the IL-12 induced pSTAT4 and GM-CSF induced pSTAT5 inhibition assays in human PBMC. The compound numbers correspond to the compound numbers in Table 1. Compounds having an activity designated as "A" provided an $IC_{50}$ 0.03-0.1 μM; compounds having an activity designated as "B" provided a $IC_{50}$ of 0.1-2 μM; and compounds having an activity designated as "C" provided an $IC_{50} > 2$ μM.

TABLE 3

Cell activity data

| Compound | Tyk2-pSTAT4 $EC_{50}$ | JAK2-pSTAT5 $EC_{50}$ |
|---|---|---|
| I-2 | NA | C |
| I-3 | NA | C |
| I-4 | B | C |
| I-5 | NA | C |
| I-6 | B | C |
| I-9 | NA | C |
| I-16 | NA | C |
| I-56 | B | B |
| I-57 | B | B |
| I-59 | B | B |
| I-60 | NA | C |
| I-61 | B | NA |
| I-62 | B | B |
| I-63 | B | B |
| I-65 | A | B |
| I-68 | NA | C |
| I-69 | B | B |
| I-70 | B | B |
| I-71 | A | B |
| I-72 | B | C |
| I-73 | B | NA |
| I-74 | NA | C |
| I-75 | NA | C |
| I-76 | A | B |
| I-77 | A | NA |
| I-78 | A | B |
| I-79 | A | B |
| I-80 | NA | C |
| I-83 | B | C |
| I-84 | A | B |
| I-85 | NA | C |
| I-86 | B | NA |
| I-88 | B | C |
| I-89 | B | C |
| I-90 | NA | C |
| I-91 | B | C |
| I-92 | A | B |
| I-93 | A | NA |
| I-95 | A | B |
| I-96 | NA | C |
| I-97 | A | B |
| I-98 | A | B |
| I-100 | A | B |
| I-101 | NA | C |
| I-103 | B | B |
| I-104 | B | B |
| I-105 | B | NA |
| I-107 | B | B |
| I-109 | NA | C |
| I-110 | NA | C |
| I-111 | A | B |
| I-112 | B | B |
| I-113 | B | B |
| I-114 | A | B |
| I-118 | A | B |
| I-119 | A | B |
| I-120 | B | B |
| I-121 | A | C |
| I-122 | B | B |
| I-123 | B | C |
| I-124 | C | C |
| I-125 | B | B |
| I-126 | B | B |
| I-127 | A | NA |
| I-128 | A | NA |
| I-129 | B | C |
| I-130 | B | B |
| I-131 | A | C |
| I-132 | B | NA |
| I-133 | NA | C |
| I-134 | B | NA |
| I-135 | B | C |
| I-136 | A | C |
| I-137 | B | C |
| I-139 | B | B |

TABLE 3-continued

Cell activity data

| Compound | Tyk2-pSTAT4 EC$_{50}$ | JAK2-pSTAT5 EC$_{50}$ |
|---|---|---|
| I-140 | B | NA |
| I-141 | B | B |
| I-142 | A | B |
| I-145 | NA | C |
| I-147 | B | B |
| I-148 | C | C |
| I-149 | B | B |
| I-150 | A | C |
| I-151 | B | C |
| I-152 | B | C |
| I-153 | A | C |
| I-154 | A | NA |
| I-155 | B | C |
| I-156 | B | B |
| I-157 | B | C |
| I-158 | B | C |
| I-159 | B | C |
| I-160 | A | NA |
| I-161 | B | B |
| I-162 | B | B |
| I-163 | B | B |
| I-164 | NA | C |
| I-165 | B | B |
| I-166 | B | B |
| I-167 | B | NA |
| I-168 | B | B |
| I-169 | A | NA |
| I-170 | A | C |
| I-171 | B | C |
| I-172 | B | C |
| I-173 | NA | C |
| I-175 | B | NA |
| I-176 | B | B |
| I-177 | C | B |
| I-178 | B | C |
| I-179 | A | C |
| I-180 | NA | C |
| I-181 | B | B |
| I-182 | A | NA |
| I-183 | A | B |
| I-184 | A | B |
| I-185 | B | B |
| I-186 | B | C |
| I-187 | B | NA |
| I-188 | B | B |
| I-189 | B | C |
| I-190 | B | B |
| I-191 | B | B |
| I-192 | NA | C |
| I-193 | B | C |
| I-194 | B | NA |
| I-195 | A | B |
| I-196 | A | B |
| I-197 | B | NA |
| I-198 | B | C |
| I-200 | A | B |
| I-201 | A | B |
| I-202 | A | B |
| I-203 | A | B |
| I-204 | A | C |
| I-205 | A | B |
| I-206 | A | B |
| I-207 | A | B |
| I-208 | B | C |
| I-209 | B | C |
| I-210 | A | B |
| I-211 | B | C |
| I-212 | B | C |
| I-213 | B | C |
| I-214 | B | C |
| I-215 | B | B |
| I-216 | A | B |
| I-217 | A | B |
| I-218 | B | B |
| I-219 | B | B |
| I-220 | B | C |
| I-221 | B | B |
| I-222 | B | NA |
| I-223 | B | B |
| I-224 | A | B |
| I-225 | B | B |
| I-226 | A | B |
| I-227 | B | B |
| I-228 | B | B |
| I-229 | B | NA |
| I-230 | B | B |
| I-231 | C | C |
| I-232 | C | B |
| I-233 | C | C |
| I-234 | B | C |
| I-235 | NA | C |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A method of alleviating an TYK2-mediated disorder, disease, or condition, wherein the TYK2-mediated disorder, disease, or condition is an autoimmune disorder selected from systemic lupus erythematosus, multiple sclerosis, psoriasis, Crohn's disease, ulcerative colitis, inflammatory bowel disease and ankylosing spondylitis, in a patient in need thereof comprising administering to said patient an effective amount of a compound of formula I, or a pharmaceutical composition thereof:

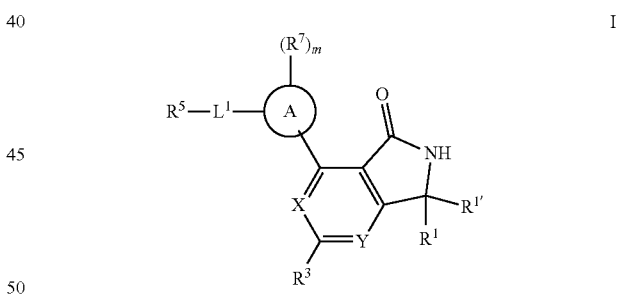

or a pharmaceutically acceptable salt thereof, wherein:
X is =C(R$^6$)—;
Y is =N—;
Ring A is phenyl; a 5-6 membered partially unsaturated monocyclic heterocyclic ring having 1-4 heteroatoms independently selected from nitrogen, oxygen, and sulfur; a 6-12 membered partially unsaturated bicyclic heterocyclic ring having 1-4 heteroatoms independently selected from nitrogen, oxygen, and sulfur; or a 5-6 membered monocyclic heteroaryl ring having 1-4 heteroatoms independently selected from nitrogen, oxygen, and sulfur;
each of R$^1$ and R$^{1'}$ is independently hydrogen, R$^2$, halogen, CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R; or R¹ and R¹' are taken together with their intervening atoms to form an optionally substituted 3-7 membered spiro-fused ring having 0-2 heteroatoms independently selected from nitrogen, oxygen, and sulfur;

each R² is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

R³ is Cy¹; wherein R³ is substituted with n instances of R⁸; R⁵ is halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, —N(R)S(O)₂R, and Cy²; wherein R⁵ is substituted with p instances of R⁹; or when Ring A is partially unsaturated, L¹R⁵, taken together, may also be absent;

each of Cy¹ and Cy² is independently phenyl; a 3-7 membered saturated or partially unsaturated monocyclic carbocyclic ring; a 6-12 membered bicyclic carbocyclic ring; a 3-7 membered saturated or partially unsaturated monocyclic heterocyclic ring having 1-2 heteroatoms independently selected from nitrogen, oxygen, and sulfur; a 6-12 membered saturated or partially unsaturated bicyclic heterocyclic ring having 1-3 heteroatoms independently selected from nitrogen, oxygen, and sulfur; or a 5-6 membered heteroaryl ring having 1-4 heteroatoms independently selected from nitrogen, oxygen, and sulfur;

each instance of R⁶ is independently hydrogen, —R², halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

each instance of R⁷ and R⁸ is independently oxo, —R², halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

each instance of R⁹ is independently oxo, $C_{1-6}$ hydroxyaliphatic, —R², halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

L¹ is a covalent bond or a $C_{1-6}$ bivalent saturated or unsaturated, straight or branched hydrocarbon chain wherein one or two methylene units of the chain are optionally and independently replaced by —N(R)—, —N(R)C(O)—, —C(O)N(R)—, —N(R)S(O)₂—, —S(O)₂N(R)—, —O—, —C(O)—, —OC(O)—, —C(O)O—, —S—, —S(O)— or —S(O)₂—;

m is 0-2;
n is 0-4;
p is 0-3; and
each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

2. The method of claim 1 wherein the autoimmune disorder is selected from multiple sclerosis, psoriasis, Crohn's disease, ulcerative colitis, inflammatory bowel disease and ankylosing spondylitis.

3. The method of claim 1 wherein Ring A is selected from the group consisting of a 5-6 membered partially unsaturated monocyclic heterocyclic ring having 1-4 heteroatoms independently selected from nitrogen, oxygen, and sulfur; a 6-12 membered partially unsaturated bicyclic heterocyclic ring having 1-4 heteroatoms independently selected from nitrogen, oxygen, and sulfur; and a 5-6 membered monocyclic heteroaryl ring having 1-4 heteroatoms independently selected from nitrogen, oxygen, and sulfur.

4. The method of claim 1 wherein R¹ and R¹' are each independently selected from the group consisting of hydrogen and —R².

5. The method of claim 1 wherein R³ is Cy¹ selected from the group consisting of phenyl; a 6-12 membered bicyclic carbocyclic ring; a 3-7 membered saturated or partially unsaturated monocyclic heterocyclic ring having 1-2 heteroatoms independently selected from nitrogen, oxygen, and sulfur; a 6-12 membered saturated or partially unsaturated bicyclic heterocyclic ring having 1-3 heteroatoms independently selected from nitrogen, oxygen, and sulfur; and a 5-6 membered heteroaryl ring having 1-4 heteroatoms independently selected from nitrogen, oxygen, and sulfur, wherein R³ is substituted with n instances of R⁸.

6. The method of claim 1 wherein R³ is substituted with n instances of R⁸ selected from the group consisting of oxo, —R², halogen, —CN, —NO₂, —OR, —SR, —NR₂, —S(O)₂R, —S(O)₂NR₂, —S(O)R, —C(O)R, C(O)NR₂, —C(O)N(R)OR, —OC(O)R, —OC(O)NR₂, —N(R)C(O)OR, —N(R)C(O)R, —N(R)C(O)NR₂, and —N(R)S(O)₂R.

7. The method of claim 6 wherein n is 0-3.

8. The method of claim 1 wherein the compound of formula I, or a pharmaceutical composition thereof is:

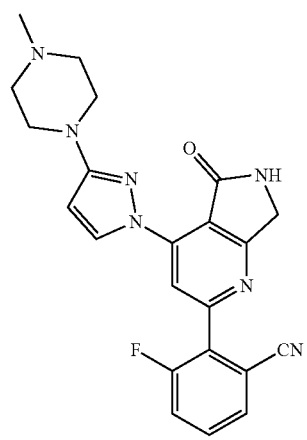

I-6

I-59
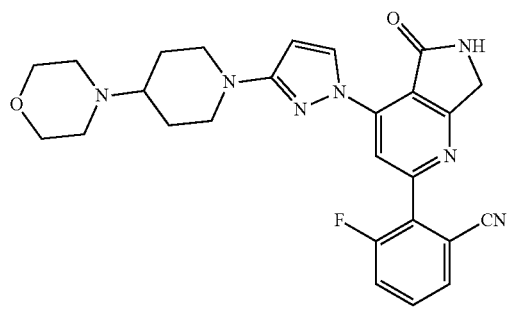
I-70
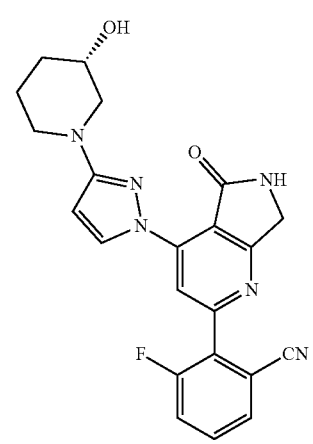
I-72
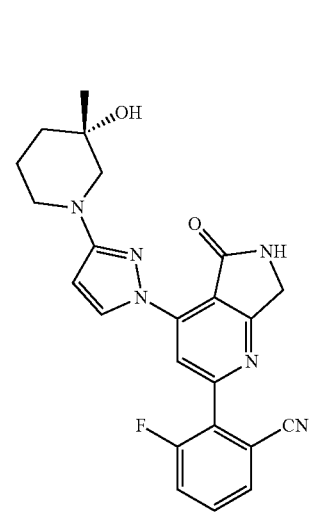
I-73
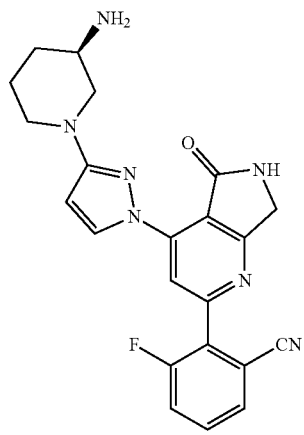
I-75
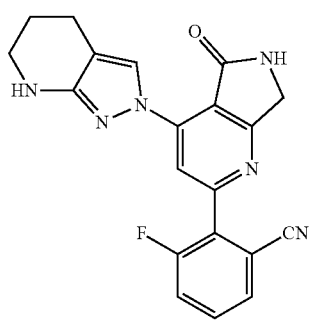
I-76
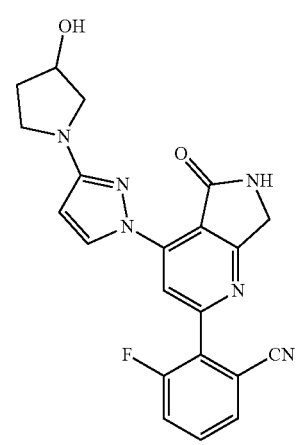
I-84
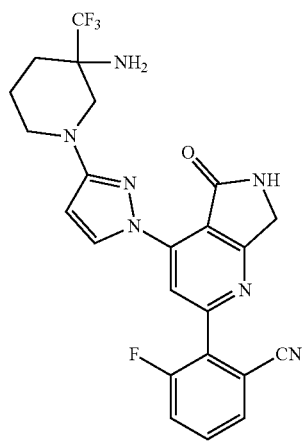

465
-continued
I-100
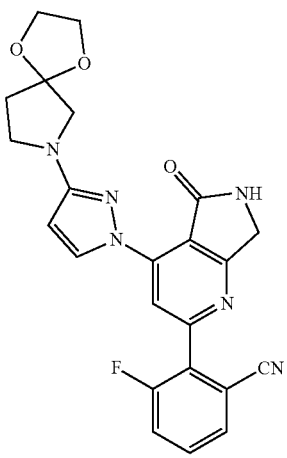
I-108
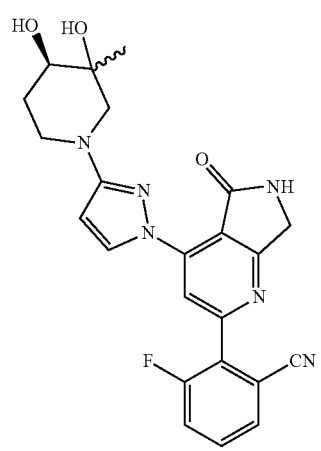
I-109
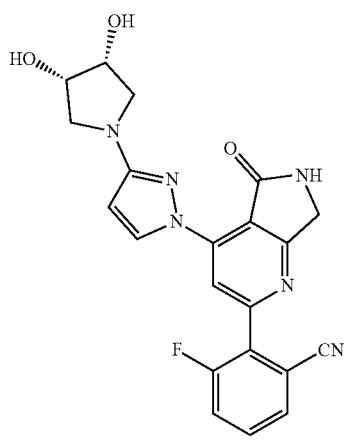
466
-continued
I-114
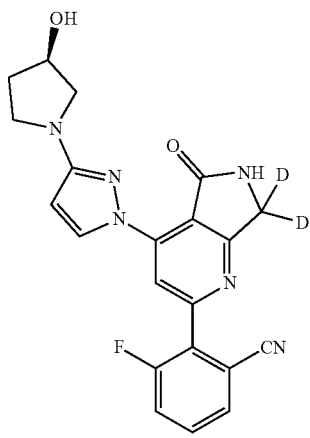
I-116
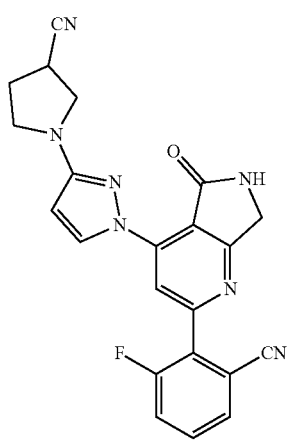
I-118
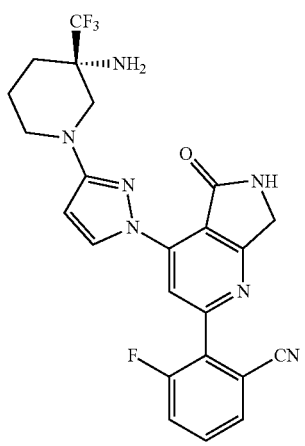

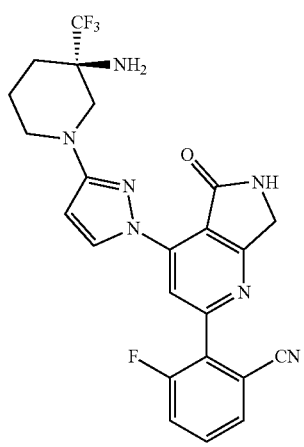
I-119
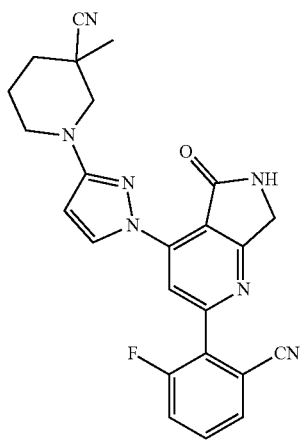
I-133
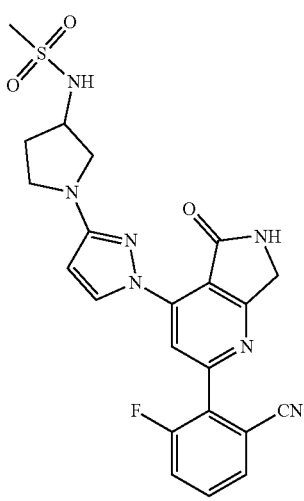
I-120
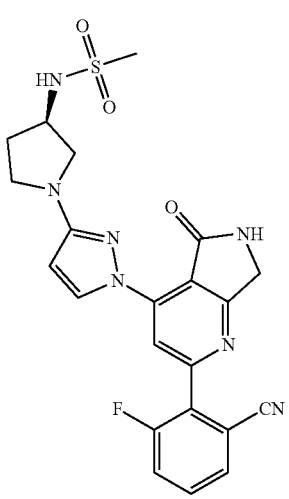
I-134
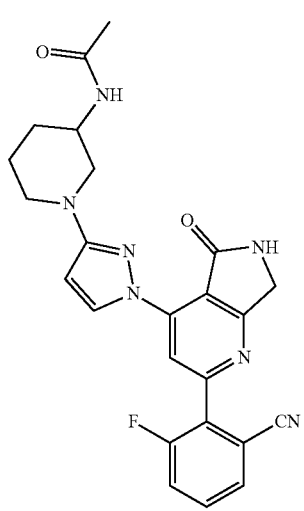
I-123
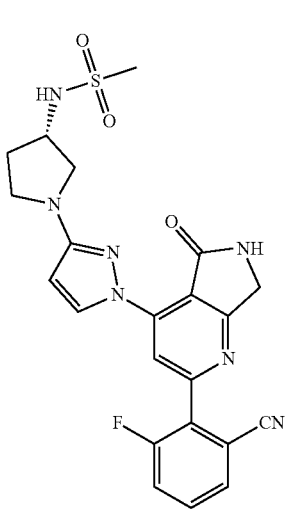
I-135

I-136
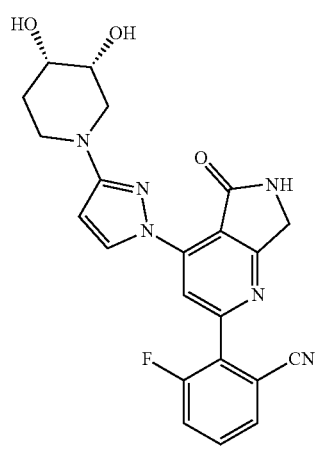
I-137
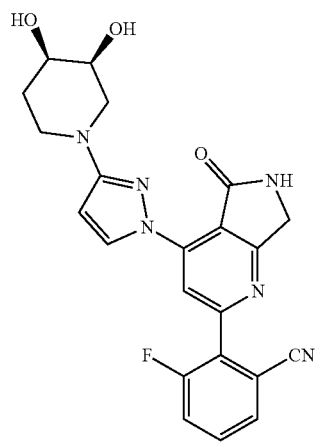
I-140
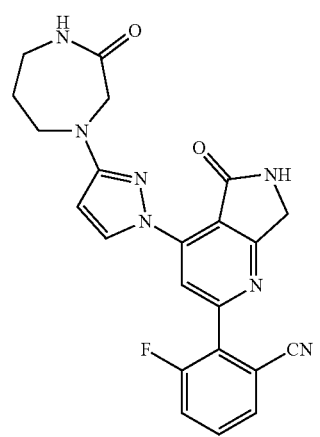
I-141
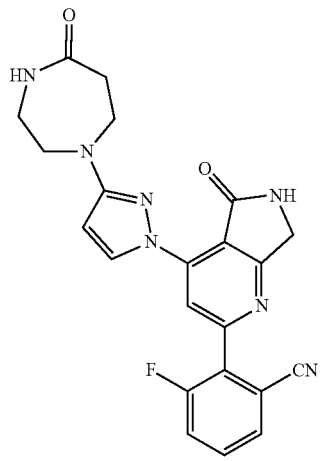
I-142
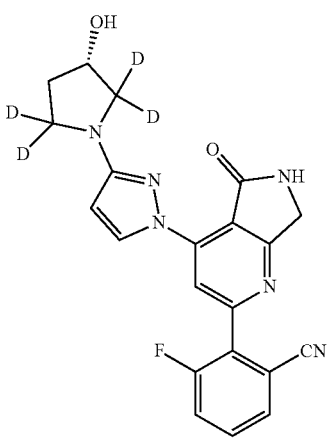
I-143
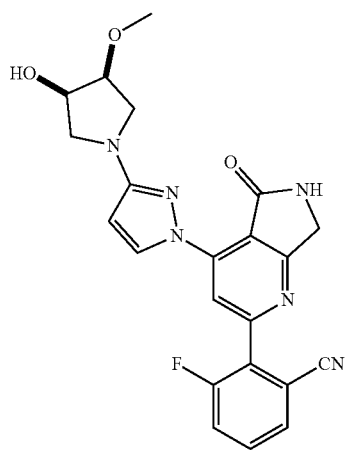

I-149
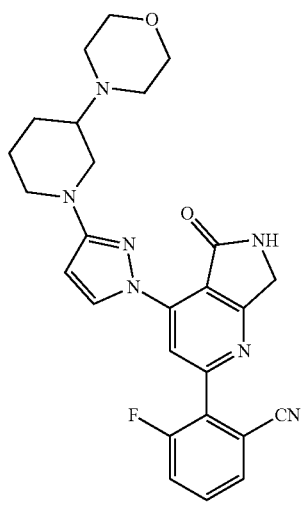
I-150
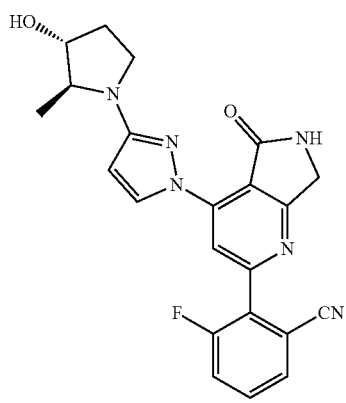
I-152
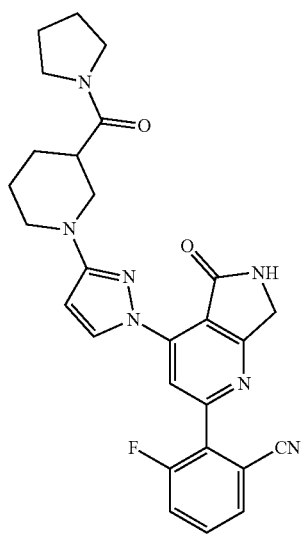
I-153
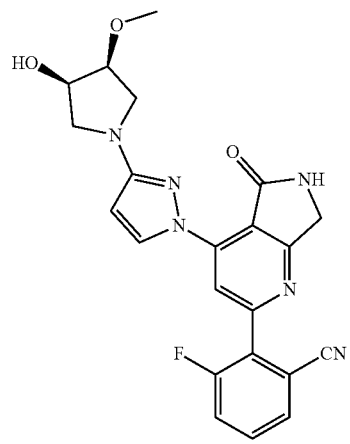
I-154
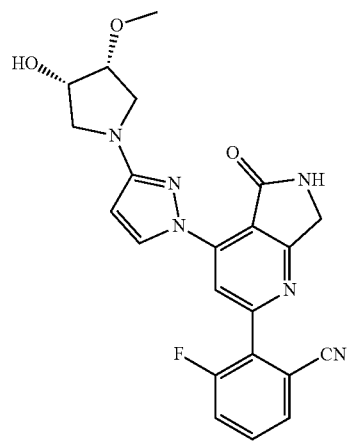
I-160
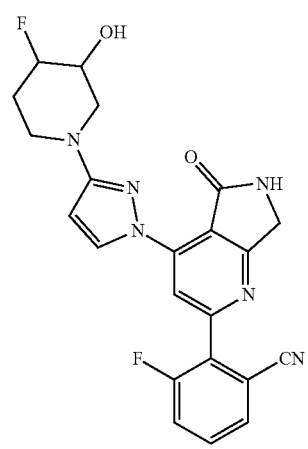

I-162
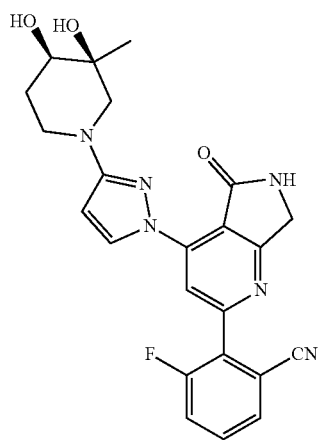
I-163
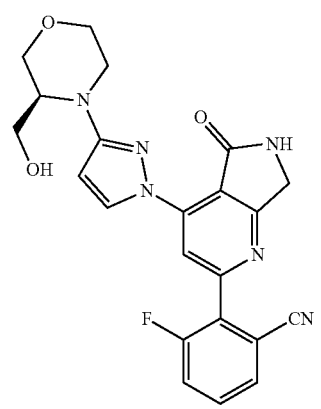
I-164
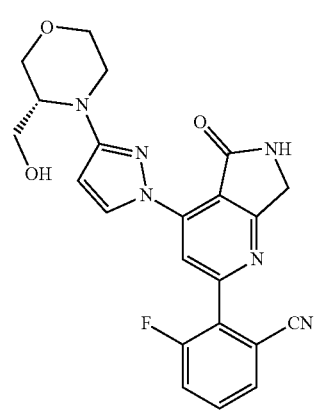
I-165
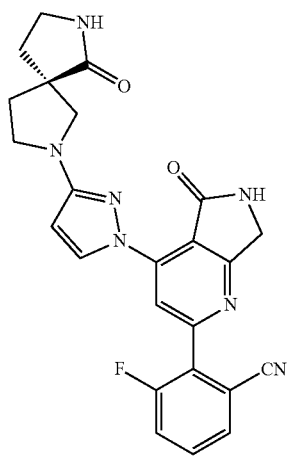
I-166
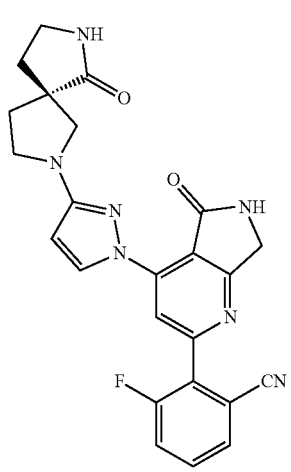
I-167
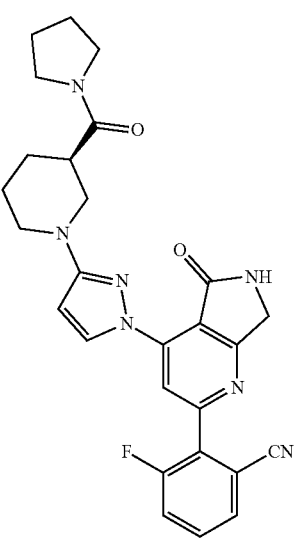

I-168
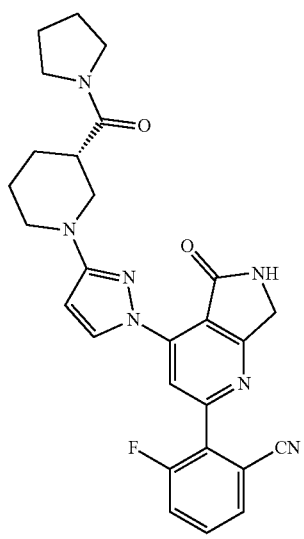
I-169
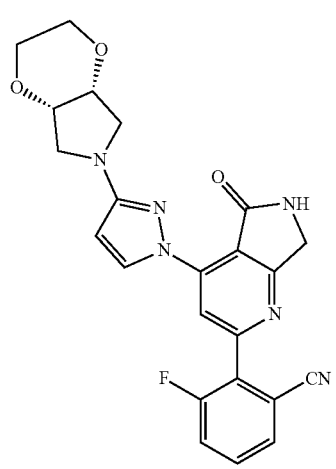
I-170
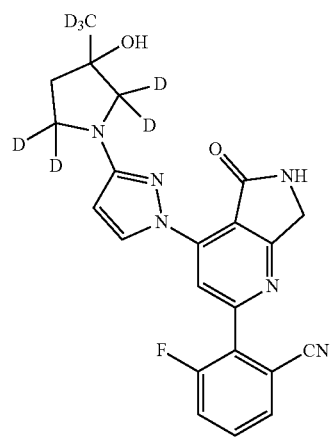
I-173
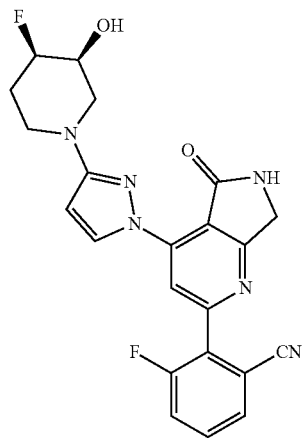
I-182
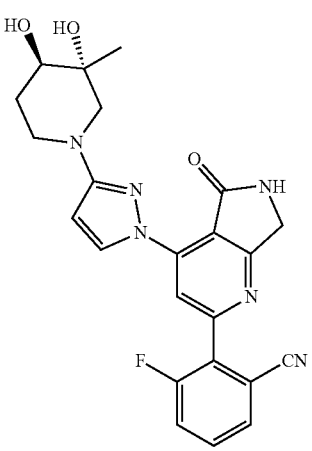
I-183
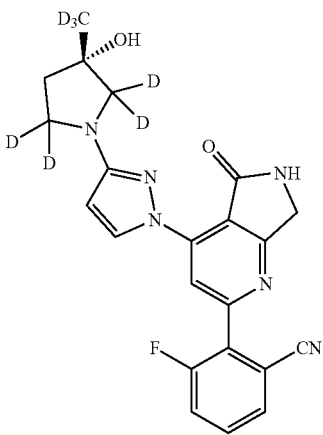

-continued
I-184
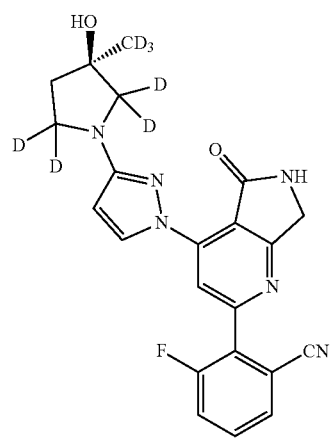
I-187
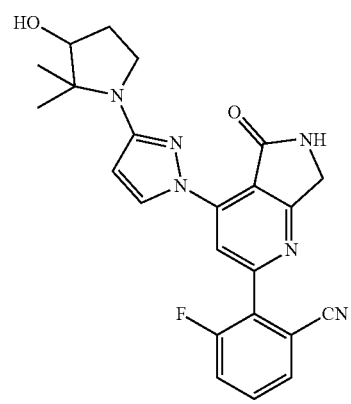
I-188
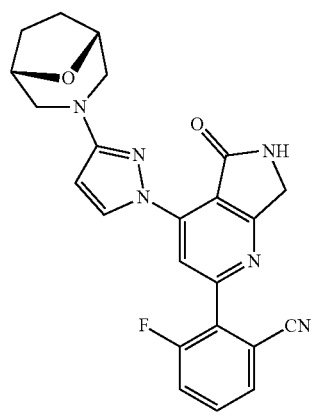
-continued
I-191
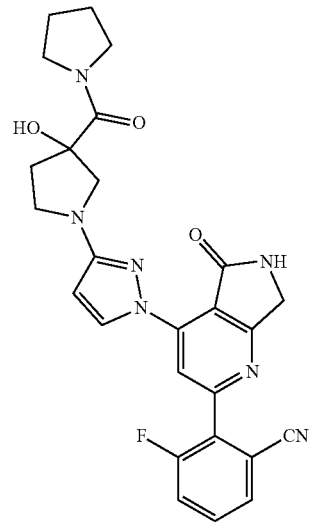
I-192
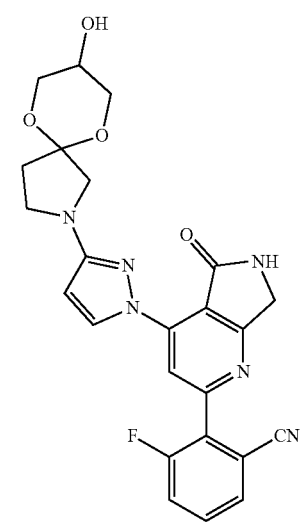
I-193
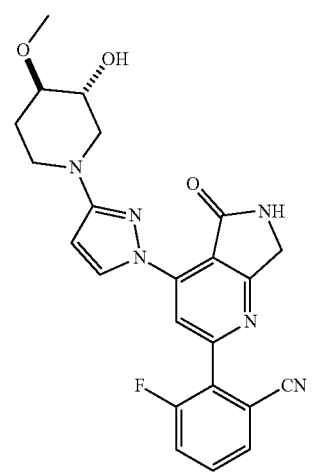

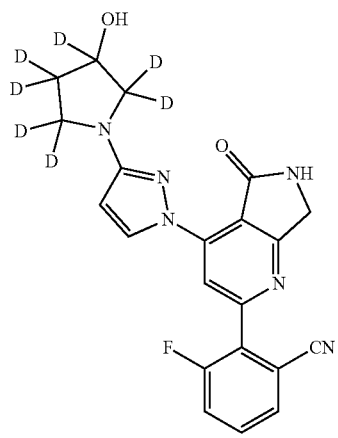
I-194
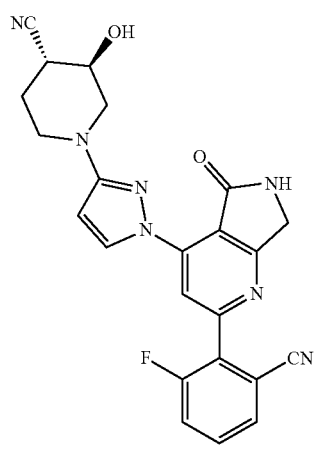
I-216
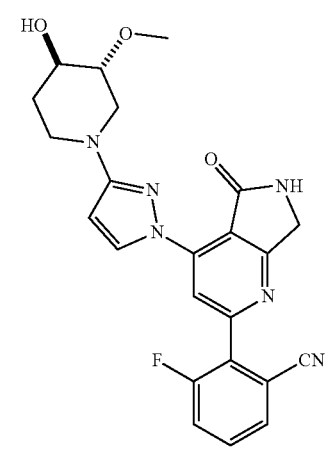
I-195
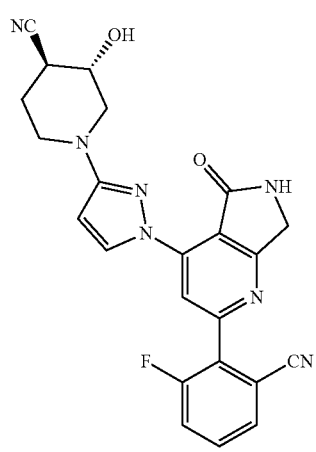
I-217
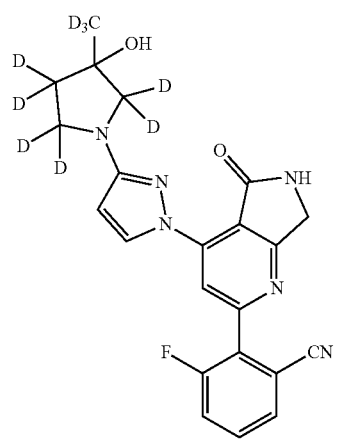
I-196
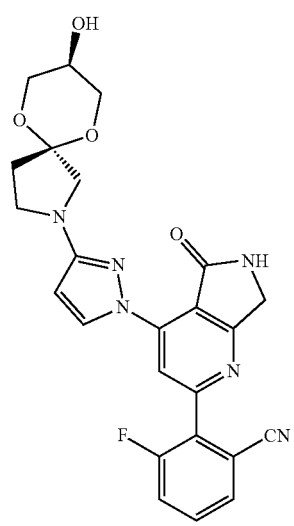
I-221

-continued
I-225
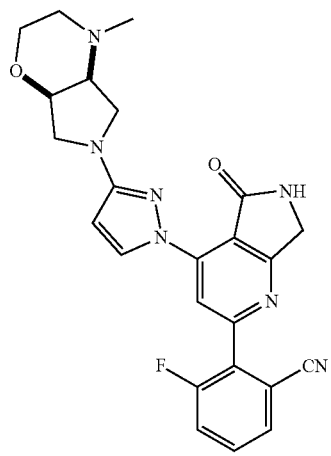
I-226
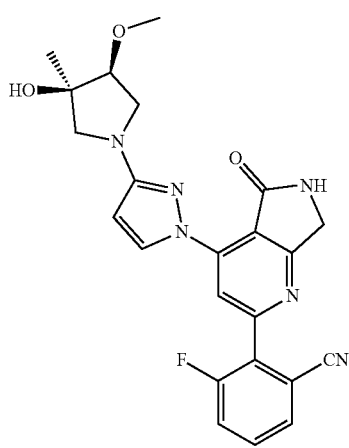
-continued
I-230
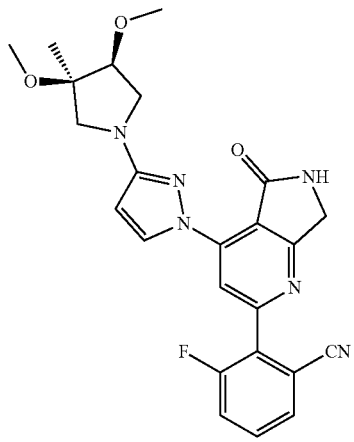
I-235
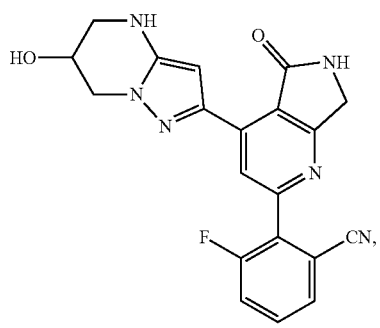
or a pharmaceutically acceptable salt thereof.
* * * * *